United States Patent
Huh et al.

(10) Patent No.: US 10,964,892 B2
(45) Date of Patent: Mar. 30, 2021

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Jungoh Huh, Daejeon (KR); Boonjae Jang, Daejeon (KR); Dong Hoon Lee, Daejeon (KR); Wonik Jeong, Daejeon (KR); Hyungjin Lee, Daejeon (KR); Minyoung Kang, Daejeon (KR); Dong Uk Heo, Daejeon (KR); Miyeon Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/126,533

(22) PCT Filed: Apr. 1, 2015

(86) PCT No.: PCT/KR2015/003255
§ 371 (c)(1),
(2) Date: Sep. 15, 2016

(87) PCT Pub. No.: WO2015/152633
PCT Pub. Date: Oct. 8, 2015

(65) Prior Publication Data
US 2017/0098777 A1     Apr. 6, 2017

(30) Foreign Application Priority Data

Apr. 4, 2014   (KR) .................. 10-2014-0040818
Jan. 23, 2015  (KR) .................. 10-2015-0011540

(51) Int. Cl.
*H01L 51/00* (2006.01)
*C09K 11/06* (2006.01)
(Continued)

(52) U.S. Cl.
CPC ........ *H01L 51/0067* (2013.01); *C07D 251/24* (2013.01); *C07D 401/14* (2013.01);
(Continued)

(58) Field of Classification Search
None
See application file for complete search history.

(56) References Cited

U.S. PATENT DOCUMENTS 6,225,467 B1   5/2001   Esteghamatian et al.
6,730,417 B2   5/2004   Hu et al.
(Continued)

FOREIGN PATENT DOCUMENTS

CN   1702065 A   11/2005
CN   1867646 A   11/2006
(Continued)

OTHER PUBLICATIONS

Hongliang Zhong et al., "New Conjugated Triazine Based Molecular Materials for Application in Optoelectronic Devices: Design, Synthesis, and Properties", The Journal of Physical Chemistry, C 2011,115, pp. 2423-2427.
(Continued)

*Primary Examiner* — Jay Yang
(74) *Attorney, Agent, or Firm* — Dentons US LLP

(57) ABSTRACT

The present specification provides a hetero-cyclic compound and an organic light emitting device comprising the same.

19 Claims, 6 Drawing Sheets

(51) Int. Cl.
  C07D 251/24 (2006.01)
  C09K 11/02 (2006.01)
  C07D 401/14 (2006.01)
  C07D 403/14 (2006.01)
  H01L 51/50 (2006.01)
(52) U.S. Cl.
  CPC .......... *C07D 403/14* (2013.01); *C09K 11/025* (2013.01); *C09K 11/06* (2013.01); *H01L 51/0052* (2013.01); *H01L 51/0054* (2013.01); *H01L 51/0058* (2013.01); *H01L 51/0077* (2013.01); *H01L 51/0085* (2013.01); *C09K 2211/1007* (2013.01); *C09K 2211/1029* (2013.01); *C09K 2211/1044* (2013.01); *C09K 2211/181* (2013.01); *C09K 2211/185* (2013.01); *H01L 51/5012* (2013.01); *H01L 51/5072* (2013.01); *H01L 51/5076* (2013.01); *H01L 51/5092* (2013.01)

(56) References Cited

U.S. PATENT DOCUMENTS

| | | | |
|---|---|---|---|
| 6,821,643 | B1 | 11/2004 | Hu et al. |
| 9,960,363 | B2 | 5/2018 | Eum et al. |
| 2003/0165715 | A1 | 9/2003 | Yoon et al. |
| 2003/0170490 | A1 | 9/2003 | Hu et al. |
| 2006/0135766 | A1 | 6/2006 | Hayoz et al. |
| 2007/0190355 | A1 | 8/2007 | Ikeda et al. |
| 2009/0162612 | A1 | 6/2009 | Hatwar et al. |
| 2010/0039026 | A1* | 2/2010 | Yang .............. C07D 239/26 313/504 |
| 2011/0037062 | A1 | 2/2011 | Fukumatsu et al. |
| 2011/0095282 | A1 | 4/2011 | Pflumm et al. |
| 2011/0121274 | A1 | 5/2011 | Parham et al. |
| 2011/0215308 | A1 | 9/2011 | Im et al. |
| 2011/0284831 | A1* | 11/2011 | Kaiser ............ H01L 51/0067 257/40 |
| 2012/0126217 | A1 | 5/2012 | Yoshida et al. |
| 2012/0214993 | A1 | 8/2012 | Aihara et al. |
| 2012/0286249 | A1 | 11/2012 | Lee et al. |
| 2013/0248830 | A1 | 9/2013 | Welsh et al. |
| 2014/0014927 | A1 | 1/2014 | Kim et al. |
| 2014/0061629 | A1 | 3/2014 | Murase et al. |
| 2014/0110694 | A1 | 4/2014 | Shin et al. |
| 2014/0367654 | A1 | 12/2014 | Kim et al. |
| 2015/0123089 | A1 | 5/2015 | Lee et al. |
| 2015/0144897 | A1 | 5/2015 | Kang et al. |
| 2015/0236273 | A1 | 8/2015 | Jang et al. |
| 2015/0243897 | A1 | 8/2015 | Montenegro et al. |
| 2015/0349270 | A1 | 12/2015 | Lee et al. |
| 2016/0072073 | A1 | 3/2016 | Lee et al. |
| 2016/0093808 | A1* | 3/2016 | Adamovich ........ H01L 51/0052 257/40 |
| 2016/0218298 | A1 | 7/2016 | Lee et al. |
| 2016/0248020 | A1 | 8/2016 | Ondari et al. |
| 2017/0005273 | A1 | 1/2017 | Hwang et al. |
| 2017/0104163 | A1 | 4/2017 | Lee et al. |
| 2018/0053900 | A1* | 2/2018 | Eum .............. H01L 51/0067 |

FOREIGN PATENT DOCUMENTS

| | | |
|---|---|---|
| CN | 1934213 A | 3/2007 |
| CN | 101656301 A | 2/2010 |
| CN | 101960637 A | 1/2011 |
| CN | 102077379 A | 5/2011 |
| CN | 102077384 A | 5/2011 |
| CN | 102201432 A | 9/2011 |
| CN | 102292841 A | 12/2011 |
| CN | 102471320 | 5/2015 |
| CN | 105392789 A | 3/2016 |
| CN | 106471093 | 3/2017 |
| EP | 2 463 351 A2 | 6/2012 |
| EP | 2749560 A1 | 7/2014 |
| EP | 2752902 A1 | 7/2014 |
| JP | 2012-513668 A | 6/2012 |
| KR | 10-2000-0051826 A | 8/2000 |
| KR | 10201100525 | 5/2011 |
| KR | 10-2011-0085174 A | 7/2011 |
| KR | 10-2011-0111093 A | 10/2011 |
| KR | 10-2011-0113469 A | 10/2011 |
| KR | 10-2012-0138673 A | 12/2012 |
| KR | 10-2013-0115160 A | 10/2013 |
| KR | 10-2013-0116041 A | 10/2013 |
| KR | 10-2014-0008126 A | 1/2014 |
| KR | 10-20140009919 | 1/2014 |
| KR | 10-2015-0002072 A | 1/2015 |
| TW | 201522317 A | 6/2015 |
| WO | 2004/077885 A2 | 9/2004 |
| WO | 2007/029798 A1 | 3/2007 |
| WO | 2009/072587 A1 | 6/2009 |
| WO | 2010/072300 A1 | 7/2010 |
| WO | 2010/102706 A1 | 9/2010 |
| WO | 2010/126270 A1 | 11/2010 |
| WO | 2011/021520 A1 | 2/2011 |
| WO | 2012/150826 A1 | 11/2012 |
| WO | 2012/173369 A2 | 12/2012 |
| WO | 2013077352 A1 | 5/2013 |
| WO | 2013/085243 A1 | 6/2013 |
| WO | 2013/154378 A1 | 10/2013 |
| WO | 2013/180503 A1 | 12/2013 |
| WO | 2014023388 A1 | 2/2014 |
| WO | 2014/185694 A1 | 11/2014 |
| WO | 2014200148 A1 | 12/2014 |
| WO | 2015005559 A1 | 1/2015 |
| WO | WO-2016/024728 A1 * | 2/2016 |
| WO | WO-2016/105141 A2 * | 6/2016 |

OTHER PUBLICATIONS

Reghu, Renji R., et al., "Glass forming donor-substituted s-triazines: Photophysical and electrochemical properties," Dyes and Pigments, 2013, 97, pp. 412-422.

Zhong, H., et al., "New Conjugated Triazine Based Molecular Materials for Application in Optoelectronic Devices: Design, Synthesis, and Properties," J. Phys. Chem., 2011, 115, pp. 2423-2427.

Ren, et al.: "Star-Shaped Donor-pi-Acceptor Conjugated Oligomers with 1,3,5-Triazine Cores: Convergent Synthesis and Multifunctional Properties", J. Phys. Chem. B, vol. 114, No. 32, 2010, pp. 10374-10383.

* cited by examiner

[Figure 1]
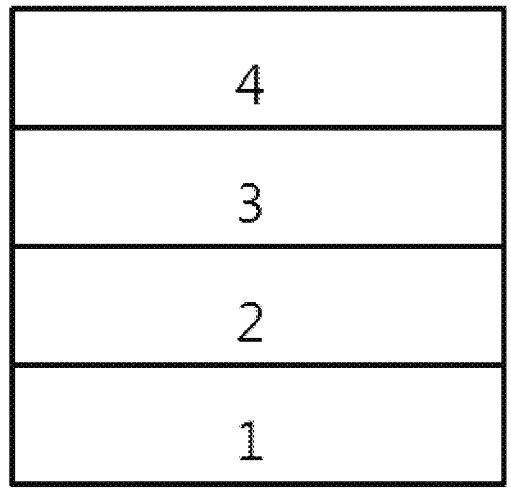
[Figure 2]
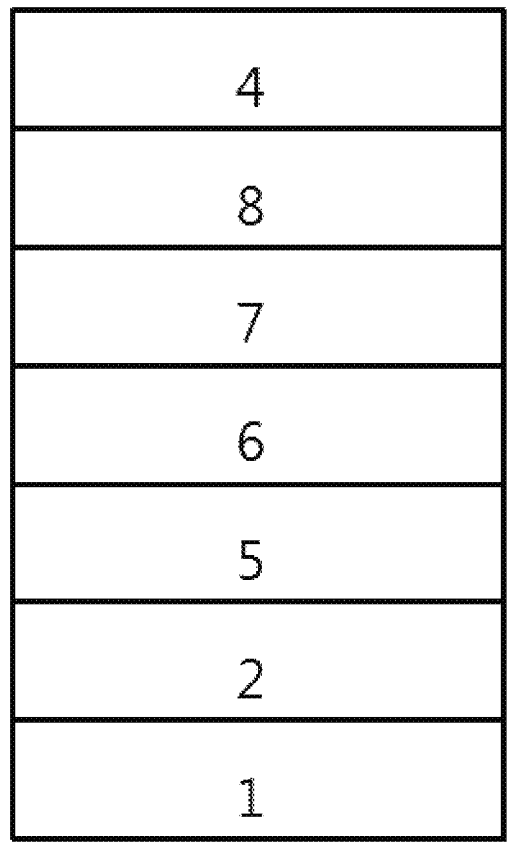

[Figure 3]
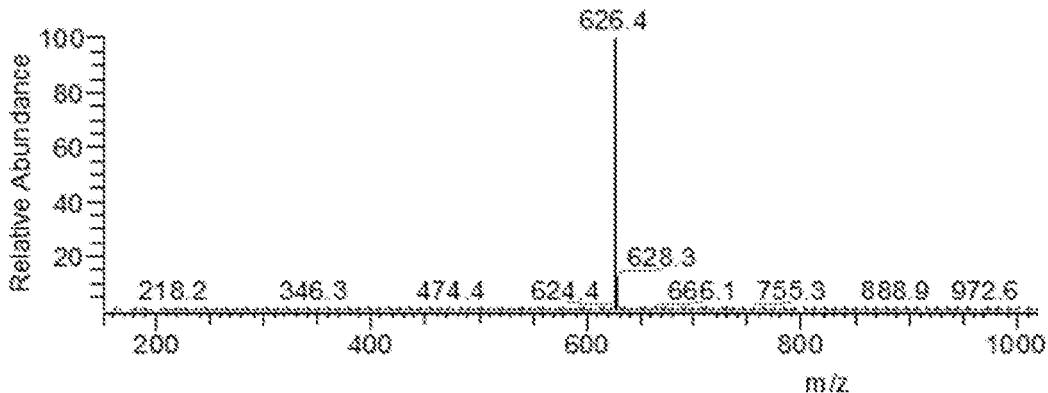
[Figure 4]
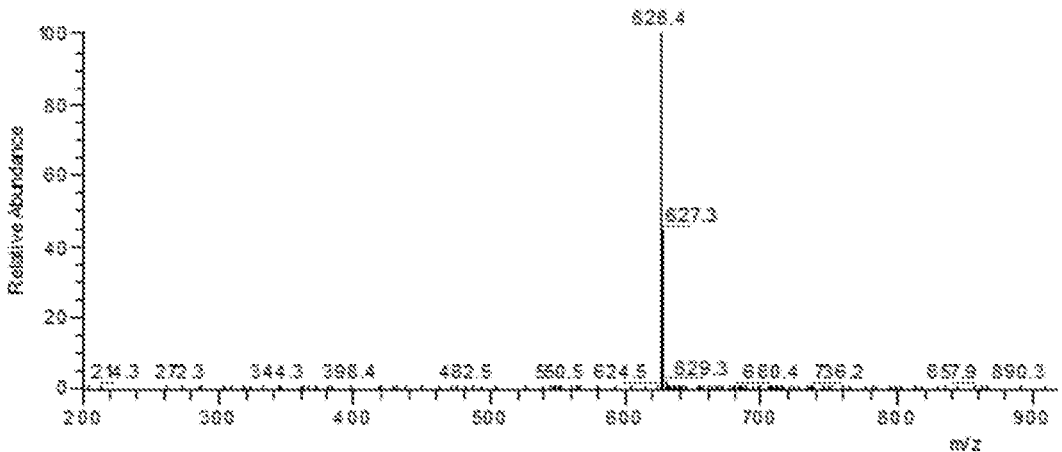
[Figure 5]
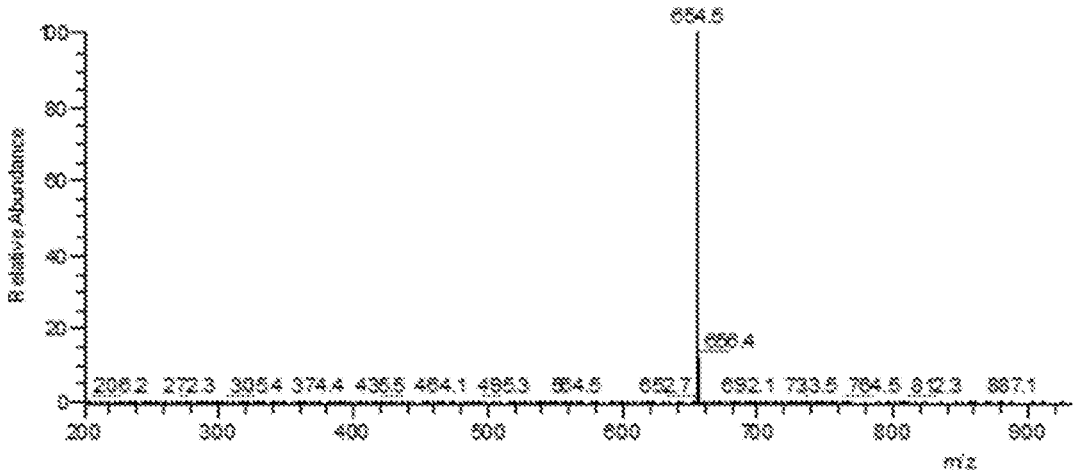

[Figure 6]
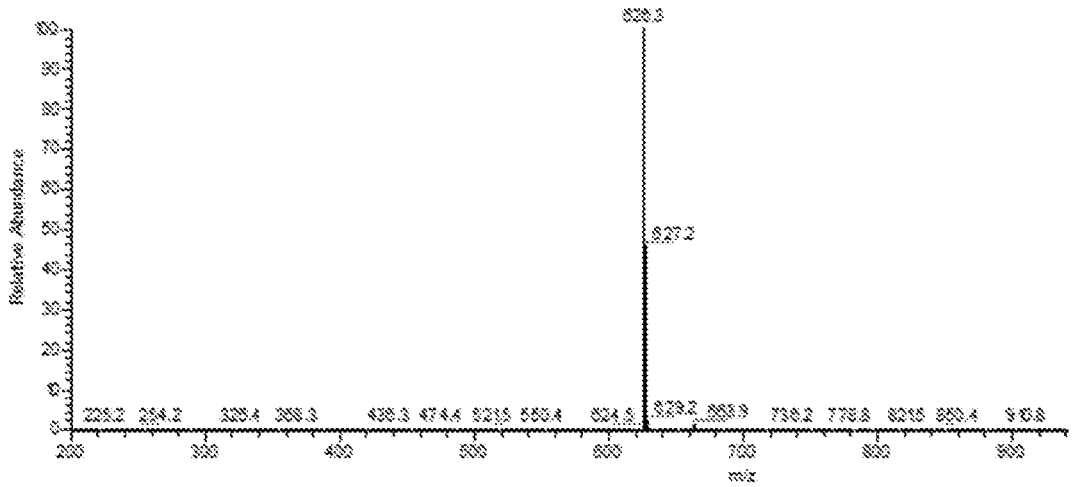
[Figure 7]
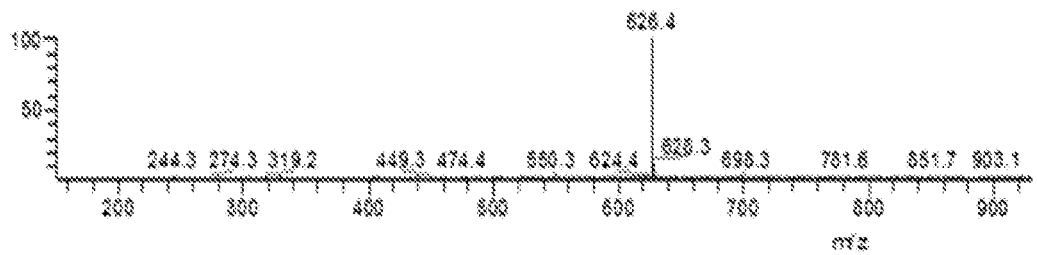
[Figure 8]
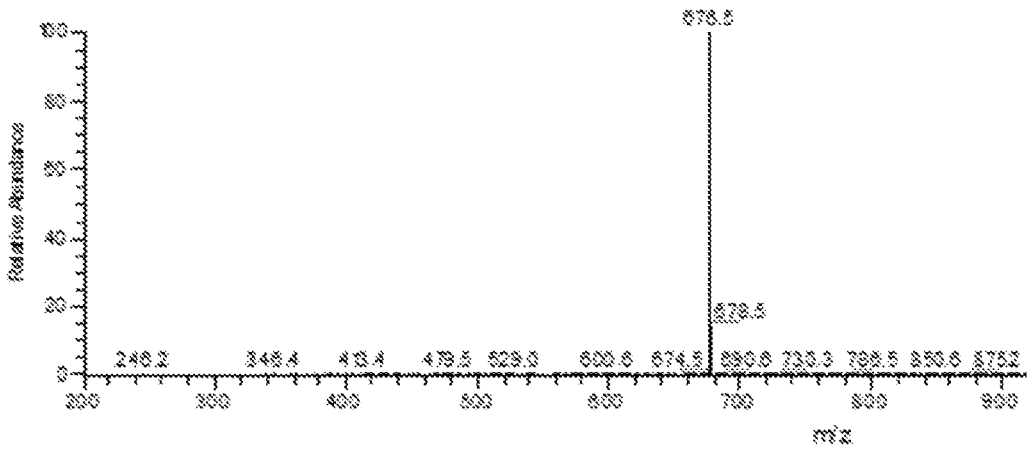

[Figure 9]
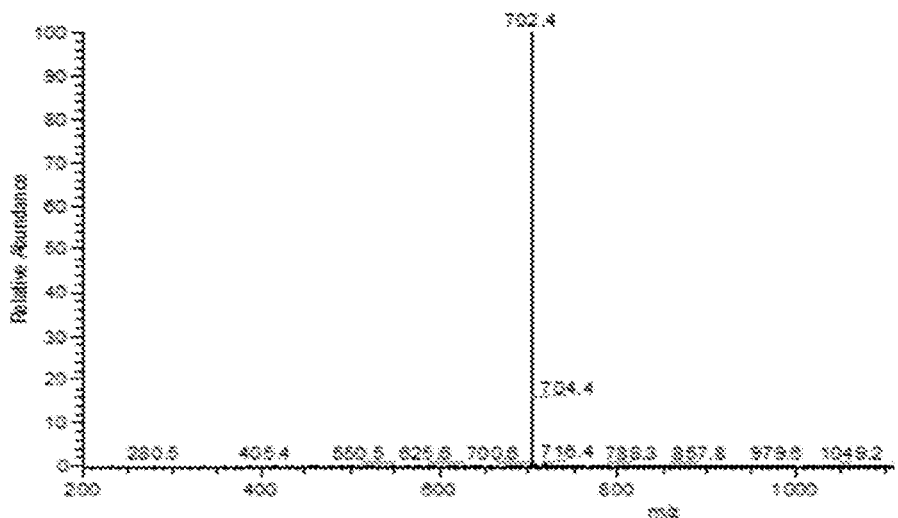
[Figure 10]
compound 1-6
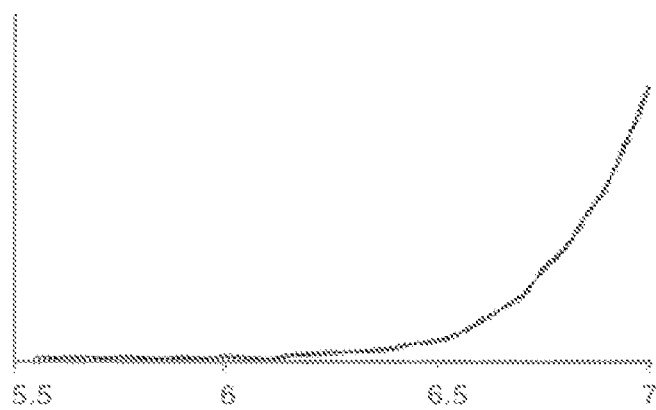
[Figure 11]
compound 1-8
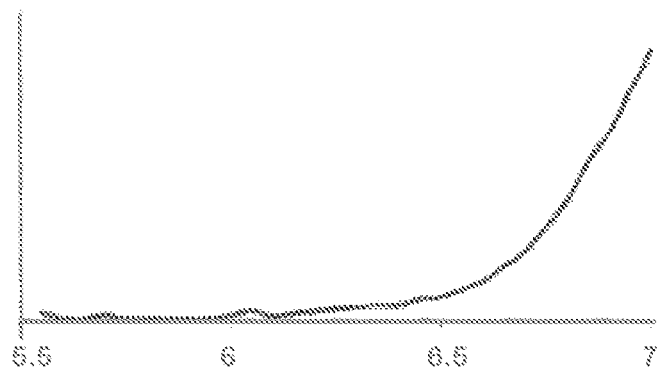

[Figure 12]
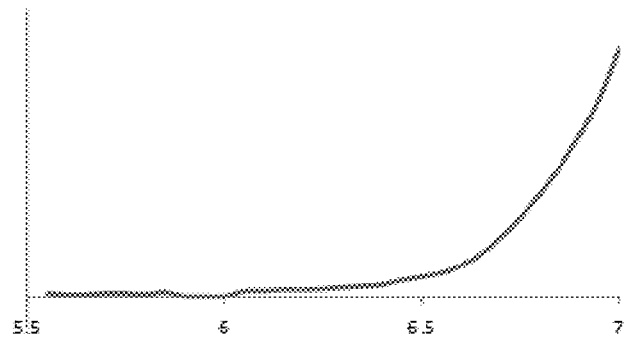
[Figure 13]
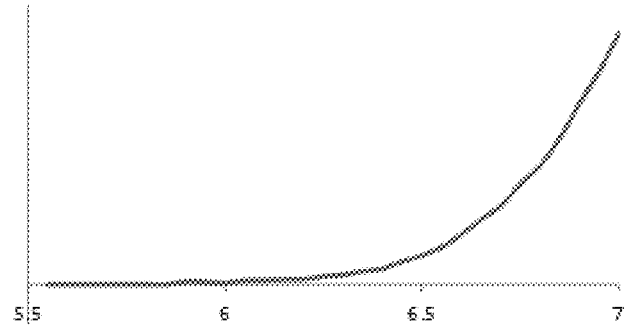

[Figure 14]
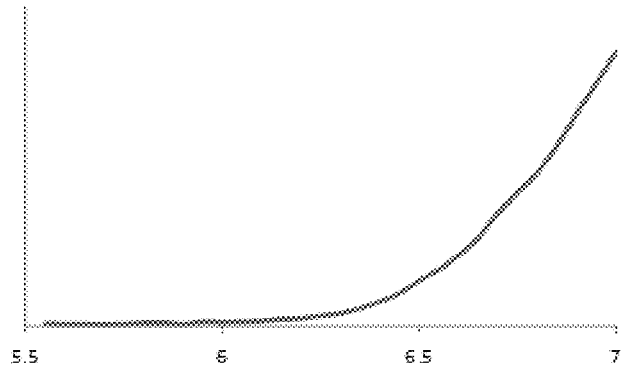

HETEROCYCLIC COMPOUND AND ORGANIC LIGHT-EMITTING DEVICE COMPRISING SAME

TECHNICAL FIELD

This application is a National Stage Application of International Application No. PCT/KR2015/003255 filed on Apr. 1, 2015, which claims the benefit of Korean Patent Application No. 10-2014-0040818 filed on Apr. 4, 2014, and Korean Patent Application No. 10-2015-0011540 filed on Jan. 23, 2015, all of which are hereby incorporated by reference in their entirety for all purposes as if fully set forth herein.

The present specification relates to a hetero-cyclic compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DISCLOSURE

Technical Problem

The present specification describes a hetero-cyclic compound and an organic light emitting device comprising the same.

Technical Solution

An exemplary embodiment of the present specification provides a compound represented by the following Formula 1:

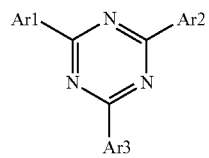

[Formula 1]

in Formula 1,

Ar1 to Ar3 are different from each other,

Ar1 and Ar2 are each independently a substituted or unsubstituted aryl group,

Ar3 is represented by the following Formula 1-1,

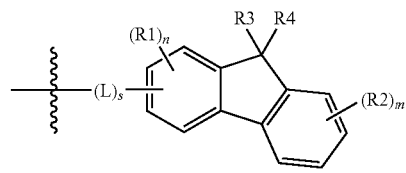

[Formula 1-1]

in Formula 1-1,

R1 and R2 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with an adjacent group to form a substituted or unsubstituted ring, R3 and R4 are the same as or different from each other, and each independently hydrogen; deuterium; a halogen group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with each other to form a substituted or unsubstituted aliphatic ring, L is a direct bond; a substituted or unsubstituted arylene; or a substituted or unsubstituted heteroarylene, n is an integer of 0 to 3, m is an integer of 0 to 4, s is an integer of 1 to 5, and when n is 2 or more, R1's are the same as or different from each other, and when m is 2 or more, R2's are the same as or different from each other, and when s is 2 or more, L's are the same as or different from each other.

Further, an exemplary embodiment of the present specification provides an organic light emitting device comprising: an anode; a cathode provided to face the anode; and one or more organic material layers provided between the anode and the cathode, in which one or more layers of the organic material layers comprise the compound of Formula 1.

Advantageous Effects

The compound described in the present specification may be used as a material for the organic material layer of the organic light emitting device. The compound according to at least one exemplary embodiment may improve the efficiency and improve low driving voltage and/or service life characteristics in the organic light emitting device. In particular, the compound described in the present specification may be used as a material for hole injection, hole transport, hole injection and transport, light emission, electron transport or electron injection, and may be used preferably as an electron transport material.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.

FIG. 3 illustrates an MS data result of 7-6 prepared in the Examples.

FIG. 4 illustrates an MS data result of Compound 1-8 prepared in the Examples.

FIG. 5 illustrates an MS data result of Compound 1-10 prepared in the Examples.

FIG. 6 illustrates an MS data result of Compound 1-18 prepared in the Examples.

FIG. 7 illustrates an MS data result of Compound 1-30 prepared in the Examples.

FIG. 8 illustrates an MS data result of Compound 1-138 prepared in the Examples.

FIG. 9 illustrates an MS data result of Compound 2-5 prepared in the Examples.

FIG. 10 illustrates a result of measurement data of the HOMO (AC3) levels of Compound 1-6.

FIG. 11 illustrates a result of measurement data of the HOMO (AC3) levels of Compound 1-8.

FIG. 12 illustrates a result of measurement data of the HOMO (AC3) levels of Compound 1-30.

FIG. 13 illustrates a result of measurement data of the HOMO (AC3) levels of Compound 1-138.

FIG. 14 illustrates a result of measurement data of the HOMO (AC3) levels of Compound 2-5.

MODE FOR INVENTION

Hereinafter, the present specification will be described in more detail.

An exemplary embodiment of the present specification provides the compound of Formula 1 represented by Formula 1. Examples of the substituents will be described below, but are not limited thereto.

In the present specification, the term "substituted or unsubstituted" means that a group is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group, or a substituent to which two or more substituents among the substituents exemplified above are linked is substituted or unsubstituted. For example, "the substituent to which two or more substituents are linked" may be a biphenyl group. That is, the biphenyl group may also be an aryl group, and may be interpreted as a substituent to which two phenyl groups are linked.

According to an exemplary embodiment of the present specification, the expression "substituted or unsubstituted" preferably means that a group is unsubstituted or substituted with one or more substituents selected from the group consisting of deuterium; a halogen group; a nitrile group; a hydroxy group; a carbonyl group; an ester group; an alkoxy group; an aryloxy group; an alkylthioxy group; an arylthioxy group; an alkylsulfoxy group; an arylsulfoxy group; a silyl group; an alkyl group; a cycloalkyl group; an alkenyl group; an aryl group; an aralkyl group; an aralkenyl group; and an alkylaryl group.

According to an exemplary embodiment of the present specification, the expression "substituted or unsubstituted" preferably means that a group is unsubstituted or substituted with one or more substituents selected from the group consisting of deuterium; an alkyl group; and an aryl group.

According to an exemplary embodiment of the present specification, the compound represented by Formula 1 may be substituted with at least one deuterium. Further, the substituent of the compound represented by Formula 1 may be substituted with at least one deuterium.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of the carbonyl group is not particularly limited, but is preferably 1 to 40. Specifically, the carbonyl group may be a compound having the following structure, but is not limited thereto.

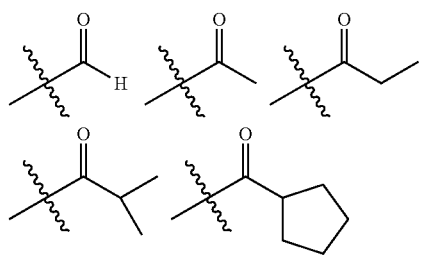

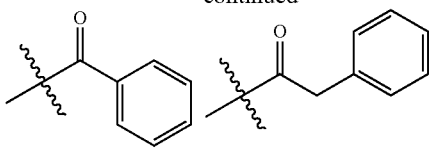

In the present specification, in the ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structure, but is not limited thereto.

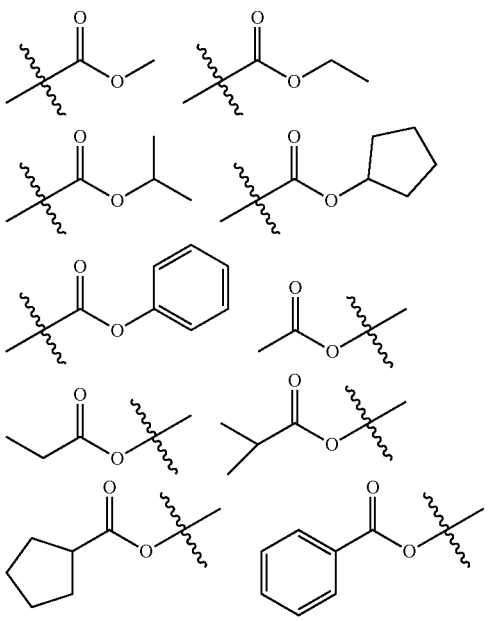

In the present specification, the number of carbon atoms of the imide group is not particularly limited, but is preferably 1 to 25. Specifically, the imide group may be a compound having the following structure, but is not limited thereto.

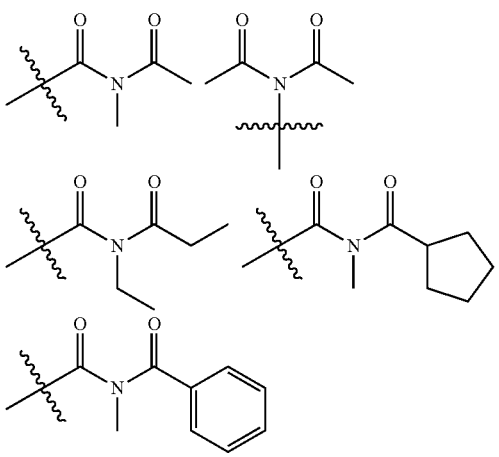

In the present specification, the silyl group may be represented by a formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be represented by a formula of —BRR'R", and R, R', and R" may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of the halogen group include fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but has preferably 3 to 60 carbon atoms, and according to an exemplary embodiment, the number of carbon atoms of the cycloalkyl group is 3 to 30. According to yet another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and two substituents may combine with each other to form a spiro structure.

When the fluorenyl group is substituted, the fluorenyl group may be

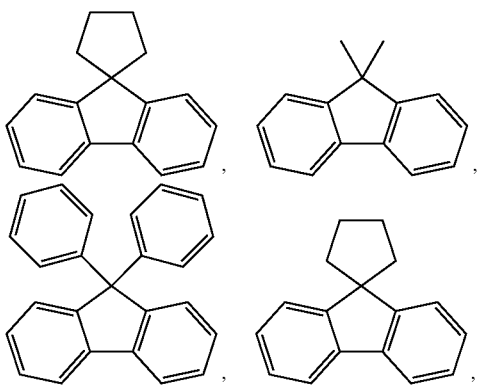

and the like. However, the fluorenyl group is not limited thereto.

In the present specification, the hetero-cyclic group is a hetero-cyclic group including one or more of O, N, S, Si, and Se as a hetero element, and the number of carbon atoms thereof is not particularly limited, but is preferably 2 to 60. Examples of the hetero-cyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described aryl group may be applied to an aryl group of an aryloxy group, an arylthioxy group, and an arylsulfoxy group.

In the present specification, the description on the above-described alkyl group may be applied to an alkyl group of an alkylthioxy group and an alkylsulfoxy group.

In the present specification, the description on the above-described aryl group may be applied to an arylene except for a divalent arylene group.

In the present specification, the description on the above-described hetero-cyclic group may be applied to a heteroarylene except for a divalent heteroarylene group.

In the present specification, the description on the above-described hetero-cyclic group may be applied to a heteroaryl group except for an aromatic group.

In the present specification, a hetero-cyclic group including one or more of O and S atoms may further include a hetero atom other than O and S atoms in the ring.

In the present specification, the meaning of combining with an adjacent group to form a ring means of combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

In the present specification, the aliphatic hydrocarbon ring means a ring composed only of carbon and hydrogen atoms as a ring which is not an aromatic group.

In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Formula 1 may be represented by the following Formula 2.

[Formula 2]

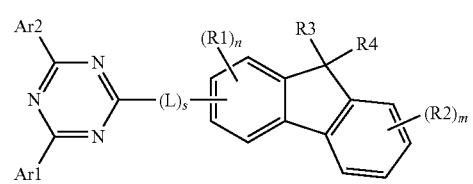

In Formula 2, the definition of Ar1, Ar2, R1 to R4, L, s, m, and n is the same as defined in Formula 1, and Ar1, Ar2, and

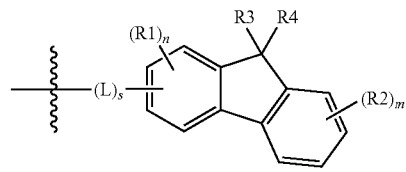

are different from each other.

According to an exemplary embodiment of the present specification, Formula 1 may be represented by any one of the following Formulae 3 to 6.

[Formula 3]
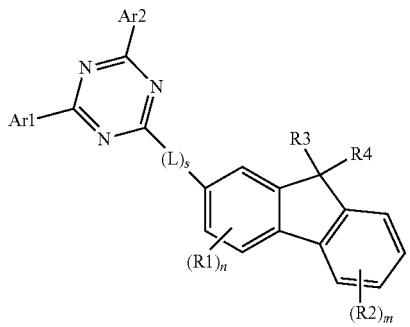

[Formula 4]
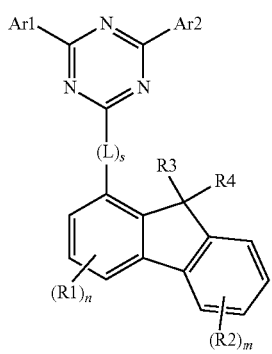

[Formula 5]
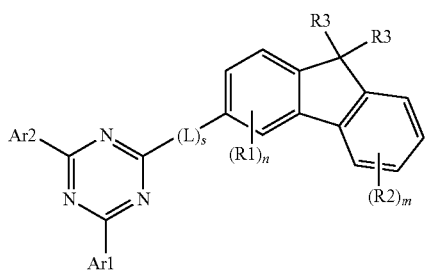

[Formula 6]
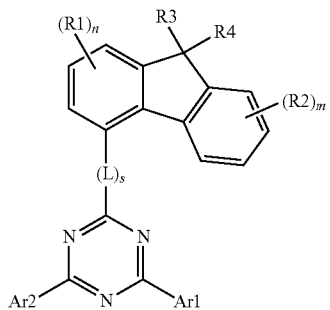

In Formulae 3 to 6, the definition of Ar1, Ar2, R1 to R4, L, s, m, and n is the same as defined in Formula 1.

According to an exemplary embodiment of the present specification, Formula 1 may be represented by the following Formula 7 or 8.

[Formula 7]
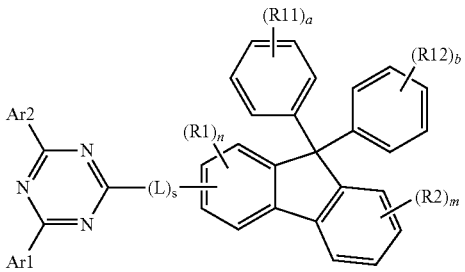

[Formula 8]
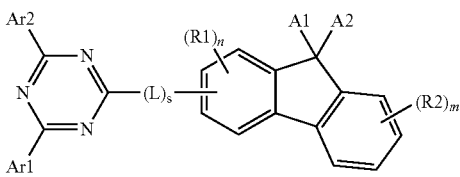

In Formulae 7 and 8, the definition of Ar1, Ar2, R1, R2, L, s, n, and m is the same as defined in Formula 1, R11 and R12 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or two or more adjacent groups combine with each other to form a substituted or unsubstituted ring, A1 and A2 are the same as or different from each other, and each independently hydrogen; or a substituted or unsubstituted alkyl group, or combine with each other to form a substituted or unsubstituted aliphatic ring, a and b are the same as or different from each other, and each independently an integer of 0 to 5, and when a and b are each 2 or more, the structures in the parenthesis are the same as or different from each other.

According to an exemplary embodiment of the present specification, A1 and A2 are the same as or different from each other, and each independently hydrogen; or a substituted or unsubstituted alkyl group.

According to an exemplary embodiment of the present specification, A1 and A2 are the same as or different from each other, and each independently hydrogen; or an alkyl group.

According to an exemplary embodiment of the present specification, A1 and A2 are the same as or different from each other, and each independently hydrogen; or a methyl group.

According to an exemplary embodiment of the present specification, Formula 7 may be represented by any one of the following Formulae 9 to 12.

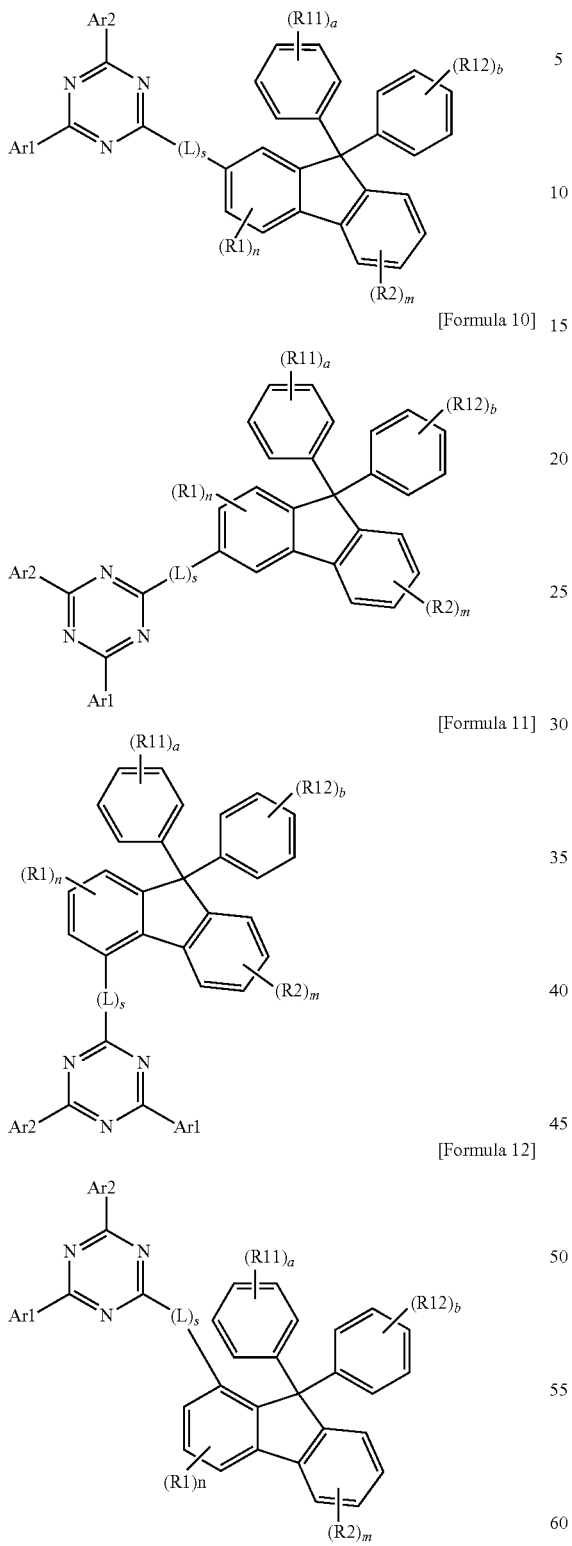

[Formula 9]

[Formula 10]

[Formula 11]

[Formula 12]

In Formulae 9 to 12,
the definition of Ar1, Ar2, R1, R2, L, s, n, and m is the same as defined in Formula 1, and
the definition of R11, R12, a and b is the same as defined in Formula 7.

According to an exemplary embodiment of the present specification, Formula 8 may be represented by any one of the following Formulae 13 to 16.

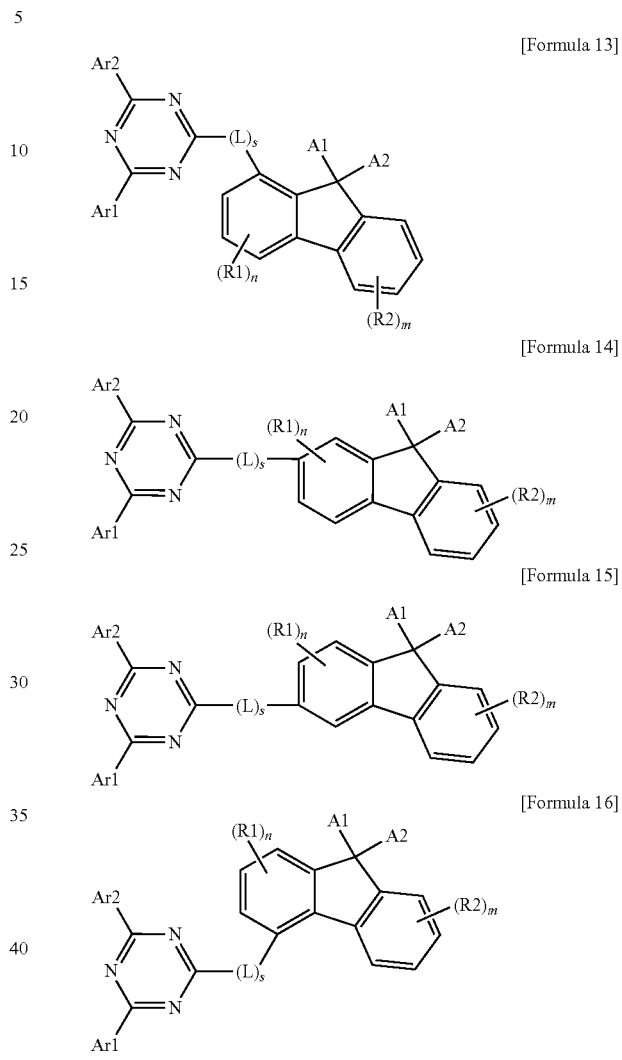

[Formula 13]

[Formula 14]

[Formula 15]

[Formula 16]

In Formulae 13 to 16,
the definition of Ar1, Ar2, R1, R2, L, s, n, and m is the same as defined in Formula 1, and
the definition of A1 and A2 is the same as defined in Formula 8.

According to an exemplary embodiment of the present specification, L is a direct bond; or a substituted or unsubstituted arylene.

According to an exemplary embodiment of the present specification, L is a direct bond; or an arylene unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group.

According to an exemplary embodiment of the present specification, L is a direct bond; or an arylene unsubstituted or substituted with one or more substituents selected from the group consisting of deuterium, an alkyl group, and an aryl group.

According to an exemplary embodiment of the present specification, L is a direct bond; or a substituted or unsubstituted monocyclic to tetracyclic arylene.

According to an exemplary embodiment of the present specification, L is a direct bond; or a substituted or unsubstituted monocyclic to tricyclic arylene.

According to an exemplary embodiment of the present specification, L is a substituted or unsubstituted arylene having 6 to 30 carbon atoms.

According to an exemplary embodiment of the present specification, L is a substituted or unsubstituted arylene having 6 to 20 carbon atoms.

According to an exemplary embodiment of the present specification, L is a direct bond; or any one selected from the following structures.

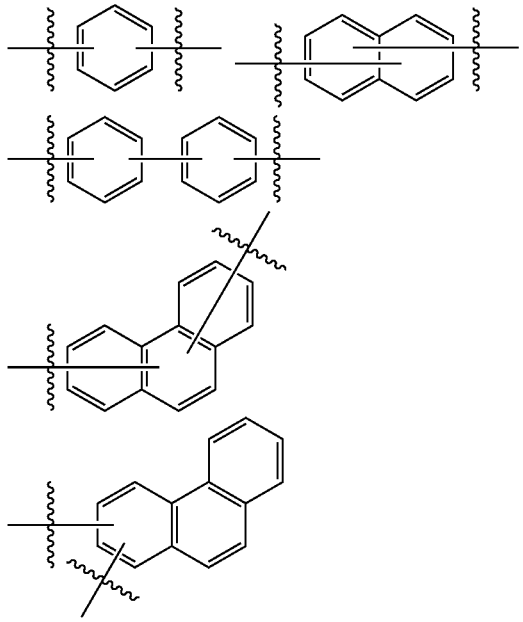

The structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, L is a direct bond; a substituted or unsubstituted phenylene; a substituted or unsubstituted biphenylylene; a substituted or unsubstituted naphthylene; or a substituted or unsubstituted phenanthrylene.

According to an exemplary embodiment of the present specification, L is a direct bond; phenylene; biphenylylene; naphthylene; or phenanthrylene.

According to an exemplary embodiment of the present specification, L is a direct bond; or a substituted or unsubstituted phenylene.

According to an exemplary embodiment of the present specification, L is a direct bond; or phenylene.

According to an exemplary embodiment of the present specification, L is a substituted or unsubstituted phenylene.

According to an exemplary embodiment of the present specification, L is phenylene.

According to an exemplary embodiment of the present specification, L is a direct bond.

According to an exemplary embodiment of the present specification, s is 0 or 1.

According to an exemplary embodiment of the present specification, s is 0.

According to an exemplary embodiment of the present specification, s is 1.

According to an exemplary embodiment of the present specification, Formula 1 may be represented by the following Formula 17.

[Formula 17]

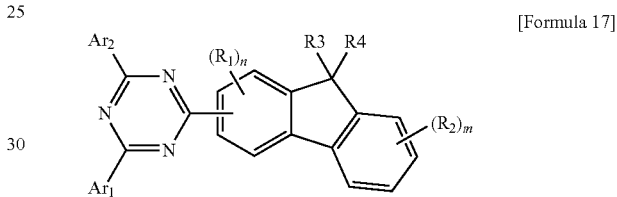

In Formula 17, the definition of Ar1, Ar2, R1 to R4, n, and m is the same as defined in Formula 1, and Ar1, Ar2, and

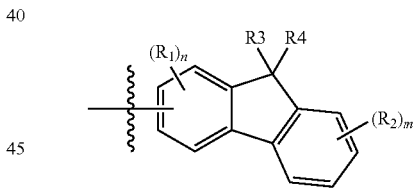

are different from each other.

According to an exemplary embodiment of the present specification, Formula 1 may be represented by any one of the following Formulae 18 to 21.

[Formula 18]

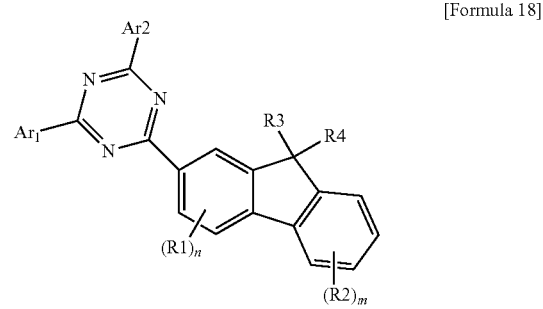

-continued

[Formula 19]

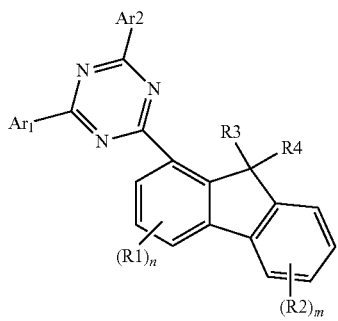

[Formula 20]

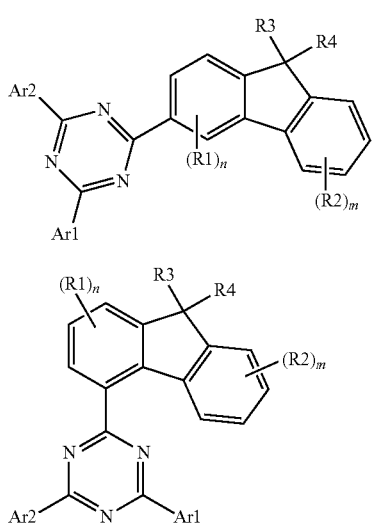

[Formula 21]

In Formulae 18 to 21, the definition of Ar1, Ar2, R1 to R4, n, and m is the same as defined in Formula 1.

According to an exemplary embodiment of the present specification, Formula 1 may be represented by the following Formula 22 or 23.

[Formula 22]

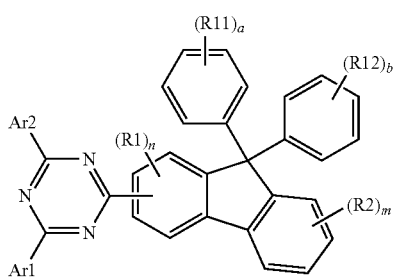

[Formula 23]

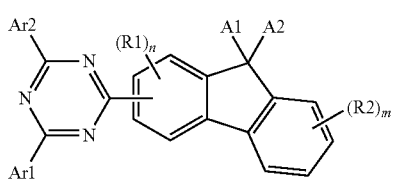

In Formulae 22 and 23, the definition of Ar1, Ar2, R1, R2, n, and m is the same as defined in Formula 1, R11 and R12 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or two or more adjacent groups combine with each other to form a substituted or unsubstituted ring, A1 and A2 are the same as or different from each other, and each independently a substituted or unsubstituted alkyl group, or combine with each other to form a substituted or unsubstituted aliphatic ring, a and b are the same as or different from each other, and each independently an integer of 0 to 5, and when a and b are each 2 or more, the structures in the parenthesis are the same as or different from each other.

According to an exemplary embodiment of the present specification, Formula 1 may be represented by the following Formula 24.

[Formula 24]

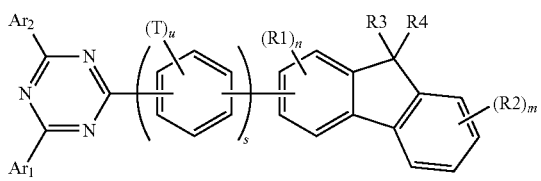

In Formula 24, the definition of Ar1, Ar2, R1 to R4, s, n, and m is the same as defined in Formula 1, T is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or two or more adjacent T's combine with each other to form a substituted or unsubstituted ring, u is an integer of 0 to 4, and when u is 2 or more, T's are the same as or different from each other.

According to an exemplary embodiment of the present specification, Formula 1 may be represented by the following Formula 25.

[Formula 25]

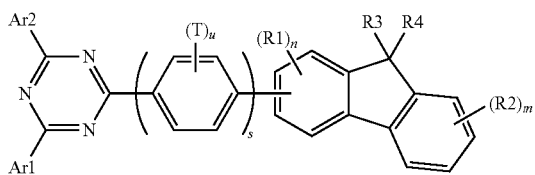

In Formula 25, the definition of Ar1, Ar2, R1 to R4, s, n, and m is the same as defined in Formula 1, T is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or two or more adjacent T's combine with each other to form a substituted or unsubstituted ring, u is an integer of 0 to 4, and when u is 2 or more, T's are the same as or different from each other.

According to an exemplary embodiment of the present specification, Formula 1 may be represented by the following Formula 26.

[Formula 26]

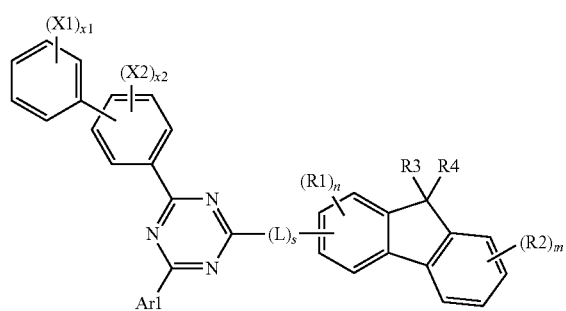

In Formula 26, the definition of R1 to R4, Ar1, L, s, m, and n is the same as defined in Formula 1, X1 and X2 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or two or more adjacent groups combine with each other to form a substituted or unsubstituted ring, x1 is an integer of 0 to 5, and x2 is an integer of 0 to 4, and when x1 is 2 or more, X1's are the same as or different from each other, and when x2 is 2 or more, X2's are the same as or different from each other.

According to an exemplary embodiment of the present specification, Formula 26 may be represented by the following Formula 27.

[Formula 27]

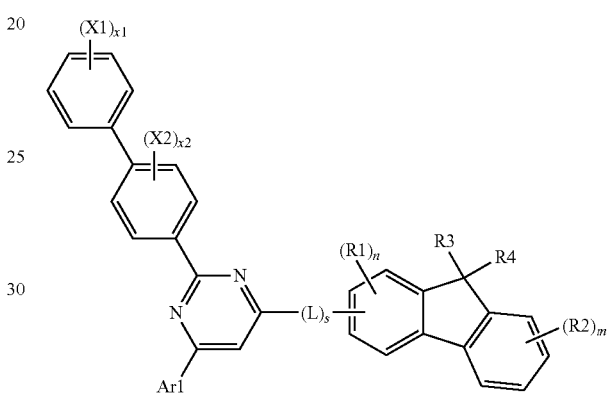

In Formula 27, the definition of R1 to R4, Ar1, L, s, m, and n is the same as defined in Formula 1, and the definition of X1, X2, x1, and x2 is the same as defined in Formula 26.

According to an exemplary embodiment of the present specification, Formula 1 may be represented by the following Formula 28.

[Formula 28]

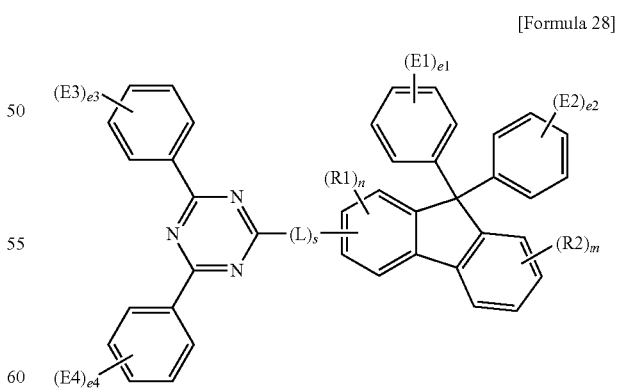

In Formula 28, the definition of L, s, R1, R2, m, and n is the same as defined in Formula 1, E1 to E4 are the same as or different from each other, and each independently hydrogen; deuterium; a halogen group;

a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted ring, e1 to e4 are the same as or different from each other, and each independently an integer of 0 to 5, and when e1 to e4 are each 2 or more, the structures in the parenthesis are the same as or different from each other.

According to an exemplary embodiment of the present specification, Formula 27 may be represented by any one of the following Formulae 27-1 to 27-4.

[Formula 27-1]

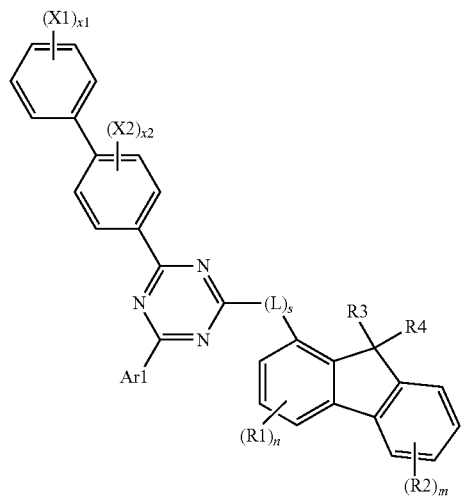

[Formula 27-2]

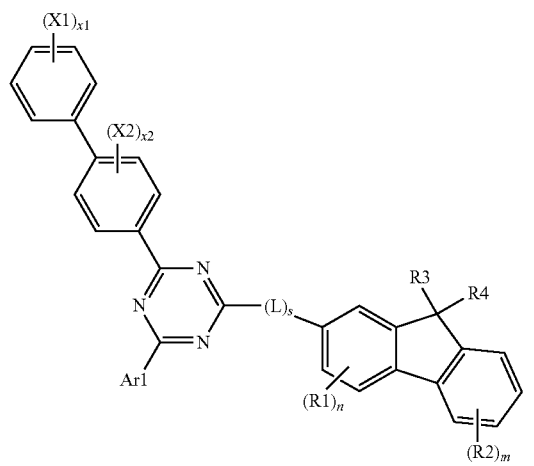

[Formula 27-3]

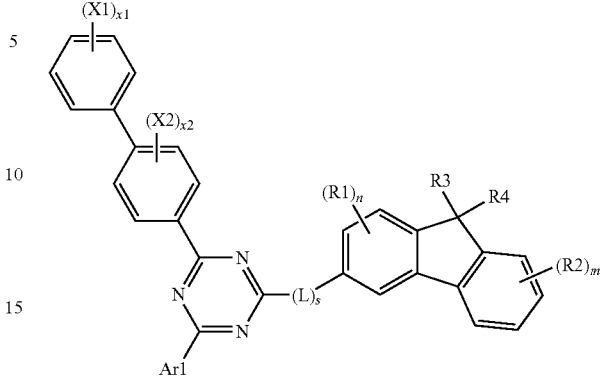

[Formula 27-4]

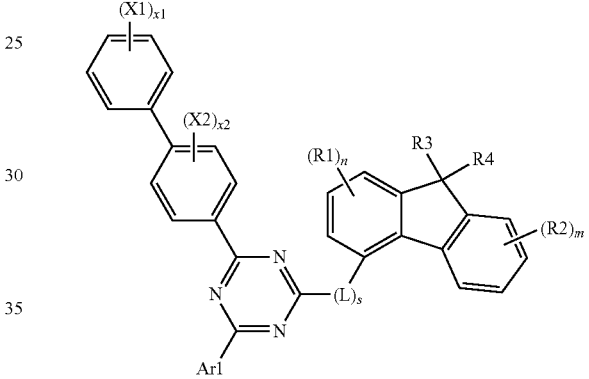

In Formulae 27-1 to 27-4, the definition of R1 to R4, Ar1, L, s, m, and n is the same as defined in Formula 1, and the definition of X1, X2, x1, and x2 is the same as defined in Formula 27.

According to an exemplary embodiment of the present specification, Formula 28 may be represented by any one of the following Formulae 28-1 to 28-4.

[Formula 28-1]

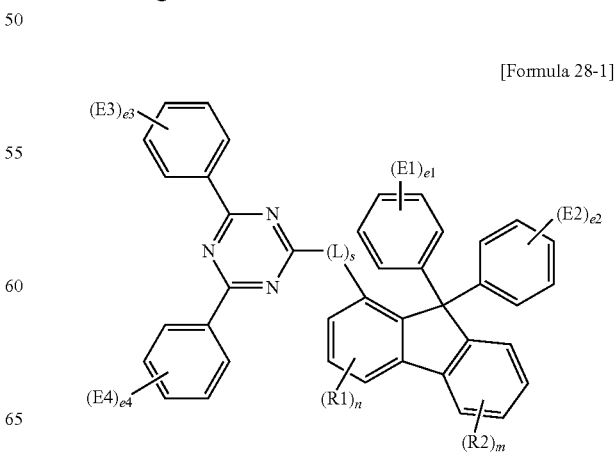

-continued

[Formula 28-2]

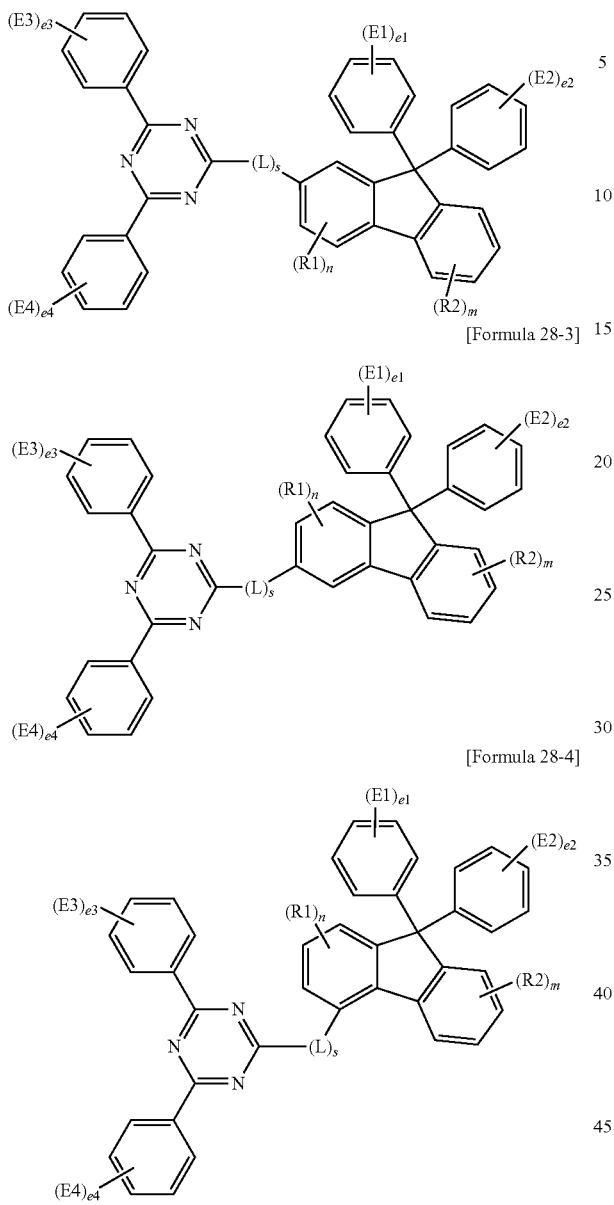

[Formula 28-3]

[Formula 28-4]

In Formulae 28-1 to 28-4, the definition of L, s, R1, R2, m, and n is the same as defined in Formula 1, and the definition of E1 to E4 and e1 to e4 is the same as defined in Formula 28.

According to an exemplary embodiment of the present specification, Formula 1-1 may be any one selected from the following structures.

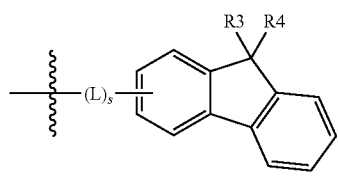

-continued

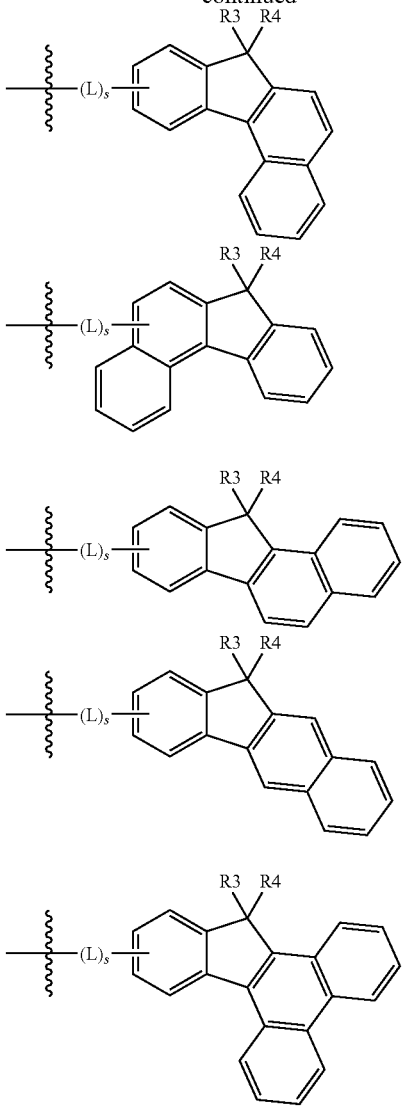

In the structural formulae, the definition of R3 and R4 is the same as defined in Formula 1, and the definition of L and s is the same as defined in Formula 1-1, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, Formula 1-1 may be any one selected from the following structures.

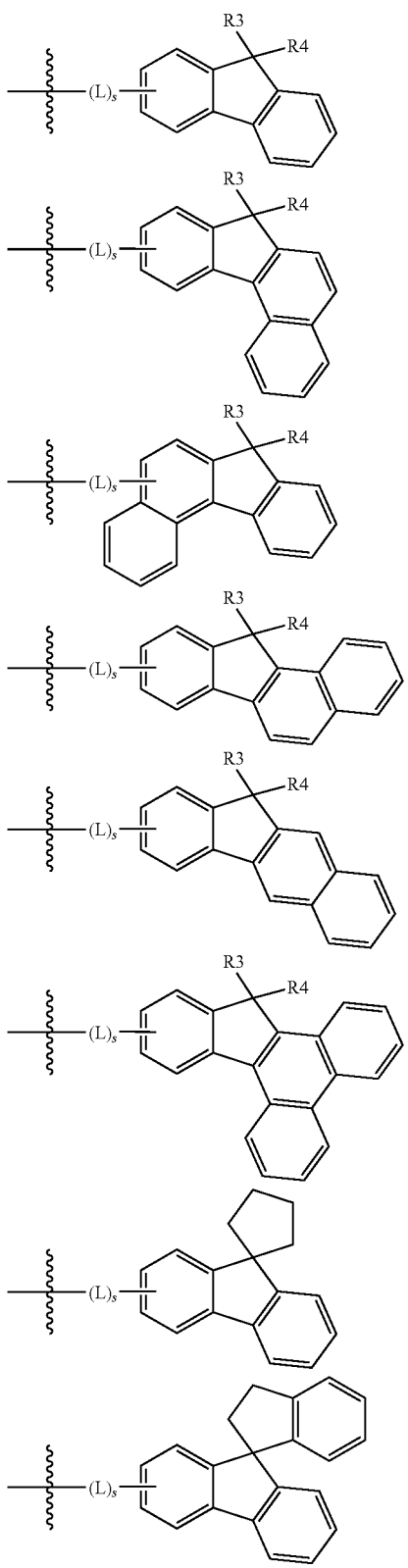

In the structural formulae, the definition of R3 and R4 is the same as defined in Formula 1, and the definition of L and s is the same as defined in Formula 1-1, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, R1 and R2 are the same as or different from each other, and each independently hydrogen; deuterium; a halogen group; a nitrile group; a nitro group; a hydroxy group; an alkyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a cycloalkyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an aryloxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkylthioxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an arylthioxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkylsulfoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an arylsulfoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkenyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a silyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a boron group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an aryl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or a hetero-cyclic group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group, or combine with an adjacent group to form a substituted or unsubstituted ring.

According to an exemplary embodiment of the present specification, R1 is hydrogen; deuterium; a substituted or unsubstituted alkyl group; or a substituted or unsubstituted aryl group, or two or more adjacent R1's combine with each other to form a substituted or unsubstituted ring.

According to an exemplary embodiment of the present specification, R1 is hydrogen; deuterium; a substituted or unsubstituted alkyl group having 1 to 30 carbon atoms; or a substituted or unsubstituted aryl group having 6 to 40 carbon atoms, or two or more adjacent R1's combine with each other to form a substituted or unsubstituted ring.

According to an exemplary embodiment of the present specification, R1 is hydrogen; deuterium; a substituted or unsubstituted alkyl group having 1 to 6 carbon atoms; or a substituted or unsubstituted aryl group having 6 to 20 carbon atoms, or two or more adjacent R1's combine with each other to form a substituted or unsubstituted ring.

According to an exemplary embodiment of the present specification, R1 is hydrogen; deuterium; an alkyl group having 1 to 6 carbon atoms; or an aryl group having 6 to 20 carbon atoms, or two or more adjacent R1's combine with each other to form a substituted or unsubstituted ring.

According to an exemplary embodiment of the present specification, R1 is hydrogen; deuterium; or an alkyl group, or two or more adjacent R1's combine with each other to form a substituted or unsubstituted ring.

According to an exemplary embodiment of the present specification, R1 is hydrogen; or deuterium.

According to an exemplary embodiment of the present specification, R1 is hydrogen, or two or more adjacent R1's combine with each other to form a substituted or unsubstituted ring.

According to an exemplary embodiment of the present specification, R1 is hydrogen, or two or more adjacent R1's combine with each other to form a ring.

According to an exemplary embodiment of the present specification, two or more adjacent R1's combine with each other to form a substituted or unsubstituted ring.

According to an exemplary embodiment of the present specification, two or more adjacent R1's combine with each other to form a ring.

According to an exemplary embodiment of the present specification, R1 is hydrogen.

According to an exemplary embodiment of the present specification, R2 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; a substituted or unsubstituted monocyclic or bicyclic hetero-cyclic group including one or more of O and S atoms; a substituted or unsubstituted pyrrole group; a substituted or unsubstituted imidazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazole group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted benzoimidazole group; or a substituted or unsubstituted phenanthroline group, or two or more adjacent R2's combine with each other to form a substituted or unsubstituted ring.

According to an exemplary embodiment of the present specification, R2 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted monocyclic or bicyclic hetero-cyclic group including one or more of O and S atoms, or two or more adjacent R2's combine with each other to form a substituted or unsubstituted ring.

According to an exemplary embodiment of the present specification, R2 is hydrogen; deuterium; or a substituted or unsubstituted aryl group; or a substituted or unsubstituted monocyclic or bicyclic hetero-cyclic group including one or more of O and S atoms, or two or more adjacent R2's combine with each other to form a substituted or unsubstituted ring.

According to an exemplary embodiment of the present specification, R2 is hydrogen; deuterium; or a substituted or unsubstituted aryl group, or two or more adjacent R2's combine with each other to form a substituted or unsubstituted ring.

According to an exemplary embodiment of the present specification, R2 is hydrogen; deuterium; or a substituted or unsubstituted aryl group having 6 to 40 carbon atoms, or two or more adjacent R2's combine with each other to form a substituted or unsubstituted ring.

According to an exemplary embodiment of the present specification, R2 is hydrogen; deuterium; or a substituted or unsubstituted aryl group having 6 to 20 carbon atoms, or two or more adjacent R2's combine with each other to form a substituted or unsubstituted ring.

According to an exemplary embodiment of the present specification, R2 is hydrogen; deuterium; or an aryl group having 6 to 20 carbon atoms, or two or more adjacent R2's combine with each other to form a substituted or unsubstituted ring.

According to an exemplary embodiment of the present specification, R2 is hydrogen; deuterium; a substituted or unsubstituted alkyl group; or a substituted or unsubstituted aryl group, or two or more adjacent R2's combine with each other to form a substituted or unsubstituted ring.

According to an exemplary embodiment of the present specification, R2 is hydrogen; deuterium; an alkyl group; or an aryl group, or two or more adjacent R2's combine with each other to form a ring.

According to an exemplary embodiment of the present specification, R2 is hydrogen; deuterium; an alkyl group; a phenyl group; or a naphthyl group, or two or more adjacent R2's combine with each other to form a substituted or unsubstituted ring.

According to an exemplary embodiment of the present specification, R2 is hydrogen; deuterium; a substituted or unsubstituted alkyl group; a substituted or unsubstituted phenyl group; or a substituted or unsubstituted naphthyl group.

According to an exemplary embodiment of the present specification, R2 is hydrogen; deuterium; an alkyl group; a phenyl group; or a naphthyl group.

According to an exemplary embodiment of the present specification, R2 is hydrogen; deuterium; a substituted or unsubstituted alkyl group; or a substituted or unsubstituted phenyl group.

According to an exemplary embodiment of the present specification, R2 is hydrogen; deuterium; an alkyl group; or a phenyl group.

According to an exemplary embodiment of the present specification, R2 is hydrogen; deuterium; or a substituted or unsubstituted alkyl group.

According to an exemplary embodiment of the present specification, R2 is hydrogen; deuterium; or an alkyl group.

According to an exemplary embodiment of the present specification, R2 is hydrogen; or deuterium.

According to an exemplary embodiment of the present specification, R2 is hydrogen.

According to an exemplary embodiment of the present specification, R3 and R4 are the same as or different from each other, and each independently hydrogen; deuterium; a halogen group; an alkyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a cycloalkyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an aryloxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkylthioxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an arylthioxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkylsulfoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an arylsulfoxy group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an alkenyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a silyl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a boron group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; an aryl group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or a hetero-cyclic group, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group, or combine with each other to form an aliphatic ring, which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group.

According to an exemplary embodiment of the present specification, R3 and R4 are the same as or different from each other, and each independently hydrogen; deuterium; a halogen group; an alkyl group, which is unsubstituted or substituted with one or more substituents selected from the group consisting of deuterium, an alkyl group, and an aryl group; an aryl group, which is unsubstituted or substituted with one or more substituents selected from the group consisting of deuterium, an alkyl group, and an aryl group; or a hetero-cyclic group, which is unsubstituted or substituted with one or more substituents selected from the group consisting of deuterium, an alkyl group, and an aryl group.

According to an exemplary embodiment of the present specification, R3 and R4 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group.

According to an exemplary embodiment of the present specification, R3 and R4 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a 5-membered substituted or unsubstituted aliphatic ring.

According to an exemplary embodiment of the present specification, R3 and R4 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a substituted or unsubstituted monocyclic or bicyclic aliphatic ring.

According to an exemplary embodiment of the present specification, R3 and R4 are the same as or different from each other, and each independently hydrogen; deuterium; a halogen group; a substituted or unsubstituted, straight-chained alkyl group having 1 to 40 carbon atoms; a substituted or unsubstituted, straight-chained alkoxy group having 1 to 40 carbon atoms; a substituted or unsubstituted, straight-chained thioalkoxy group having 1 to 40 carbon atoms; a substituted or unsubstituted, branched mono or poly cycloalkyl group having 3 to 40 carbon atoms; a substituted or unsubstituted, branched alkenyl group having to 40 carbon atoms; a substituted or unsubstituted, branched alkoxy group having 3 to 40 carbon atoms; a substituted or unsubstituted, branched thioalkoxy group having 3 to 40 carbon atoms; a 6 to 40-membered substituted or unsubstituted aryl group; a 5 to 40-membered substituted or unsubstituted hetero-cyclic group; a 5 to 40-membered substituted or unsubstituted aryloxy group; or a 5 to 40-membered substituted or unsubstituted heteroaryloxy group.

According to an exemplary embodiment of the present specification, R3 and R4 are the same as or different from each other, and each independently hydrogen; a substituted or unsubstituted alkyl group; a substituted or unsubstituted aryl group; or a substituted or unsubstituted hetero-cyclic group.

According to an exemplary embodiment of the present specification, R3 and R4 are the same as or different from each other, and each independently hydrogen; a substituted or unsubstituted alkyl group; or a substituted or unsubstituted aryl group.

According to an exemplary embodiment of the present specification, R3 and R4 are the same as or different from each other, and each independently hydrogen; a substituted or unsubstituted alkyl group; a substituted or unsubstituted aryl group having 6 to 20 carbon atoms; or a substituted or unsubstituted hetero-cyclic group.

According to an exemplary embodiment of the present specification, R3 and R4 are the same as or different from each other, and each independently hydrogen; an alkyl group; an aryl group having 6 to 20 carbon atoms, which is unsubstituted or substituted with an alkyl group; or a hetero-cyclic group.

According to an exemplary embodiment of the present specification, R3 and R4 are the same as or different from each other, and each independently hydrogen; an alkyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R3 and R4 are the same as or different from each other, and each independently hydrogen; an alkyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R3 and R4 are the same as or different from each other, and each independently hydrogen; an alkyl group; a phenyl group, which is unsubstituted or substituted with an alkyl group; a biphenyl group; or a naphthyl group, or combine with each other to form an aliphatic ring.

According to an exemplary embodiment of the present specification, R3 and R4 are the same as or different from each other, and each independently hydrogen; a methyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R3 and R4 are the same as or different from each other, and each independently hydrogen; a methyl group; a phenyl group, which is unsubstituted or substituted with an alkyl group; a biphenyl group; or a naphthyl group, or combine with each other to form an aliphatic ring.

According to an exemplary embodiment of the present specification, R3 and R4 are the same as or different from each other, and each independently hydrogen; a methyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R3 and R4 are the same as or different from each other, and each independently hydrogen; a methyl group; a phenyl group; a phenyl group substituted with a methyl group; a biphenyl group; or a naphthyl group, or combine with each other to form an aliphatic ring.

According to an exemplary embodiment of the present specification, R3 and R4 are the same as or different from each other, and each independently hydrogen; a methyl group; a phenyl group; a phenyl group substituted with a methyl group; a biphenyl group; or a naphthyl group, or combine with each other to form a 5-membered aliphatic ring.

According to an exemplary embodiment of the present specification, R3 and R4 are the same as or different from each other, and each independently a substituted or unsubstituted alkyl group; or a substituted or unsubstituted aryl group.

According to an exemplary embodiment of the present specification, R3 and R4 are the same as or different from each other, and each independently an alkyl group; or a substituted or unsubstituted phenyl group.

According to an exemplary embodiment of the present specification, R3 and R4 are the same as or different from each other, and each independently an alkyl group; a phenyl group; or a phenyl group substituted with a methyl group.

According to an exemplary embodiment of the present specification, R3 and R4 are the same as or different from each other, and each independently a methyl group; a phenyl group; or a phenyl group substituted with a methyl group.

According to an exemplary embodiment of the present specification, R3 and R4 are the same as each other, and a substituted or unsubstituted alkyl group; or a substituted or unsubstituted aryl group.

According to an exemplary embodiment of the present specification, R3 and R4 are the same as each other, and a substituted or unsubstituted alkyl group; or a substituted or unsubstituted phenyl group.

According to an exemplary embodiment of the present specification, R3 and R4 are the same as each other, and an alkyl group; or a substituted or unsubstituted phenyl group.

According to an exemplary embodiment of the present specification, R3 and R4 are the same as each other, and an alkyl group; a phenyl group; or a phenyl group substituted with a methyl group.

According to an exemplary embodiment of the present specification, R3 and R4 are the same as each other, and a methyl group; a phenyl group; or a phenyl group substituted with a methyl group.

According to an exemplary embodiment of the present specification, Ar1 and Ar2 are different from each other, and each independently a substituted or unsubstituted aryl group.

According to an exemplary embodiment of the present specification, Ar1 and Ar2 are different from each other, and each independently an aryl group, which is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, Ar1 and Ar2 are different from each other, and each independently an aryl group, which is unsubstituted or substituted with one or more substituents selected from the group consisting of deuterium, an alkyl group, and an aryl group.

According to an exemplary embodiment of the present specification, Ar1 and Ar2 are the same as each other, and each independently a substituted or unsubstituted aryl group, and at least one of Ar1 and Ar2 is an aryl group, which is unsubstituted or substituted with deuterium.

According to an exemplary embodiment of the present specification, Ar1 and Ar2 are different from each other, and each independently an aryl group, which is unsubstituted or substituted with deuterium.

According to an exemplary embodiment of the present specification, Ar1 and Ar2 are different from each other, and each independently a substituted or unsubstituted monocyclic to tetracyclic aryl group.

According to an exemplary embodiment of the present specification, Ar1 and Ar2 are different from each other, and each independently an aryl group, which is unsubstituted or substituted with an aryl group.

According to an exemplary embodiment of the present specification, Ar1 and Ar2 are different from each other, and each independently a monocyclic to tetracyclic aryl group, which is unsubstituted or substituted with an aryl group.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; or a substituted or unsubstituted fluorenyl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; a chrysenyl group; or a fluorenyl group, which is unsubstituted or substituted with an alkyl group or an aryl group.

According to an exemplary embodiment of the present specification, Ar1 and Ar2 are different from each other, and each independently a phenyl group, which is unsubstituted or substituted with an aryl group; a naphthyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a phenanthryl group, which is unsubstituted or substituted with an aryl group; or a chrysenyl group, which is unsubstituted or substituted with an aryl group.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; or a substituted or unsubstituted chrysenyl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; or a chrysenyl group.

According to an exemplary embodiment of the present specification, Ar1 and Ar2 are different from each other, and each independently a substituted or unsubstituted phenyl group; a substituted or unsubstituted biphenyl group; a substituted or unsubstituted terphenyl group; a substituted or unsubstituted naphthyl group; or a substituted or unsubstituted phenanthryl group.

According to an exemplary embodiment of the present specification, Ar1 and Ar2 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 and Ar2 are different from each other, and each independently a phenyl group; a biphenyl group; a terphenyl group; a terphenyl group substituted with a phenyl group; a naphthyl group; a phenanthryl group; a phenyl group substituted with a naphthyl group; or a biphenyl group substituted with a phenyl group.

According to an exemplary embodiment of the present specification, Ar1 is an aryl group.

According to an exemplary embodiment of the present specification, Ar1 is a monocyclic to tricyclic aryl group.

According to an exemplary embodiment of the present specification, Ar1 is a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar1 is a phenyl group; a biphenyl group; a naphthyl group; or a phenanthryl group.

According to an exemplary embodiment of the present specification, Ar1 is a substituted or unsubstituted phenyl group.

According to an exemplary embodiment of the present specification, Ar1 is a substituted or unsubstituted biphenyl group.

According to an exemplary embodiment of the present specification, Ar1 is a substituted or unsubstituted naphthyl group.

According to an exemplary embodiment of the present specification, Ar1 is a substituted or unsubstituted phenanthryl group.

According to an exemplary embodiment of the present specification, when Ar1 is a substituted or unsubstituted phenyl group, Ar2 is a substituted or unsubstituted biphenyl group; a substituted or unsubstituted terphenyl group; a substituted or unsubstituted quarterphenyl group; a substituted or unsubstituted naphthyl group; a substituted or unsubstituted phenanthryl group; or a substituted phenyl group.

According to an exemplary embodiment of the present specification, when Ar1 is a phenyl group, Ar2 is a biphenyl group; a terphenyl group; a terphenyl group substituted with a phenyl group; a quarterphenyl group; a naphthyl group; phenanthryl group; or a phenyl group substituted with a naphthyl group.

According to an exemplary embodiment of the present specification, when Ar1 is a substituted or unsubstituted biphenyl group, Ar2 is a substituted or unsubstituted terphenyl group; a substituted or unsubstituted biphenyl group; a substituted phenyl group; a substituted or unsubstituted naphthyl group; or a substituted or unsubstituted phenanthryl group.

According to an exemplary embodiment of the present specification, when Ar1 is a biphenyl group, Ar2 is a terphenyl group; a biphenyl group; a phenyl group substituted with a naphthyl group; a phenyl group substituted with a phenanthryl group; a biphenyl group substituted with a naphthyl group; a naphthyl group; a naphthyl group substituted with a phenyl group; or a phenanthryl group.

According to an exemplary embodiment of the present specification, when Ar1 is a substituted or unsubstituted naphthyl group, Ar2 is a substituted or unsubstituted biphenyl group; a substituted phenyl group; a substituted or unsubstituted terphenyl group; a substituted or unsubstituted phenanthryl group; or a substituted or unsubstituted quarterphenyl group.

According to an exemplary embodiment of the present specification, when Ar1 is a naphthyl group, Ar2 is a biphenyl group; a phenyl group substituted with a naphthyl group; a phenyl group substituted with a phenanthryl group; a terphenyl group; a biphenyl group substituted with a naphthyl group; a phenanthryl group substituted with a phenyl group; a phenanthryl group; a quarterphenyl group; or a terphenyl group substituted with a phenyl group.

According to an exemplary embodiment of the present specification, when Ar1 is a substituted or unsubstituted phenanthryl group, Ar2 is a substituted or unsubstituted biphenyl group; a substituted phenyl group; a substituted or unsubstituted terphenyl group; or a substituted or unsubstituted quarterphenyl group.

According to an exemplary embodiment of the present specification, when Ar1 is a phenanthryl group, Ar2 is a biphenyl group; a phenyl group substituted with a phenanthryl group; a phenyl group substituted with a naphthyl group; a terphenyl group; a quarterphenyl group; or a terphenyl group substituted with a phenyl group.

According to an exemplary embodiment of the present specification, Ar2 is a substituted or unsubstituted phenyl group; a substituted or unsubstituted biphenyl group; a substituted or unsubstituted terphenyl group; a substituted or unsubstituted quarterphenyl group; a substituted or unsubstituted naphthyl group; or a substituted or unsubstituted phenanthryl group.

According to an exemplary embodiment of the present specification, Ar2 is a phenyl group; a biphenyl group; a terphenyl group; a quarterphenyl group; a naphthyl group; or a phenanthryl group.

According to an exemplary embodiment of the present specification, at least one of Ar1 and Ar2 is a substituted or unsubstituted biphenyl group.

According to an exemplary embodiment of the present specification, Ar1 is a phenyl group, which is unsubstituted or substituted with an aryl group; a biphenyl group, which is unsubstituted or substituted with an aryl group; a naphthyl group, which is unsubstituted or substituted with an aryl group; or a phenanthryl group, which is unsubstituted or substituted with an aryl group, and Ar2 is a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 is a phenyl group, and Ar2 is a biphenyl group.

According to an exemplary embodiment of the present specification, the compound represented by any one of Formulae 1 to 28 has a glass transition temperature of preferably 80° C. or more, and more preferably 100° C. or more.

According to an exemplary embodiment of the present specification, the compound represented by any one of Formulae 1 to 28 may be used for an electron transporting layer of an organic light emitting device. Further, according to an exemplary embodiment of the present specification, the compound represented by any one of Formulae 1 to 28 may be used for an electron controlling layer of an organic light emitting device.

According to an exemplary embodiment of the present specification, the compound represented by any one of Formulae 1 to 28 has a HOMO level of 6.0 eV or more, and more preferably 6.0 eV to 7.0 eV.

In the experimental examples of the present specification, it was confirmed that the compound represented by any one of Formulae 1 to 28 has a HOMO level of 6.0 eV or more, which is a deep HOMO level, and the result is shown in Table 1.

In the present specification, the energy level means the size of energy. Accordingly, even when the energy level is expressed in the negative (-) direction from the vacuum level, it is interpreted that the energy level means an absolute value of the corresponding energy value. For example, the HOMO energy level means the distance from the vacuum level to the highest occupied molecular orbital.

In an exemplary embodiment of the present specification, the HOMO level may be measured by using an atmospheric pressure photoelectron spectrometer AC3 (manufactured by Riken Keiki Co., Ltd.). Specifically, the HOMO level may be measured by irradiating light on a material, and measuring the amount of electron produced due to separation of a charge at that time.

According to an exemplary embodiment of the present specification, the triplet energy of the compound represented by any one of Formulae 1 to 28 is 2.2 eV or more.

In the experimental examples of the present specification, it was confirmed that the triplet energy of the compound represented by any one of Formulae 1 to 28 is 2.2 eV or more, and the result is shown in Table 1.

In an exemplary embodiment of the present specification, the triplet energy ($E_T$) may be measured by using the low temperature photoluminescence method. The triplet energy may be obtained by measuring the λ edge value and using the following conversion formula.

$$E_T(eV)=1239.85/(\lambda\ edge)$$

When a phosphorescence spectrum is expressed by taking the phosphorescence intensity in the longitudinal axis and the wavelength in the lateral axis, a tangent line is drawn with respect to an increase at the short wavelength side of the phosphorescence spectrum, the term "λ edge" in the conversion formula means a wavelength value of a cross-section of the tangent line and the lateral axis (unit nm).

In another exemplary embodiment of the present specification, the triplet energy ($E_T$) may also be obtained by the quantum chemical calculation. The quantum chemical calculation may be performed by using a quantum chemical calculation program Gaussian 03 manufactured by U.S. Gaussian Corporation. In the calculation, the density functional theory (DFT) is used, and a calculated value of the triplet energy may be obtained by the time-dependent-density functional theory (TD-DFT) with respect to a structure optimized using B3LYP as a functional and 6-31G* as a basis function.

In another exemplary embodiment of the present specification, the phosphorescence spectrum is not observed in a specific organic compound in some cases, and in the organic compound, it is possible to assume and use the triplet energy ($E_T$) obtained by using the quantum chemical calculation as shown above.

According to an exemplary embodiment of the present invention, the compound of Formula 1 may be any one selected from the following Compounds 1-1 to 1-627.

| Compound | ---Ar1 | ---Ar2 | ---Ar3 |
|---|---|---|---|
| 1-1 | 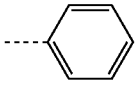 | 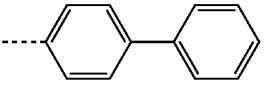 | 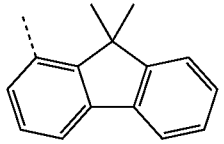 |
| 1-2 | 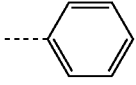 | 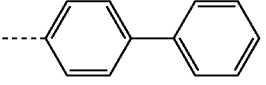 | 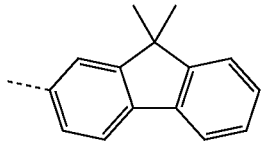 |
| 1-3 | 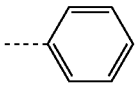 | 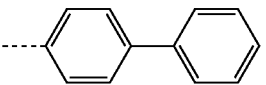 | 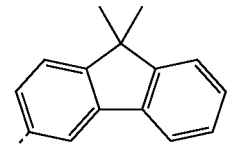 |
| 1-4 | 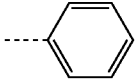 | 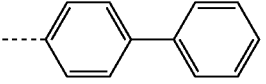 | 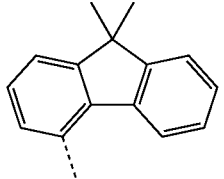 |
| 1-5 | 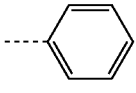 | 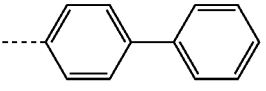 | 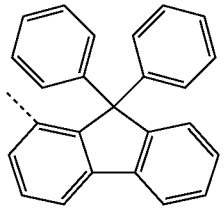 |
| 1-6 | 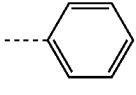 | 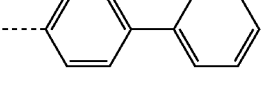 | 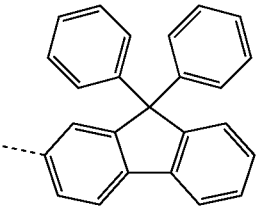 |
| 1-7 | 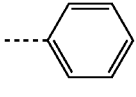 | 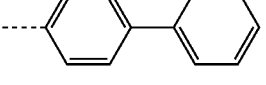 | 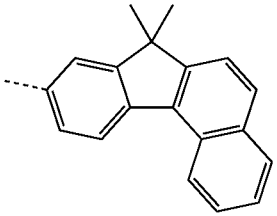 |
| 1-8 | 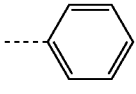 | 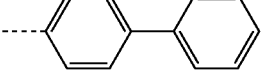 | 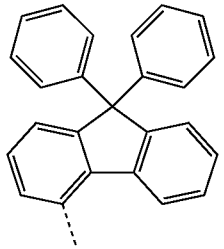 |

-continued

| Compound | ---Ar1 | ---Ar2 | ---Ar3 |
|---|---|---|---|
| 1-9 | phenyl | 4-biphenyl | 4,4-dimethyl-4H-benzo[c]fluorenyl |
| 1-10 | phenyl | 4-biphenyl | 9,9-bis(4-methylphenyl)fluoren-2-yl |
| 1-11 | phenyl | 4-biphenyl | 9,9-bis(4-methylphenyl)fluoren-3-yl |
| 1-12 | phenyl | 4-biphenyl | 9,9-bis(4-methylphenyl)fluoren-4-yl |
| 1-13 | phenyl | 3-biphenyl | 9,9-dimethylfluoren-1-yl |
| 1-14 | phenyl | 3-biphenyl | 9,9-dimethylfluoren-2-yl |

-continued
| Compound | ---Ar1 | ---Ar2 | ---Ar3 |
|---|---|---|---|
| 1-15 | 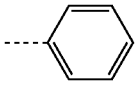 | 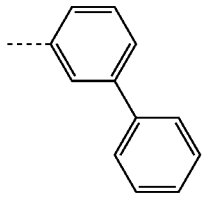 | 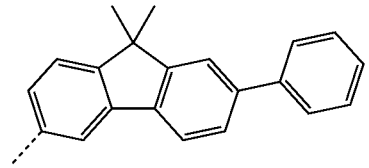 |
| 1-16 | 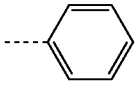 | 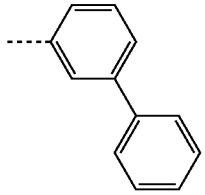 | 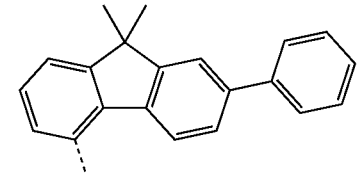 |
| 1-17 | 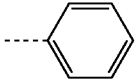 | 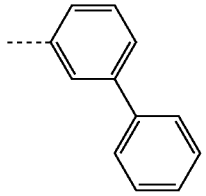 | 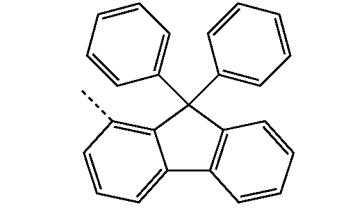 |
| 1-18 | 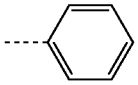 | 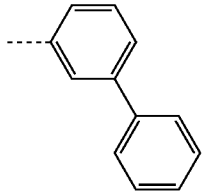 | 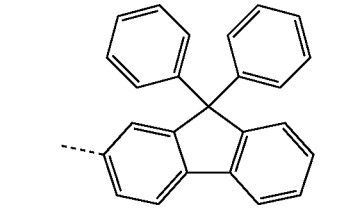 |
| 1-19 | 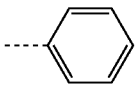 | 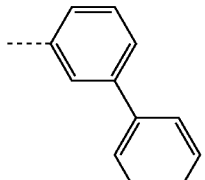 | 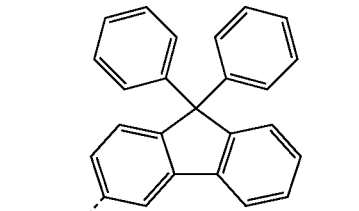 |
| 1-20 | 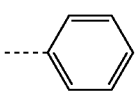 | 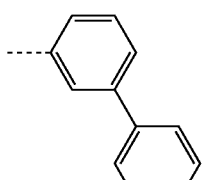 | 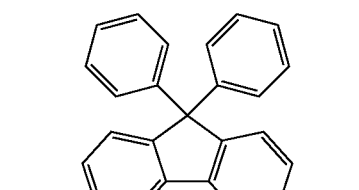 |
| 1-21 | 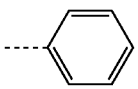 | 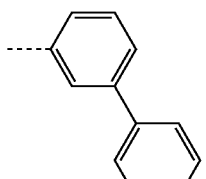 | 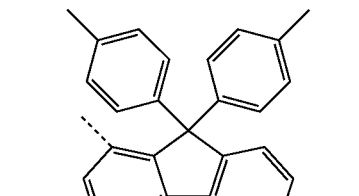 |

-continued
| Compound | ---Ar1 | ---Ar2 | ---Ar3 |
|---|---|---|---|
| 1-22 | 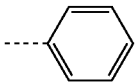 | 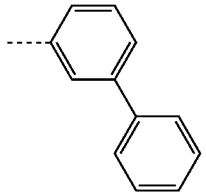 | 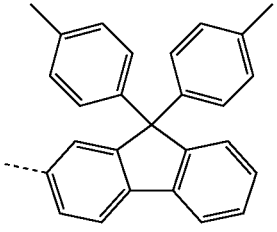 |
| 1-23 | 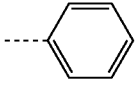 | 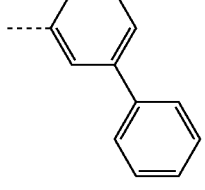 | 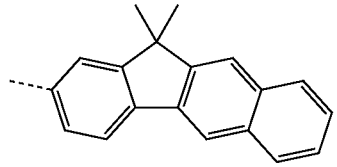 |
| 1-24 | 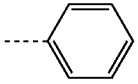 | 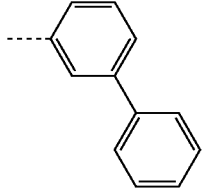 | 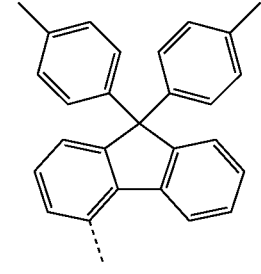 |
| 1-25 | 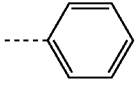 | 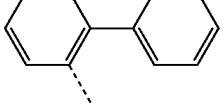 | 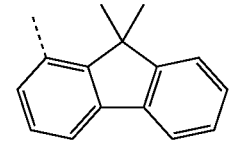 |
| 1-26 | 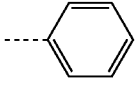 | 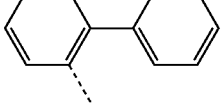 | 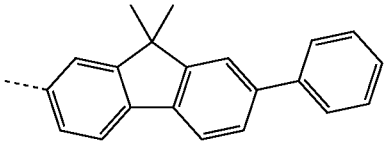 |
| 1-27 | 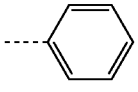 | 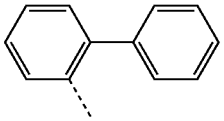 | 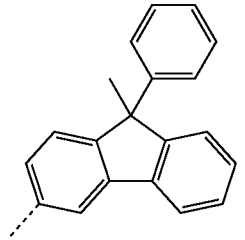 |
| 1-28 | 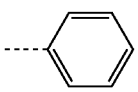 | 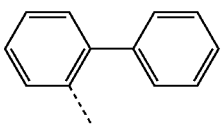 | 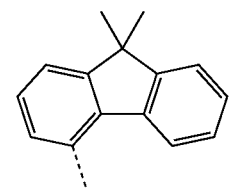 |

-continued

| Compound | ---Ar1 | ---Ar2 | ---Ar3 |
| --- | --- | --- | --- |
| 1-29 | phenyl | 2-biphenyl | 9,9-diphenylfluoren-1-yl |
| 1-30 | phenyl | 2-biphenyl | 9,9-diphenylfluoren-2-yl |
| 1-31 | phenyl | 2-biphenyl | dimethyl-dibenzofluorenyl |
| 1-32 | phenyl | 2-biphenyl | 9,9-diphenylfluoren-4-yl |
| 1-33 | phenyl | 2-biphenyl | dimethyl-benzofluorenyl |
| 1-34 | phenyl | 2-biphenyl | 9,9-di(p-tolyl)fluoren-2-yl |

-continued

| Compound | ---Ar1 | ---Ar2 | ---Ar3 |
|---|---|---|---|
| 1-35 | | | |
| 1-36 | | | |
| 1-37 | | | |
| 1-38 | | | |
| 1-39 | | | |
| 1-40 | | | |
| 1-41 | | | |

-continued
| Compound | ---Ar1 | ---Ar2 | ---Ar3 |
|---|---|---|---|
| 1-42 | 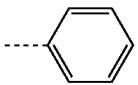 | 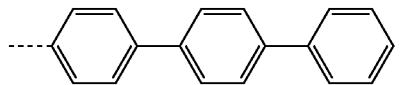 | 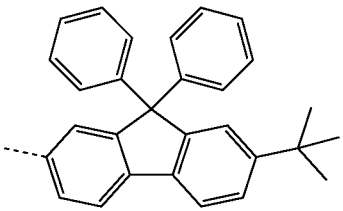 |
| 1-43 | 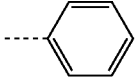 | 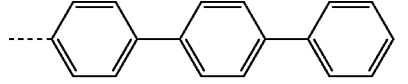 | 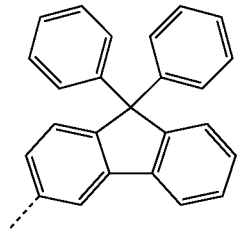 |
| 1-44 | 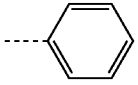 | 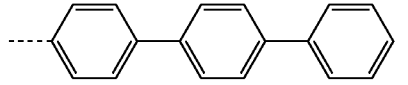 | 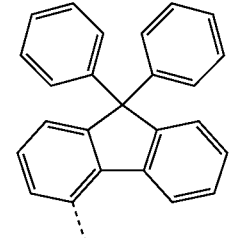 |
| 1-45 | 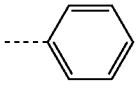 | 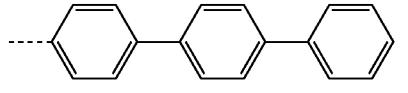 | 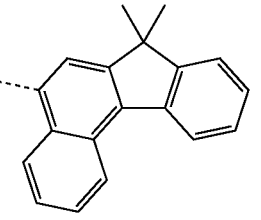 |
| 1-46 | 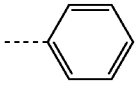 | 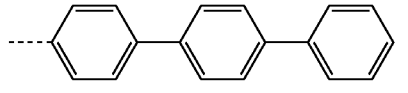 | 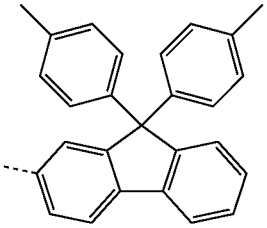 |
| 1-47 | 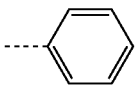 | 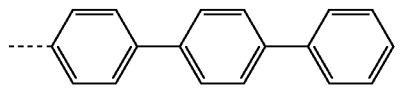 | 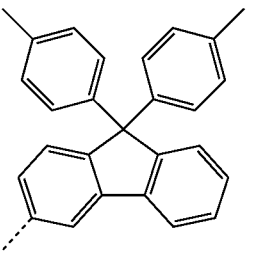 |

-continued
| Compound | ---Ar1 | ---Ar2 | ---Ar3 |
|---|---|---|---|
| 1-48 | 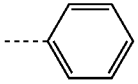 | 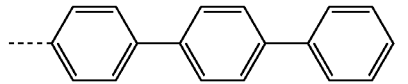 | 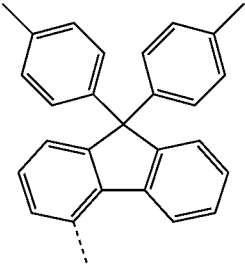 |
| 1-49 | 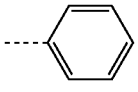 | 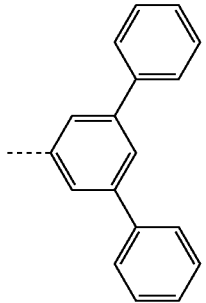 | 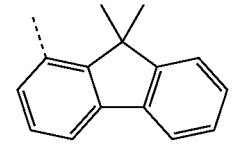 |
| 1-50 | 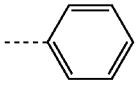 | 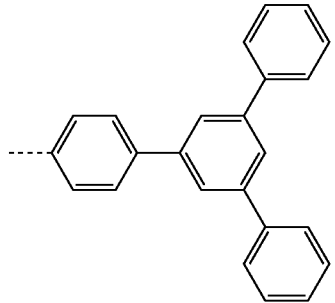 | 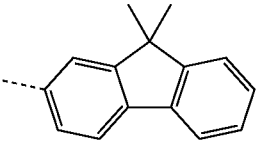 |
| 1-51 | 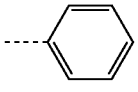 | 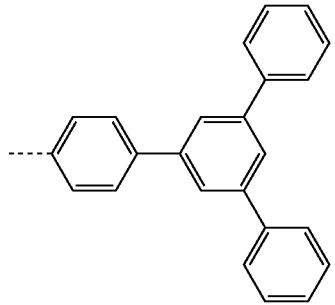 | 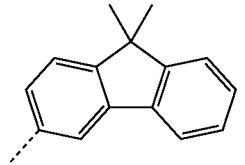 |
| 1-52 | 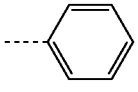 | 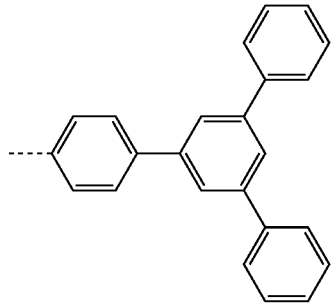 | 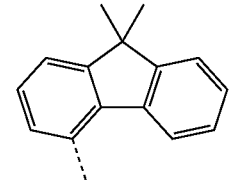 |

-continued

| Compound | ---Ar1 | ---Ar2 | ---Ar3 |
|---|---|---|---|
| 1-53 | | | |
| 1-54 | | | |
| 1-55 | | | |
| 1-56 | | | |
| 1-57 | | | |

| Compound | ---Ar1 | ---Ar2 | ---Ar3 |
|---|---|---|---|
| 1-58 | 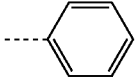 | 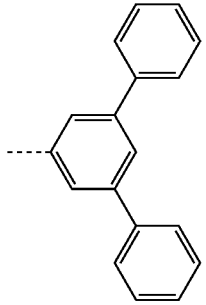 | 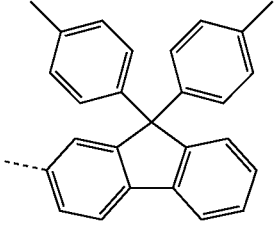 |
| 1-59 | 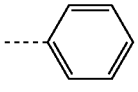 | 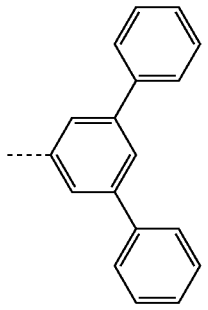 | 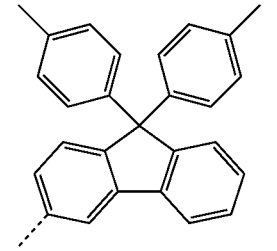 |
| 1-60 | 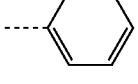 | 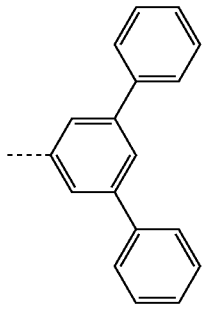 | 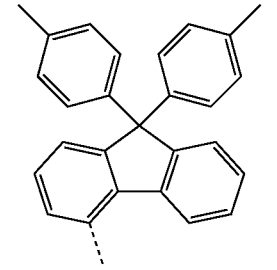 |
| 1-61 | 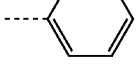 | 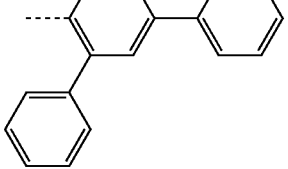 | 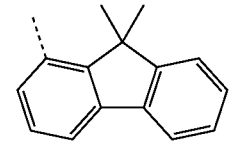 |
| 1-62 | 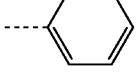 | 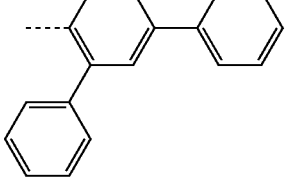 | 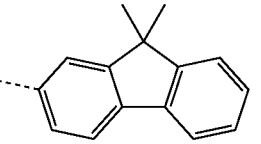 |
| 1-63 | 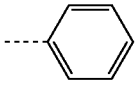 | 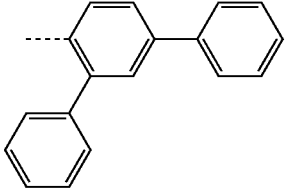 | 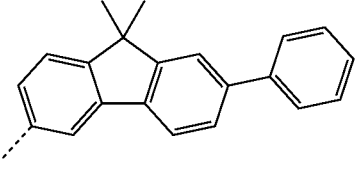 |

-continued

| Compound | ---Ar1 | ---Ar2 | ---Ar3 |
|---|---|---|---|
| 1-64 | phenyl | 2,4-biphenyl-substituted phenyl | 9,9-dimethylfluorenyl (4-position) |
| 1-65 | phenyl | 2,4-biphenyl-substituted phenyl | dimethyl-dibenzo[g,p]chrysene-type fluorene |
| 1-66 | phenyl | 2,4-biphenyl-substituted phenyl | 9,9-diphenylfluoren-2-yl |
| 1-67 | phenyl | 2,4-biphenyl-substituted phenyl | 9,9-diphenylfluoren-3-yl |
| 1-68 | phenyl | 2,4-biphenyl-substituted phenyl | 9,9-diphenylfluoren-4-yl |
| 1-69 | phenyl | 2,4-biphenyl-substituted phenyl | 11,11-dimethyl-11H-benzo[a]fluorenyl |

-continued
| Compound | ---Ar1 | ---Ar2 | ---Ar3 |
|---|---|---|---|
| 1-70 | 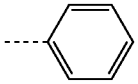 | 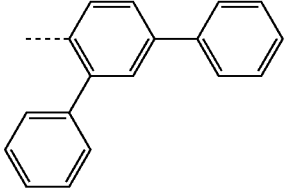 | 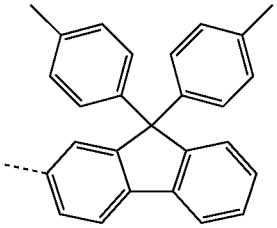 |
| 1-71 | 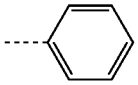 | 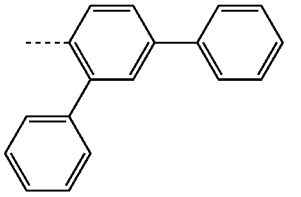 | 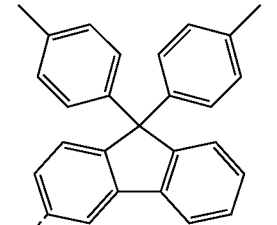 |
| 1-72 | 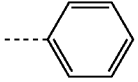 | 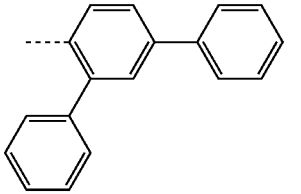 | 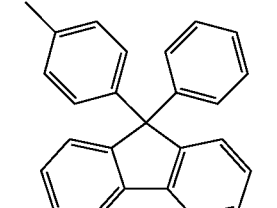 |
| 1-73 | 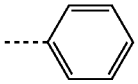 | 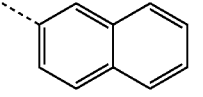 | 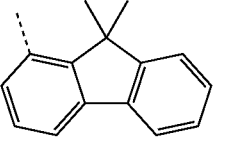 |
| 1-74 | 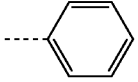 | 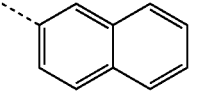 | 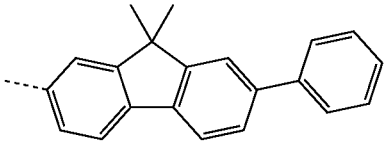 |
| 1-75 | 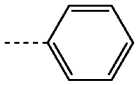 | 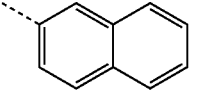 | 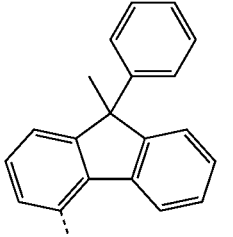 |
| 1-76 | 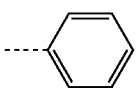 | 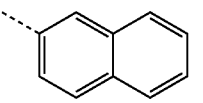 | 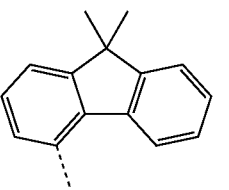 |

-continued

| Compound | ---Ar1 | ---Ar2 | ---Ar3 |
|---|---|---|---|
| 1-77 | phenyl | 2-naphthyl | 9,9-diphenylfluoren-1-yl |
| 1-78 | phenyl | 2-naphthyl | 9,9-diphenylfluoren-2-yl |
| 1-79 | phenyl | 2-naphthyl | 9,9-diphenylfluoren-3-yl |
| 1-80 | phenyl | 2-naphthyl | 9,9-diphenylfluoren-4-yl |
| 1-81 | phenyl | 2-naphthyl | 9,9-di(p-tolyl)fluoren-1-yl |
| 1-82 | phenyl | 2-naphthyl | 9,9-di(p-tolyl)fluoren-2-yl |

-continued
| Compound | ---Ar1 | ---Ar2 | ---Ar3 |
|---|---|---|---|
| 1-83 | 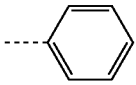 | 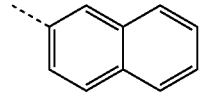 | 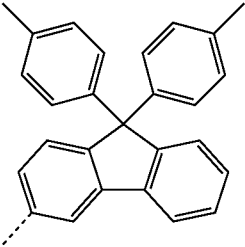 |
| 1-84 | 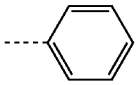 | 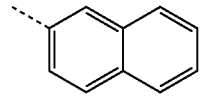 | 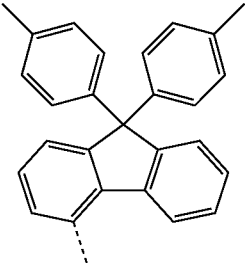 |
| 1-85 | 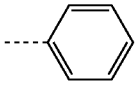 | 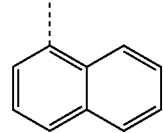 | 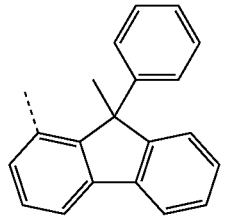 |
| 1-86 | 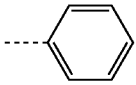 | 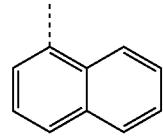 | 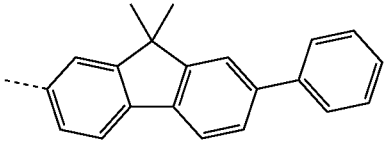 |
| 1-87 | 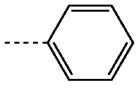 | 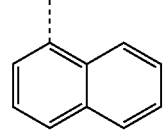 | 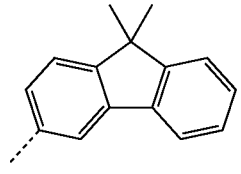 |
| 1-88 | 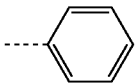 | 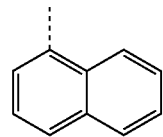 | 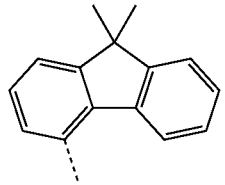 |
| 1-89 | 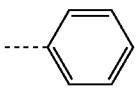 | 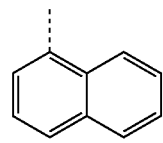 | 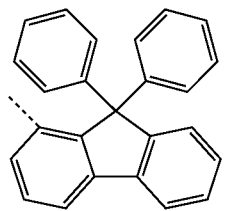 |

-continued
| Compound | ---Ar1 | ---Ar2 | ---Ar3 |
|---|---|---|---|
| 1-90 | 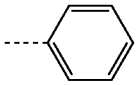 | 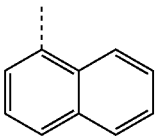 | 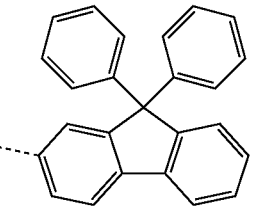 |
| 1-91 | 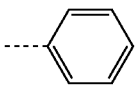 | 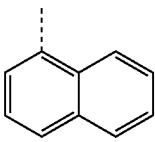 | 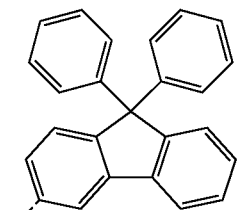 |
| 1-92 | 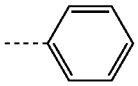 | 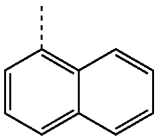 | 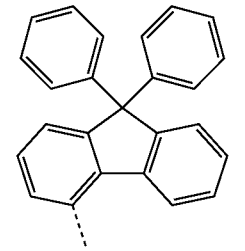 |
| 1-93 | 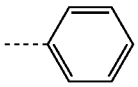 | 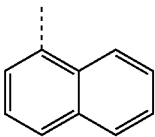 | 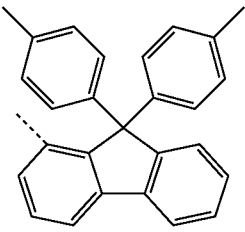 |
| 1-94 | 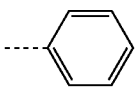 | 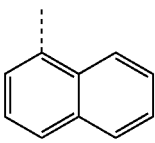 | 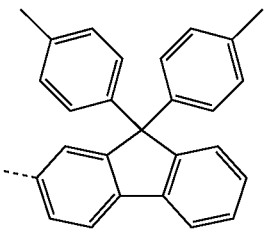 |
| 1-95 | 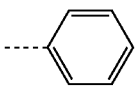 | 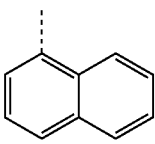 | 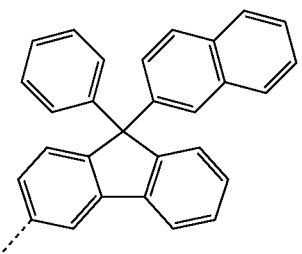 |

-continued
| Compound | ---Ar1 | ---Ar2 | ---Ar3 |
|---|---|---|---|
| 1-96 | 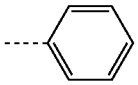 | 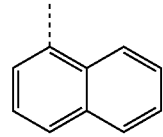 | 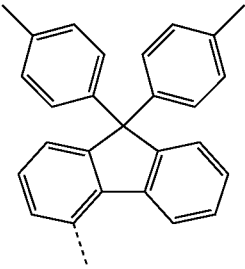 |
| 1-97 | 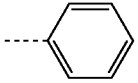 | 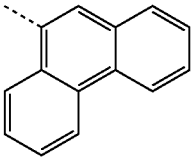 | 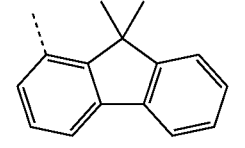 |
| 1-98 | 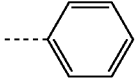 | 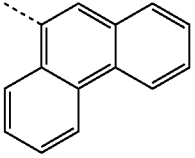 | 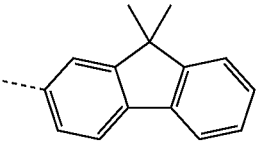 |
| 1-99 | 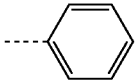 | 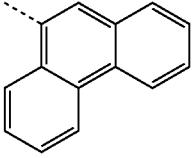 | 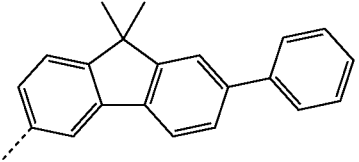 |
| 1-100 | 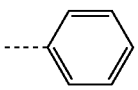 | 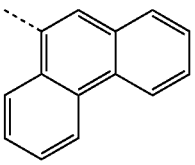 | 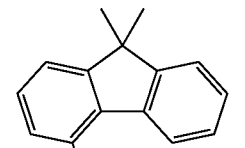 |
| 1-101 | 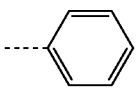 | 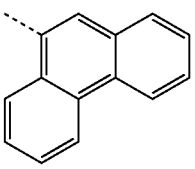 | 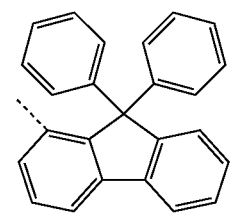 |
| 1-102 | 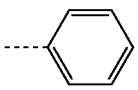 | 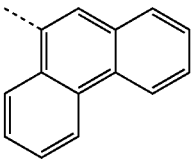 | 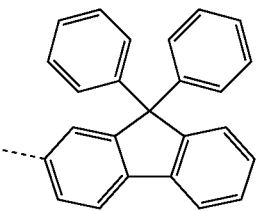 |

-continued
| Compound | ---Ar1 | ---Ar2 | ---Ar3 |
|---|---|---|---|
| 1-103 | 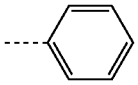 | 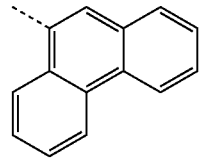 | 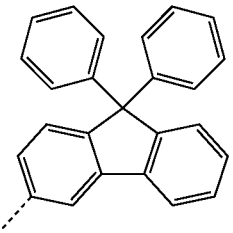 |
| 1-104 | 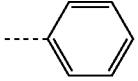 | 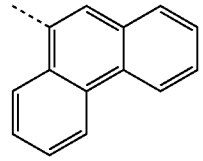 | 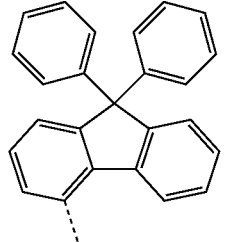 |
| 1-105 | 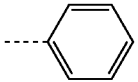 | 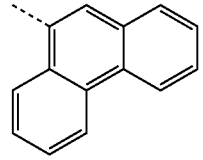 | 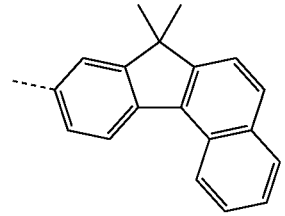 |
| 1-106 | 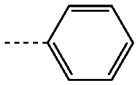 | 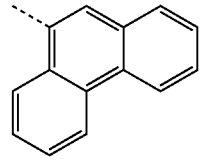 | 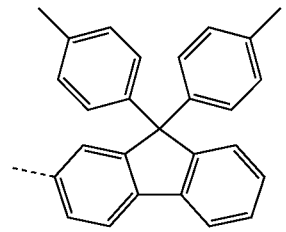 |
| 1-107 | 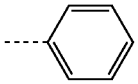 | 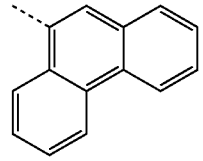 | 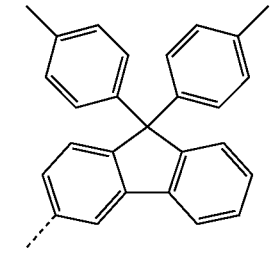 |
| 1-108 | 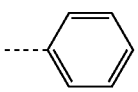 | 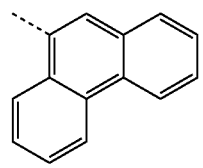 | 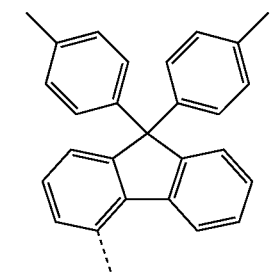 |

-continued
| Compound | ---Ar1 | ---Ar2 | ---Ar3 |
|---|---|---|---|
| 1-109 | 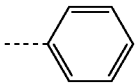 | 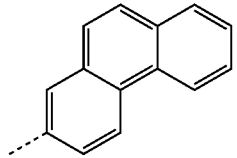 | 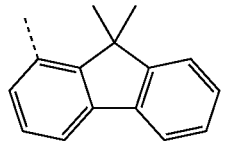 |
| 1-110 | 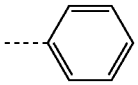 | 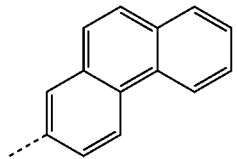 | 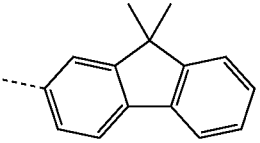 |
| 1-111 | 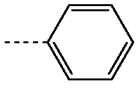 | 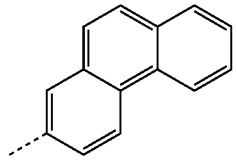 | 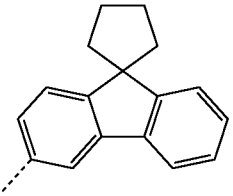 |
| 1-112 | 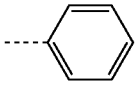 | 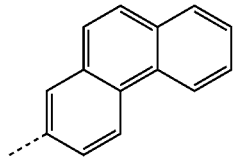 | 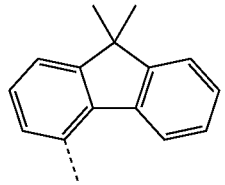 |
| 1-113 | 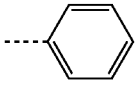 | 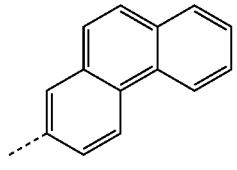 | 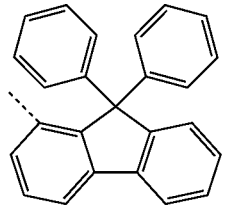 |
| 1-114 | 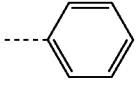 | 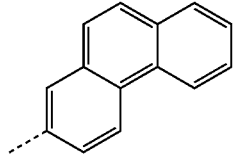 | 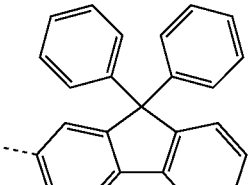 |
| 1-115 | 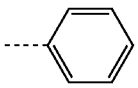 | 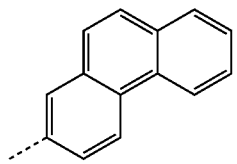 | 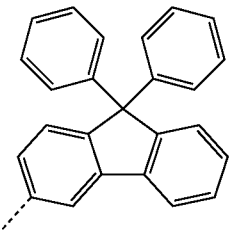 |

-continued
| Compound | ---Ar1 | ---Ar2 | ---Ar3 |
|---|---|---|---|
| 1-116 | 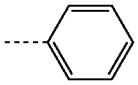 | 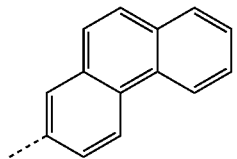 | 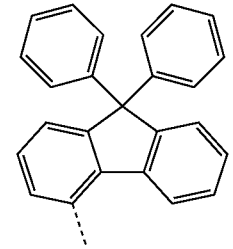 |
| 1-117 | 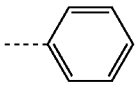 | 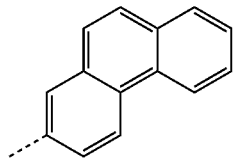 | 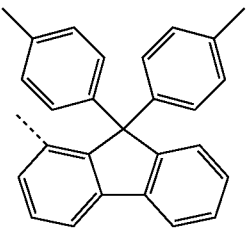 |
| 1-118 | 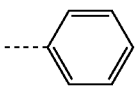 | 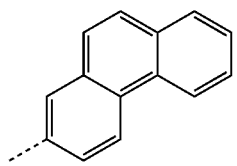 | 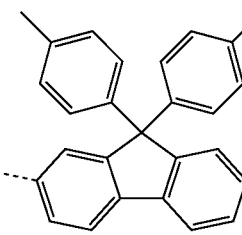 |
| 1-119 | 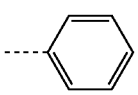 | 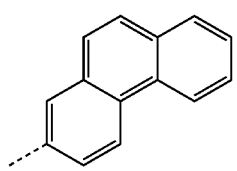 | 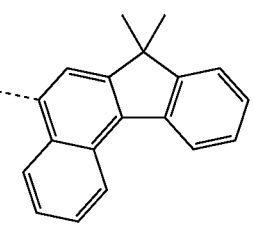 |
| 1-120 | 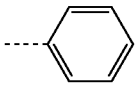 | 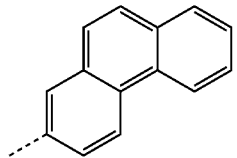 | 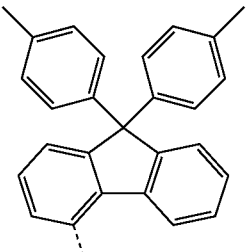 |
| 1-121 | 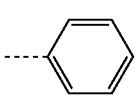 | 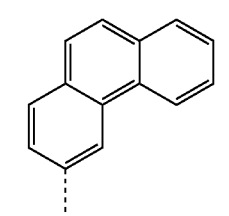 | 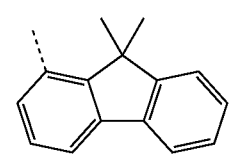 |

-continued
| Compound | ---Ar1 | ---Ar2 | ---Ar3 |
|---|---|---|---|
| 1-122 | 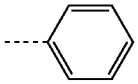 | 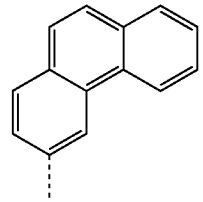 | 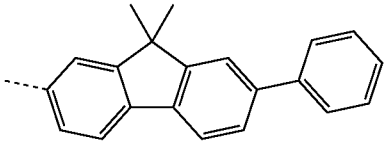 |
| 1-123 | 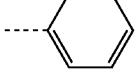 | 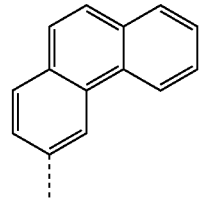 | 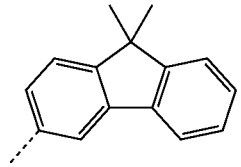 |
| 1-124 | 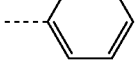 | 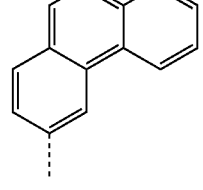 | 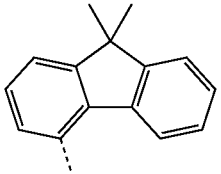 |
| 1-125 | 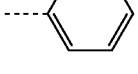 | 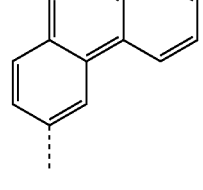 | 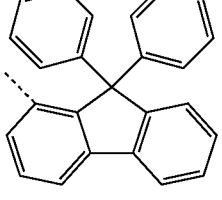 |
| 1-126 | 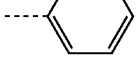 | 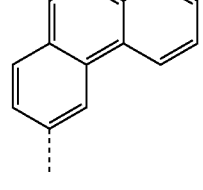 | 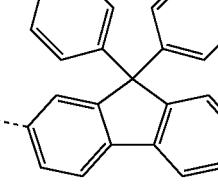 |
| 1-127 | 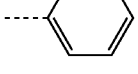 | 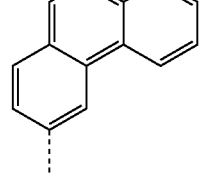 | 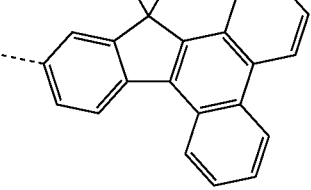 |
| 1-128 | 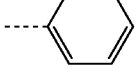 | 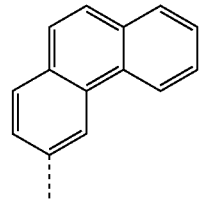 | 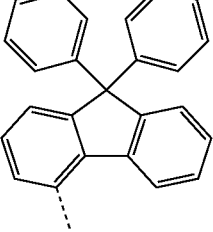 |

-continued
| Compound | ---Ar1 | ---Ar2 | ---Ar3 |
|---|---|---|---|
| 1-129 | 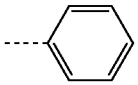 | 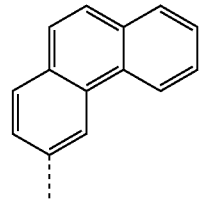 | 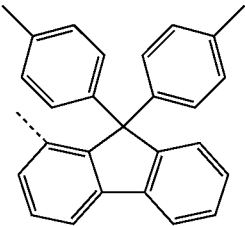 |
| 1-130 | 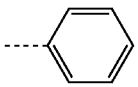 | 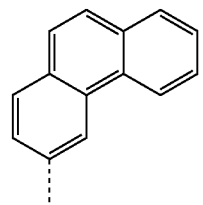 | 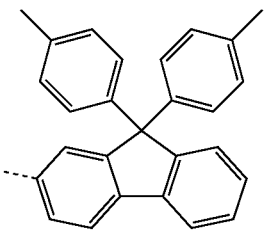 |
| 1-131 | 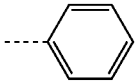 | 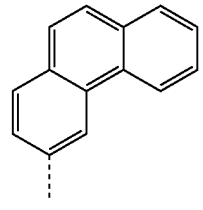 | 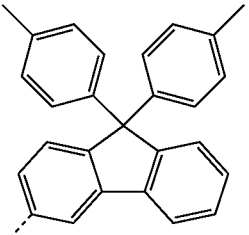 |
| 1-132 | 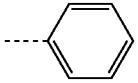 | 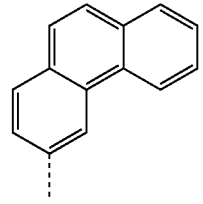 | 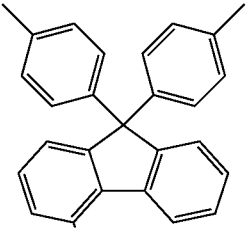 |
| 1-133 | 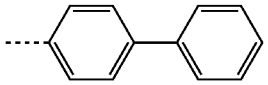 | 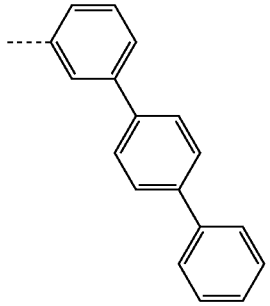 | 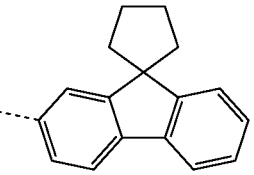 |
| 1-134 | 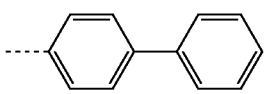 | 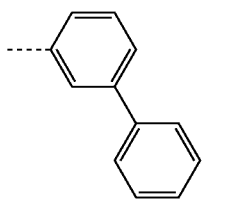 | 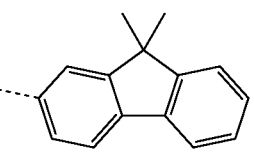 |

-continued

| Compound | ---Ar1 | ---Ar2 | ---Ar3 |
|---|---|---|---|
| 1-135 | biphenyl | biphenyl | 9,9-dimethylfluorene |
| 1-136 | biphenyl | biphenyl | 9,9-dimethylfluorene |
| 1-137 | biphenyl | biphenyl | 9,9-diphenylfluorene |
| 1-138 | phenyl | 4-(2-naphthyl)phenyl | 9,9-diphenylfluorene |
| 1-139 | biphenyl | biphenyl | 9,9-diphenylfluorene |
| 1-140 | biphenyl | biphenyl | 9,9-diphenylfluorene |
| 1-141 | biphenyl | biphenyl | 9,9-di(p-tolyl)fluorene |

-continued

| Compound | ---Ar1 | ---Ar2 | ---Ar3 |
|---|---|---|---|
| 1-142 | biphenyl | biphenyl | 9,9-bis(4-methylphenyl)fluoren-2-yl |
| 1-143 | biphenyl | 3-(naphthalen-1-yl)phenyl | 9,9-diphenylfluoren-2-yl |
| 1-144 | biphenyl | biphenyl | 9,9-bis(4-methylphenyl)fluoren-4-yl |
| 1-145 | biphenyl | 2-biphenyl | 9,9-dimethylfluoren-1-yl |
| 1-146 | biphenyl | 2-biphenyl | 9,9-dimethylfluoren-2-yl |
| 1-147 | biphenyl | 2-biphenyl | 9,9-dimethylfluoren-3-yl |
| 1-148 | biphenyl | 2-biphenyl | 9,9-dimethylfluoren-4-yl |

-continued
| Compound | ---Ar1 | ---Ar2 | ---Ar3 |
|---|---|---|---|
| 1-149 | 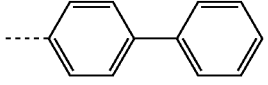 | 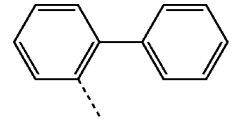 | 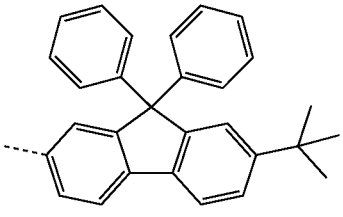 |
| 1-150 | 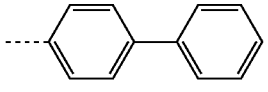 | 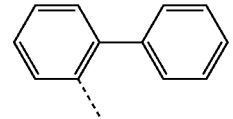 | 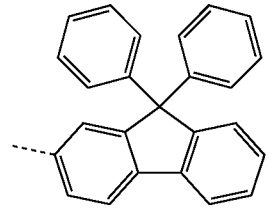 |
| 1-151 | 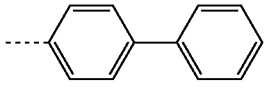 | 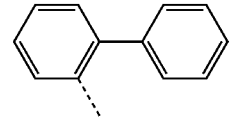 | 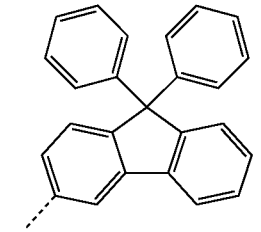 |
| 1-152 | 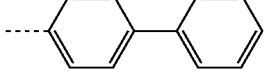 | 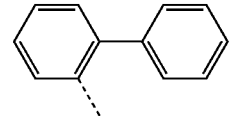 | 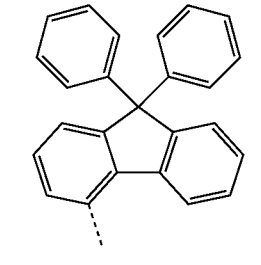 |
| 1-153 | 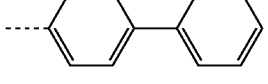 | 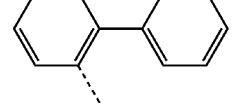 | 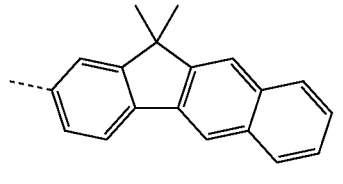 |
| 1-154 | 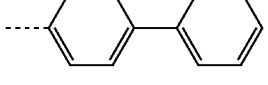 | 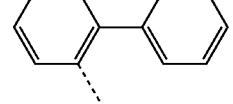 | 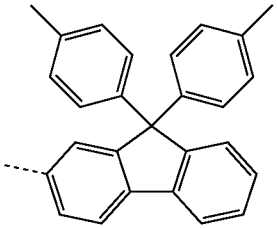 |

-continued

| Compound | ---Ar1 | ---Ar2 | ---Ar3 |
|---|---|---|---|
| 1-155 | | | |
| 1-156 | | | |
| 1-157 | | | |
| 1-158 | | | |
| 1-159 | | | |
| 1-160 | | | |
| 1-161 | | | |

-continued

| Compound | ---Ar1 | ---Ar2 | ---Ar3 |
|---|---|---|---|
| 1-162 | biphenyl | p-terphenyl | 9,9-diphenylfluoren-2-yl |
| 1-163 | biphenyl | p-terphenyl | 9,9-diphenylfluoren-3-yl |
| 1-164 | biphenyl | p-terphenyl | 9,9-diphenylfluoren-4-yl |
| 1-165 | biphenyl | 4-(naphthalen-1-yl)phenyl-phenyl | 9,9-di(p-tolyl)fluoren-1-yl |
| 1-166 | biphenyl | p-terphenyl | 9,9-di(p-tolyl)fluoren-2-yl |
| 1-167 | biphenyl | p-terphenyl | 9,9-dimethyl-benzo[a]fluorenyl |

-continued

| Compound | ---Ar1 | ---Ar2 | ---Ar3 |
|---|---|---|---|
| 1-168 | biphenyl | p-terphenyl | 9,9-di(p-tolyl)fluoren-4-yl |
| 1-169 | biphenyl | 1,1':3',1''-terphenyl-5'-yl | 9,9-dimethylfluoren-1-yl |
| 1-170 | biphenyl | 1,1':3',1''-terphenyl-5'-yl | 9,9-dimethylfluoren-2-yl |
| 1-171 | biphenyl | 1,1':3',1''-terphenyl-5'-yl | spiro[cyclopentane-1,9'-fluoren]-2'-yl |
| 1-172 | biphenyl | 1,1':3',1''-terphenyl-5'-yl | 9,9-dimethylfluoren-4-yl |

-continued

| Compound | ---Ar1 | ---Ar2 | ---Ar3 |
| --- | --- | --- | --- |
| 1-173 | biphenyl | 1,3,5-terphenyl | 9,9-diphenylfluoren-1-yl |
| 1-174 | biphenyl | 1,3,5-terphenyl | 9,9-diphenylfluoren-2-yl |
| 1-175 | biphenyl | 1,3,5-terphenyl | 9,9-diphenylfluoren-3-yl |
| 1-176 | biphenyl | 1,3,5-terphenyl | 9,9-diphenylfluoren-4-yl |
| 1-177 | biphenyl | 1,3,5-terphenyl | 9,9-dimethyl-9H-tribenzo[a,c]fluorenyl |

-continued

| Compound | ---Ar1 | ---Ar2 | ---Ar3 |
|---|---|---|---|
| 1-178 | biphenyl | 3,5-diphenylphenyl | 9,9-diphenyl-fluoren-2-yl |
| 1-179 | biphenyl | 3,5-diphenylphenyl | 11,11-dimethyl-benzo[a]fluorenyl |
| 1-180 | biphenyl | 3,5-diphenylphenyl | 9,9-di(p-tolyl)-fluoren-4-yl |
| 1-181 | biphenyl | 2,4-diphenylphenyl | 9,9-dimethyl-fluoren-1-yl |
| 1-182 | biphenyl | 2,4-diphenylphenyl | 9,9-dimethyl-fluoren-2-yl |
| 1-183 | biphenyl | 2,4-diphenylphenyl | 9,9-dimethyl-fluoren-3-yl |

-continued
| Compound | ---Ar1 | ---Ar2 | ---Ar3 |
|---|---|---|---|
| 1-184 | 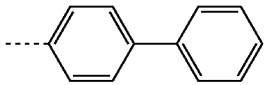 | 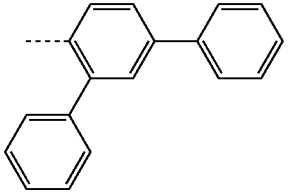 | 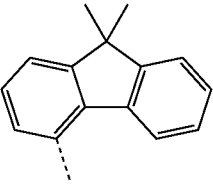 |
| 1-185 | 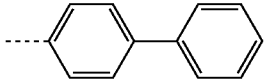 | 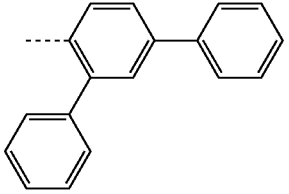 | 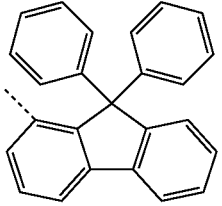 |
| 1-186 | 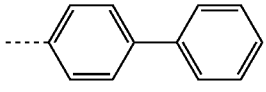 | 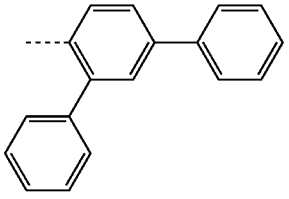 | 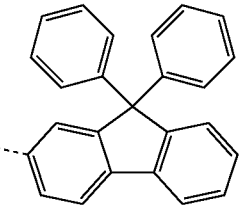 |
| 1-187 | 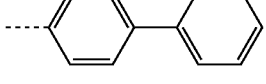 | 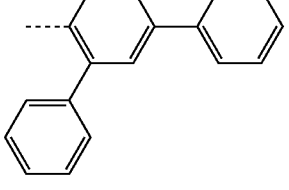 | 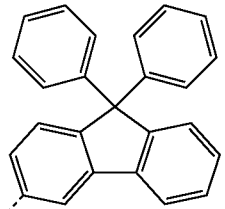 |
| 1-188 | 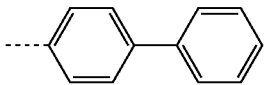 | 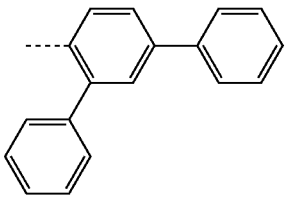 | 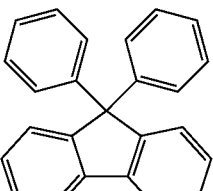 |
| 1-189 | 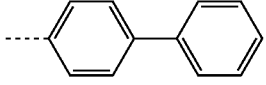 | 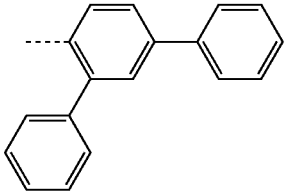 | 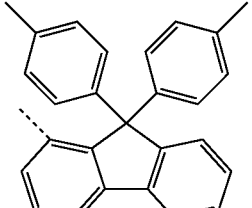 |

-continued

| Compound | ---Ar1 | ---Ar2 | ---Ar3 |
|---|---|---|---|
| 1-190 | biphenyl | 2,6-diphenylphenyl | 9,9-bis(4-methylphenyl)fluoren-2-yl |
| 1-191 | biphenyl | 3,4-diphenylphenyl | 9,9-bis(4-methylphenyl)fluoren-3-yl |
| 1-192 | biphenyl | 2,6-diphenylphenyl | 9,9-bis(4-methylphenyl)fluoren-4-yl |
| 1-193 | biphenyl | naphthalen-2-yl | 9,9-dimethylfluoren-1-yl |
| 1-194 | biphenyl | naphthalen-2-yl | 9,9-dimethylfluoren-2-yl |
| 1-195 | biphenyl | 2,2'-binaphthyl | 9,9-dimethylfluoren-3-yl |
| 1-196 | biphenyl | naphthalen-2-yl | 9,9-dimethylfluoren-4-yl |

-continued

| Compound | ---Ar1 | ---Ar2 | ---Ar3 |
| --- | --- | --- | --- |
| 1-197 | biphenyl | 2-naphthyl | 9,9-diphenylfluoren-1-yl |
| 1-198 | biphenyl | 2-naphthyl | 9,9-diphenylfluoren-2-yl |
| 1-199 | biphenyl | 6-phenylnaphthalen-2-yl | 9,9-diphenylfluoren-3-yl |
| 1-200 | biphenyl | 6-phenylnaphthalen-2-yl | 9,9-diphenylfluoren-4-yl |
| 1-201 | biphenyl | 2-naphthyl | 9,9-di(p-tolyl)fluoren-1-yl |
| 1-202 | biphenyl | 2-naphthyl | 9,9-di(p-tolyl)fluoren-2-yl |

-continued
| Compound | ---Ar1 | ---Ar2 | ---Ar3 |
|---|---|---|---|
| 1-203 | 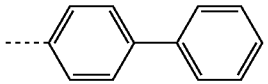 | 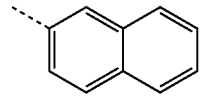 | 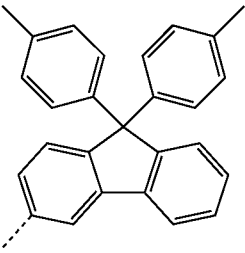 |
| 1-204 | 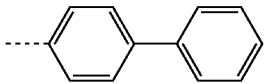 | 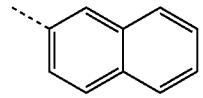 | 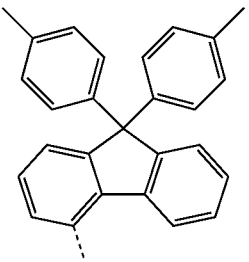 |
| 1-205 | 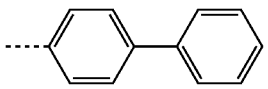 | 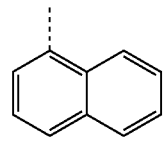 | 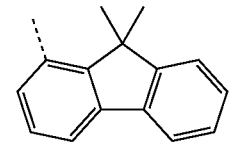 |
| 1-206 | 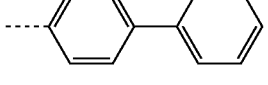 | 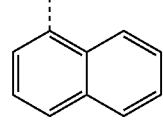 | 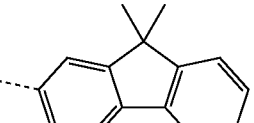 |
| 1-207 | 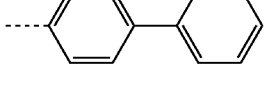 | 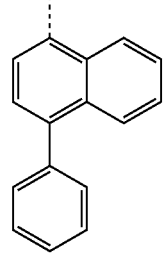 | 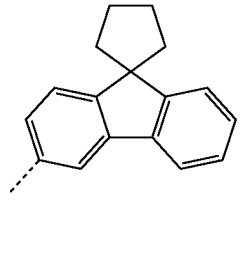 |
| 1-208 | 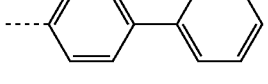 | 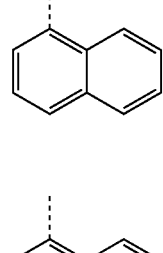 | 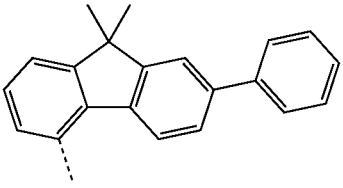 |
| 1-209 | 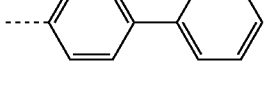 | 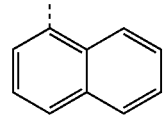 | 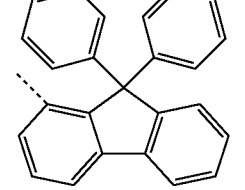 |

-continued
| Compound | ---Ar1 | ---Ar2 | ---Ar3 |
|---|---|---|---|
| 1-210 | 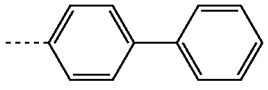 | 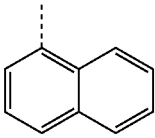 | 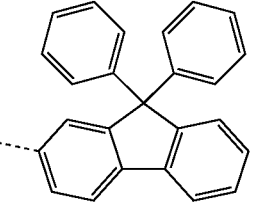 |
| 1-211 | 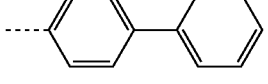 | 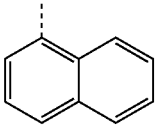 | 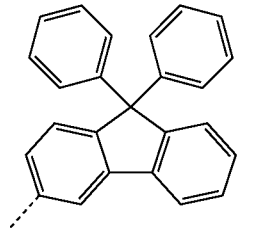 |
| 1-212 | 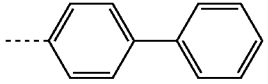 | 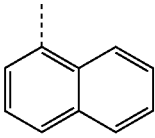 | 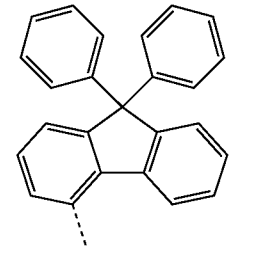 |
| 1-213 | 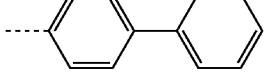 | 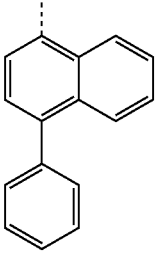 | 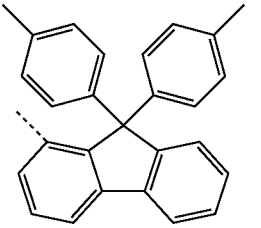 |
| 1-214 | 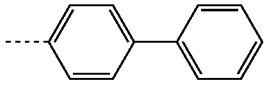 | 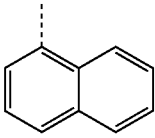 | 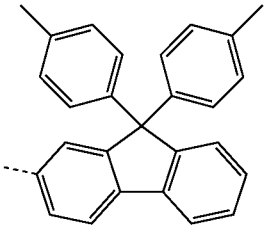 |
| 1-215 | 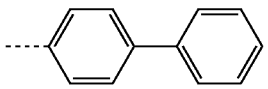 | 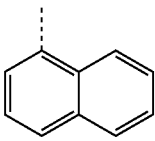 | 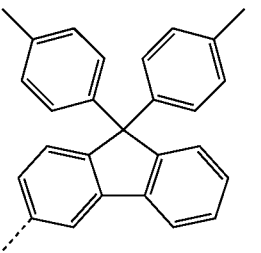 |

-continued

| Compound | ---Ar1 | ---Ar2 | ---Ar3 |
| --- | --- | --- | --- |
| 1-216 | biphenyl | naphthyl | 9,9-di(p-tolyl)fluorenyl |
| 1-217 | biphenyl | phenanthrenyl | 9,9-dimethylfluorenyl |
| 1-218 | biphenyl | phenanthrenyl | 9,9-dimethylfluorenyl |
| 1-219 | biphenyl | phenanthrenyl | 9,9-dimethylfluorenyl |
| 1-220 | biphenyl | phenyl-phenanthrenyl | 9,9-dimethylfluorenyl |
| 1-221 | biphenyl | phenanthrenyl | 9,9-di(p-tolyl)fluorenyl |
| 1-222 | biphenyl | phenanthrenyl | 9,9-diphenylfluorenyl |

-continued

| Compound | ---Ar1 | ---Ar2 | ---Ar3 |
|---|---|---|---|
| 1-223 | biphenyl | phenanthrenyl | 9,9-diphenylfluorenyl |
| 1-224 | biphenyl | phenanthrenyl | 9,9-diphenylfluorenyl |
| 1-225 | biphenyl | phenanthrenyl | 9,9-di(p-tolyl)fluorenyl |
| 1-226 | biphenyl | phenanthrenyl | 9,9-di(p-tolyl)fluorenyl |
| 1-227 | biphenyl | phenanthrenyl | 9,9-dimethyl-benzofluorenyl |
| 1-228 | biphenyl | phenanthrenyl | 9,9-di(p-tolyl)fluorenyl |

-continued
| Compound | ---Ar1 | ---Ar2 | ---Ar3 |
|---|---|---|---|
| 1-229 | 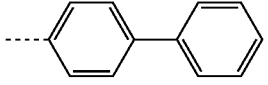 | 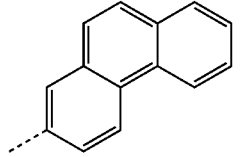 | 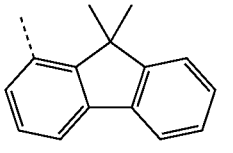 |
| 1-230 | 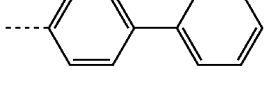 | 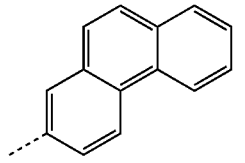 | 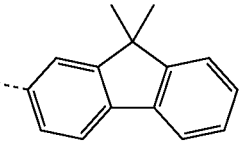 |
| 1-231 | 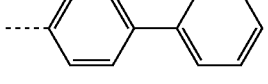 | 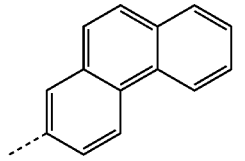 | 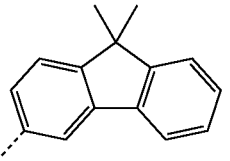 |
| 1-232 | 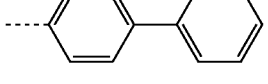 | 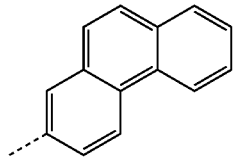 | 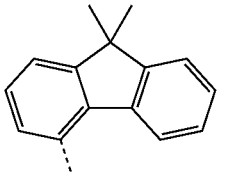 |
| 1-233 | 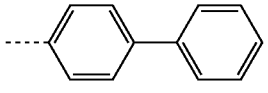 | 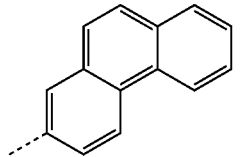 | 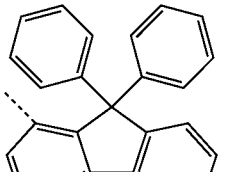 |
| 1-234 | 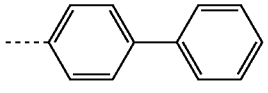 | 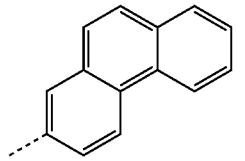 | 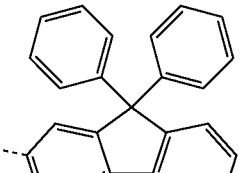 |
| 1-235 | 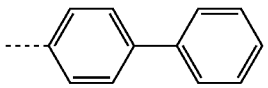 | 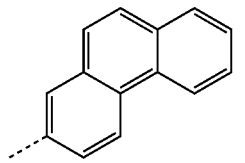 | 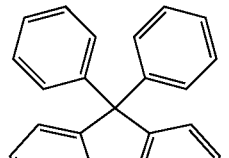 |

-continued

| Compound | ---Ar1 | ---Ar2 | ---Ar3 |
|---|---|---|---|
| 1-236 | biphenyl | phenanthrene | 9,9-diphenylfluorene |
| 1-237 | biphenyl | phenanthrene | 9,9-dimethylbenzo[c]fluorene |
| 1-238 | biphenyl | phenanthrene | 9,9-di(p-tolyl)fluorene |
| 1-239 | biphenyl | phenanthrene | 9,9-di(p-tolyl)fluorene |
| 1-240 | biphenyl | phenanthrene | 9,9-di(p-tolyl)fluorene |
| 1-241 | biphenyl | phenanthrene | 9,9-dimethylfluorene |

-continued

| Compound | ---Ar1 | ---Ar2 | ---Ar3 |
|---|---|---|---|
| 1-242 | biphenyl | phenanthrene | 9,9-dimethylfluorene (2-position) |
| 1-243 | biphenyl | phenanthrene | 9,9-dimethylfluorene (3-position) |
| 1-244 | biphenyl | phenanthrene | 9,9-dimethylfluorene (4-position) |
| 1-245 | biphenyl | phenanthrene | 9,9-diphenylfluorene (1-position) |
| 1-246 | biphenyl | phenanthrene | 9,9-diphenylfluorene (2-position) |
| 1-247 | biphenyl | phenanthrene | 9,9-diphenyl-2-tert-butylfluorene |
| 1-248 | biphenyl | phenanthrene | 9,9-diphenylfluorene (4-position) |

-continued

| Compound | ---Ar1 | ---Ar2 | ---Ar3 |
|---|---|---|---|
| 1-249 | biphenyl | phenanthrene | 9,9-dimethyl-benzo[b]fluorene |
| 1-250 | biphenyl | phenanthrene | 9,9-di(p-tolyl)fluorene |
| 1-251 | biphenyl | phenanthrene | 9,9-di(p-tolyl)fluorene |
| 1-252 | biphenyl | phenanthrene | 9,9-di(p-tolyl)fluorene |
| 1-253 | naphthalene | biphenyl | 9,9-dimethylfluorene |
| 1-254 | naphthalene | biphenyl | 9,9-dimethylfluorene |

-continued
| Compound | ---Ar1 | ---Ar2 | ---Ar3 |
|---|---|---|---|
| 1-255 | 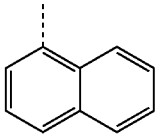 | 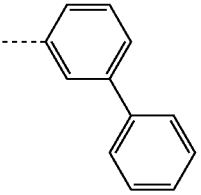 | 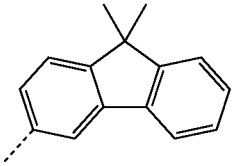 |
| 1-256 | 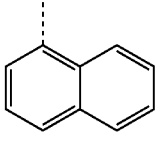 | 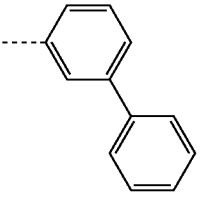 | 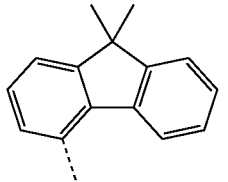 |
| 1-257 | 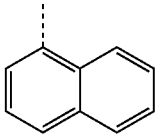 | 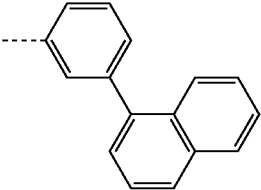 | 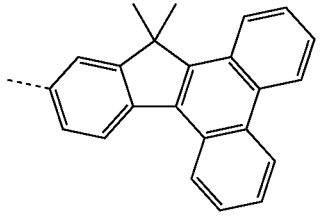 |
| 1-258 | 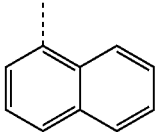 | 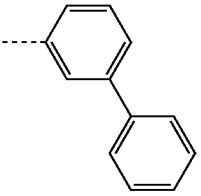 | 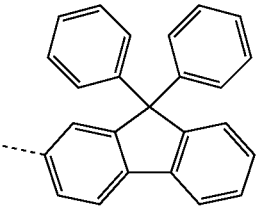 |
| 1-259 | 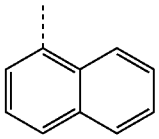 | 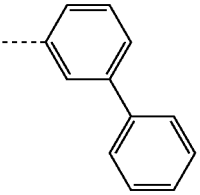 | 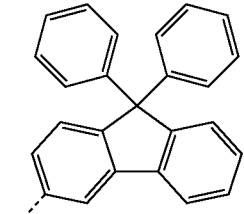 |
| 1-260 | 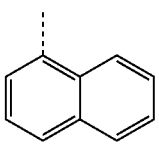 | 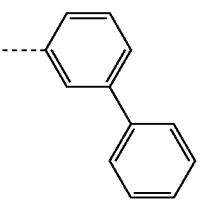 | 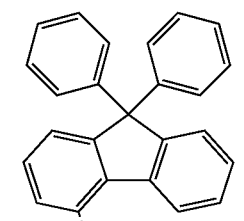 |
| 1-261 | 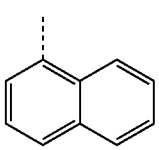 | 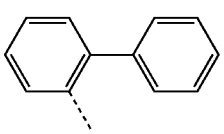 | 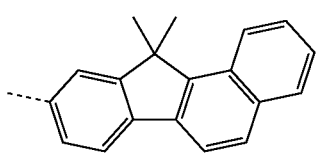 |

-continued
| Compound | ---Ar1 | ---Ar2 | ---Ar3 |
|---|---|---|---|
| 1-262 | 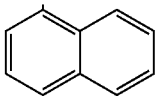 | 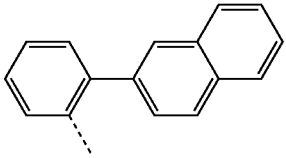 | 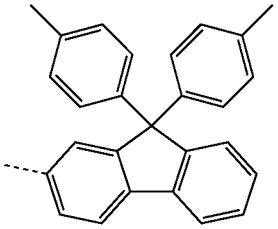 |
| 1-263 | 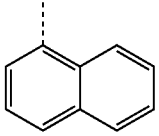 | 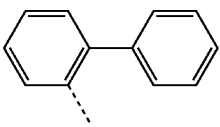 | 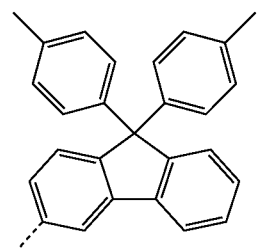 |
| 1-264 | 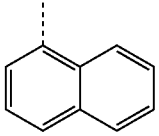 | 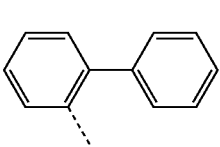 | 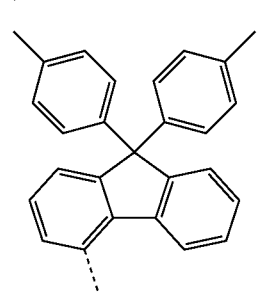 |
| 1-265 | 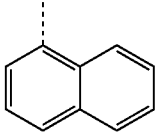 | 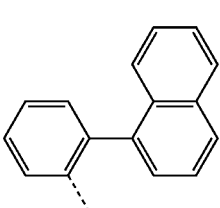 | 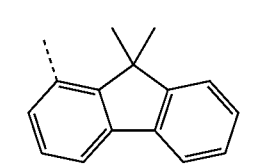 |
| 1-266 | 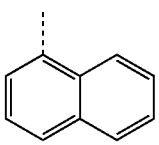 | 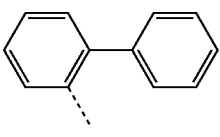 | 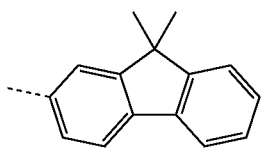 |
| 1-267 | 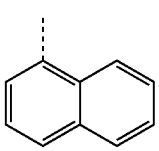 | 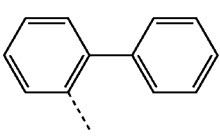 | 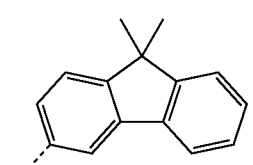 |
| 1-268 | 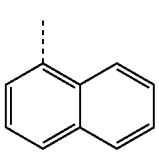 | 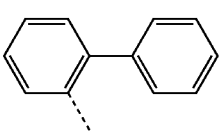 | 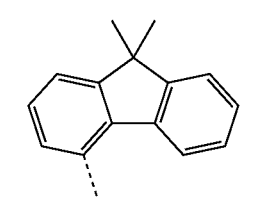 |

-continued

| Compound | ---Ar1 | ---Ar2 | ---Ar3 |
|---|---|---|---|
| 1-269 | 1-naphthyl | 2-biphenyl | 9,9-diphenylfluoren-1-yl |
| 1-270 | 1-naphthyl | 2-biphenyl | 9,9-diphenylfluoren-2-yl |
| 1-271 | 1-naphthyl | 2-biphenyl | 9,9-diphenylfluoren-3-yl |
| 1-272 | 1-naphthyl | 2-(9-phenanthryl)phenyl | 9,9-diphenylfluoren-4-yl |
| 1-273 | 1-naphthyl | 2-biphenyl | 9,9-dimethylbenzo[c]fluorenyl |
| 1-274 | 1-naphthyl | 2-biphenyl | 9,9-di(p-tolyl)fluoren-2-yl |

-continued
| Compound | ---Ar1 | ---Ar2 | ---Ar3 |
|---|---|---|---|
| 1-275 | 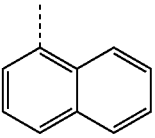 | 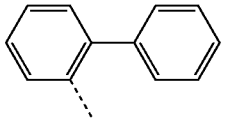 | 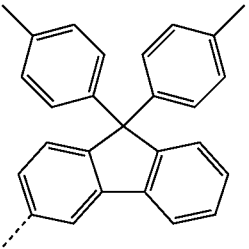 |
| 1-276 | 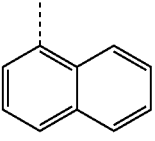 | 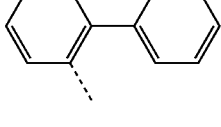 | 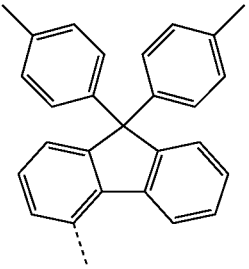 |
| 1-277 | 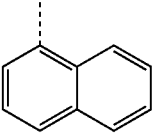 | 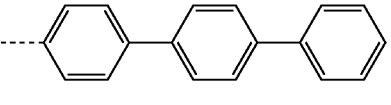 | 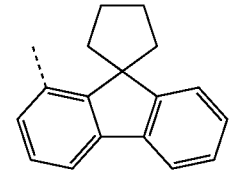 |
| 1-278 | 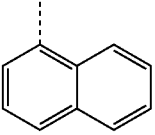 | 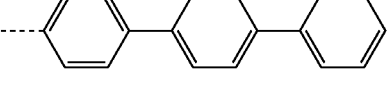 | 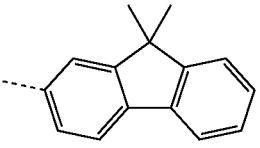 |
| 1-279 | 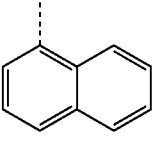 | 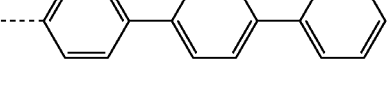 | 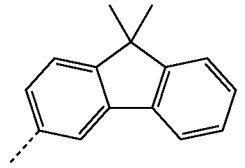 |
| 1-280 | 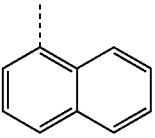 | 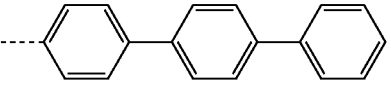 | 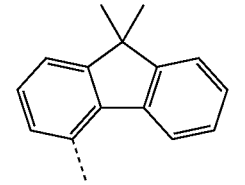 |
| 1-281 | 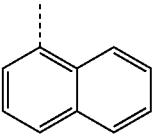 | 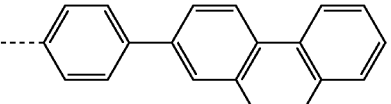 | 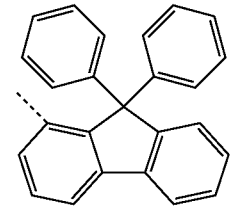 |

-continued

| Compound | ---Ar1 | ---Ar2 | ---Ar3 |
|---|---|---|---|
| 1-282 | 1-naphthyl | p-terphenyl | 9,9-diphenylfluoren-2-yl |
| 1-283 | 1-naphthyl | p-terphenyl | 9,9-diphenylfluoren-3-yl |
| 1-284 | 1-naphthyl | p-terphenyl | 9,9-diphenylfluoren-4-yl |
| 1-285 | 1-naphthyl | p-terphenyl | 9,9-di(p-tolyl)fluoren-2-yl |
| 1-286 | 1-naphthyl | p-terphenyl | 9,9-di(p-tolyl)fluoren-2-yl |
| 1-287 | 1-naphthyl | 4-(phenanthren-2-yl)phenyl | 9,9-di(p-tolyl)fluoren-3-yl |

-continued
| Compound | ---Ar1 | ---Ar2 | ---Ar3 |
|---|---|---|---|
| 1-288 | 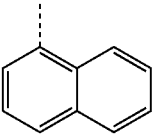 | 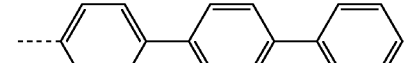 | 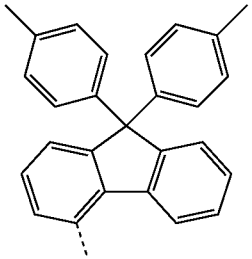 |
| 1-289 | 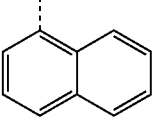 | 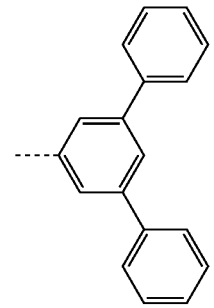 | 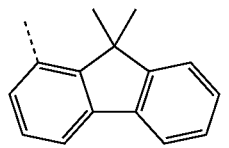 |
| 1-290 | 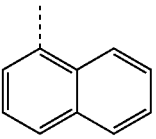 | 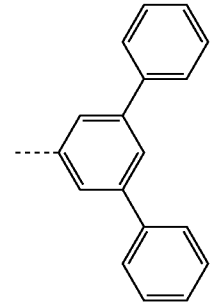 | 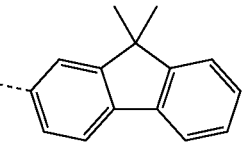 |
| 1-291 | 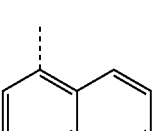 | 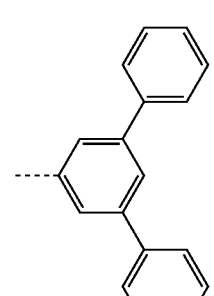 | 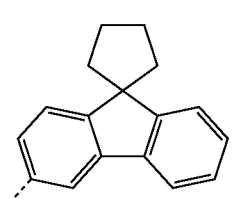 |
| 1-292 | 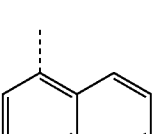 | 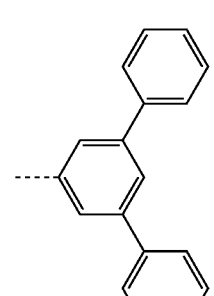 | 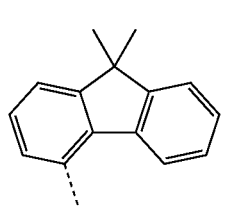 |

-continued
| Compound | ---Ar1 | ---Ar2 | ---Ar3 |
|---|---|---|---|
| 1-293 | 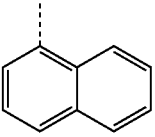 | 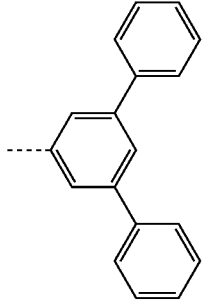 | 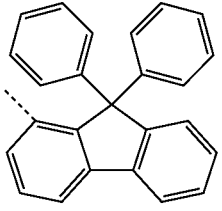 |
| 1-294 | 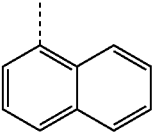 | 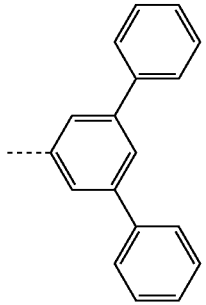 | 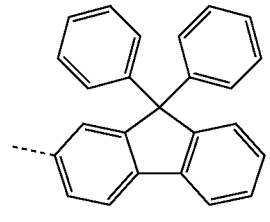 |
| 1-295 | 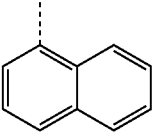 | 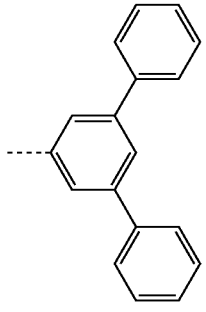 | 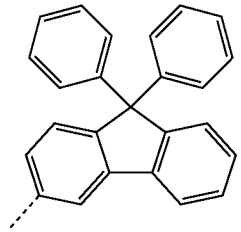 |
| 1-296 | 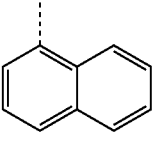 | 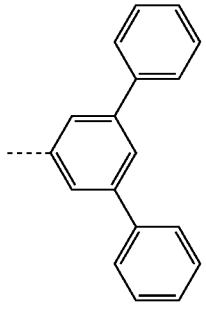 | 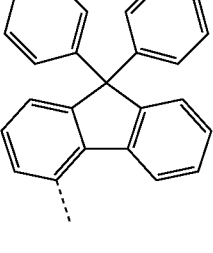 |
| 1-297 | 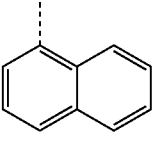 | 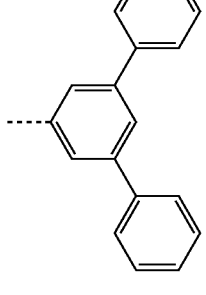 | 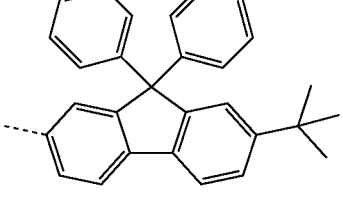 |

-continued
| Compound | ---Ar1 | ---Ar2 | ---Ar3 |
|---|---|---|---|
| 1-298 | 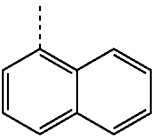 | 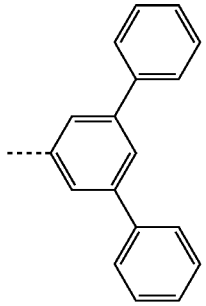 | 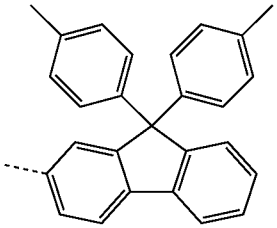 |
| 1-299 | 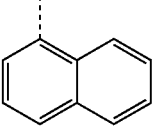 | 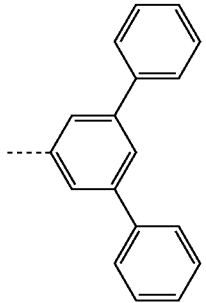 | 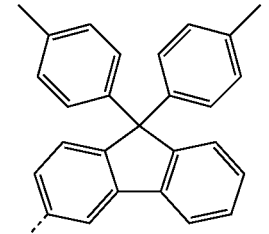 |
| 1-300 | 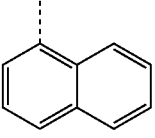 | 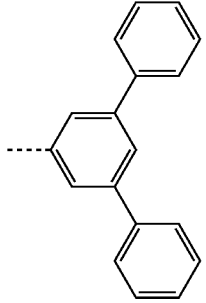 | 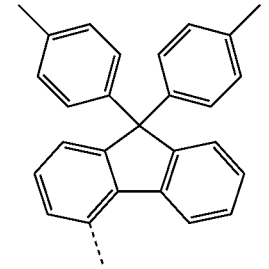 |
| 1-301 | 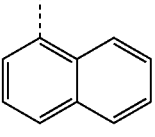 | 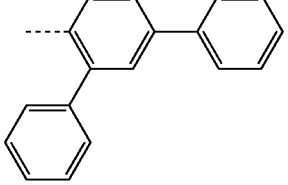 | 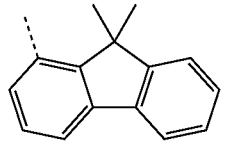 |
| 1-302 | 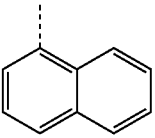 | 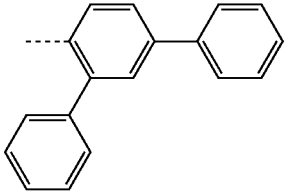 | 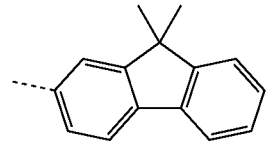 |
| 1-303 | 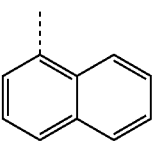 | 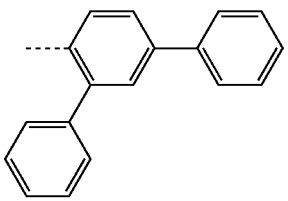 | 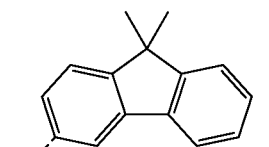 |

-continued
| Compound | ---Ar1 | ---Ar2 | ---Ar3 |
|---|---|---|---|
| 1-304 | 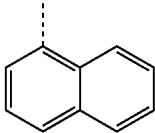 | 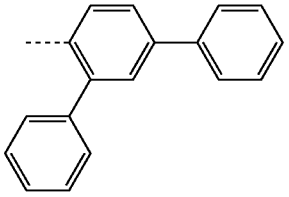 | 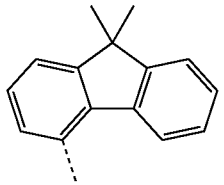 |
| 1-305 | 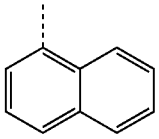 | 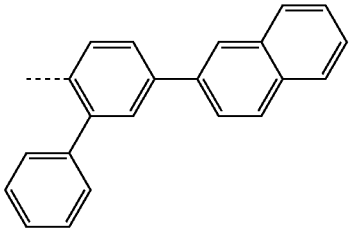 | 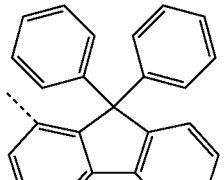 |
| 1-306 | 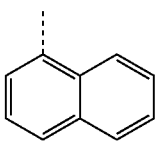 | 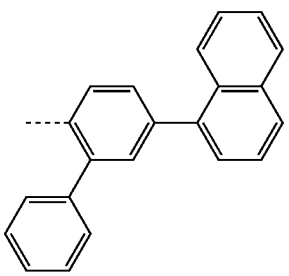 | 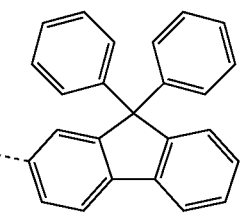 |
| 1-307 | 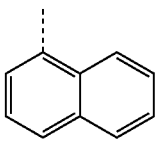 | 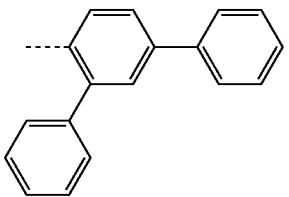 | 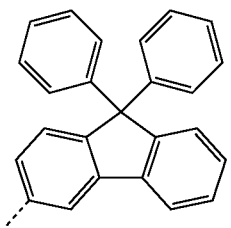 |
| 1-308 | 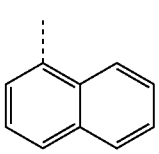 | 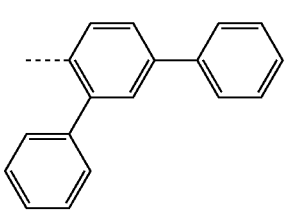 | 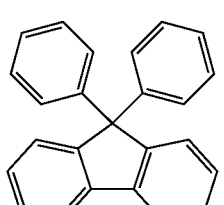 |
| 1-309 | 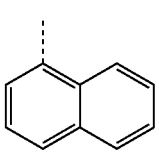 | 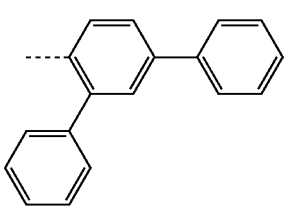 | 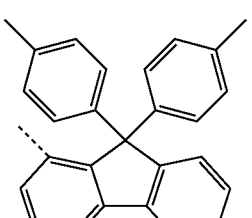 |

-continued
| Compound | ---Ar1 | ---Ar2 | ---Ar3 |
|---|---|---|---|
| 1-310 | 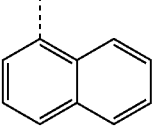 | 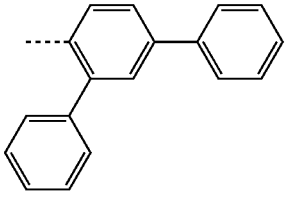 | 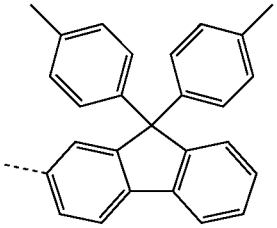 |
| 1-311 | 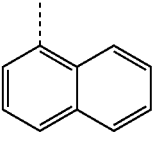 | 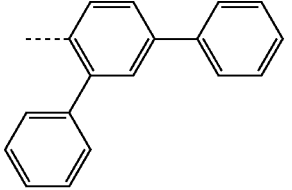 | 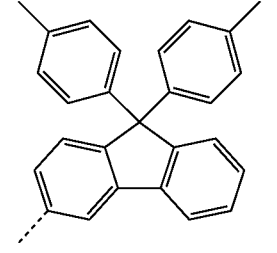 |
| 1-312 | 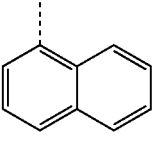 | 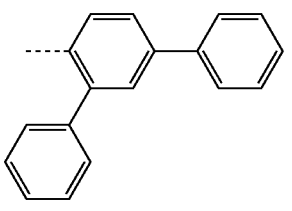 | 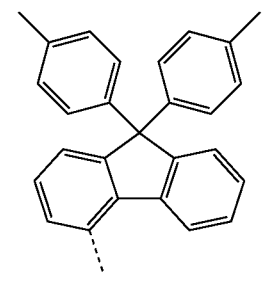 |
| 1-313 | 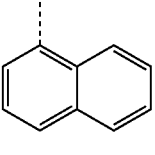 | 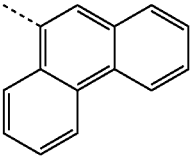 | 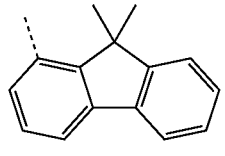 |
| 1-314 | 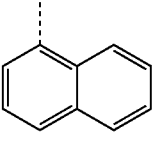 | 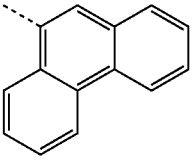 | 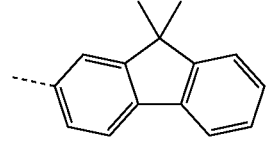 |
| 1-315 | 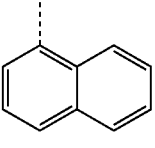 | 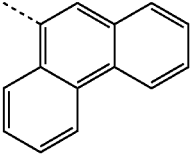 | 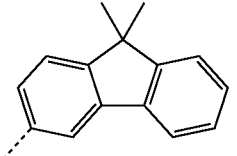 |
| 1-316 | 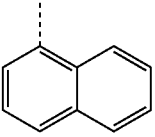 | 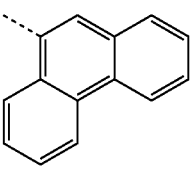 | 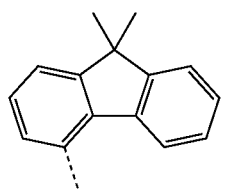 |

-continued
| Compound | ---Ar1 | ---Ar2 | ---Ar3 |
|---|---|---|---|
| 1-317 | 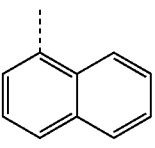 | 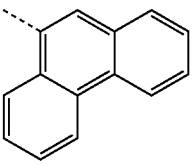 | 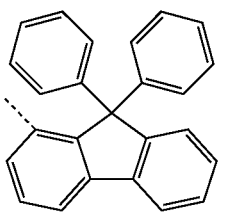 |
| 1-318 | 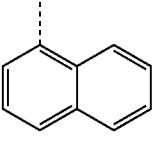 | 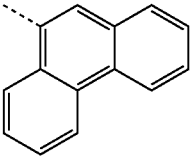 | 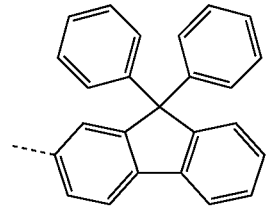 |
| 1-319 | 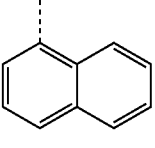 | 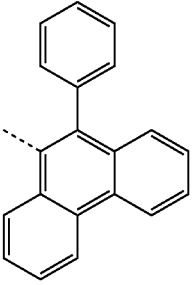 | 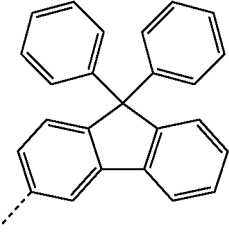 |
| 1-320 | 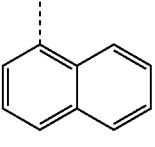 | 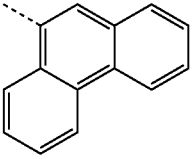 | 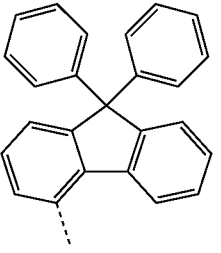 |
| 1-321 | 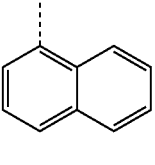 | 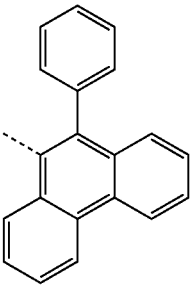 | 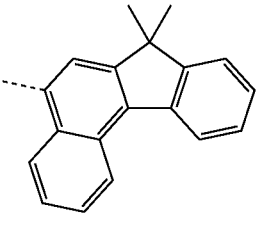 |
| 1-322 | 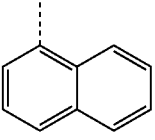 | 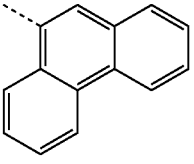 | 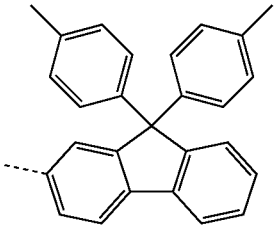 |

-continued
| Compound | ---Ar1 | ---Ar2 | ---Ar3 |
|---|---|---|---|
| 1-323 | 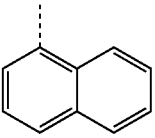 | 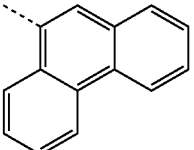 | 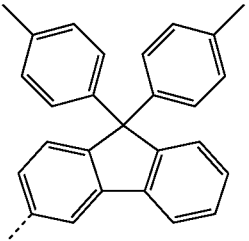 |
| 1-324 | 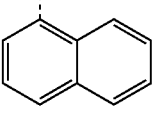 | 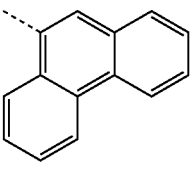 | 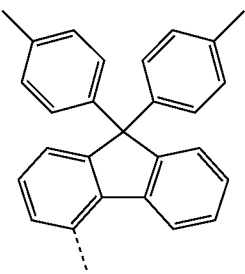 |
| 1-325 | 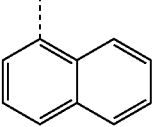 | 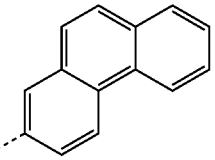 | 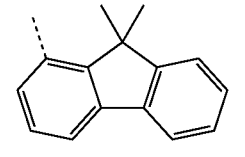 |
| 1-326 | 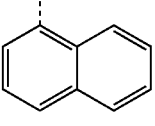 | 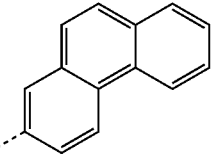 | 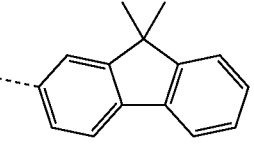 |
| 1-327 | 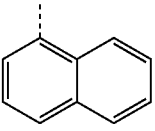 | 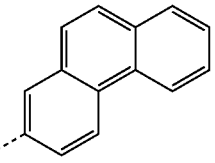 | 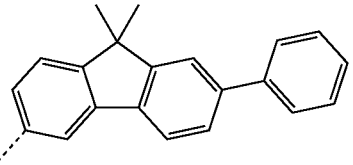 |
| 1-328 | 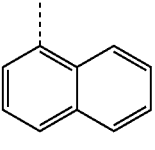 | 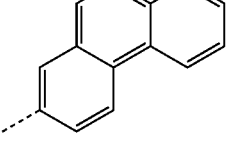 | 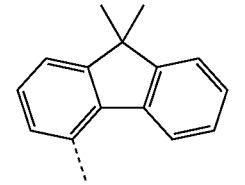 |
| 1-329 | 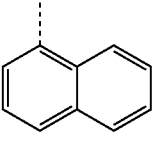 | 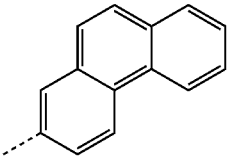 | 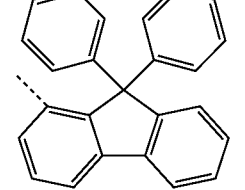 |

-continued

| Compound | ---Ar1 | ---Ar2 | ---Ar3 |
|---|---|---|---|
| 1-330 | naphthalen-1-yl | phenanthren-3-yl | 9,9-diphenylfluoren-2-yl |
| 1-331 | naphthalen-1-yl | phenanthren-3-yl | 9,9-diphenylfluoren-3-yl |
| 1-332 | naphthalen-1-yl | phenanthren-3-yl | 9,9-diphenylfluoren-4-yl |
| 1-333 | naphthalen-1-yl | phenanthren-3-yl | 9,9-di(p-tolyl)fluoren-1-yl |
| 1-334 | naphthalen-1-yl | phenanthren-3-yl | 9,9-di(p-tolyl)fluoren-2-yl |
| 1-335 | naphthalen-1-yl | phenanthren-3-yl | 11,11-dimethyl-11H-benzo[b]fluoren-2-yl |

-continued
| Compound | ---Ar1 | ---Ar2 | ---Ar3 |
|---|---|---|---|
| 1-336 |  |  |  |
| 1-337 |  |  |  |
| 1-338 |  |  |  |
| 1-339 |  |  |  |
| 1-340 |  |  |  |
| 1-341 |  |  |  |
| 1-342 |  |  |  |

147
148
-continued
| Compound | ---Ar1 | ---Ar2 | ---Ar3 |
|---|---|---|---|
| 1-343 | 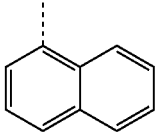 | 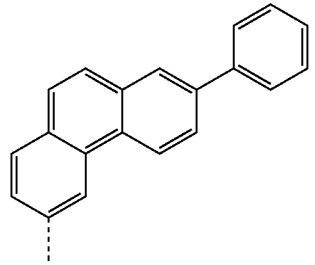 | 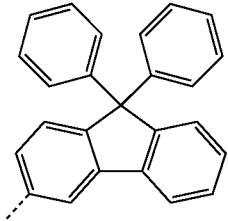 |
| 1-344 | 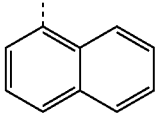 | 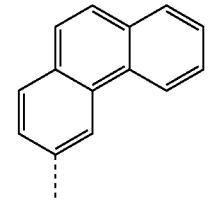 | 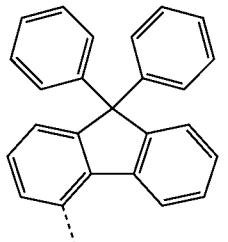 |
| 1-345 | 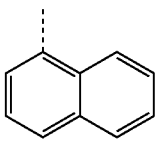 | 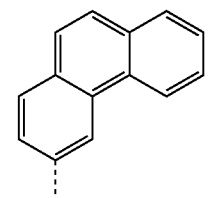 | 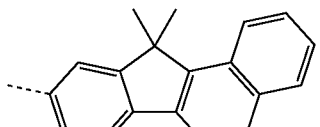 |
| 1-346 | 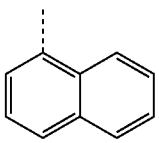 | 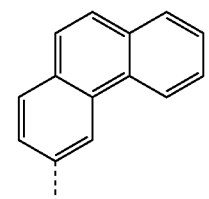 | 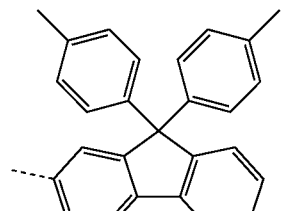 |
| 1-347 | 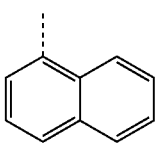 | 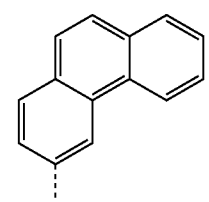 | 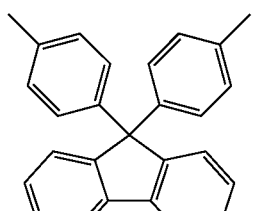 |
| 1-348 | 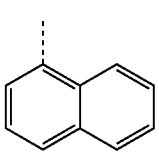 | 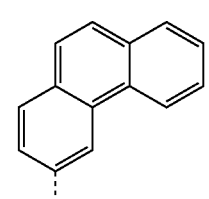 | 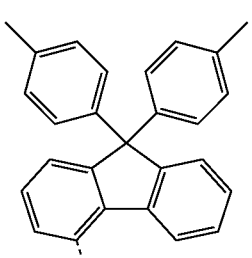 |

-continued
| Compound | ---Ar1 | ---Ar2 | ---Ar3 |
|---|---|---|---|
| 1-349 | 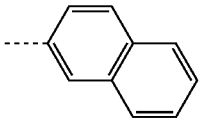 | 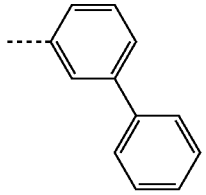 | 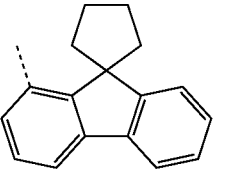 |
| 1-350 | 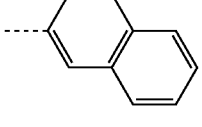 | 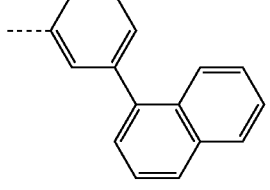 | 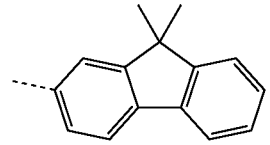 |
| 1-351 | 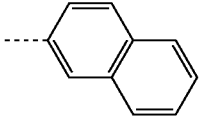 | 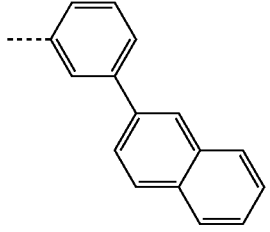 | 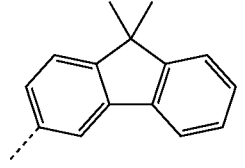 |
| 1-352 | 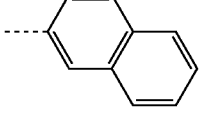 | 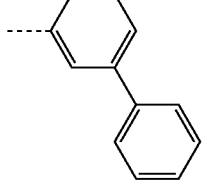 | 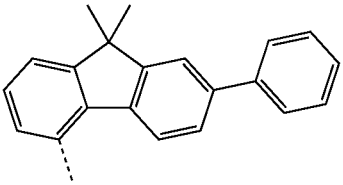 |
| 1-353 | 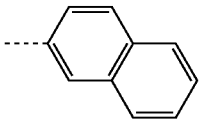 | 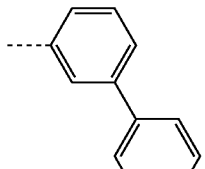 | 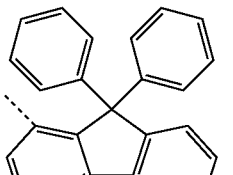 |
| 1-354 | 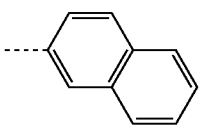 | 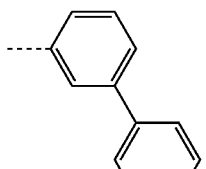 | 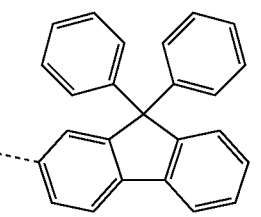 |
| 1-355 | 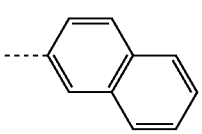 | 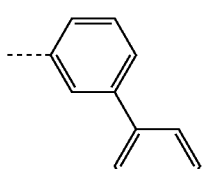 | 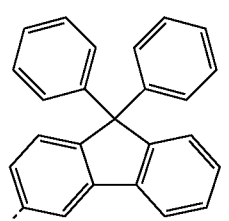 |

-continued
| Compound | ---Ar1 | ---Ar2 | ---Ar3 |
|---|---|---|---|
| 1-356 | 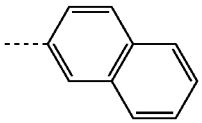 | 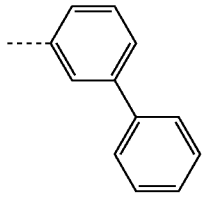 | 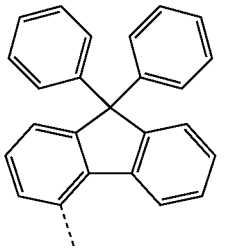 |
| 1-357 | 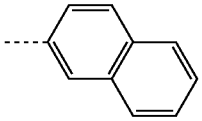 | 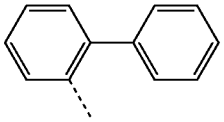 | 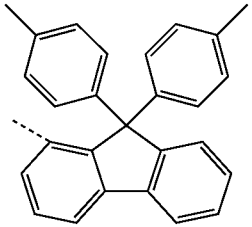 |
| 1-358 | 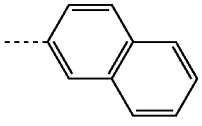 | 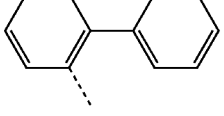 | 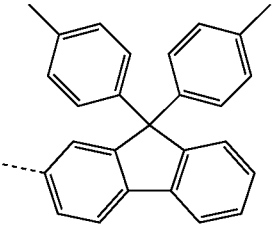 |
| 1-359 | 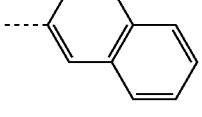 | 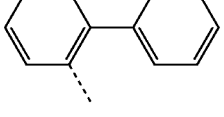 | 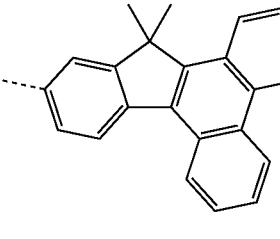 |
| 1-360 | 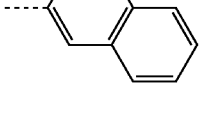 | 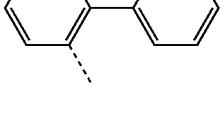 | 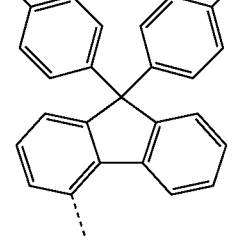 |
| 1-361 | 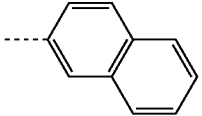 | 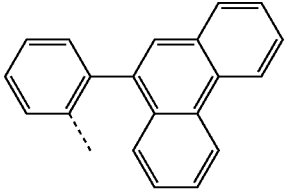 | 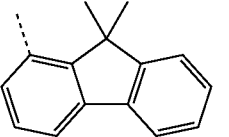 |

-continued
| Compound | ---Ar1 | ---Ar2 | ---Ar3 |
|---|---|---|---|
| 1-362 | 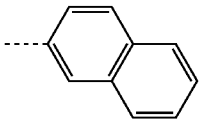 | 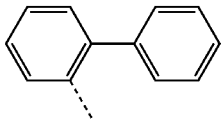 | 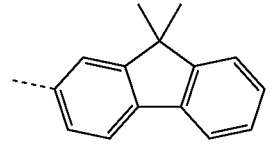 |
| 1-363 | 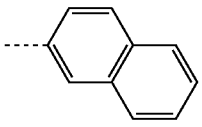 | 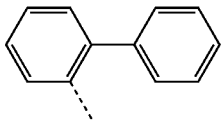 | 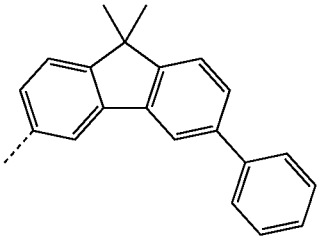 |
| 1-364 | 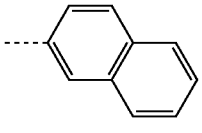 | 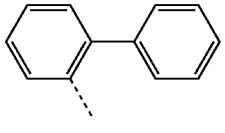 | 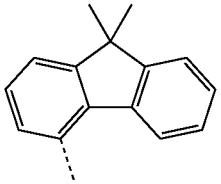 |
| 1-365 | 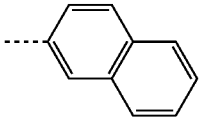 | 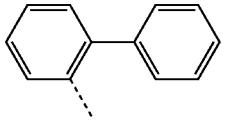 | 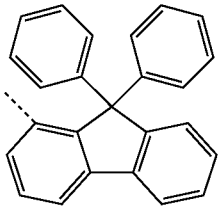 |
| 1-366 | 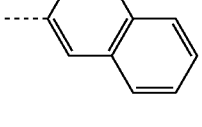 | 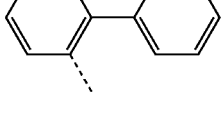 | 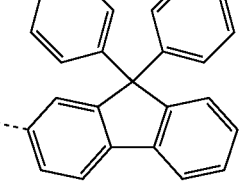 |
| 1-367 | 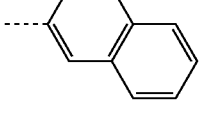 | 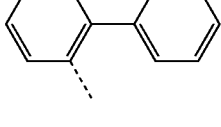 | 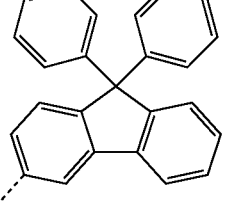 |
| 1-368 | 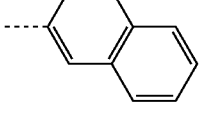 | 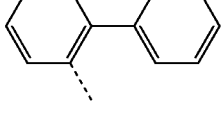 | 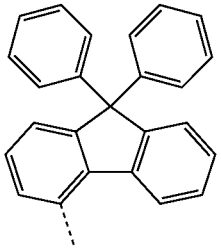 |

-continued
| Compound | ---Ar1 | ---Ar2 | ---Ar3 |
|---|---|---|---|
| 1-369 | 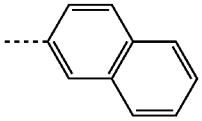 | 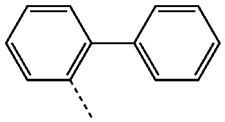 | 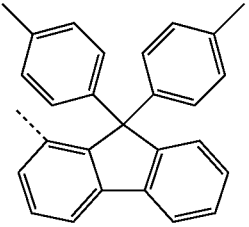 |
| 1-370 | 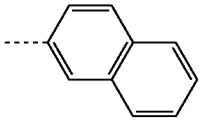 | 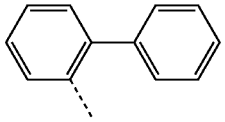 | 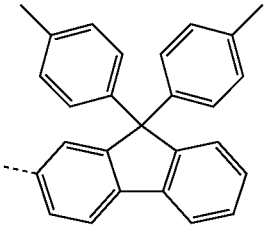 |
| 1-371 | 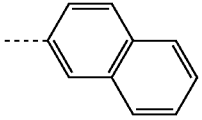 | 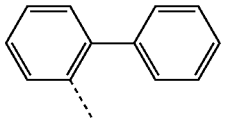 | 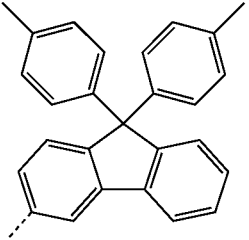 |
| 1-372 | 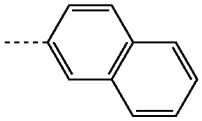 | 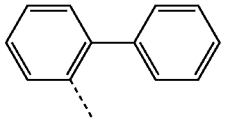 | 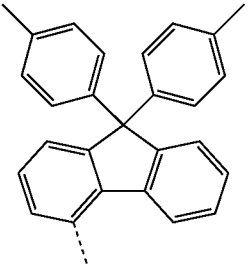 |
| 1-373 | 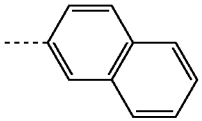 | 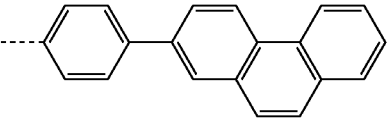 | 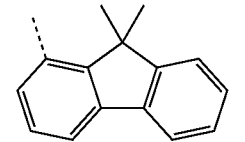 |
| 1-374 | 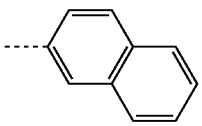 | 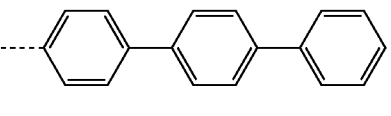 | 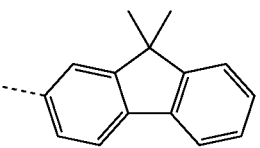 |
| 1-375 | 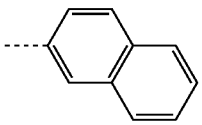 | 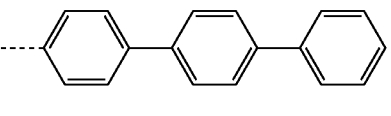 | 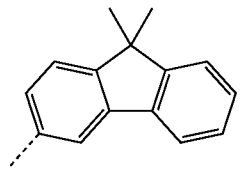 |

-continued
| Compound | ---Ar1 | ---Ar2 | ---Ar3 |
|---|---|---|---|
| 1-376 | 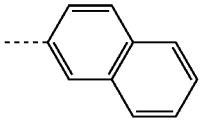 | 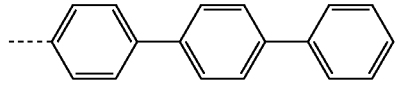 | 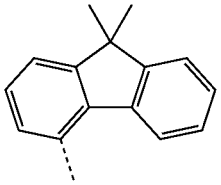 |
| 1-377 | 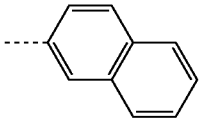 | 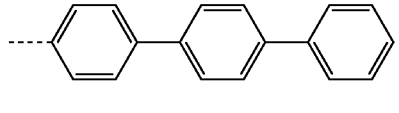 | 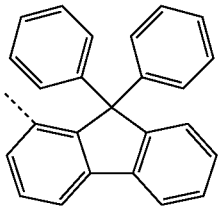 |
| 1-378 | 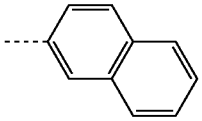 | 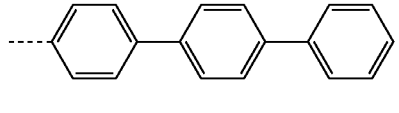 | 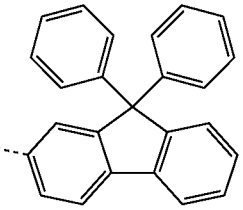 |
| 1-379 | 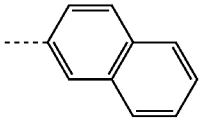 | 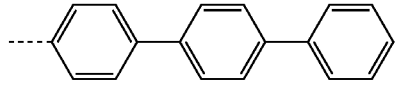 | 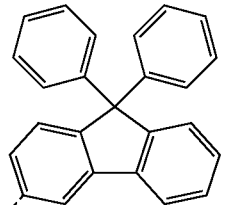 |
| 1-380 | 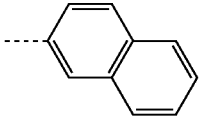 | 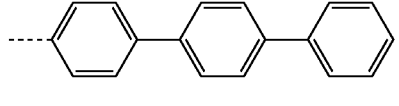 | 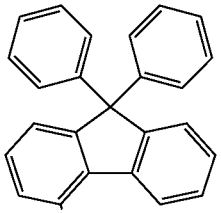 |
| 1-381 | 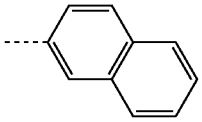 | 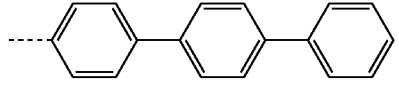 | 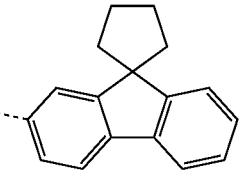 |
| 1-382 | 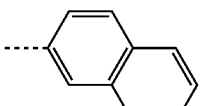 | 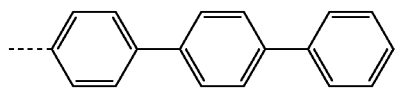 | 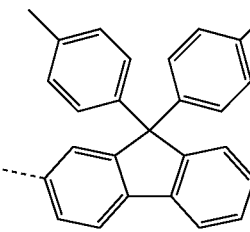 |

| Compound | ---Ar1 | ---Ar2 | ---Ar3 |
|---|---|---|---|
| 1-383 | 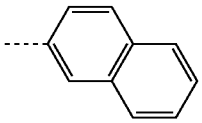 | 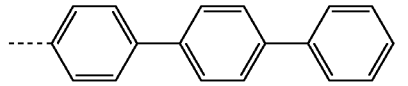 | 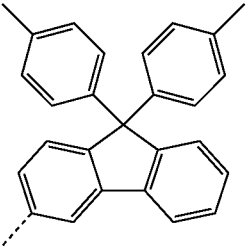 |
| 1-384 | 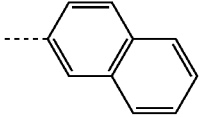 | 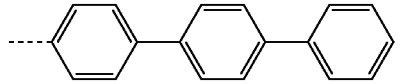 | 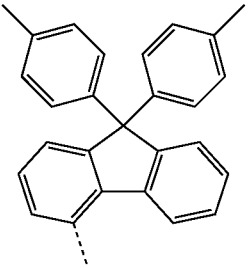 |
| 1-385 | 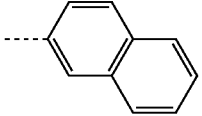 | 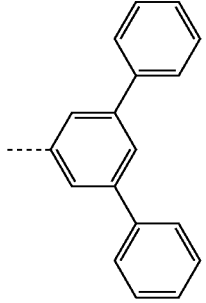 | 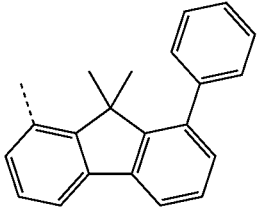 |
| 1-386 | 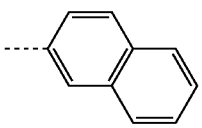 | 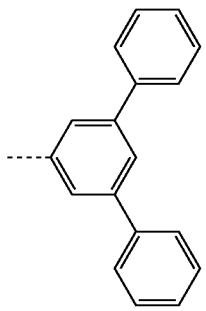 | 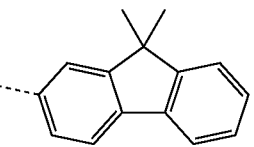 |
| 1-387 | 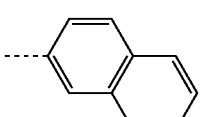 | 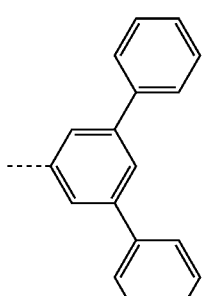 | 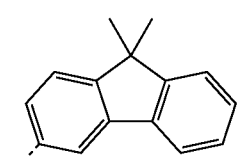 |

-continued
| Compound | ---Ar1 | ---Ar2 | ---Ar3 |
|---|---|---|---|
| 1-388 | 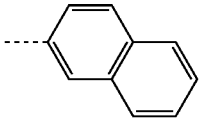 | 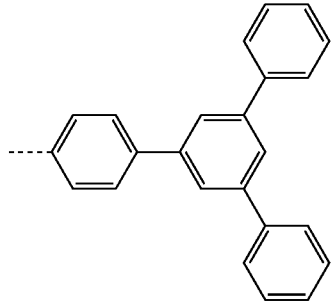 | 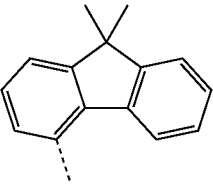 |
| 1-389 | 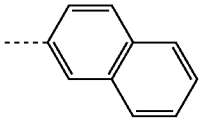 | 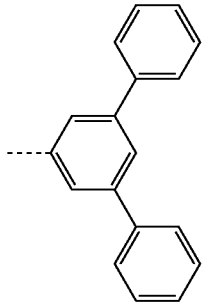 | 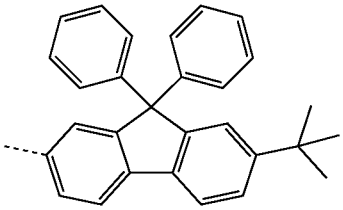 |
| 1-390 | 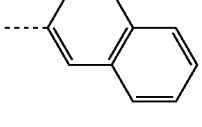 | 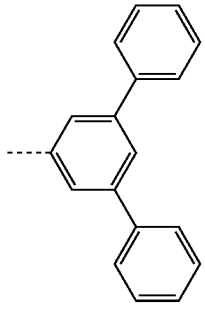 | 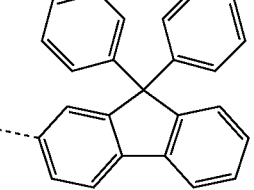 |
| 1-391 | 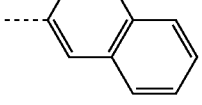 | 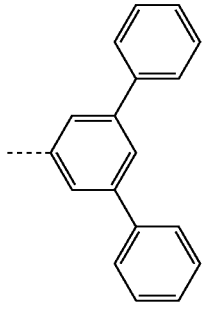 | 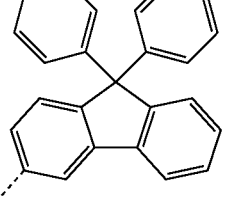 |
| 1-392 | 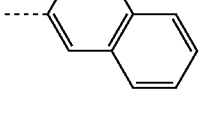 | 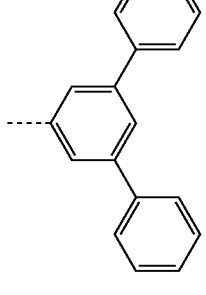 | 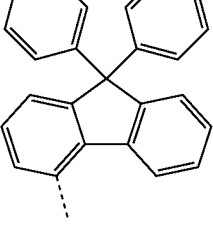 |

-continued
| Compound | ---Ar1 | ---Ar2 | ---Ar3 |
|---|---|---|---|
| 1-393 | 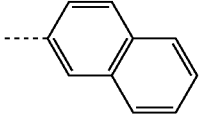 | 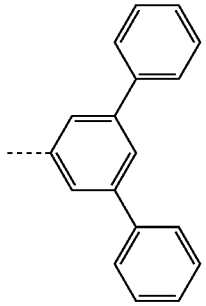 | 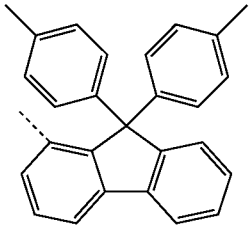 |
| 1-394 | 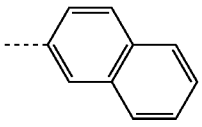 | 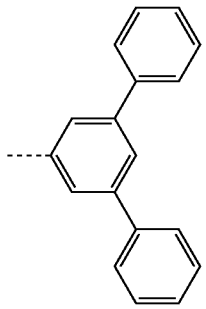 | 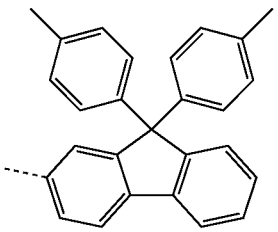 |
| 1-395 | 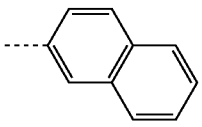 | 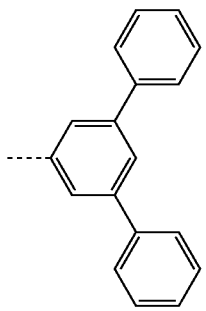 | 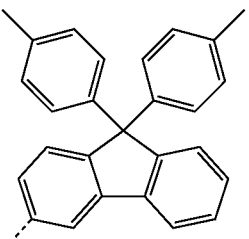 |
| 1-396 | 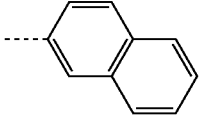 | 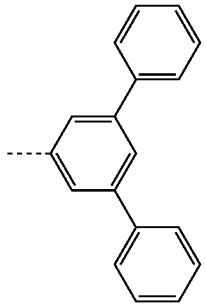 | 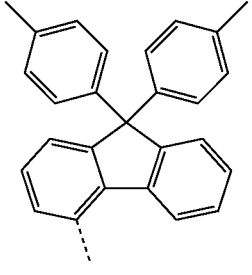 |
| 1-397 | 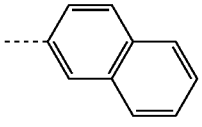 | 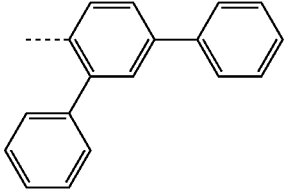 | 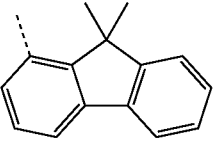 |

-continued
| Compound | ---Ar1 | ---Ar2 | ---Ar3 |
|---|---|---|---|
| 1-398 | 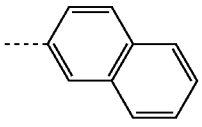 | 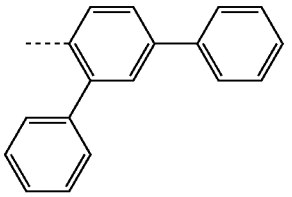 | 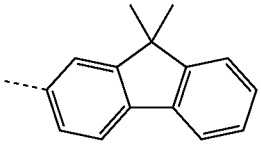 |
| 1-399 | 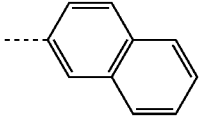 | 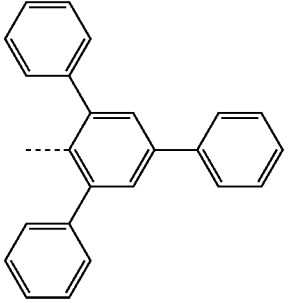 | 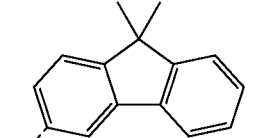 |
| 1-400 | 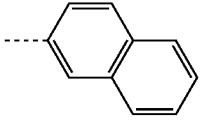 | 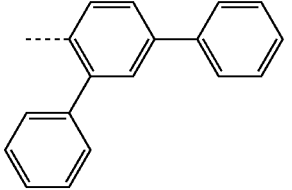 | 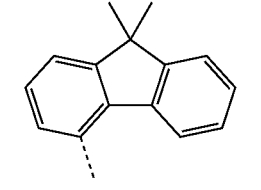 |
| 1-401 | 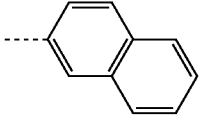 | 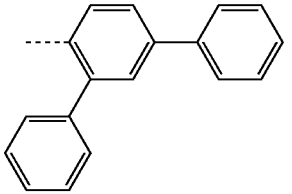 | 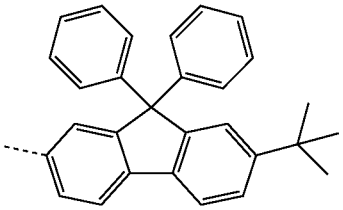 |
| 1-402 | 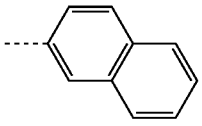 | 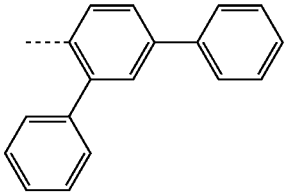 | 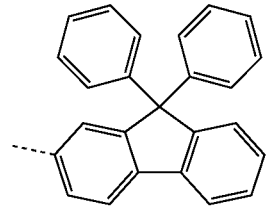 |
| 1-403 | 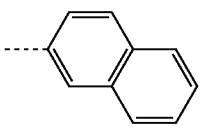 | 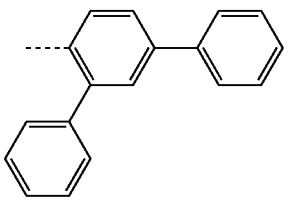 | 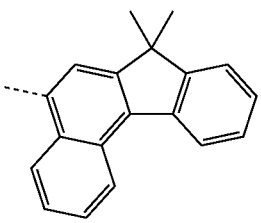 |

-continued
| Compound | ---Ar1 | ---Ar2 | ---Ar3 |
|---|---|---|---|
| 1-404 | 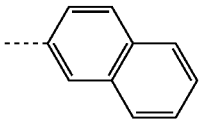 | 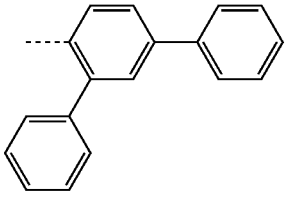 | 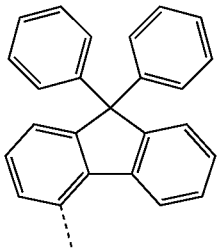 |
| 1-405 | 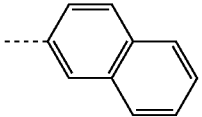 | 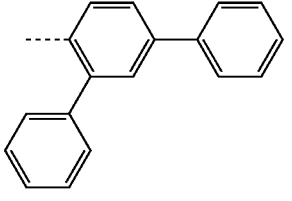 | 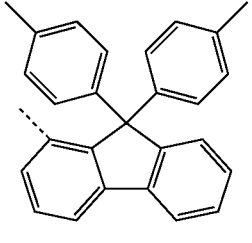 |
| 1-406 | 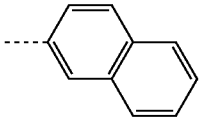 | 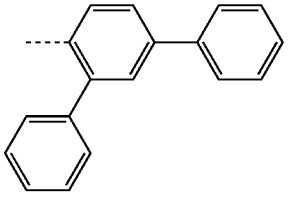 | 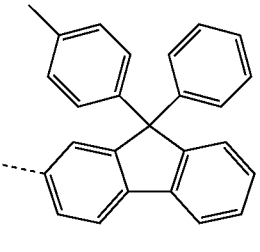 |
| 1-407 | 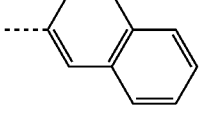 | 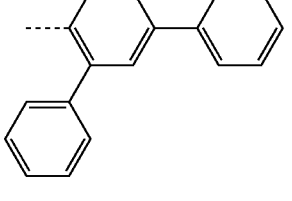 | 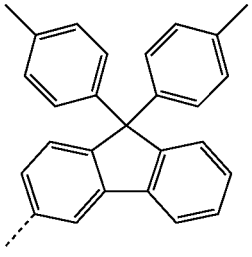 |
| 1-408 | 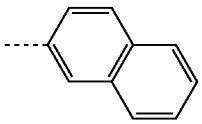 | 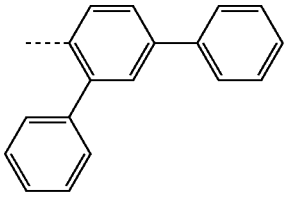 | 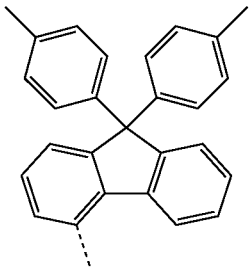 |
| 1-409 | 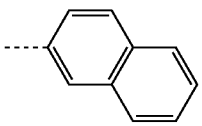 | 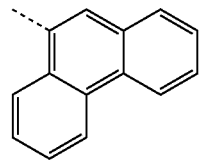 | 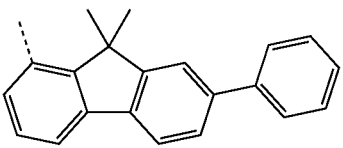 |

-continued

| Compound | ---Ar1 | ---Ar2 | ---Ar3 |
|---|---|---|---|
| 1-410 | naphthyl | phenanthrenyl | 9,9-dimethylfluorenyl |
| 1-411 | naphthyl | phenanthrenyl | 9,9-dimethylfluorenyl |
| 1-412 | naphthyl | phenanthrenyl | 9,9-dimethylfluorenyl |
| 1-413 | naphthyl | phenanthrenyl | 9,9-diphenylfluorenyl |
| 1-414 | naphthyl | phenanthrenyl | 9,9-diphenylfluorenyl |
| 1-415 | naphthyl | phenanthrenyl | 9,9-diphenylfluorenyl |
| 1-416 | naphthyl | phenanthrenyl | 9,9-diphenylfluorenyl |

-continued
| Compound | ---Ar1 | ---Ar2 | ---Ar3 |
|---|---|---|---|
| 1-417 | 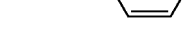 | 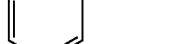 | 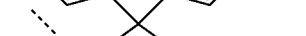 |
| 1-418 | 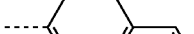 | 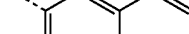 | 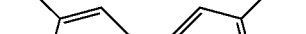 |
| 1-419 | 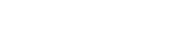 | 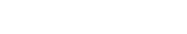 | 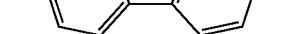 |
| 1-420 | 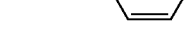 | 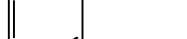 | 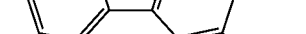 |
| 1-421 | 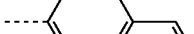 | 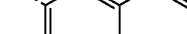 | 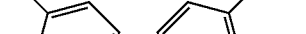 |
| 1-422 | 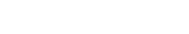 | 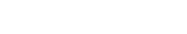 | 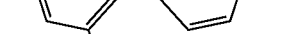 |
| 1-423 | 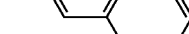 | 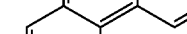 | 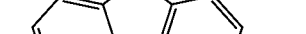 |

-continued
| Compound | ---Ar1 | ---Ar2 | ---Ar3 |
|---|---|---|---|
| 1-424 | 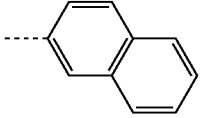 | 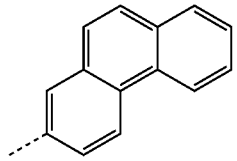 | 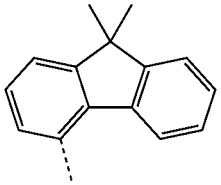 |
| 1-425 | 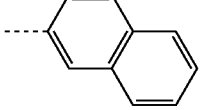 | 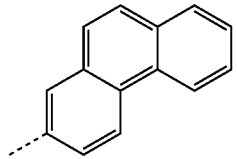 | 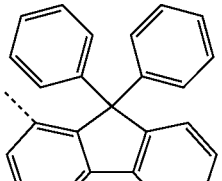 |
| 1-426 | 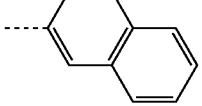 | 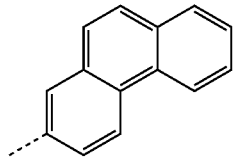 | 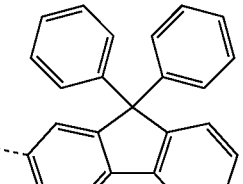 |
| 1-427 | 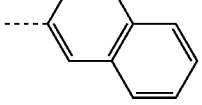 | 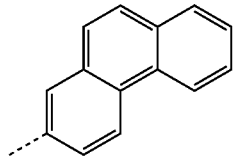 | 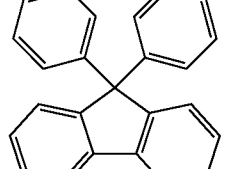 |
| 1-428 | 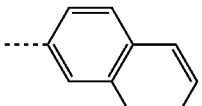 | 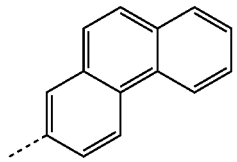 | 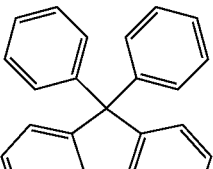 |
| 1-429 | 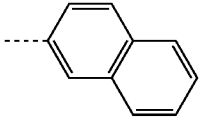 | 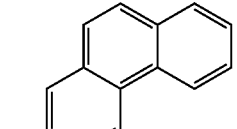 | 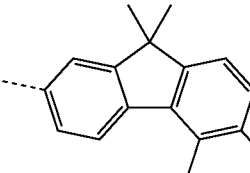 |

-continued
| Compound | ---Ar1 | ---Ar2 | ---Ar3 |
|---|---|---|---|
| 1-430 | 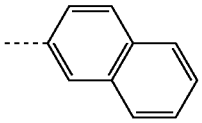 | 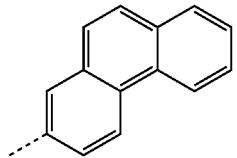 | 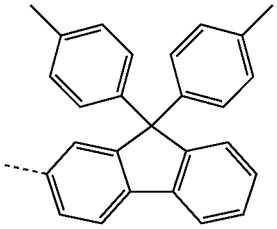 |
| 1-431 | 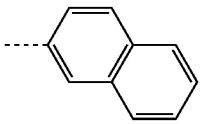 | 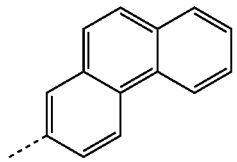 | 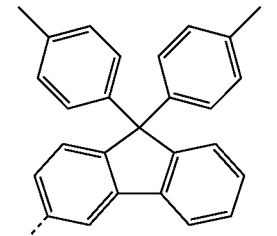 |
| 1-432 | 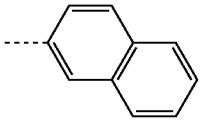 | 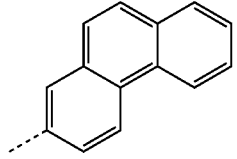 | 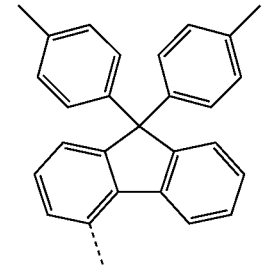 |
| 1-433 | 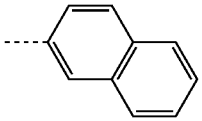 | 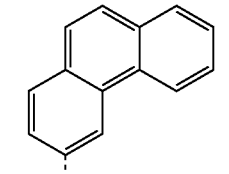 | 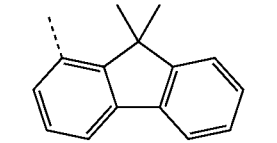 |
| 1-434 | 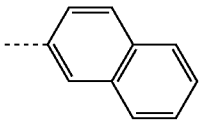 | 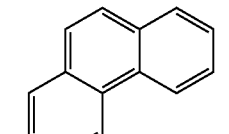 | 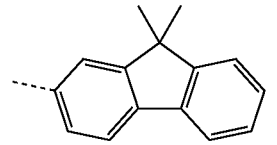 |
| 1-435 | 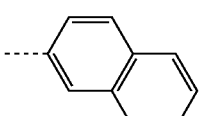 | 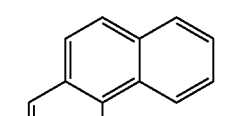 | 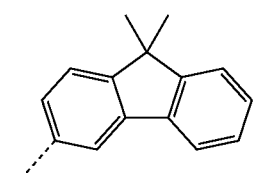 |

-continued

| Compound | ---Ar1 | ---Ar2 | ---Ar3 |
| --- | --- | --- | --- |
| 1-436 | naphthalene | phenanthrene | 9,9-dimethylfluorene |
| 1-437 | naphthalene | phenanthrene | 9,9-diphenylfluorene |
| 1-438 | naphthalene | phenanthrene | 9,9-diphenylfluorene |
| 1-439 | naphthalene | phenanthrene | 9,9-diphenylfluorene |
| 1-440 | naphthalene | phenanthrene | 9,9-diphenylfluorene |
| 1-441 | naphthalene | phenanthrene | 9,9-di(p-tolyl)fluorene |

-continued
| Compound | ---Ar1 | ---Ar2 | ---Ar3 |
|---|---|---|---|
| 1-442 | 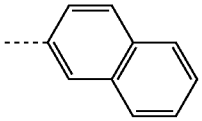 | 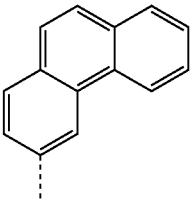 | 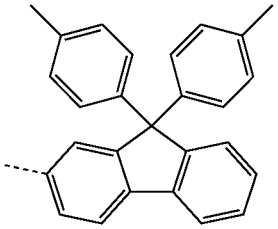 |
| 1-443 | 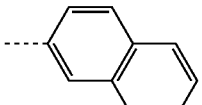 | 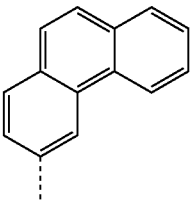 | 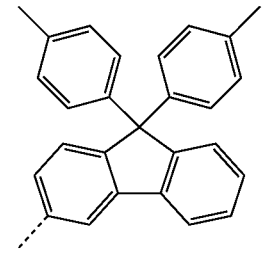 |
| 1-444 | 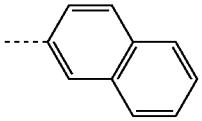 | 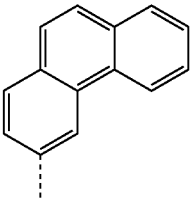 | 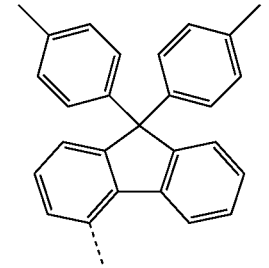 |
| 1-445 | 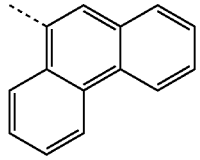 | 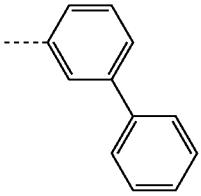 | 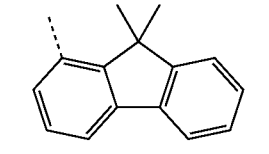 |
| 1-446 | 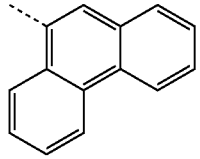 | 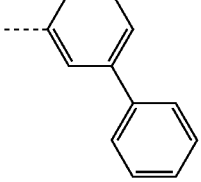 | 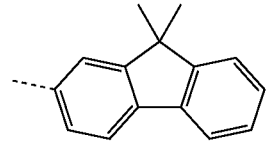 |
| 1-447 | 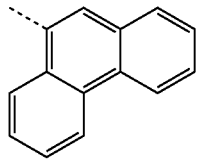 | 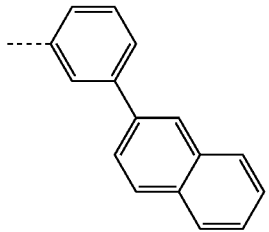 | 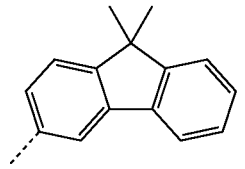 |

-continued

| Compound | ---Ar1 | ---Ar2 | ---Ar3 |
|---|---|---|---|
| 1-448 | | | |
| 1-449 | | | |
| 1-450 | | | |
| 1-451 | | | |
| 1-452 | | | |
| 1-453 | | | |

-continued
| Compound | ---Ar1 | ---Ar2 | ---Ar3 |
|---|---|---|---|
| 1-454 | 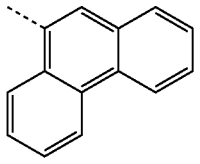 | 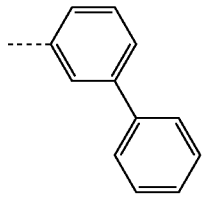 | 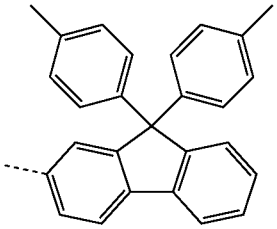 |
| 1-455 | 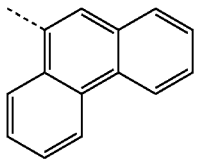 | 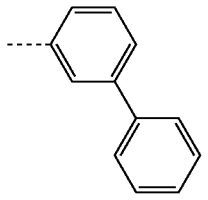 | 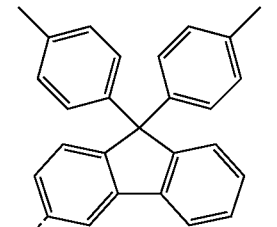 |
| 1-456 | 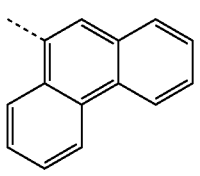 | 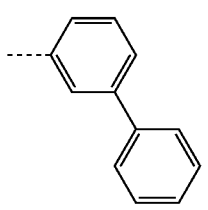 | 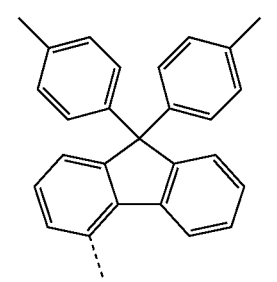 |
| 1-457 | 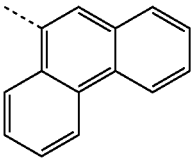 | 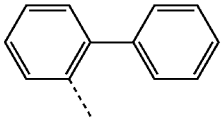 | 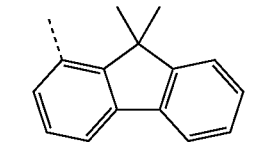 |
| 1-458 | 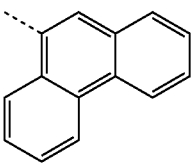 | 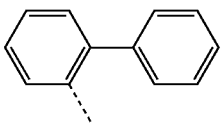 | 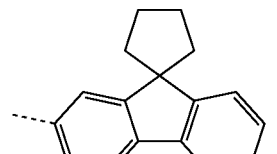 |
| 1-459 | 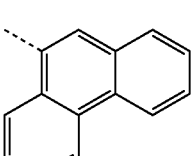 | 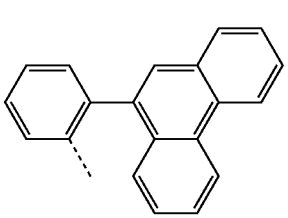 | 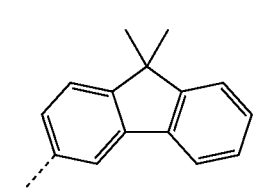 |
| 1-460 | 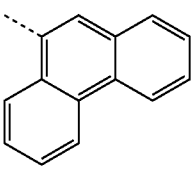 | 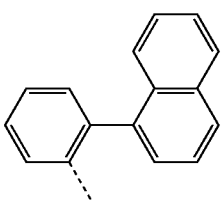 | 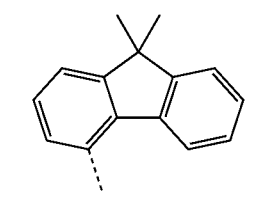 |

-continued
| Compound | ---Ar1 | ---Ar2 | ---Ar3 |
|---|---|---|---|
| 1-461 | 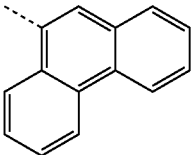 | 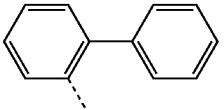 | 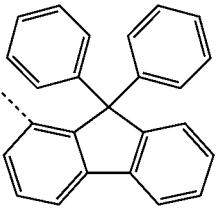 |
| 1-462 | 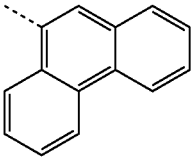 | 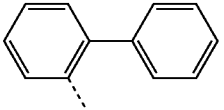 | 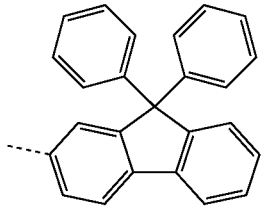 |
| 1-463 | 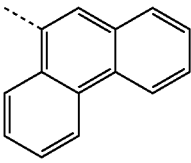 | 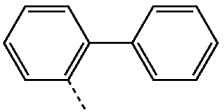 | 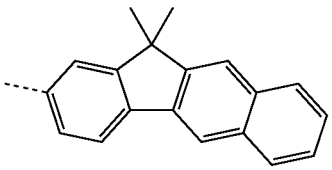 |
| 1-464 | 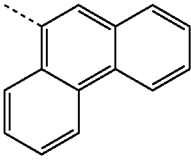 | 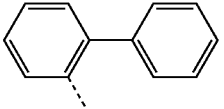 | 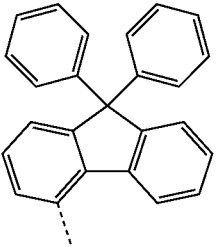 |
| 1-465 | 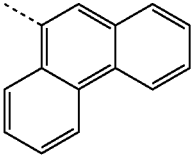 | 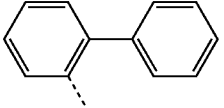 | 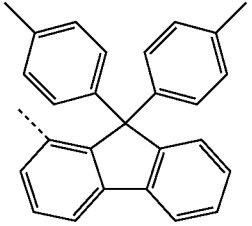 |
| 1-466 | 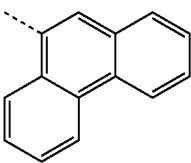 | 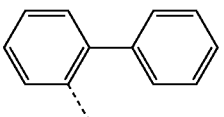 | 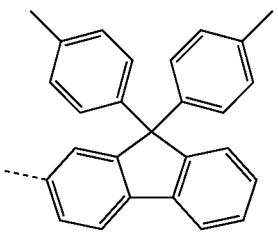 |

-continued

| Compound | ---Ar1 | ---Ar2 | ---Ar3 |
|---|---|---|---|
| 1-467 | phenanthrene | 2-biphenyl | 9,9-di(p-tolyl)fluorene |
| 1-468 | phenanthrene | 2-biphenyl | 9,9-di(m-tolyl)fluorene |
| 1-469 | phenanthrene | p-terphenyl | 9,9-dimethylfluorene |
| 1-470 | phenanthrene | p-terphenyl | fluorene |
| 1-471 | phenanthrene | p-terphenyl | 9,9-dimethylfluorene |
| 1-472 | phenanthrene | 4-(4-naphthalenyl)phenyl-phenyl | 9,9-dimethylfluorene |
| 1-473 | phenanthrene | p-terphenyl | dimethyl-dibenzo[g,p]chrysene/fluorene derivative |

-continued
| Compound | ---Ar1 | ---Ar2 | ---Ar3 |
|---|---|---|---|
| 1-474 | 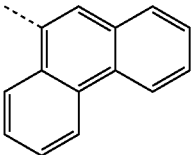 | 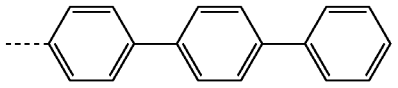 | 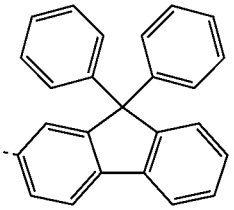 |
| 1-475 | 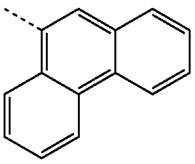 | 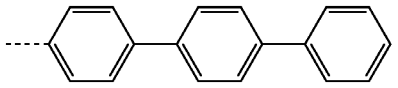 | 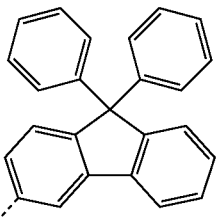 |
| 1-476 | 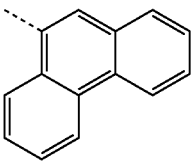 | 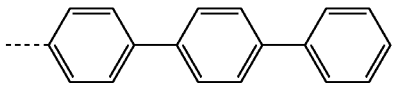 | 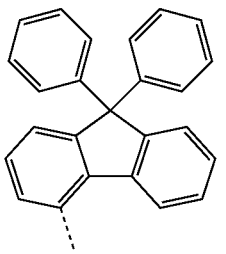 |
| 1-477 | 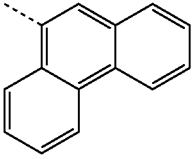 | 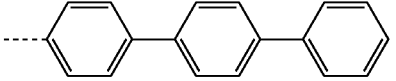 | 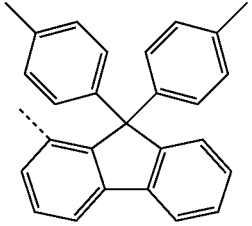 |
| 1-478 | 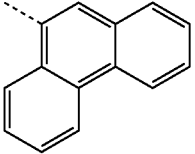 | 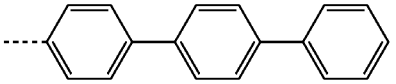 | 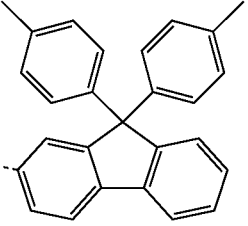 |
| 1-479 | 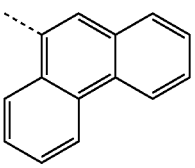 | 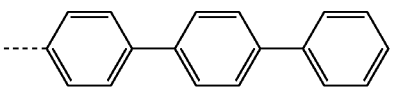 | 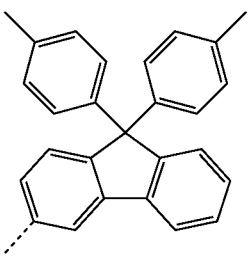 |

-continued
| Compound | ---Ar1 | ---Ar2 | ---Ar3 |
|---|---|---|---|
| 1-480 | 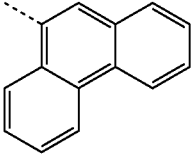 | 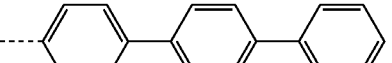 | 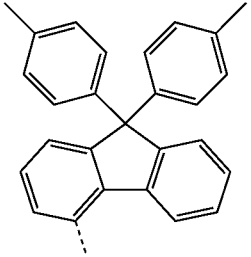 |
| 1-481 | 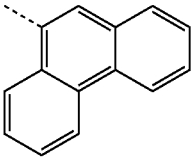 | 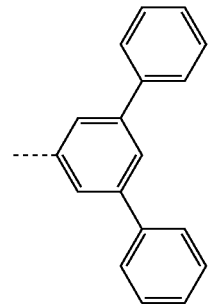 | 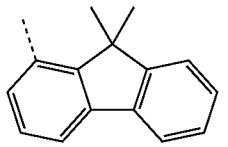 |
| 1-482 | 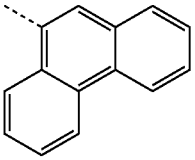 | 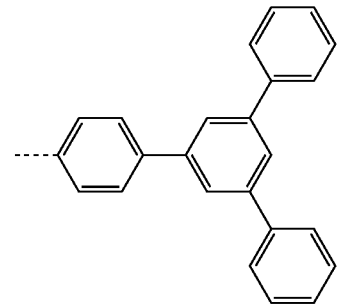 | 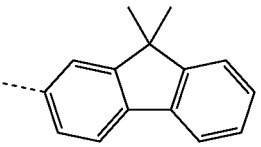 |
| 1-483 | 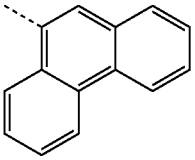 | 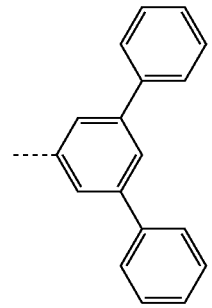 | 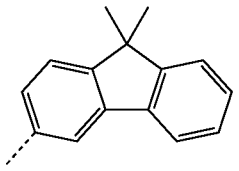 |
| 1-484 | 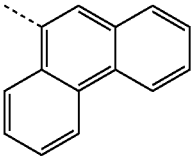 | 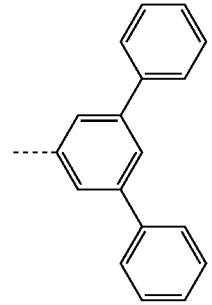 | 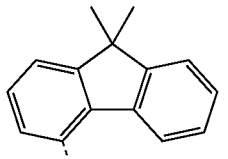 |

-continued
| Compound | ---Ar1 | ---Ar2 | ---Ar3 |
|---|---|---|---|
| 1-485 | 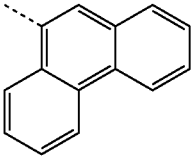 | 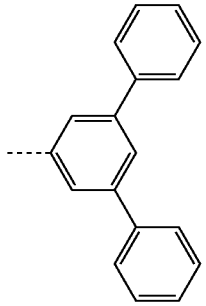 | 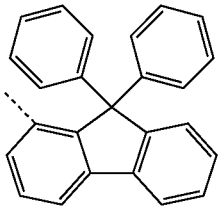 |
| 1-486 | 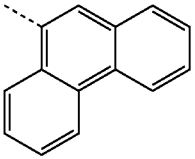 | 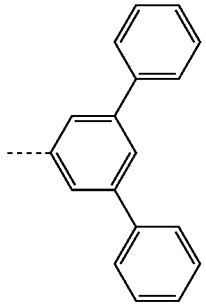 | 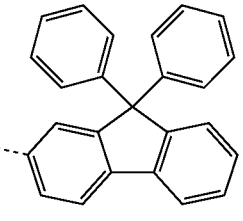 |
| 1-487 | 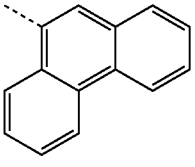 | 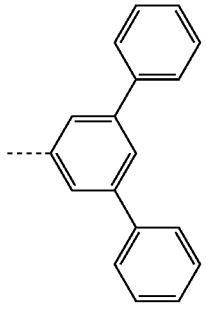 | 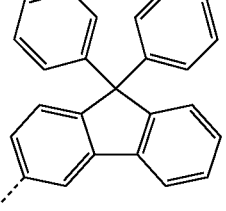 |
| 1-488 | 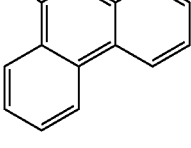 | 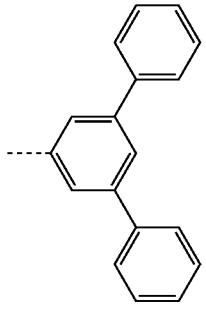 | 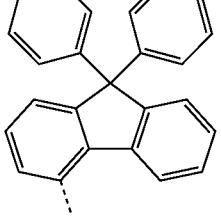 |
| 1-489 | 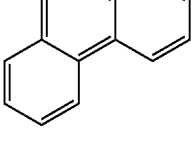 | 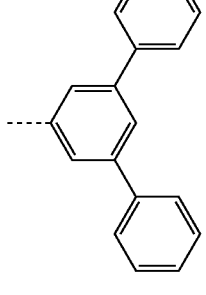 | 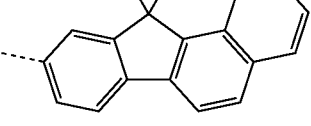 |

-continued

| Compound | ---Ar1 | ---Ar2 | ---Ar3 |
| --- | --- | --- | --- |
| 1-490 | | | |
| 1-491 | | | |
| 1-492 | | | |
| 1-493 | | | |
| 1-494 | | | |

-continued
| Compound | ---Ar1 | ---Ar2 | ---Ar3 |
|---|---|---|---|
| 1-495 | 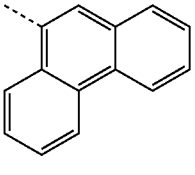 | 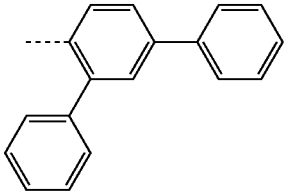 | 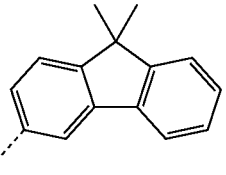 |
| 1-496 | 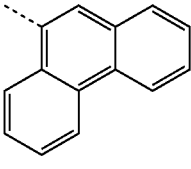 | 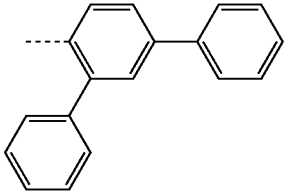 | 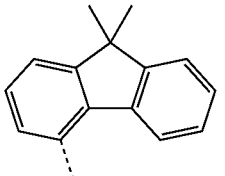 |
| 1-497 | 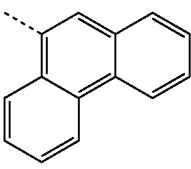 | 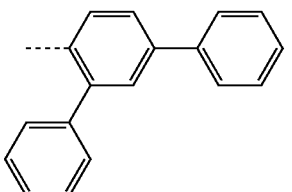 | 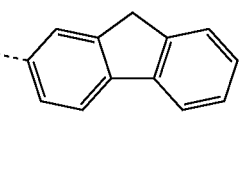 |
| 1-498 | 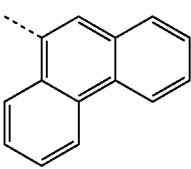 | 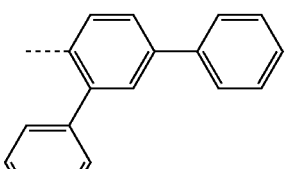 | 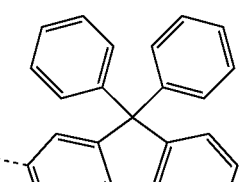 |
| 1-499 | 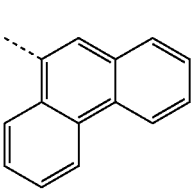 | 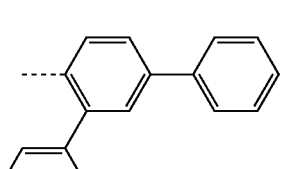 | 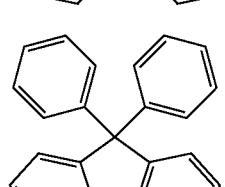 |
| 1-500 | 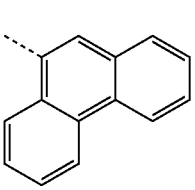 | 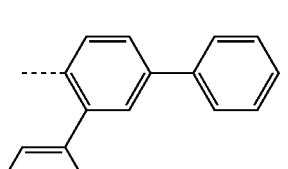 | 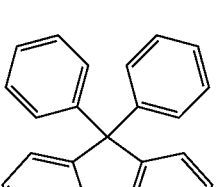 |
| 1-501 | 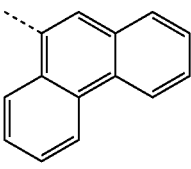 | 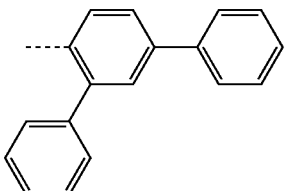 | 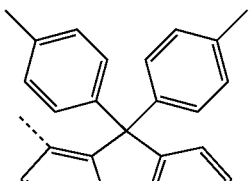 |

-continued

| Compound | ---Ar1 | ---Ar2 | ---Ar3 |
|---|---|---|---|
| 1-502 | | | |
| 1-503 | | | |
| 1-504 | | | |
| 1-505 | | | |
| 1-506 | | | |
| 1-507 | | | |

-continued
| Compound | ---Ar1 | ---Ar2 | ---Ar3 |
|---|---|---|---|
| 1-508 | 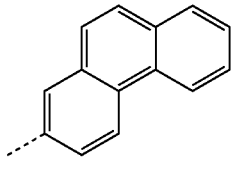 | 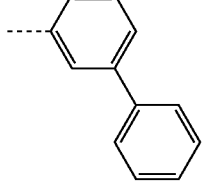 | 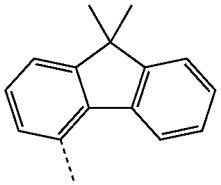 |
| 1-509 | 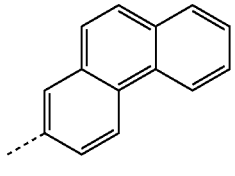 | 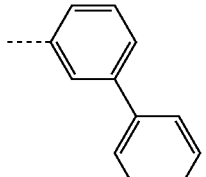 | 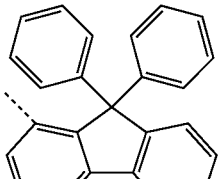 |
| 1-510 | 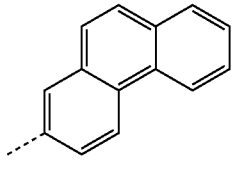 | 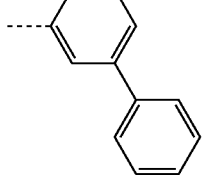 | 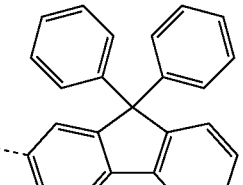 |
| 1-511 | 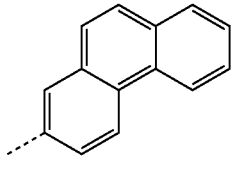 | 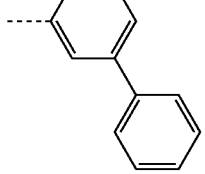 | 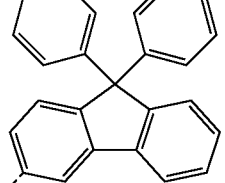 |
| 1-512 | 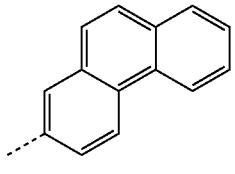 | 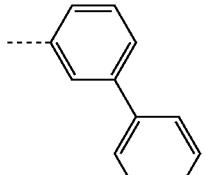 | 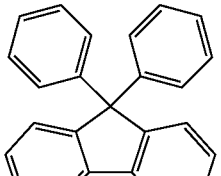 |
| 1-513 | 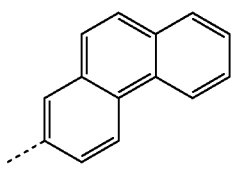 | 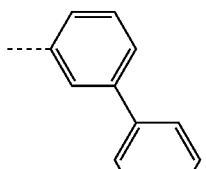 | 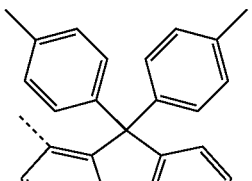 |

-continued
| Compound | ---Ar1 | ---Ar2 | ---Ar3 |
|---|---|---|---|
| 1-514 | 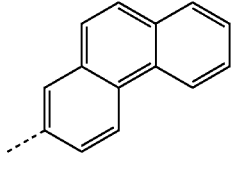 | 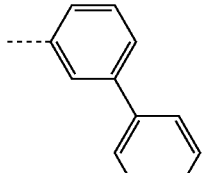 | 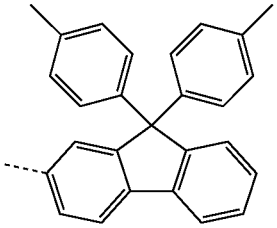 |
| 1-515 | 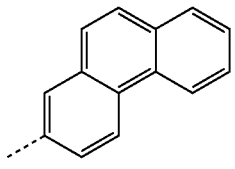 | 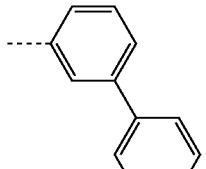 | 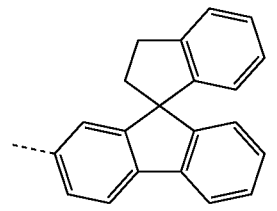 |
| 1-516 | 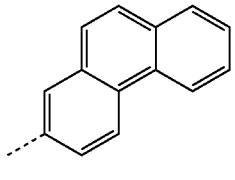 | 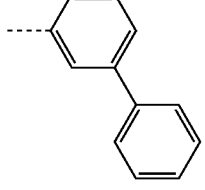 | 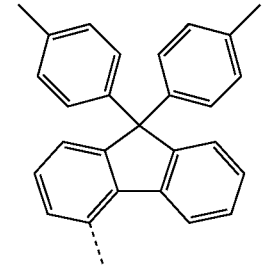 |
| 1-517 | 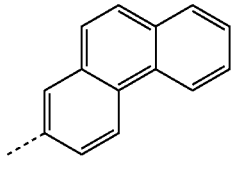 | 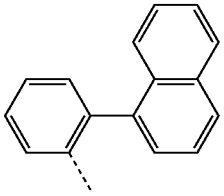 | 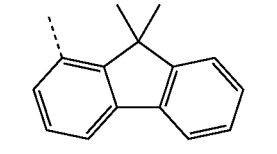 |
| 1-518 | 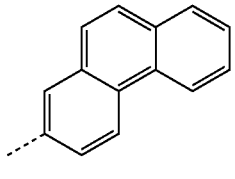 | 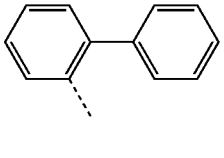 | 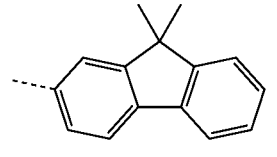 |
| 1-519 | 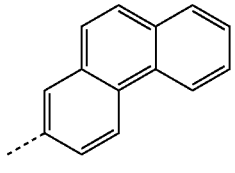 | 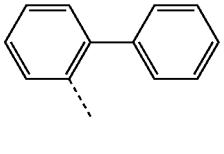 | 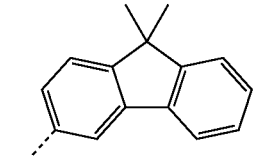 |
| 1-520 | 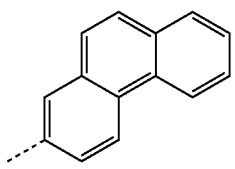 | 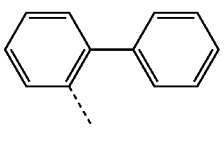 | 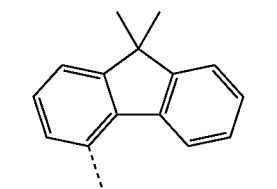 |

| Compound | ---Ar1 | ---Ar2 | ---Ar3 |
|---|---|---|---|
| 1-521 | phenanthrene | 2-biphenyl | 9,9-dimethyl-benzo-fused fluorene |
| 1-522 | phenanthrene | 2-biphenyl | 9,9-diphenylfluorene (2-yl) |
| 1-523 | phenanthrene | 2-biphenyl | 9,9-diphenylfluorene (3-yl) |
| 1-524 | phenanthrene | 2-biphenyl | 9,9-diphenylfluorene (4-yl) |
| 1-525 | phenanthrene | 2-biphenyl | 9,9-bis(4-methylphenyl)fluorene (1-yl) |
| 1-526 | phenanthrene | 2-biphenyl | 9,9-bis(4-methylphenyl)fluorene (2-yl) |

-continued
| Compound | ---Ar1 | ---Ar2 | ---Ar3 |
|---|---|---|---|
| 1-527 | 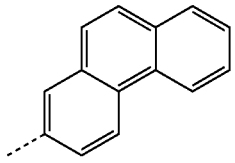 | 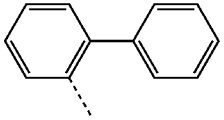 | 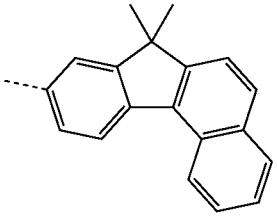 |
| 1-528 | 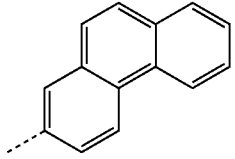 | 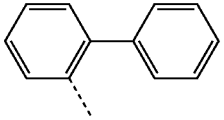 | 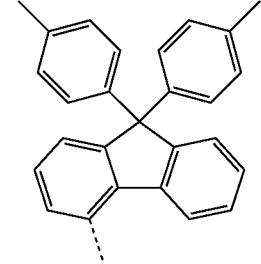 |
| 1-529 | 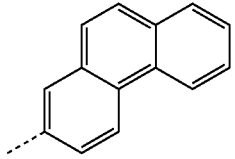 | 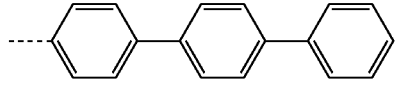 | 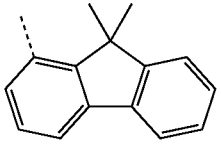 |
| 1-530 | 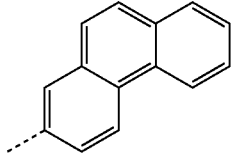 | 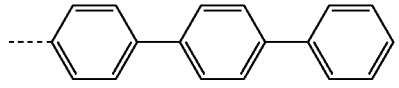 | 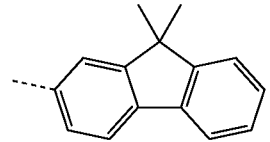 |
| 1-531 | 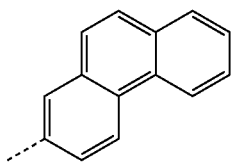 | 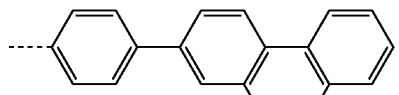 | 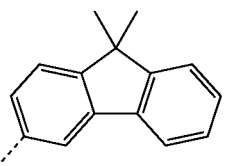 |
| 1-532 | 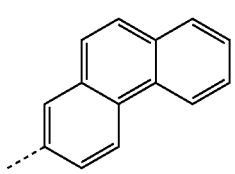 | 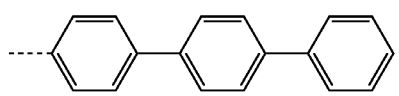 | 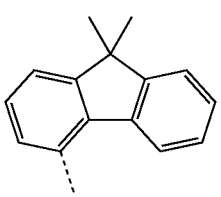 |
| 1-533 | 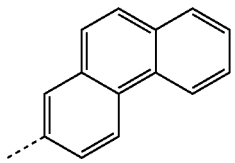 | 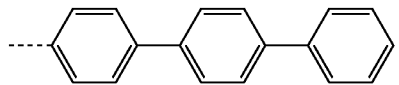 | 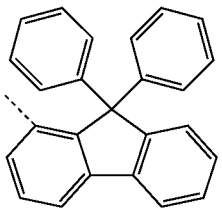 |

-continued
| Compound | ---Ar1 | ---Ar2 | ---Ar3 |
|---|---|---|---|
| 1-534 | 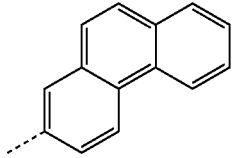 | 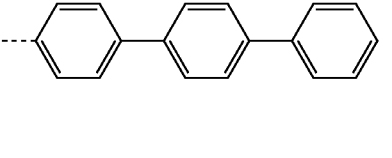 | 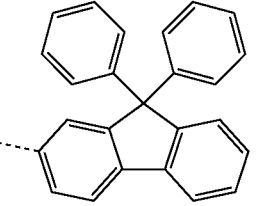 |
| 1-535 | 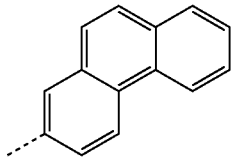 | 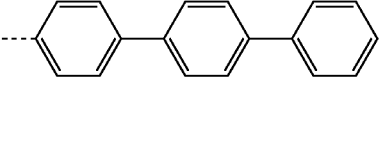 | 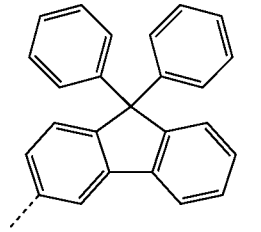 |
| 1-536 | 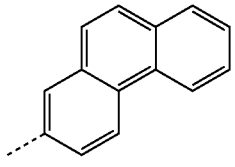 | 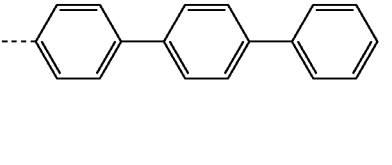 | 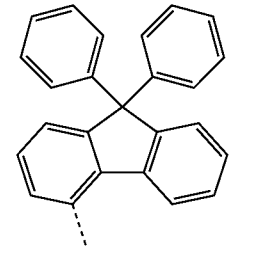 |
| 1-537 | 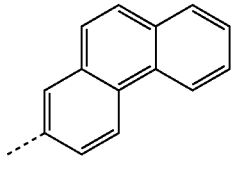 | 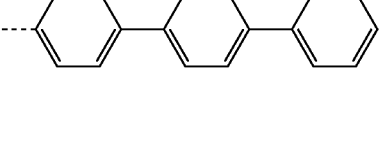 | 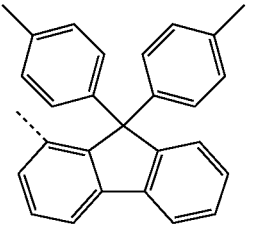 |
| 1-538 | 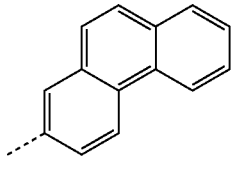 | 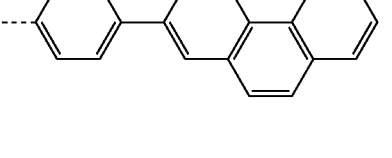 | 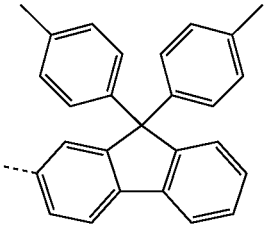 |
| 1-539 | 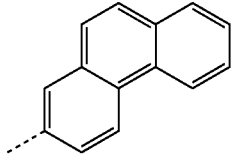 | 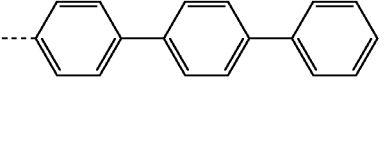 | 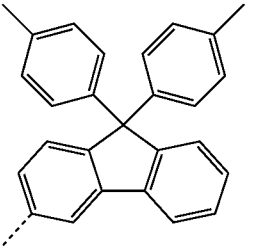 |

| Compound | ---Ar1 | ---Ar2 | ---Ar3 |
|---|---|---|---|
| 1-540 | phenanthrene | p-terphenyl | 9,9-bis(p-tolyl)fluorene |
| 1-541 | phenanthrene | 1,1':3',1''-terphenyl | 9,9-dimethylfluorene |
| 1-542 | phenanthrene | 1,1':3',1''-terphenyl | 9,9-dimethylfluorene |
| 1-543 | phenanthrene | 1,1':3',1''-terphenyl | 9,9-dimethylfluorene |
| 1-544 | phenanthrene | 1,1':3',1''-terphenyl | 9,9-dimethylfluorene |

-continued
| Compound | ---Ar1 | ---Ar2 | ---Ar3 |
|---|---|---|---|
| 1-545 | 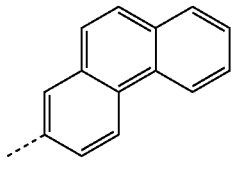 | 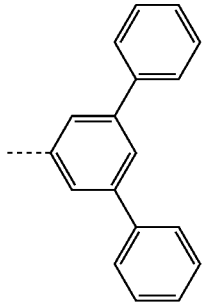 | 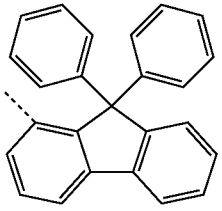 |
| 1-546 | 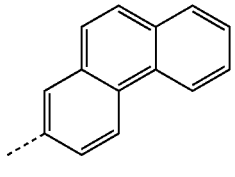 | 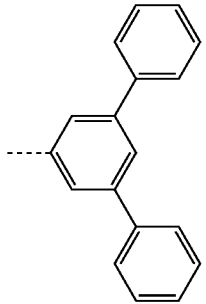 | 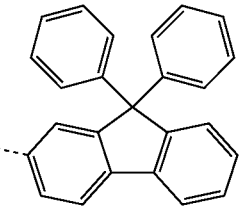 |
| 1-547 | 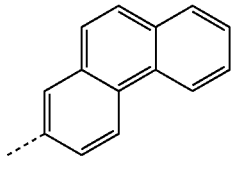 | 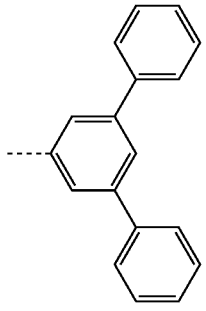 | 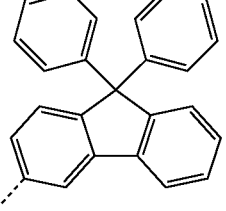 |
| 1-548 | 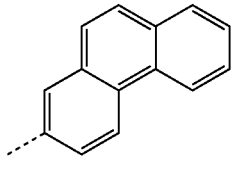 | 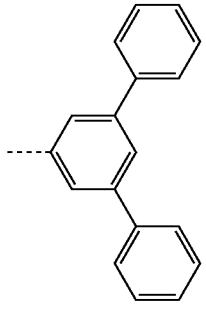 | 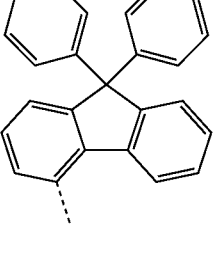 |
| 1-549 | 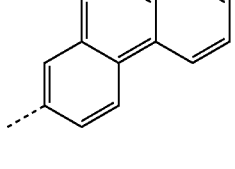 | 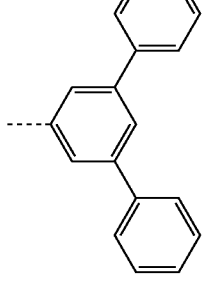 | 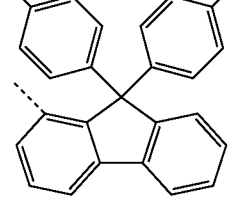 |

-continued

| Compound | ---Ar1 | ---Ar2 | ---Ar3 |
| --- | --- | --- | --- |
| 1-550 | phenanthrene | m-terphenyl | 9,9-bis(4-methylphenyl)fluorene |
| 1-551 | phenanthrene | m-terphenyl | 9,9-bis(4-methylphenyl)fluorene |
| 1-552 | phenanthrene | m-terphenyl | 9,9-bis(4-methylphenyl)fluorene |
| 1-553 | phenanthrene | 1,1':2',1''-terphenyl | 9,9-dimethylfluorene |
| 1-554 | phenanthrene | 1,1':2',1''-terphenyl | 9,9-dimethylfluorene |
| 1-555 | phenanthrene | 1,1':2',1''-terphenyl | 9,9-dimethylfluorene |

US 10,964,892 B2
-continued
| Compound | ---Ar1 | ---Ar2 | ---Ar3 |
|---|---|---|---|
| 1-556 | 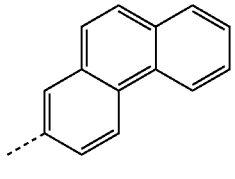 | 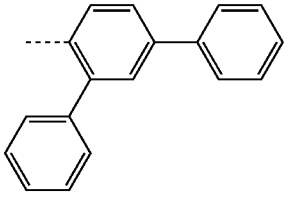 | 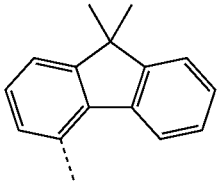 |
| 1-557 | 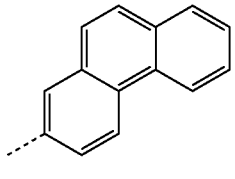 | 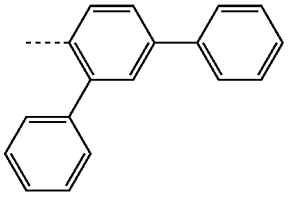 | 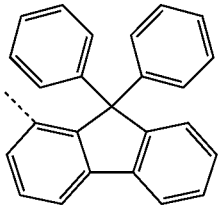 |
| 1-558 | 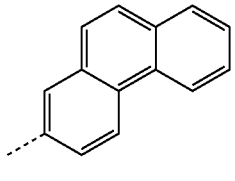 | 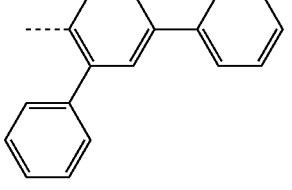 | 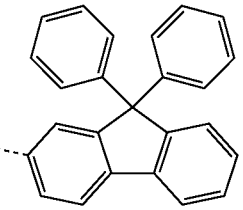 |
| 1-559 | 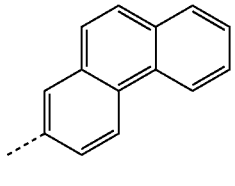 | 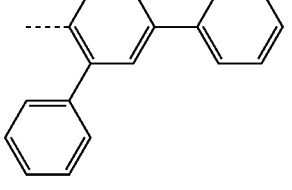 | 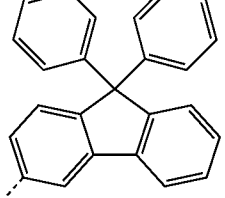 |
| 1-560 | 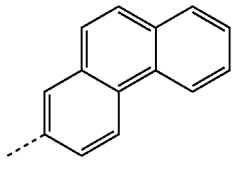 | 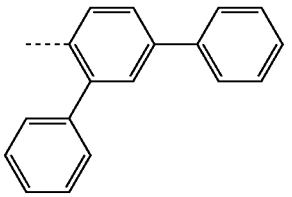 | 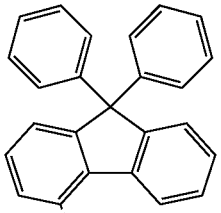 |
| 1-561 | 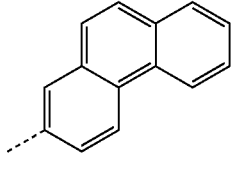 | 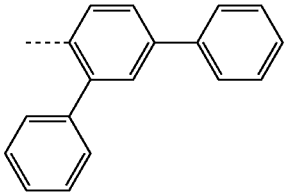 | 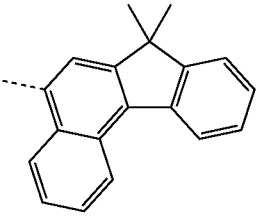 |

| Compound | ---Ar1 | ---Ar2 | ---Ar3 |
|---|---|---|---|
| 1-562 | | | |
| 1-563 | | | |
| 1-564 | | | |
| 1-565 | | | |
| 1-566 | | | |
| 1-567 | | | |

-continued
| Compound | ---Ar1 | ---Ar2 | ---Ar3 |
|---|---|---|---|
| 1-568 | 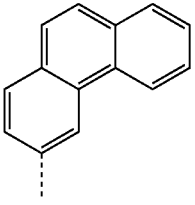 | 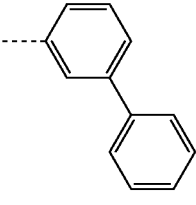 | 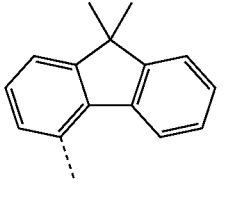 |
| 1-569 | 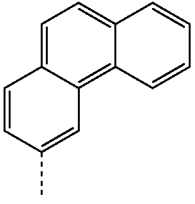 | 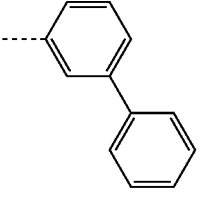 | 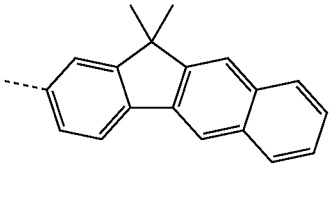 |
| 1-570 | 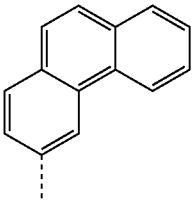 | 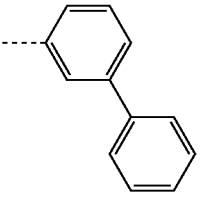 | 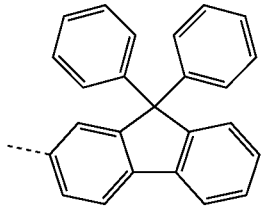 |
| 1-571 | 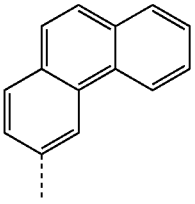 | 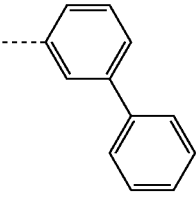 | 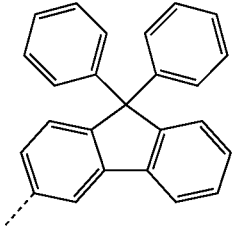 |
| 1-572 | 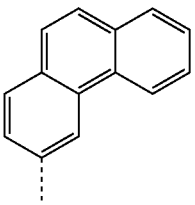 | 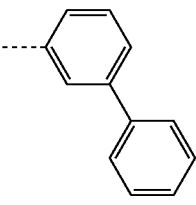 | 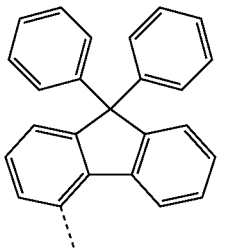 |
| 1-573 | 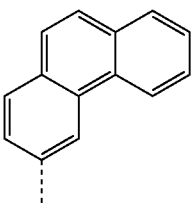 | 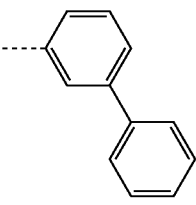 | 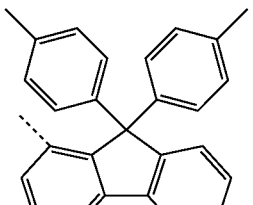 |

-continued
| Compound | ---Ar1 | ---Ar2 | ---Ar3 |
|---|---|---|---|
| 1-574 | 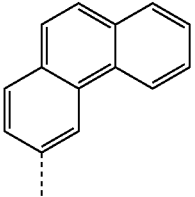 | 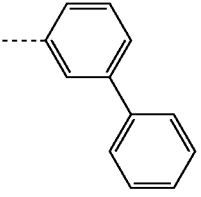 | 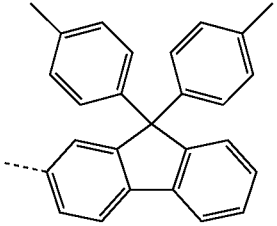 |
| 1-575 | 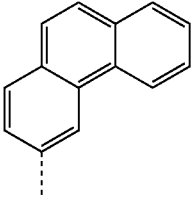 | 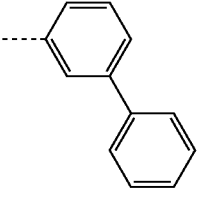 | 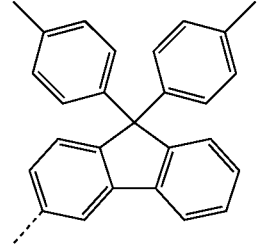 |
| 1-576 | 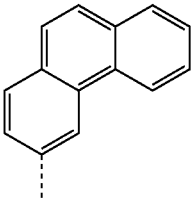 | 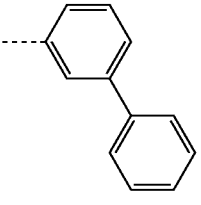 | 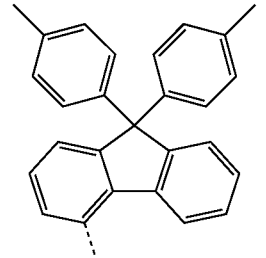 |
| 1-577 | 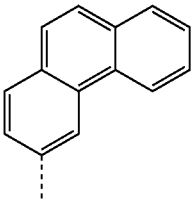 | 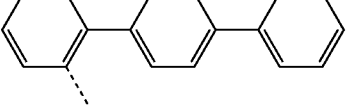 | 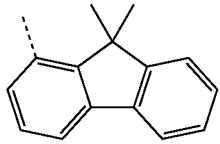 |
| 1-578 | 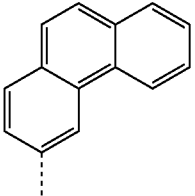 | 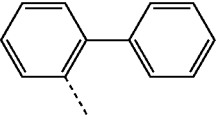 | 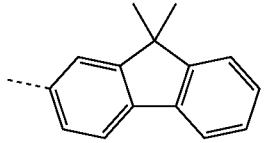 |
| 1-579 | 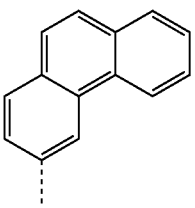 | 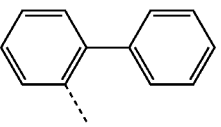 | 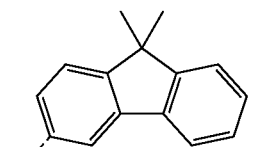 |

225 226
-continued
| Compound | ---Ar1 | ---Ar2 | ---Ar3 |
|---|---|---|---|
| 1-580 | 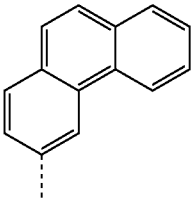 | 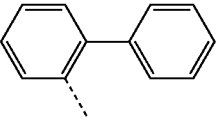 | 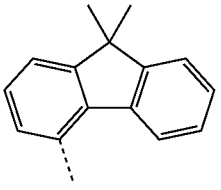 |
| 1-581 | 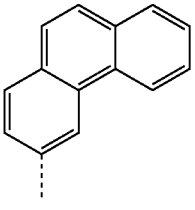 | 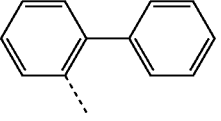 | 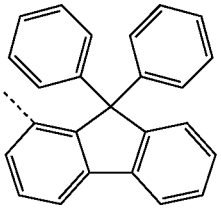 |
| 1-582 | 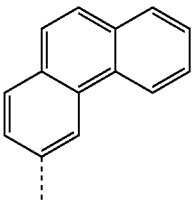 | 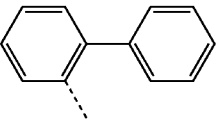 | 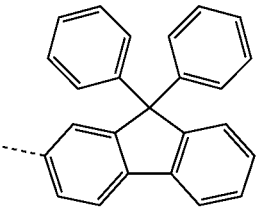 |
| 1-583 | 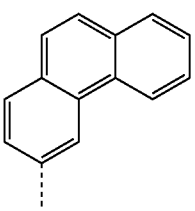 | 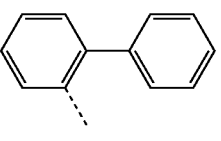 | 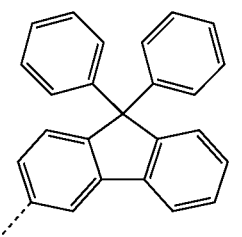 |
| 1-584 | 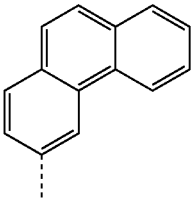 | 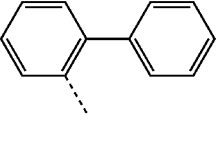 | 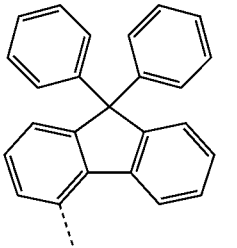 |
| 1-585 | 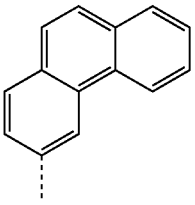 | 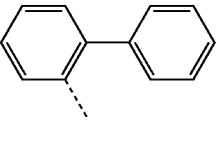 | 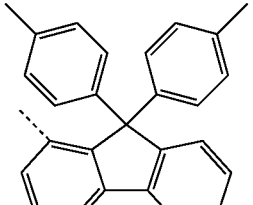 |

-continued
| Compound | ---Ar1 | ---Ar2 | ---Ar3 |
|---|---|---|---|
| 1-586 | 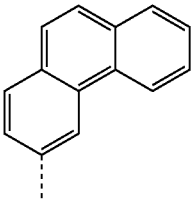 | 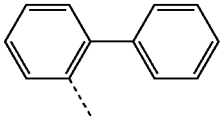 | 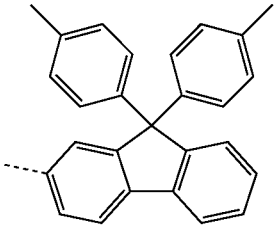 |
| 1-587 | 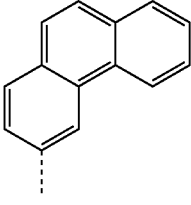 | 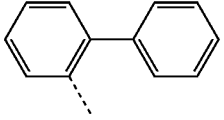 | 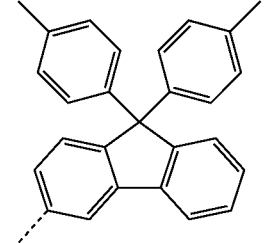 |
| 1-588 | 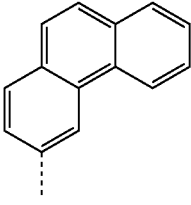 | 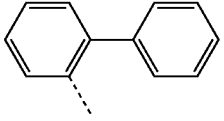 | 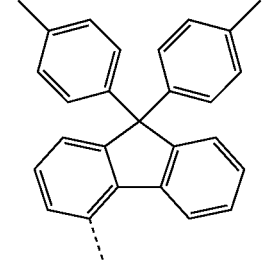 |
| 1-589 | 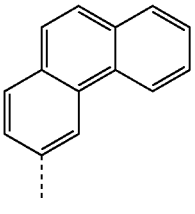 | 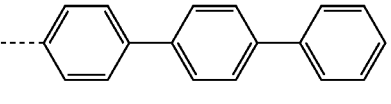 | 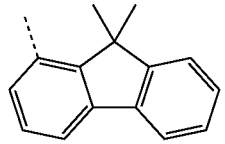 |
| 1-590 | 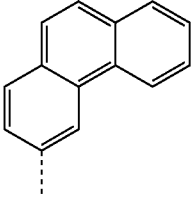 | 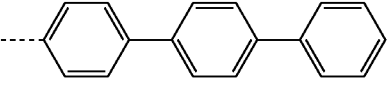 | 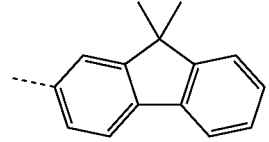 |
| 1-591 | 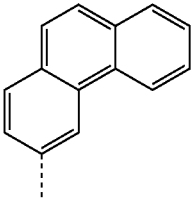 | 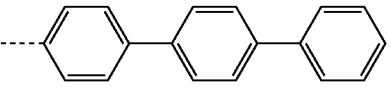 | 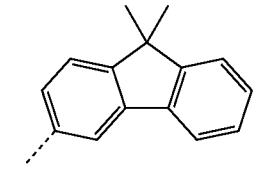 |

-continued

| Compound | ---Ar1 | ---Ar2 | ---Ar3 |
|---|---|---|---|
| 1-592 | phenanthrene | p-terphenyl | 9,9-dimethylfluorene |
| 1-593 | phenanthrene | p-terphenyl | 9,9-di(p-tolyl)fluorene |
| 1-594 | phenanthrene | p-terphenyl | 9,9-diphenylfluorene |
| 1-595 | phenanthrene | p-terphenyl | 9,9-diphenylfluorene |
| 1-596 | phenanthrene | p-terphenyl | 9,9-diphenylfluorene |
| 1-597 | phenanthrene | p-terphenyl | dimethyl-benzofluorene |

-continued
| Compound | ---Ar1 | ---Ar2 | ---Ar3 |
|---|---|---|---|
| 1-598 | 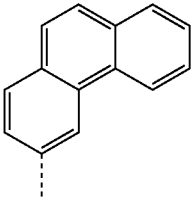 | 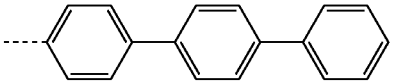 | 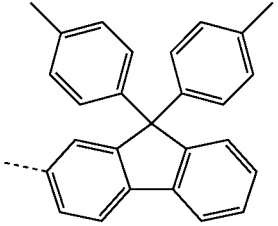 |
| 1-599 | 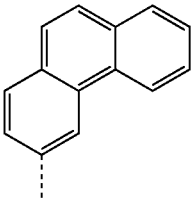 | 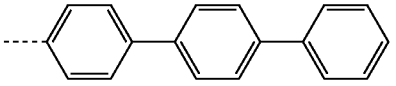 | 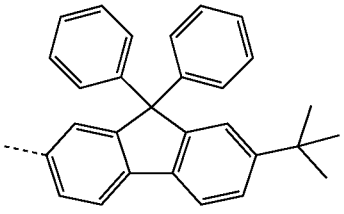 |
| 1-600 | 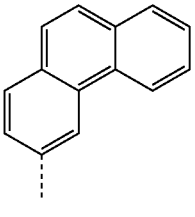 | 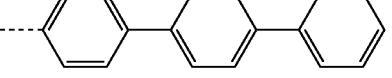 | 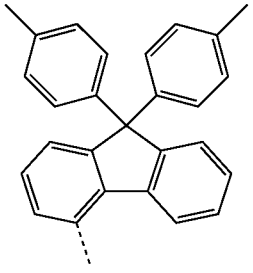 |
| 1-601 | 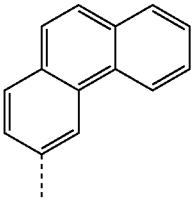 | 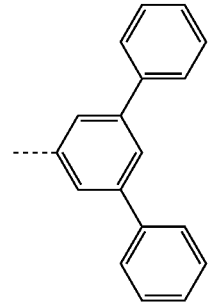 | 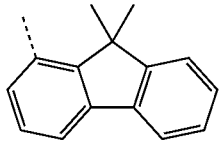 |
| 1-602 | 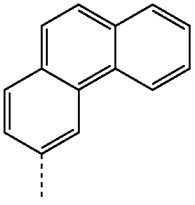 | 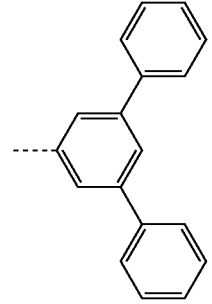 | 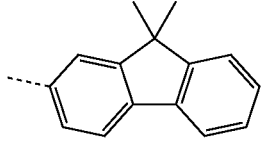 |

-continued

| Compound | ---Ar1 | ---Ar2 | ---Ar3 |
|---|---|---|---|
| 1-603 | phenanthrene | 5'-phenyl-[1,1':3',1''-terphenyl] | 9,9-dimethyl-fluorene |
| 1-604 | phenanthrene | [1,1':3',1''-terphenyl] | 9,9-dimethyl-fluorene |
| 1-605 | phenanthrene | [1,1':3',1''-terphenyl] | 9,9-diphenyl-fluorene |
| 1-606 | phenanthrene | [1,1':3',1''-terphenyl] | 9,9-diphenyl-fluorene |
| 1-607 | phenanthrene | [1,1':3',1''-terphenyl] | 9,9-diphenyl-fluorene |

-continued
| Compound | ---Ar1 | ---Ar2 | ---Ar3 |
|---|---|---|---|
| 1-608 | 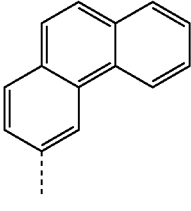 | 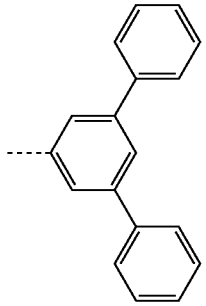 | 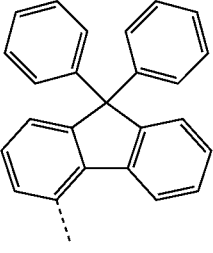 |
| 1-609 | 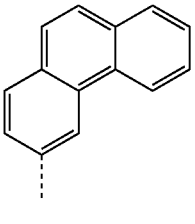 | 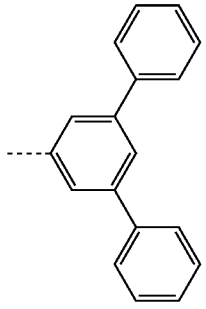 | 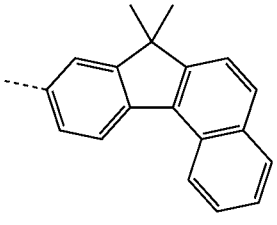 |
| 1-610 | 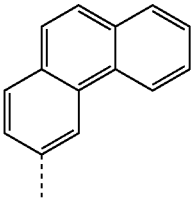 | 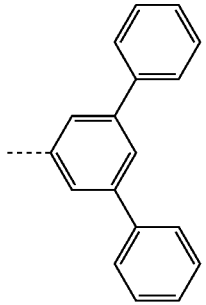 | 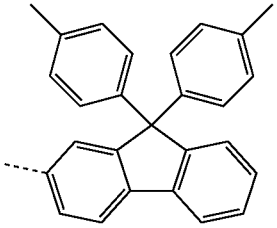 |
| 1-611 | 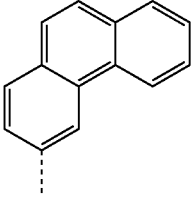 | 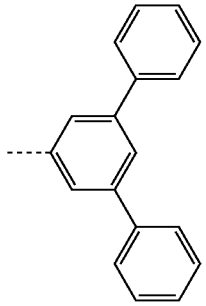 | 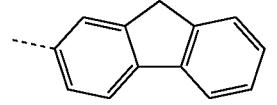 |
| 1-612 | 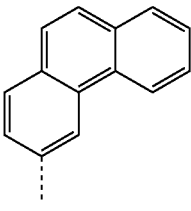 | 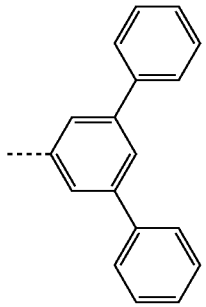 | 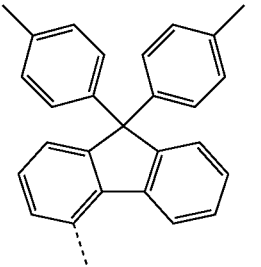 |

-continued

| Compound | ---Ar1 | ---Ar2 | ---Ar3 |
|---|---|---|---|
| 1-613 | phenanthrene | m-terphenyl (1,3-diphenylbenzene) | 9,9-dimethylfluorene (1-position) |
| 1-614 | phenanthrene | m-terphenyl (1,3-diphenylbenzene) | 9,9-dimethylfluorene (2-position) |
| 1-615 | phenanthrene | 1,3,5-triphenylbenzene | 9,9-dimethylfluorene (3-position) |
| 1-616 | phenanthrene | m-terphenyl (1,3-diphenylbenzene) | 9,9-dimethylfluorene (4-position) |
| 1-617 | phenanthrene | m-terphenyl (1,3-diphenylbenzene) | 9,9-diphenylfluorene |
| 1-618 | phenanthrene | m-terphenyl (1,3-diphenylbenzene) | 9,9-diphenylfluorene |

-continued
| Compound | ---Ar1 | ---Ar2 | ---Ar3 |
|---|---|---|---|
| 1-619 | 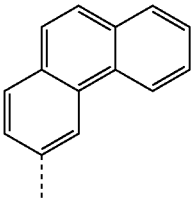 | 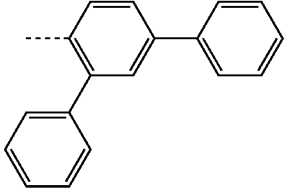 | 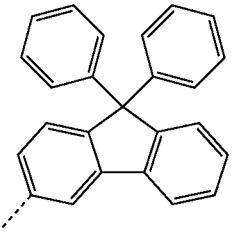 |
| 1-620 | 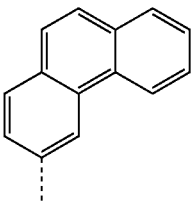 | 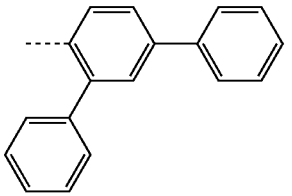 | 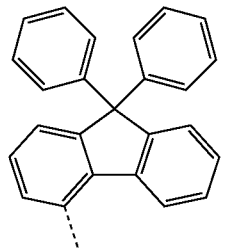 |
| 1-621 | 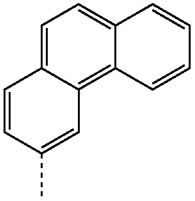 | 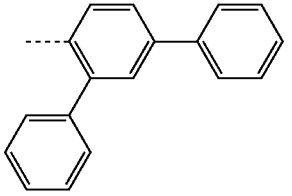 | 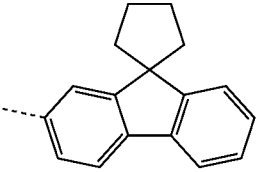 |
| 1-622 | 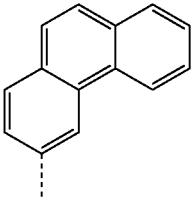 | 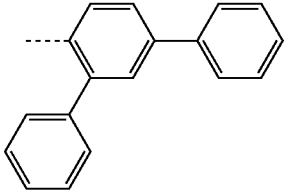 | 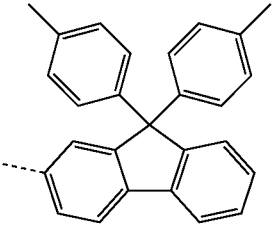 |
| 1-623 | 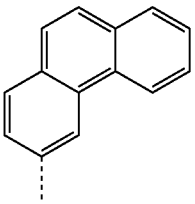 | 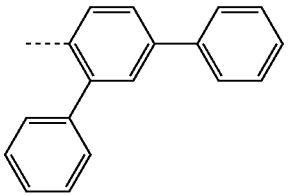 | 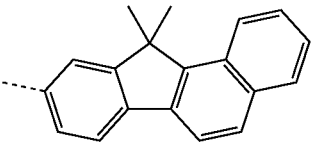 |
| 1-624 | 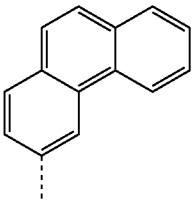 | 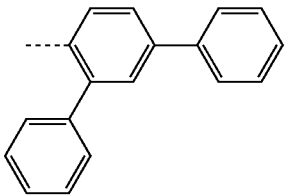 | 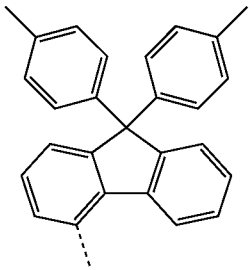 |

| Compound | ---Ar1 | ---Ar2 | ---Ar3 |
|---|---|---|---|
| 1-625 | (C6D5-) | (biphenyl-4-yl) | (9,9-diphenylfluoren-2-yl) |
| 1-626 | (C6D5-) | (biphenyl-4-yl) | (9,9-diphenylfluoren-4-yl) |
| 1-627 | (phenyl) | (2,3,5,6-tetradeutero-biphenyl-4-yl) | (9,9-di-p-tolylfluoren-2-yl) |

According to an exemplary embodiment of the present invention, the compound of Formula 1 may be any one selected from the following Compounds 2-1 to 2-363.

| Compound | ----Ar1 | ----Ar2 | ----Ar3 |
|---|---|---|---|
| 2-1 | (phenyl) | (biphenyl-4-yl) | (9,9-dimethylfluoren-1-yl)phenyl |
| 2-2 | (phenyl) | (biphenyl-4-yl) | (9,9-dimethylfluoren-2-yl)phenyl |

-continued
| Compound | ----Ar1 | ----Ar2 | ----Ar3 |
|---|---|---|---|
| 2-3 | 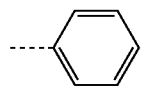 | 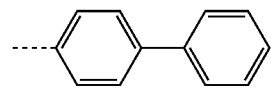 | 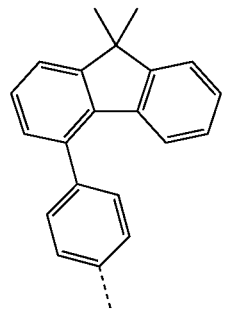 |
| 2-4 | 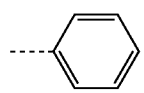 | 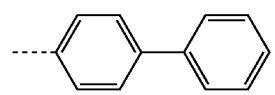 | 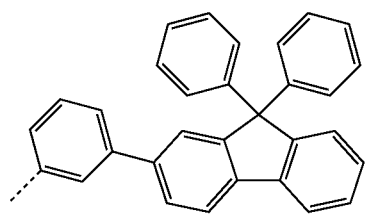 |
| 2-5 | 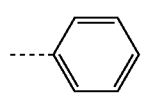 | 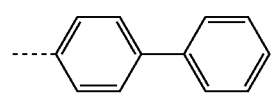 | 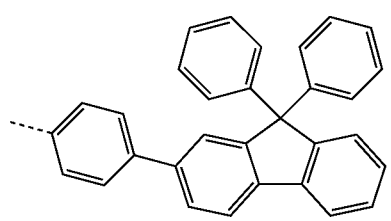 |
| 2-6 | 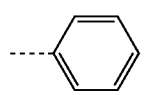 | 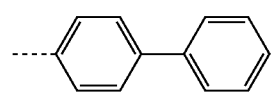 | 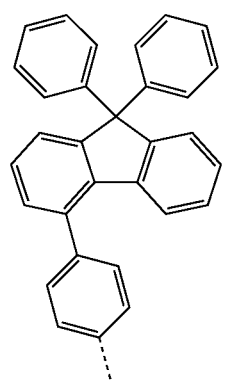 |
| 2-7 | 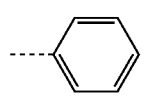 | 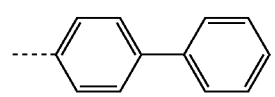 | 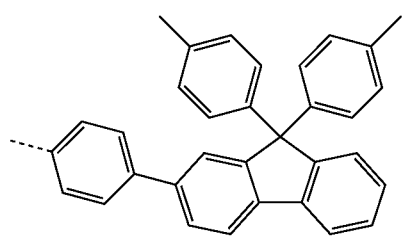 |

-continued
| Compound | ----Ar1 | ----Ar2 | ----Ar3 |
|---|---|---|---|
| 2-8 | 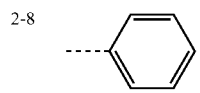 | 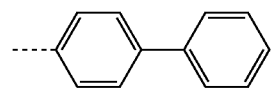 | 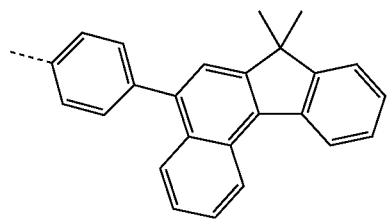 |
| 2-9 | 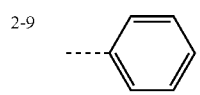 | 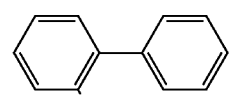 | 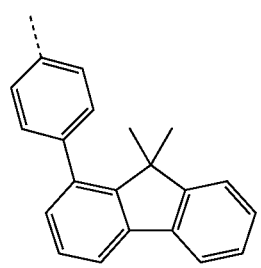 |
| 2-10 | 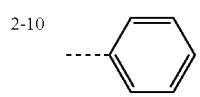 | 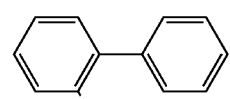 | 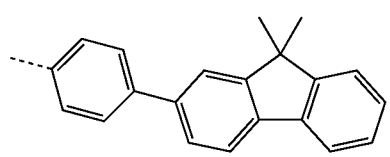 |
| 2-11 | 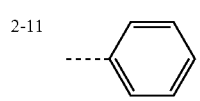 | 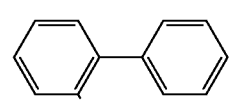 | 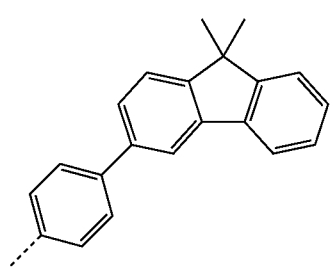 |
| 2-12 | 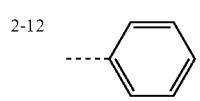 | 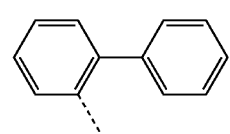 | 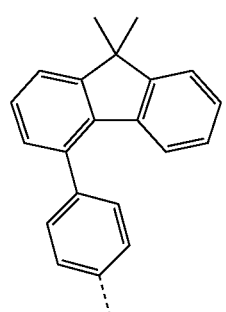 |
| 2-13 | 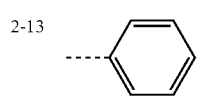 | 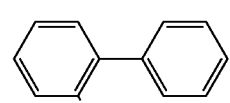 | 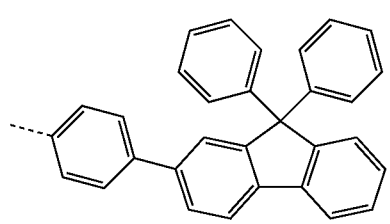 |

-continued
| Compound | ----Ar1 | ----Ar2 | ----Ar3 |
|---|---|---|---|
| 2-14 | 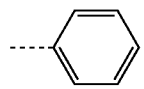 | 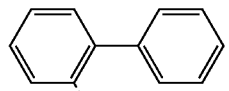 | 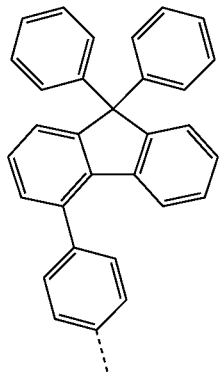 |
| 2-15 | 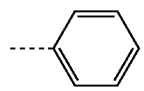 | 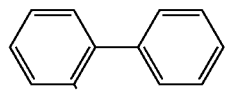 | 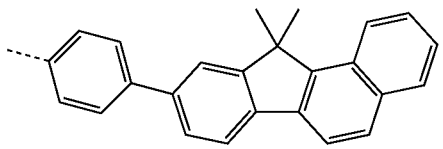 |
| 2-16 | 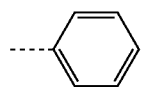 | 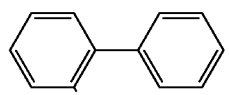 | 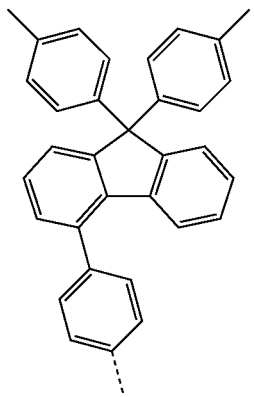 |
| 2-17 | 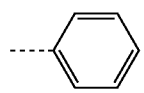 | 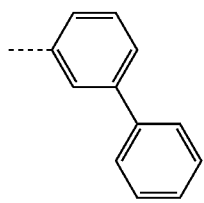 | 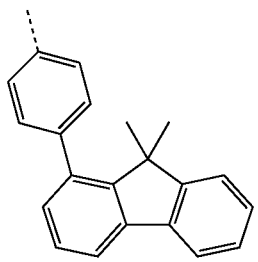 |
| 2-18 | 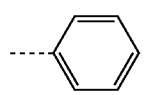 | 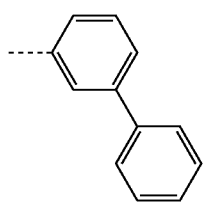 | 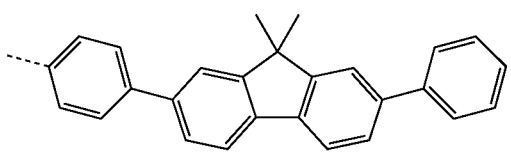 |

-continued
| Compound | ----Ar1 | ----Ar2 | ----Ar3 |
|---|---|---|---|
| 2-19 | 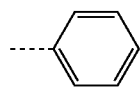 | 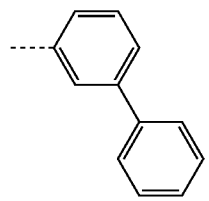 | 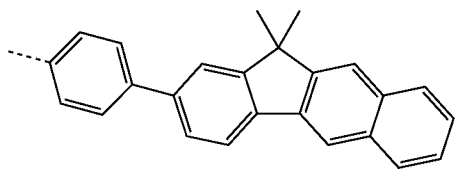 |
| 2-20 | 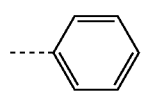 | 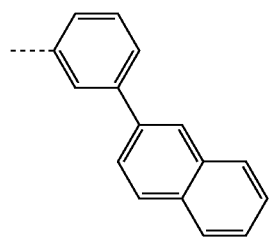 | 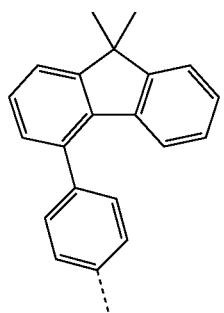 |
| 2-21 | 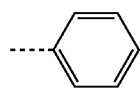 | 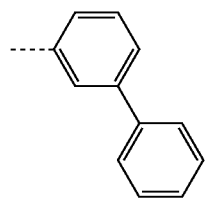 | 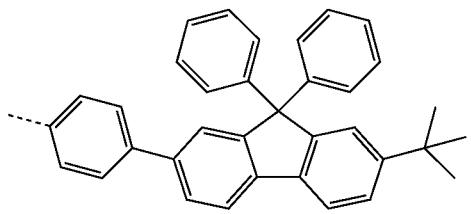 |
| 2-22 | 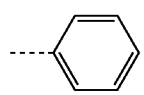 | 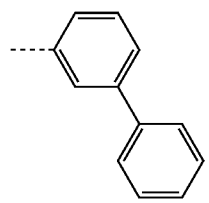 | 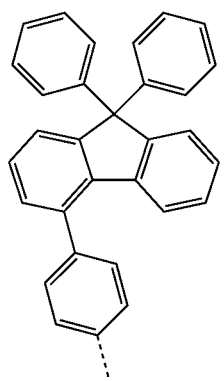 |
| 2-23 | 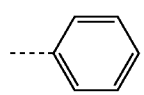 | 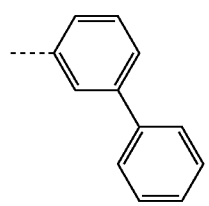 | 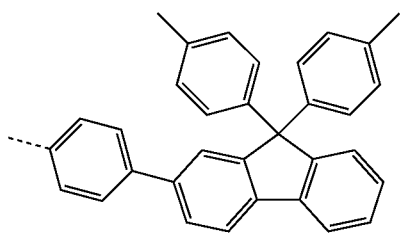 |

-continued
| Compound | ----Ar1 | ----Ar2 | ----Ar3 |
|---|---|---|---|
| 2-24 | 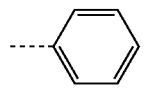 | 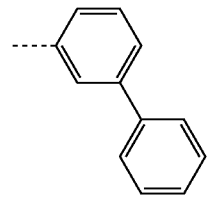 | 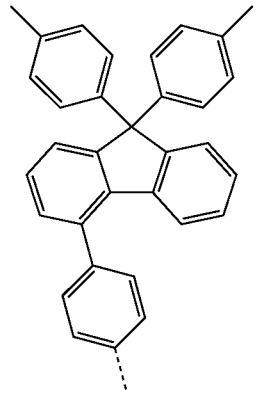 |
| 2-25 | 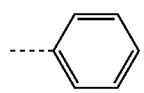 | 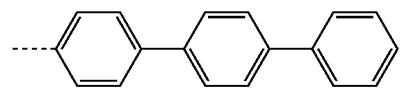 | 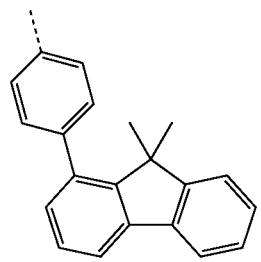 |
| 2-26 | 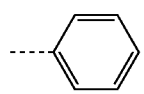 | 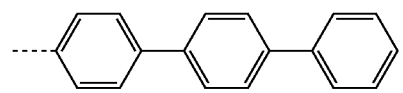 | 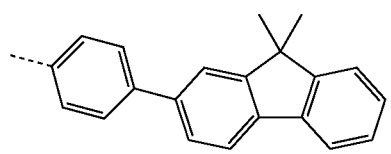 |
| 2-27 | 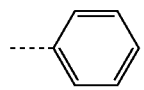 | 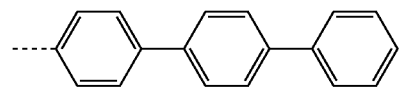 | 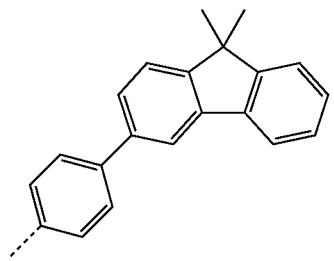 |
| 2-28 | 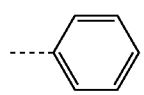 | 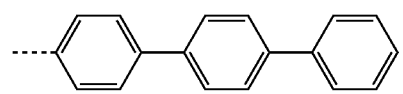 | 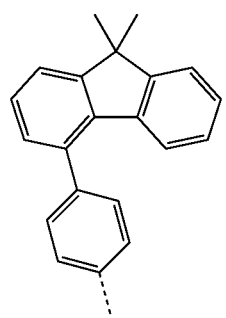 |

-continued
| Compound | ----Ar1 | ----Ar2 | ----Ar3 |
|---|---|---|---|
| 2-29 | 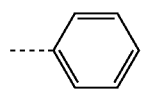 | 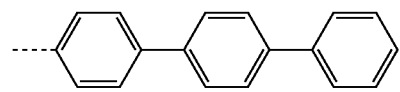 | 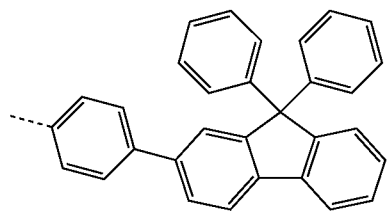 |
| 2-30 | 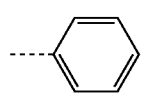 | 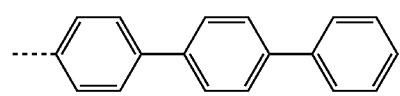 | 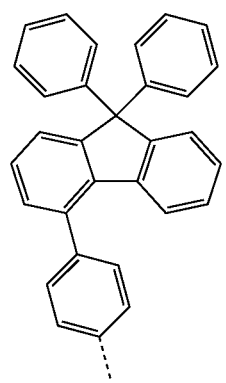 |
| 2-31 | 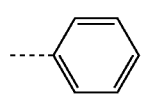 | 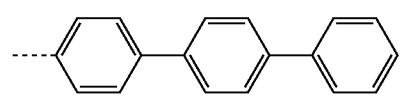 | 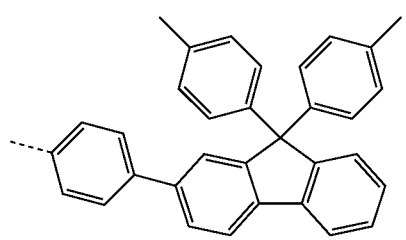 |
| 2-32 | 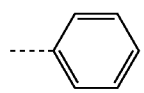 | 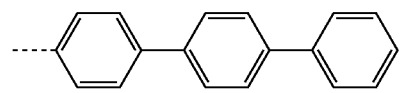 | 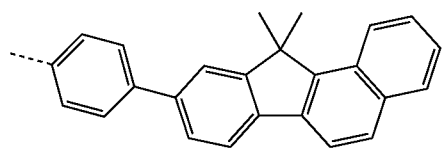 |
| 2-33 | 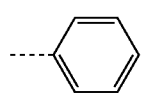 | 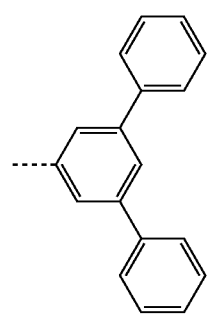 | 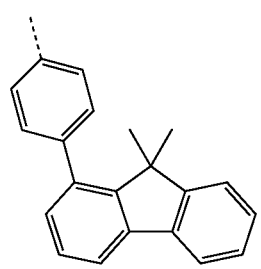 |

-continued
| Compound | ----Ar1 | ----Ar2 | ----Ar3 |
|---|---|---|---|
| 2-34 | 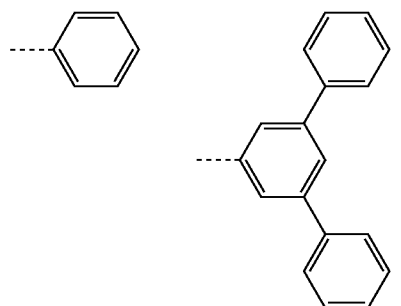 | 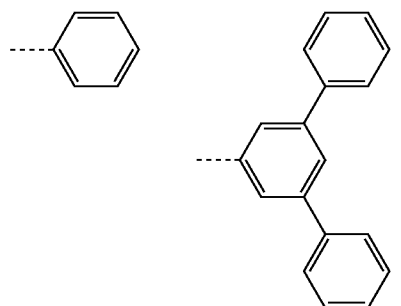 | 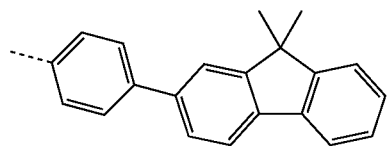 |
| 2-35 | 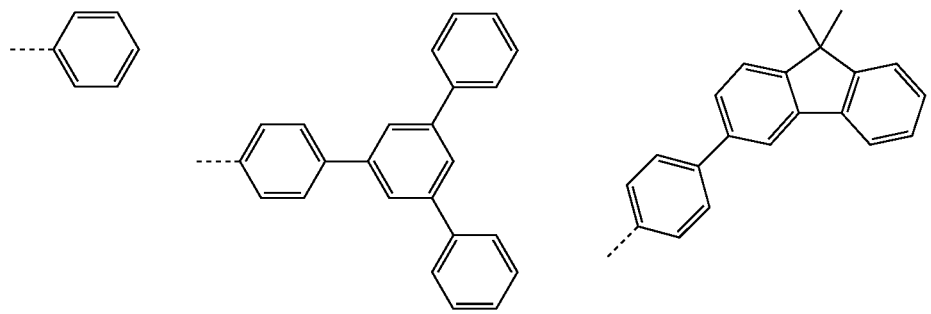 | | 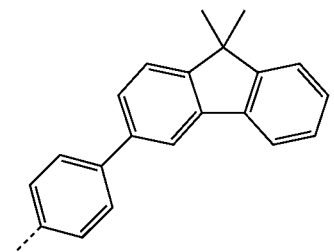 |
| 2-36 | 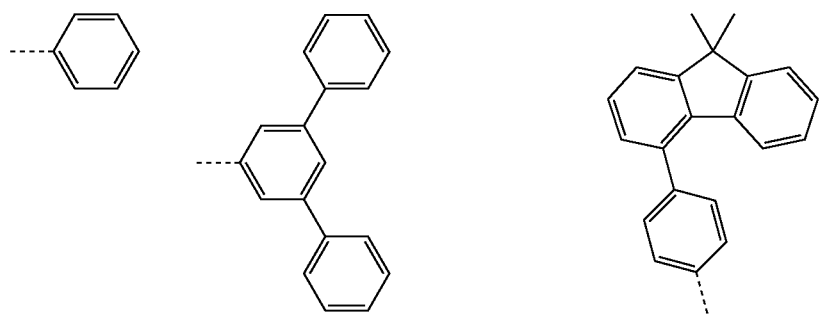 | | 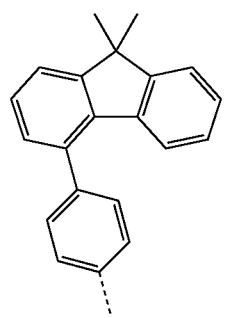 |
| 2-37 | 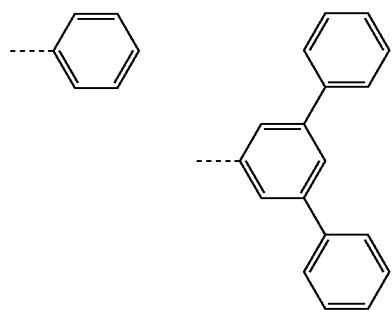 | | 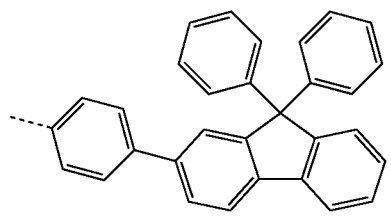 |

-continued
| Compound | ----Ar1 | ----Ar2 | ----Ar3 |
|---|---|---|---|
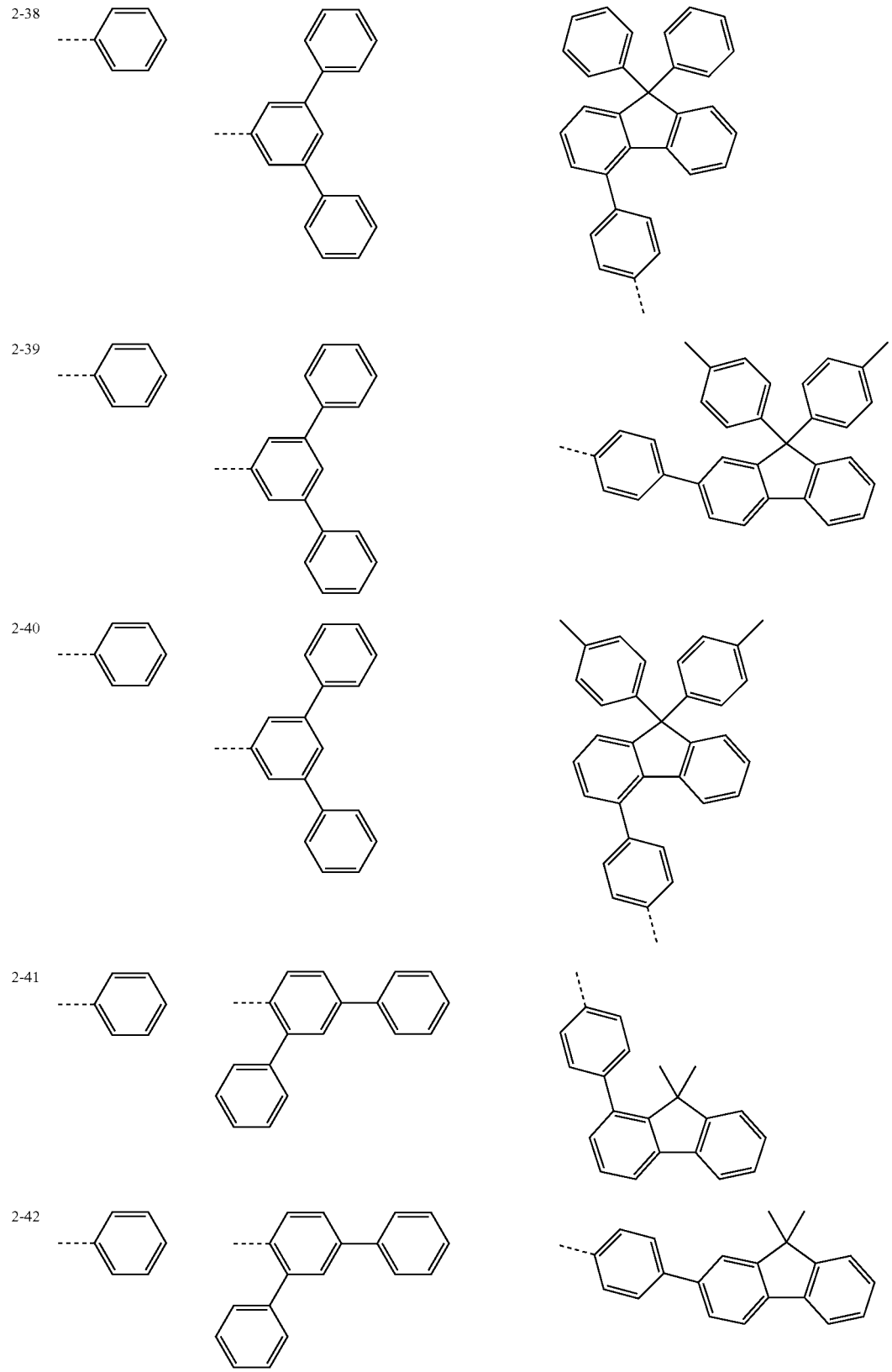

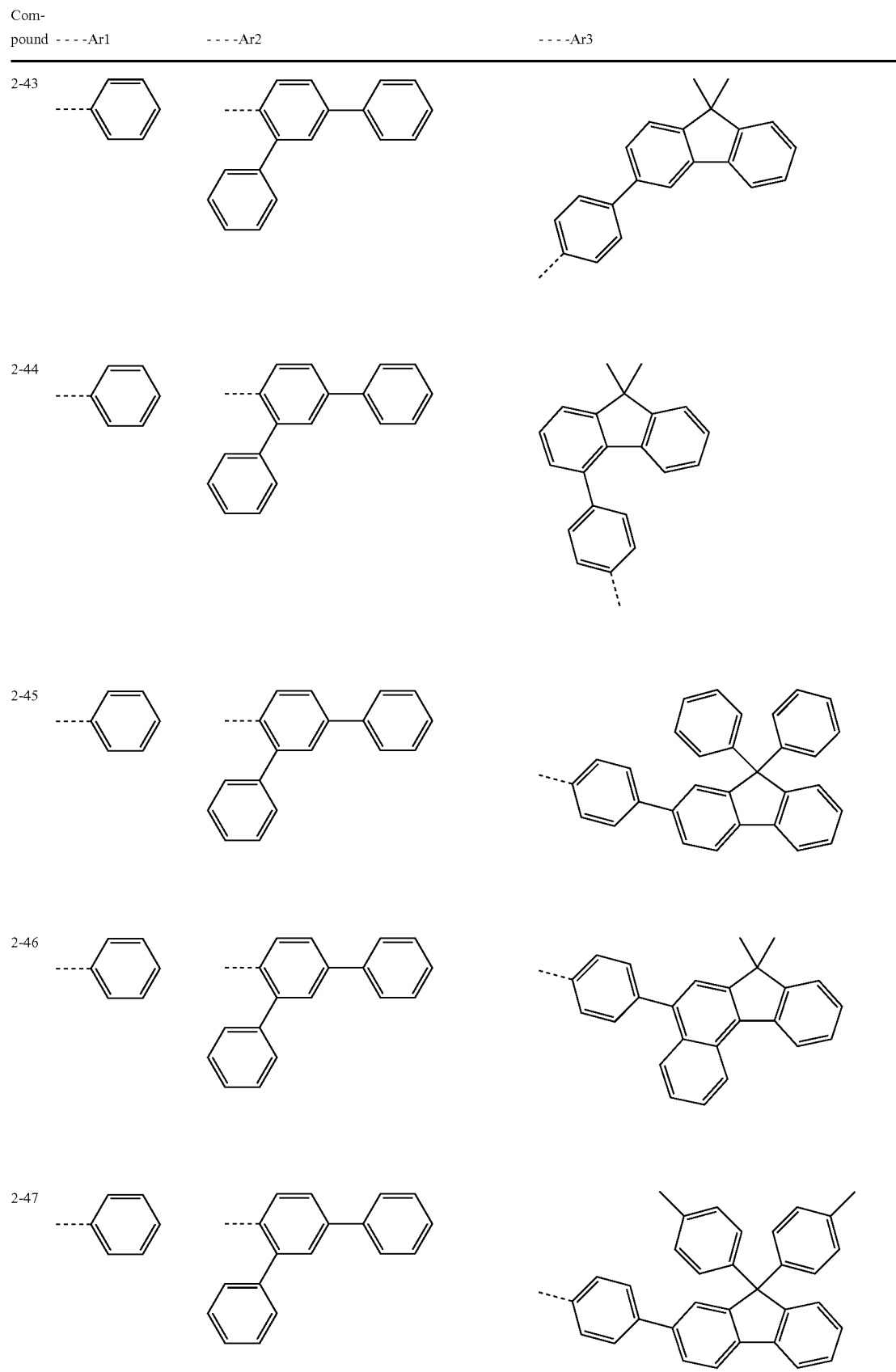

-continued
| Compound | ----Ar1 | ----Ar2 | ----Ar3 |
|---|---|---|---|
2-48
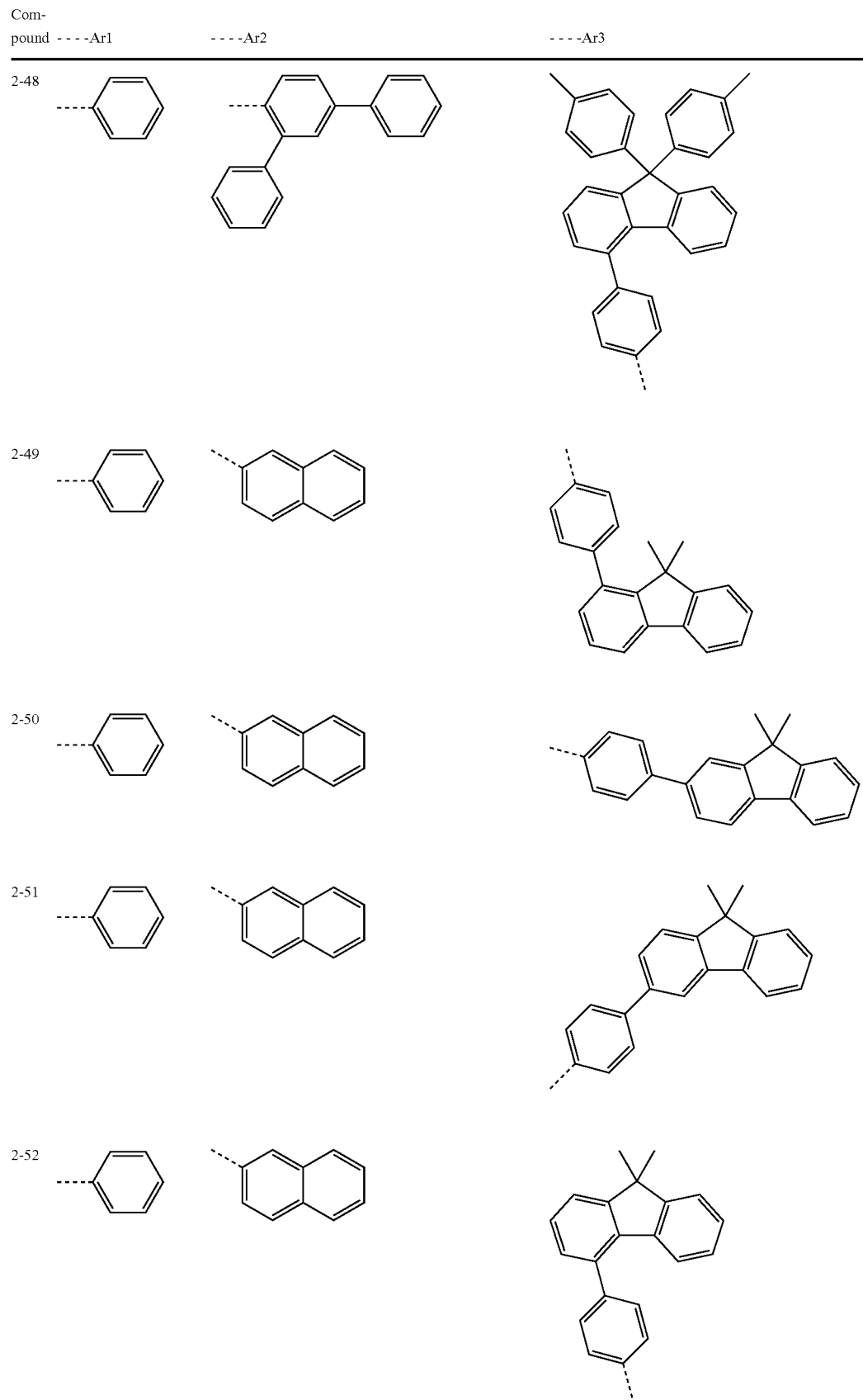

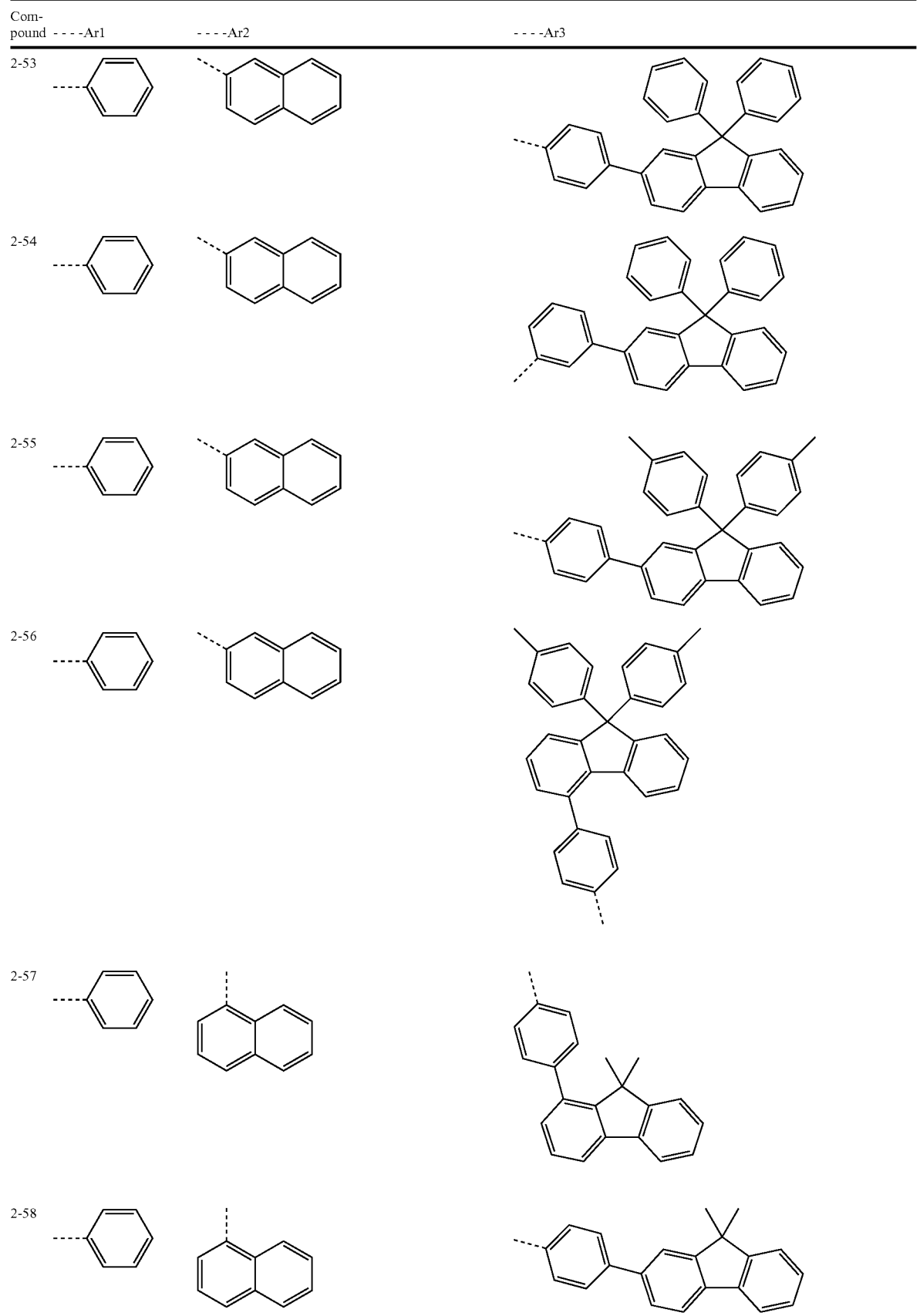

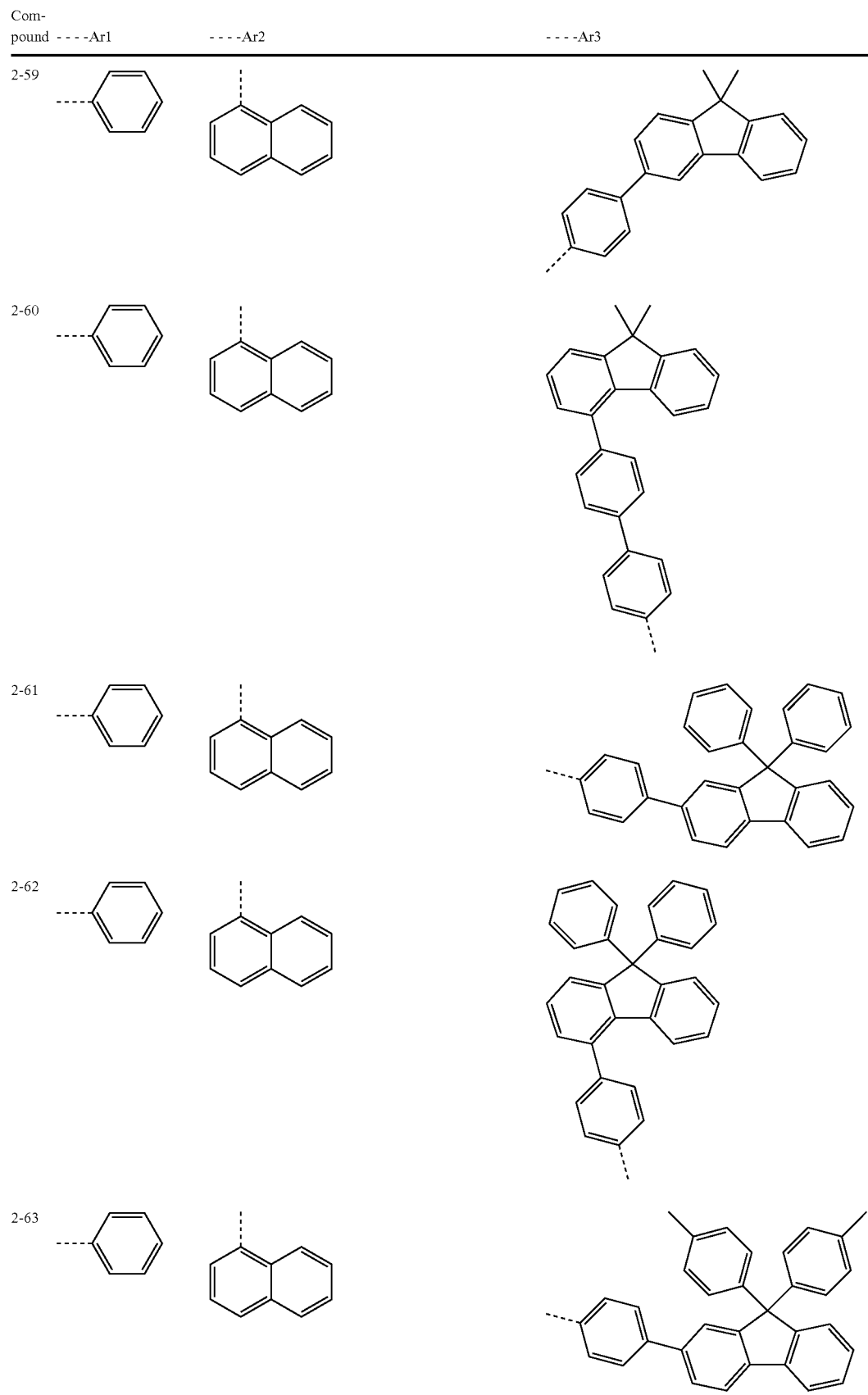

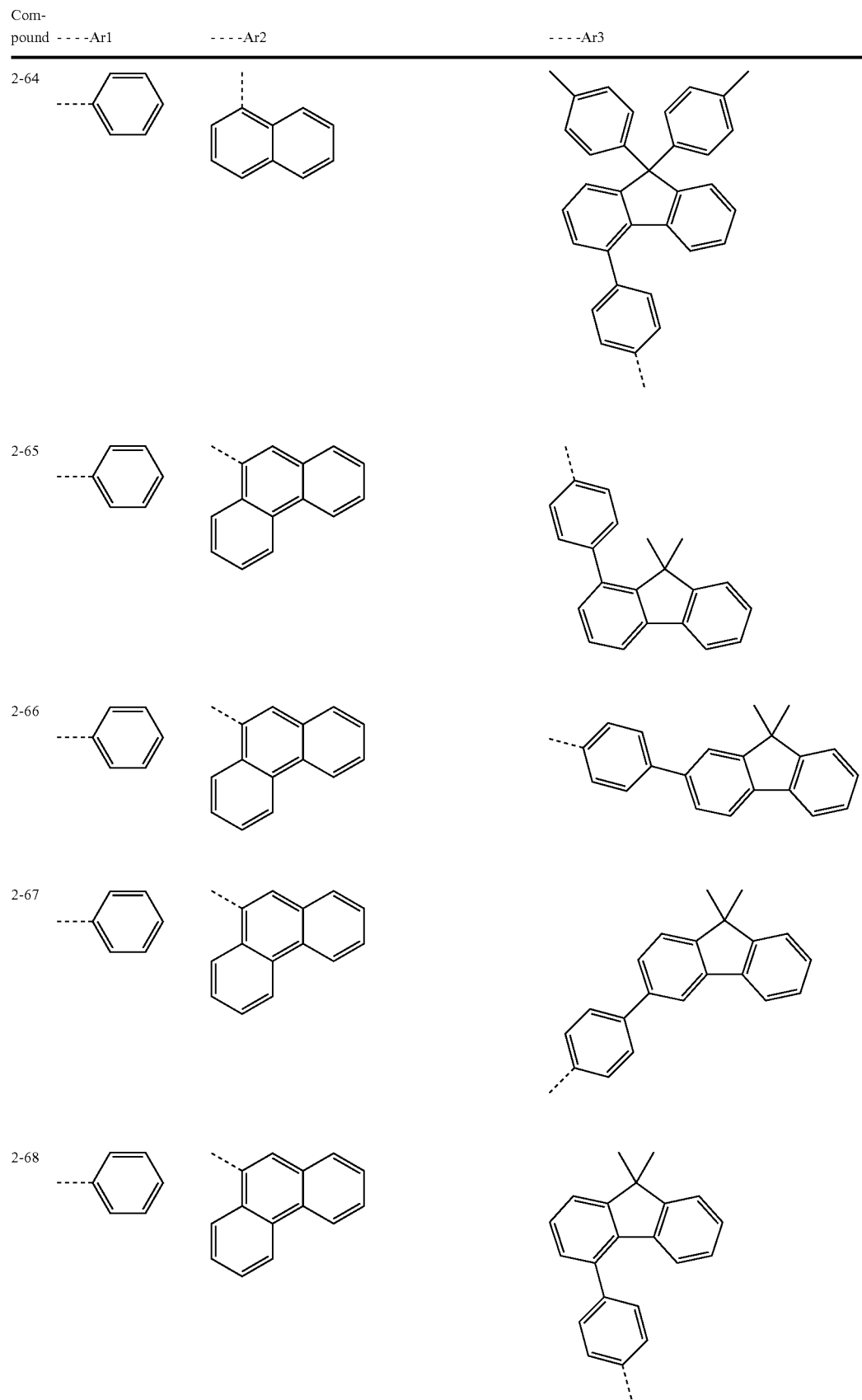

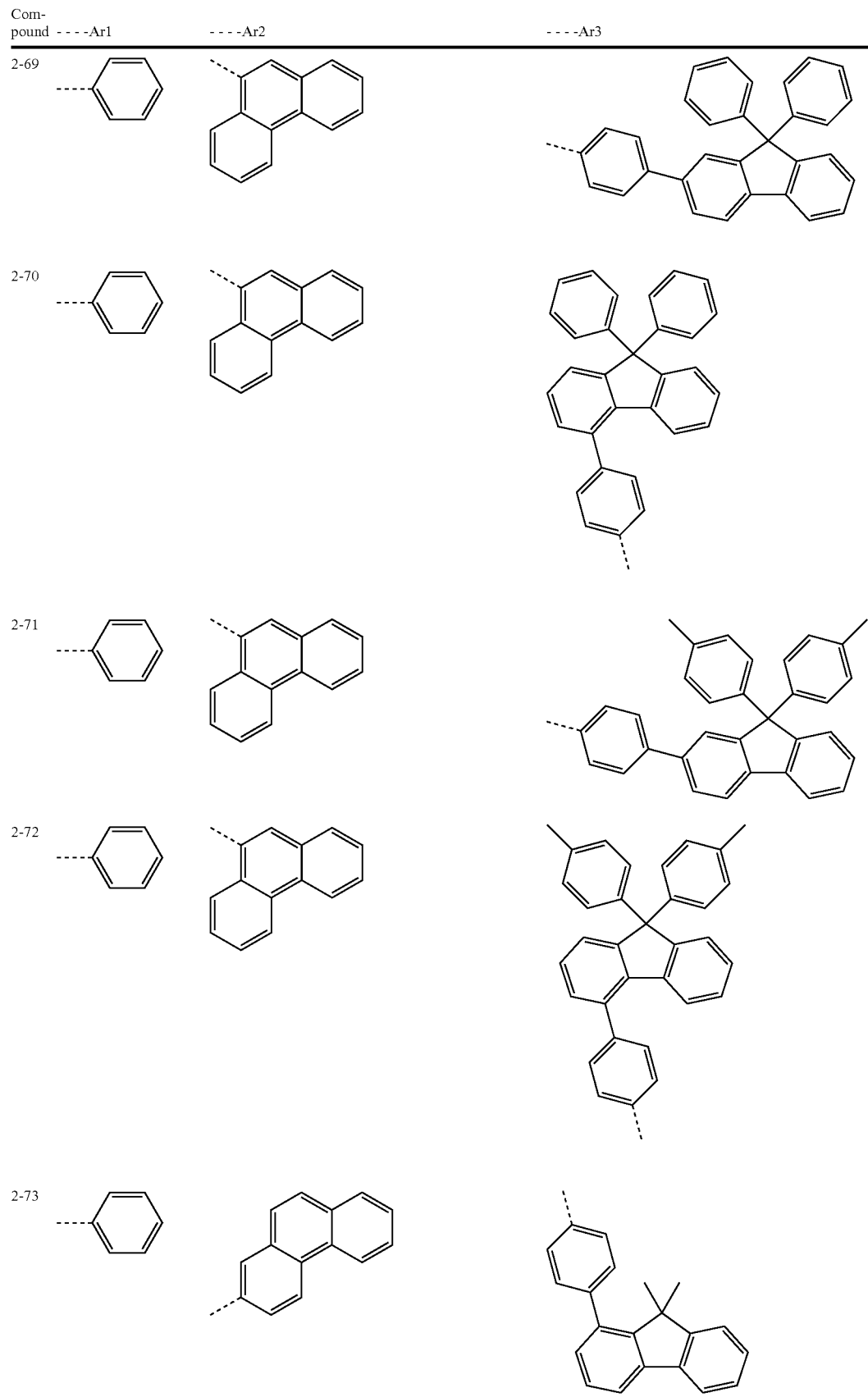

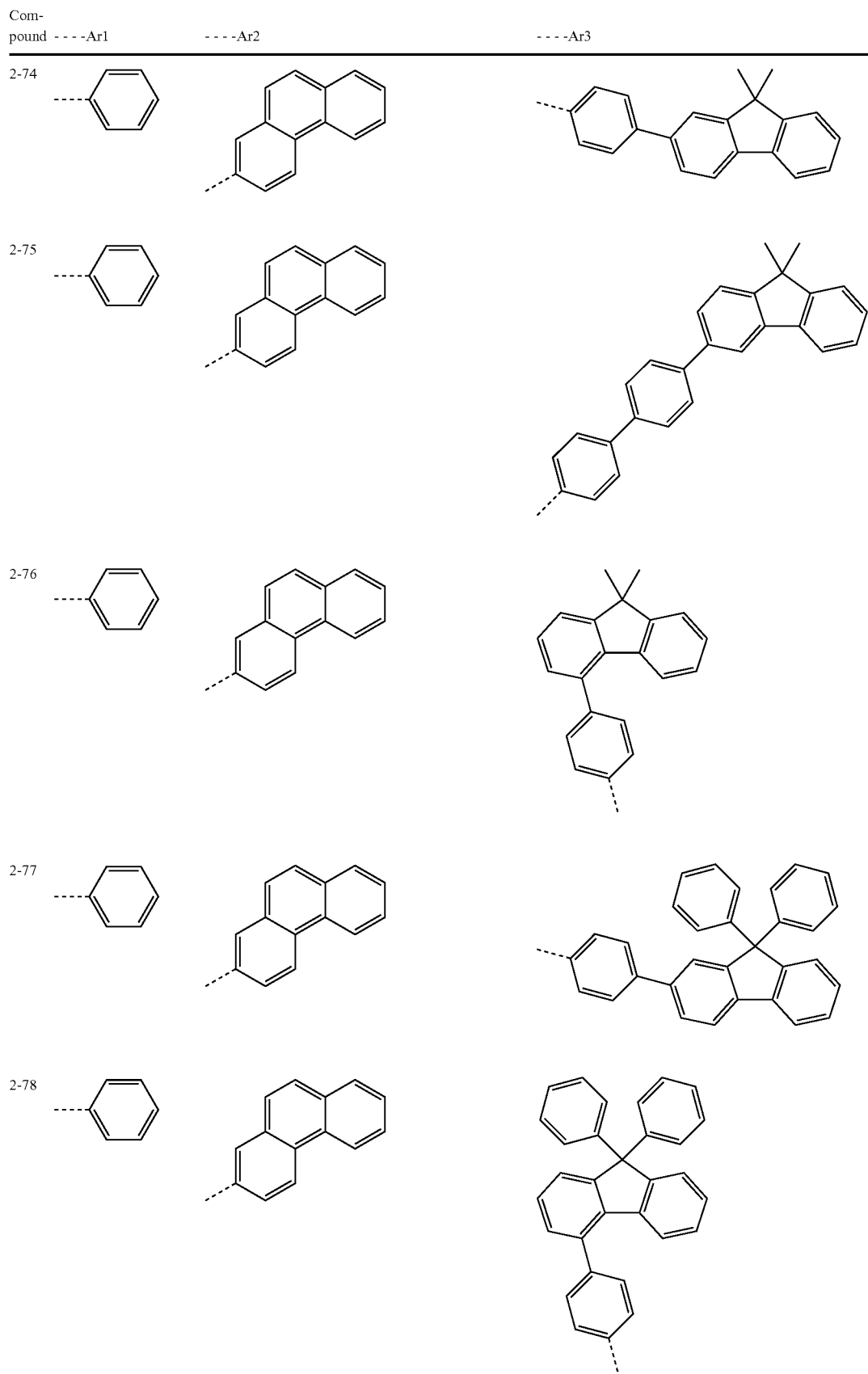

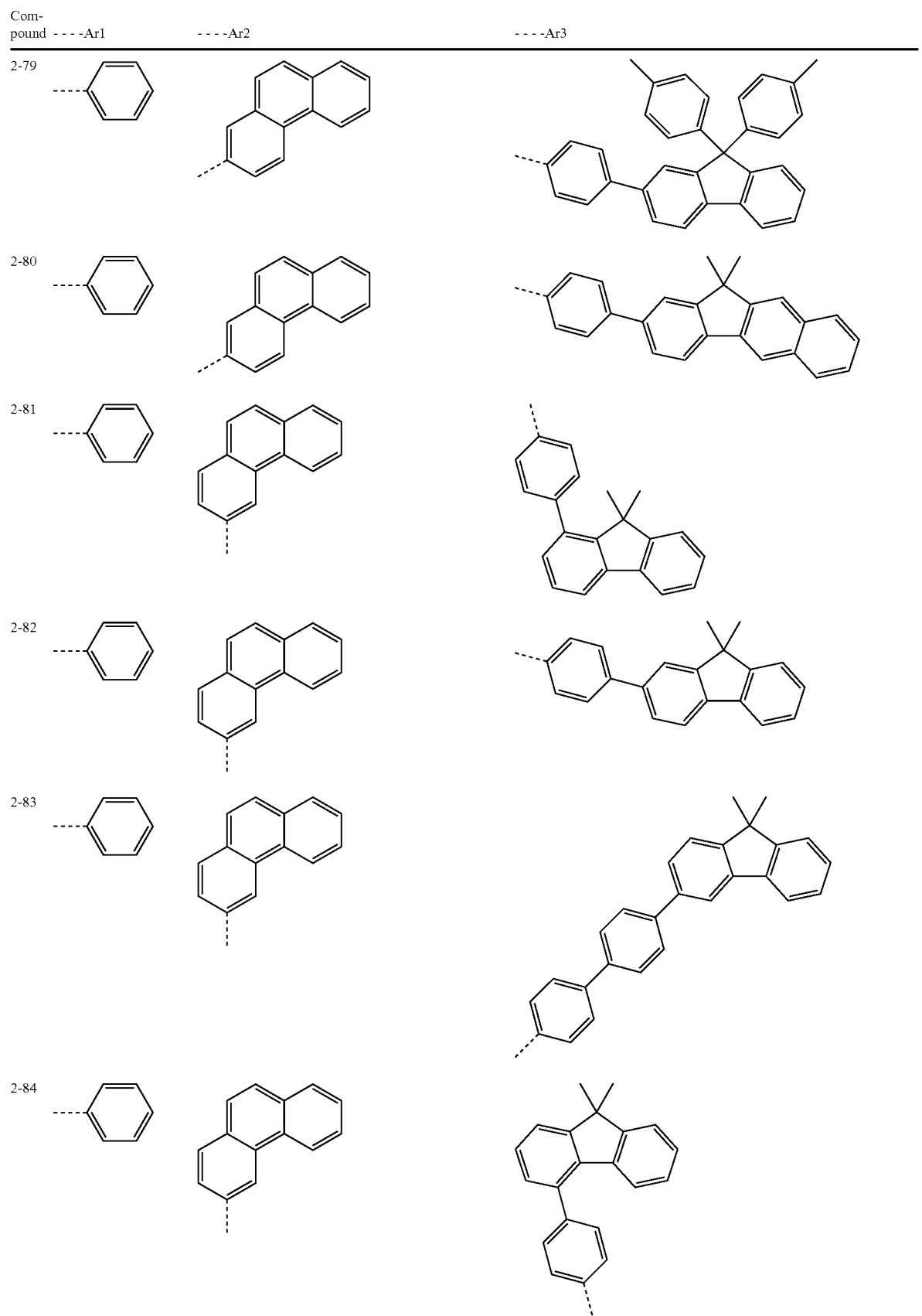

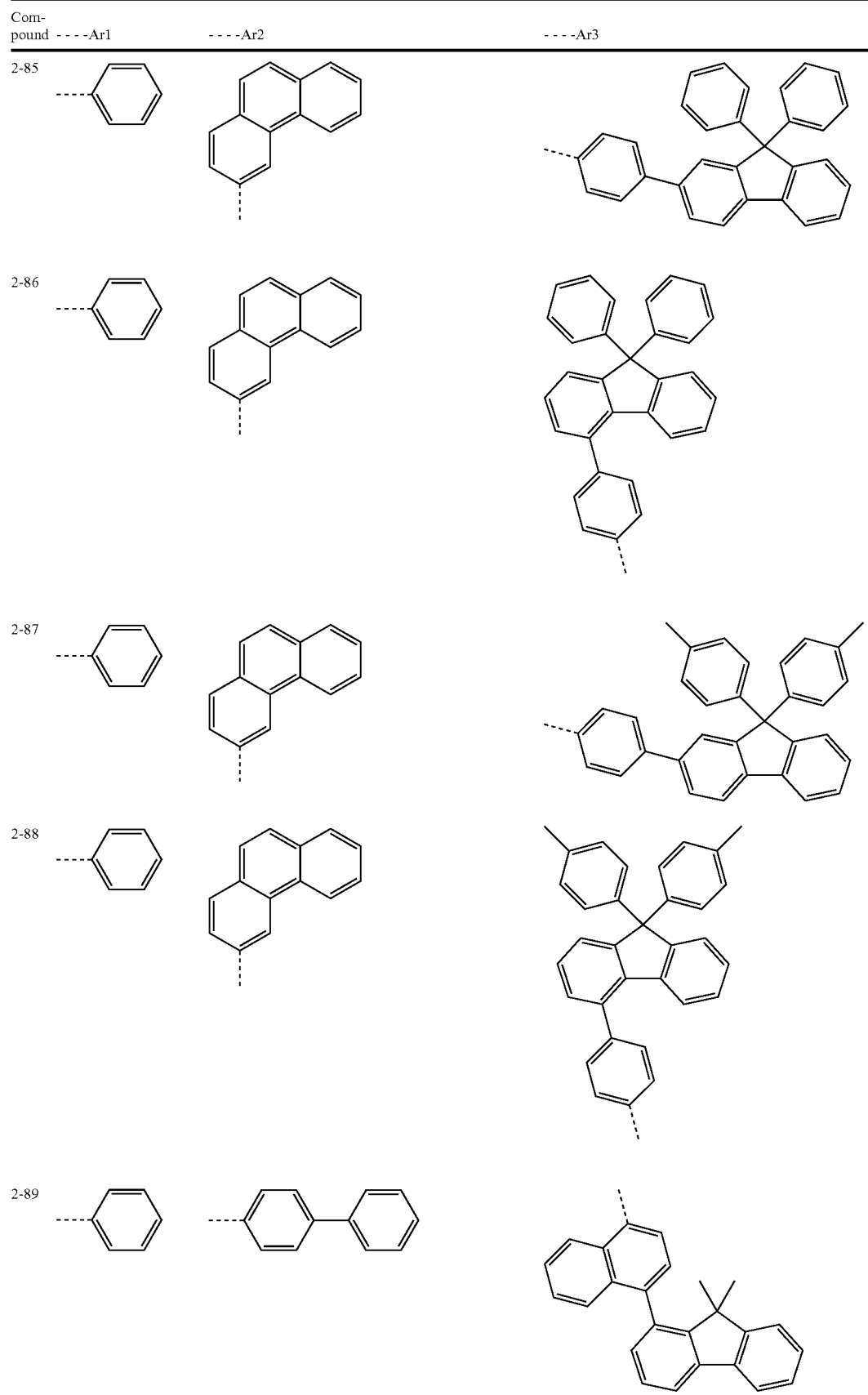

-continued
| Compound | ----Ar1 | ----Ar2 | ----Ar3 |
|---|---|---|---|
| 2-90 | 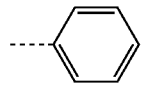 | 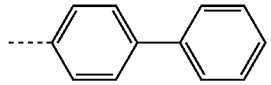 | 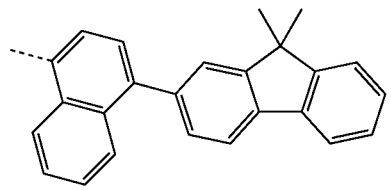 |
| 2-91 | 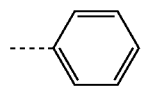 | 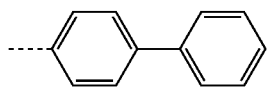 | 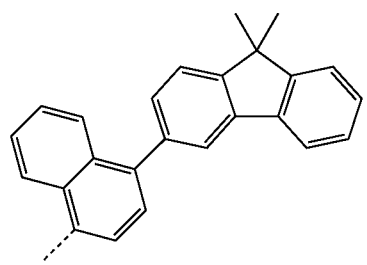 |
| 2-92 | 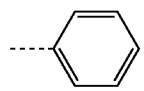 | 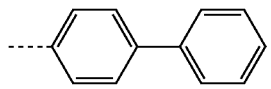 | 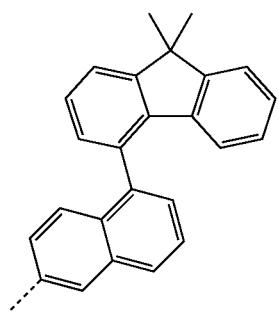 |
| 2-93 | 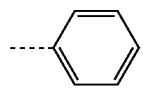 | 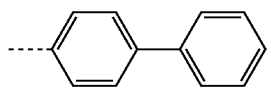 | 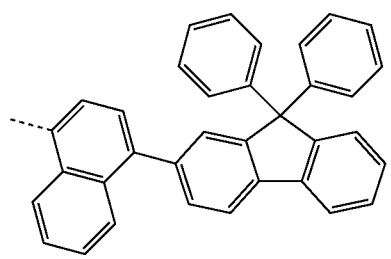 |
| 2-94 | 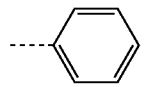 | 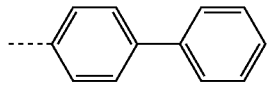 | 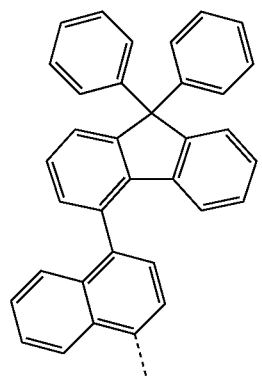 |

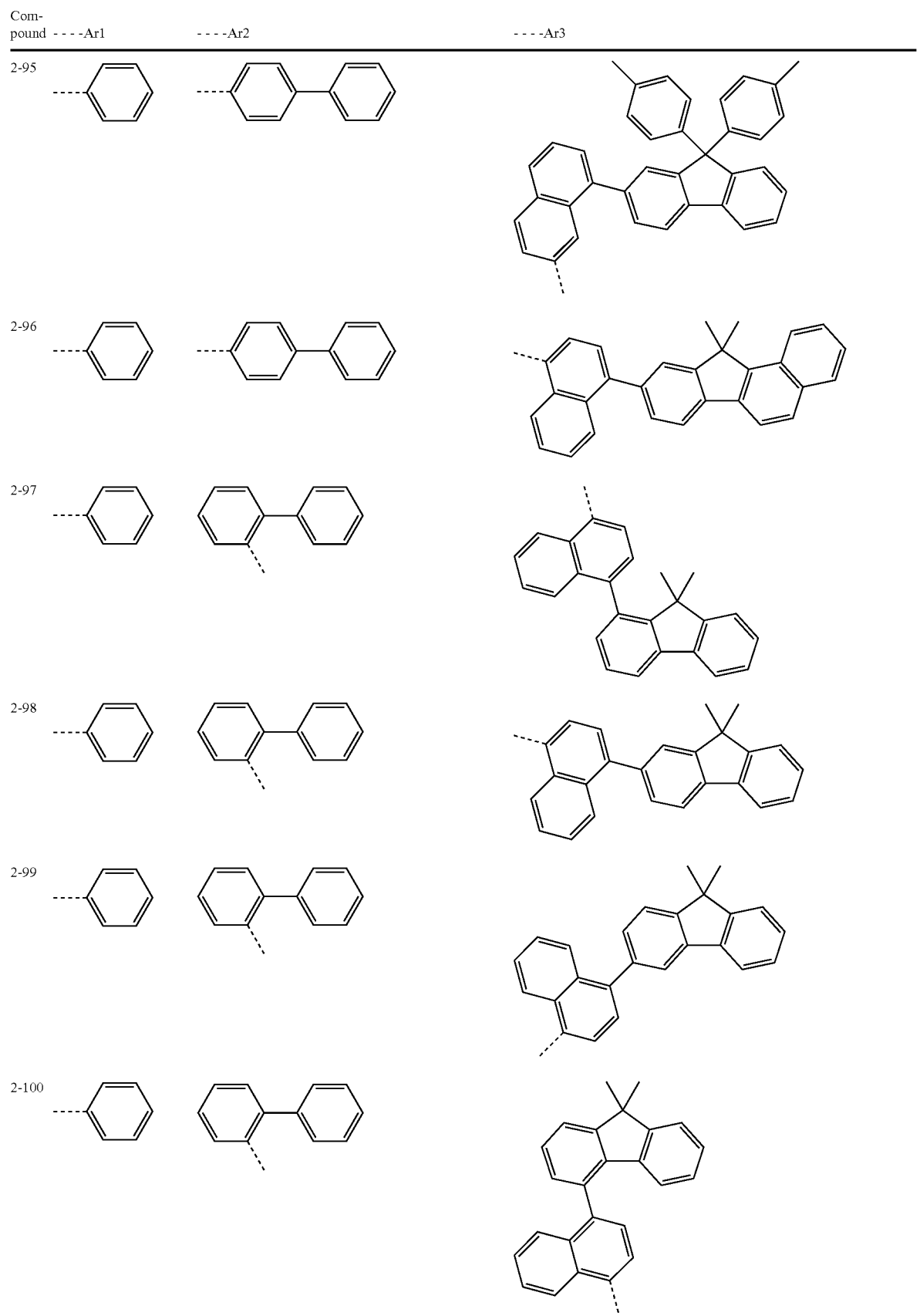

-continued
| Compound | ----Ar1 | ----Ar2 | ----Ar3 |
|---|---|---|---|
| 2-101 | 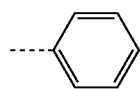 | 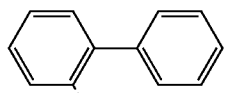 | 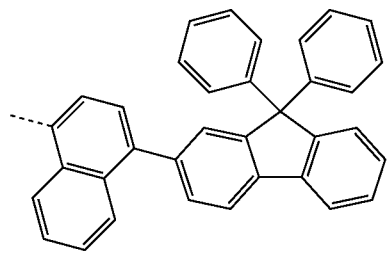 |
| 2-102 | 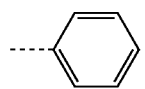 | 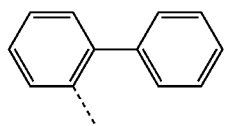 | 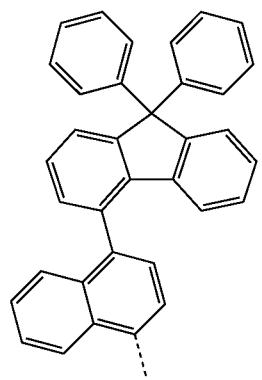 |
| 2-103 | 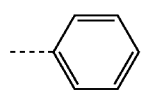 | 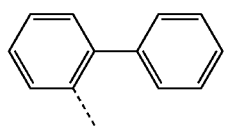 | 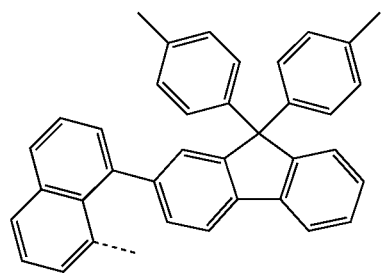 |
| 2-104 | 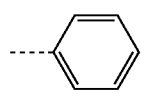 | 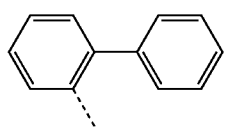 | 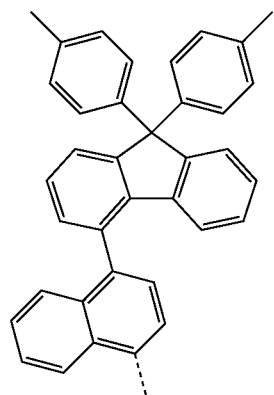 |

-continued
| Compound | ----Ar1 | ----Ar2 | ----Ar3 |
|---|---|---|---|
| 2-105 |  |  |  |
| 2-106 |  |  |  |
| 2-107 |  |  | 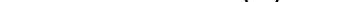 |
| 2-108 |  |  | 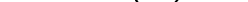 |
| 2-109 |  |  | 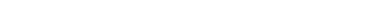 |

-continued
| Compound | ----Ar1 | ----Ar2 | ----Ar3 |
|---|---|---|---|
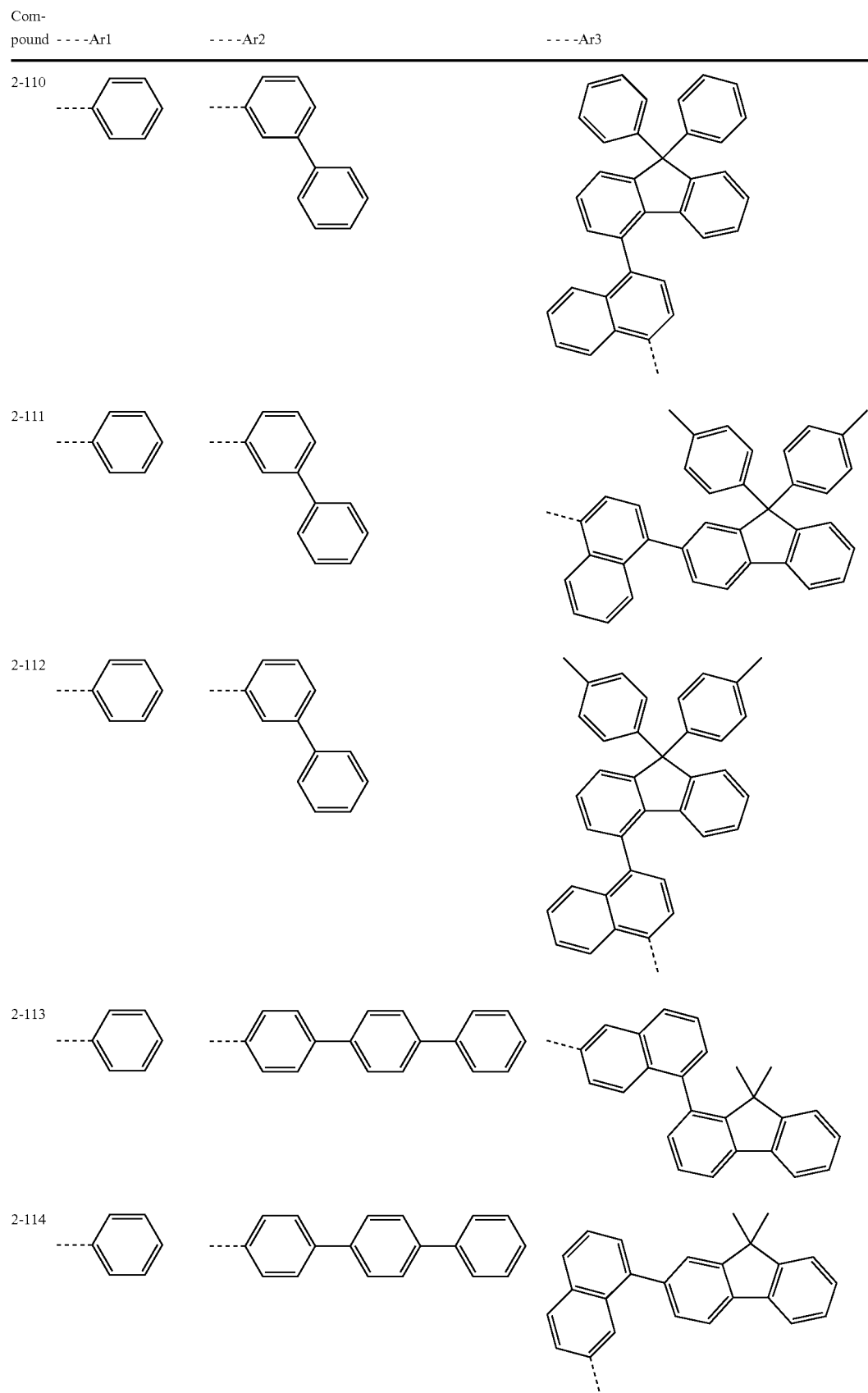

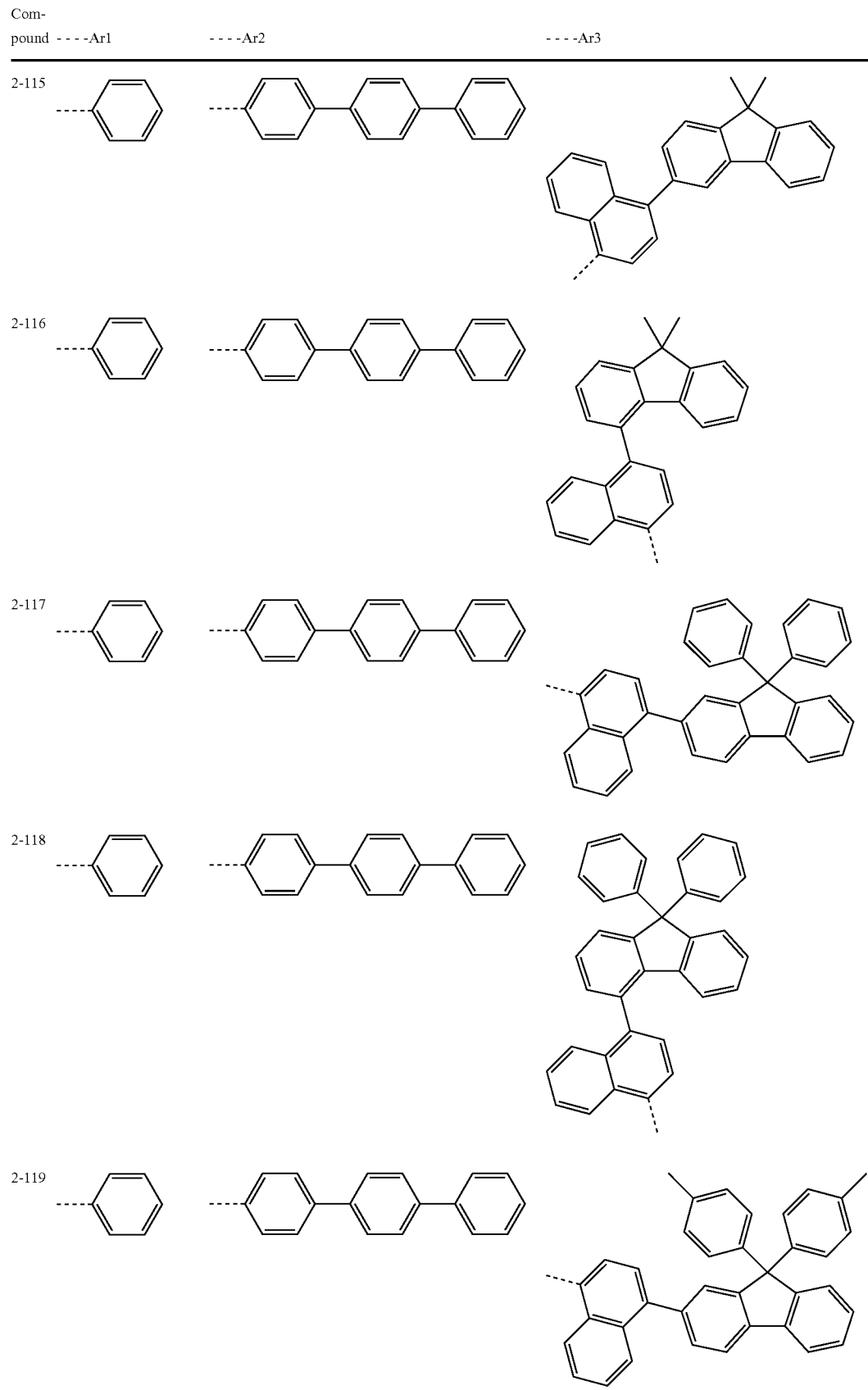

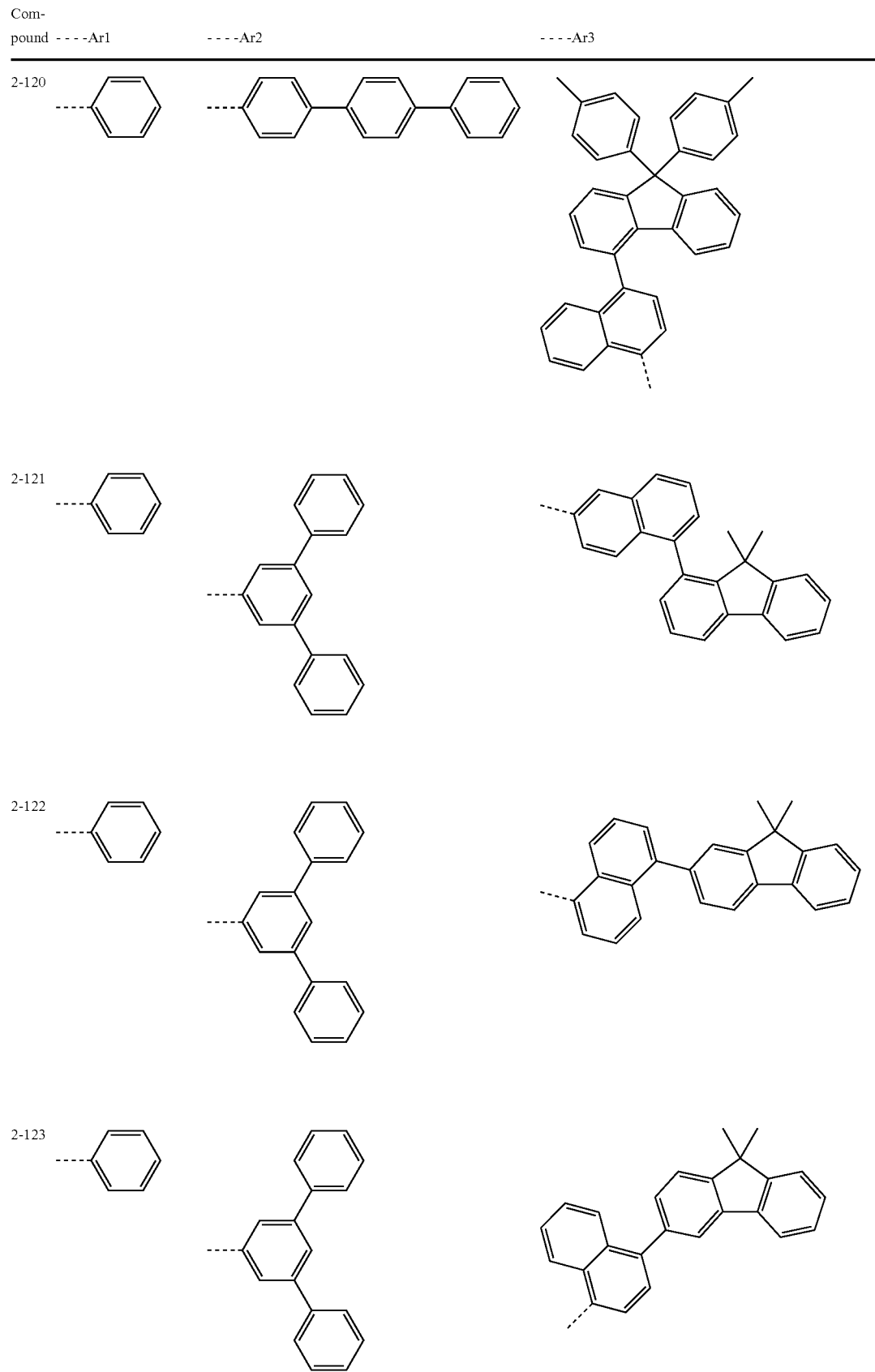

| Compound | ----Ar1 | ----Ar2 | ----Ar3 |
|---|---|---|---|
| 2-124 | 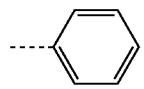 | 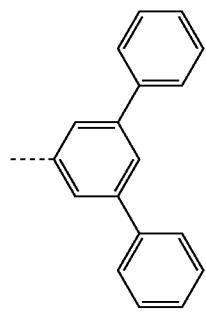 | 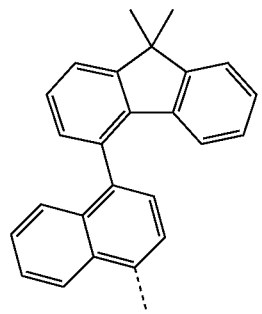 |
| 2-125 | 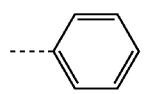 | 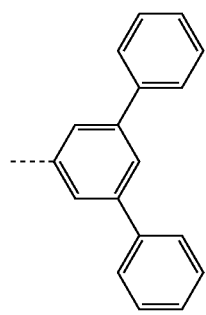 | 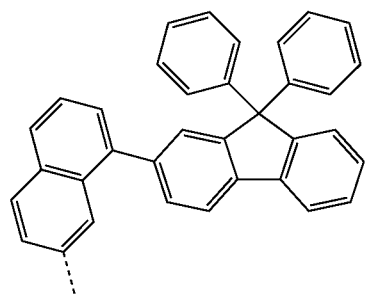 |
| 2-126 | 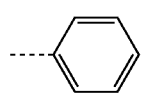 | 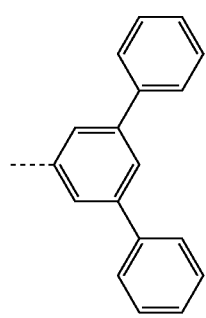 | 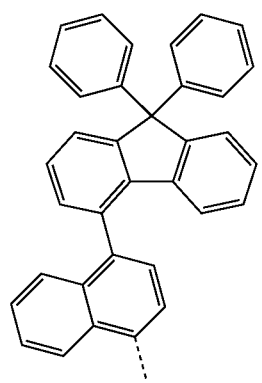 |
| 2-127 | 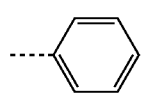 | 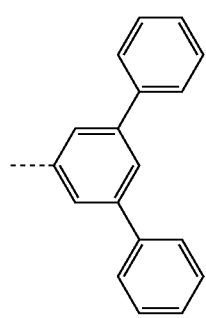 | 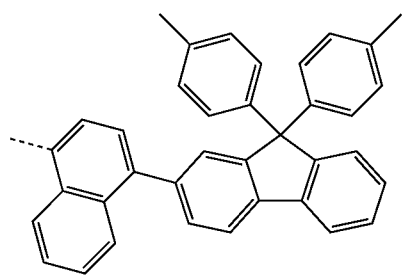 |

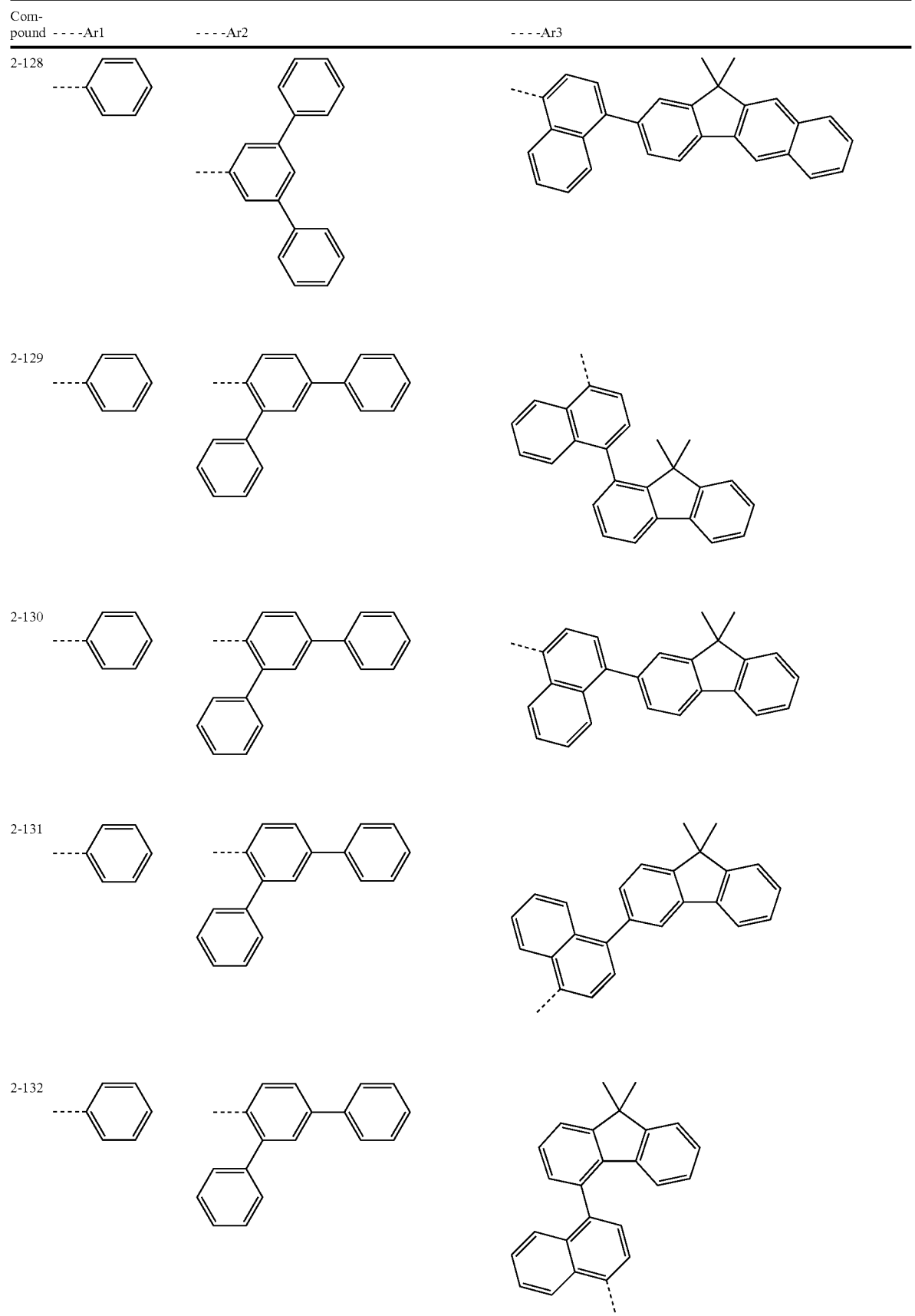

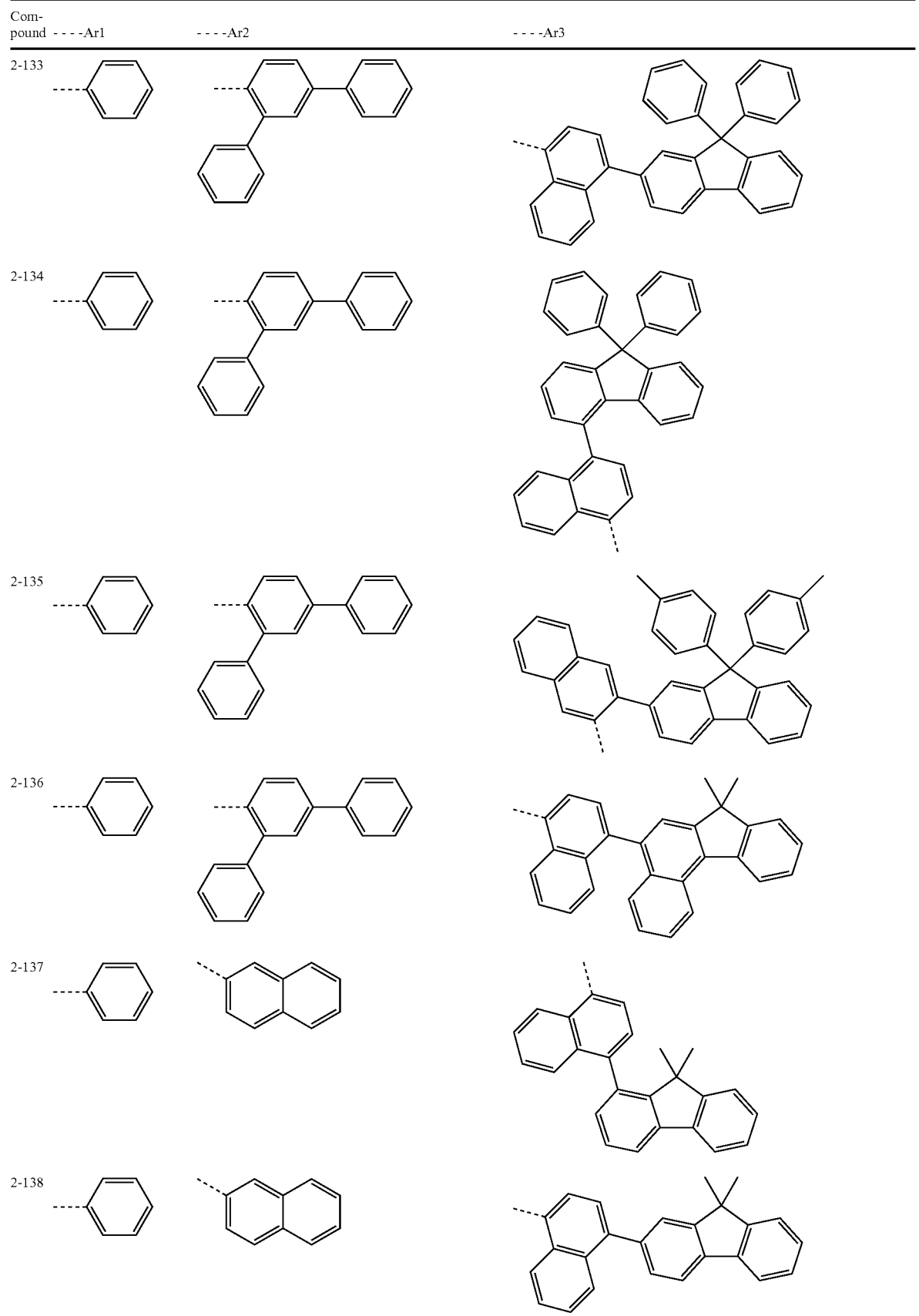

-continued
| Compound | ----Ar1 | ----Ar2 | ----Ar3 |
|---|---|---|---|
| 2-139 | 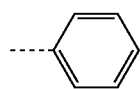 | 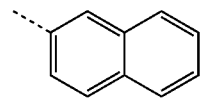 | 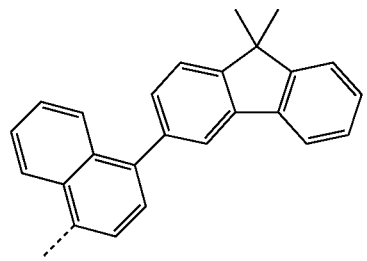 |
| 2-140 | 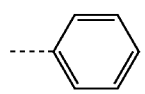 | 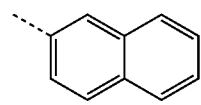 | 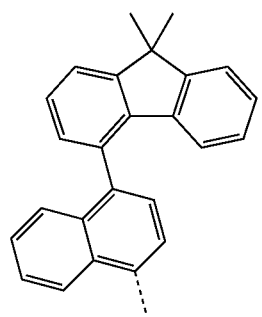 |
| 2-141 | 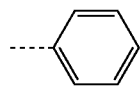 | 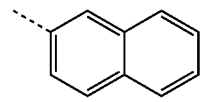 | 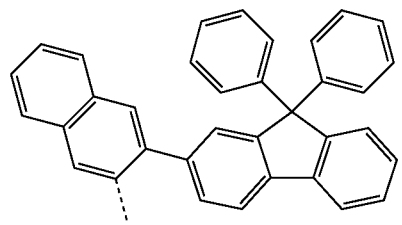 |
| 2-142 | 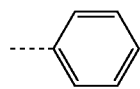 | 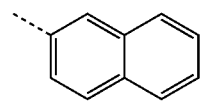 | 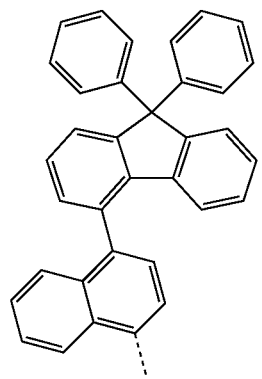 |
| 2-143 | 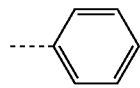 | 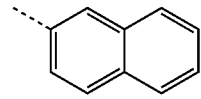 | 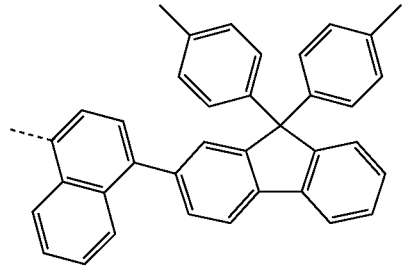 |

-continued
| Compound | ----Ar1 | ----Ar2 | ----Ar3 |
|---|---|---|---|
| 2-144 | 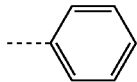 | 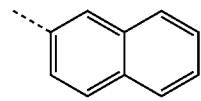 | 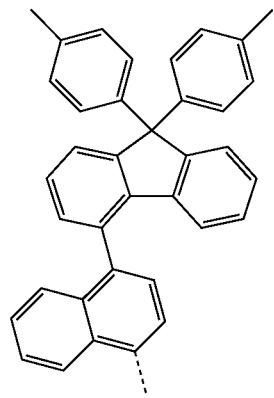 |
| 2-145 | 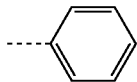 | 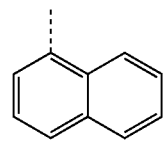 | 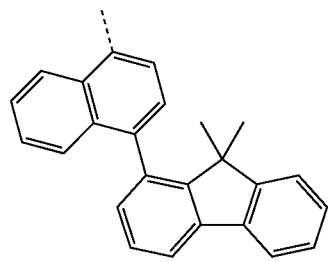 |
| 2-146 | 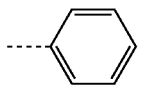 | 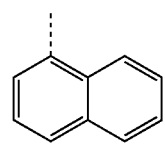 | 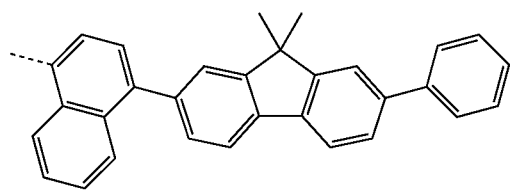 |
| 2-147 | 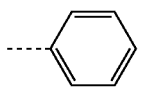 | 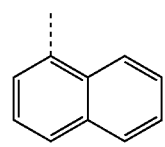 | 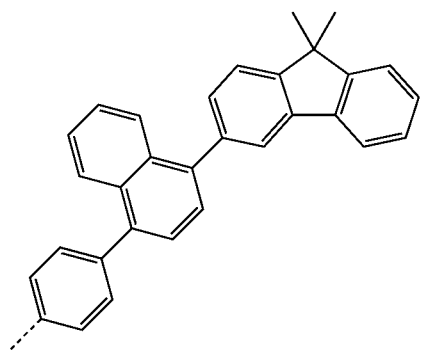 |
| 2-148 | 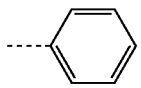 | 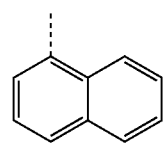 | 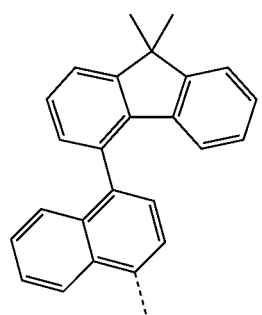 |

-continued
| Compound | ----Ar1 | ----Ar2 | ----Ar3 |
|---|---|---|---|
| 2-149 | | | |
| 2-150 | | | |
| 2-151 | | | |
| 2-152 | | | |
| 2-153 | | | |
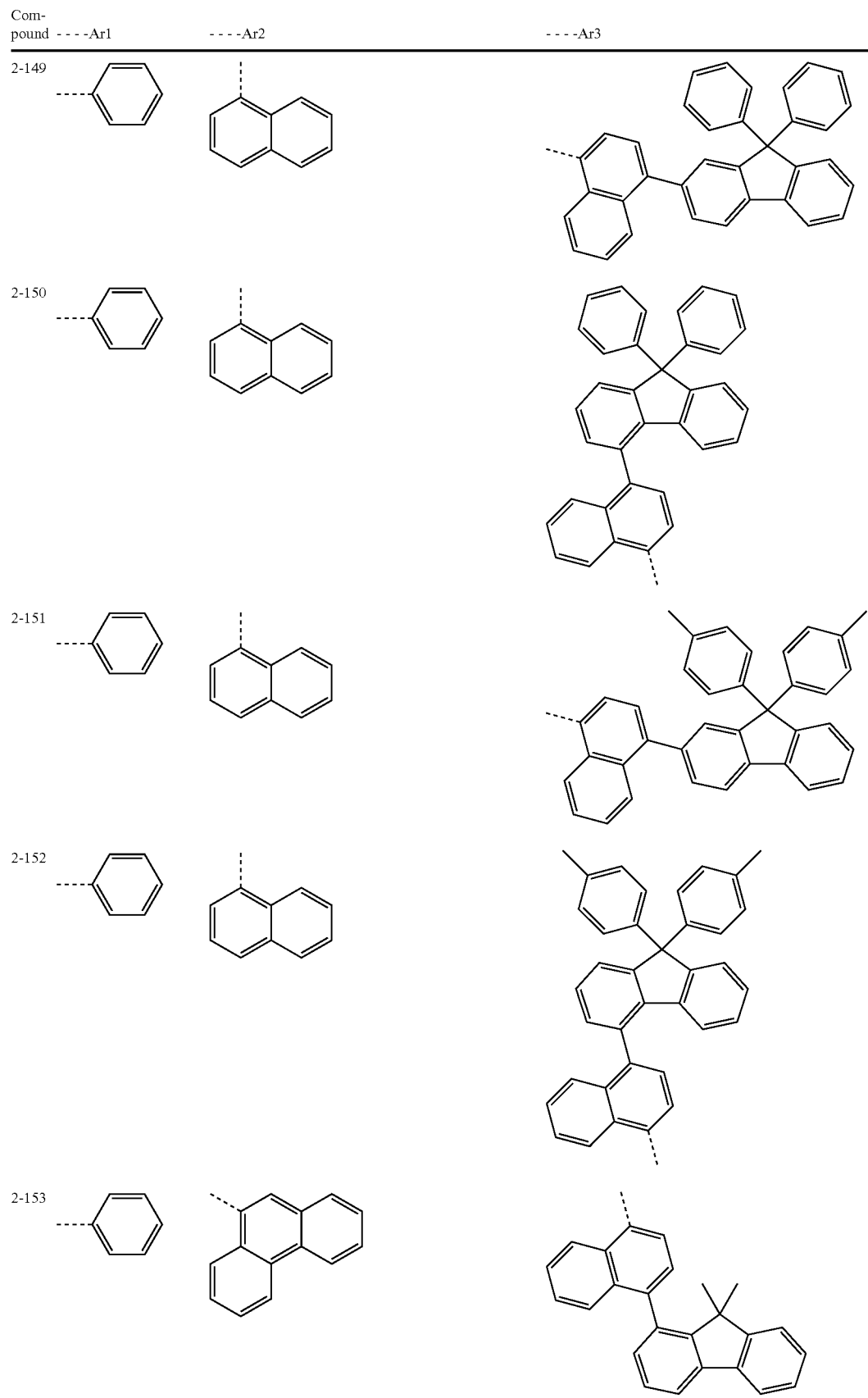

-continued
| Compound | ----Ar1 | ----Ar2 | ----Ar3 |
|---|---|---|---|
| 2-154 | 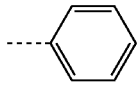 | 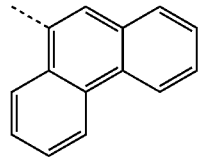 | 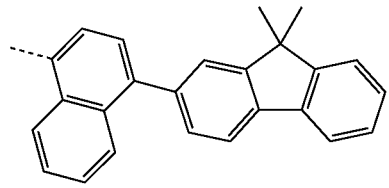 |
| 2-155 | 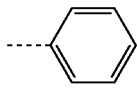 | 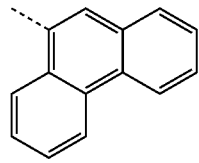 | 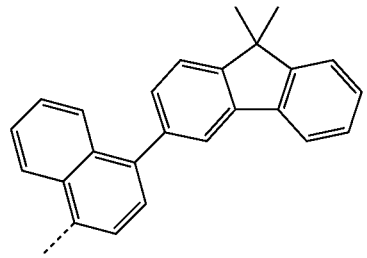 |
| 2-156 | 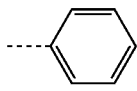 | 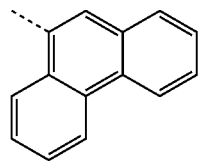 | 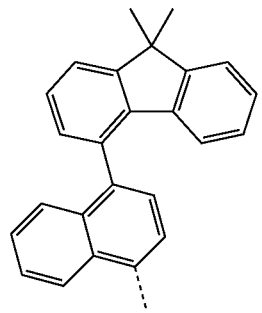 |
| 2-157 | 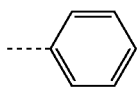 | 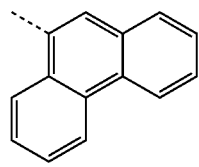 | 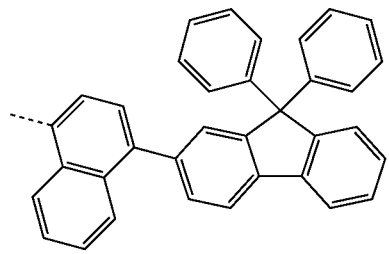 |
| 2-158 | 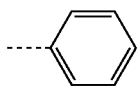 | 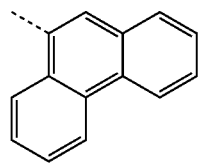 | 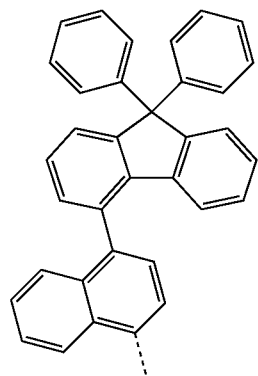 |

-continued
| Compound | ----Ar1 | ----Ar2 | ----Ar3 |
|---|---|---|---|
| 2-159 | 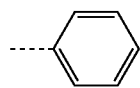 | 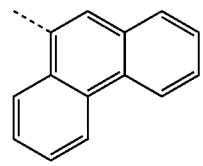 | 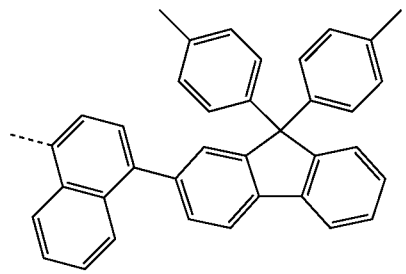 |
| 2-160 | 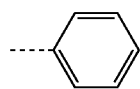 | 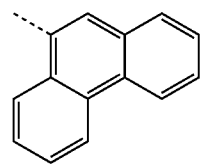 | 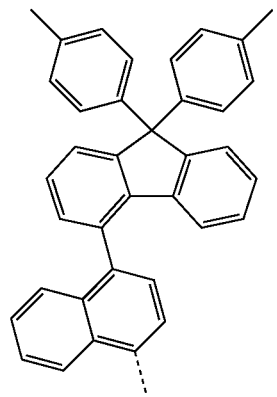 |
| 2-161 | 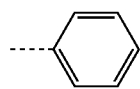 | 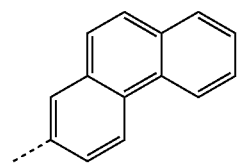 | 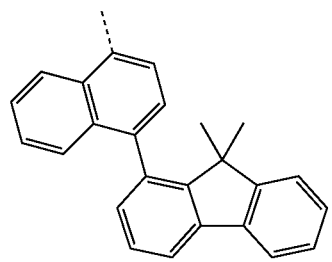 |
| 2-162 | 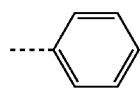 | 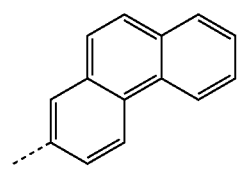 | 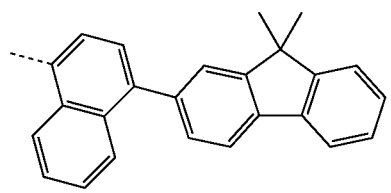 |
| 2-163 | 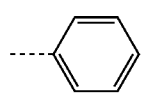 | 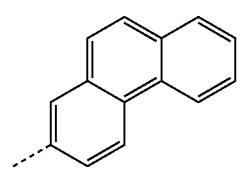 | 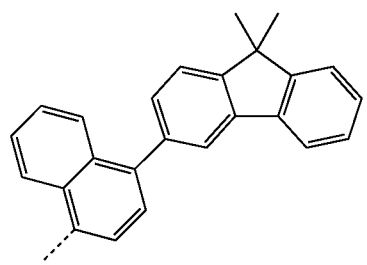 |

-continued
| Com-pound | ----Ar1 | ----Ar2 | ----Ar3 |
|---|---|---|---|
| 2-164 | 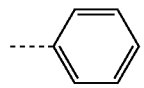 | 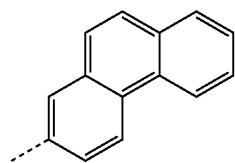 | 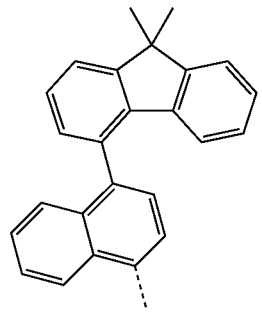 |
| 2-165 | 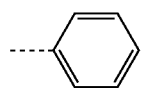 | 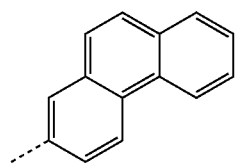 | 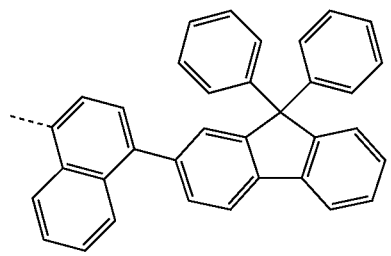 |
| 2-166 | 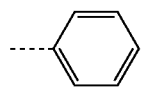 | 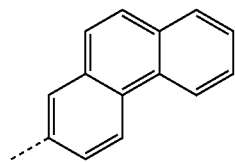 | 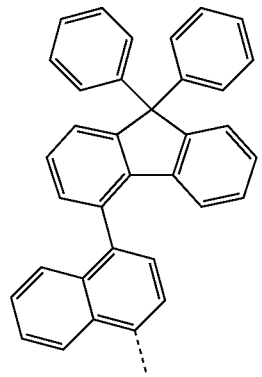 |
| 2-167 | 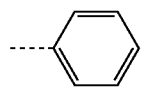 | 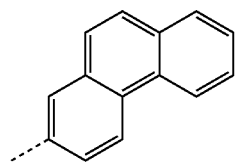 | 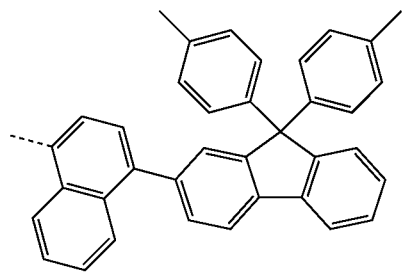 |

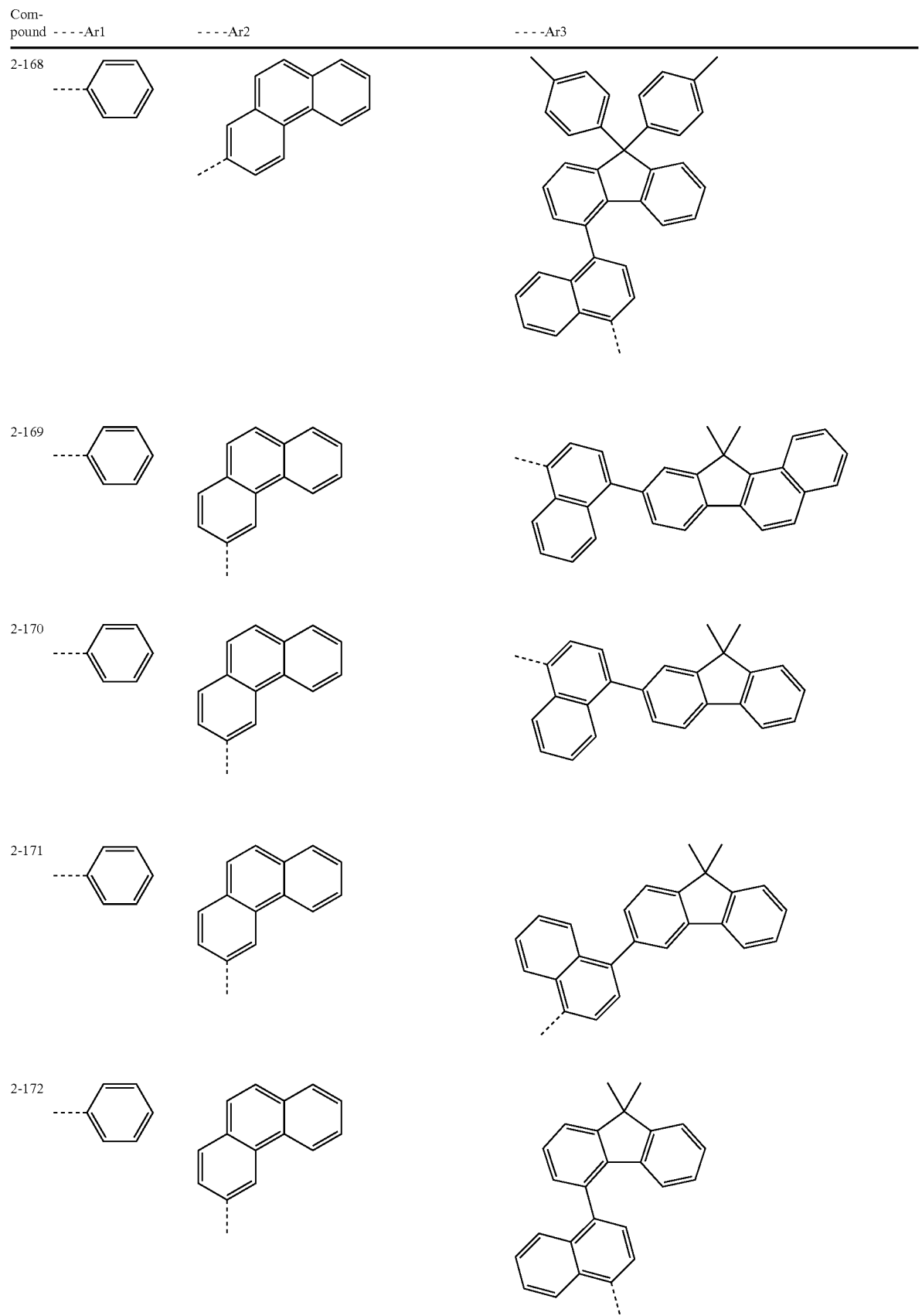

-continued
| Compound | ----Ar1 | ----Ar2 | ----Ar3 |
|---|---|---|---|
2-173
2-174
2-175
2-176
2-177
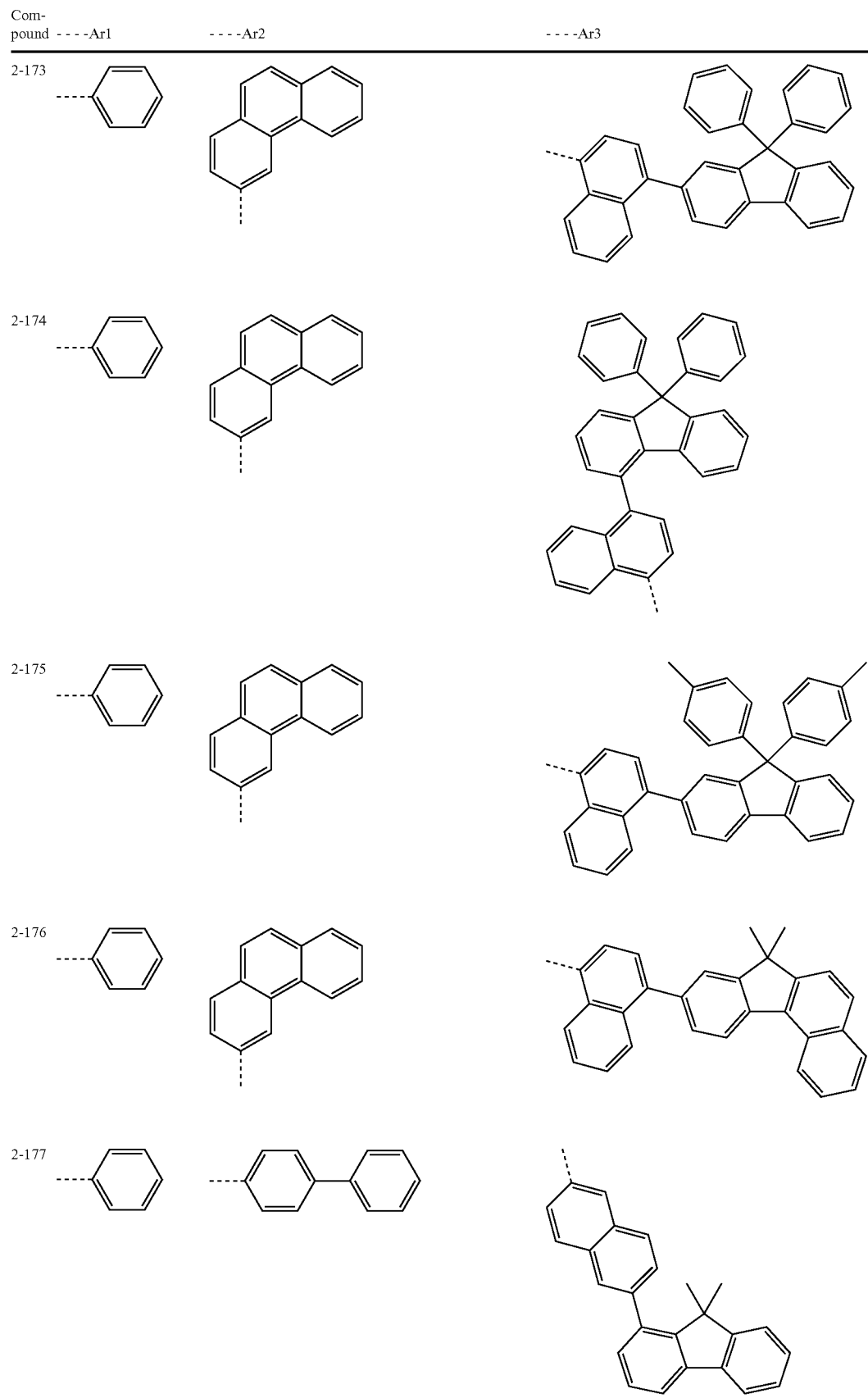

| Compound | ----Ar1 | ----Ar2 | ----Ar3 |
|---|---|---|---|
| 2-178 | 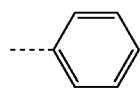 | 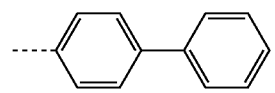 | 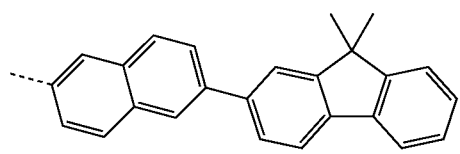 |
| 2-179 | 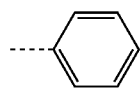 | 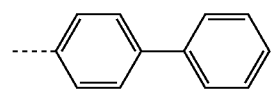 | 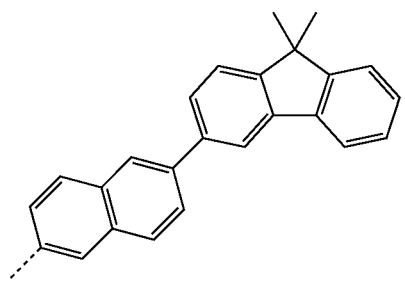 |
| 2-180 | 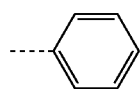 | 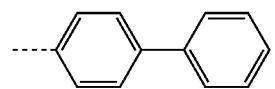 | 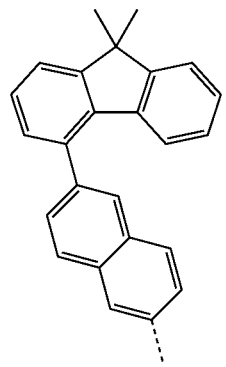 |
| 2-181 | 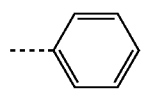 | 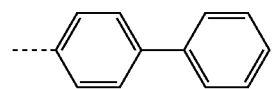 | 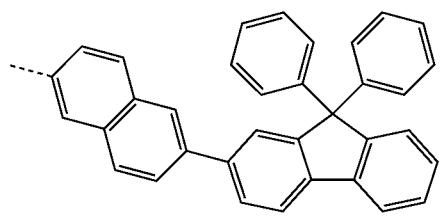 |
| 2-182 | 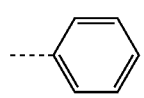 | 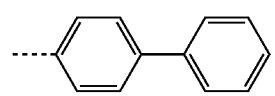 | 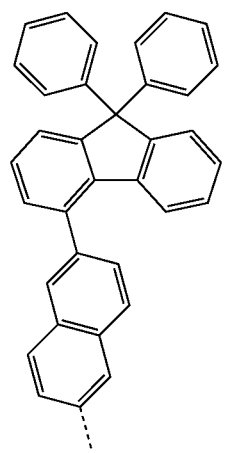 |

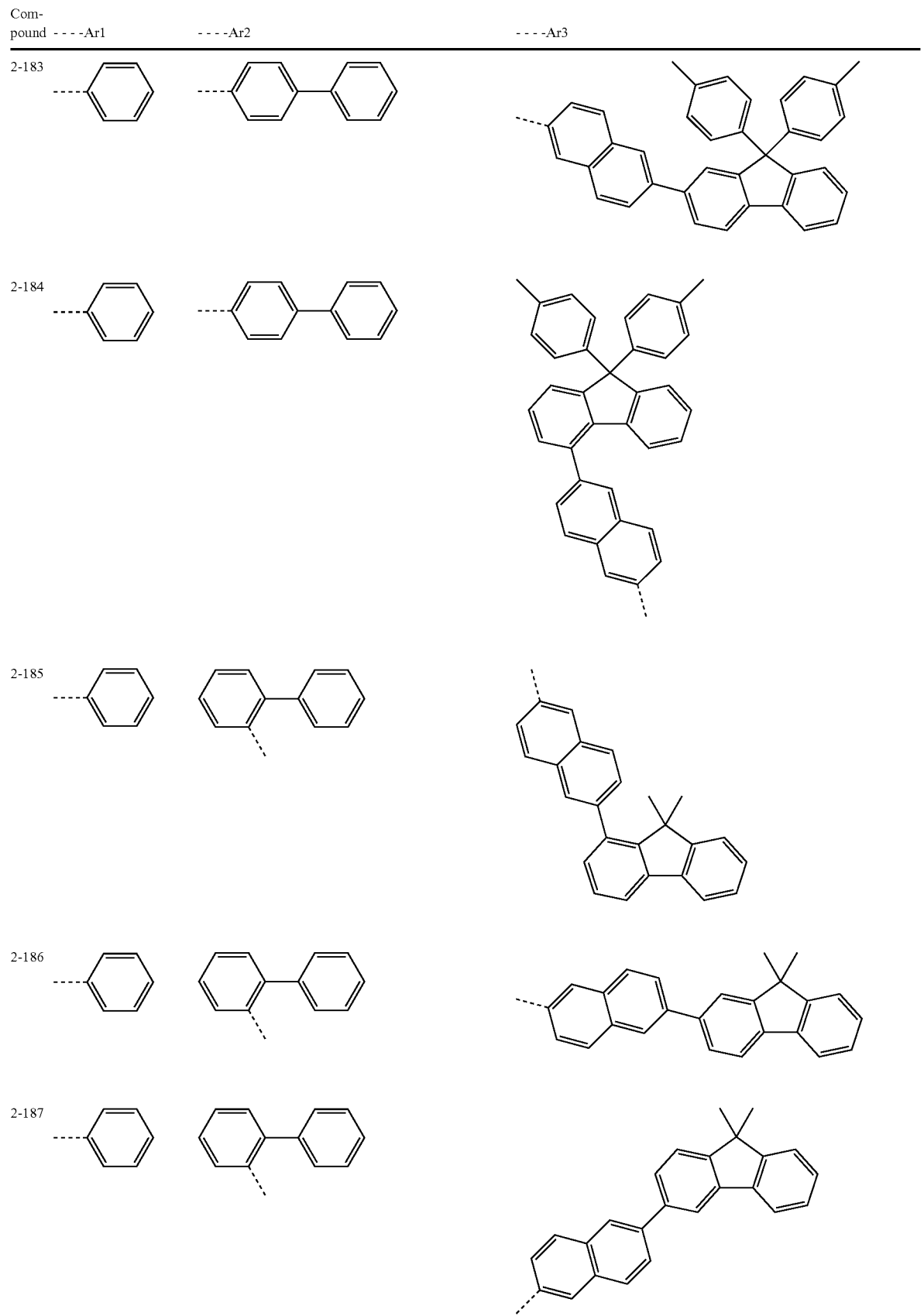

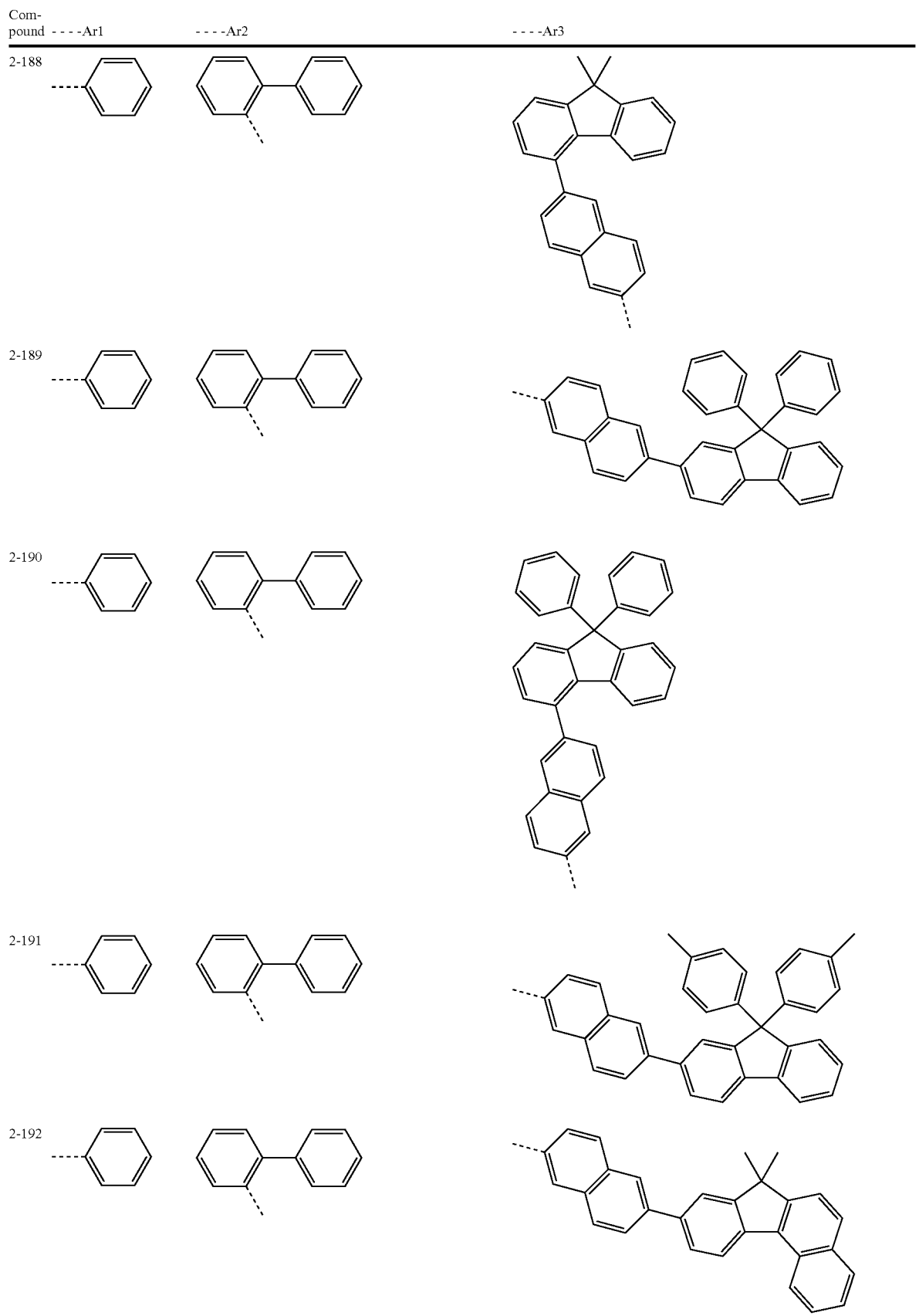

-continued
| Compound | ----Ar1 | ----Ar2 | ----Ar3 |
|---|---|---|---|
| 2-193 | | | |
| 2-194 | | | |
| 2-195 | | | |
| 2-196 | | | |
| 2-197 | | | |
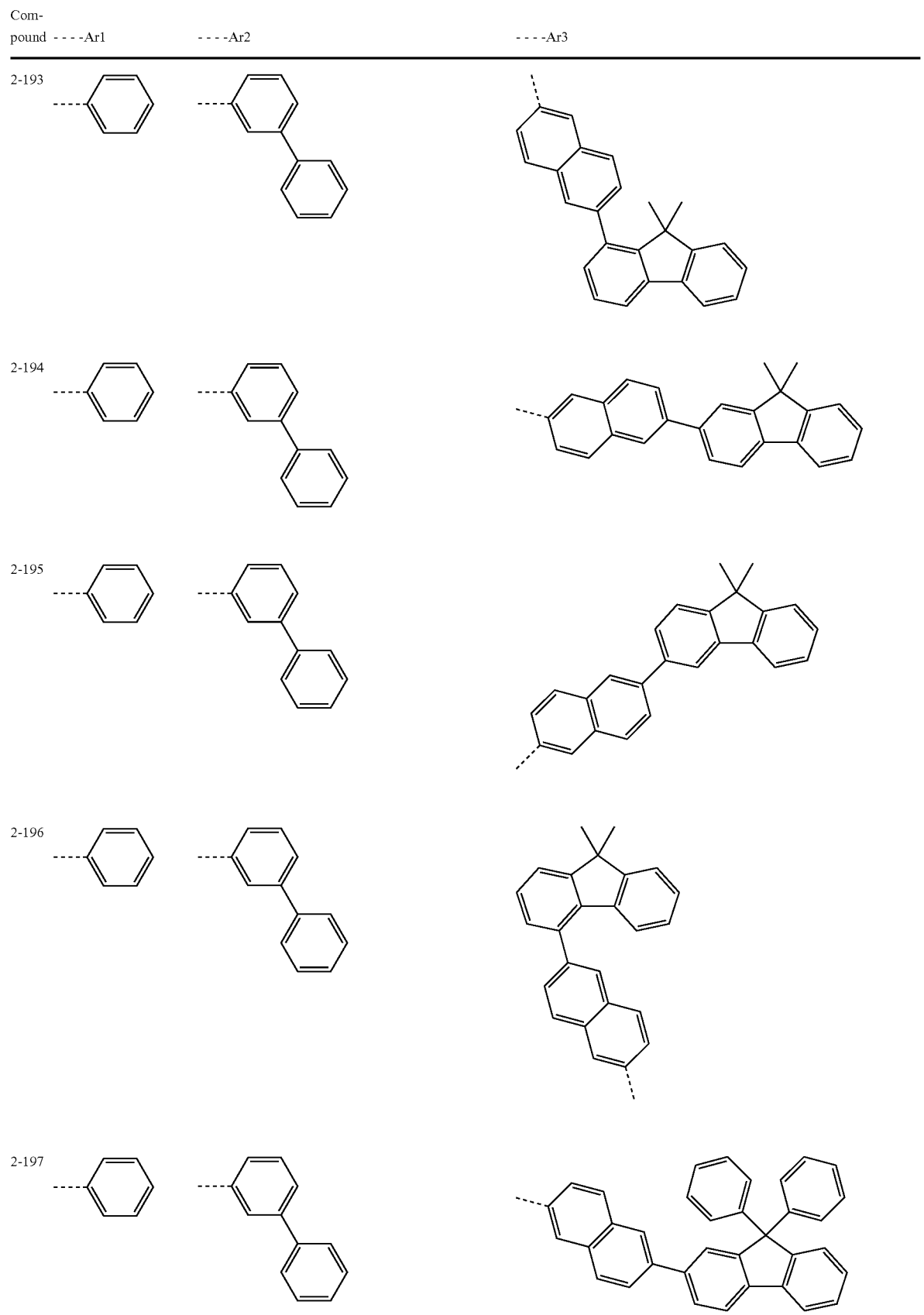

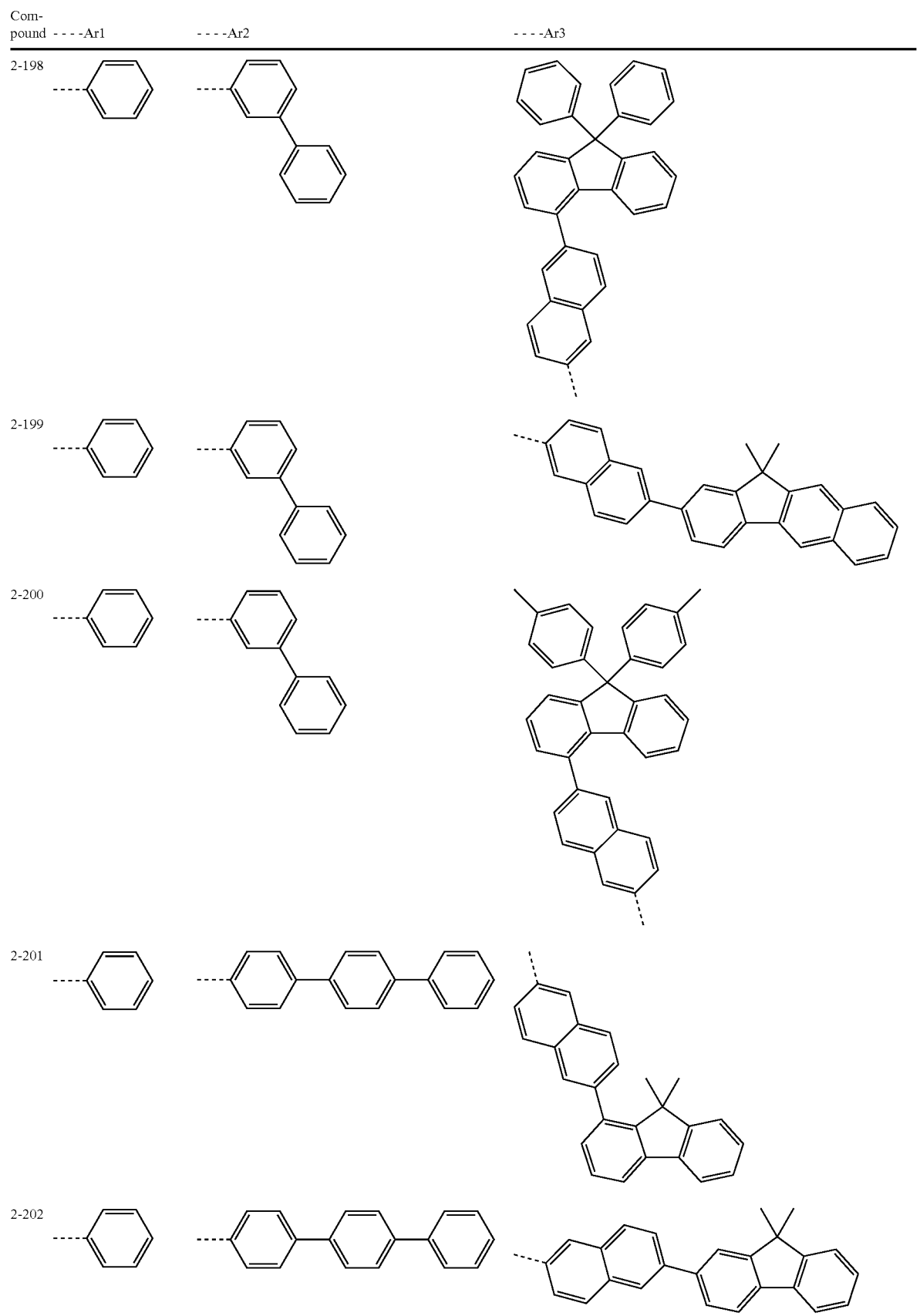

-continued
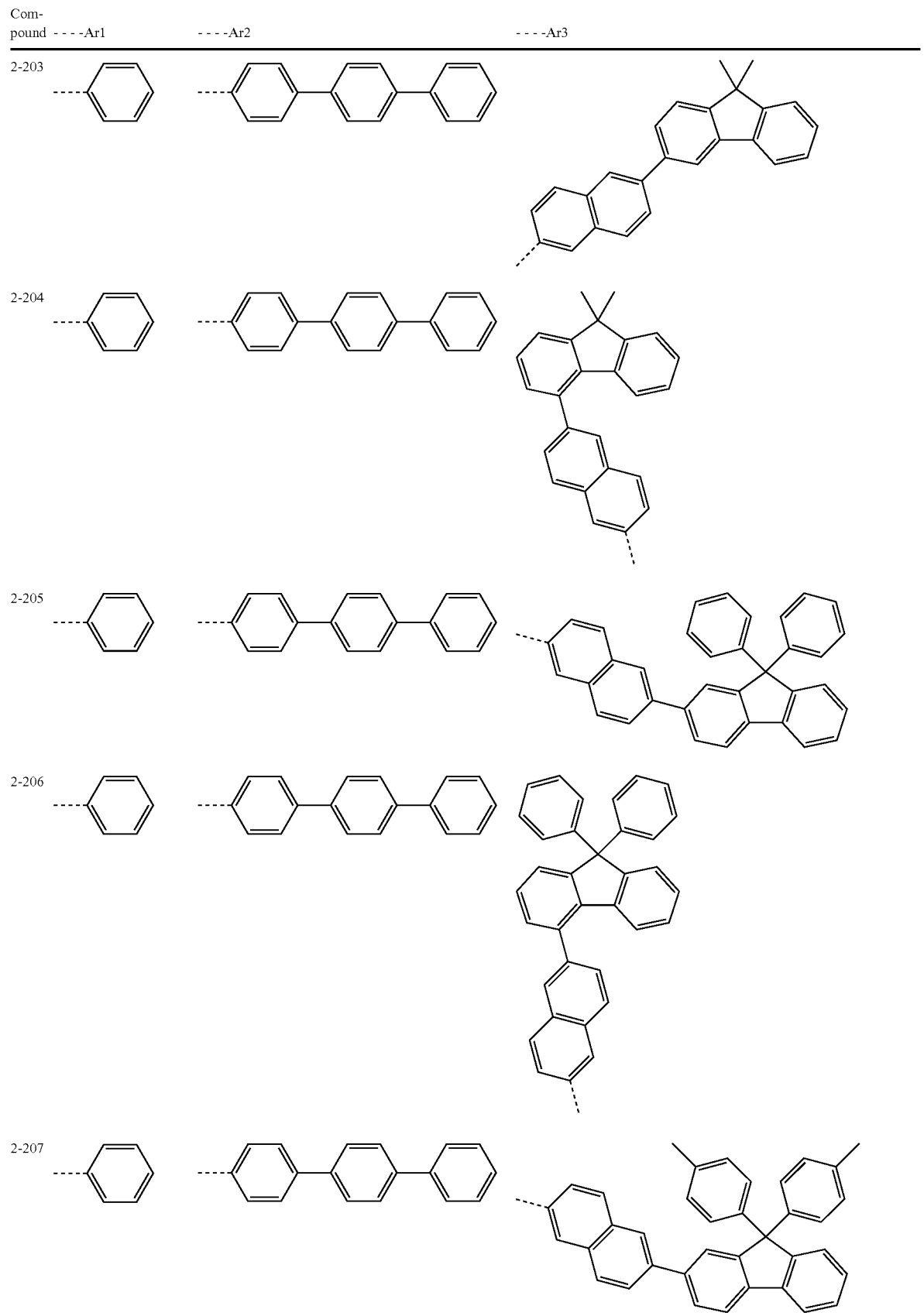

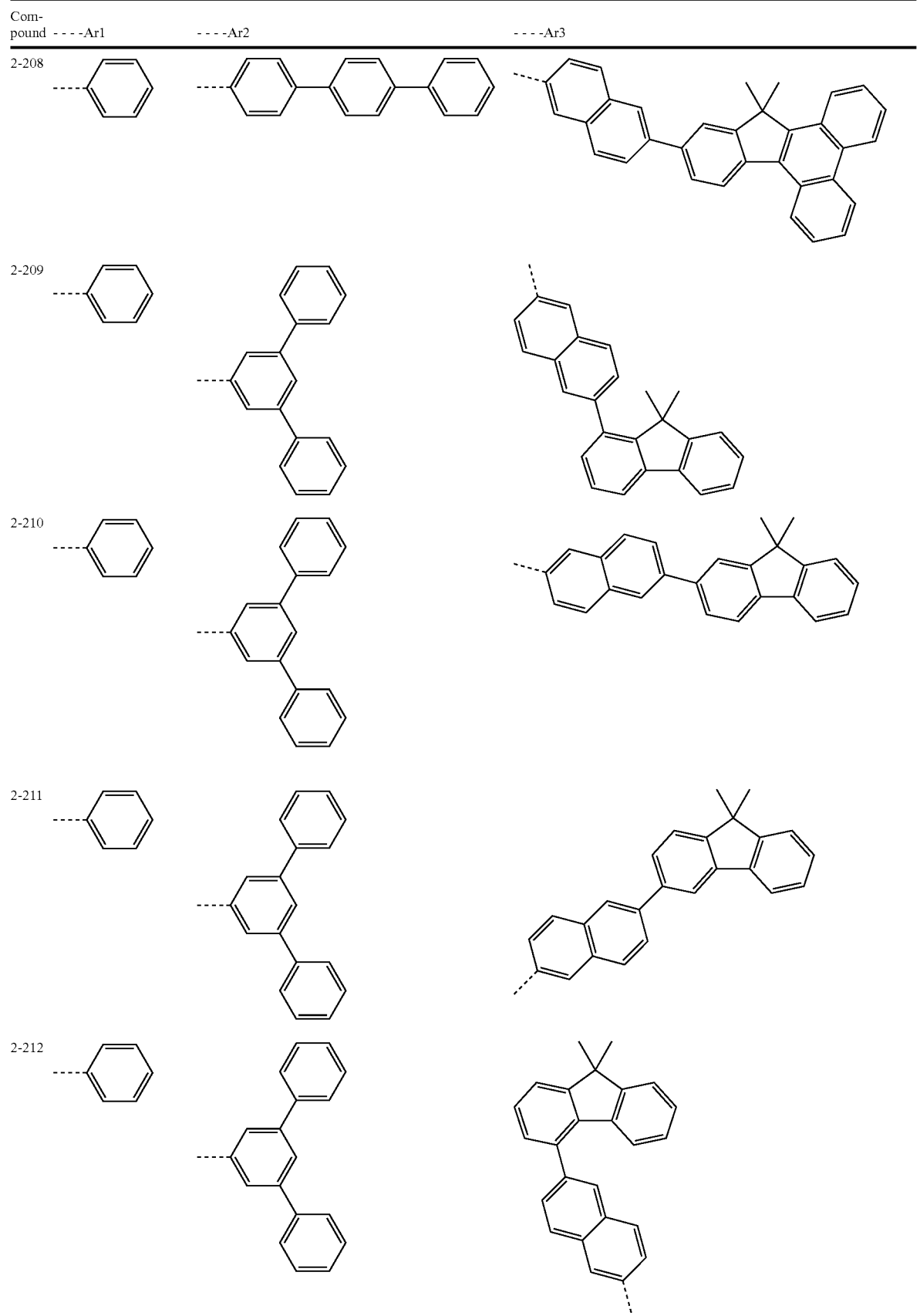

-continued
| Compound | ----Ar1 | ----Ar2 | ----Ar3 |
|---|---|---|---|
| 2-213 | 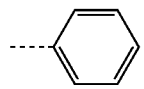 | 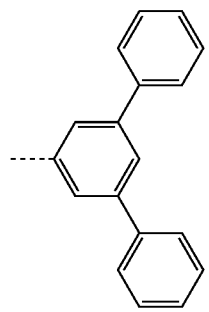 | 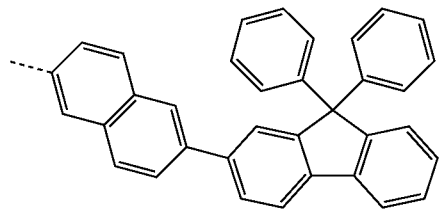 |
| 2-214 | 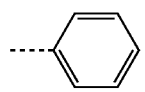 | 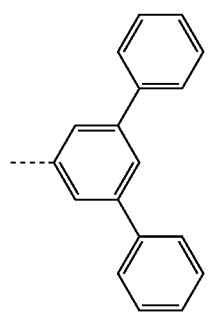 | 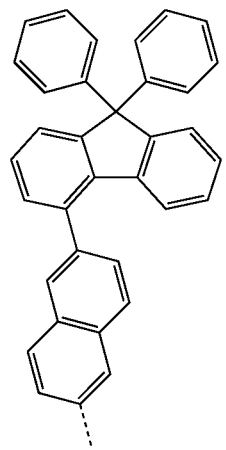 |
| 2-215 | 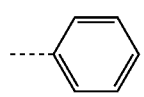 | 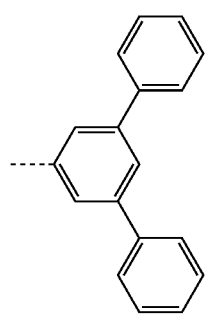 | 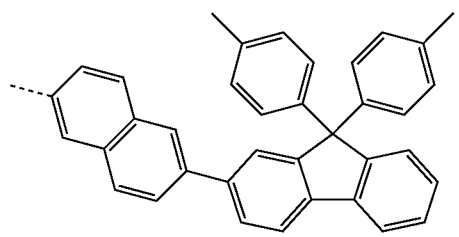 |
| 2-216 | 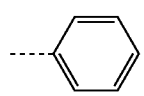 | 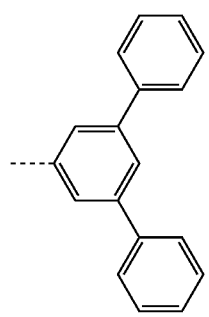 | 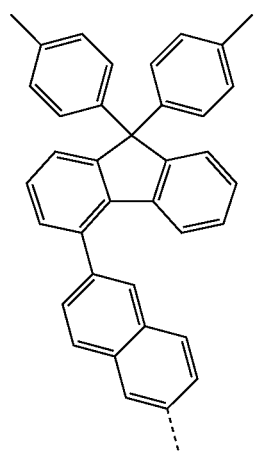 |

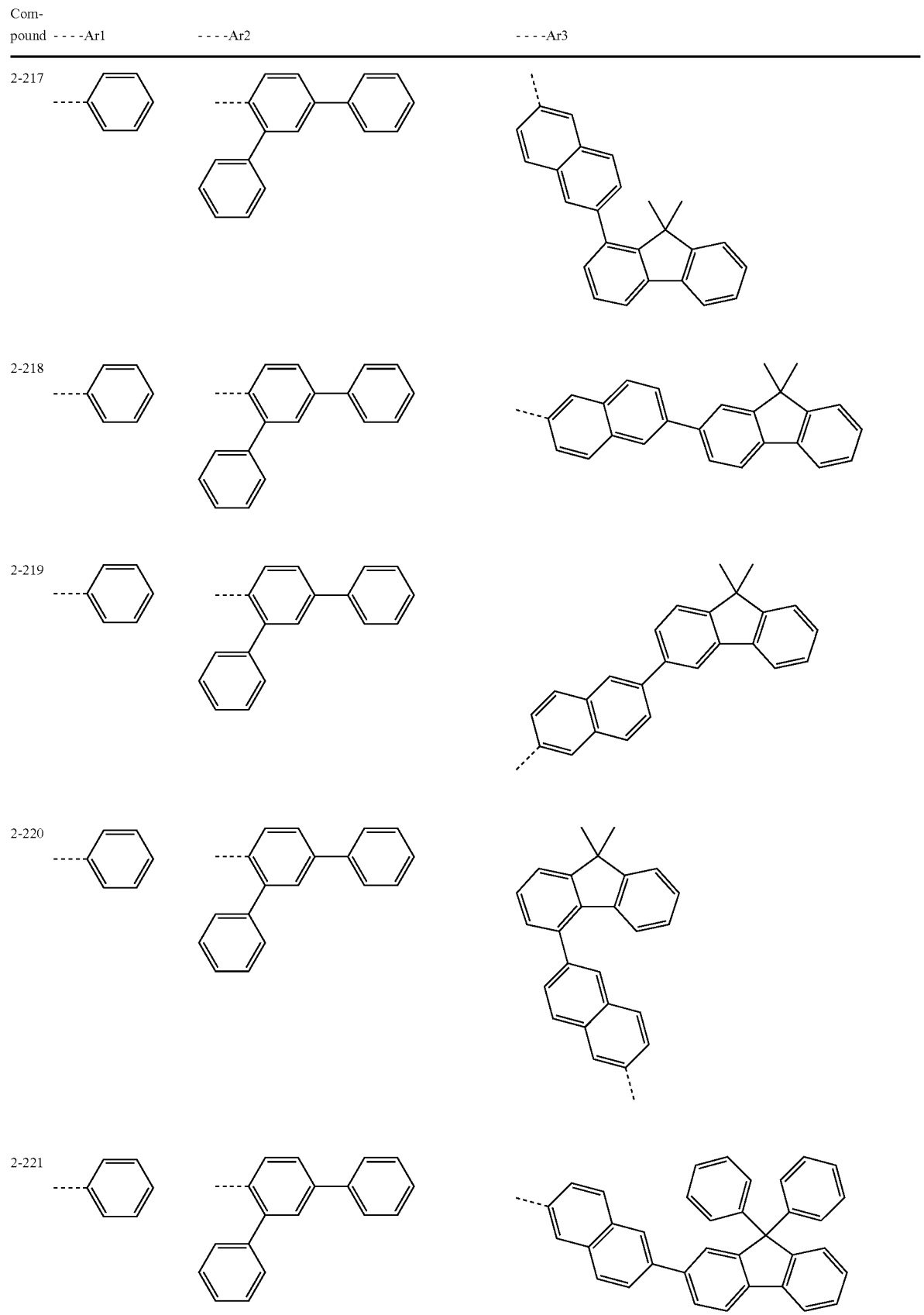

-continued
| Compound | ----Ar1 | ----Ar2 | ----Ar3 |
|---|---|---|---|
| 2-222 | 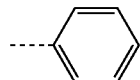 | 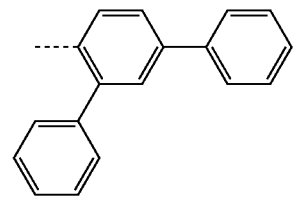 | 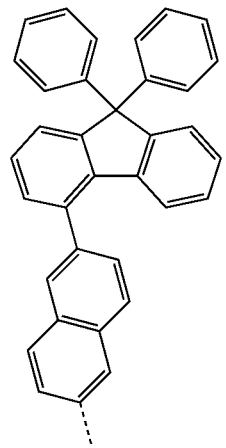 |
| 2-223 | 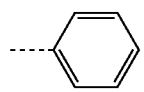 | 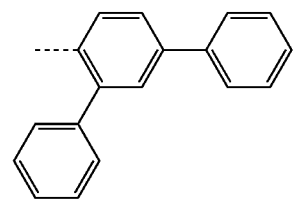 | 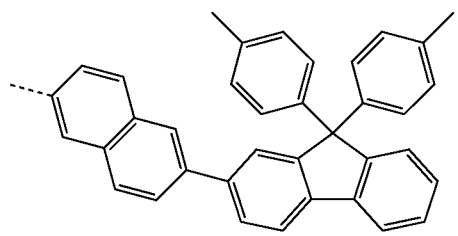 |
| 2-224 | 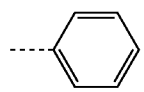 | 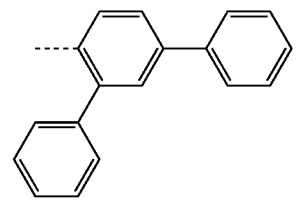 | 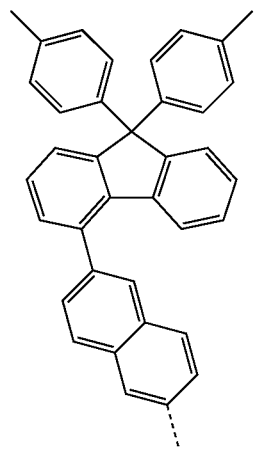 |
| 2-225 | 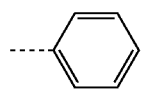 | 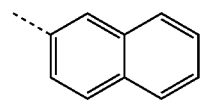 | 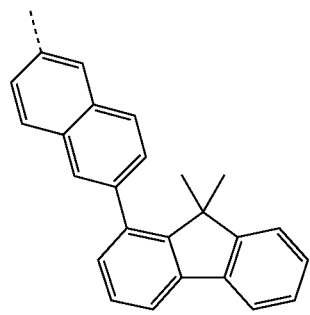 |

-continued
| Compound | ----Ar1 | ----Ar2 | ----Ar3 |
|---|---|---|---|
| 2-226 | 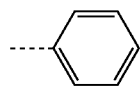 | 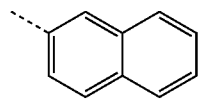 | 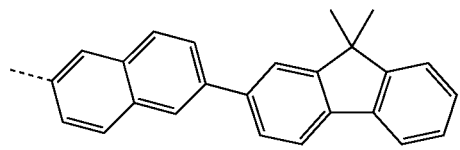 |
| 2-227 | 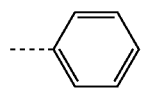 | 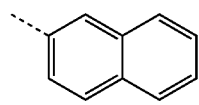 | 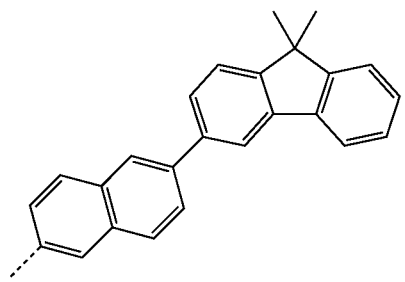 |
| 2-228 | 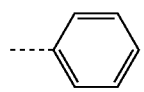 | 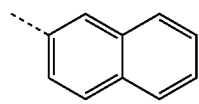 | 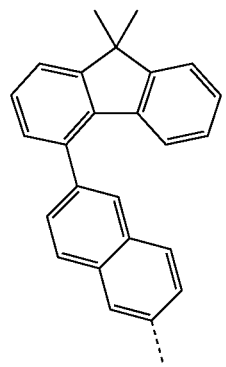 |
| 2-229 | 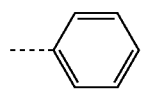 | 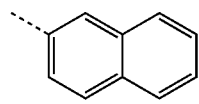 | 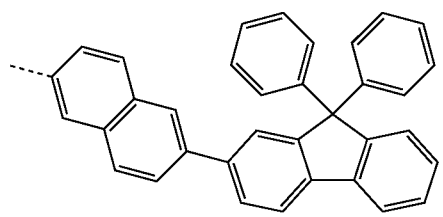 |
| 2-230 | 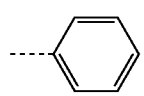 | 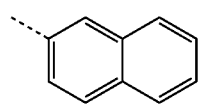 | 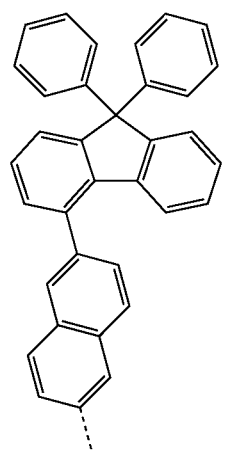 |

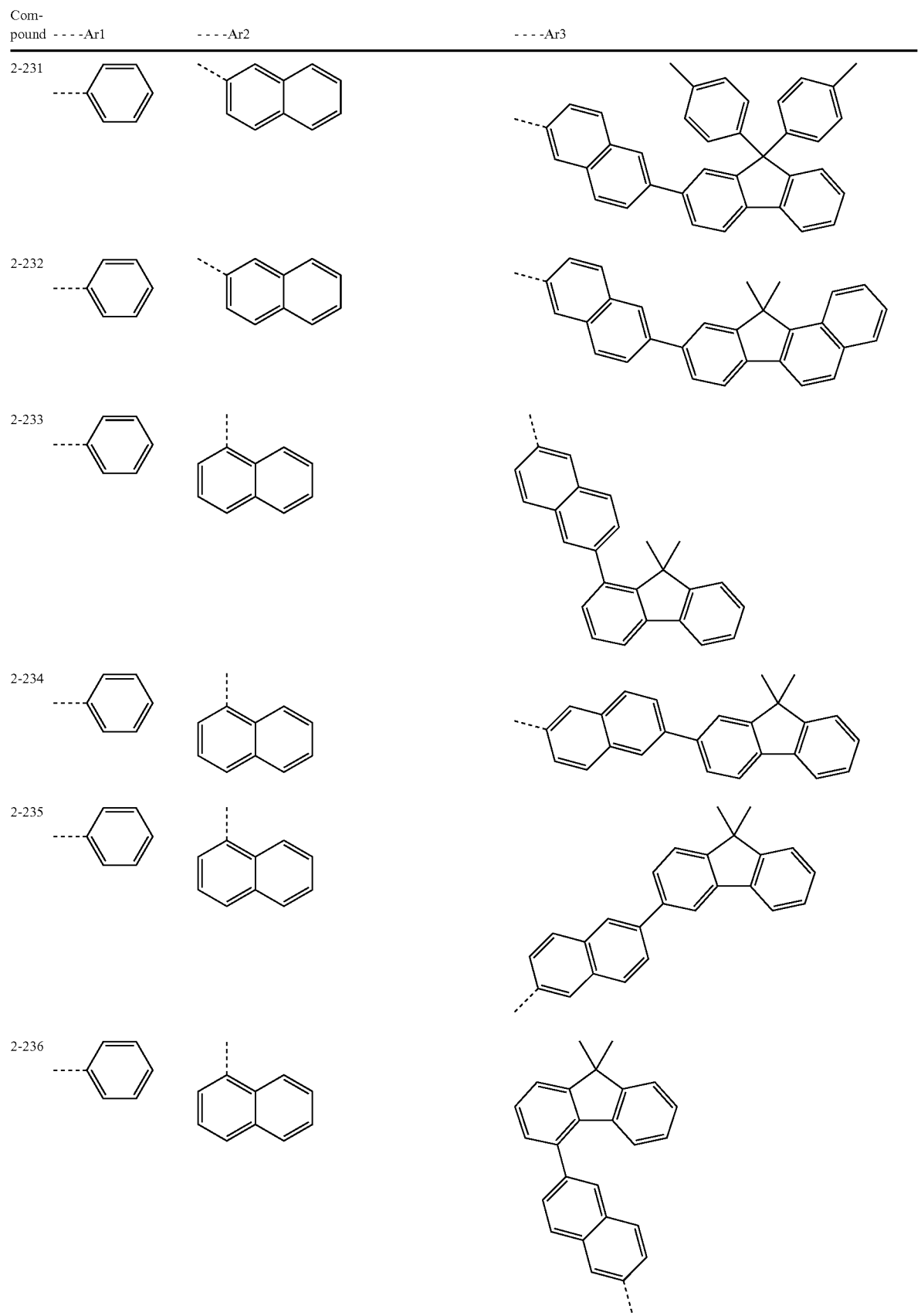

-continued
| Compound | ----Ar1 | ----Ar2 | ----Ar3 |
|---|---|---|---|
| 2-237 | 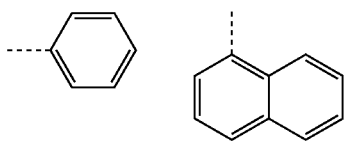 | | 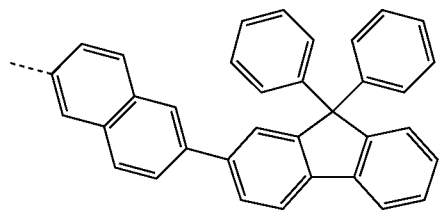 |
| 2-238 | 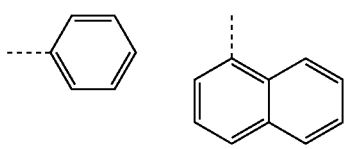 | | 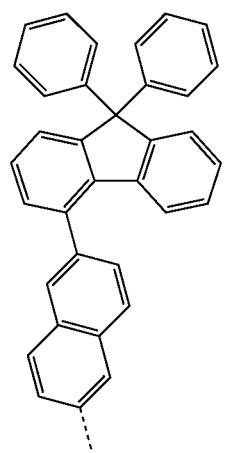 |
| 2-239 | 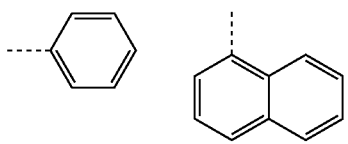 | | 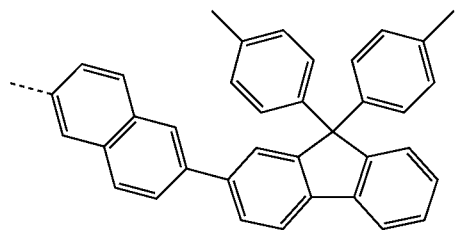 |
| 2-240 | 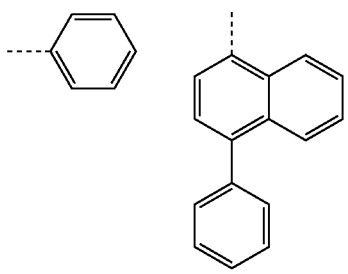 | | 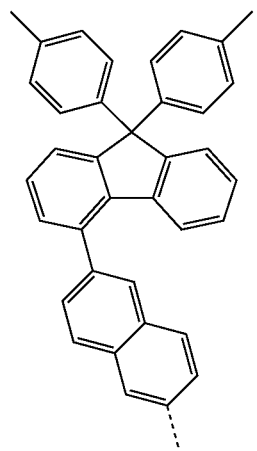 |

-continued
| Compound | ----Ar1 | ----Ar2 | ----Ar3 |
|---|---|---|---|
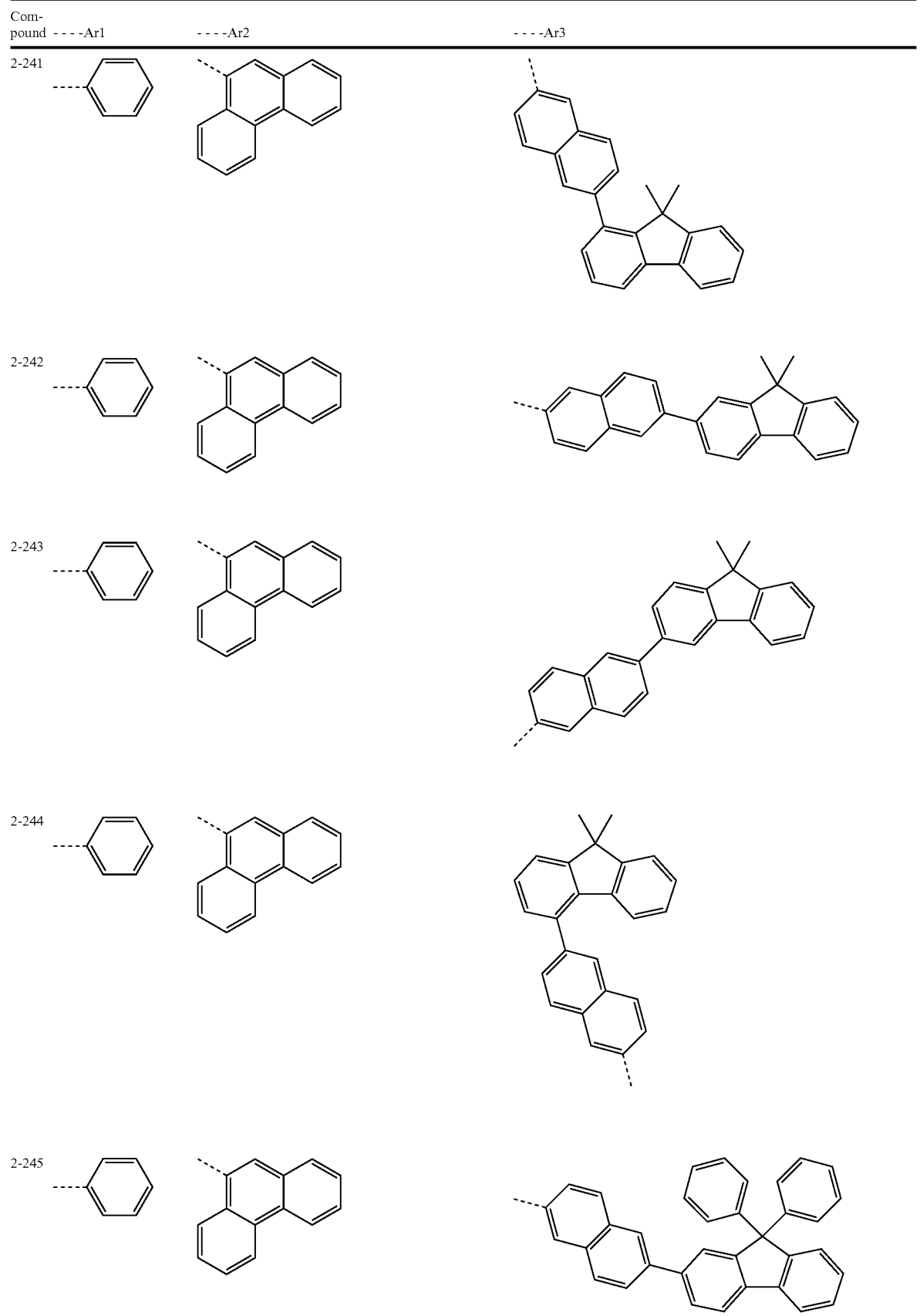

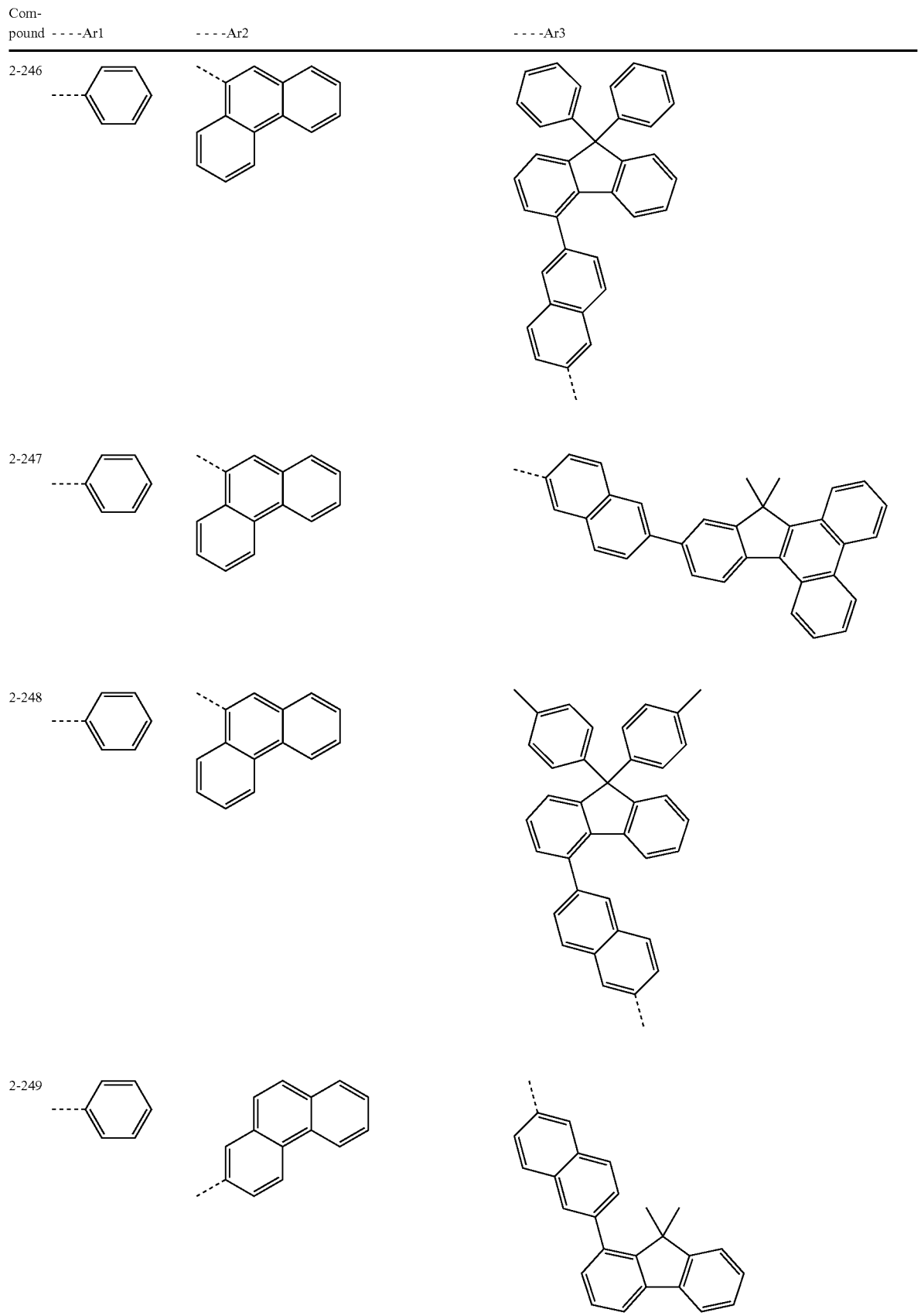

| Compound | ----Ar1 | ----Ar2 | ----Ar3 |
|---|---|---|---|
| 2-250 | 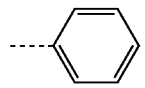 | 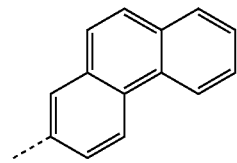 | 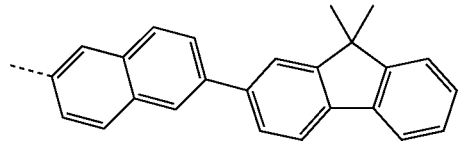 |
| 2-251 | 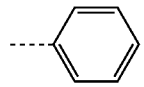 | 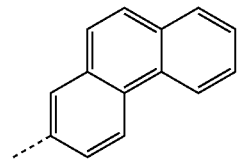 | 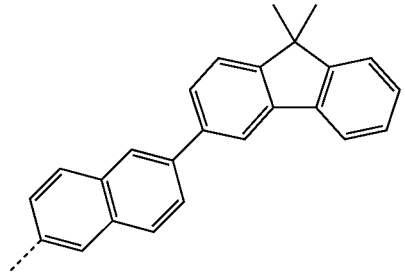 |
| 2-252 | 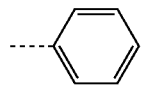 | 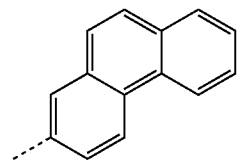 | 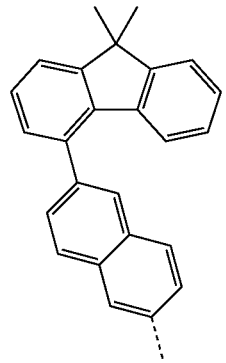 |
| 2-253 | 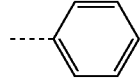 | 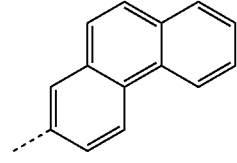 | 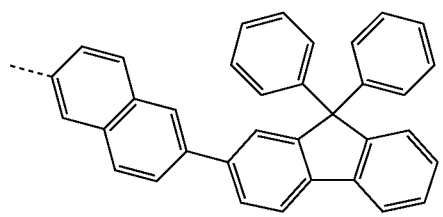 |
| 2-254 | 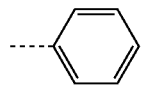 | 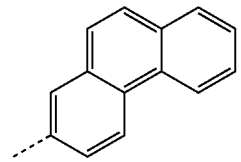 | 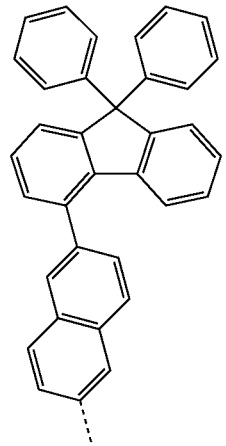 |

-continued
| Com-pound | ----Ar1 | ----Ar2 | ----Ar3 |
|---|---|---|---|
| 2-255 | 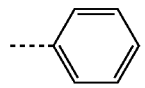 | 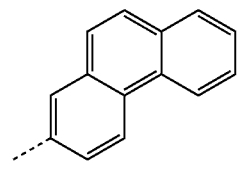 | 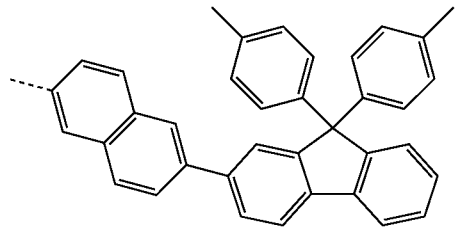 |
| 2-256 | 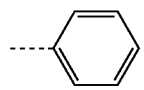 | 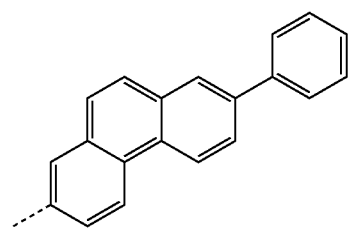 | 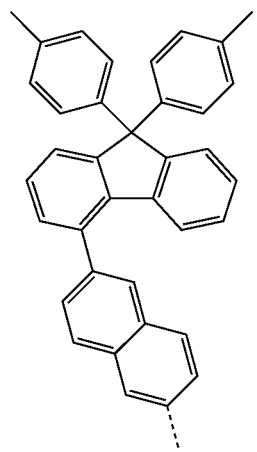 |
| 2-257 | 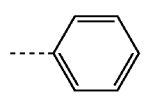 | 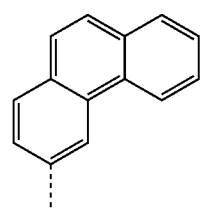 | 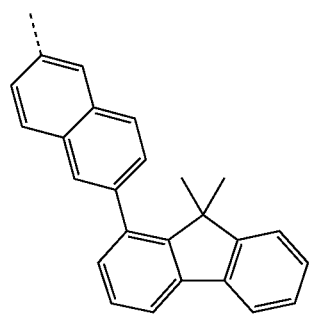 |
| 2-258 | 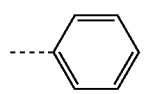 | 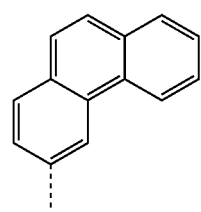 | 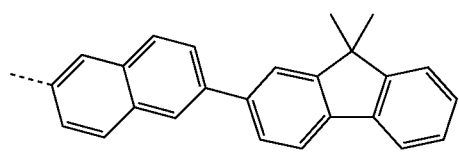 |
| 2-259 | 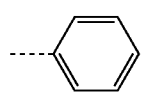 | 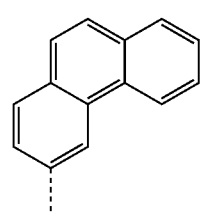 | 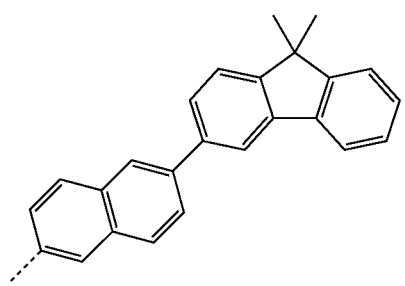 |

-continued
| Compound | ----Ar1 | ----Ar2 | ----Ar3 |
|---|---|---|---|
| 2-260 | 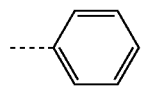 | 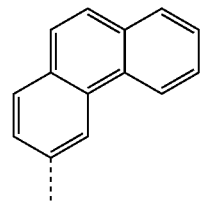 | 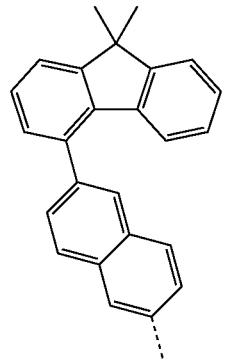 |
| 2-261 | 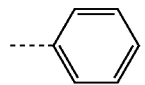 | 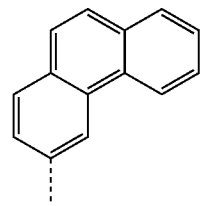 | 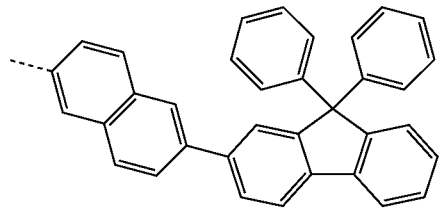 |
| 2-262 | 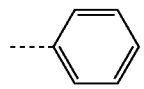 | 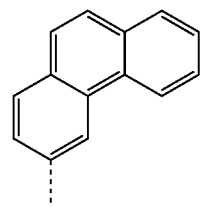 | 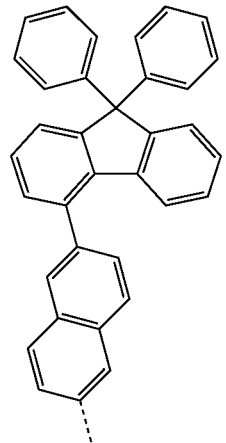 |
| 2-263 | 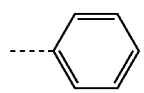 | 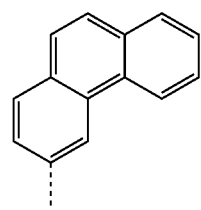 | 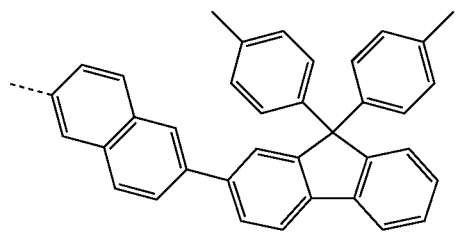 |

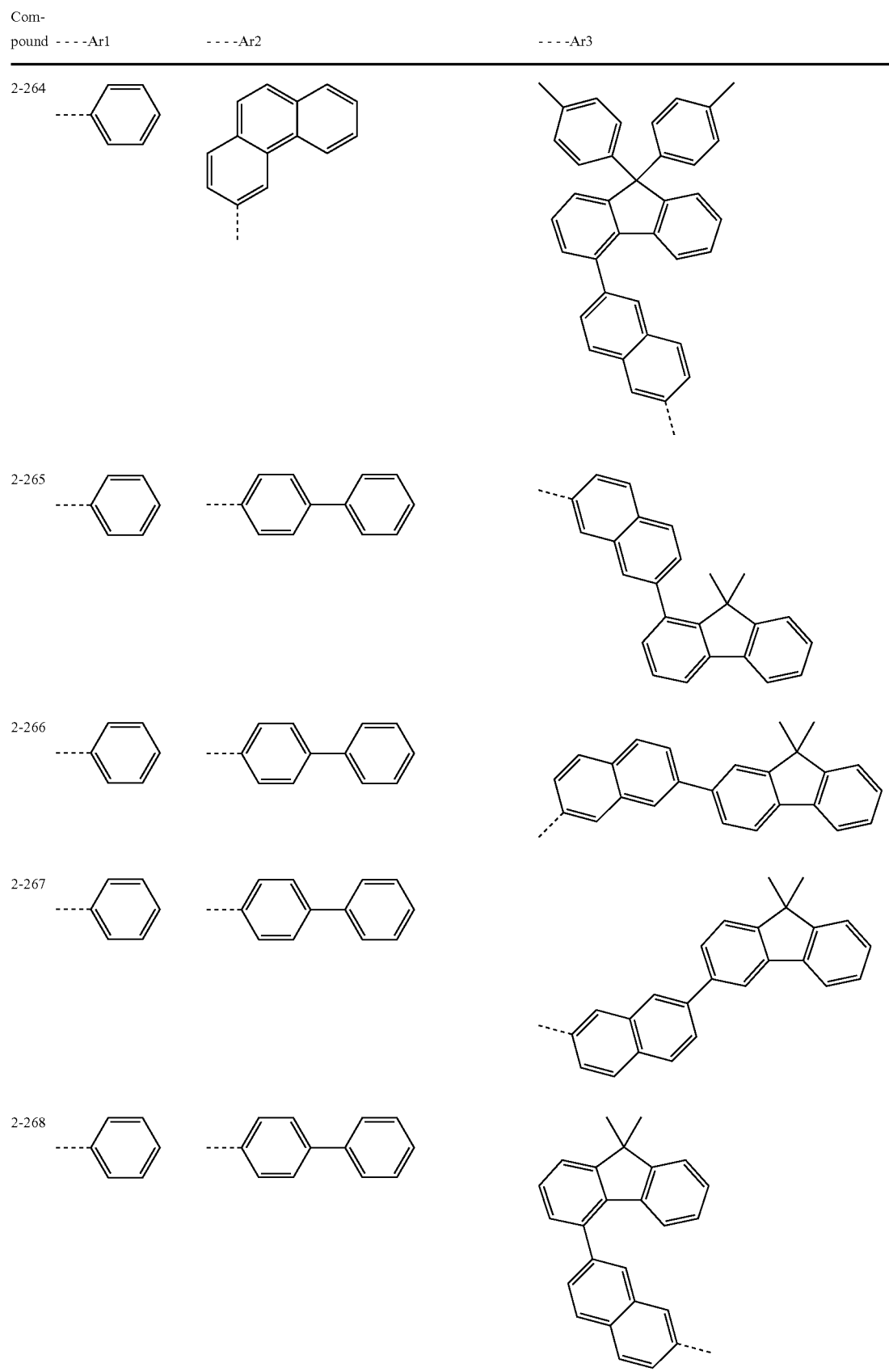

-continued
| Compound | ----Ar1 | ----Ar2 | ----Ar3 |
|---|---|---|---|
| 2-269 | 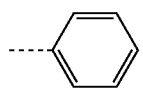 | 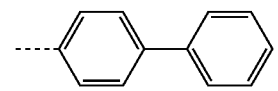 | 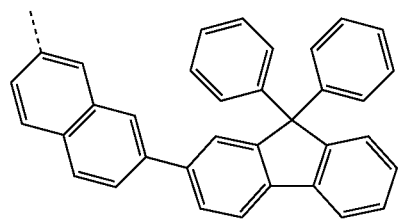 |
| 2-270 | 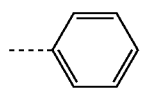 | 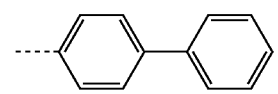 | 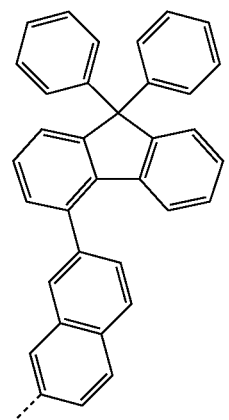 |
| 2-271 | 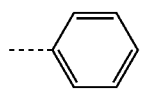 | 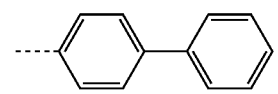 | 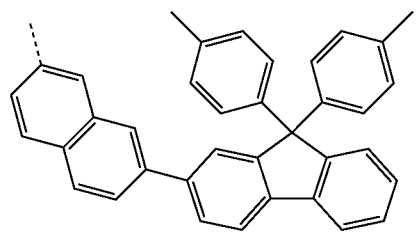 |
| 2-272 | 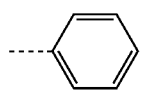 | 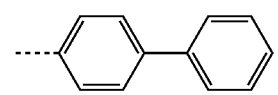 | 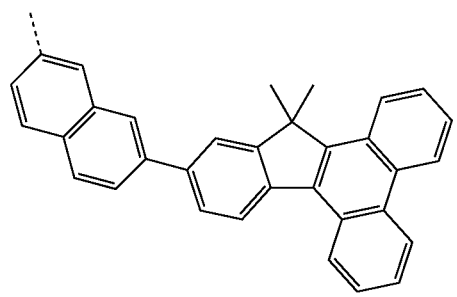 |
| 2-273 | 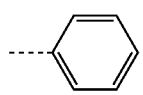 | 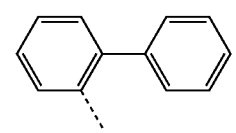 | 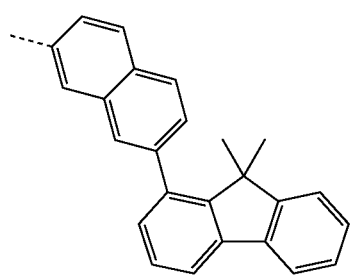 |

-continued
| Compound | ----Ar1 | ----Ar2 | ----Ar3 |
|---|---|---|---|
| 2-274 | 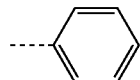 | 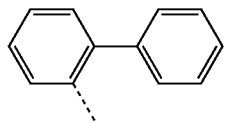 | 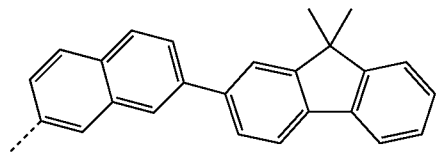 |
| 2-275 | 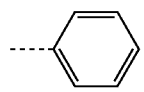 | 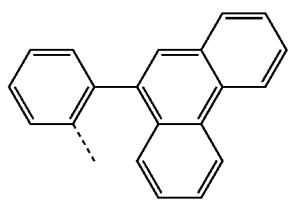 | 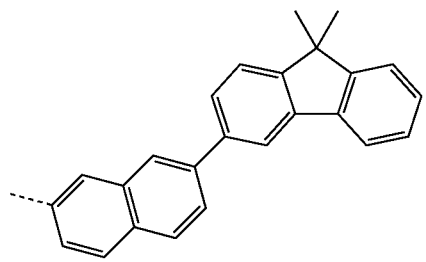 |
| 2-276 | 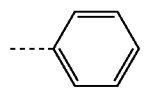 | 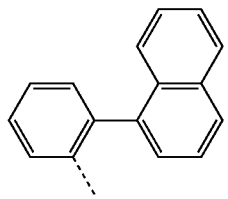 | 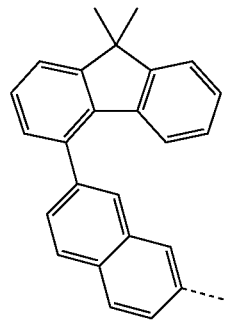 |
| 2-277 | 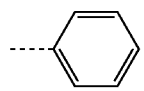 | 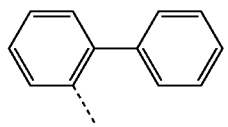 | 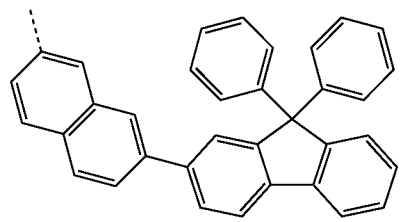 |
| 2-278 | 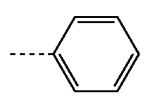 | 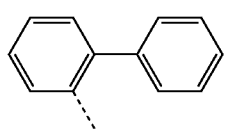 | 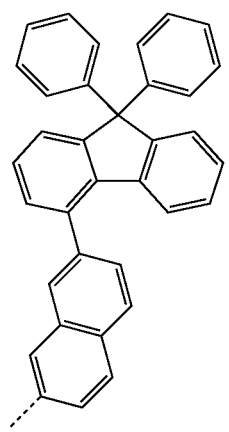 |

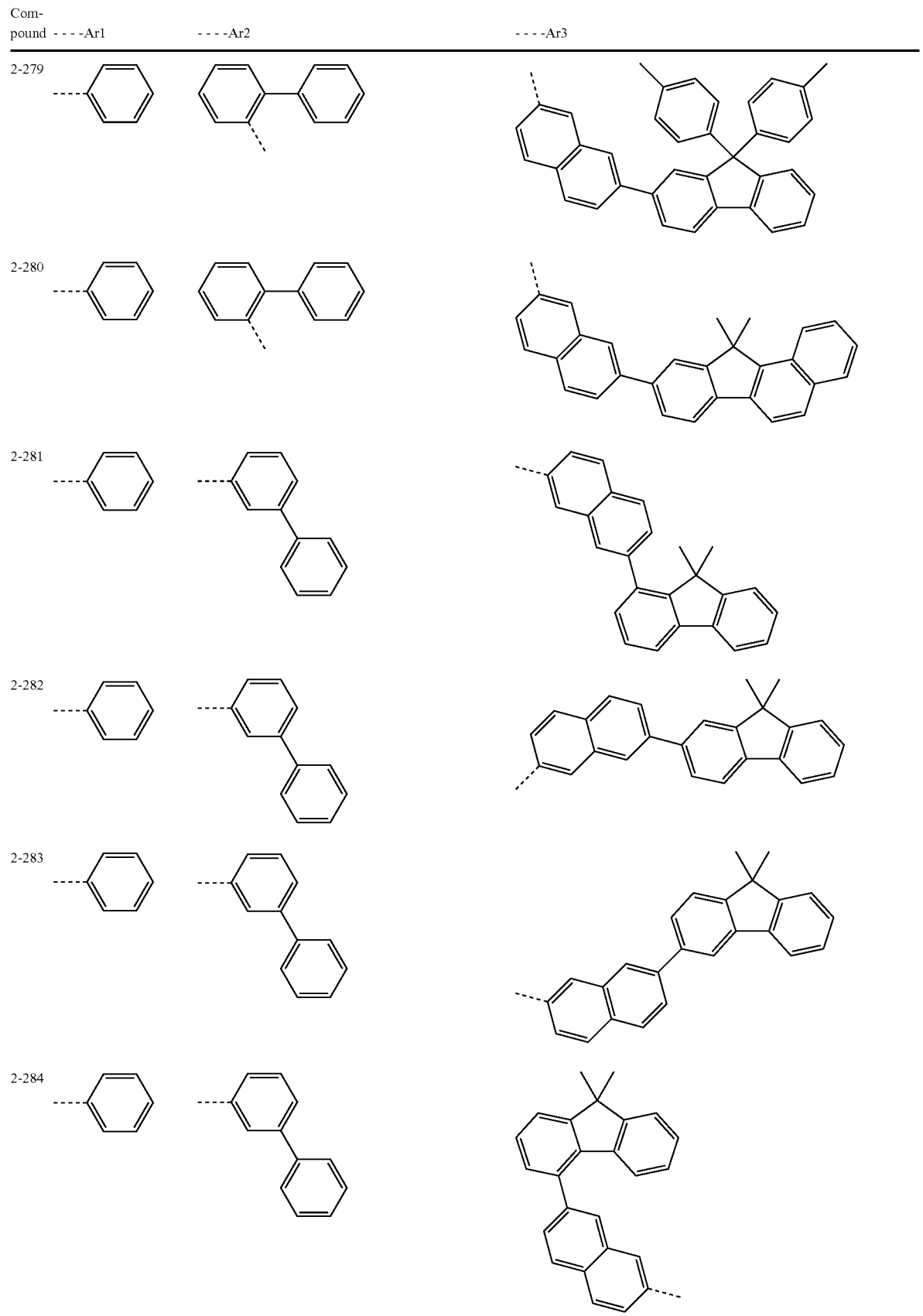

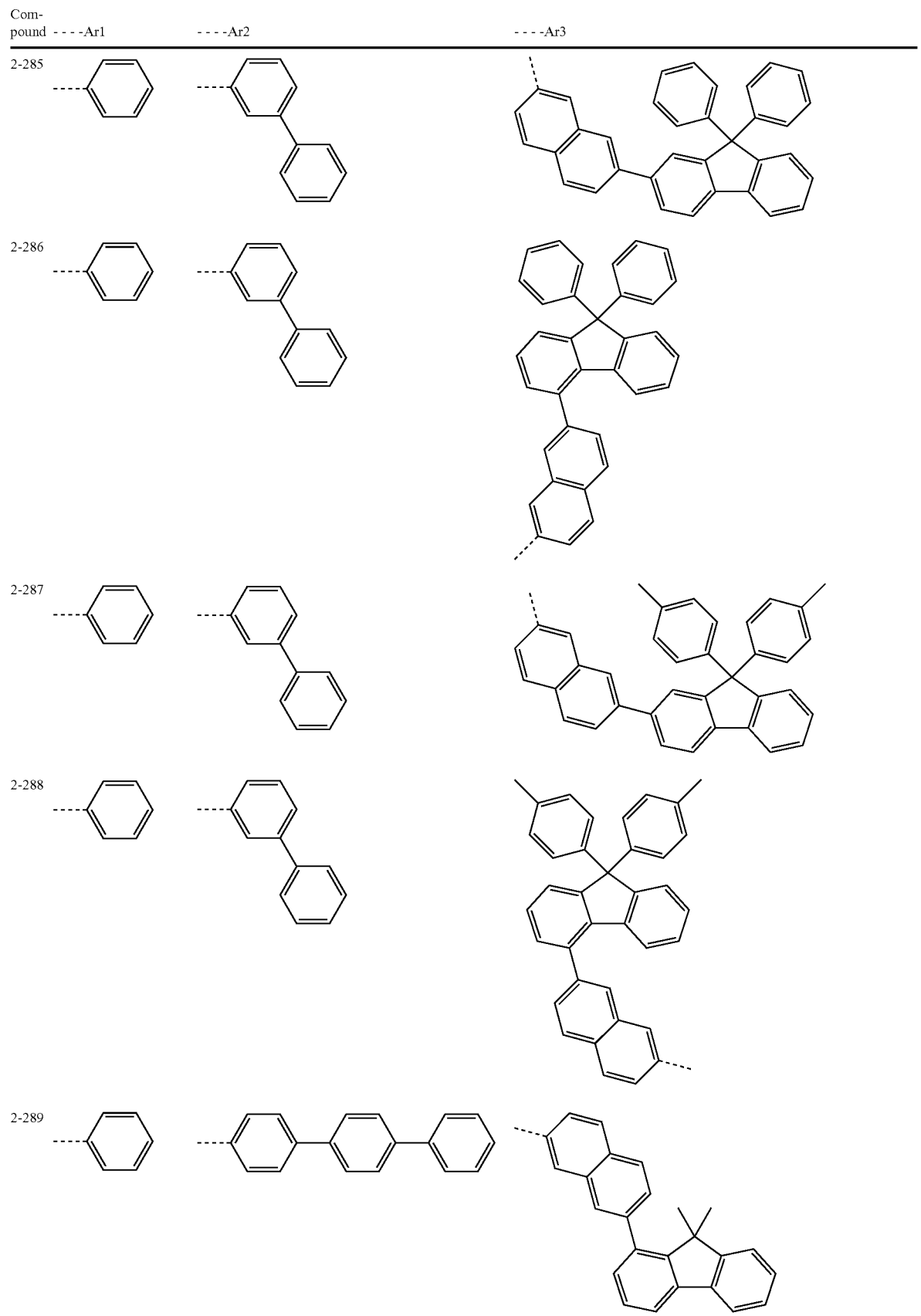

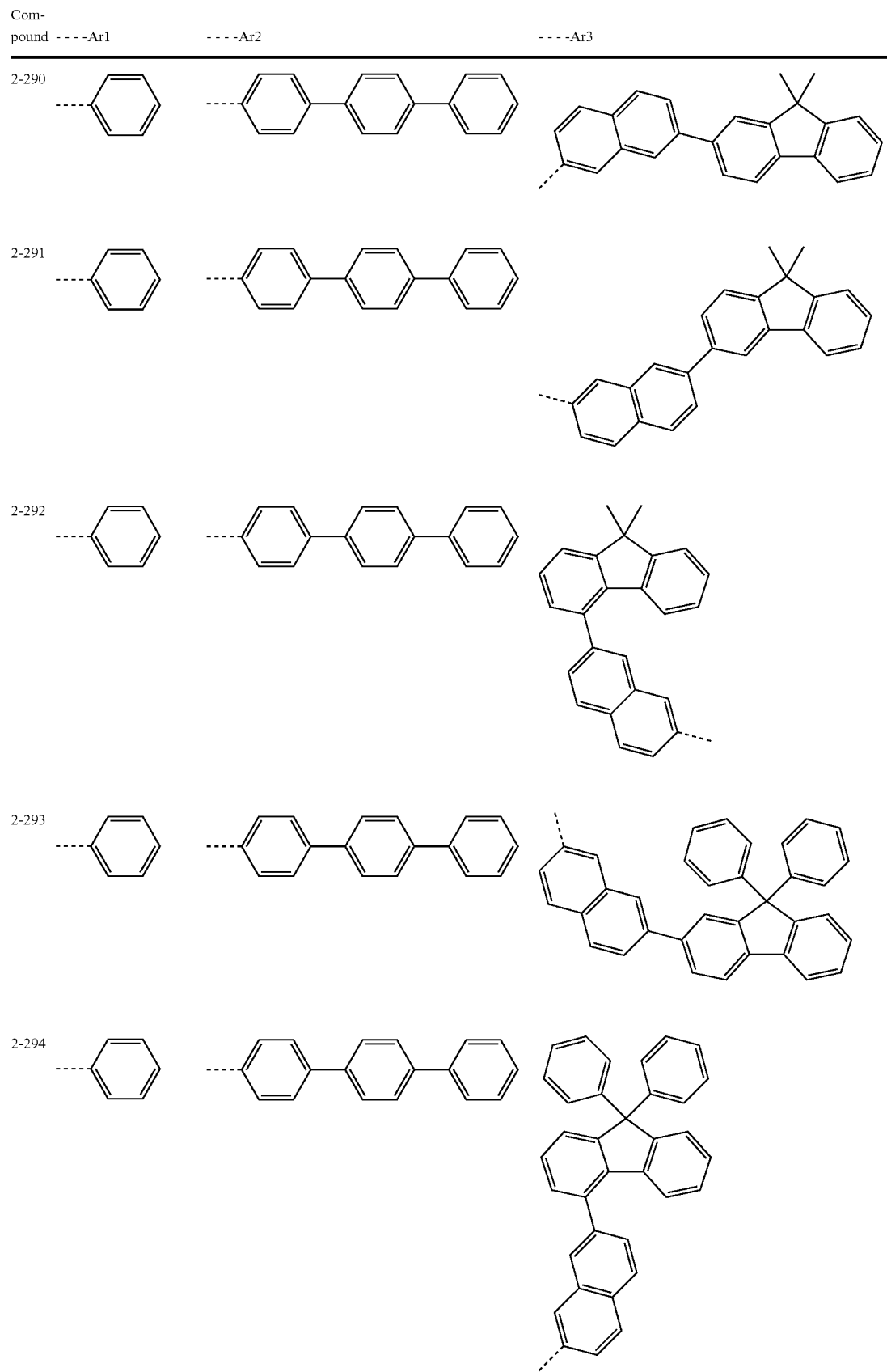

| Compound | ----Ar1 | ----Ar2 | ----Ar3 |
|---|---|---|---|
| 2-295 | 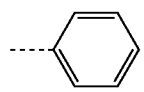 | 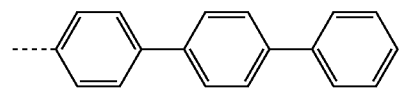 | 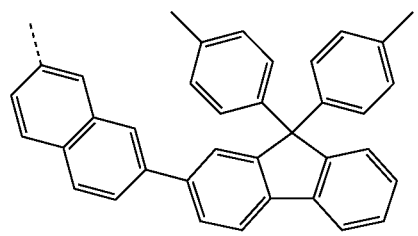 |
| 2-296 | 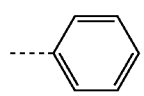 | 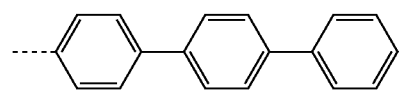 | 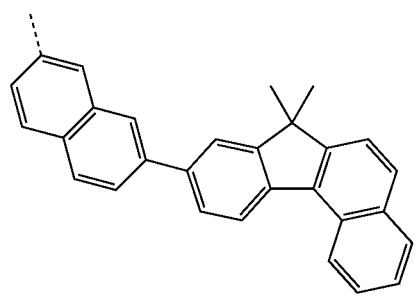 |
| 2-297 | 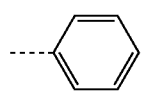 | 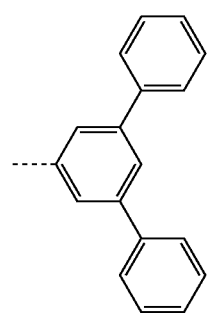 | 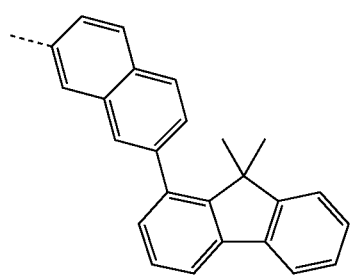 |
| 2-298 | 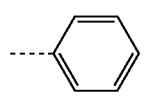 | 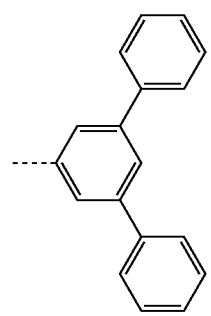 | 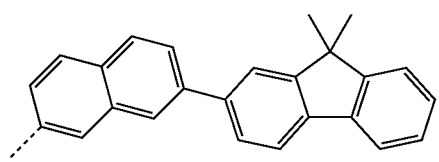 |
| 2-299 | 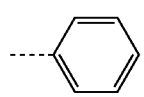 | 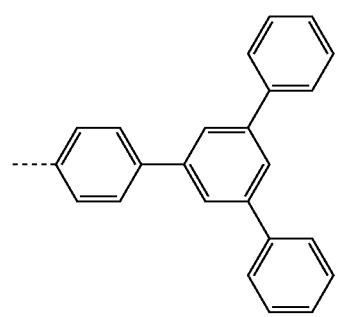 | 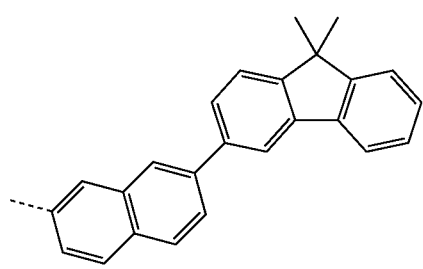 |

-continued
| Compound | ----Ar1 | ----Ar2 | ----Ar3 |
|---|---|---|---|
| 2-300 | | | |
| 2-301 | | | |
| 2-302 | | | |
| 2-303 | | | |
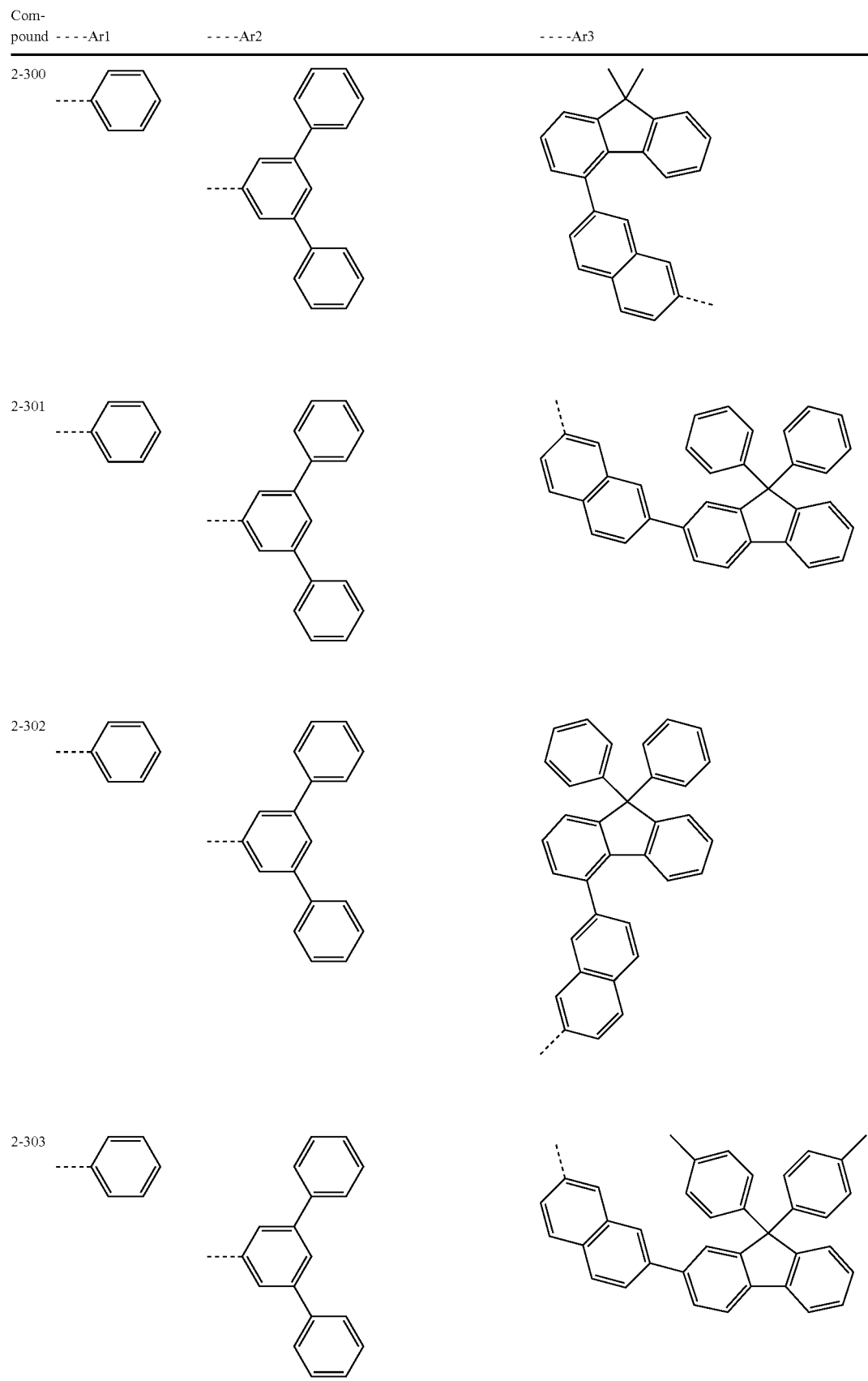

-continued
| Compound | ----Ar1 | ----Ar2 | ----Ar3 |
|---|---|---|---|
| 2-304 | 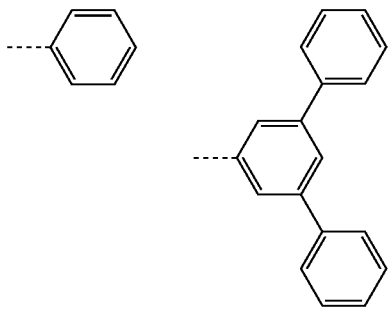 | 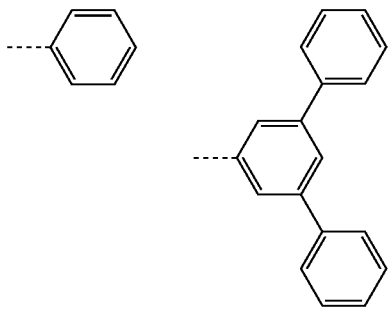 | 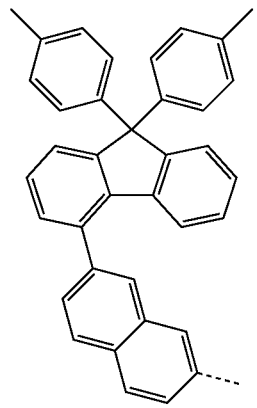 |
| 2-305 | 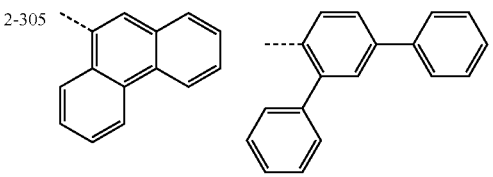 | 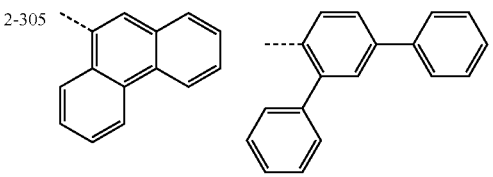 | 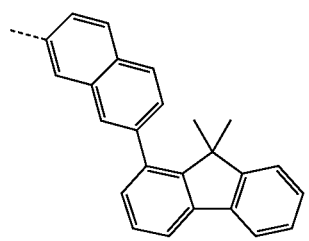 |
| 2-306 | 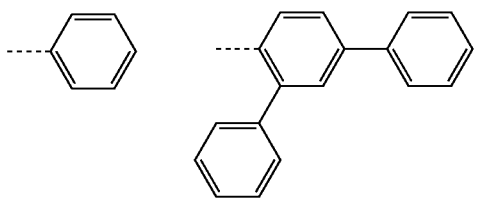 | 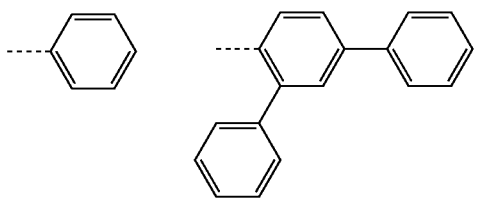 | 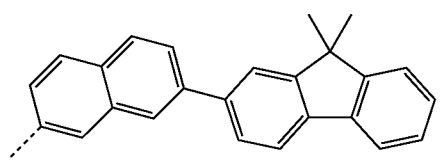 |
| 2-307 | 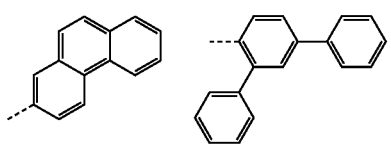 | 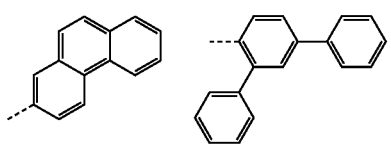 | 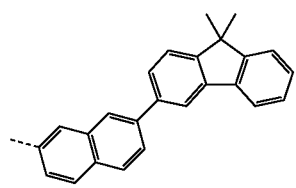 |
| 2-308 | 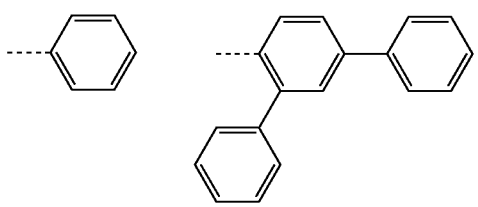 | 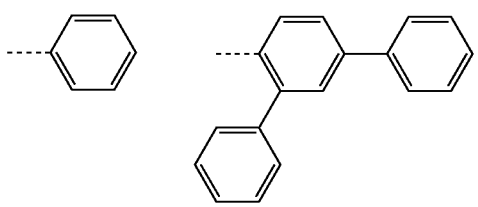 | 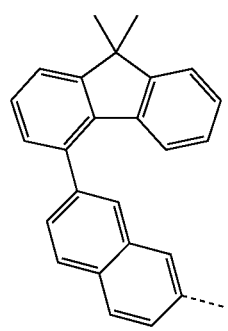 |

-continued
| Compound | ----Ar1 | ----Ar2 | ----Ar3 |
|---|---|---|---|
| 2-309 | | | |
| 2-310 | | | |
| 2-311 | | | |
| 2-312 | | | |
| 2-313 | | | |
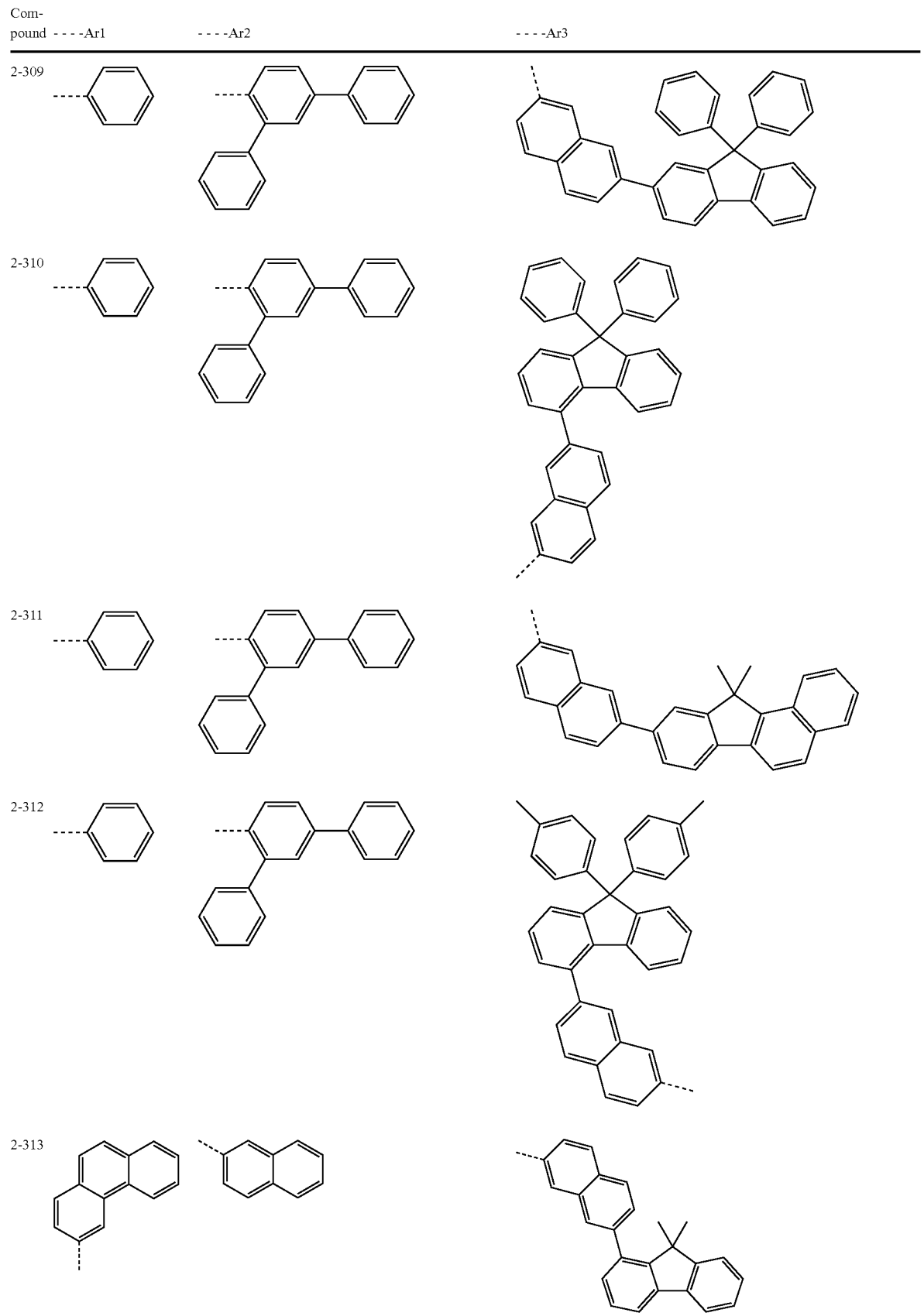

-continued
| Compound | ----Ar1 | ----Ar2 | ----Ar3 |
|---|---|---|---|
| 2-314 | 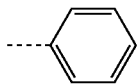 | 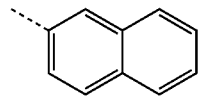 | 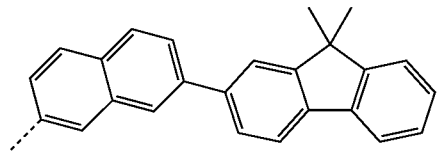 |
| 2-315 | 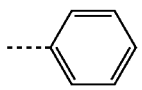 | 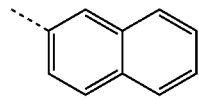 | 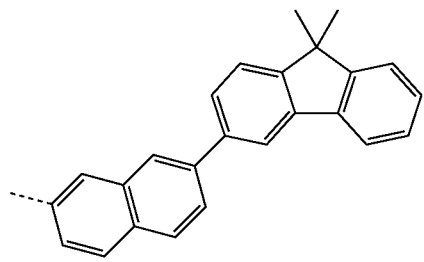 |
| 2-316 | 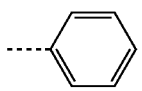 | 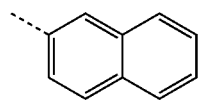 | 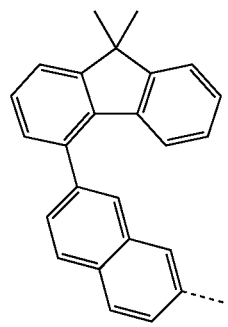 |
| 2-317 | 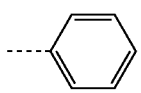 | 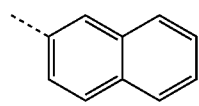 | 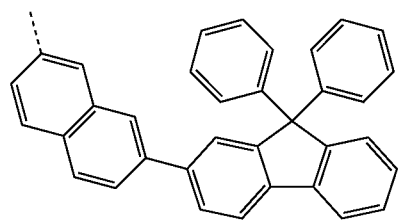 |
| 2-318 | 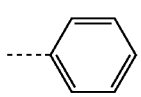 | 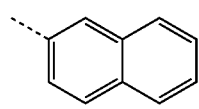 | 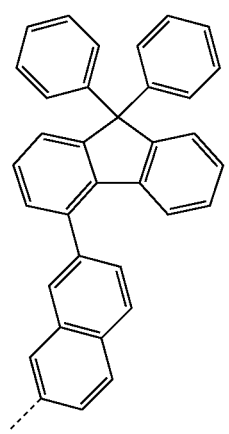 |

-continued
| Compound | ----Ar1 | ----Ar2 | ----Ar3 |
|---|---|---|---|
| 2-319 | 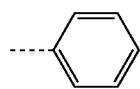 | 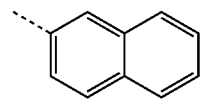 | 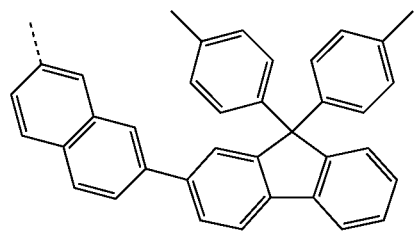 |
| 2-320 | 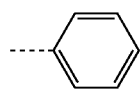 | 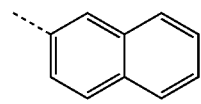 | 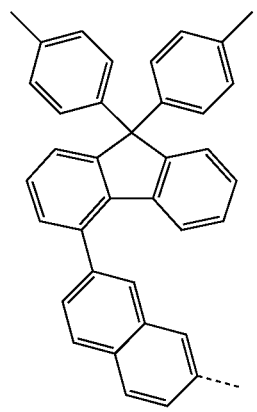 |
| 2-321 | 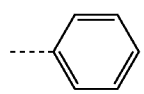 | 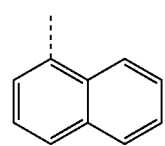 | 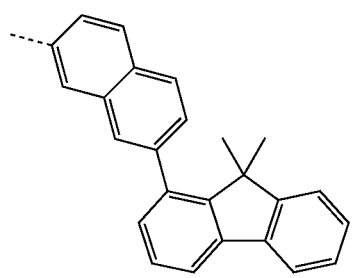 |
| 2-322 | 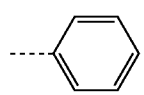 | 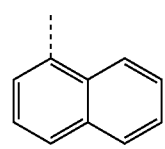 | 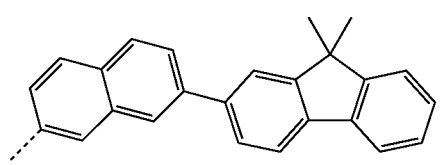 |
| 2-323 | 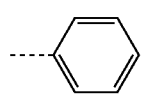 | 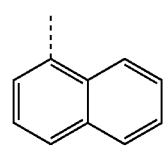 | 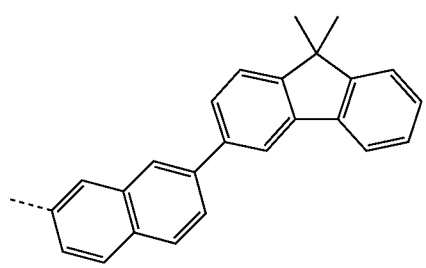 |

| Compound | ----Ar1 | ----Ar2 | ----Ar3 |
|---|---|---|---|
| 2-324 | 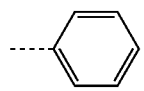 | 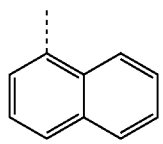 | 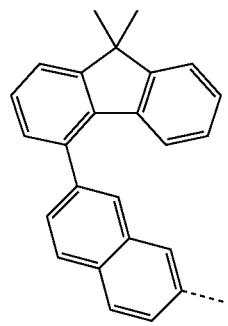 |
| 2-325 | 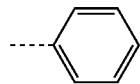 | 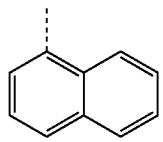 | 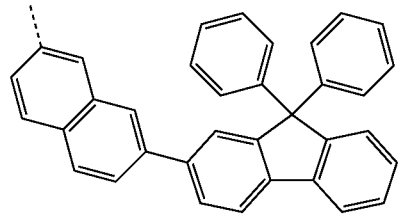 |
| 2-326 | 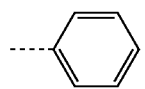 | 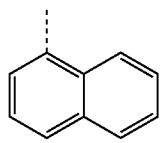 | 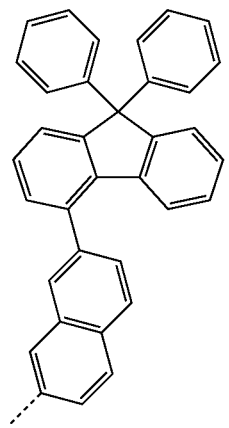 |
| 2-327 | 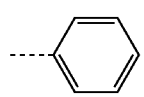 | 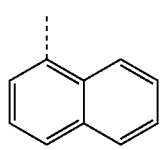 | 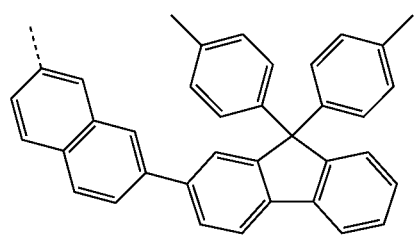 |

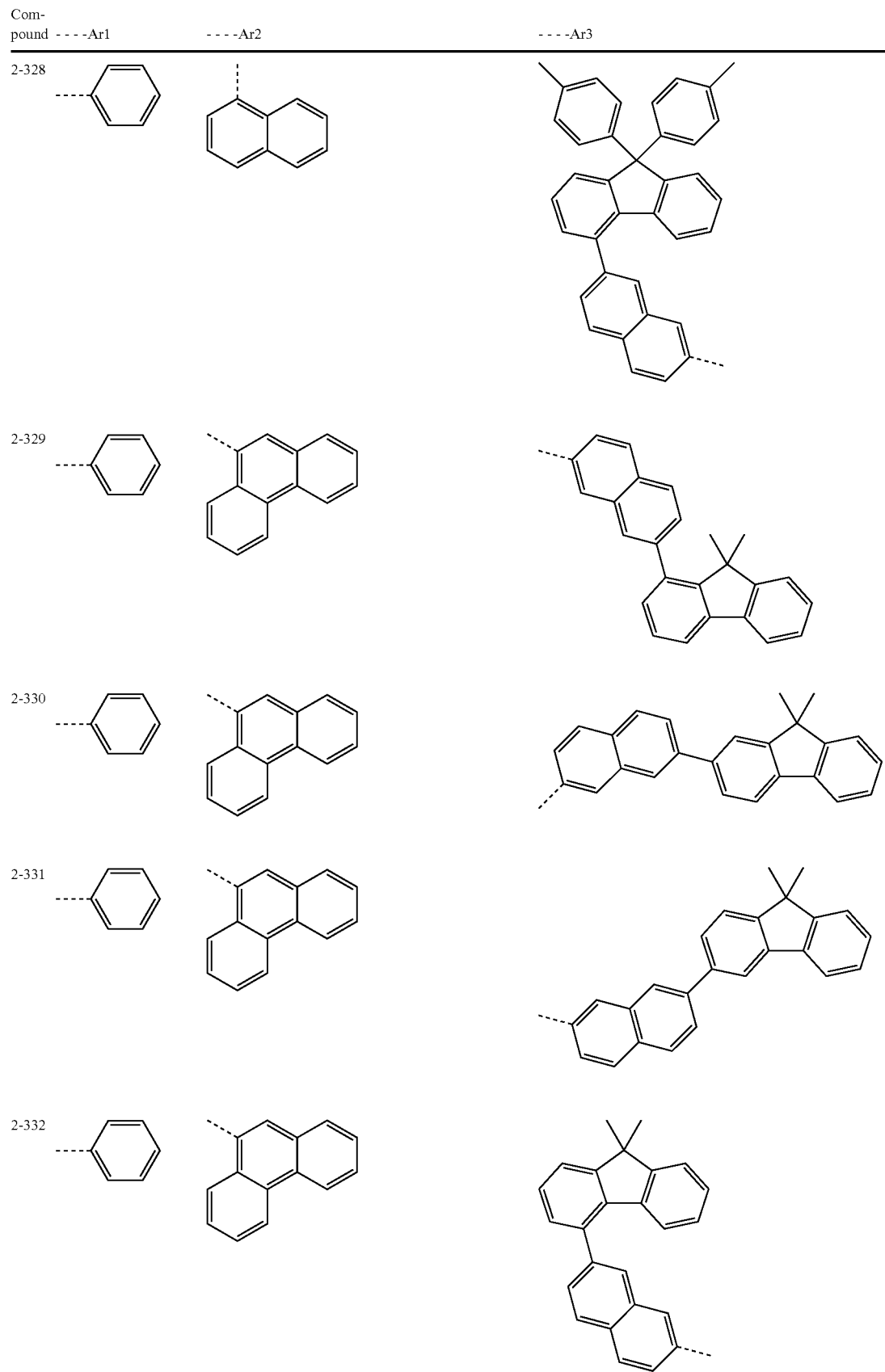

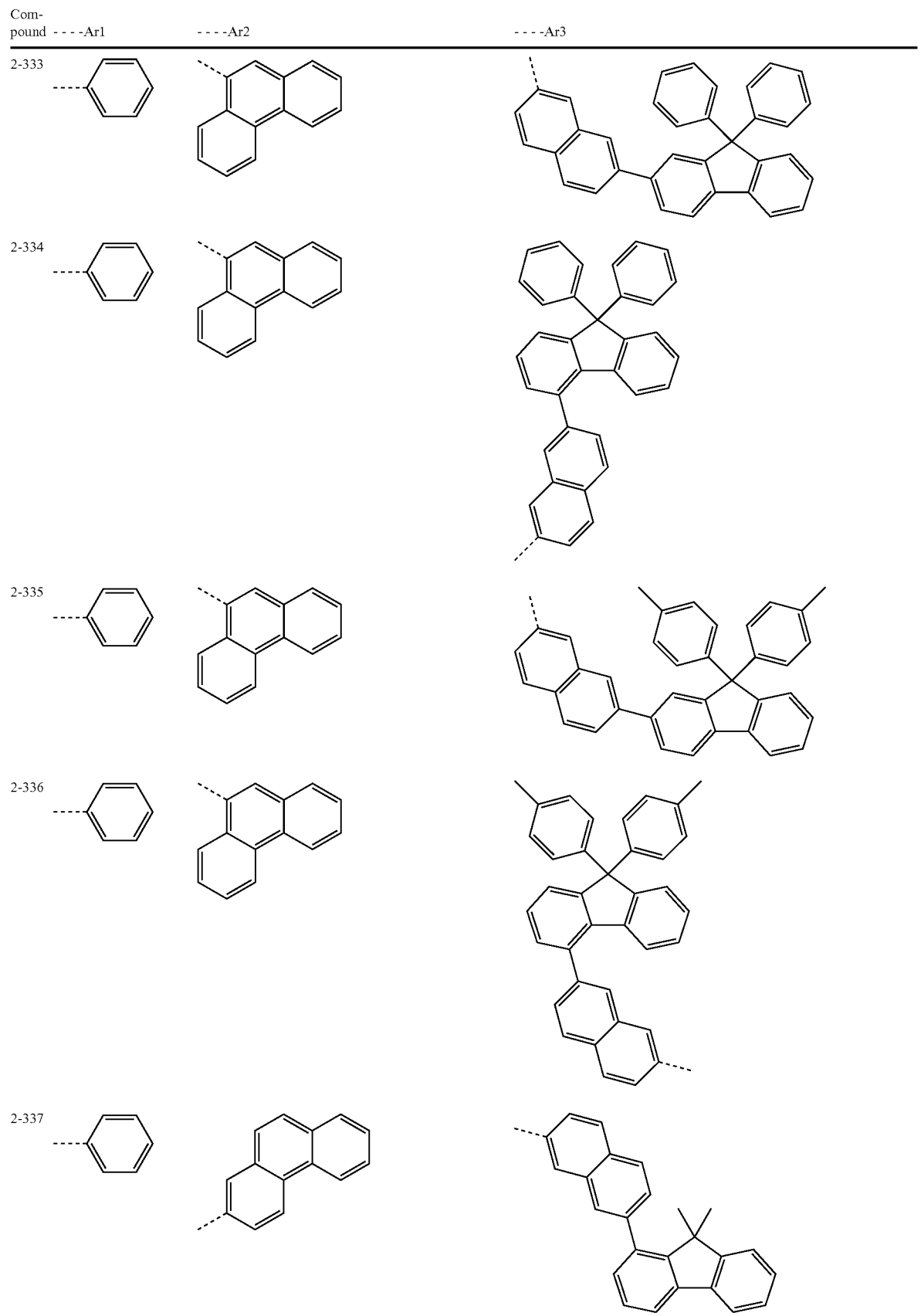

-continued
| Compound | ----Ar1 | ----Ar2 | ----Ar3 |
|---|---|---|---|
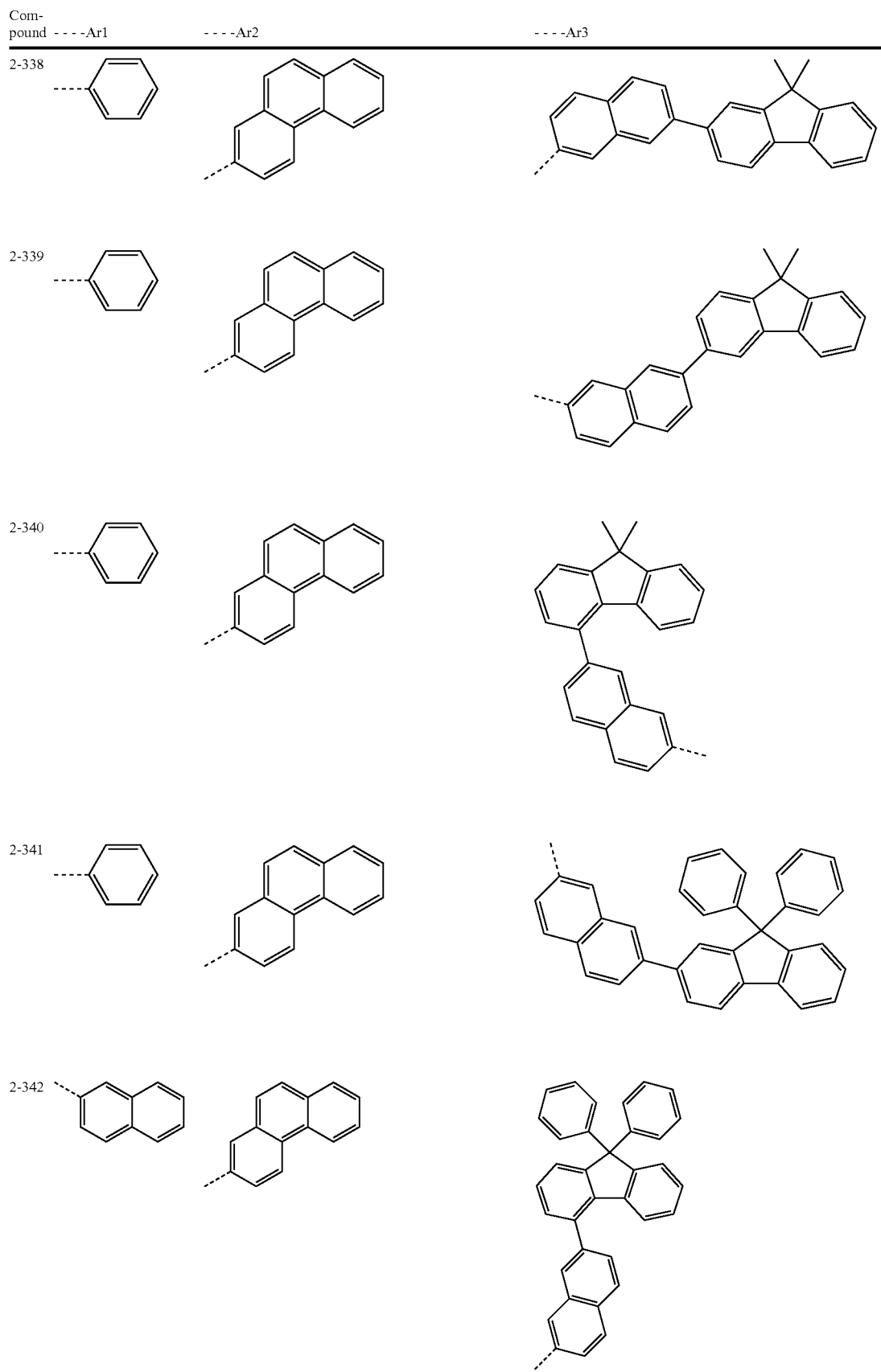

-continued
| Compound | ----Ar1 | ----Ar2 | ----Ar3 |
|---|---|---|---|
| 2-343 | 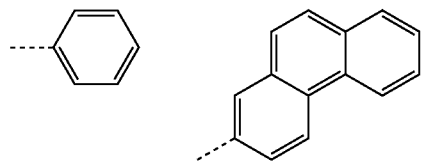 | | 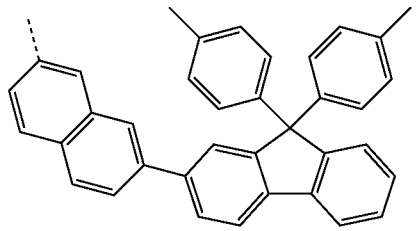 |
| 2-344 | 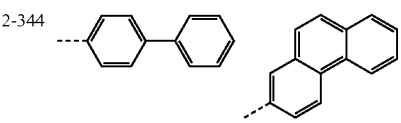 | | 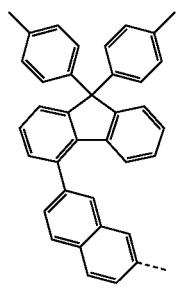 |
| 2-345 | 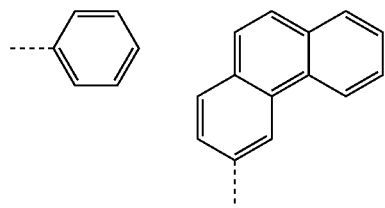 | | 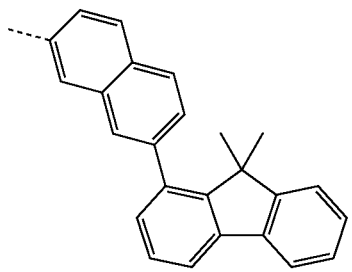 |
| 2-346 | 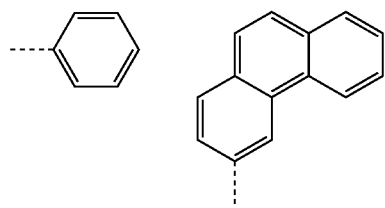 | | 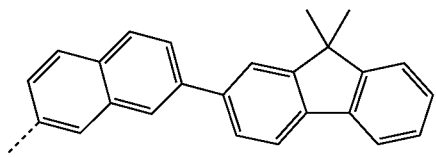 |
| 2-347 | 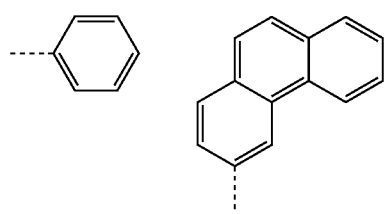 | | 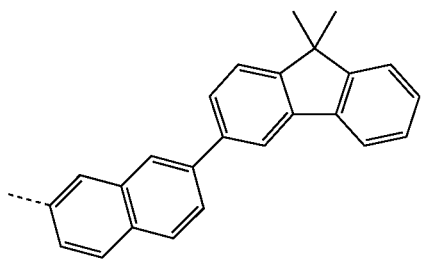 |

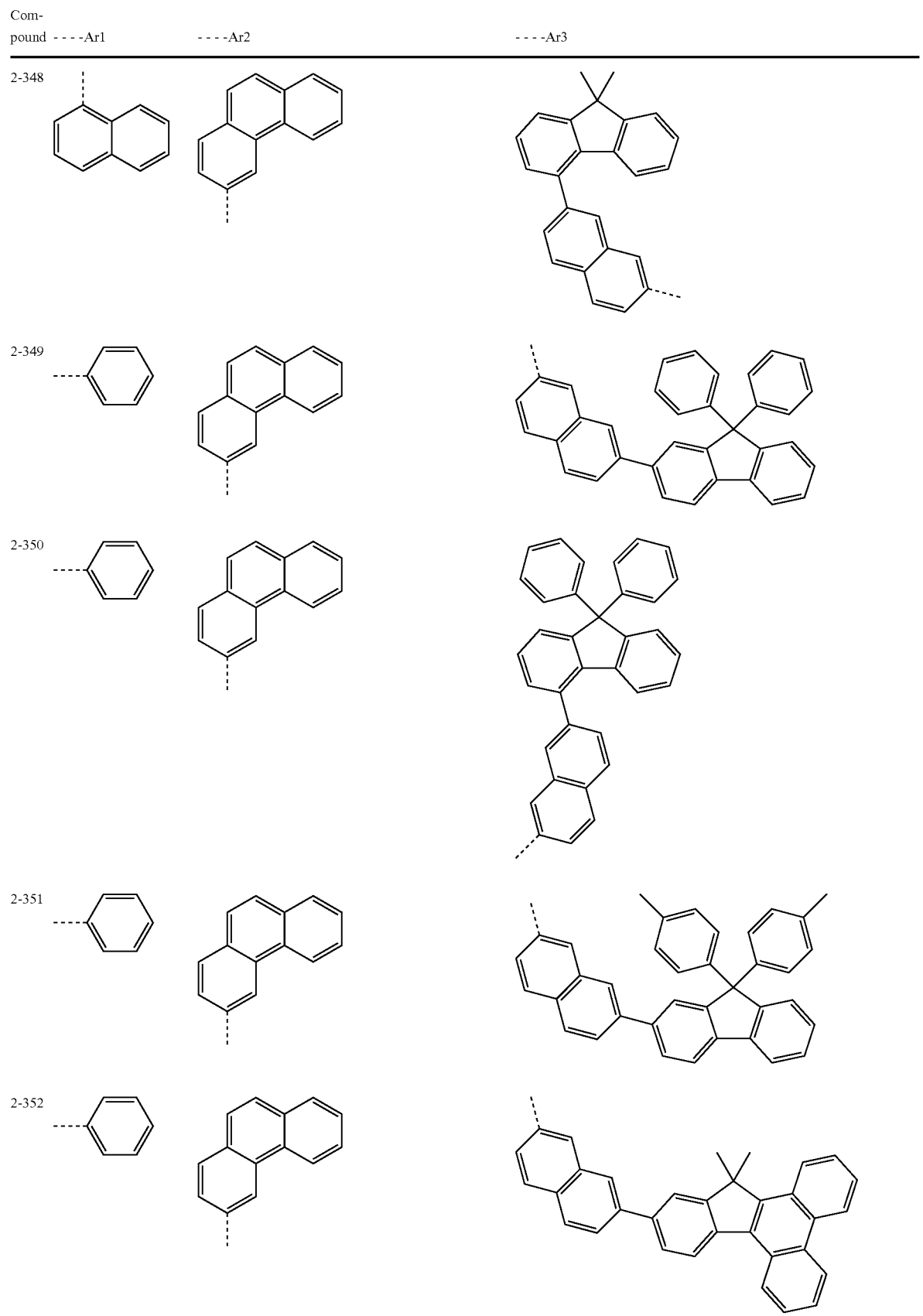

-continued
| Compound | ----Ar1 | ----Ar2 | ----Ar3 |
|---|---|---|---|
| 2-353 | 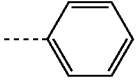 | 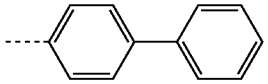 | 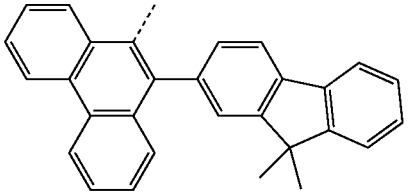 |
| 2-354 | 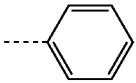 | 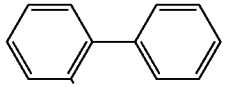 | 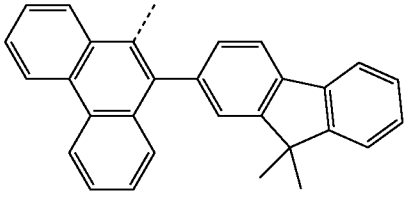 |
| 2-355 | 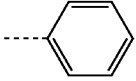 | 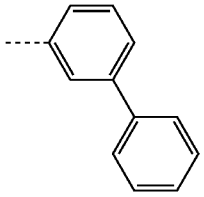 | 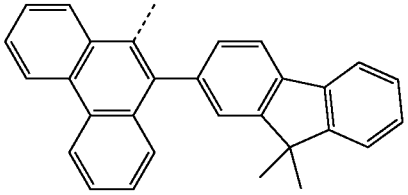 |
| 2-356 | 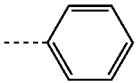 | 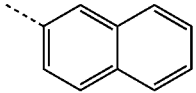 | 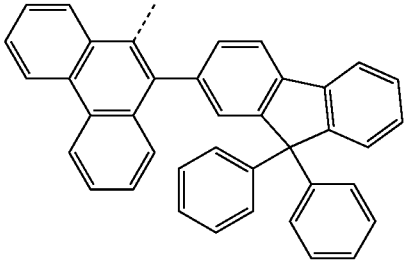 |
| 2-357 | 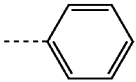 | 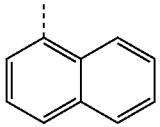 | 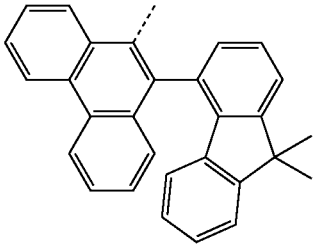 |
| 2-358 | 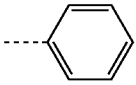 | 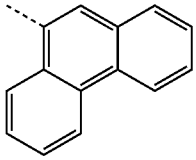 | 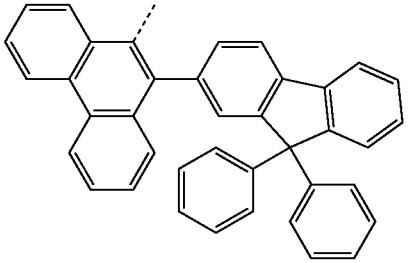 |

| Compound | ----Ar1 | ----Ar2 | ----Ar3 |
|---|---|---|---|
| 2-359 | | | |
| 2-360 | | | |
| 2-361 | | | |
| 2-362 | | | |
| 2-363 | | | |
The compound represented by Formula 1 may be prepared based on the Preparation Examples to be described below. According to an exemplary embodiment, the compound may be prepared by the method such as the following Reaction Formula 1.
[Reaction Formula 1]
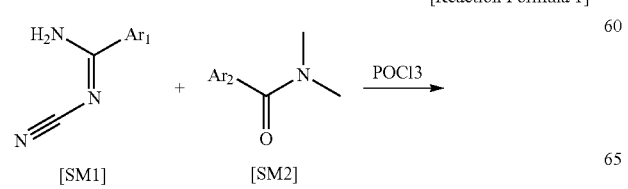
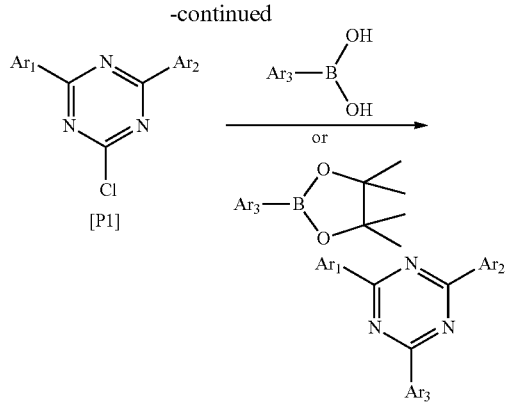

In the reaction formula, the definition of Ar1 to Ar3 is the same as that in Formula 1.

Specifically, according to an exemplary embodiment of the present specification, a compound of [P1] may be prepared by reacting the compound [SM1] and the compound [SM2] with an equivalent amount of phosphorus oxychloride at a temperature of 70° C. or more. Thereafter, a compound in which Ar1 to Ar3 of Formula 1 are asymmetric with each other may be prepared by using a palladium catalyst reaction to couple an aromatic compound substituted with boronic acid or a boronic acid derivative with the compound of [P1].

One of the important characteristics of an organic material used in the organic light emitting device is that an amorphous deposition film needs to be formed. An organic material having high crystallinity has a disadvantage in that a film is non-uniformly deposited during the deposition, and thus, the driving voltage is largely increased when a device is driven, and the service life of the diode is decreased, and thus the diode quickly deteriorates. In order to alleviate the disadvantage, an amorphous film needs to be formed.

Thus, the present inventors have confirmed that an asymmetric material in a triazine derivative structure does not exhibit crystallinity. According to an exemplary embodiment of the present specification, it was confirmed that the compound represented by any one of Formulae 1 to 28 has an asymmetrical structure in which Ar1 to Ar3 are different from each other, and in the case of an organic light emitting device including the same, a device is stably driven.

In addition, the present specification provides an organic light emitting device including the compound of any one of Formulae 1 to 28.

An exemplary embodiment of the present specification provides an organic light emitting device including: an anode; a cathode; and one or more organic material layers provided between the anode and the cathode, one or more layers of the organic material layers include the compound of any one of Formulae 1 to 28.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, an electron controlling layer, and the like as organic material layers. However, the structure of the organic light emitting device is not limited thereto.

According to an exemplary embodiment of the present specification, the organic material layer includes an electron transporting layer or an electron injection layer, and the electron transporting layer or the electron injection layer includes the compound of any one of Formulae 1 to 28.

According to an exemplary embodiment of the present specification, the organic material layer includes an electron transporting layer, an electron injection layer, or a layer which simultaneously transports and injects electrons, and one more layers of the electron transporting layer, the electron injection layer, and the layer, which simultaneously transports and injects electrons, include the compound of any one of Formulae 1 to 28.

According to an exemplary embodiment of the present specification, the organic material layer includes one or two or more layers selected from the group consisting of an electron transporting layer; an electron injection layer; a layer which simultaneously injects and transports electrons; and an electron controlling layer, and one or more layers of the electron transporting layer, the electron injection layer, the layer which simultaneously injects and transports electrons, and the electron controlling layer include the compound of any one of Formulae 1 to 28.

According to an exemplary embodiment of the present specification, the organic material layer may further include one or more selected from the group consisting of an electron injection layer, an electron transporting layer, and a layer which simultaneously injects and transports electrons between the light emitting layer and the anode or between the light emitting layer and the cathode.

According to an exemplary embodiment of the present specification, in an organic light emitting device including: an anode; a cathode provided to face the anode; a light emitting layer provided between the anode and the cathode; and two or more organic material layers provided between the light emitting layer and the anode or between the light emitting layer and the cathode, at least one of the two or more organic material layers includes the compound of any one of Formulae 1 to 28.

In an exemplary embodiment of the present specification, as the two or more organic material layers, two or more may be selected from the group consisting of an electron transporting layer, an electron injection layer, a layer which simultaneously transports and injects electrons, and an electron controlling layer.

In an exemplary embodiment of the present specification, the organic material layer includes two or more electron transporting layers, and at least one of the two or more electron transporting layers includes the compound of any one of Formulae 1 to 28. Specifically, in an exemplary embodiment of the present specification, the compound of any one of Formulae 1 to 28 may also be included in one layer of the two or more electron transporting layers, and may be included in each of the two or more electron transporting layers.

Furthermore, in an exemplary embodiment of the present specification, when the compound of any one of Formulae 1 to 28 is included in each of the two or more electron transporting layers, the other materials except for the compound of any one of Formulae 1 to 28 may be the same as or different from each other.

In another exemplary embodiment, the organic material layer includes a light emitting layer and an electron transporting layer, and the electron transporting layer includes the compound of any one of Formulae 1 to 28.

According to an exemplary embodiment of the present specification, the organic light emitting device includes an electron transporting layer provided between the light emitting layer and the cathode, and the electron transporting layer includes the compound of any one of Formulae 1 to 28.

According to an exemplary embodiment of the present specification, the organic light emitting device includes: a light emitting layer provided between an anode and the cathode; an electron transporting layer provided between the light emitting layer and the cathode; and an electron controlling layer provided between the electron transporting layer and the light emitting layer, and the electron controlling layer includes the compound of any one of Formulae 1 to 28.

According to an exemplary embodiment of the present specification, the electron controlling layer is provided to be in contact with a light emitting layer, and the electron controlling layer includes the compound of any one of Formulae 1 to 28.

According to an exemplary embodiment of the present specification, the organic light emitting device includes: a light emitting layer provided between an anode and the cathode; an electron transporting layer provided between the light emitting layer and the cathode; and an electron controlling layer provided between the electron transporting layer and the light emitting layer, and the electron controlling layer includes the compound of Formula 3.

According to an exemplary embodiment of the present specification, the organic light emitting device includes: a light emitting layer provided between an anode and the cathode; an electron transporting layer provided between the light emitting layer and the cathode; and an electron controlling layer provided between the electron transporting layer and the light emitting layer, and the electron controlling layer includes a compound of the following Formula 3-1.

[Formula 3-1]

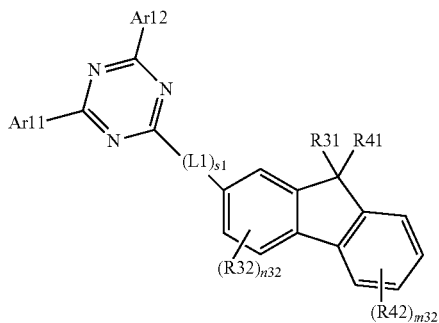

In Formula 3-1,

Ar11 and Ar12 are different from each other, and each independently a substituted or unsubstituted aryl group, L1 is a direct bond; a substituted or unsubstituted arylene; or a substituted or unsubstituted heteroarylene, R32 and R42 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with an adjacent group to form a substituted or unsubstituted ring, R31 and R41 are the same as or different from each other, and each independently hydrogen; deuterium; a halogen group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with each other to form a substituted or unsubstituted aliphatic ring, n32 is an integer of 0 to 3 and n42 is an integer of 0 to 4, and s1 is an integer of 1 to 5, and when n32, n42, and s1 are each 2 or more, the structures in the parenthesis are the same as or different from each other.

According to an exemplary embodiment of the present specification, L1 is a direct bond; or a substituted or unsubstituted arylene.

According to an exemplary embodiment of the present specification, L1 is a direct bond; or a substituted or unsubstituted monocyclic to tetracyclic arylene.

According to an exemplary embodiment of the present specification, L1 is a direct bond; or a substituted or unsubstituted monocyclic to tricyclic arylene.

According to an exemplary embodiment of the present specification, L1 is a substituted or unsubstituted arylene having 6 to 30 carbon atoms.

According to an exemplary embodiment of the present specification, L1 is a substituted or unsubstituted arylene having 6 to 20 carbon atoms.

According to an exemplary embodiment of the present specification, L1 is a direct bond; a substituted or unsubstituted phenylene; a substituted or unsubstituted biphenylylene; a substituted or unsubstituted naphthylene; or a substituted or unsubstituted phenanthrylene.

According to an exemplary embodiment of the present specification, L1 is a direct bond; phenylene; biphenylylene; naphthylene; or phenanthrylene.

According to an exemplary embodiment of the present specification, L1 is a direct bond; or a substituted or unsubstituted phenylene.

According to an exemplary embodiment of the present specification, L1 is a direct bond; or phenylene.

According to an exemplary embodiment of the present specification, L1 is a substituted or unsubstituted phenylene.

According to an exemplary embodiment of the present specification, L1 is phenylene.

According to an exemplary embodiment of the present specification, L1 is a direct bond.

According to an exemplary embodiment of the present specification, R32 is hydrogen; deuterium; a substituted or unsubstituted alkyl group; or a substituted or unsubstituted aryl group, or two or more adjacent R32's combine with each other to form a substituted or unsubstituted ring.

According to an exemplary embodiment of the present specification, R32 is hydrogen; deuterium; a substituted or unsubstituted alkyl group having 1 to 30 carbon atoms; or a substituted or unsubstituted aryl group having 6 to 40 carbon atoms, or two or more adjacent R32's combine with each other to form a substituted or unsubstituted ring.

According to an exemplary embodiment of the present specification, R32 is hydrogen; deuterium; a substituted or unsubstituted alkyl group having 1 to 6 carbon atoms; or a substituted or unsubstituted aryl group having 6 to 20 carbon atoms, or two or more adjacent R32's combine with each other to form a substituted or unsubstituted ring.

According to an exemplary embodiment of the present specification, R32 is hydrogen; deuterium; an alkyl group having 1 to 6 carbon atoms; or an aryl group having 6 to 20 carbon atoms, or two or more adjacent R32's combine with each other to form a substituted or unsubstituted ring.

According to an exemplary embodiment of the present specification, R32 is hydrogen; deuterium; or an alkyl group, or two or more adjacent R32's combine with each other to form a substituted or unsubstituted ring.

According to an exemplary embodiment of the present specification, R32 is hydrogen; or deuterium.

According to an exemplary embodiment of the present specification, R32 is hydrogen, or two or more adjacent R32's combine with each other to form a substituted or unsubstituted ring.

According to an exemplary embodiment of the present specification, R32 is hydrogen, or two or more adjacent R32's combine with each other to form a ring.

According to an exemplary embodiment of the present specification, two or more adjacent R32's combine with each other to form a substituted or unsubstituted ring.

According to an exemplary embodiment of the present specification, two or more adjacent R32's combine with each other to form a ring.

According to an exemplary embodiment of the present specification, R32 is hydrogen.

According to an exemplary embodiment of the present specification, R42 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; a substituted or unsubstituted monocyclic or bicyclic hetero-cyclic group including one or more of O and S atoms; a substituted or unsubstituted pyrrole group; a substituted or unsubstituted imidazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazole group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted benzoimidazole group; or a substituted or unsubstituted phenanthroline group, or two or more adjacent R42's combine with each other to form a substituted or unsubstituted ring.

According to an exemplary embodiment of the present specification, R42 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted monocyclic or bicyclic hetero-cyclic group including one or more of O and S atoms, or two or more adjacent R42's combine with each other to form a substituted or unsubstituted ring.

According to an exemplary embodiment of the present specification, R42 is hydrogen; deuterium; or a substituted or unsubstituted aryl group; or a substituted or unsubstituted monocyclic or bicyclic hetero-cyclic group including one or more of O and S atoms, or two or more adjacent R42's combine with each other to form a substituted or unsubstituted ring.

According to an exemplary embodiment of the present specification, R42 is hydrogen; deuterium; or a substituted or unsubstituted aryl group, or two or more adjacent R42's combine with each other to form a substituted or unsubstituted ring.

According to an exemplary embodiment of the present specification, R42 is hydrogen; deuterium; or a substituted or unsubstituted aryl group having 6 to 40 carbon atoms, or two or more adjacent R42's combine with each other to form a substituted or unsubstituted ring.

According to an exemplary embodiment of the present specification, R42 is hydrogen; deuterium; or a substituted or unsubstituted aryl group having 6 to 20 carbon atoms, or two or more adjacent R42's combine with each other to form a substituted or unsubstituted ring.

According to an exemplary embodiment of the present specification, R42 is hydrogen; deuterium; or an aryl group having 6 to 20 carbon atoms, or two or more adjacent R42's combine with each other to form a substituted or unsubstituted ring.

According to an exemplary embodiment of the present specification, R42 is hydrogen; deuterium; a substituted or unsubstituted alkyl group; or a substituted or unsubstituted aryl group, or two or more adjacent R42's combine with each other to form a substituted or unsubstituted ring.

According to an exemplary embodiment of the present specification, R42 is hydrogen; deuterium; an alkyl group; or an aryl group, or two or more adjacent R42's combine with each other to form a ring.

According to an exemplary embodiment of the present specification, R42 is hydrogen; deuterium; an alkyl group; a phenyl group; or a naphthyl group, or two or more adjacent R42's combine with each other to form a substituted or unsubstituted ring.

According to an exemplary embodiment of the present specification, R42 is hydrogen; deuterium; a substituted or unsubstituted alkyl group; a substituted or unsubstituted phenyl group; or a substituted or unsubstituted naphthyl group.

According to an exemplary embodiment of the present specification, R42 is hydrogen; deuterium; an alkyl group; a phenyl group; or a naphthyl group.

According to an exemplary embodiment of the present specification, R42 is hydrogen; deuterium; a substituted or unsubstituted alkyl group; or a substituted or unsubstituted phenyl group.

According to an exemplary embodiment of the present specification, R42 is hydrogen; deuterium; an alkyl group; or a phenyl group.

According to an exemplary embodiment of the present specification, R42 is hydrogen; deuterium; or a substituted or unsubstituted alkyl group.

According to an exemplary embodiment of the present specification, R42 is hydrogen; deuterium; or an alkyl group.

According to an exemplary embodiment of the present specification, R42 is hydrogen; or deuterium.

According to an exemplary embodiment of the present specification, R42 is hydrogen.

According to an exemplary embodiment of the present specification, R31 and R41 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group.

According to an exemplary embodiment of the present specification, R31 and R41 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a 5-membered substituted or unsubstituted aliphatic ring.

According to an exemplary embodiment of the present specification, R31 and R41 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a substituted or unsubstituted monocyclic or bicyclic aliphatic ring.

According to an exemplary embodiment of the present specification, R31 and R41 are the same as or different from each other, and each independently hydrogen; deuterium; a halogen group; a substituted or unsubstituted, straight-chained alkyl group having 1 to 40 carbon atoms; a substituted or unsubstituted, straight-chained alkoxy group having 1 to 40 carbon atoms; a substituted or unsubstituted, straight-chained thioalkoxy group having 1 to 40 carbon atoms; a substituted or unsubstituted, branched mono or poly cycloalkyl group having 3 to 40 carbon atoms; a substituted or unsubstituted, branched alkenyl group having to 40 carbon atoms; a substituted or unsubstituted, branched alkoxy group having 3 to 40 carbon atoms; a substituted or unsubstituted, branched thioalkoxy group having 3 to 40 carbon atoms; a 6 to 40-membered substituted or unsubstituted aryl group; a 5 to 40-membered substituted or unsubstituted hetero-cyclic group; a 5 to 40-membered substituted or unsubstituted aryloxy group; or a 5 to 40-membered substituted or unsubstituted heteroaryloxy group. According to an exemplary embodiment of the present specification, R31 and R41 are the same as or different from each other, and each independently hydrogen; a substituted or unsubstituted alkyl group; a substituted or unsubstituted aryl group; or a substituted or unsubstituted hetero-cyclic group.

According to an exemplary embodiment of the present specification, R31 and R41 are the same as or different from each other, and each independently hydrogen; a substituted or unsubstituted alkyl group; or a substituted or unsubstituted aryl group.

According to an exemplary embodiment of the present specification, R31 and R41 are the same as or different from each other, and each independently hydrogen; a substituted or unsubstituted alkyl group; a substituted or unsubstituted aryl group having 6 to 20 carbon atoms; or a substituted or unsubstituted hetero-cyclic group.

According to an exemplary embodiment of the present specification, R31 and R41 are the same as or different from each other, and each independently hydrogen; an alkyl group; an aryl group having 6 to 20 carbon atoms, which is unsubstituted or substituted with an alkyl group; or a hetero-cyclic group.

According to an exemplary embodiment of the present specification, R31 and R41 are the same as or different from each other, and each independently hydrogen; an alkyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R31 and R41 are the same as or different from each other, and each independently hydrogen; an alkyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R31 and R41 are the same as or different from each other, and each independently hydrogen; an alkyl group; a phenyl group, which is unsubstituted or substituted with an alkyl group; a biphenyl group; or a naphthyl group, or combine with each other to form an aliphatic ring.

According to an exemplary embodiment of the present specification, R31 and R41 are the same as or different from each other, and each independently hydrogen; a methyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R31 and R41 are the same as or different from each other, and each independently hydrogen; a methyl group; a phenyl group, which is unsubstituted or substituted with an alkyl group; a biphenyl group; or a naphthyl group, or combine with each other to form an aliphatic ring.

According to an exemplary embodiment of the present specification, R31 and R41 are the same as or different from each other, and each independently hydrogen; a methyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R31 and R41 are the same as or different from each other, and each independently hydrogen; a methyl group; a phenyl group; a phenyl group substituted with a methyl group; a biphenyl group; or a naphthyl group, or combine with each other to form an aliphatic ring.

According to an exemplary embodiment of the present specification, R31 and R41 are the same as or different from each other, and each independently hydrogen; a methyl group; a phenyl group; a phenyl group substituted with a methyl group; a biphenyl group; or a naphthyl group, or combine with each other to form a 5-membered aliphatic ring. According to an exemplary embodiment of the present specification, R31 and R41 are the same as or different from each other, and each independently a substituted or unsubstituted alkyl group; or a substituted or unsubstituted aryl group.

According to an exemplary embodiment of the present specification, R31 and R41 are the same as or different from each other, and each independently an alkyl group; or a substituted or unsubstituted phenyl group.

According to an exemplary embodiment of the present specification, R31 and R41 are the same as or different from each other, and each independently an alkyl group; a phenyl group; or a phenyl group substituted with a methyl group.

According to an exemplary embodiment of the present specification, R31 and R41 are the same as or different from each other, and each independently a methyl group; a phenyl group; or a phenyl group substituted with a methyl group.

According to an exemplary embodiment of the present specification, R31 and R41 are the same as each other, and a substituted or unsubstituted alkyl group; or a substituted or unsubstituted aryl group.

According to an exemplary embodiment of the present specification, R31 and R41 are the same as each other, and a substituted or unsubstituted alkyl group; or a substituted or unsubstituted phenyl group.

According to an exemplary embodiment of the present specification, R31 and R41 are the same as each other, and an alkyl group; or a substituted or unsubstituted phenyl group.

According to an exemplary embodiment of the present specification, R31 and R41 are the same as each other, and an alkyl group; a phenyl group; or a phenyl group substituted with a methyl group.

According to an exemplary embodiment of the present specification, R31 and R41 are the same as each other, and a methyl group; a phenyl group; or a phenyl group substituted with a methyl group.

According to an exemplary embodiment of the present specification, Ar11 and Ar12 are different from each other, and each independently a substituted or unsubstituted aryl group.

According to an exemplary embodiment of the present specification, Ar11 and Ar12 are different from each other, and each independently a substituted or unsubstituted monocyclic to tetracyclic aryl group.

According to an exemplary embodiment of the present specification, Ar11 and Ar12 are different from each other, and each independently an aryl group, which is unsubstituted or substituted with an aryl group.

According to an exemplary embodiment of the present specification, Ar11 and Ar12 are different from each other, and each independently a substituted or unsubstituted monocyclic to tetracyclic aryl group.

According to an exemplary embodiment of the present specification, Ar11 and Ar12 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; or a substituted or unsubstituted fluorenyl group.

According to an exemplary embodiment of the present specification, Ar11 and Ar12 are different from each other, and each independently a phenyl group; a naphthyl group; a biphenyl group; a terphenyl group; a quarterphenyl group; a phenanthryl group; a chrysenyl group; or a fluorenyl group, which is unsubstituted or substituted with an alkyl group or an aryl group.

According to an exemplary embodiment of the present specification, Ar11 and Ar12 are different from each other, and each independently a phenyl group, which is unsubstituted or substituted with an aryl group; a naphthyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a phenanthryl group, which is unsubstituted or substituted with an aryl group; or a chrysenyl group, which is unsubstituted or substituted with an aryl group.

According to an exemplary embodiment of the present specification, Ar11 and Ar12 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; or a substituted or unsubstituted chrysenyl group.

According to an exemplary embodiment of the present specification, Ar11 and Ar12 are different from each other, and each independently a phenyl group; a naphthyl group; a biphenyl group; a terphenyl group; a quarterphenyl group; a phenanthryl group; or a chrysenyl group.

According to an exemplary embodiment of the present specification, Ar11 and Ar12 are different from each other, and each independently a substituted or unsubstituted phenyl group; a substituted or unsubstituted biphenyl group; a substituted or unsubstituted terphenyl group; a substituted or unsubstituted naphthyl group; or a substituted or unsubstituted phenanthryl group.

According to an exemplary embodiment of the present specification, Ar11 and Ar12 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar11 and Ar12 are different from each other, and each independently a phenyl group; a biphenyl group; a terphenyl group; a terphenyl group substituted with a phenyl group; a naphthyl group; a phenanthryl group; a phenyl group substituted with a naphthyl group; or a biphenyl group substituted with a phenyl group.

According to an exemplary embodiment of the present specification, Ar11 is an aryl group.

According to an exemplary embodiment of the present specification, Ar11 is a monocyclic to tricyclic aryl group.

According to an exemplary embodiment of the present specification, Ar11 is a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar11 is a phenyl group; a biphenyl group; a naphthyl group; or a phenanthryl group.

According to an exemplary embodiment of the present specification, Ar11 is a substituted or unsubstituted phenyl group.

According to an exemplary embodiment of the present specification, Ar11 is a substituted or unsubstituted biphenyl group.

According to an exemplary embodiment of the present specification, Ar11 is a substituted or unsubstituted naphthyl group.

According to an exemplary embodiment of the present specification, Ar11 is a substituted or unsubstituted phenanthryl group.

According to an exemplary embodiment of the present specification, when Ar11 is a substituted or unsubstituted phenyl group, Ar12 is a substituted or unsubstituted biphenyl group; a substituted or unsubstituted terphenyl group; a substituted or unsubstituted quarterphenyl group; a substituted or unsubstituted naphthyl group; a substituted or unsubstituted phenanthryl group; or a substituted phenyl group.

According to an exemplary embodiment of the present specification, when Ar11 is a phenyl group, Ar12 is a biphenyl group; a terphenyl group; a terphenyl group substituted with a phenyl group; a quarterphenyl group; a naphthyl group; a phenanthryl group; or a phenyl group substituted with a naphthyl group.

According to an exemplary embodiment of the present specification, when Ar11 is a substituted or unsubstituted biphenyl group, Ar12 is a substituted or unsubstituted terphenyl group; a substituted or unsubstituted biphenyl group; a substituted phenyl group; a substituted or unsubstituted naphthyl group; or a substituted or unsubstituted phenanthryl group.

According to an exemplary embodiment of the present specification, when Ar11 is a biphenyl group, Ar12 is a terphenyl group; a biphenyl group; a phenyl group substituted with a naphthyl group; a phenyl group substituted with a phenanthryl group; a biphenyl group substituted with a naphthyl group; a naphthyl group; a naphthyl group substituted with a phenyl group; or a phenanthryl group.

According to an exemplary embodiment of the present specification, when Ar11 is a substituted or unsubstituted naphthyl group, Ar12 is a substituted or unsubstituted biphenyl group; a substituted phenyl group; a substituted or unsubstituted terphenyl group; a substituted or unsubstituted phenanthryl group; or a substituted or unsubstituted quarterphenyl group.

According to an exemplary embodiment of the present specification, when Ar11 is a naphthyl group, Ar12 is a biphenyl group; a phenyl group substituted with a naphthyl group; a phenyl group substituted with a phenanthryl group; a terphenyl group; a biphenyl group substituted with a naphthyl group; a phenanthryl group substituted with a phenyl group; a phenanthryl group; a quarterphenyl group; or a terphenyl group substituted with a phenyl group.

According to an exemplary embodiment of the present specification, when Ar11 is a substituted or unsubstituted phenanthryl group, Ar12 is a substituted or unsubstituted biphenyl group; a substituted phenyl group; a substituted or unsubstituted terphenyl group; or a substituted or unsubstituted quarterphenyl group.

According to an exemplary embodiment of the present specification, when Ar11 is a phenanthryl group, Ar12 is a biphenyl group; a phenyl group substituted with a phenanthryl group; a phenyl group substituted with a naphthyl group; a terphenyl group; a quarterphenyl group; or a terphenyl group substituted with a phenyl group.

According to an exemplary embodiment of the present specification, Ar12 is a substituted or unsubstituted phenyl group; a substituted or unsubstituted biphenyl group; a substituted or unsubstituted terphenyl group; a substituted or unsubstituted quarterphenyl group; a substituted or unsubstituted naphthyl group; or a substituted or unsubstituted phenanthryl group.

According to an exemplary embodiment of the present specification, Ar12 is a phenyl group; a biphenyl group; a terphenyl group; a quarterphenyl group; a naphthyl group; or a phenanthryl group.

According to an exemplary embodiment of the present specification, at least one of Ar11 and Ar12 is a substituted or unsubstituted biphenyl group.

According to an exemplary embodiment of the present specification, Ar11 is a phenyl group, which is unsubstituted or substituted with an aryl group; a biphenyl group, which is unsubstituted or substituted with an aryl group; a naphthyl group, which is unsubstituted or substituted with an aryl group; or a phenanthryl group, which is unsubstituted or substituted with an aryl group, and Ar12 is a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar11 is a phenyl group and Ar12 is a biphenyl group.

According to an exemplary embodiment of the present specification, the electron controlling layer is provided to be in contact with a light emitting layer, and the electron controlling layer includes the compound of Formula 3-1.

According to an exemplary embodiment of the present specification, the organic light emitting device includes a light emitting layer provided between an anode and the cathode; an electron transporting layer provided between the light emitting layer and the cathode; and an electron controlling layer provided between the electron transporting layer and the light emitting layer, and the electron transporting layer includes the compound of any one of Formulae 1 to 28.

According to an exemplary embodiment of the present specification, the electron controlling layer is provided to be in contact with a light emitting layer, and the electron transporting layer includes the compound of any one of Formulae 1 to 28.

According to an exemplary embodiment of the present specification, the organic light emitting device includes a light emitting layer provided between the anode and the cathode; an electron transporting layer provided between the light emitting layer and the cathode; and an electron controlling layer provided between the electron transporting layer and the light emitting layer, and the electron controlling layer includes the compound of Formula 6.

According to an exemplary embodiment of the present specification, the organic light emitting device includes a light emitting layer provided between the anode and the cathode; an electron transporting layer provided between the light emitting layer and the cathode; and an electron controlling layer provided between the electron transporting layer and the light emitting layer, and the electron transporting layer includes a compound of the following Formula 6-1.

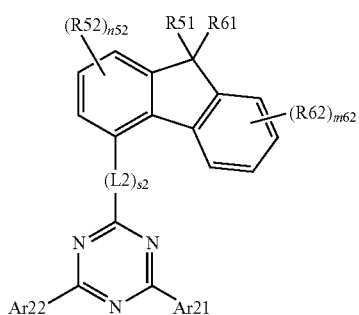

[Formula 6-1]

In Formula 6-1,

Ar21 and Ar22 are different from each other, and each independently a substituted or unsubstituted aryl group, L2 is a direct bond; a substituted or unsubstituted arylene; or a substituted or unsubstituted heteroarylene, R52 and R62 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with an adjacent group to form a substituted or unsubstituted ring, R51 and R61 are the same as or different from each other, and each independently hydrogen; deuterium; a halogen group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted hetero-cyclic group, or combine with each other to form a substituted or unsubstituted aliphatic ring, n52 is an integer of 0 to 3 and n62 is an integer of 0 to 4, and s2 is an integer of 1 to 5, and when n52, n62, and s2 are each 2 or more, the structures in the parenthesis are the same as or different from each other.

According to an exemplary embodiment of the present specification, L2 is a direct bond; or a substituted or unsubstituted arylene.

According to an exemplary embodiment of the present specification, L2 is a direct bond; or a substituted or unsubstituted monocyclic to tetracyclic arylene.

According to an exemplary embodiment of the present specification, L2 is a direct bond; or a substituted or unsubstituted monocyclic to tricyclic arylene.

According to an exemplary embodiment of the present specification, L2 is a substituted or unsubstituted arylene having 6 to 30 carbon atoms.

According to an exemplary embodiment of the present specification, L2 is a substituted or unsubstituted arylene having 6 to 20 carbon atoms.

According to an exemplary embodiment of the present specification, L2 is a direct bond; a substituted or unsubstituted phenylene; a substituted or unsubstituted biphenylylene; a substituted or unsubstituted naphthylene; or a substituted or unsubstituted phenanthrylene.

According to an exemplary embodiment of the present specification, L2 is a direct bond; phenylene; biphenylylene; naphthylene; or phenanthrylene.

According to an exemplary embodiment of the present specification, L2 is a direct bond; or a substituted or unsubstituted phenylene.

According to an exemplary embodiment of the present specification, L2 is a direct bond; or phenylene.

According to an exemplary embodiment of the present specification, L2 is a substituted or unsubstituted phenylene.

According to an exemplary embodiment of the present specification, L2 is phenylene.

According to an exemplary embodiment of the present specification, L2 is a direct bond.

According to an exemplary embodiment of the present specification, R52 is hydrogen; deuterium; a substituted or unsubstituted alkyl group; or a substituted or unsubstituted aryl group, or two or more adjacent R52's combine with each other to form a substituted or unsubstituted ring.

According to an exemplary embodiment of the present specification, R52 is hydrogen; deuterium; a substituted or unsubstituted alkyl group having 1 to 30 carbon atoms; or a substituted or unsubstituted aryl group having 6 to 40 carbon atoms, or two or more adjacent R52's combine with each other to form a substituted or unsubstituted ring.

According to an exemplary embodiment of the present specification, R52 is hydrogen; deuterium; a substituted or unsubstituted alkyl group having 1 to 6 carbon atoms; or a substituted or unsubstituted aryl group having 6 to 20 carbon atoms, or two or more adjacent R52's combine with each other to form a substituted or unsubstituted ring.

According to an exemplary embodiment of the present specification, R52 is hydrogen; deuterium; an alkyl group having 1 to 6 carbon atoms; or an aryl group having 6 to 20 carbon atoms, or two or more adjacent R52's combine with each other to form a substituted or unsubstituted ring.

According to an exemplary embodiment of the present specification, R52 is hydrogen; deuterium; or an alkyl group, or two or more adjacent R52's combine with each other to form a substituted or unsubstituted ring.

According to an exemplary embodiment of the present specification, R52 is hydrogen; or deuterium.

According to an exemplary embodiment of the present specification, R52 is hydrogen, or two or more adjacent R52's combine with each other to form a substituted or unsubstituted ring.

According to an exemplary embodiment of the present specification, R52 is hydrogen, or two or more adjacent R52's combine with each other to form a ring.

According to an exemplary embodiment of the present specification, two or more adjacent R52's combine with each other to form a substituted or unsubstituted ring.

According to an exemplary embodiment of the present specification, two or more adjacent R52's combine with each other to form a ring.

According to an exemplary embodiment of the present specification, R52 is hydrogen.

According to an exemplary embodiment of the present specification, R62 is hydrogen; deuterium; a halogen group;

a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; a substituted or unsubstituted monocyclic or bicyclic hetero-cyclic group including one or more of O and S atoms; a substituted or unsubstituted pyrrole group; a substituted or unsubstituted imidazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazole group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted benzoimidazole group; or a substituted or unsubstituted phenanthroline group, or two or more adjacent R62's combine with each other to form a substituted or unsubstituted ring.

According to an exemplary embodiment of the present specification, R62 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted monocyclic or bicyclic hetero-cyclic group including one or more of O and S atoms, or two or more adjacent R62's combine with each other to form a substituted or unsubstituted ring.

According to an exemplary embodiment of the present specification, R62 is hydrogen; deuterium; or a substituted or unsubstituted aryl group; or a substituted or unsubstituted monocyclic or bicyclic hetero-cyclic group including one or more of O and S atoms, or two or more adjacent R62's combine with each other to form a substituted or unsubstituted ring.

According to an exemplary embodiment of the present specification, R62 is hydrogen; deuterium; or a substituted or unsubstituted aryl group, or two or more adjacent R62's combine with each other to form a substituted or unsubstituted ring.

According to an exemplary embodiment of the present specification, R62 is hydrogen; deuterium; or a substituted or unsubstituted aryl group having 6 to 40 carbon atoms, or two or more adjacent R62's combine with each other to form a substituted or unsubstituted ring.

According to an exemplary embodiment of the present specification, R62 is hydrogen; deuterium; or a substituted or unsubstituted aryl group having 6 to 20 carbon atoms, or two or more adjacent R62's combine with each other to form a substituted or unsubstituted ring.

According to an exemplary embodiment of the present specification, R62 is hydrogen; deuterium; or an aryl group having 6 to 20 carbon atoms, or two or more adjacent R62's combine with each other to form a substituted or unsubstituted ring.

According to an exemplary embodiment of the present specification, R62 is hydrogen; deuterium; a substituted or unsubstituted alkyl group; or a substituted or unsubstituted aryl group, or two or more adjacent R62's combine with each other to form a substituted or unsubstituted ring.

According to an exemplary embodiment of the present specification, R62 is hydrogen; deuterium; an alkyl group; or an aryl group, or two or more adjacent R62's combine with each other to form a ring.

According to an exemplary embodiment of the present specification, R62 is hydrogen; deuterium; an alkyl group; a phenyl group; or a naphthyl group, or two or more adjacent R62's combine with each other to form a substituted or unsubstituted ring.

According to an exemplary embodiment of the present specification, R62 is hydrogen; deuterium; a substituted or unsubstituted alkyl group; a substituted or unsubstituted phenyl group; or a substituted or unsubstituted naphthyl group.

According to an exemplary embodiment of the present specification, R62 is hydrogen; deuterium; an alkyl group; a phenyl group; or a naphthyl group.

According to an exemplary embodiment of the present specification, R62 is hydrogen; deuterium; a substituted or unsubstituted alkyl group; or a substituted or unsubstituted phenyl group.

According to an exemplary embodiment of the present specification, R62 is hydrogen; deuterium; an alkyl group; or a phenyl group.

According to an exemplary embodiment of the present specification, R62 is hydrogen; deuterium; or a substituted or unsubstituted alkyl group.

According to an exemplary embodiment of the present specification, R62 is hydrogen; deuterium; or an alkyl group.

According to an exemplary embodiment of the present specification, R62 is hydrogen; or deuterium.

According to an exemplary embodiment of the present specification, R62 is hydrogen.

According to an exemplary embodiment of the present specification, R51 and R61 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group.

According to an exemplary embodiment of the present specification, R51 and R61 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a 5-membered substituted or unsubstituted aliphatic ring.

According to an exemplary embodiment of the present specification, R51 and R61 are the same as or different from each other, and each independently hydrogen; deuterium; a halogen group; a substituted or unsubstituted alkyl group; a substituted or unsubstituted alkoxy group; a substituted or unsubstituted thioalkoxy group; a substituted or unsubstituted cycloalkyl group; a substituted or unsubstituted alkenyl group; a substituted or unsubstituted aryl group; a substituted or unsubstituted hetero-cyclic group; a substituted or unsubstituted aryloxy group; or a substituted or unsubstituted heteroaryloxy group, or combine with each other to form a substituted or unsubstituted monocyclic or bicyclic aliphatic ring.

According to an exemplary embodiment of the present specification, R51 and R61 are the same as or different from each other, and each independently hydrogen; deuterium; a halogen group; a substituted or unsubstituted, straight-chained alkyl group having 1 to 40 carbon atoms; a substituted or unsubstituted, straight-chained alkoxy group having 1 to 40 carbon atoms; a substituted or unsubstituted, straight-chained thioalkoxy group having 1 to 40 carbon atoms; a substituted or unsubstituted, branched mono or poly cycloalkyl group having 3 to 40 carbon atoms; a substituted or unsubstituted, branched alkenyl group having 3 to 40 carbon atoms; a substituted or unsubstituted, branched alkoxy group having 3 to 40 carbon atoms; a substituted or unsubstituted, branched thioalkoxy group having 3 to 40 carbon atoms; a 6 to 40-membered substituted or unsubstituted aryl group; a 5 to 40-membered substituted or unsubstituted hetero-cyclic group; a 5 to 40-membered substituted or unsubstituted aryloxy group; or a 5 to 40-membered substituted or unsubstituted heteroaryloxy group.

According to an exemplary embodiment of the present specification, R51 and R61 are the same as or different from each other, and each independently hydrogen; a substituted or unsubstituted alkyl group; a substituted or unsubstituted aryl group; or a substituted or unsubstituted hetero-cyclic group.

According to an exemplary embodiment of the present specification, R51 and R61 are the same as or different from each other, and each independently hydrogen; a substituted or unsubstituted alkyl group; or a substituted or unsubstituted aryl group.

According to an exemplary embodiment of the present specification, R51 and R61 are the same as or different from each other, and each independently hydrogen; a substituted or unsubstituted alkyl group; a substituted or unsubstituted aryl group having 6 to 20 carbon atoms; or a substituted or unsubstituted hetero-cyclic group.

According to an exemplary embodiment of the present specification, R51 and R61 are the same as or different from each other, and each independently hydrogen; an alkyl group; an aryl group having 6 to 20 carbon atoms, which is unsubstituted or substituted with an alkyl group; or a heterocyclic group.

According to an exemplary embodiment of the present specification, R51 and R61 are the same as or different from each other, and each independently hydrogen; an alkyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R51 and R61 are the same as or different from each other, and each independently hydrogen; an alkyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R51 and R61 are the same as or different from each other, and each independently hydrogen; an alkyl group; a phenyl group, which is unsubstituted or substituted with an alkyl group; a biphenyl group; or a naphthyl group, or combine with each other to form an aliphatic ring.

According to an exemplary embodiment of the present specification, R51 and R61 are the same as or different from each other, and each independently hydrogen; a methyl group; a substituted or unsubstituted phenyl group; a substituted or unsubstituted biphenyl group; or a substituted or unsubstituted naphthyl group, or combine with each other to form a 5-membered aliphatic ring.

According to an exemplary embodiment of the present specification, R51 and R61 are the same as or different from each other, and each independently hydrogen; a methyl group; a phenyl group, which is unsubstituted or substituted with an alkyl group; a biphenyl group; or a naphthyl group, or combine with each other to form an aliphatic ring.

According to an exemplary embodiment of the present specification, R51 and R61 are the same as or different from each other, and each independently hydrogen; a methyl group; a phenyl group, which is unsubstituted or substituted with an alkyl group; a biphenyl group; or a naphthyl group, or combine with each other to form a substituted or unsubstituted monocyclic or bicyclic ring.

According to an exemplary embodiment of the present specification, R51 and R61 are the same as or different from each other, and each independently hydrogen; a methyl group; a phenyl group; a phenyl group substituted with a methyl group; a biphenyl group; or a naphthyl group, or combine with each other to form an aliphatic ring.

According to an exemplary embodiment of the present specification, R51 and R61 are the same as or different from each other, and each independently hydrogen; a methyl group; a phenyl group; a phenyl group substituted with a methyl group; a biphenyl group; or a naphthyl group, or combine with each other to form a 5-membered aliphatic ring.

According to an exemplary embodiment of the present specification, R51 and R61 are the same as or different from each other, and each independently a substituted or unsubstituted alkyl group; or a substituted or unsubstituted aryl group.

According to an exemplary embodiment of the present specification, R51 and R61 are the same as or different from each other, and each independently an alkyl group; or a substituted or unsubstituted phenyl group.

According to an exemplary embodiment of the present specification, R51 and R61 are the same as or different from each other, and each independently an alkyl group; a phenyl group; or a phenyl group substituted with a methyl group.

According to an exemplary embodiment of the present specification, R51 and R61 are the same as or different from each other, and each independently a methyl group; a phenyl group; or a phenyl group substituted with a methyl group.

According to an exemplary embodiment of the present specification, R51 and R61 are the same as each other, and a substituted or unsubstituted alkyl group; or a substituted or unsubstituted aryl group.

According to an exemplary embodiment of the present specification, R51 and R61 are the same as each other, and a substituted or unsubstituted alkyl group; or a substituted or unsubstituted phenyl group.

According to an exemplary embodiment of the present specification, R51 and R61 are the same as each other, and an alkyl group; or a substituted or unsubstituted phenyl group.

According to an exemplary embodiment of the present specification, R51 and R61 are the same as each other, and an alkyl group; a phenyl group; or a phenyl group substituted with a methyl group.

According to an exemplary embodiment of the present specification, R51 and R61 are the same as each other, and a methyl group; a phenyl group; or a phenyl group substituted with a methyl group.

According to an exemplary embodiment of the present specification, Ar21 and Ar22 are different from each other, and each independently a substituted or unsubstituted aryl group.

According to an exemplary embodiment of the present specification, Ar21 and Ar22 are different from each other, and each independently a substituted or unsubstituted monocyclic to tetracyclic aryl group.

According to an exemplary embodiment of the present specification, Ar21 and Ar22 are different from each other, and each independently an aryl group, which is unsubstituted or substituted with an aryl group.

According to an exemplary embodiment of the present specification, Ar21 and Ar22 are different from each other, and each independently a monocyclic to tetracyclic aryl group, which is unsubstituted or substituted with an aryl group.

According to an exemplary embodiment of the present specification, Ar21 and Ar22 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; or a substituted or unsubstituted fluorenyl group.

According to an exemplary embodiment of the present specification, Ar21 and Ar22 are different from each other, and each independently a phenyl group; a naphthyl group; a biphenyl group; a terphenyl group; a quarterphenyl group; a phenanthryl group; a chrysenyl group; or a fluorenyl group, which is unsubstituted or substituted with an alkyl group or an aryl group.

According to an exemplary embodiment of the present specification, Ar21 and Ar22 are different from each other, and each independently a phenyl group, which is unsubstituted or substituted with an aryl group; a naphthyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a phenanthryl group, which is unsubstituted or substituted with an aryl group; or a chrysenyl group, which is unsubstituted or substituted with an aryl group.

According to an exemplary embodiment of the present specification, Ar21 and Ar22 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; or a substituted or unsubstituted chrysenyl group.

According to an exemplary embodiment of the present specification, Ar21 and Ar22 are different from each other, and each independently a phenyl group; a naphthyl group; a biphenyl group; a terphenyl group; a quarterphenyl group; a phenanthryl group; or a chrysenyl group.

According to an exemplary embodiment of the present specification, Ar21 and Ar22 are different from each other, and each independently a substituted or unsubstituted phenyl group; a substituted or unsubstituted biphenyl group; a substituted or unsubstituted terphenyl group; a substituted or unsubstituted naphthyl group; or a substituted or unsubstituted phenanthryl group.

According to an exemplary embodiment of the present specification, Ar21 and Ar22 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar21 and Ar22 are different from each other, and each independently a phenyl group; a biphenyl group; a terphenyl group; a terphenyl group substituted with a phenyl group; a naphthyl group; a phenanthryl group; a phenyl group substituted with a naphthyl group; or a biphenyl group substituted with a phenyl group.

According to an exemplary embodiment of the present specification, Ar21 is an aryl group.

According to an exemplary embodiment of the present specification, Ar21 is a monocyclic to tricyclic aryl group.

According to an exemplary embodiment of the present specification, Ar21 is a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar21 is a phenyl group; a biphenyl group; a naphthyl group; or a phenanthryl group.

According to an exemplary embodiment of the present specification, Ar21 is a substituted or unsubstituted phenyl group.

According to an exemplary embodiment of the present specification, Ar21 is a substituted or unsubstituted biphenyl group.

According to an exemplary embodiment of the present specification, Ar21 is a substituted or unsubstituted naphthyl group.

According to an exemplary embodiment of the present specification, Ar21 is a substituted or unsubstituted phenanthryl group.

According to an exemplary embodiment of the present specification, when Ar21 is a substituted or unsubstituted phenyl group, Ar22 is a substituted or unsubstituted biphenyl group; a substituted or unsubstituted terphenyl group; a substituted or unsubstituted quarterphenyl group; a substituted or unsubstituted naphthyl group; a substituted or unsubstituted phenanthryl group; or a substituted phenyl group.

According to an exemplary embodiment of the present specification, when Ar21 is a phenyl group, Ar22 is a biphenyl group; a terphenyl group; a terphenyl group substituted with a phenyl group; a quarterphenyl group; a naphthyl group; a phenanthryl group; or a phenyl group substituted with a naphthyl group.

According to an exemplary embodiment of the present specification, when Ar21 is a substituted or unsubstituted biphenyl group, Ar22 is a substituted or unsubstituted terphenyl group; a substituted or unsubstituted biphenyl group; a substituted phenyl group; a substituted or unsubstituted naphthyl group; or a substituted or unsubstituted phenanthryl group.

According to an exemplary embodiment of the present specification, when Ar21 is a biphenyl group, Ar22 is a terphenyl group; a biphenyl group; a phenyl group substituted with a naphthyl group; a phenyl group substituted with a phenanthryl group; a biphenyl group substituted with a naphthyl group; a naphthyl group; a naphthyl group substituted with a phenyl group; or a phenanthryl group.

According to an exemplary embodiment of the present specification, when Ar21 is a substituted or unsubstituted naphthyl group, Ar22 is a substituted or unsubstituted biphenyl group; a substituted phenyl group; a substituted or unsubstituted terphenyl group; a substituted or unsubstituted phenanthryl group; or a substituted or unsubstituted quarterphenyl group.

According to an exemplary embodiment of the present specification, when Ar21 is a naphthyl group, Ar22 is a biphenyl group; a phenyl group substituted with a naphthyl group; a phenyl group substituted with a phenanthryl group; a terphenyl group; a biphenyl group substituted with a naphthyl group; a phenanthryl group substituted with a phenyl group; a phenanthryl group; a quarterphenyl group; or a terphenyl group substituted with a phenyl group.

According to an exemplary embodiment of the present specification, when Ar21 is a substituted or unsubstituted phenanthryl group, Ar22 is a substituted or unsubstituted biphenyl group; a substituted phenyl group; a substituted or unsubstituted terphenyl group; or a substituted or unsubstituted quarterphenyl group.

According to an exemplary embodiment of the present specification, when Ar21 is a phenanthryl group, Ar22 is a biphenyl group; a phenyl group substituted with a phenanthryl group; a phenyl group substituted with a naphthyl group; a terphenyl group; a quarterphenyl group; or a terphenyl group substituted with a phenyl group.

According to an exemplary embodiment of the present specification, Ar22 is a substituted or unsubstituted phenyl group; a substituted or unsubstituted biphenyl group; a substituted or unsubstituted terphenyl group; a substituted or unsubstituted quarterphenyl group; a substituted or unsubstituted naphthyl group; or a substituted or unsubstituted phenanthryl group.

According to an exemplary embodiment of the present specification, Ar22 is a phenyl group; a biphenyl group; a terphenyl group; a quarterphenyl group; a naphthyl group; or a phenanthryl group.

According to an exemplary embodiment of the present specification, at least one of Ar21 and Ar22 is a substituted or unsubstituted biphenyl group.

According to an exemplary embodiment of the present specification, Ar21 is a phenyl group, which is unsubstituted or substituted with an aryl group; a biphenyl group, which is unsubstituted or substituted with an aryl group; a naphthyl group, which is unsubstituted or substituted with an aryl group; or a phenanthryl group, which is unsubstituted or substituted with an aryl group, and Ar22 is a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar21 is a phenyl group and Ar22 is a biphenyl group.

According to an exemplary embodiment of the present specification, the electron controlling layer is provided to be in contact with a light emitting layer, and the electron transporting layer includes the compound of Formula 6-1.

According to an exemplary embodiment of the present specification, the organic light emitting device includes a light emitting layer provided between an anode and the cathode; an electron transporting layer provided between the light emitting layer and the cathode; and an electron controlling layer provided between the electron transporting layer and the light emitting layer, the electron transporting layer includes the compound of any one of Formulae 1 to 28, and the electron controlling layer includes the compound of any one of Formulae 1 to 28. In this case, the compounds included in each layer may be the same as or different from each other.

In another exemplary embodiment of the present specification, the organic material layer includes an electron transporting layer and an electron controlling layer, and at least one of the electron transporting layer and the electron controlling layer includes the compound of any one of Formulae 1 to 28. Specifically, in an exemplary embodiment of the present specification, the compound of any one of Formulae 1 to 28 may also be included in one layer of the electron transporting layer and the electron controlling layer, and may also be included in each of the electron transporting layer and the electron controlling layer. In this case, the compounds included in each layer may be the same as or different from each other.

Specifically, according to an exemplary embodiment of the present specification, the organic material layer includes an electron transporting layer and an electron controlling layer, the electron controlling layer is provided to be in contact with a light emitting layer, the electron controlling layer the compound of Formula 3-1, and the electron transporting layer includes the compound of Formula 6-1.

According to an exemplary embodiment of the present specification, the organic light emitting device includes two or more organic material layers between a light emitting layer and a cathode, and at least one of the two or more organic material layers includes the compound of any one of Formulae 1 to 28.

According to an exemplary embodiment of the present specification, as the organic material layer, two layers or two or more layers may be selected from the group consisting of an electron transporting layer, an electron injection layer, a layer which simultaneously transports and injects electrons, and an electron controlling layer, and when the compound of any one of Formulae 1 to 28 is each included in the two layers or the two or more layers, the other materials except for the compound of any one of Formulae 1 to 28 may be the same as or different from each other.

In an exemplary embodiment of the present specification, the organic material layer includes two or more electron transporting layers, and at least one of the two or more electron transporting layers includes the compound of any one of Formulae 1 to 28. Specifically, in an exemplary embodiment of the present specification, the compound of any one of Formulae 1 to 28 may also be included in one layer of the two or more electron transporting layers, and may be included in each of the two or more electron transporting layers. In this case, the compounds included in each layer may be the same as or different from each other.

An organic light emitting device according to another exemplary embodiment of the present specification includes: an anode; a cathode; and one or more organic material layers provided between the anode and the cathode, in which one or more layers of the organic material layers include the compound of any one of Formulae 1 to 28, which has a HOMO energy level of 6 eV to 7 eV.

An organic light emitting device according to another exemplary embodiment of the present specification includes: an anode; a cathode; a light emitting layer provided between the anode and the cathode; and an electron transporting layer provided between the light emitting layer and the cathode, the light emitting layer includes a host, and the electron transporting layer includes the compound of any one of Formulae 1 to 28, which is different from the host and has a HOMO energy level of 6 eV to 7 eV.

An organic light emitting device according to still another exemplary embodiment includes: an anode; a cathode; a light emitting layer provided between the anode and the cathode; and an electron controlling layer provided between the light emitting layer and the cathode, the light emitting layer includes a host, and the electron controlling layer includes the compound of any one of Formulae 1 to 28, which is different from the host and has a HOMO energy level of 6 eV to 7 eV.

In the Experimental Examples of the present specification, it was confirmed that the HOMO level of the compound of any one of Formulae 1 to 28 is 6 eV or more, which is a deep HOMO level. It was confirmed that such a deep HOMO level exhibits high efficiency by effectively blocking holes from the light emitting layer. It was confirmed that such a hole blocking effect enhances the stability of the device and thus also increases the service life.

According to an exemplary embodiment of the present specification, the light emitting layer includes a host and a dopant, and the HOMO energy level of the compound of any one of Formulae 1 to 28 is larger than the HOMO energy level of the host.

According to an exemplary embodiment of the present specification, the light emitting layer includes a host and a dopant, and the difference between the HOMO energy level of the host and the HOMO energy level of the hetero-cyclic compound represented by Formula 1 is 0.2 eV or more. As described above, when the difference in HOMO energy level between the host material of the light emitting layer and the hetero-cyclic compound represented by Formula 1 is 0.2 eV or more, holes may be further effectively blocked from the light emitting layer, and thus, it is possible to provide an organic light emitting device having high light emitting efficiency and a long service life.

Even in the Experimental Examples of the present specification, it was confirmed that when the compound of any one of Formulae 1 to 28 is used with a light emitting layer, holes are effectively blocked by having a deeper HOMO level than that of the host compound of the light emitting layer. For example, in the case of a blue fluorescent host, an anthracene derivative is usually used, and these anthracene derivatives generally have a HOMO level of less than 6 eV. In this case, it was confirmed that when the compound of any one of Formulae 1 to 28, which has a HOMO level of 6 eV or more, is used for an organic light emitting device as an electron controlling layer, the hole blocking effect is high.

Further, it was confirmed that even a phosphorescent host of the combination of carbazole-heteroaryl, which is usually used, has a HOMO level of less than 5.9 eV, and when the compound of any one of Formulae 1 to 28, which has a HOMO level of 6 eV or more, is used as an electron controlling layer in an organic light emitting device which uses the material as a host of the light emitting layer, the hole blocking effect is high. It was confirmed that all of the following compounds [ET-1-A], [ET-1-B], [ET-2-A], [ET-2-B], and [ET-3-F], which are anthracene derivatives suggested as the Comparative Examples, have a HOMO level of less than 6 eV, and these compounds having a low HOMO level have low device efficiency.

An organic light emitting device according to another exemplary embodiment of the present specification includes: an anode; a cathode; and one or more organic material layers provided between the anode and the cathode, in which one or more layers of the organic material layers include the compound of any one of Formulae 1 to 28, which has a triplet energy ($E_T$) of 2.2 eV or more.

An organic light emitting device according to still another exemplary embodiment of the present specification includes: an anode; a cathode; a light emitting layer provided between the anode and the cathode; and an electron transporting layer provided between the light emitting layer and the cathode, the light emitting layer includes a host, and the electron transporting layer includes the compound of any one of Formulae 1 to 28, which is different from the host and has a triplet energy ($E_T$) of 2.2 eV or more.

An organic light emitting device according to yet another exemplary embodiment of the present specification includes: an anode; a cathode; a light emitting layer provided between the anode and the cathode; and an electron controlling layer provided between the light emitting layer and the cathode, the light emitting layer includes a host, and the electron controlling layer includes the compound of any one of Formulae 1 to 28, which is different from the host and has a triplet energy ($E_T$) of 2.2 eV or more.

In the Experimental Examples of the present specification, it was confirmed that the triplet energy of the compound of any one of Formulae 1 to 28 is 2.2 eV or more. The compound of any one of Formulae 1 to 28, which has triplet energy in these various ranges efficiently blocks a triplet exciton of the light emitting layer in an effective manner in an organic light emitting device such as a blue fluorescent light emitting device, a red phosphorescent light emitting device, and a green phosphorescent light emitting device, thereby exhibiting high efficiency. In addition, the triplet exciton blocking effect may enhance the stability of the device and thus also increase the service life thereof.

According to an exemplary embodiment of the present specification, the light emitting layer includes a host and a dopant, and the triplet energy of the compound represented by any one of Formulae 1 to 28 is larger than the triplet energy of the host.

According to an exemplary embodiment of the present specification, when the triplet energy of the compound represented by any one of Formulae 1 to 28 is larger than that of the host compound of the light emitting layer, the triplet exciton of the light emitting layer may be effectively blocked.

Even in the Experimental Examples of the present specification, it was confirmed that when the compound of any one of Formulae 1 to 28 is used with a light emitting layer, the triplet excitons of the light emitting layer are effectively blocked by having a larger triplet energy than that of the host compound of the light emitting layer. For example, in the case of a blue fluorescent host, an anthracene derivative is usually used. It was confirmed that these anthracene derivatives generally have a triplet energy level of less than 1.9 eV, and when the compound of any one of Formulae 1 to 28, which has a triplet energy level of 2.2 eV or more, is used for an organic light emitting device as an electron controlling layer, the triplet exciton blocking effect is so high that the device efficiency is improved. It was confirmed that all of the following compounds [ET-1-A], [ET-1-B], [ET-2-A], [ET-2-B], and [ET-3-F], which are anthracene derivatives suggested as the Comparative Examples have triplet energy of less than 1.9 eV, and when a compound having such low triplet energy is used for an organic light emitting device, the device efficiency is low.

According to an exemplary embodiment of the present specification, an electron transporting layer including the compound of any one of Formulae 1 to 28 may be doped with a donor, and the donor refers to an n-type dopant.

In the present specification, the donor doping is for facilitating extraction of electrons from the negative electrode by doping the electron transporting layer with a donor metal compound or a donor complex.

According to an exemplary embodiment of the present specification, the electron transporting layer; the electron injection layer; the layer which simultaneously transports and injects electrons; or the electron controlling layer may include the compound of any one of Formulae 1 to 28 as a host, and include an n-type dopant as a dopant.

According to an exemplary embodiment of the present specification, the n-type dopant includes an alkali metal, an alkali metal compound, an alkaline earth metal, an alkaline earth metal compound, or a combination thereof.

Furthermore, according to an exemplary embodiment of the present specification, as the n-type dopant, one or two or more may be selected from the group consisting of Li, Na, K, Rb, Cs, Mg, Ca, Sr, Ba, La, Nd, Sm, Eu, Tb, Yb, LiF, Li$_2$O, CsF, or the following compounds, but the n-type dopant is not limited thereto.

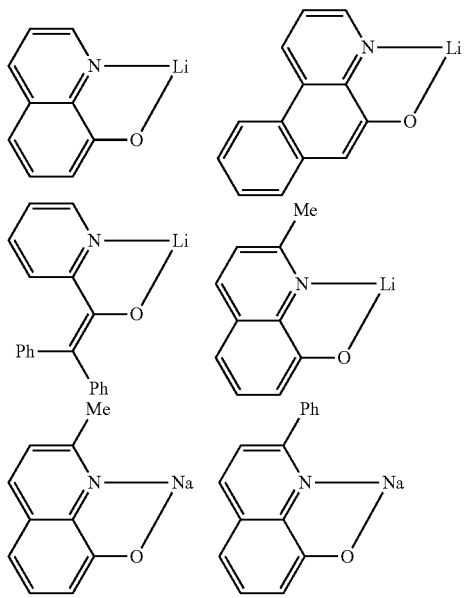

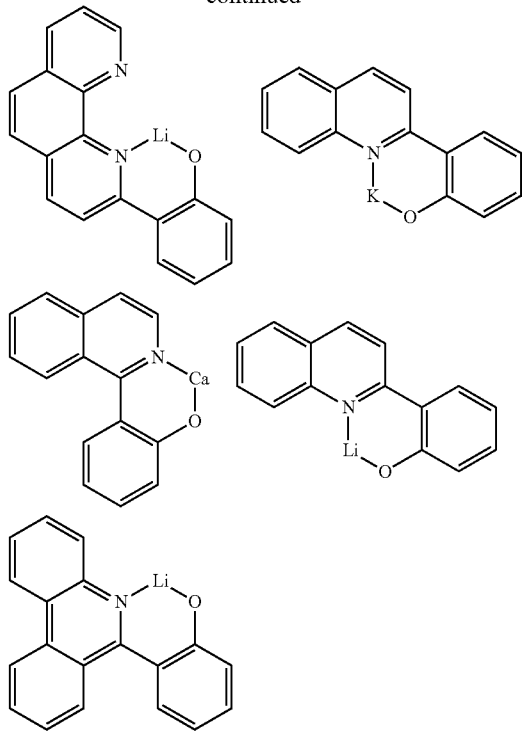

According to an exemplary embodiment of the present specification, the compound represented by any one of Formulae 1 to 28 and the n-type dopant may be stacked on an organic light emitting device at a weight ratio of 9:1 to 1:9.

According to an exemplary embodiment of the present specification, the n-type dopants may be either alone or in combination of two or more thereof.

An exemplary embodiment of the present specification provides an organic light emitting device including: an anode; a cathode; and two or more organic material layers provided between the anode and the cathode, in which the organic material layer includes an electron transporting layer and an electron controlling layer, the electron transporting layer includes the compound of any one of Formulae 1 to 28 as a host and an n-type dopant as a dopant, and the electron controlling layer is different from the electron transporting layer.

An exemplary embodiment of the present specification provides an organic light emitting device including: an anode; a cathode; and two or more organic material layers provided between the anode and the cathode, in which the organic material layer includes an electron transporting layer and an electron controlling layer, the electron controlling layer includes the compound of any one of Formulae 1 to 28 as a host and an n-type dopant as a dopant, and the electron transporting layer is different from the electron controlling layer.

According to another exemplary embodiment, the organic light emitting device may be an organic light emitting device having a structure (normal type) in which a positive electrode, one or more organic material layers, and a negative electrode are sequentially stacked on a substrate.

According to still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 1, an anode 2, a light emitting layer 3, and a cathode 4. In the structure, the compound may be included in the light emitting layer.

FIG. 2 illustrates an example of an organic light emitting device composed of a substrate 1, an anode 2, a hole injection layer 5, a hole transporting layer 6, a light emitting layer 7, an electron transporting layer 8, and a cathode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of any one of Formulae 1 to 28.

When the organic light emitting device includes a plurality of organic material layers, the organic material layer may be formed of the same material or different materials.

The organic light emitting device of the present specification may be manufactured by the materials and methods known in the art, except that one or more layers of the organic material layers include the compound of any one of Formulae 1 to 28, that is, the compound represented by any one of Formulae 1 to 28.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form a positive electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a negative electrode, thereon. In addition to the method described above, an organic light emitting device may be made by subsequently depositing a negative electrode material, an organic material layer, and a positive electrode material on a substrate.

Further, the compound of any one of Formulae 1 to 28 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be manufactured by sequentially stacking a negative electrode material, an organic material layer, and a positive electrode material on a substrate (International Publication No. 2003/012890). However, the manufacturing method is not limited thereto.

In an exemplary embodiment of the present specification, the anode is a positive electrode, and the cathode is a negative electrode.

In another exemplary embodiment, the anode is a negative electrode, and the cathode is a positive electrode. As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or LiO$_2$/Al, and the like, but are not limited thereto.

The hole injection material is a layer which injects holes from an electrode, and is preferably a compound which has a capability of transporting holes, and thus has an effect of injecting holes at positive electrode and an excellent effect of injecting holes for the light emitting layer or the light emitting material, prevents excitons produced from the light emitting layer from moving to an electron injection layer or an electron injection material, and is excellent in forming a thin film. It is preferred that the highest occupied molecular orbital (HOMO) of the hole injection material is between the work function of the positive electrode material and the HOMO of an adjacent organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The electron transporting layer is a layer which receives holes from the hole injection layer and transports holes to the light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

According to an exemplary embodiment of the present specification, the organic light emitting device performs phosphorescent light emission or fluorescent light emission, and the light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto. Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like having an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which receives electrons from an electron injection layer and transports electrons to a light emitting layer, and an electron transporting material is a material which may receive electrons well from a negative electrode and may transfer electrons to a light emitting layer, and is suitably a material which has large mobility for the electrons. Specific examples thereof include: an Al complex of 8-hydroxyquinoline; a complex including $Alq_3$; an organic radical compound; and a hydroxyflavone-metal complex, but are not limited thereto. The electron transporting layer may be used with any desired cathode material, as used according to the related art. In particular, examples of an appropriate cathode material are a typical material which has a low work function, followed by an aluminum layer or a silver layer. Specific examples thereof include cesium, barium, calcium, ytterbium, and samarium, in each case followed by an aluminum layer or a silver layer.

According to an exemplary embodiment of the present specification, the electron controlling layer serves to effectively receive electrons from an electron transporting layer, and control the electron mobility, thereby serving to control the amount of electrons transferred to the light emitting layer. Further, the electron controlling layer may simultaneously serve as a hole barrier, which allows holes supplied from the light emitting layer not to be transferred to the electron transporting layer. This may maximize the balance between holes and electrons in the light emitting layer and thus may increase the light emitting efficiency, and may enhance the service life of a device through the hole stability of the electron controlling layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to the hole injection layer, and is also excellent in forming a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Formula 1 may be included in an organic solar cell or an organic transistor in addition to the organic light emitting device.

The preparation of the compound represented by Formula 1 and the organic light emitting device including the same will be specifically described in the following Examples. However, the following Examples are provided for illustrating the present specification, and the range of the present specification is not limited thereby.

PREPARATION EXAMPLES

<Preparation Example 1-1> Preparation of [Compound 1-1]

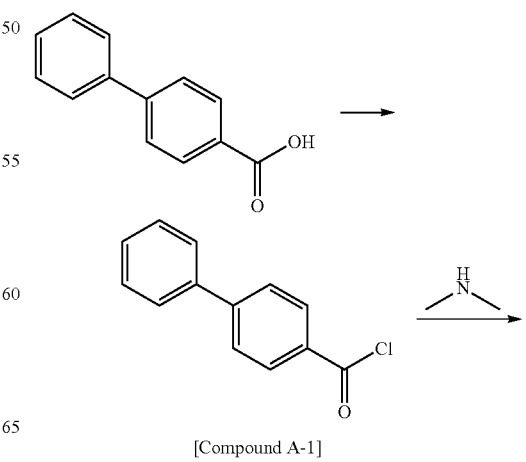

[Compound A-1]

-continued

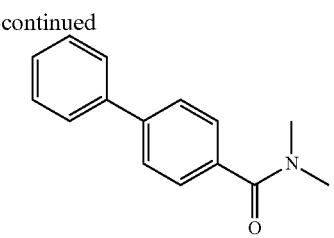

[Compound A-2]

[1,1'-biphenyl]-4-carboxylic acid (30 g, 151 mmol) was put into thionyl chloride (400 mL), and then the resulting mixture was refluxed and stirred for 2 hours. After the mixture was cooled to normal temperature, a solid produced by distilling the mixture was washed with diethyl ether, and then dried, thereby preparing [Compound A-1] (29.4 g, yield 90%, MS: $[M+H]^+=217$).

After a 2.0 M solution of diethylamine (74.8 mL, 150 mmol) and triethylamine (37.9 mL, 272 mmol) were put into 500 mL of diethyl ether, [Compound A-1] (29.4 g, 136 mmol) was slowly added dropwise thereto, and the resulting mixture was stirred for 30 minutes. The produced solid was filtered, and then the filtrate was distilled, thereby preparing [Compound A-2] (26 g, yield 85%, MS: $[M+H]^+=226$).

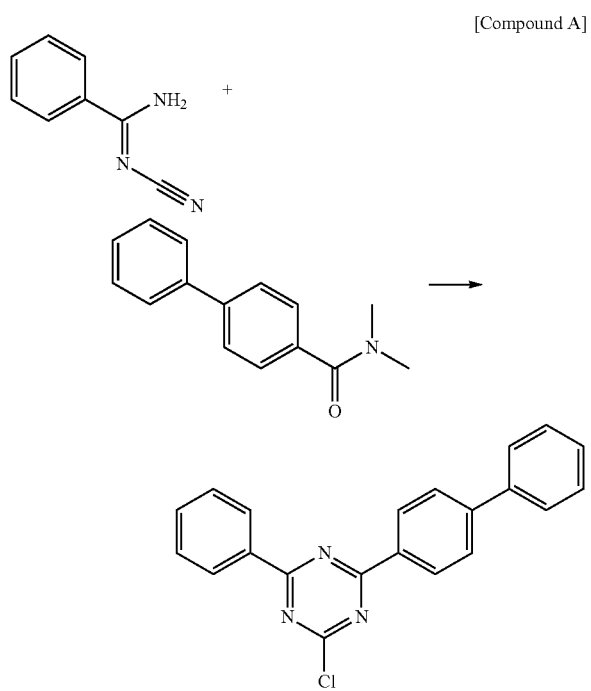

[Compound A]

N'-cyanobenzimidamide (16.8 g, 116 mmol), [Compound A-2] (26 g, 116 mmol), and phosphorus oxychloride (12 mL, 128 mmol) were put into 500 mL of acetonitrile, and then the resulting mixture was stirred and refluxed for 1 hour. After the mixture was cooled to normal temperature, a solid produced was filtered and washed with water and ethanol, and then dried, thereby preparing [Compound A] (32.7 g, yield 82%, MS: $[M+H]^+=344$).

[Compound A] (10 g, 29 mmol) and (9,9-dimethyl-9H-fluoren-1-yl)boronic acid (7.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-1] (12.5 g, yield 86%, MS: $[M+H]^+=502$).

<Preparation Example 1-2> Preparation of [Compound 1-2]

[Compound A] (10 g, 29 mmol) and (9,9-dimethyl-9H-fluoren-2-yl)boronic acid (7.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1-2] (12.5 g, yield 81%, MS: $[M+H]^+=502$).

<Preparation Example 1-3> Preparation of [Compound 1-3]

[Compound A] (10 g, 29 mmol) and (9,9-dimethyl-9H-fluoren-3-yl)boronic acid (7.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 1-3] (11.2 g, yield 77%, MS: $[M+H]^+=502$).

<Preparation Example 1-4> Preparation of [Compound 1-4]

[Compound A] (10 g, 29 mmol) and (9,9-dimethyl-9H-fluoren-4-yl)boronic acid (7.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1-4] (10.9 g, yield 75%, MS: $[M+H]^+=502$).

<Preparation Example 1-5> Preparation of [Compound 1-6]

[Compound A] (10 g, 29 mmol) and (9,9-diphenyl-9H-fluoren-2-yl)boronic acid (11.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-6] (16.0 g, yield 88%, MS: $[M+H]^+=626$).

<Preparation Example 1-6> Preparation of [Compound 1-8]

[Compound A] (10 g, 29 mmol) and (9,9-diphenyl-9H-fluoren-4-yl)boronic acid (11.6 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-8] (15.2 g, yield 84%, MS: [M+H]$^+$=626).

<Preparation Example 1-7> Preparation of [Compound 1-10]

[Compound A] (10 g, 29 mmol) and (9,9-di-p-tolyl-9H-fluoren-2-yl)boronic acid (12.5 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 1-10] (14.2 g, yield 75%, MS: [M+H]$^+$=654).

<Preparation Example 1-8> Preparation of [Compound 1-12]

[Compound A] (10 g, 29 mmol) and (9,9-di-p-tolyl-9H-fluoren-2-yl)boronic acid (12.5 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-12] (13.8 g, yield 73%, MS: [M+H]$^+$=654).

<Preparation Example 1-9> Preparation of [Compound 1-18]

[Compound B] was prepared in the same manner as in <Preparation Example 1> by using [1,1'-biphenyl]-3-carboxylic acid. (MS: [M+H]$^+$=344)

[Compound B]

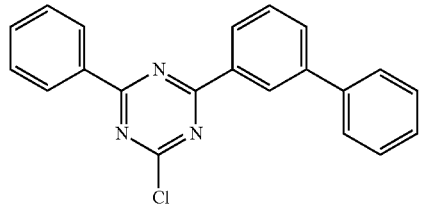

[Compound B] (10 g, 29 mmol) and (9,9-diphenyl-9H-fluoren-2-yl)boronic acid (11.6 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-18] (14.9 g, yield 82%, MS: [M+H]$^+$=626).

<Preparation Example 1-10> Preparation of [Compound 1-20]

[Compound B] (10 g, 29 mmol) and (9,9-diphenyl-9H-fluoren-4-yl)boronic acid (11.6 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-20] (13.8 g, yield 76%, MS: [M+H]$^+$=626).

<Preparation Example 1-11> Preparation of [Compound 1-22]

[Compound B] (10 g, 29 mmol) and (9,9-di-p-tolyl-9H-fluoren-2-yl)boronic acid (12.5 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 1-22] (13.8 g, yield 73%, MS: [M+H]$^+$=654).

<Preparation Example 1-12> Preparation of [Compound 1-26]

[Compound C] was prepared in the same manner as in <Preparation Example 1> by using [1,1'-biphenyl]-2-carboxylic acid. (MS: [M+H]$^+$=344)

[Compound C]

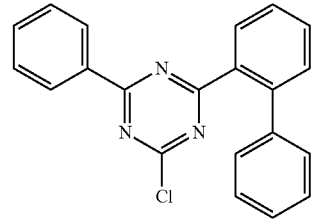

[Compound C] (10 g, 29 mmol) and (9,9-dimethyl-7-phenyl-9H-fluoren-2-yl)boronic acid (10.1 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 1-26] (12.4 g, yield 74%, MS: [M+H]$^+$=578).

<Preparation Example 1-13> Preparation of [Compound 1-30]

[Compound C] (10 g, 29 mmol) and (9,9-diphenyl-9H-fluoren-2-yl)boronic acid (10.5 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-30] (14.2 g, yield 78%, MS: [M+H]$^+$=626).

<Preparation Example 1-14> Preparation of [Compound 1-32]

[Compound C] (10 g, 29 mmol) and (9,9-diphenyl-9H-fluoren-4-yl)boronic acid (10.5 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-32] (12.9 g, yield 71%, MS: $[M+H]^+=626$).

<Preparation Example 1-15> Preparation of [Compound 1-34]

[Compound C] (10 g, 29 mmol) and (9,9-di-p-tolyl-9H-fluoren-2-yl)boronic acid (12.5 g, 32 mmol) were put into 100 mL of THF. 50 mL of 2 M $K_2CO_3$ and 0.7 g of $Pd(PPh_3)_4$ were put thereinto, and then the resulting mixture was stirred and refluxed for 12 hours. The mixture was cooled to normal temperature, and then a solid produced by filtering the mixture was recrystallized with chloroform and ethanol, thereby preparing [Compound 1-34] (13.3 g, yield 70%, MS: $[M+H]^+=654$).

<Preparation Example 1-16> Preparation of [Compound 1-40]

[Compound D] was prepared in the same manner as in <Preparation Example 1> by using [1,1':4',1''-terphenyl]-4-carboxylic acid. (MS: $[M+H]^+=420$)

[Compound D]

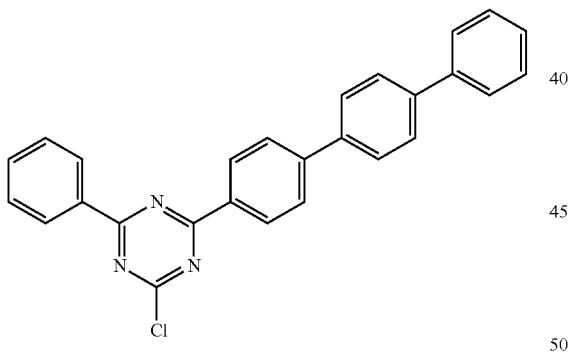

[Compound D] (10 g, 24 mmol) and (9,9-dimethyl-9H-fluoren-4-yl)boronic acid (6.2 g, 26 mmol) were put into 100 mL of THF. 50 mL of 2 M $K_2CO_3$ and 0.6 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-40] (10.7 g, yield 77%, MS: $[M+H]^+=578$).

<Preparation Example 1-17> Preparation of [Compound 1-50]

[Compound E] was prepared in the same manner as in <Preparation Example 1> by using 5'-phenyl-[1,1':3',1''-terphenyl]-4-carboxylic acid. (MS: $[M+H]^+=496$)

[Compound E]

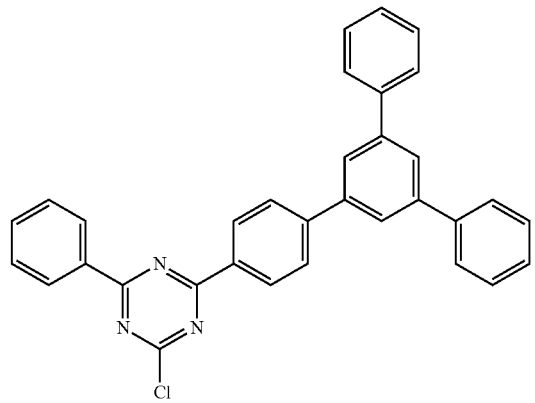

[Compound E] (10 g, 20 mmol) and (9,9-dimethyl-9H-fluoren-2-yl)boronic acid (5.2 g, 22 mmol) were put into 100 mL of THF. 50 mL of 2 M $K_2CO_3$ and 0.5 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-50] (9.2 g, yield 70%, MS: $[M+H]^+=654$).

<Preparation Example 1-18> Preparation of [Compound 1-54]

[Compound F] was prepared in the same manner as in <Preparation Example 1> by using [1,1':3',1''-terphenyl]-5'-carboxylic acid. (MS: $[M+H]^+=420$)

[Compound F]

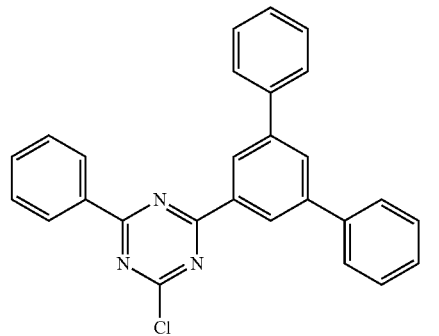

[Compound F] (10 g, 24 mmol) and (9,9-diphenyl-9H-fluoren-2-yl)boronic acid (9.4 g, 26 mmol) were put into 100 mL of THF. 50 mL of 2 M $K_2CO_3$ and 0.6 g of $Pd(PPh_3)_4$ were put thereinto, and then the resulting mixture was stirred and refluxed for 12 hours. The mixture was cooled to normal temperature, and then a solid produced by filtering the mixture was recrystallized with chloroform and ethanol, thereby preparing [Compound 1-54] (13.0 g, yield 77%, MS: $[M+H]^+=702$).

<Preparation Example 1-19> Preparation of [Compound 1-56]

[Compound F] (10 g, 24 mmol) and (9,9-diphenyl-9H-fluoren-4-yl)boronic acid (9.4 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 14 hours. The mixture was cooled to normal temperature, and then a solid produced by filtering the mixture was recrystallized with chloroform and ethanol, thereby preparing [Compound 1-56] (13.3 g, yield 79%, MS: [M+H]$^+$=702).

<Preparation Example 1-20> Preparation of [Compound 1-67]

[Compound G] was prepared in the same manner as in <Preparation Example 1> by using [1,1':3',1''-terphenyl]-4'-carboxylic acid. (MS: [M+H]$^+$=420)

[Compound G]

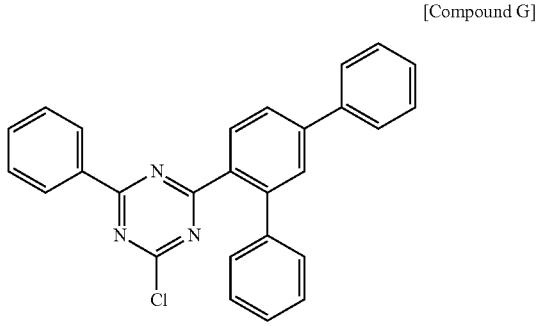 [SMILES: Clc1nc(-c2ccccc2)nc(-c2ccc(-c3ccccc3)cc2-c2ccccc2)n1]

[Compound G] (10 g, 24 mmol) and (9,9-diphenyl-9H-fluoren-3-yl)boronic acid (9.4 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 12 hours. The mixture was cooled to normal temperature, and then a solid produced by filtering the mixture was recrystallized with chloroform and ethanol, thereby preparing [Compound 1-67] (12.6 g, yield 75%, MS: [M+H]$^+$=702).

<Preparation Example 1-21> Preparation of [Compound 1-82]

[Compound H] was prepared in the same manner as in <Preparation Example 1> by using 2-naphthoic acid. (MS: [M+H]$^+$=318)

[Compound H]

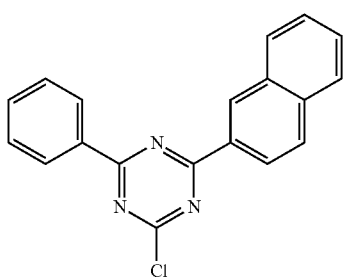

[Compound H] (10 g, 31 mmol) and (9,9-di-p-tolyl-9H-fluoren-2-yl)boronic acid (13.3 g, 34 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 1-82] (15.8 g, yield 81%, MS: [M+H]$^+$=628).

<Preparation Example 1-22> Preparation of [Compound 1-90]

[Compound I] was prepared in the same manner as in <Preparation Example 1> by using 1-naphthoic acid. (MS: [M+H]$^+$=318)

[Compound I]

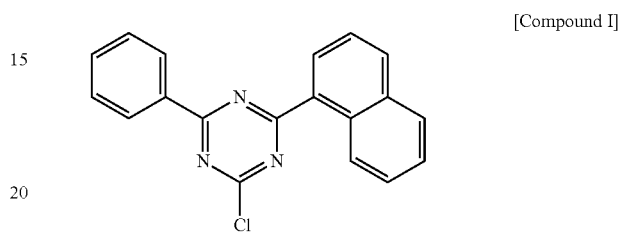

[Compound I] (10 g, 31 mmol) and (9,9-diphenyl-9H-fluoren-2-yl)boronic acid (12.3 g, 34 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-90] (13.0 g, yield 70%, MS: [M+H]$^+$=600).

<Preparation Example 1-23> Preparation of [Compound 1-92]

[Compound H] (10 g, 31 mmol) and (9,9-diphenyl-9H-fluoren-4-yl)boronic acid (12.3 g, 34 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-92] (14.7 g, yield 79%, MS: [M+H]$^+$=600).

<Preparation Example 1-24> Preparation of [Compound 1-94]

[Compound H] (10 g, 31 mmol) and (9,9-di-p-tolyl-9H-fluoren-2-yl)boronic acid (13.3 g, 34 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 1-94] (13.2 g, yield 68%, MS: [M+H]$^+$=628).

<Preparation Example 1-25> Preparation of [Compound 1-102]

[Compound J] was prepared in the same manner as in <Preparation Example 1> by using phenanthrene-9-carboxylic acid. (MS: [M+H]$^+$=368)

[Compound J]

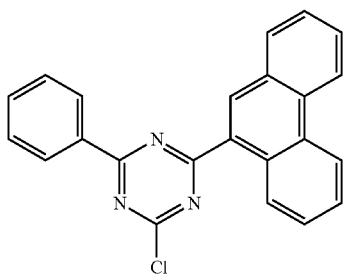

[Compound J] (10 g, 27 mmol) and (9,9-diphenyl-9H-fluoren-2-yl)boronic acid (10.9 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 1-102] (13.2 g, yield 75%, MS: $[M+H]^+$=650).

<Preparation Example 1-26> Preparation of [Compound 1-116]

[Compound K] was prepared in the same manner as in <Preparation Example 1> by using phenanthrene-2-carboxylic acid. (MS: $[M+H]^+$=368)

[Compound K]

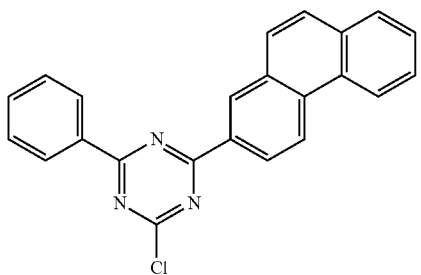

[Compound K] (10 g, 27 mmol) and (9,9-diphenyl-9H-fluoren-4-yl)boronic acid (10.9 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-116] (13.7 g, yield 78%, MS: $[M+H]^+$=650).

<Preparation Example 1-27> Preparation of [Compound 1-122]

[Compound L] was prepared in the same manner as in <Preparation Example 1> by using phenanthrene-2-carboxylic acid. (MS: $[M+H]^+$=368)

[Compound L]

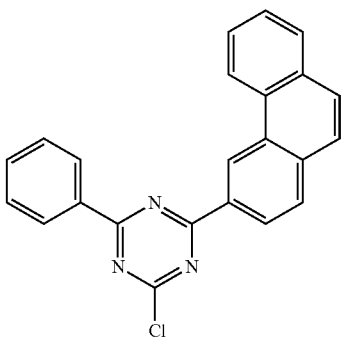

[Compound L] (10 g, 27 mmol) and (9,9-dimethyl-7-phenyl-9H-fluoren-2-yl)boronic acid (9.4 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 1-122] (12.8 g, yield 79%, MS: $[M+H]^+$=602).

<Preparation Example 1-28> Preparation of [Compound 1-126]

[Compound L] (10 g, 27 mmol) and (9,9-diphenyl-9H-fluoren-2-yl)boronic acid (10.9 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-126] (13.3 g, yield 76%, MS: $[M+H]^+$=650).

<Preparation Example 1-29> Preparation of [Compound 1-128]

[Compound L] (10 g, 27 mmol) and (9,9-diphenyl-9H-fluoren-4-yl)boronic acid (10.9 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 12 hours. The mixture was cooled to normal temperature, and then a solid produced by filtering the mixture was recrystallized with chloroform and ethanol, thereby preparing [Compound 1-128] (12.3 g, yield 70%, MS: $[M+H]^+$=650).

<Preparation Example 1-30> Preparation of [Compound 1-130]

[Compound L] (10 g, 27 mmol) and (9,9-di-p-tolyl-9H-fluoren-2-yl)boronic acid (11.7 g, 30 mmol) were put into 100 mL of THF. 50 mL of 2 M $K_2CO_3$ and 0.6 g of $Pd(PPh_3)_4$ were put thereinto, and then the resulting mixture was stirred and refluxed for 14 hours. The mixture was cooled to normal temperature, and then a solid produced by filtering the mixture was recrystallized with chloroform and ethanol, thereby preparing [Compound 1-130] (12.3 g, yield 67%, MS: $[M+H]^+$=678).

<Preparation Example 1-31> Preparation of [Compound 1-134]

[Compound M] was prepared in the same manner as in <Preparation Example 1> by using N'-cyano-[1,1'-biphenyl]-4-carboximidamide and [1,1'-biphenyl]-3-carboxylic acid. (MS: [M+H]⁺=420)

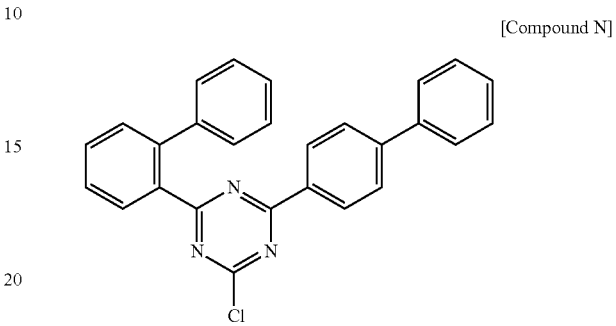

[Compound M]

[Compound M] (10 g, 24 mmol) and (9,9-dimethyl-9H-fluoren-2-yl)boronic acid (6.4 g, 27 mmol) were put into 100 mL of THF. 50 mL of 2 M K₂CO₃ and 0.6 g of Pd(PPh₃)₄ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-134] (10.1 g, yield 73%, MS: [M+H]⁺=578).

<Preparation Example 1-32> Preparation of [Compound 1-138]

[Compound V] was prepared in the same manner as in <Preparation Example 1> by using (9,9-diphenyl-9H-fluoren-2-yl)carboxylic acid. (MS: [M+H]⁺=509)

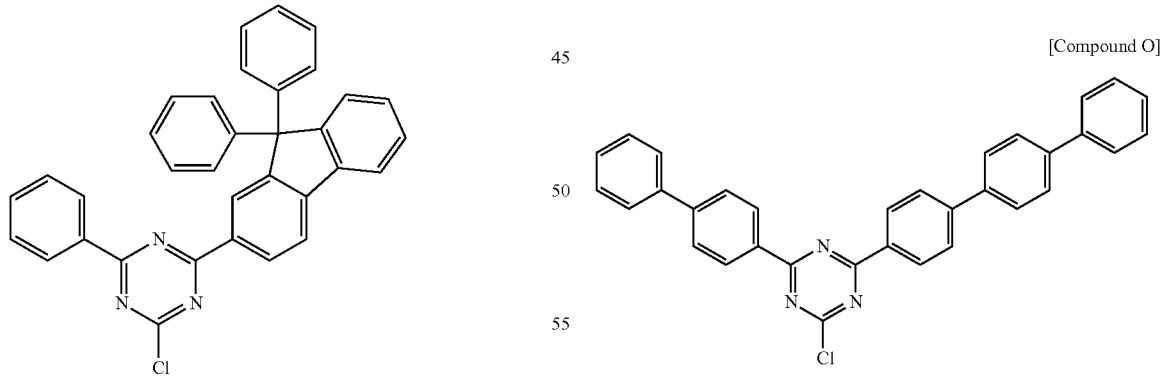

[Compound V]

[Compound V] (10 g, 20 mmol) and (4-(naphthalen-2-yl)phenyl)boronic acid (5.5 g, 22 mmol) were put into 100 mL of THF. 50 mL of 2 M K₂CO₃ and 0.5 g of Pd(PPh₃)₄ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1-138] (10.3 g, yield 76%, MS: [M+H]⁺=676).

<Preparation Example 1-33> Preparation of [Compound 1-154]

[Compound N] was prepared in the same manner as in <Preparation Example 1> by using N'-cyano-[1,1'-biphenyl]-4-carboximidamide and [1,1'-biphenyl]-2-carboxylic acid. (MS: [M+H]⁺=420)

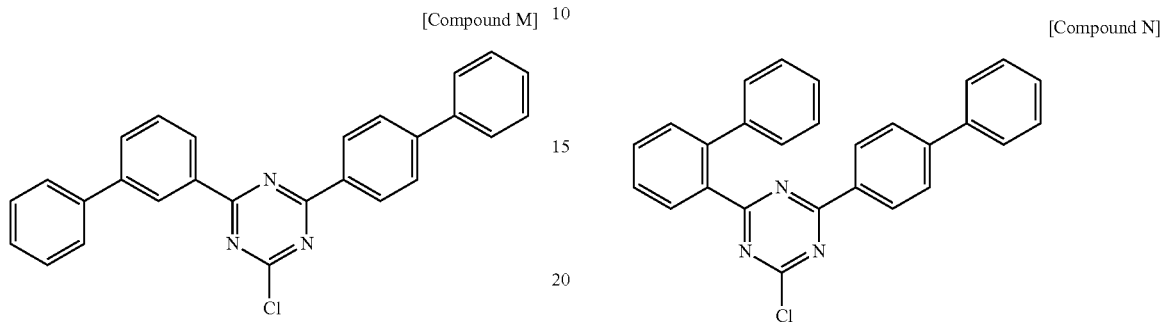

[Compound N]

[Compound N] (10 g, 24 mmol) and (9,9-di-p-tolyl-9H-fluoren-2-yl)boronic acid (10.5 g, 27 mmol) were put into 100 mL of THF. 50 mL of 2 M K₂CO₃ and 0.6 g of Pd(PPh₃)₄ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 1-154] (12.3 g, yield 70%, MS: [M+H]⁺=730).

<Preparation Example 1-34> Preparation of [Compound 1-160]

[Compound O] was prepared in the same manner as in <Preparation Example 1> by using N'-cyano-[1,1'-biphenyl]-4-carboximidamide and [1,1':4',1''-terphenyl]-4-carboxylic acid. (MS: [M+H]⁺=496)

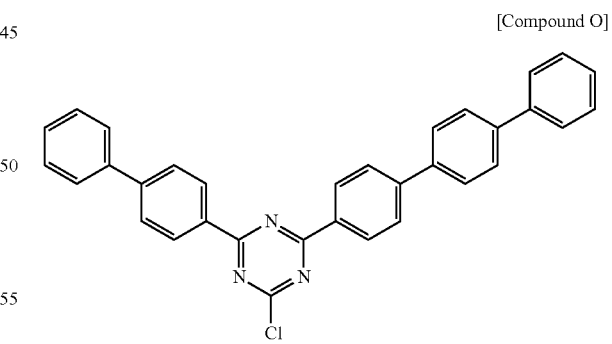

[Compound O]

[Compound O] (10 g, 20 mmol) and (9,9-dimethyl-9H-fluoren-4-yl)boronic acid (5.2 g, 22 mmol) were put into 100 mL of THF. 50 mL of 2 M K₂CO₃ and 0.5 g of Pd(PPh₃)₄ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1-160] (8.6 g, yield 66%, MS: [M+H]⁺=654).

<Preparation Example 1-35> Preparation of [Compound 1-170]

[Compound P] was prepared in the same manner as in <Preparation Example 1> by using N'-cyano-[1,1'-biphenyl]-4-carboximidamide and [1,1':3',1''-terphenyl]-5'-carboxylic acid. (MS: [M+H]$^+$=496)

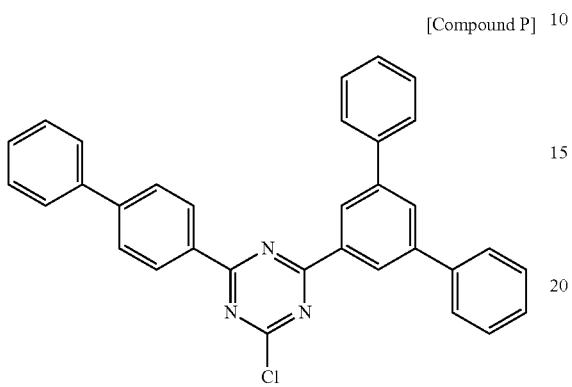

[Compound P]

[Compound P] (10 g, 20 mmol) and (9,9-dimethyl-9H-fluoren-2-yl)boronic acid (5.2 g, 22 mmol) were put into 100 mL of THF. 50 mL of 2 M K$_2$CO$_3$ and 0.5 g of Pd(PPh$_3$)$_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1-170] (9.2 g, yield 70%, MS: [M+H]$^+$=654).

<Preparation Example 1-36> Preparation of [Compound 1-198]

[Compound Q] was prepared in the same manner as in <Preparation Example 1> by using N'-cyano-[1,1'-biphenyl]-4-carboximidamide and 2-naphthoic acid. (MS: [M+H]$^+$=394)

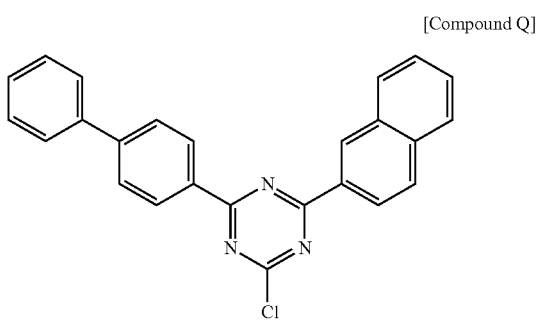 [SMILES: Clc1nc(-c2ccc(-c3ccccc3)cc2)nc(-c2ccc3ccccc3c2)n1]

[Compound Q]

[Compound Q] (10 g, 25 mmol) and (9,9-diphenyl-9H-fluoren-2-yl)boronic acid (10.1 g, 28 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 1-198] (12.7 g, yield 75%, MS: [M+H]$^+$=676).

<Preparation Example 1-37> Preparation of [Compound 1-229]

[Compound R] was prepared in the same manner as in <Preparation Example 1> by using N'-cyano-[1,1'-biphenyl]-4-carboximidamide and phenanthrene-2-carboxylic acid. (MS: [M+H]$^+$=444)

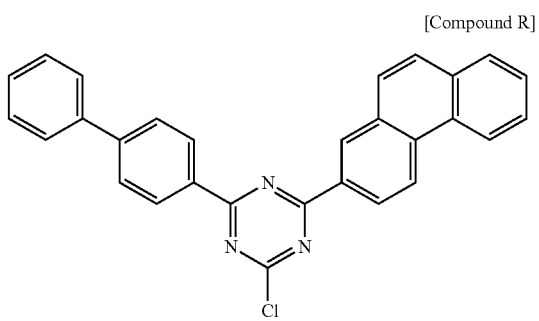 [SMILES: Clc1nc(-c2ccc(-c3ccccc3)cc2)nc(-c2ccc3c(ccc4ccccc43)c2)n1]

[Compound R]

[Compound R] (10 g, 23 mmol) and (9,9-dimethyl-9H-fluoren-1-yl)boronic acid (6.0 g, 25 mmol) were put into 100 mL of THF. 50 mL of 2 M K$_2$CO$_3$ and 0.5 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-229] (10.8 g, yield 78%, MS: [M+H]$^+$=602).

<Preparation Example 1-38> Preparation of [Compound 1-237]

[Compound R] (10 g, 23 mmol) and (7,7-dimethyl-7H-benzo[c]fluoren-5-yl)boronic acid (7.2 g, 25 mmol) were put into 100 mL of THF. 50 mL of 2 M K$_2$CO$_3$ and 0.5 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-237] (10.5 g, yield 70%, MS: [M+H]$^+$=652).

<Preparation Example 1-39> Preparation of [Compound 1-279]

[Compound S] was prepared in the same manner as in <Preparation Example 1> by using N'-cyano-1-naphthimidamide and [1,1':4',1''-terphenyl]-4-carboxylic acid. (MS: [M+H]$^+$=470)

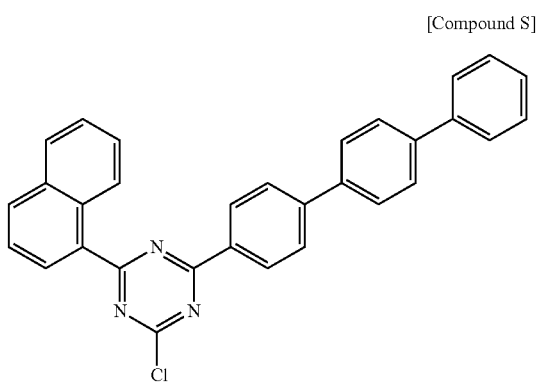 [SMILES: Clc1nc(-c2ccc(-c3ccc(-c4ccccc4)cc3)cc2)nc(-c2cccc3ccccc23)n1]

[Compound S]

[Compound S] (10 g, 21 mmol) and (9,9-dimethyl-9H-fluoren-3-yl)boronic acid (5.5 g, 23 mmol) were put into 100 mL of THF. 50 mL of 2 M $K_2CO_3$ and 0.5 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 1-279] (10.4 g, yield 79%, MS: $[M+H]^+$=628).

<Preparation Example 1-40> Preparation of [Compound 1-341]

[Compound T] was prepared in the same manner as in <Preparation Example 1> by using N'-cyano-1-naphthimidamide and phenanthrene-3-carboxylic acid. (MS: $[M+H]^+$=418)

[Compound T]

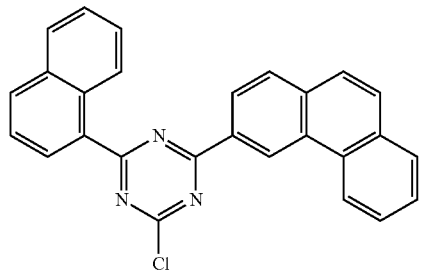

[Compound T] (10 g, 24 mmol) and (9,9-diphenyl-9H-fluoren-1-yl)boronic acid (8.7 g, 23 mmol) were put into 150 mL of THF. 50 mL of 2 M $K_2CO_3$ and 0.6 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-341] (13.6 g, yield 81%, MS: $[M+H]^+$=700).

<Preparation Example 1-41> Preparation of [Compound 1-345]

[Compound T] (10 g, 24 mmol) and (11,11-dimethyl-11H-benzo[a]fluoren-9-yl)boronic acid (7.5 g, 26 mmol) were put into 150 mL of THF. 50 mL of 2 M $K_2CO_3$ and 0.6 g of $Pd(PPh_3)_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 1-345] (10.1 g, yield 67%, MS: $[M+H]^+$=626).

<Preparation Example 1-42> Preparation of [Compound 1-482]

[Compound U] was prepared in the same manner as in <Preparation Example 1> by using N'-cyanophenanthrene-9-carboximidamide and 5'-phenyl-[1,1':3',1''-terphenyl]-4-carboxylic acid. (MS: $[M+H]^+$=597)

[Compound U]

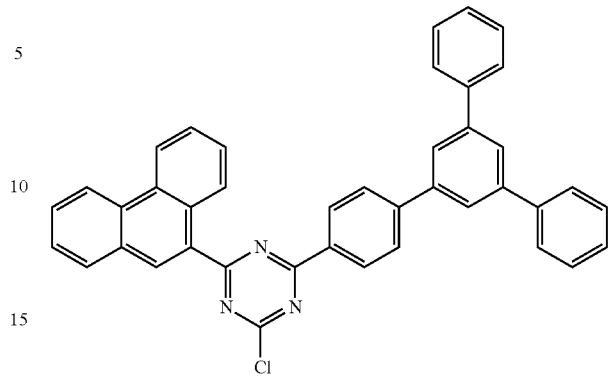

[Compound U] (15 g, 25 mmol) and (9,9-dimethyl-9H-fluoren-2-yl)boronic acid (6.7 g, 28 mmol) were put into 100 mL of THF. 50 mL of 2 M $K_2CO_3$ and 0.6 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 1-482] (12.8 g, yield 68%, MS: $[M+H]^+$=753).

<Preparation Example 1-43> Preparation of [Compound 1-625]

[Compound V] was prepared in the same manner as in <Preparation Example 1> by using N'-cyanobenzimidamide-2,3,4,5,6-d5 and [1,1'-biphenyl]-4-carboxylic acid. (MS: $[M+H]^+$=349)

[Compound V]

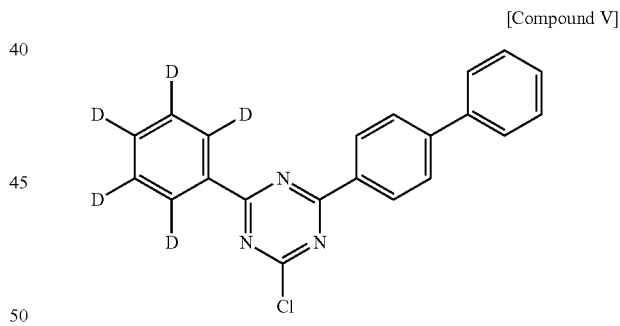

[Compound T] (10 g, 29 mmol) and (9,9-diphenyl-9H-fluoren-2-yl)boronic acid (10.4 g, 29 mmol) were put into 100 mL of THF. 50 mL of 2 M $K_2CO_3$ and 0.7 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 1-625] (12.2 g, yield 69%, MS: $[M+H]^+$=631).

<Preparation Example 2-1> Preparation of [Compound 2-2]

[Compound A] (10 g, 29 mmol) and (4-(9,9-dimethyl-9H-fluoren-2-yl)phenyl)boronic acid (9.1 g, 31 mmol) were put into 100 mL of THF. 50 mL of 2 M $K_2CO_3$ and 0.7 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 2-2] (12.7 g, yield 76%, MS: [M+H]$^+$=578).

<Preparation Example 2-2> Preparation of [Compound 2-4]

[Compound A] (10 g, 29 mmol) and (3-(9,9-diphenyl-9H-fluoren-2-yl)phenyl)boronic acid (13.6 g, 31 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-2] (14.5 g, yield 71%, MS: [M+H]$^+$=702).

<Preparation Example 2-3> Preparation of [Compound 2-5]

[Compound A] (10 g, 29 mmol) and (4-(9,9-diphenyl-9H-fluoren-2-yl)phenyl)boronic acid (13.6 g, 31 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 2-5] (14.9 g, yield 73%, MS: [M+H]$^+$=702).

<Preparation Example 2-4> Preparation of [Compound 2-6]

[Compound A] (10 g, 29 mmol) and (4-(9,9-diphenyl-9H-fluoren-4-yl)phenyl)boronic acid (13.6 g, 31 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-6] (14.0 g, yield 69%, MS: [M+H]$^+$=702).

<Preparation Example 2-5> Preparation of [Compound 2-8]

[Compound A] (10 g, 29 mmol) and (4-(7,7-dimethyl-7H-benzo[c]fluoren-5-yl)phenyl)boronic acid (11.3 g, 31 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-8] (11.2 g, yield 66%, MS: [M+H]$^+$=628).

<Preparation Example 2-6> Preparation of [Compound 2-11]

[Compound C] (10 g, 29 mmol) and (4-(9,9-dimethyl-9H-fluoren-3-yl)phenyl)boronic acid (9.1 g, 31 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 2-11] (12.4 g, yield 74%, MS: [M+H]$^+$=578).

<Preparation Example 2-7> Preparation of [Compound 2-28]

[Compound D] (10 g, 24 mmol) and (4-(9,9-dimethyl-9H-fluoren-4-yl)phenyl)boronic acid (8.2 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-28] (12.4 g, yield 74%, MS: [M+H]$^+$=654).

<Preparation Example 2-8> Preparation of [Compound 2-38]

[Compound F] (10 g, 24 mmol) and (4-(9,9-diphenyl-9H-fluoren-4-yl)phenyl)boronic acid (11.4 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-38] (13 g, yield 70%, MS: [M+H]$^+$=778).

<Preparation Example 2-9> Preparation of [Compound 2-55]

[Compound H] (10 g, 32 mmol) and (4-(9,9-di-p-tolyl-9H-fluoren-2-yl)phenyl)boronic acid (16.3 g, 35 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-55] (17.3 g, yield 77%, MS: [M+H]$^+$=704).

<Preparation Example 2-10> Preparation of [Compound 2-70]

[Compound J] (10 g, 27 mmol) and (4-(9,9-diphenyl-9H-fluoren-4-yl)phenyl)boronic acid (13.1 g, 30 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-70] (15.7 g, yield 80%, MS: [M+H]$^+$=726).

<Preparation Example 2-11> Preparation of [Compound 2-90]

[Compound A] (10 g, 29 mmol) and (4-(9,9-dimethyl-9H-fluoren-2-yl)naphthalen-1-yl)boronic acid (11.7 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-90] (17.2 g, yield 76%, MS: [M+H]$^+$=780).

<Preparation Example 2-12> Preparation of [Compound 2-99]

[Compound C] (10 g, 29 mmol) and (4-(9,9-dimethyl-9H-fluoren-3-yl)naphthalen-1-yl)boronic acid (11.7 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-99] (16 g, yield 71%, MS: [M+H]$^+$=780).

<Preparation Example 2-13> Preparation of [Compound 2-106]

[Compound B] (10 g, 29 mmol) and (4-(9,9-dimethyl-9H-fluoren-2-yl)naphthalen-1-yl)boronic acid (11.7 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-106] (17.9 g, yield 79%, MS: [M+H]$^+$=780).

<Preparation Example 2-14> Preparation of [Compound 2-113]

[Compound D] (10 g, 24 mmol) and (5-(9,9-dimethyl-9H-fluoren-1-yl)naphthalen-2-yl)boronic acid (9.5 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 2-113] (11.8 g, yield 70%, MS: [M+H]$^+$=704).

<Preparation Example 2-15> Preparation of [Compound 2-122]

[Compound F] (10 g, 24 mmol) and (5-(9,9-dimethyl-9H-fluoren-2-yl)naphthalen-1-yl)boronic acid (9.5 g, 26 mmol) were put into 100 mL of THF. 50 mL of 2 M K$_2$CO$_3$ and 0.6 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-122] (11.2 g, yield 66%, MS: [M+H]$^+$=704).

<Preparation Example 2-16> Preparation of [Compound 2-141]

[Compound H] (10 g, 32 mmol) and (3-(9,9-dimethyl-9H-fluoren-2-yl)naphthalen-2-yl)boronic acid (17 g, 35 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 2-141] (16.7 g, yield 72%, MS: [M+H]$^+$=726).

<Preparation Example 2-17> Preparation of [Compound 2-146]

[Compound I] (10 g, 32 mmol) and (4-(9,9-dimethyl-7-phenyl-9H-fluoren-2-yl)naphthalen-1-yl)boronic acid (15.4 g, 35 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 11 hours. The mixture was cooled to normal temperature, and then a solid produced by filtering the mixture was recrystallized with chloroform and ethanol, thereby preparing [Compound 2-146] (17.1 g, yield 79%, MS: [M+H]$^+$=678).

<Preparation Example 2-18> Preparation of [Compound 2-178]

[Compound A] (10 g, 29 mmol) and (6-(9,9-dimethyl-9H-fluoren-2-yl)naphthalen-2-yl)boronic acid (11.7 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-178] (14 g, yield 77%, MS: [M+H]$^+$=628).

<Preparation Example 2-19> Preparation of [Compound 2-227]

[Compound H] (10 g, 32 mmol) and (6-(9,9-dimethyl-9H-fluoren-2-yl)naphthalen-3-yl)boronic acid (12.7 g, 35 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 2-227] (14.0 g, yield 73%, MS: [M+H]$^+$=602).

<Preparation Example 2-20> Preparation of [Compound 2-269]

[Compound A] (10 g, 29 mmol) and (7-(9,9-diphenyl-9H-fluoren-2-yl)naphthalen-2-yl)boronic acid (14.2 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-269] (17.2 g, yield 79%, MS: [M+H]$^+$=752).

<Preparation Example 2-21> Preparation of [Compound 2-282]

[Compound B] (10 g, 29 mmol) and (7-(9,9-dimethyl-9H-fluoren-2-yl)naphthalen-2-yl)boronic acid (11.7 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 2-282] (13.7 g, yield 75%, MS: [M+H]$^+$=628).

<Preparation Example 2-22> Preparation of [Compound 2-353]

[Compound A] (10 g, 29 mmol) and (10-(9,9-dimethyl-9H-fluoren-2-yl)phenanthren-9-yl)boronic acid (13.3 g, 32 mmol) were put into 100 mL of THF. 50 mL of 2 M K$_2$CO$_3$ and 0.7 g of Pd(PPh$_3$)$_4$ were put thereinto, and then the resulting mixture was stirred and refluxed for 13 hours. The mixture was cooled to normal temperature, and then a solid produced by filtering the mixture was recrystallized with chloroform and ethanol, thereby preparing [Compound 2-353] (13.8 g, yield 70%, MS: [M+H]$^+$=678).

The HOMO level and triplet energy (E$_T$) values of the compound, which were measured through the Experimental Examples of the present specification, are shown in the following Table 1.

TABLE 1

| Compound | HOMO (eV) | E$_T$ (eV) |
|---|---|---|
| 1-1 | 6.45 | 2.80 |
| 1-2 | 6.43 | 2.64 |
| 1-3 | 6.45 | 2.79 |
| 1-6 | 6.37 | 2.62 |
| 1-8 | 6.38 | 2.78 |
| 1-10 | 6.33 | 2.62 |
| 1-12 | 6.39 | 2.78 |
| 1-18 | 6.37 | 2.62 |
| 1-20 | 6.41 | 2.78 |
| 1-22 | 6.35 | 2.61 |
| 1-26 | 6.30 | 2.60 |
| 1-30 | 6.44 | 2.62 |
| 1-32 | 6.43 | 2.78 |
| 1-34 | 6.40 | 2.61 |
| 1-40 | 6.35 | 2.79 |
| 1-50 | 6.39 | 2.63 |
| 1-54 | 6.35 | 2.62 |
| 1-56 | 6.37 | 2.78 |
| 1-67 | 6.38 | 2.57 |
| 1-82 | 6.27 | 2.43 |
| 1-90 | 6.29 | 2.46 |
| 1-92 | 6.30 | 2.46 |
| 1-94 | 6.27 | 2.46 |
| 1-102 | 6.27 | 2.46 |
| 1-116 | 6.29 | 2.57 |
| 1-122 | 6.32 | 2.47 |
| 1-126 | 6.31 | 2.46 |
| 1-128 | 6.32 | 2.47 |
| 1-130 | 6.29 | 2.46 |
| 1-134 | 6.35 | 2.61 |
| 1-138 | 6.29 | 2.47 |
| 1-154 | 6.33 | 2.63 |
| 1-160 | 6.37 | 2.79 |
| 1-170 | 6.36 | 2.64 |
| 1-198 | 6.30 | 2.46 |
| 1-229 | 6.32 | 2.57 |
| 1-237 | 6.28 | 2.46 |
| 1-279 | 6.31 | 2.46 |
| 1-341 | 6.27 | 2.43 |
| 1-345 | 6.20 | 2.43 |
| 1-482 | 6.31 | 2.46 |
| 1-625 | 6.38 | 2.61 |
| 2-2 | 6.28 | 2.60 |
| 2-4 | 6.29 | 2.63 |
| 2-5 | 6.22 | 2.62 |
| 2-6 | 6.25 | 2.70 |
| 2-8 | 6.24 | 2.70 |
| 2-11 | 6.20 | 2.46 |
| 2-28 | 6.32 | 2.71 |
| 2-38 | 6.30 | 2.70 |
| 2-55 | 6.18 | 2.43 |
| 2-70 | 6.22 | 2.46 |
| 2-90 | 6.20 | 2.46 |
| 2-99 | 6.23 | 2.46 |
| 2-106 | 6.20 | 2.45 |
| 2-113 | 6.25 | 2.44 |
| 2-122 | 6.24 | 2.45 |
| 2-141 | 6.15 | 2.43 |
| 2-146 | 6.12 | 2.44 |
| 2-178 | 6.20 | 2.43 |
| 2-227 | 6.17 | 2.44 |
| 2-269 | 6.13 | 2.44 |
| 2-282 | 6.19 | 2.45 |
| 2-353 | 6.15 | 2.44 |

EXAMPLE

Example 1-1

A glass substrate thinly coated with indium tin oxide (ITO) to have a thickness of 500 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 minutes, and then transported to a vacuum evaporator.

The following Compound [HAT] was thermally vacuum deposited to a thickness of 50 Å on the transparent ITO electrode, which was prepared as described above, thereby forming a hole injection layer. The following Compounds [NPB] (1,000 Å) and [HT-A] (400 Å) were sequentially vacuum deposited on the hole injection layer, thereby forming a hole transporting layer.

Subsequently, the following Compounds [RH] and [RD] were vacuum deposited at a weight ratio of 30:1 to have a film thickness of 350 Å on the hole transporting layer, thereby forming a light emitting layer.

[Compound 1-1] was vacuum deposited on the light emitting layer, thereby forming an electron controlling layer having a thickness of 200 Å. Compounds [ET-1-A] and [LiQ] were vacuum deposited at a weight ratio of 1:1 on the electron controlling layer, thereby forming an electron transporting layer having a thickness of 150 Å. Lithium fluoride (LiF) and aluminum were subsequently deposited to have a thickness of 10 Å and 1,000 Å, respectively, on the electron transporting layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec, and at 2 Å/sec, respectively, and the degree of vacuum during the deposition was maintained at $1 \times 10^{-7}$ to $5 \times 10^{-8}$ torr, thereby manufacturing an organic light emitting device.

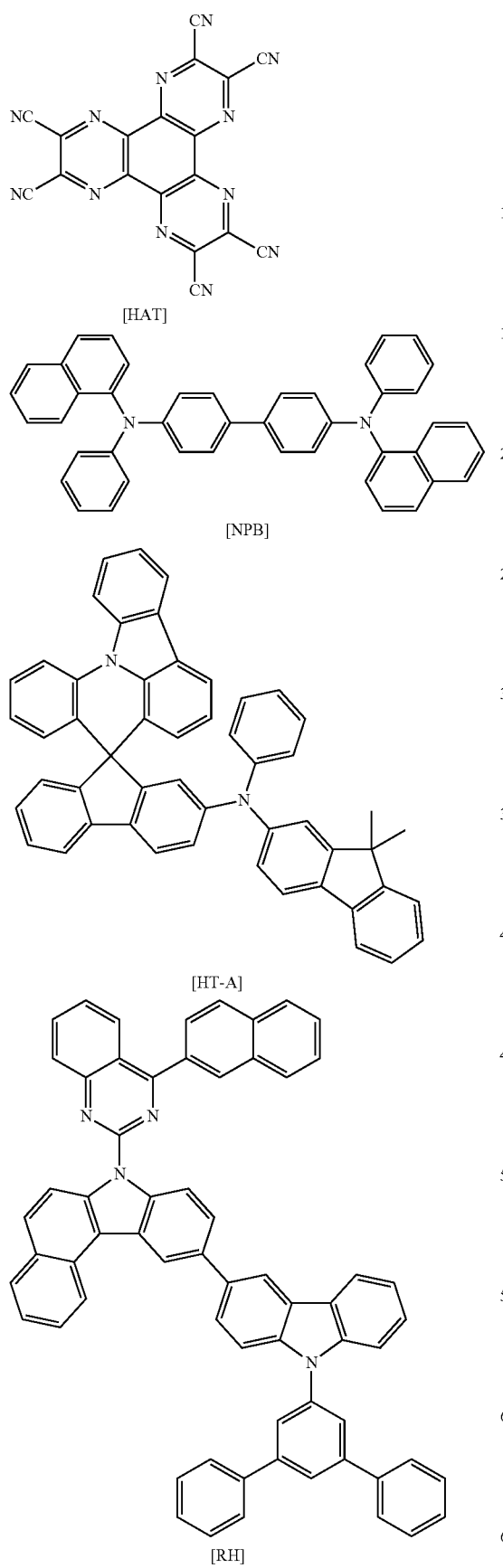
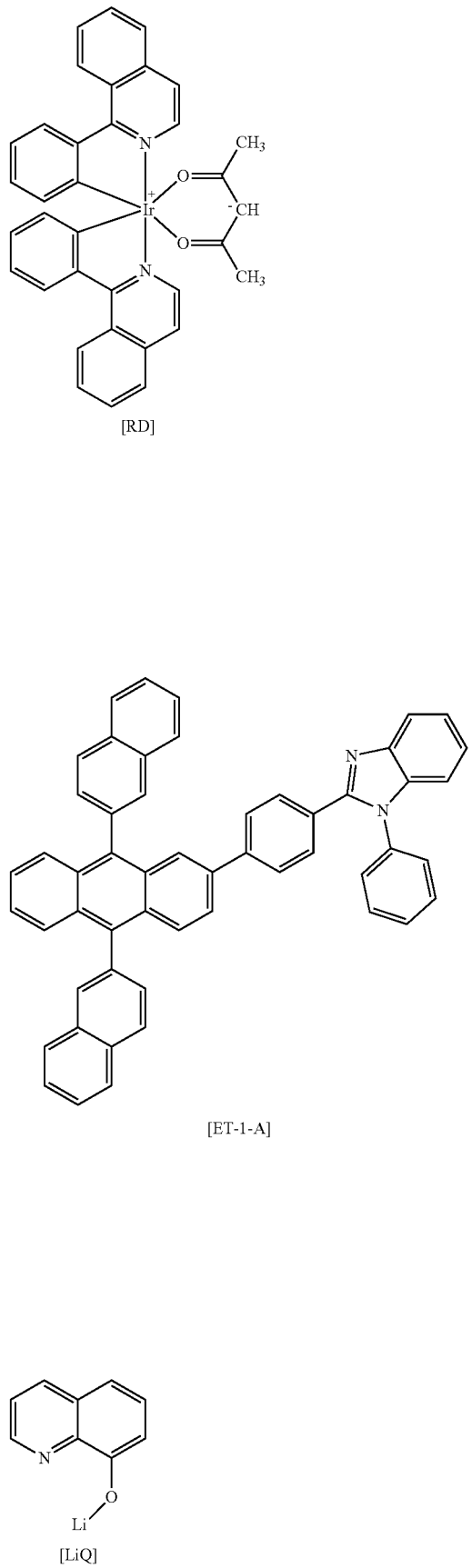

-continued

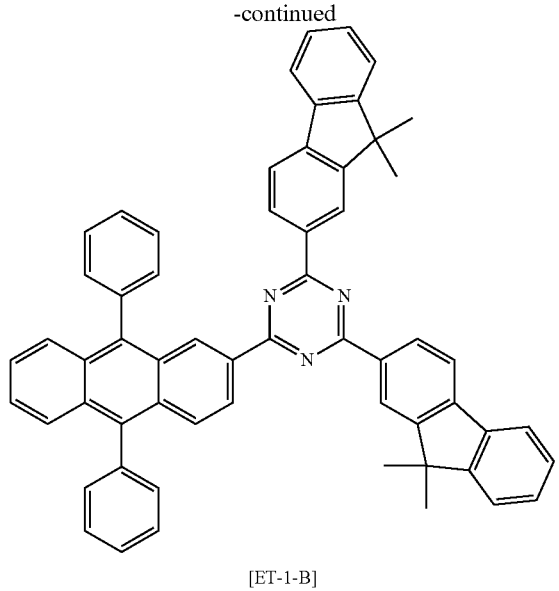

[ET-1-B]

[ET-1-C]

Example 1-2

An organic light emitting device was manufactured in the same manner as in [Example 1-1], except that [Compound 1-3] was used instead of [Compound 1-1] of [Example 1-1].

Example 1-3

An organic light emitting device was manufactured in the same manner as in [Example 1-1], except that [Compound 1-82] was used instead of [Compound 1-1] of [Example 1-1].

Example 1-4

An organic light emitting device was manufactured in the same manner as in [Example 1-1], except that [Compound 1-122] was used instead of [Compound 1-1] of [Example 1-1].

Example 1-5

An organic light emitting device was manufactured in the same manner as in [Example 1-1], except that [Compound 1-229] was used instead of [Compound 1-1] of [Example 1-1].

Example 1-6

An organic light emitting device was manufactured in the same manner as in [Example 1-1], except that [Compound 1-237] was used instead of [Compound 1-1] of [Example 1-1].

Example 1-7

An organic light emitting device was manufactured in the same manner as in [Example 1-1], except that [Compound 1-279] was used instead of [Compound 1-1] of [Example 1-1].

Example 1-8

An organic light emitting device was manufactured in the same manner as in [Example 1-1], except that [Compound 1-345] was used instead of [Compound 1-1] of [Example 1-1].

Example 1-9

An organic light emitting device was manufactured in the same manner as in [Example 1-1], except that [Compound 1-482] was used instead of [Compound 1-1] of [Example 1-1].

Example 1-10

An organic light emitting device was manufactured in the same manner as in [Example 1-1], except that [Compound 2-8] was used instead of [Compound 1-1] of [Example 1-1].

Example 1-11

An organic light emitting device was manufactured in the same manner as in [Example 1-1], except that [Compound 2-11] was used instead of [Compound 1-1] of [Example 1-1].

Example 1-12

An organic light emitting device was manufactured in the same manner as in [Example 1-1], except that [Compound 2-99] was used instead of [Compound 1-1] of [Example 1-1].

Example 1-13

An organic light emitting device was manufactured in the same manner as in [Example 1-1], except that [Compound 2-113] was used instead of [Compound 1-1] of [Example 1-1].

Example 1-14

An organic light emitting device was manufactured in the same manner as in [Example 1-1], except that [Compound 2-141] was used instead of [Compound 1-1] of [Example 1-1].

Example 1-15

An organic light emitting device was manufactured in the same manner as in [Example 1-1], except that [Compound 2-146] was used instead of [Compound 1-1] of [Example 1-1].

Example 1-16

An organic light emitting device was manufactured in the same manner as in [Example 1-1], except that [Compound 2-178] was used instead of [Compound 1-1] of [Example 1-1].

Example 1-17

An organic light emitting device was manufactured in the same manner as in [Example 1-1], except that [Compound 2-227] was used instead of [Compound 1-1] of [Example 1-1].

Example 1-18

An organic light emitting device was manufactured in the same manner as in [Example 1-1], except that [Compound 2-282] was used instead of [Compound 1-1] of [Example 1-1].

Example 1-19

An organic light emitting device was manufactured in the same manner as in [Example 1-1], except that [Compound 1-6] and [Compound 1-8] were used instead of [Compound 1-1] and [ET-1-A] of [Example 1-1], respectively.

Example 1-20

An organic light emitting device was manufactured in the same manner as in [Example 1-1], except that [Compound 1-6] and [Compound 1-6] were used instead of [Compound 1-1] and [ET-1-A] of [Example 1-1], respectively.

Example 1-21

An organic light emitting device was manufactured in the same manner as in [Example 1-1], except that [Compound 1-54] and [Compound 1-116] were used instead of [Compound 1-1] and [ET-1-A] of [Example 1-1], respectively.

Comparative Example 1-1

An organic light emitting device was manufactured in the same manner as in [Example 1-1], except that [ET-1-A] was used instead of [Compound 1-1] of [Example 1-1].

Comparative Example 1-2

An organic light emitting device was manufactured in the same manner as in [Example 1-1], except that [ET-1-B] was used instead of [Compound 1-1] of [Example 1-1].

Comparative Example 1-3

An organic light emitting device was manufactured in the same manner as in [Example 1-1], except that [ET-1-C] was used instead of [Compound 1-1] of [Example 1-1].

For the organic light emitting devices manufactured by the above-described method, the driving voltage and the light emitting efficiency were measured at a current density of 10 mA/cm$^2$, and a time ($T_{95}$) for reaching a 95% value compared to the initial luminance was measured at a current density of 20 mA/cm$^2$. The results are shown in the following Table 2.

TABLE 2

| | Voltage (V) | Efficiency (Cd/A) | Color coordinate (x, y) | Service life (h) $T_{95}$ at 20 mA/cm$^2$ |
|---|---|---|---|---|
| Example 1-1 | 5.62 | 22.1 | (0.675, 0.319) | 232 |
| Example 1-2 | 5.65 | 22.6 | (0.675, 0.318) | 220 |
| Example 1-3 | 5.34 | 23.2 | (0.675, 0.317) | 255 |
| Example 1-4 | 5.43 | 23.7 | (0.675, 0.318) | 253 |
| Example 1-5 | 5.71 | 21.1 | (0.675, 0.319) | 232 |
| Example 1-6 | 5.35 | 22.9 | (0.675, 0.318) | 254 |
| Example 1-7 | 5.63 | 19.8 | (0.675, 0.320) | 242 |
| Example 1-8 | 5.43 | 22.7 | (0.675, 0.319) | 261 |
| Example 1-9 | 5.32 | 23.3 | (0.675, 0.319) | 260 |
| Example 1-10 | 5.45 | 24.0 | (0.675, 0.318) | 271 |
| Example 1-11 | 5.81 | 22.5 | (0.675, 0.320) | 226 |
| Example 1-12 | 5.73 | 22.8 | (0.675, 0.319) | 218 |
| Example 1-13 | 5.66 | 20.5 | (0.675, 0.320) | 221 |
| Example 1-14 | 5.35 | 22.9 | (0.675, 0.319) | 244 |
| Example 1-15 | 5.45 | 23.3 | (0.675, 0.318) | 252 |
| Example 1-16 | 5.31 | 24.5 | (0.675, 0.317) | 272 |
| Example 1-17 | 5.87 | 21.0 | (0.675, 0.319) | 232 |
| Example 1-18 | 5.42 | 23.5 | (0.675, 0.317) | 249 |
| Example 1-19 | 4.82 | 27.4 | (0.675, 0.317) | 277 |
| Example 1-20 | 5.02 | 25.1 | (0.675, 0.316) | 265 |
| Example 1-21 | 5.11 | 24.8 | (0.675, 0.316) | 241 |
| Comparative Example 1-1 | 6.57 | 17.5 | (0.675, 0.321) | 187 |
| Comparative Example 1-2 | 6.45 | 18.5 | (0.675, 0.321) | 152 |
| Comparative Example 1-3 | 6.38 | 18.7 | (0.675, 0.319) | 168 |

From the result of the table, it can be confirmed that the compound represented by Formula 1 according to an exemplary embodiment of the present specification may be used for the electron controlling layer in the organic phosphorescent light emitting device. It can be confirmed that an organic phosphorescent light emitting device using the same has higher efficiency, a lower driving voltage, and a longer service life than the case where a symmetrical triazine compound is used for the electron controlling layer. Further, it can be confirmed that even the case where the compound represented by Formula 1 is used for the electron controlling layer and the electron transporting layer has high efficiency, a low driving voltage, and a long service life. In particular, the compound represented by Formula 1 according to the present invention was excellent in thermal stability, and had a deep HOMO level of 6.0 eV or more, and high triplet energy ($E_T$) and hole stability, thereby exhibiting excellent characteristics.

In particular, according to an exemplary embodiment of the present specification, the case where the compound represented by Formula 3 is used for the electron controlling layer has higher efficiency, a lower driving voltage, and a longer service life than the case where the compounds represented by Formulae 4 to 6 are used for the electron controlling layer.

Example 2-1

Formula [HAT] was thermally vacuum deposited to a thickness of 50 Å on a transparent ITO electrode, which was prepared as in [Example 1-1], thereby forming a hole injection layer. Compounds [NPB] (1,000 Å) and [HT-A] (200 Å) were sequentially vacuum deposited on the hole injection layer, thereby forming a hole transporting layer.

Subsequently, the following Compounds [GH] and [GD] were vacuum deposited at a weight ratio of 10:1 to have a film thickness of 300 Å on the hole transporting layer, thereby forming a light emitting layer.

[Compound 1-2] was vacuum deposited on the light emitting layer, thereby forming an electron controlling layer having a thickness of 200 Å. The following Compounds [ET-2-A] and [LiQ] were vacuum deposited at a weight ratio of 1:1 on the electron controlling layer, thereby forming an electron transporting layer having a thickness of 150 Å. Lithium fluoride (LiF) and aluminum were subsequently deposited to have a thickness of 10 Å and 1,000 Å, respectively, on the electron transporting layer, thereby forming a negative electrode.

An organic light emitting device was manufactured in the same manner as in [Example 1-1] in terms of the deposition rate of the organic material and degree of vacuum in the aforementioned procedure.

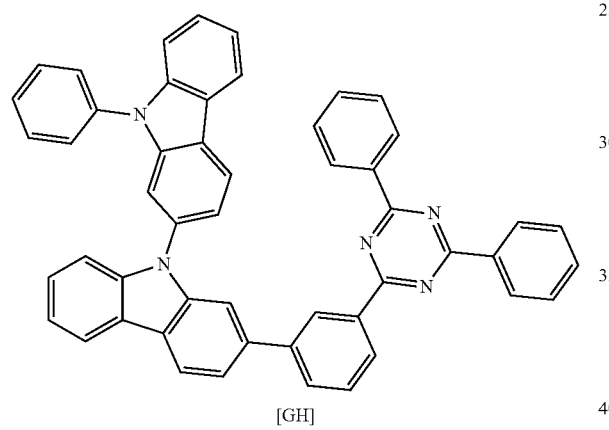

[GH]

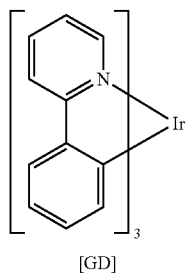

[GD]

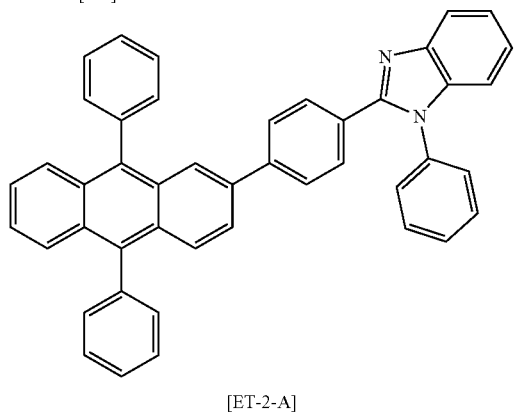

[ET-2-A]

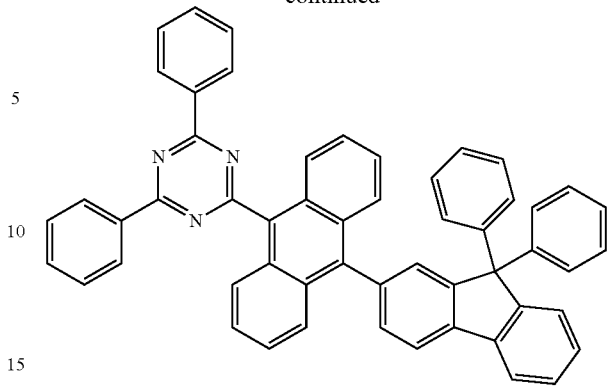

[ET-2-B]

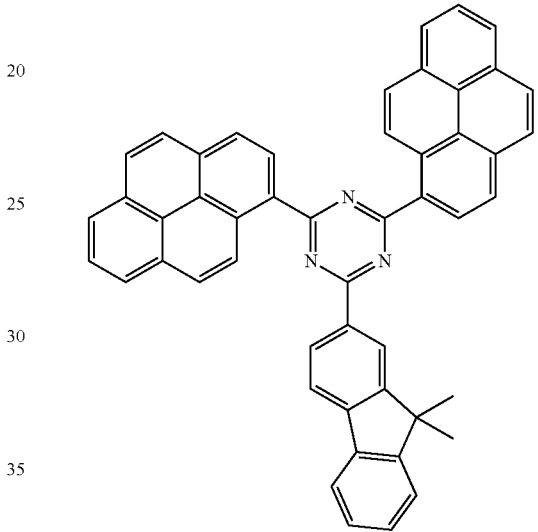

[ET-2-C]

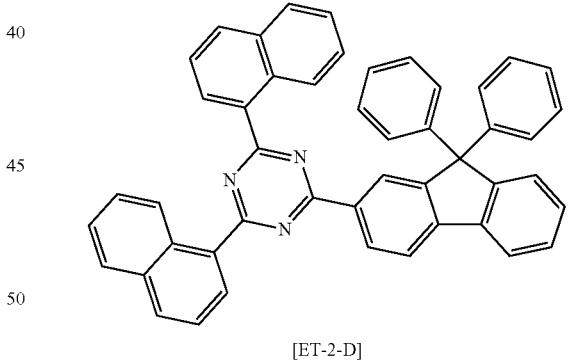

[ET-2-D]

Example 2-2

An organic light emitting device was manufactured in the same manner as in [Example 2-1], except that [Compound 1-26] was used instead of [Compound 1-2] of [Example 2-1].

Example 2-3

An organic light emitting device was manufactured in the same manner as in [Example 2-1], except that [Compound 1-40] was used instead of [Compound 1-2] of [Example 2-1].

Example 2-4

An organic light emitting device was manufactured in the same manner as in [Example 2-1], except that [Compound 1-50] was used instead of [Compound 1-2] of [Example 2-1].

Example 2-5

An organic light emitting device was manufactured in the same manner as in [Example 2-1], except that [Compound 1-67] was used instead of [Compound 1-2] of [Example 2-1].

Example 2-6

An organic light emitting device was manufactured in the same manner as in [Example 2-1], except that [Compound 1-160] was used instead of [Compound 1-2] of [Example 2-1].

Example 2-7

An organic light emitting device was manufactured in the same manner as in [Example 2-1], except that [Compound 1-170] was used instead of [Compound 1-2] of [Example 2-1].

Example 2-8

An organic light emitting device was manufactured in the same manner as in [Example 2-1], except that [Compound 2-2] was used instead of [Compound 1-2] of [Example 2-1].

Example 2-9

An organic light emitting device was manufactured in the same manner as in [Example 2-1], except that [Compound 2-4] was used instead of [Compound 1-2] of [Example 2-1].

Example 2-10

An organic light emitting device was manufactured in the same manner as in [Example 2-1], except that [Compound 2-5] was used instead of [Compound 1-2] of [Example 2-1].

Example 2-11

An organic light emitting device was manufactured in the same manner as in [Example 2-1], except that [Compound 2-6] was used instead of [Compound 1-2] of [Example 2-1].

Example 2-12

An organic light emitting device was manufactured in the same manner as in [Example 2-1], except that [Compound 2-28] was used instead of [Compound 1-2] of [Example 2-1].

Example 2-13

An organic light emitting device was manufactured in the same manner as in [Example 2-1], except that [Compound 2-38] was used instead of [Compound 1-2] of [Example 2-1].

Example 2-14

An organic light emitting device was manufactured in the same manner as in [Example 2-1], except that [Compound 1-6] instead of [Compound 1-2] of [Example 2-1] and Compound [LiQ] (lithium quinolate) were vacuum deposited and used at a weight ratio of 1:1.

Example 2-15

An organic light emitting device was manufactured in the same manner as in [Example 2-1], except that [Compound 1-8] instead of [Compound 1-2] of [Example 2-1] and Compound [LiQ] (lithium quinolate) were vacuum deposited and used at a weight ratio of 1:1.

Example 2-16

An organic light emitting device was manufactured in the same manner as in [Example 2-1], except that [Compound 1-6] was used instead of [Compound 1-2] of [Example 2-1].

Comparative Example 2-1

An organic light emitting device was manufactured in the same manner as in [Example 2-1], except that [ET-2-A] was used instead of [Compound 1-2] of [Example 2-1].

Comparative Example 2-2

An organic light emitting device was manufactured in the same manner as in [Example 2-1], except that [ET-2-B] was used instead of [Compound 1-2] of [Example 2-1].

Comparative Example 2-3

An organic light emitting device was manufactured in the same manner as in [Example 2-1], except that [ET-2-C] was used instead of [Compound 1-2] of [Example 2-1].

Comparative Example 2-4

An organic light emitting device was manufactured in the same manner as in [Example 2-1], except that [ET-2-D] was used instead of [Compound 1-2] of [Example 2-1].

For the organic light emitting devices manufactured by the above-described method, the driving voltage and the light emitting efficiency were measured at a current density of 10 mA/cm$^2$, and a time ($T_{95}$) for reaching a 95% value compared to the initial luminance was measured at a current density of 20 mA/cm$^2$. The results are shown in the following Table 3.

TABLE 3

| | Voltage (V) | Efficiency (Cd/A) | Color coordinate (x, y) | Service life (h) $T_{95}$ at 20 mA/cm$^2$ |
|---|---|---|---|---|
| Example 2-1 | 4.42 | 38.2 | (0.322, 0.613) | 46.2 |
| Example 2-2 | 4.63 | 37.9 | (0.322, 0.612) | 38.9 |
| Example 2-3 | 4.71 | 34.8 | (0.322, 0.615) | 35.7 |
| Example 2-4 | 4.69 | 36.9 | (0.322, 0.612) | 50.1 |
| Example 2-5 | 4.75 | 35.1 | (0.322, 0.613) | 39.2 |
| Example 2-6 | 4.85 | 34.5 | (0.322, 0.614) | 41.9 |
| Example 2-7 | 4.65 | 37.3 | (0.322, 0.612) | 47.5 |
| Example 2-8 | 4.37 | 38.1 | (0.322, 0.611) | 51.7 |
| Example 2-9 | 4.59 | 37.8 | (0.322, 0.612) | 45.8 |
| Example 2-10 | 4.32 | 38.8 | (0.322, 0.611) | 52.9 |

TABLE 3-continued

| | Voltage (V) | Efficiency (Cd/A) | Color coordinate (x, y) | Service life (h) $T_{95}$ at 20 mA/cm$^2$ |
|---|---|---|---|---|
| Example 2-11 | 4.61 | 35.5 | (0.322, 0.613) | 42.7 |
| Example 2-12 | 4.68 | 34.1 | (0.322, 0.614) | 40.8 |
| Example 2-13 | 4.73 | 33.9 | (0.322, 0.615) | 44.5 |
| Example 2-14 | 4.13 | 42.9 | (0.322, 0.612) | 72.1 |
| Example 2-15 | 4.27 | 40.2 | (0.322, 0.612) | 61.5 |
| Example 2-16 | 4.30 | 39.8 | (0.322, 0.612) | 55.7 |
| Comparative Example 2-1 | 5.21 | 28.5 | (0.322, 0.614) | 33.8 |
| Comparative Example 2-2 | 5.82 | 21.2 | (0.322, 0.615) | 27.1 |
| Comparative Example 2-3 | 5.45 | 26.4 | (0.322, 0.614) | 30.1 |
| Comparative Example 2-4 | 4.97 | 30.8 | (0.322, 0.613) | 31.8 |

From the result of the table, it can be confirmed that the compound represented by Formula 1 according to an exemplary embodiment of the present specification may be used for the electron controlling layer in the organic phosphorescent light emitting device. It can be confirmed that an organic phosphorescent light emitting device using the same has higher efficiency, a lower driving voltage, and a longer service life than the case where a symmetrical triazine compound is used for the electron controlling layer. In particular, the compound represented by Formula according to the present invention was excellent in thermal stability, and had a deep HOMO level of 6.0 eV or more, and high triplet energy ($E_T$) and hole stability, thereby exhibiting excellent characteristics.

Further, from the result of the Table, the compound represented by Formula 1 according to the present invention may be used in mixture with an n-type dopant for the electron controlling layer in the organic green phosphorescent light emitting device, and accordingly, the compound represented by Formula 1 has a low driving voltage and high efficiency, and may improve stability of the device by hole stability of the compound.

In particular, according to an exemplary embodiment of the present specification, the case where the compound represented by Formula 3 is used for the electron controlling layer has higher efficiency, a lower driving voltage, and a longer service life than the case where the compounds represented by Formulae 4 to 6 are used for the electron controlling layer.

Example 3-1

The following Compound Formula [HI-A] was thermally vacuum deposited to a thickness of 600 Å on a transparent ITO electrode, which was prepared as in [Example 1-1], thereby forming a hole injection layer. Compound [HAT] (50 Å) and the following Compound [HT-B] (600 Å) were sequentially vacuum deposited on the hole injection layer, thereby forming a hole transporting layer.

Subsequently, the following compounds [BH] and [BD] were vacuum deposited at a weight ratio of 25:1 to have a film thickness of 200 Å on the hole transporting layer, thereby forming a light emitting layer.

Compound [Formula 1-6] and Compound [LiQ] (lithium quinolate) were vacuum deposited at a weight ratio of 1:1 on the light emitting layer, thereby forming an electron injection and transporting layer having a thickness of 350 Å. Lithium fluoride (LiF) and aluminum were subsequently deposited to have a thickness of 10 Å and 1,000 Å, respectively, on the electron injection and transporting layer, thereby forming a negative electrode.

An organic light emitting device was manufactured in the same manner as in [Example 1-1] in terms of the deposition rate of the organic material and degree of vacuum in the aforementioned procedure.

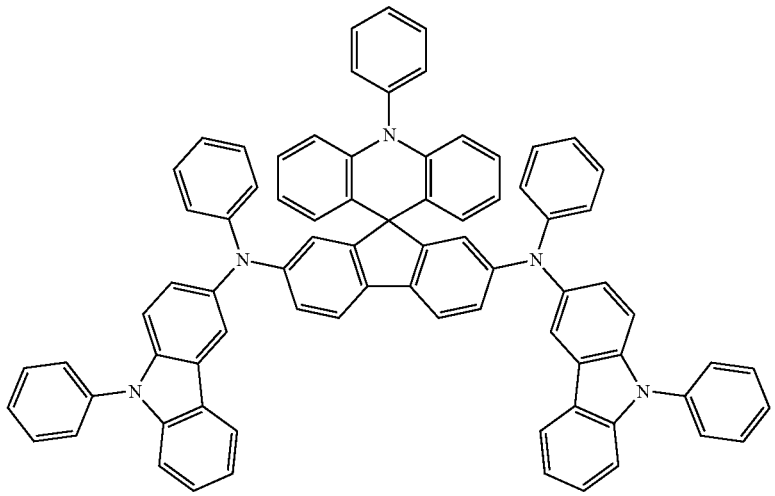

[HT-A]

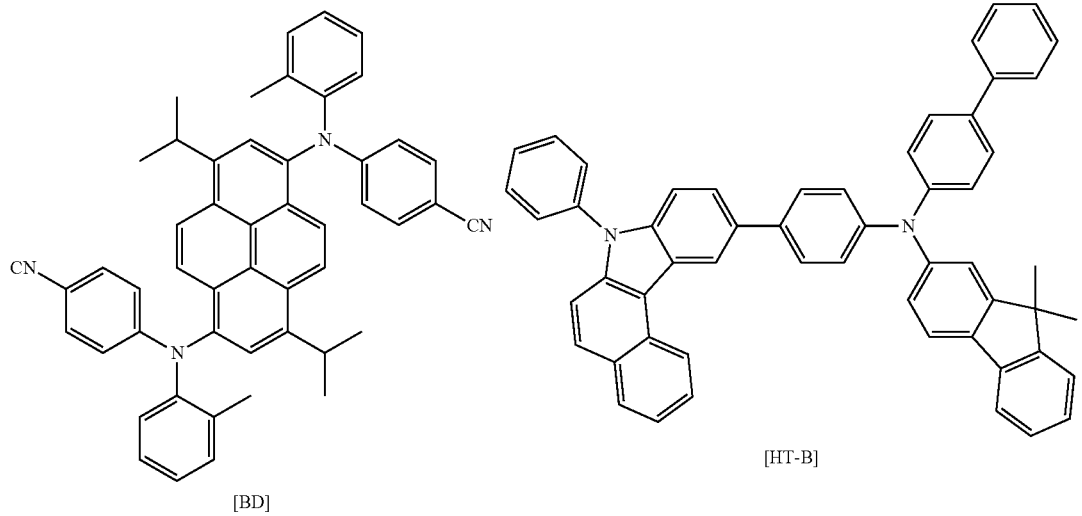
[BD]  [HT-B]
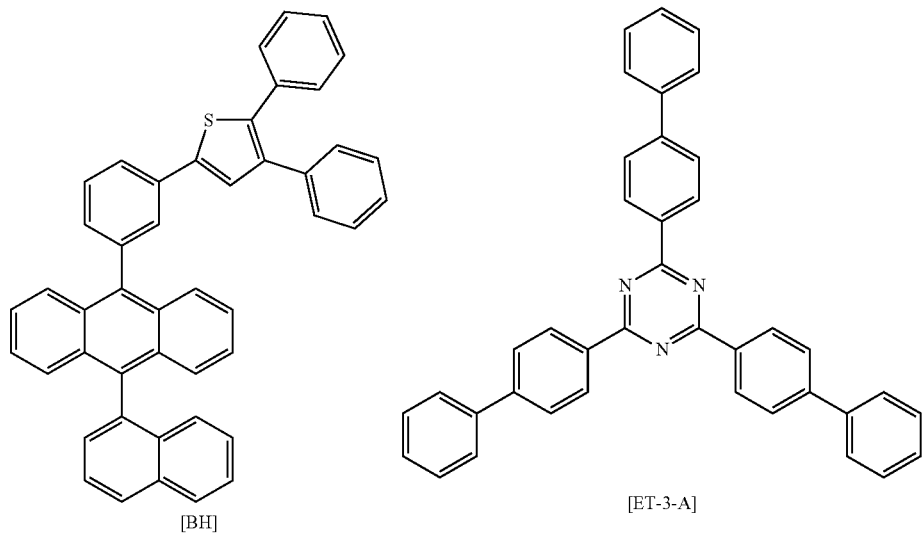
[BH]  [ET-3-A]
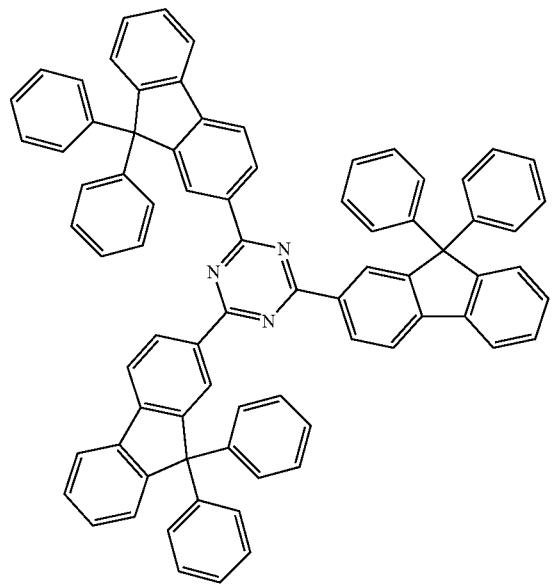
[ET-3-B]

-continued
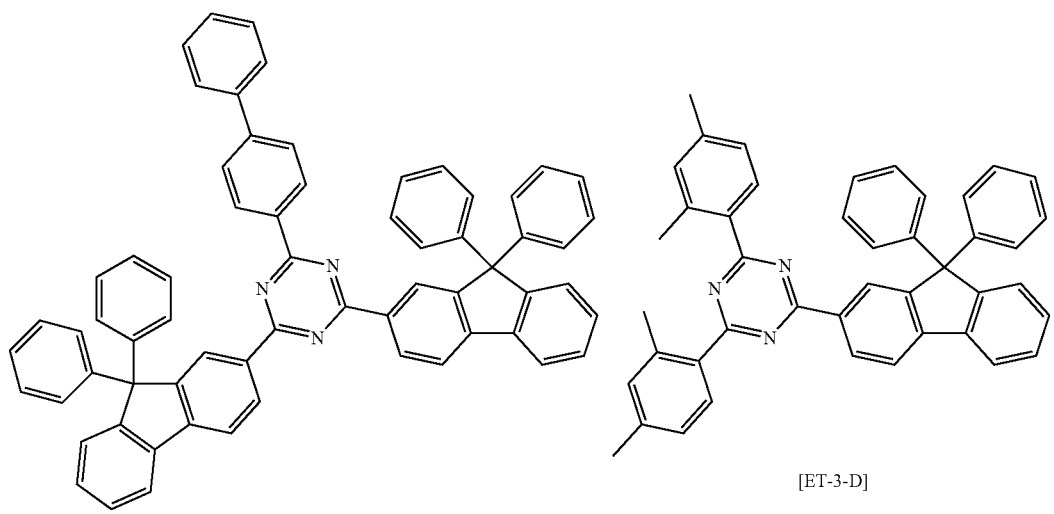
[ET-3-C]  [ET-3-D]
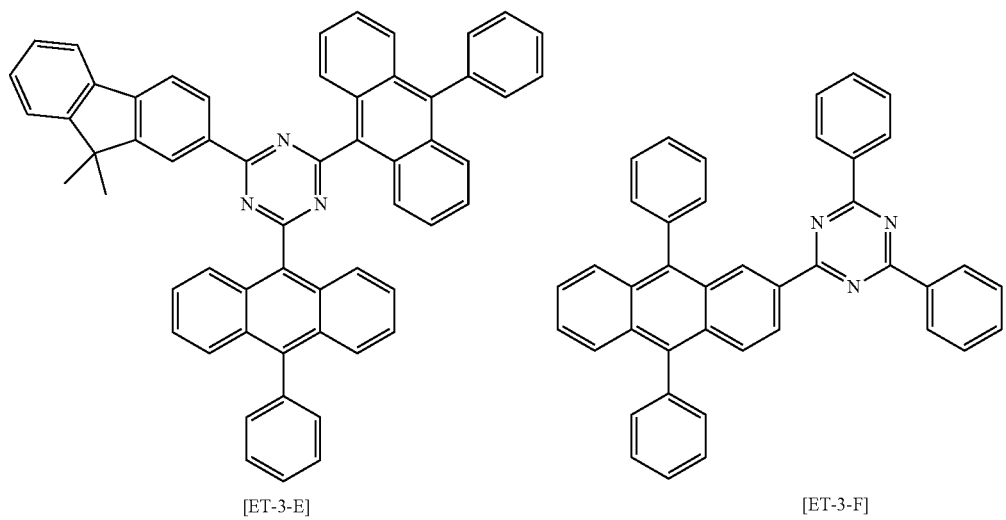
[ET-3-E]  [ET-3-F]
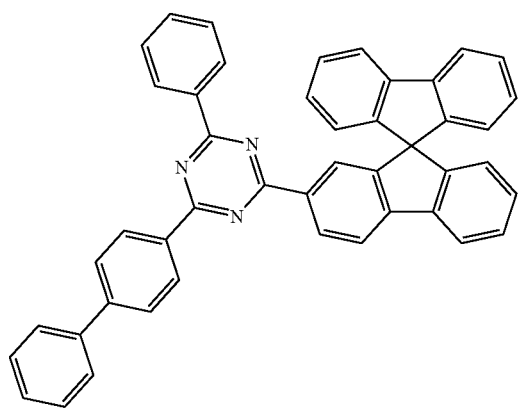
[ET-3-G]

Example 3-2

An organic light emitting device was manufactured in the same manner as in [Example 3-1], except that [Compound 1-8] was used instead of [Compound 1-6] of [Example 3-1].

Example 3-3

An organic light emitting device was manufactured in the same manner as in [Example 3-1], except that [Compound 1-10] was used instead of [Compound 1-6] of [Example 3-1].

Example 3-4

An organic light emitting device was manufactured in the same manner as in [Example 3-1], except that [Compound 1-12] was used instead of [Compound 1-6] of [Example 3-1].

Example 3-5

An organic light emitting device was manufactured in the same manner as in [Example 3-1], except that [Compound 1-20] was used instead of [Compound 1-6] of [Example 3-1].

Example 3-6

An organic light emitting device was manufactured in the same manner as in [Example 3-1], except that [Compound 1-22] was used instead of [Compound 1-6] of [Example 3-1].

Example 3-7

An organic light emitting device was manufactured in the same manner as in [Example 3-1], except that [Compound 1-32] was used instead of [Compound 1-6] of [Example 3-1].

Example 3-8

An organic light emitting device was manufactured in the same manner as in [Example 3-1], except that [Compound 1-34] was used instead of [Compound 1-6] of [Example 3-1].

Example 3-9

An organic light emitting device was manufactured in the same manner as in [Example 3-1], except that [Compound 1-54] was used instead of [Compound 1-6] of [Example 3-1].

Example 3-10

An organic light emitting device was manufactured in the same manner as in [Example 3-1], except that [Compound 1-90] was used instead of [Compound 1-6] of [Example 3-1].

Example 3-11

An organic light emitting device was manufactured in the same manner as in [Example 3-1], except that [Compound 1-92] was used instead of [Compound 1-6] of [Example 3-1].

Example 3-13

An organic light emitting device was manufactured in the same manner as in [Example 3-1], except that [Compound 1-102] was used instead of [Compound 1-6] of [Example 3-1].

Example 3-14

An organic light emitting device was manufactured in the same manner as in [Example 3-1], except that [Compound 1-128] was used instead of [Compound 1-6] of [Example 3-1].

Example 3-15

An organic light emitting device was manufactured in the same manner as in [Example 3-1], except that [Compound 1-130] was used instead of [Compound 1-6] of [Example 3-1].

Example 3-16

An organic light emitting device was manufactured in the same manner as in [Example 3-1], except that [Compound 1-154] was used instead of [Compound 1-6] of [Example 3-1].

Example 3-17

An organic light emitting device was manufactured in the same manner as in [Example 3-1], except that [Compound 1-198] was used instead of [Compound 1-6] of [Example 3-1].

Example 3-18

An organic light emitting device was manufactured in the same manner as in [Example 3-1], except that [Compound 1-341] was used instead of [Compound 1-6] of [Example 3-1].

Example 3-19

An organic light emitting device was manufactured in the same manner as in [Example 3-1], except that [Compound 2-55] was used instead of [Compound 1-6] of [Example 3-1].

Example 3-20

An organic light emitting device was manufactured in the same manner as in [Example 3-1], except that [Compound 2-70] was used instead of [Compound 1-6] of [Example 3-1].

Example 3-21

An organic light emitting device was manufactured in the same manner as in [Example 3-1], except that [Compound 2-90] was used instead of [Compound 1-6] of [Example 3-1].

Example 3-22

An organic light emitting device was manufactured in the same manner as in [Example 3-1], except that [Compound 2-353] was used instead of [Compound 1-6] of [Example 3-1].

Example 3-23

An organic light emitting device was manufactured in the same manner as in [Example 3-1], except that [Compound 1-625] was used instead of [Compound 1-6] of [Example 3-1].

Comparative Example 3-1

An organic light emitting device was manufactured in the same manner as in [Example 3-1], except that [ET-3-A] was used instead of [Compound 1-6] of [Example 3-1].

Comparative Example 3-2

An organic light emitting device was manufactured in the same manner as in [Example 3-1], except that [ET-3-B] was used instead of [Compound 1-6] of [Example 3-1].

Comparative Example 3-3

An organic light emitting device was manufactured in the same manner as in [Example 3-1], except that [ET-3-C] was used instead of [Compound 1-6] of [Example 3-1].

Comparative Example 3-4

An organic light emitting device was manufactured in the same manner as in [Example 3-1], except that [ET-3-D] was used instead of [Compound 1-6] of [Example 3-1].

Comparative Example 3-5

An organic light emitting device was manufactured in the same manner as in [Example 3-1], except that [ET-3-E] was used instead of [Compound 1-6] of [Example 3-1].

Comparative Example 3-6

An organic light emitting device was manufactured in the same manner as in [Example 3-1], except that [ET-3-F] was used instead of [Compound 1-6] of [Example 3-1].

Comparative Example 3-7

An organic light emitting device was manufactured in the same manner as in [Example 3-1], except that [ET-1-A] was used instead of [Compound 1-6] of [Example 3-1].

Comparative Example 3-8

An organic light emitting device was manufactured in the same manner as in [Example 3-1], except that [ET-3-G] was used instead of [Compound 1-6] of [Example 3-1].

For the organic light emitting devices manufactured by the above-described method, the driving voltage and the light emitting efficiency were measured at a current density of 10 mA/cm$^2$, and a time ($T_{90}$) for reaching a 90% value compared to the initial luminance measured at a current density of 20 mA/cm$^2$. The results are shown in the following Table 4.

TABLE 4

| | Voltage (V) | Efficiency (Cd/A) | Color coordinate (x, y) | Service life (h) $T_{90}$ at 20 mA/cm$^2$ |
|---|---|---|---|---|
| Example 3-1 | 4.50 | 5.45 | (0.142, 0.097) | 167 |
| Example 3-2 | 4.30 | 5.79 | (0.142, 0.096) | 180 |
| Example 3-3 | 4.49 | 5.40 | (0.142, 0.098) | 143 |
| Example 3-4 | 4.35 | 5.61 | (0.142, 0.096) | 154 |
| Example 3-5 | 4.52 | 5.68 | (0.142, 0.096) | 152 |
| Example 3-6 | 4.59 | 5.32 | (0.142, 0.098) | 142 |
| Example 3-7 | 4.55 | 5.66 | (0.142, 0.096) | 145 |
| Example 3-8 | 4.65 | 5.45 | (0.142, 0.097) | 153 |
| Example 3-9 | 4.69 | 5.36 | (0.142, 0.099) | 169 |
| Example 3-10 | 4.62 | 5.39 | (0.142, 0.097) | 150 |
| Example 3-11 | 4.48 | 5.52 | (0.142, 0.096) | 168 |
| Example 3-13 | 4.72 | 5.35 | (0.142, 0.097) | 143 |
| Example 3-14 | 4.55 | 5.47 | (0.142, 0.097) | 141 |
| Example 3-15 | 4.69 | 5.38 | (0.142, 0.096) | 156 |
| Example 3-16 | 4.66 | 5.41 | (0.142, 0.097) | 148 |
| Example 3-17 | 4.52 | 5.32 | (0.142, 0.099) | 138 |
| Example 3-18 | 4.75 | 5.45 | (0.142, 0.097) | 165 |
| Example 3-19 | 4.61 | 5.39 | (0.142, 0.098) | 155 |
| Example 3-20 | 4.52 | 5.65 | (0.142, 0.096) | 177 |
| Example 3-21 | 4.55 | 5.41 | (0.142, 0.097) | 156 |
| Example 3-22 | 4.59 | 5.29 | (0.142, 0.097) | 175 |
| Example 3-23 | 4.51 | 5.43 | (0.142, 0.097) | 170 |
| Comparative Example 3-1 | 5.55 | 4.52 | (0.142, 0.098) | 92 |
| Comparative Example 3-2 | 5.75 | 4.32 | (0.142, 0.100) | 101 |
| Comparative Example 3-3 | 5.42 | 4.77 | (0.142, 0.099) | 110 |
| Comparative Example 3-4 | 4.81 | 5.02 | (0.142, 0.097) | 85 |
| Comparative Example 3-5 | 6.25 | 3.55 | (0.142, 0.098) | 88 |
| Comparative Example 3-6 | 5.94 | 3.80 | (0.142, 0.102) | 65 |
| Comparative Example 3-7 | 5.01 | 4.58 | (0.142, 0.098) | 133 |
| Comparative Example 3-8 | 4.88 | 5.11 | (0.142, 0.097) | 105 |

From the result of the table, it can be confirmed that the compound represented by Formula 1 according to an exemplary embodiment of the present specification may be used for an organic layer of the organic light emitting device which may simultaneously inject and transport electrons. It can be confirmed that an organic light emitting device using the same has higher efficiency, a lower driving voltage, and a longer service life than the case where a symmetrical triazine compound is used for an organic layer which may simultaneously inject and transport electrons. In particular, the compound represented by Formula 1 according to the present invention was excellent in thermal stability, and had a deep HOMO level of 6.0 eV or more, and high triplet energy ($E_T$) and hole stability, thereby exhibiting excellent characteristics. When the compound is used in the organic layer which simultaneously injects and transports electrons, the compound may be used in a mixture with an n-type dopant. Accordingly, the compound represented by Formula 1 has a low driving voltage and high efficiency, and may improve stability of the device by hole stability of the compound.

Further, according to the document (J. AM. CHEM. SOC. 2003, 125, 3710-3711), it can be confirmed that a disubstituted fluorenyl group has higher electron mobility than that of a spirobifluorenyl group. Accordingly, it could be confirmed that [Compound 1-8] and [Compound 1-10] transport electrons more efficiently than the compound of [ET-3-G] used in Comparative Example 3-8 and thus exhibit high efficiency, and the service life thereof is also improved.

Example 4-1

Compound [HI-A] was thermally vacuum deposited to a thickness of 600 Å on a transparent ITO electrode, which was prepared as in [Example 1-1], thereby forming a hole injection layer. Compound [HAT] (50 Å) and Compound [HT-B] (600 Å) were sequentially vacuum deposited on the hole injection layer, thereby forming a hole transporting layer. Subsequently, the following Compounds [BH] and [BD] were vacuum deposited at a weight ratio of 25:1 to have a film thickness of 200 Å on the hole transporting layer, thereby forming a light emitting layer.

The following Compound [ET-A] was vacuum deposited to a thickness of 50 Å on the light emitting layer, thereby forming an electron controlling layer. Compound [Formula 1-6] and Compound [LiQ] (lithium quinolate) were vacuum deposited at a weight ratio of 1:1 on the electron controlling layer, thereby forming an electron transporting and injection layer having a thickness of 300 Å. Lithium fluoride (LiF) and aluminum were subsequently deposited to have a thickness of 10 Å and 1,000 Å, respectively, on the electron transporting and injection layer, thereby forming a negative electrode.

An organic light emitting device was manufactured in the same manner as in [Example 1-1] in terms of the deposition rate of the organic material and degree of vacuum in the aforementioned procedure.

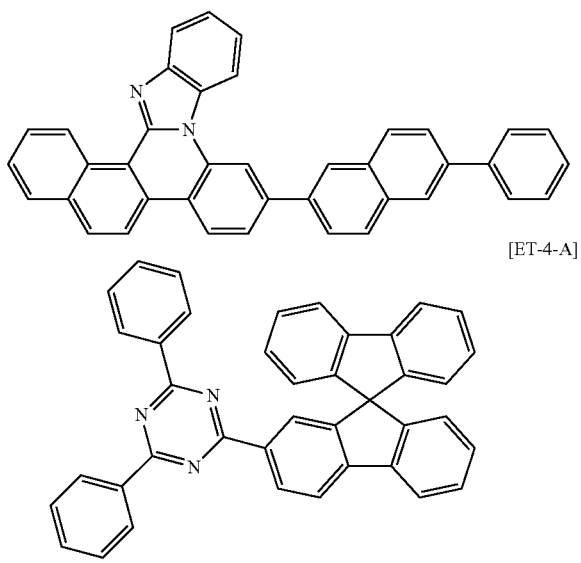

[ET-A]

[ET-4-A]

Example 4-2

An organic light emitting device was manufactured in the same manner as in [Example 4-1], except that [Compound 1-8] was used instead of [Compound 1-6] of [Example 4-1].

Example 4-3

An organic light emitting device was manufactured in the same manner as in [Example 4-1], except that [Compound 1-18] was used instead of [Compound 1-6] of [Example 4-1].

Example 4-4

An organic light emitting device was manufactured in the same manner as in [Example 4-1], except that [Compound 1-30] was used instead of [Compound 1-6] of [Example 4-1].

Example 4-5

An organic light emitting device was manufactured in the same manner as in [Example 4-1], except that [Compound 1-56] was used instead of [Compound 1-6] of [Example 4-1].

Example 4-6

An organic light emitting device was manufactured in the same manner as in [Example 4-1], except that [Compound 1-116] was used instead of [Compound 1-6] of [Example 4-1].

Example 4-7

An organic light emitting device was manufactured in the same manner as in [Example 4-1], except that [Compound 1-126] was used instead of [Compound 1-6] of [Example 4-1].

Example 4-8

An organic light emitting device was manufactured in the same manner as in [Example 4-1], except that [Compound 1-138] was used instead of [Compound 1-6] of [Example 4-1].

Example 4-9

An organic light emitting device was manufactured in the same manner as in [Example 4-1], except that [Compound 1-170] was used instead of [Compound 1-6] of [Example 4-1].

Example 4-10

An organic light emitting device was manufactured in the same manner as in [Example 4-1], except that [Compound 2-5] was used instead of [Compound 1-6] of [Example 4-1].

Example 4-11

An organic light emitting device was manufactured in the same manner as in [Example 4-1], except that [Compound 2-269] was used instead of [Compound 1-6] of [Example 4-1].

Comparative Example 4-1

An organic light emitting device was manufactured in the same manner as in [Example 4-1], except that [ET-1-A] was used instead of [Compound 1-6] of [Example 4-1].

Comparative Example 4-2

An organic light emitting device was manufactured in the same manner as in [Example 4-1], except that [ET-1-C] was used instead of [Compound 1-6] of [Example 4-1].

Comparative Example 4-3

An organic light emitting device was manufactured in the same manner as in [Example 4-1], except that [ET-2-C] was used instead of [Compound 1-6] of [Example 4-1].

Comparative Example 4-4

An organic light emitting device was manufactured in the same manner as in [Example 4-1], except that [ET-3-B] was used instead of [Compound 1-6] of [Example 4-1].

Comparative Example 4-5

An organic light emitting device was manufactured in the same manner as in [Example 4-1], except that [ET-3-F] was used instead of [Compound 1-6] of [Example 4-1].

Comparative Example 4-6

An organic light emitting device was manufactured in the same manner as in [Example 4-1], except that [ET-4-A] was used instead of [Compound 1-6] of [Example 4-1].

For the organic light emitting devices manufactured by the above-described method, the driving voltage and the light emitting efficiency were measured at a current density of 10 mA/cm$^2$, and a time ($T_{90}$) for reaching a 90% value compared to the initial luminance was measured at a current density of 20 mA/cm$^2$. The results are shown in the following Table 5.

TABLE 5

| | Voltage (V) | Efficiency (Cd/A) | Color coordinate (x, y) | Service life (h) $T_{90}$ at 20 mA/cm$^2$ |
|---|---|---|---|---|
| Example 4-1 | 4.61 | 6.75 | (0.142, 0.098) | 190 |
| Example 4-2 | 4.40 | 6.98 | (0.142, 0.096) | 202 |
| Example 4-3 | 4.81 | 6.50 | (0.142, 0.097) | 178 |
| Example 4-4 | 4.65 | 6.62 | (0.142, 0.097) | 169 |
| Example 4-5 | 4.59 | 6.57 | (0.142, 0.096) | 205 |
| Example 4-6 | 4.62 | 6.54 | (0.142, 0.096) | 215 |
| Example 4-7 | 4.85 | 6.27 | (0.142, 0.098) | 180 |
| Example 4-8 | 4.70 | 6.40 | (0.142, 0.097) | 179 |
| Example 4-9 | 4.80 | 6.35 | (0.142, 0.099) | 165 |
| Example 4-10 | 4.65 | 6.36 | (0.142, 0.097) | 187 |
| Example 4-11 | 4.71 | 6.30 | (0.142, 0.099) | 193 |
| Comparative Example 4-1 | 5.28 | 5.51 | (0.142, 0.099) | 122 |
| Comparative Example 4-2 | 5.15 | 5.62 | (0.142, 0.099) | 147 |
| Comparative Example 4-3 | 5.51 | 5.30 | (0.142, 0.098) | 101 |
| Comparative Example 4-4 | 5.42 | 5.21 | (0.142, 0.100) | 128 |
| Comparative Example 4-5 | 5.81 | 4.22 | (0.142, 0.101) | 152 |
| Comparative Example 4-6 | 4.88 | 6.49 | (0.142, 0.097) | 90 |

From the result of the table, it can be confirmed that the compound represented by any one of Formulae 1 to according to an exemplary embodiment of the present specification may be used for a layer which simultaneously injects and transports electrons between an electron controlling layer and a negative electrode of an organic light emitting device. It can be confirmed that an organic light emitting device according to an exemplary embodiment of the present specification has higher efficiency, a lower driving voltage, and a longer service life than the case where a symmetrical triazine compound is used for the electron controlling layer. In particular, the compound of any one of Formulae 1 to 28 according to an exemplary embodiment of the present specification was excellent in thermal stability, and had a deep HOMO level of 6 eV or more, and high triplet energy ($E_T$) and hole stability, thereby exhibiting excellent characteristics.

That is, one of the important characteristics of the organic material used for the organic light emitting device is that an amorphous deposition film needs to be formed, and an organic material having high crystallinity has a disadvantage in that a film is non-uniformly deposited during the deposition, and thus, the driving voltage is largely increased when a device is driven, and the service life of the device is decreased, and thus the device quickly deteriorates. In order to alleviate the disadvantage, an amorphous film needs to be formed, and the present inventors have found that an asymmetric material in a triazine derivative structure does not exhibit crystallinity, and has confirmed that according to an exemplary embodiment of the present specification, the compound of any one of Formulae 1 to 28 has an asymmetrical structure in which Ar1 to Ar3 are different from each other, and an organic light emitting device including the same is stably driven.

Furthermore, according to an exemplary embodiment of the present specification, when the compound represented by any one of Formulae 1 to 28 is used for the electron transporting layer, the compound may be used in mixture with an n-type dopant. Accordingly, the compound of any one of Formulae 1 to 28 has improved electron injection characteristics and thus has a low driving voltage and high efficiency, and may improve stability of the device.

In particular, according to an exemplary embodiment of the present specification, the case where the compound represented by Formula 6 is used for the electron transporting layer has higher efficiency, a lower driving voltage, and a longer service life than the case where the compounds represented by Formulae 3 to 5 are used for the electron transporting layer.

EXPLANATION OF REFERENCE NUMERALS AND SYMBOLS

1: Substrate
2: Anode
3: Light emitting layer
4: Cathode
5: Hole injection layer
6: Hole transporting layer
7: Light emitting layer
8: Electron transporting layer

The invention claimed is:
1. A compound of any one of Formulae 3 to 6:

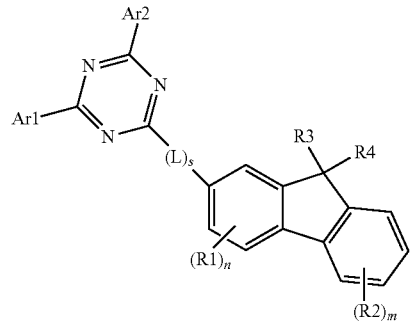

Formula 3

Formula 4

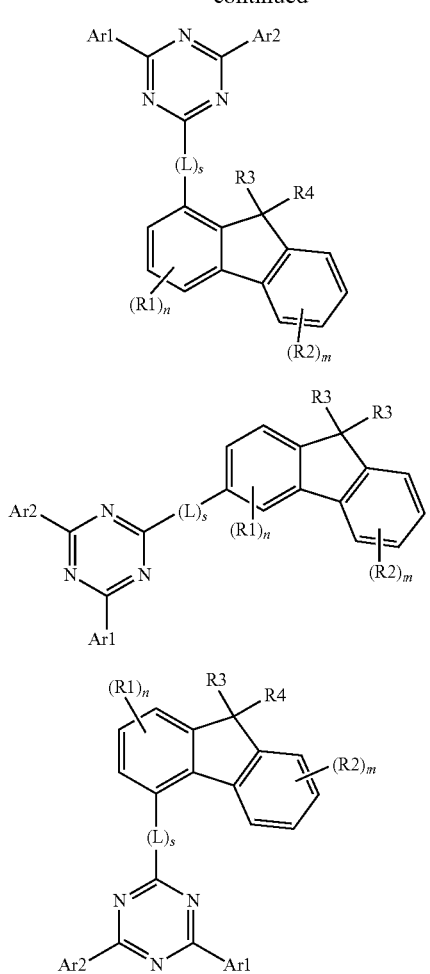

Formula 5

Formula 6 wherein in Formula 3 to 6:
Ar1 and Ar2 are different from each other, and each independently is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
R1 is hydrogen or deuterium, or two or more adjacent R1s combine with each other to form a benzene ring;
R2 is hydrogen, deuterium, a C1 to C6 alkyl group, a phenyl group, a naphthyl group, or a biphenyl group, or two or more adjacent R2s combine with each other to form a benzene ring;
R3 and R4 are the same as or different from each other, and each independently is hydrogen, deuterium, a C1 to C6 alkyl group, a phenyl group, a naphthyl group, or a biphenyl group, which is unsubstituted or substituted with deuterium or an C1-C6 alkyl group;
L is a direct bond, a phenylene, a biphenylene, a naphthylene, or a phenanthrylene, which is unsubstituted or substituted with deuterium;
n is an integer of 0 to 3;
m is an integer of 0 to 4;
s is an integer of 1 to 5; and
when n is 2 or more, the R1's are the same as or different from each other, and
when m is 2 or more, the R2's are the same as or different from each other, and
when s is 2 or more, the L's are the same as or different from each other.

2. A compound of Formula 7 or 8:

[Formula 7]

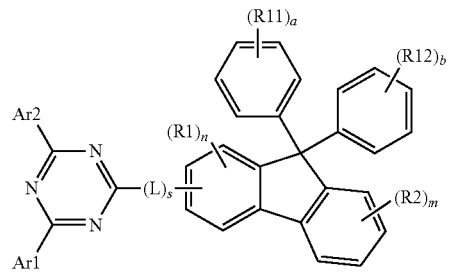

[Formula 8]

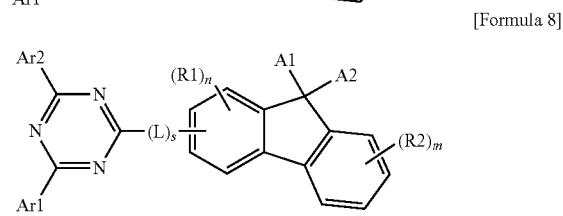

wherein in Formulae 7 and 8:
Ar1 and Ar2 are different from each other, and each independently is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
R1 is hydrogen or deuterium, or two or more adjacent R1s combine with each other to form a benzene ring;
R2 is hydrogen, deuterium, a C1 to C6 alkyl group, a phenyl group, a naphthyl group, or a biphenyl group, or two or more adjacent R2s combine with each other to form a benzene ring;
L is a direct bond, a phenylene, a biphenylene, a naphthylene, or a phenanthrylene, which is unsubstituted or substituted with deuterium;
R11 and R12 are the same as or different from each other, and each independently is hydrogen, deuterium, or a C1-C6 alkyl group, or two or more adjacent groups combine with each other to form a benzene ring,
A1 and A2 are the same as or different from each other, and each independently is hydrogen, deuterium, or a C1-C6 alkyl group,
a and b are the same as or different from each other, and each independently is 0 or 1; and
n is an integer of 0 to 3;
m is an integer of 0 to 4; and
s is an integer of 1 to 5;
when n is 2 or more, the R1's are the same as or different from each other, and
when m is 2 or more, the R2's are the same as or different from each other, and
when s is 2 or more, the L's are the same as or different from each other, and
when a is 2 or more, the R11's are the same as or different from each other, and when b is 2 or more, the R12's are the same as or different from each other.

3. The compound of claim 1, wherein L is a direct bond, or any one structure selected from the following structures:

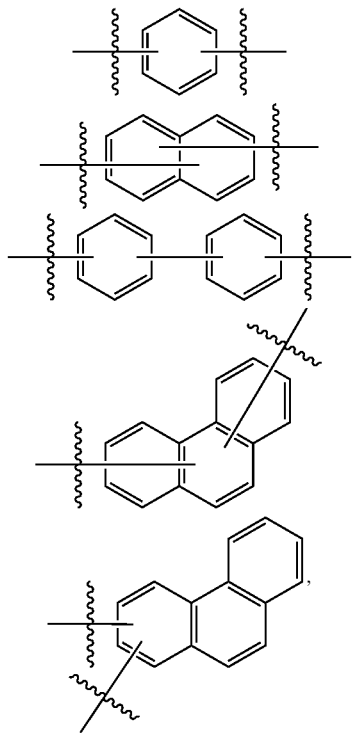

wherein the structures are unsubstituted or substituted with deuterium.

4. A compound of Formula 24:

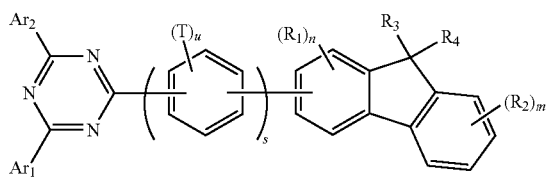

[Formula 24]

wherein in Formula 24:
Ar1 and Ar2 are different from each other, and each independently is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
R1 is hydrogen or deuterium, or two or more adjacent R1s combine with each other to form a benzene ring;
R2 is hydrogen, deuterium, a C1 to C6 alkyl group, a phenyl group, a naphthyl group, or a biphenyl group, or two or more adjacent R2s combine with each other to form a benzene ring;
R3 and R4 are the same as or different from each other, and each independently is hydrogen, deuterium, a C1 to C6 alkyl group, a phenyl group, a naphthyl group, or a biphenyl group, which is unsubstituted or substituted with deuterium or an C1-C6 alkyl group;
T is hydrogen, or deuterium;
s is an integer of 1 to 5;
u is an integer of 0 to 4; and
when u is 2 or more, T's are the same as or different from each other.

5. A compound of Formula 26:

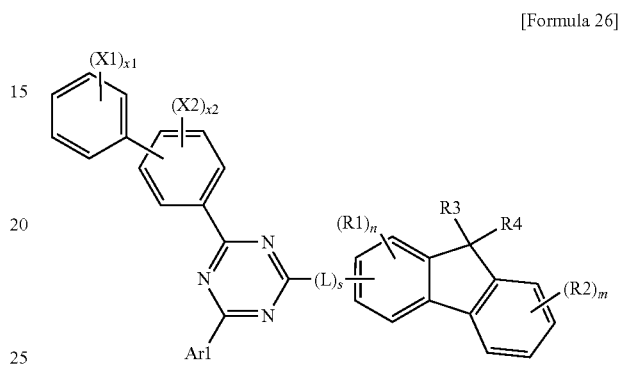

[Formula 26]

wherein in Formula 26:
Ar1 is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
R1 is hydrogen or deuterium, or two or more adjacent R1s combine with each other to form a benzene ring;
R2 is hydrogen, deuterium, a C1 to C6 alkyl group, a phenyl group, a naphthyl group, or a biphenyl group, or two or more adjacent R2s combine with each other to form a benzene ring;
R3 and R4 are the same as or different from each other, and each independently is hydrogen, deuterium, a C1 to C6 alkyl group, a phenyl group, a naphthyl group, or a biphenyl group, which is unsubstituted or substituted with deuterium or an C1-C6 alkyl group;
X1 and X2 are the same as or different from each other, and each independently is hydrogen, deuterium, a phenyl group, a naphthyl group, a terphenyl group, or a phenanthryl group;

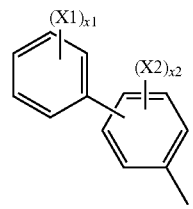

and Ar1 are different from each other;
x1 is an integer of 0 to 5;
x2 is an integer of 0 to 4;
n is an integer of 1 to 3;
m is an integer of 1 to 4;
s is an integer of 1 to 5; and when n is 2 or more, the R1's are the same as or different from each other; and when m is 2 or more, the R2's are the same as or different from each other; and when s is 2 or more, the L's are the same as or different from each other; and when x1 is 2 or more, the X's are the same as or different from each other; and when x2 is 2 or more, the X2's are the same as or different from each other.

6. The compound of claim 1, wherein Ar1 is a phenyl group, a biphenyl group, a naphthyl group, or a phenanthryl group, which is unsubstituted or substituted with a phenyl group, a naphthyl group, a terphenyl group or a phenanthryl group; and Ar2 is a phenyl group, a biphenyl group, a terphenyl group, quaterphenyl group, a naphthyl group, or a phenanthryl group, which is unsubstituted or substituted with a phenyl group, a naphthyl group, a terphenyl group or a phenanthryl group.

7. The compound of claim 1, wherein the compound of any one of Formulae 3 to 6 is a compound of Formula 1:

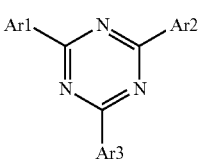

[Formula 1]

that is any one selected from the following compounds:

-continued
| Compound | ----Ar1 | ----Ar2 | ----Ar3 |
|---|---|---|---|
| 1-7 | 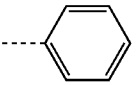 | 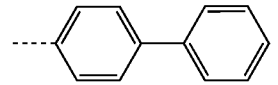 | 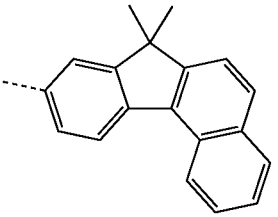 |
| 1-8 | 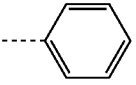 | 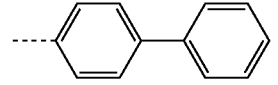 | 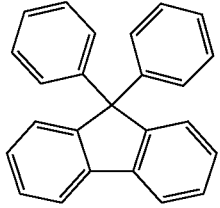 |
| 1-9 | 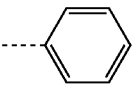 | 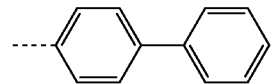 | 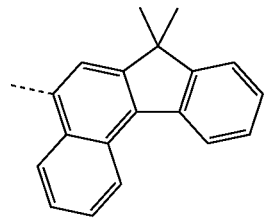 |
| 1-10 | 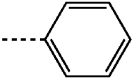 | 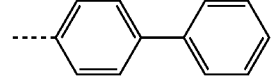 | 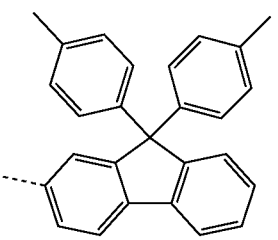 |
| 1-11 | 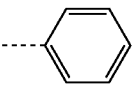 | 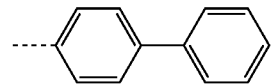 | 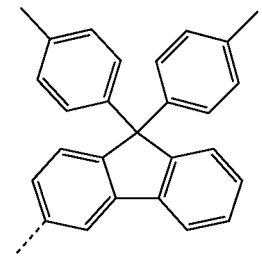 |
| 1-12 | 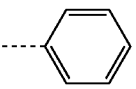 | 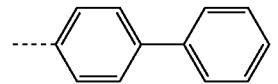 | 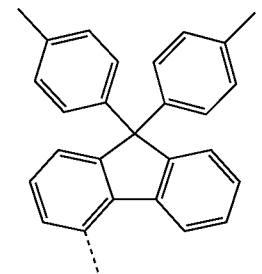 |

-continued

| Compound | ----Ar1 | ----Ar2 | ----Ar3 |
|---|---|---|---|
| 1-13 | phenyl | biphenyl | 9,9-dimethylfluorene (1-position) |
| 1-14 | phenyl | biphenyl | 9,9-dimethylfluorene (2-position) |
| 1-15 | phenyl | biphenyl | 2-phenyl-9,9-dimethylfluorene |
| 1-16 | phenyl | biphenyl | 2-phenyl-9,9-dimethylfluorene |
| 1-17 | phenyl | biphenyl | 9,9-diphenylfluorene (1-position) |
| 1-18 | phenyl | biphenyl | 9,9-diphenylfluorene (2-position) |
| 1-19 | phenyl | biphenyl | 9,9-diphenylfluorene |

-continued

| Compound | ---Ar1 | ---Ar2 | ---Ar3 |
|---|---|---|---|
| 1-20 | phenyl | biphenyl-3-yl | 9,9-diphenylfluoren-4-yl |
| 1-21 | phenyl | biphenyl-3-yl | 9,9-di(p-tolyl)fluoren-1-yl |
| 1-22 | phenyl | biphenyl-3-yl | 9,9-di(p-tolyl)fluoren-2-yl |
| 1-23 | phenyl | biphenyl-3-yl | 9,9-dimethyl-9H-benzo[b]fluoren-2-yl |
| 1-24 | phenyl | biphenyl-3-yl | 9,9-di(p-tolyl)fluoren-4-yl |
| 1-25 | phenyl | biphenyl-2-yl | 9,9-dimethylfluoren-1-yl |
| 1-26 | phenyl | biphenyl-2-yl | 9,9-dimethyl-7-phenylfluoren-2-yl |

-continued
| Compound | - - - Ar1 | - - - Ar2 | - - - Ar3 |
|---|---|---|---|
| 1-27 | 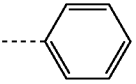 | 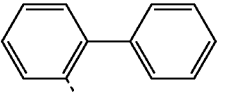 | 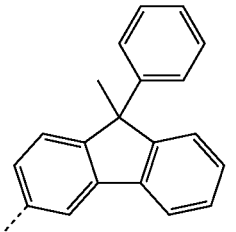 |
| 1-28 | 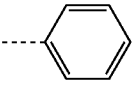 | 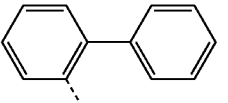 | 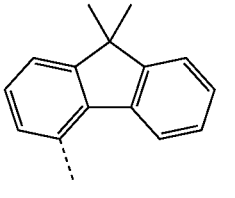 |
| 1-29 | 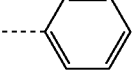 | 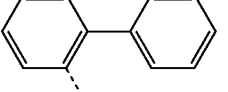 | 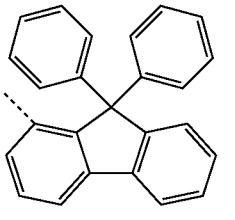 |
| 1-30 | 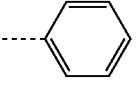 | 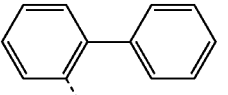 | 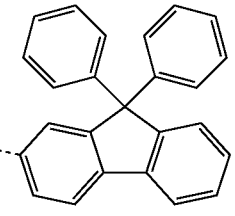 |
| 1-32 | 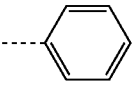 | 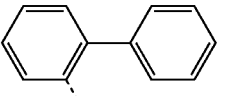 | 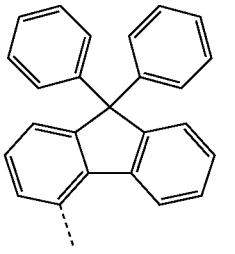 |
| 1-33 | 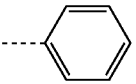 | 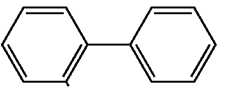 | 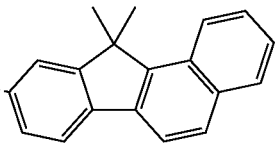 |
| 1-34 | 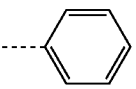 | 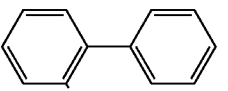 | 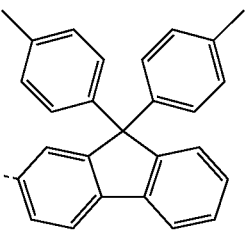 |

| Compound | ---Ar1 | ---Ar2 | ---Ar3 |
|---|---|---|---|
| 1-35 | 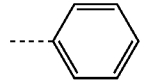 | 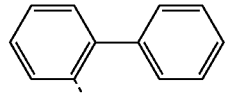 | 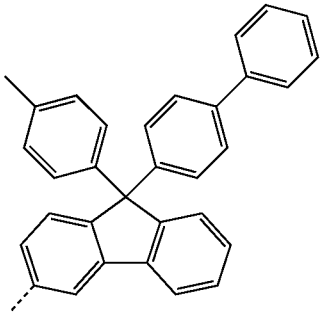 |
| 1-36 | 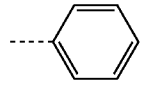 | 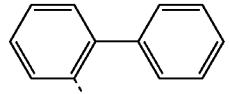 | 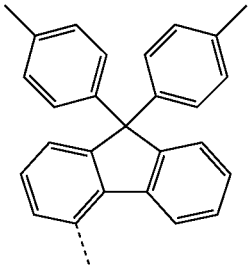 |
| 1-37 | 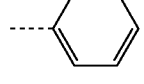 | 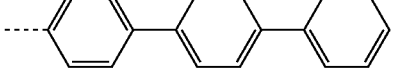 | 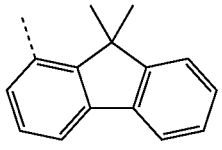 |
| 1-38 | 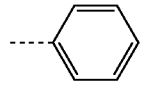 | 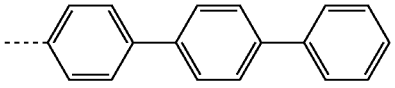 | 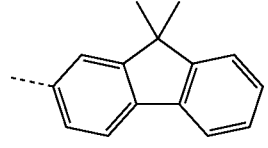 |
| 1-39 | 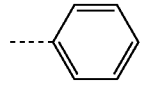 | 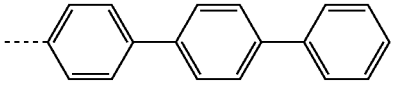 | 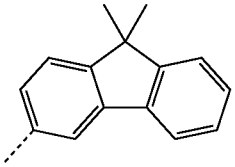 |
| 1-40 | 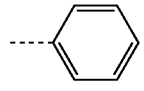 | 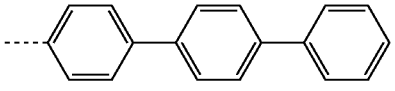 | 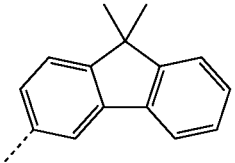 |
| 1-41 | 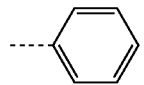 | 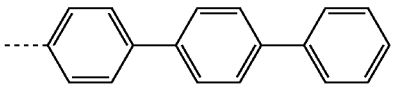 | 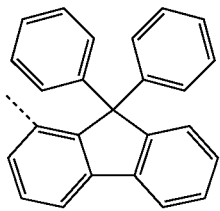 |

-continued
| Compound | ---Ar1 | ---Ar2 | ---Ar3 |
|---|---|---|---|
| 1-42 | 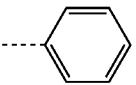 | 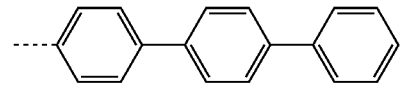 | 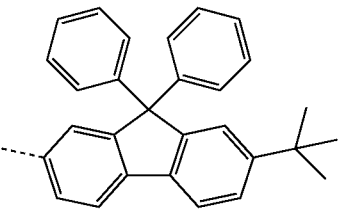 |
| 1-43 | 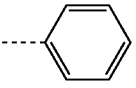 | 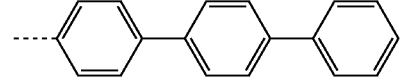 | 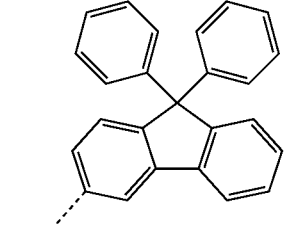 |
| 1-44 | 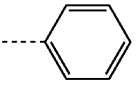 | 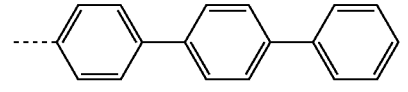 | 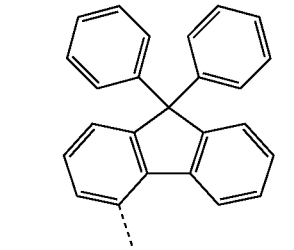 |
| 1-45 | 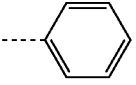 | 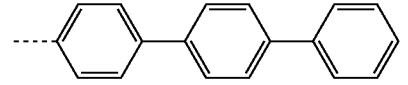 | 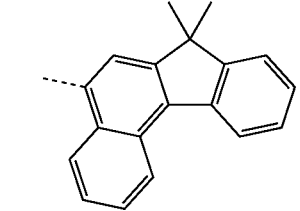 |
| 1-46 | 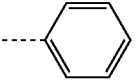 | 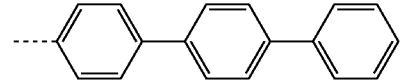 | 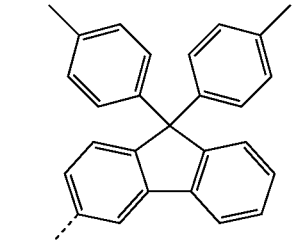 |
| 1-47 | 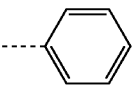 | 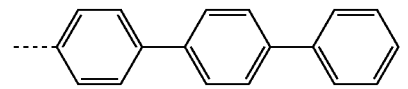 | 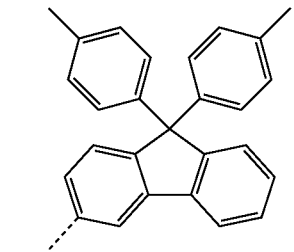 |

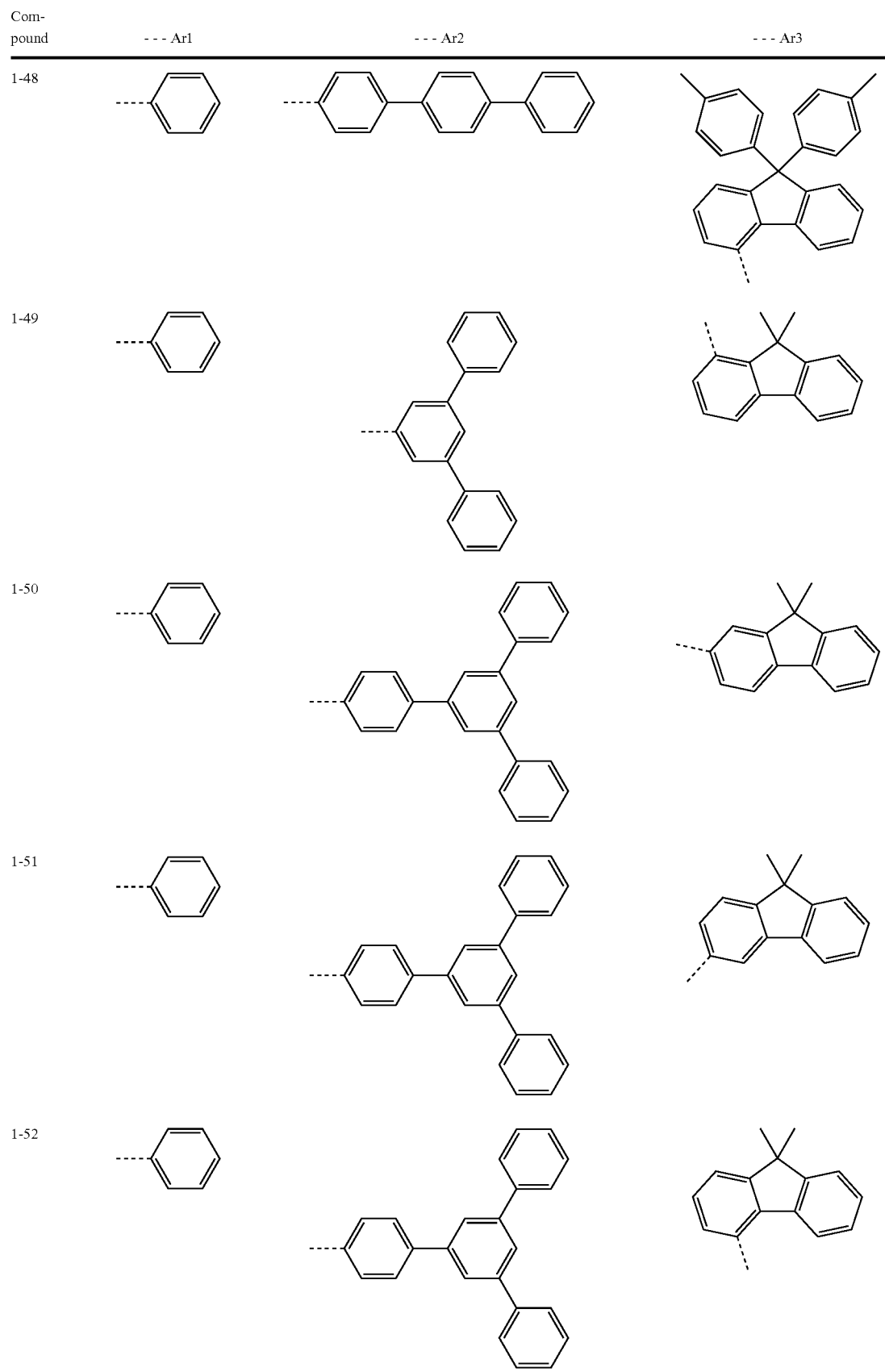

-continued

| Compound | ---Ar1 | ---Ar2 | ---Ar3 |
|---|---|---|---|
| 1-53 | phenyl | 3,5-diphenylphenyl | 9,9-diphenyl-fluoren-1-yl |
| 1-54 | phenyl | 3,5-diphenylphenyl | 9,9-diphenyl-fluoren-2-yl |
| 1-55 | phenyl | 3,5-diphenylphenyl | 9,9-diphenyl-fluoren-3-yl |
| 1-56 | phenyl | 3,5-diphenylphenyl | 9,9-diphenyl-fluoren-4-yl |
| 1-57 | phenyl | 3,5-diphenylphenyl | 9,9-dimethyl-benzo[b]fluorenyl |

-continued

| Compound | - - - Ar1 | - - - Ar2 | - - - Ar3 |
|---|---|---|---|
| 1-58 | | | |
| 1-59 | | | |
| 1-60 | | | |
| 1-61 | | | |
| 1-62 | | | |
| 1-63 | | | |

-continued

| Compound | ---Ar1 | ---Ar2 | ---Ar3 |
|---|---|---|---|
| 1-64 | phenyl | m-terphenyl (branched) | 9,9-dimethylfluoren-4-yl |
| 1-66 | phenyl | m-terphenyl (branched) | 9,9-diphenylfluoren-2-yl |
| 1-67 | phenyl | m-terphenyl (branched) | 9,9-diphenylfluoren-3-yl |
| 1-68 | phenyl | m-terphenyl (branched) | 9,9-diphenylfluoren-4-yl |
| 1-69 | phenyl | m-terphenyl (branched) | 11,11-dimethyl-11H-benzo[a]fluorenyl |
| 1-70 | phenyl | m-terphenyl (branched) | 9,9-di(p-tolyl)fluoren-2-yl |

-continued

| Compound | ---Ar1 | ---Ar2 | ---Ar3 |
|---|---|---|---|
| 1-71 | phenyl | m-terphenyl | 9,9-bis(p-tolyl)fluoren-3-yl |
| 1-72 | phenyl | m-terphenyl | 9,9-bis(p-tolyl)fluoren-4-yl |
| 1-73 | phenyl | naphthalen-2-yl | 9,9-dimethylfluoren-1-yl |
| 1-74 | phenyl | naphthalen-2-yl | 9,9-dimethyl-7-phenylfluoren-2-yl |
| 1-75 | phenyl | naphthalen-2-yl | 9-methyl-9-phenylfluoren-4-yl |
| 1-76 | phenyl | naphthalen-2-yl | 9,9-dimethylfluoren-4-yl |
| 1-77 | phenyl | naphthalen-2-yl | 9,9-diphenylfluoren-1-yl |

US 10,964,892 B2
493                                                                                                494
-continued
| Compound | --- Ar1 | --- Ar2 | --- Ar3 |
|---|---|---|---|
| 1-78 | 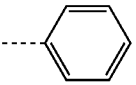 | 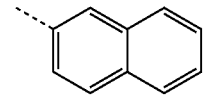 | 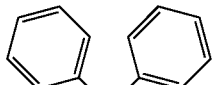 |
| 1-79 | 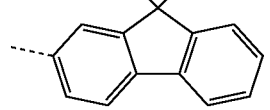 | 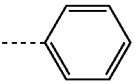 | 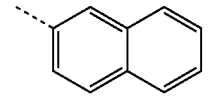 |
| 1-80 | 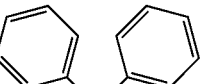 | 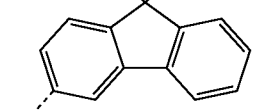 | 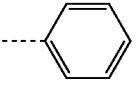 |
| 1-81 | 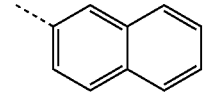 | 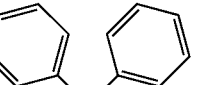 | 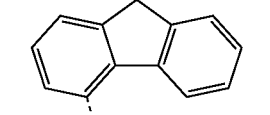 |
| 1-82 | 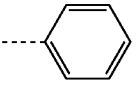 | 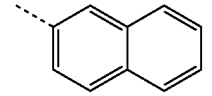 | 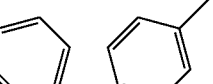 |
| 1-83 | 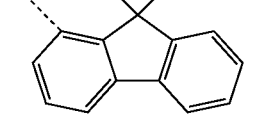 | 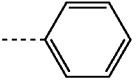 | 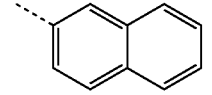 |

-continued
| Compound | ---Ar1 | ---Ar2 | ---Ar3 |
|---|---|---|---|
| 1-84 | 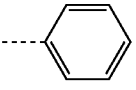 | 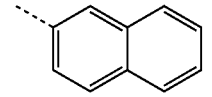 | 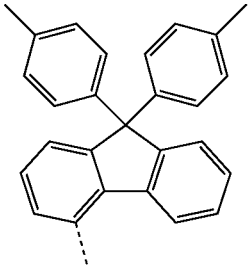 |
| 1-85 | 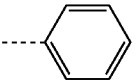 | 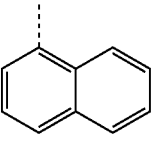 | 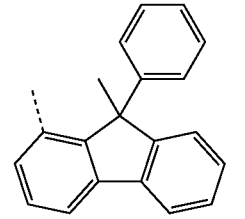 |
| 1-86 | 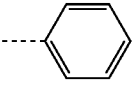 | 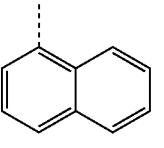 | 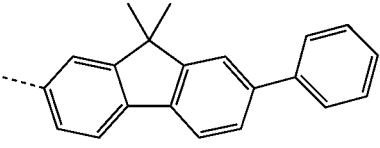 |
| 1-87 | 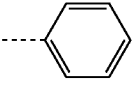 | 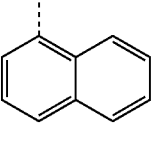 | 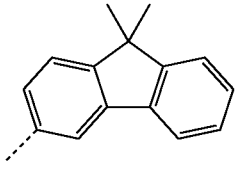 |
| 1-88 | 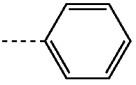 | 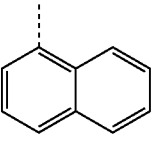 | 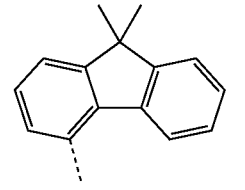 |
| 1-89 | 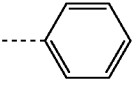 | 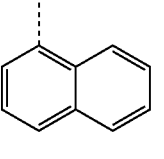 | 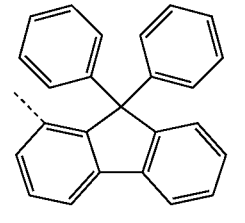 |
| 1-90 | 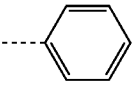 | 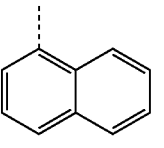 | 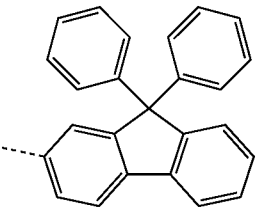 |

-continued

| Compound | ---Ar1 | ---Ar2 | ---Ar3 |
|---|---|---|---|
| 1-91 | phenyl | 1-naphthyl | 9,9-diphenylfluorenyl |
| 1-92 | phenyl | 1-naphthyl | 9,9-diphenylfluorenyl |
| 1-93 | phenyl | 1-naphthyl | 9,9-di(p-tolyl)fluorenyl |
| 1-94 | phenyl | 1-naphthyl | 9,9-di(p-tolyl)fluorenyl |
| 1-95 | phenyl | 1-naphthyl | 9-phenyl-9-(2-naphthyl)fluorenyl |
| 1-96 | phenyl | 1-naphthyl | 9,9-di(p-tolyl)fluorenyl |

-continued
| Compound | ---Ar1 | ---Ar2 | ---Ar3 |
|---|---|---|---|
| 1-97 | 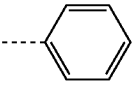 | 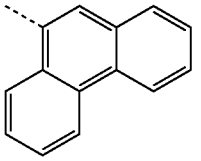 | 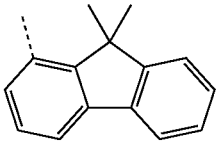 |
| 1-98 | 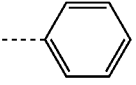 | 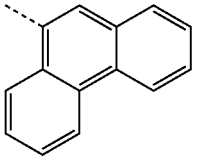 | 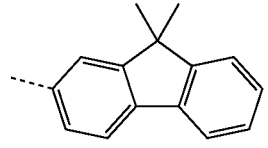 |
| 1-99 | 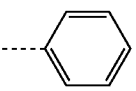 | 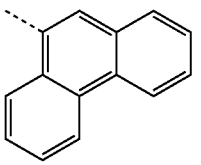 | 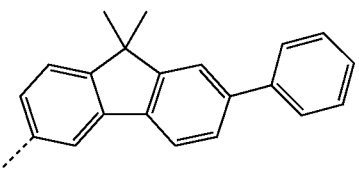 |
| 1-100 | 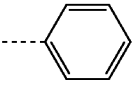 | 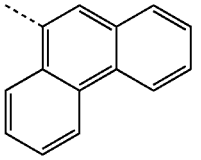 | 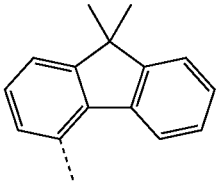 |
| 1-101 | 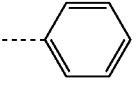 | 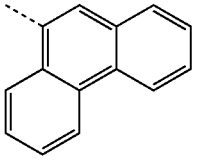 | 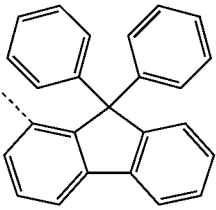 |
| 1-102 | 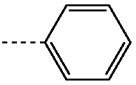 | 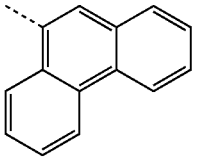 | 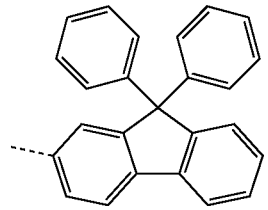 |
| 1-103 | 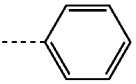 | 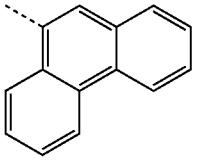 | 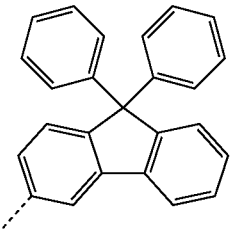 |

-continued
| Compound | ---Ar1 | ---Ar2 | ---Ar3 |
|---|---|---|---|
| 1-104 | 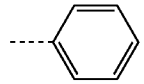 | 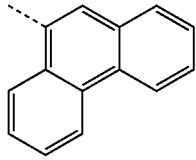 | 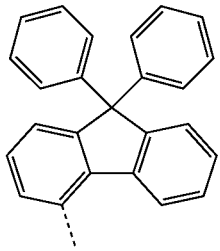 |
| 1-105 | 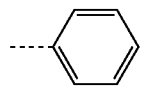 | 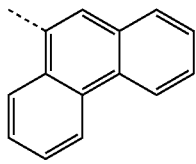 | 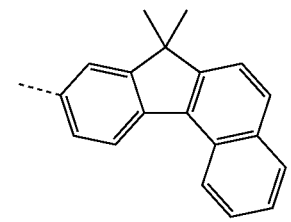 |
| 1-106 | 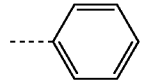 | 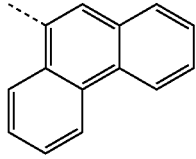 | 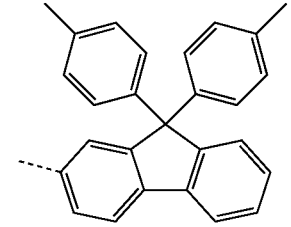 |
| 1-107 | 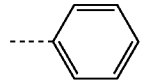 | 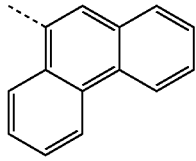 | 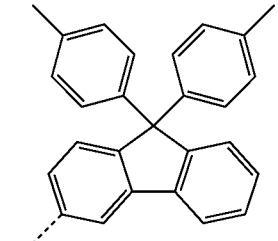 |
| 1-108 | 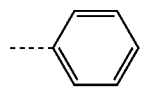 | 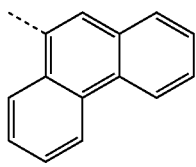 | 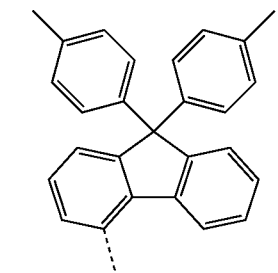 |
| 1-109 | 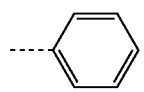 | 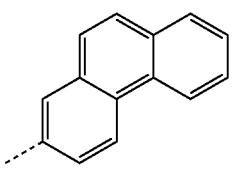 | 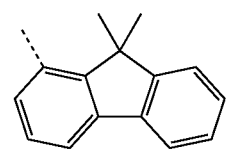 |

-continued
| Compound | - - - Ar1 | - - - Ar2 | - - - Ar3 |
|---|---|---|---|
| 1-110 | 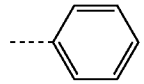 | 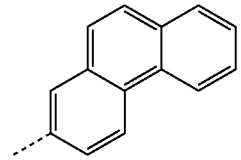 | 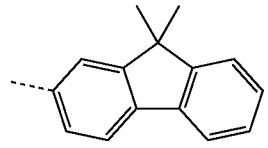 |
| 1-112 | 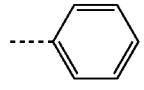 | 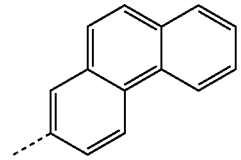 | 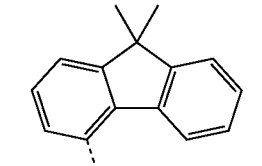 |
| 1-113 | 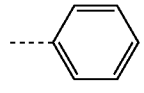 | 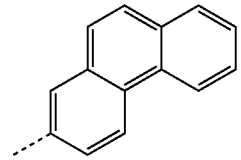 | 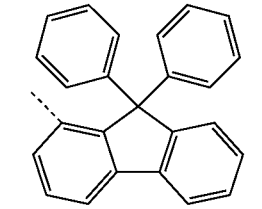 |
| 1-114 | 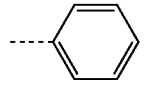 | 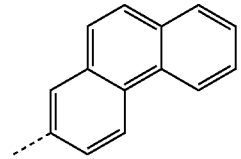 | 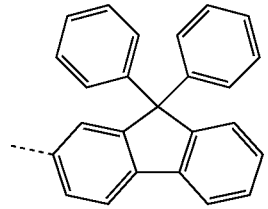 |
| 1-115 | 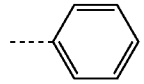 | 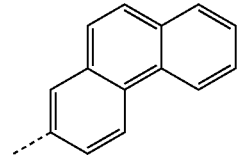 | 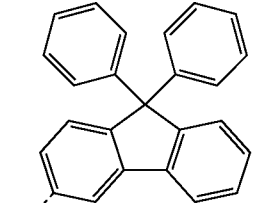 |
| 1-116 | 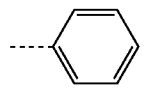 | 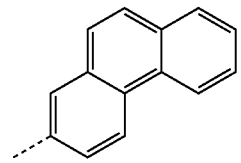 | 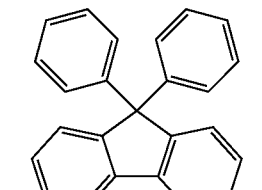 |
| 1-117 | 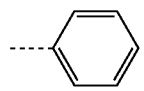 | 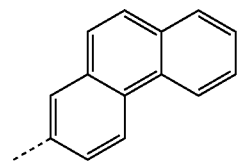 | 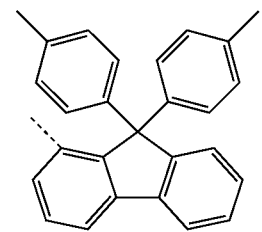 |

-continued
| Compound | - - - Ar1 | - - - Ar2 | - - - Ar3 |
|---|---|---|---|
| 1-118 | 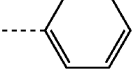 | 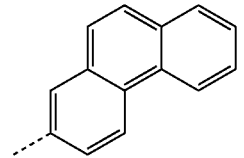 | 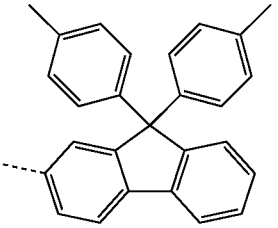 |
| 1-119 | 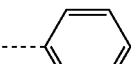 | 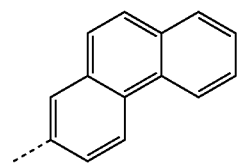 | 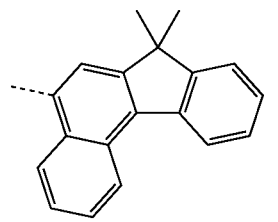 |
| 1-120 | 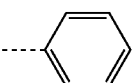 | 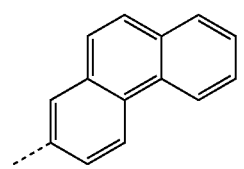 | 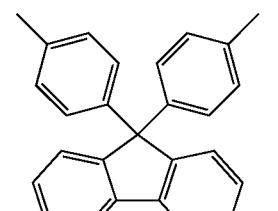 |
| 1-121 | 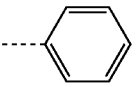 | 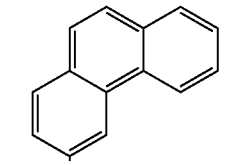 | 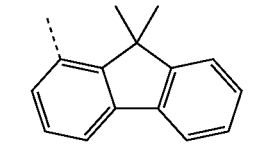 |
| 1-122 | 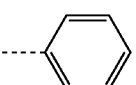 | 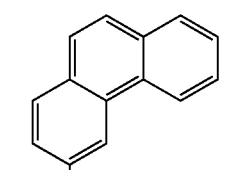 | 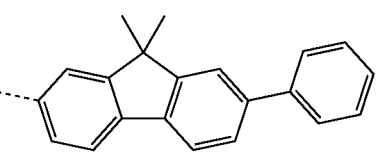 |
| 1-123 | 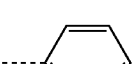 | 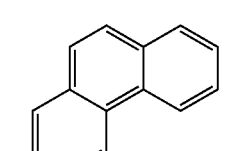 | 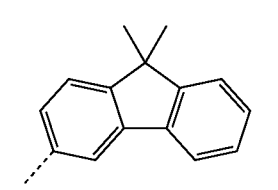 |
| 1-124 | 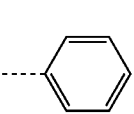 | 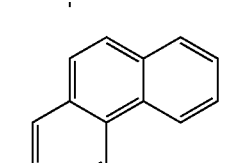 | 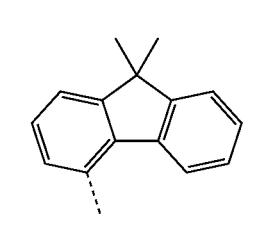 |

-continued
| Compound | - - - Ar1 | - - - Ar2 | - - - Ar3 |
|---|---|---|---|
| 1-125 | 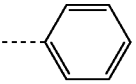 | 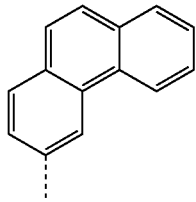 | 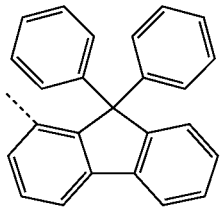 |
| 1-126 | 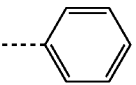 | 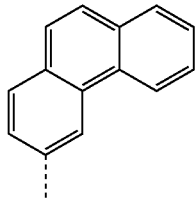 | 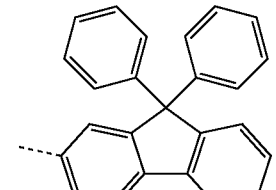 |
| 1-128 | 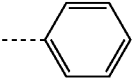 | 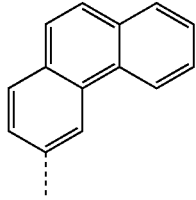 | 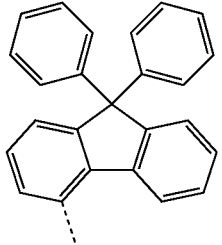 |
| 1-129 | 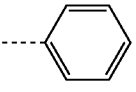 | 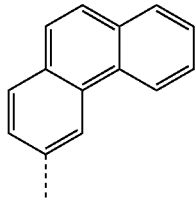 | 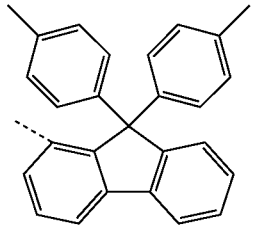 |
| 1-130 | 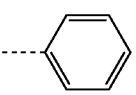 | 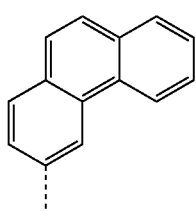 | 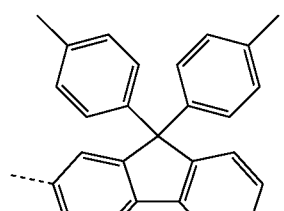 |
| 1-131 | 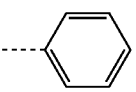 | 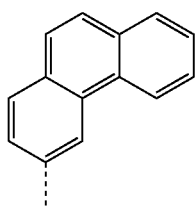 | 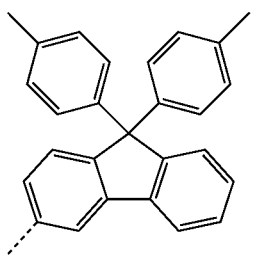 |

-continued

| Compound | ---Ar1 | ---Ar2 | ---Ar3 |
|---|---|---|---|
| 1-132 | phenyl | phenanthrenyl | 9,9-di(p-tolyl)fluorenyl |
| 1-134 | 4-biphenyl | 3-biphenyl | 9,9-dimethylfluoren-2-yl |
| 1-135 | 4-biphenyl | 3-biphenyl | 9,9-dimethylfluoren-3-yl |
| 1-136 | 4-biphenyl | 2-biphenyl | 9,9-dimethylfluoren-4-yl |
| 1-137 | 4-biphenyl | 3-biphenyl | 9,9-diphenylfluoren-1-yl |
| 1-138 | phenyl | 4-(naphthalen-2-yl)phenyl | 9,9-diphenylfluoren-2-yl |
| 1-139 | 4-biphenyl | 3-biphenyl | 9,9-diphenylfluoren-3-yl |

-continued

| Compound | --- Ar1 | --- Ar2 | --- Ar3 |
|---|---|---|---|
| 1-140 | 4-biphenyl | 3-biphenyl | 9,9-diphenylfluoren-4-yl |
| 1-141 | 4-biphenyl | 3-biphenyl | 9,9-di(p-tolyl)fluoren-2-yl |
| 1-142 | 4-biphenyl | 3-biphenyl | 9,9-di(p-tolyl)fluoren-2-yl |
| 1-143 | 4-biphenyl | 3-(naphthalen-1-yl)phenyl | 9,9-diphenylfluoren-2-yl |
| 1-144 | 4-biphenyl | 3-biphenyl | 9,9-di(p-tolyl)fluoren-4-yl |
| 1-145 | 4-biphenyl | 2-biphenyl | 9,9-dimethylfluoren-1-yl |
| 1-146 | 4-biphenyl | 2-biphenyl | 9,9-dimethylfluoren-2-yl |

-continued
| Compound | --- Ar1 | --- Ar2 | --- Ar3 |
|---|---|---|---|
| 1-147 | 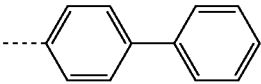 | 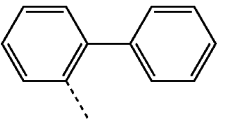 | 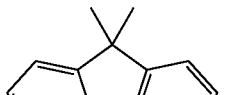 |
| 1-148 | 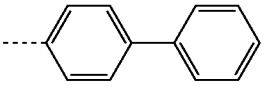 | 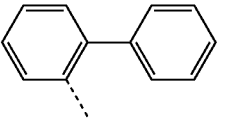 | 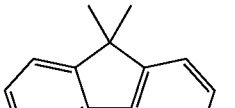 |
| 1-149 | 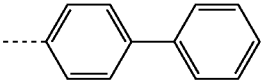 | 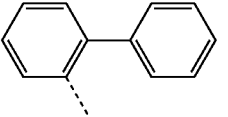 | 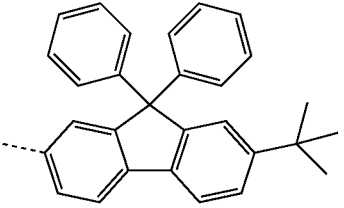 |
| 1-150 | 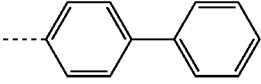 | 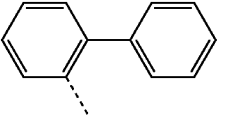 | 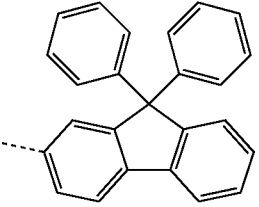 |
| 1-151 | 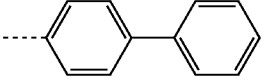 | 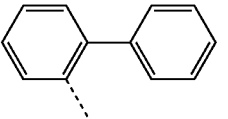 | 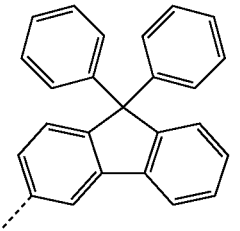 |
| 1-152 | 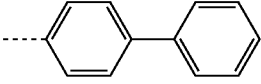 | 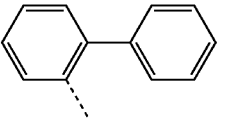 | 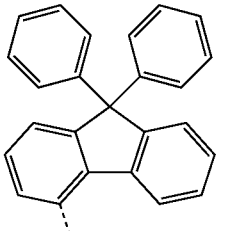 |
| 1-153 | 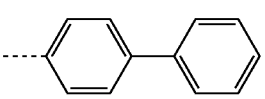 | 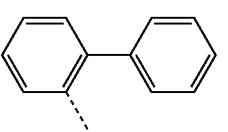 | 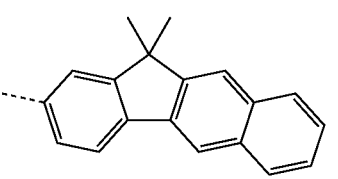 |

-continued

| Compound | ---Ar1 | ---Ar2 | ---Ar3 |
|---|---|---|---|
| 1-154 | | | |
| 1-155 | | | |
| 1-156 | | | |
| 1-157 | | | |
| 1-158 | | | |
| 1-159 | | | |
| 1-160 | | | |

-continued
| Compound | - - - Ar1 | - - - Ar2 | - - - Ar3 |
|---|---|---|---|
| 1-161 | 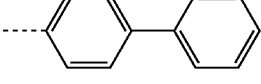 | 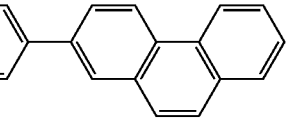 | 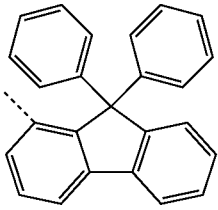 |
| 1-162 | 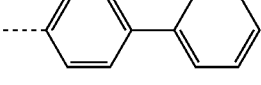 | 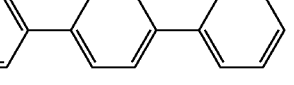 | 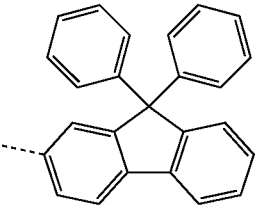 |
| 1-163 | 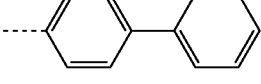 | 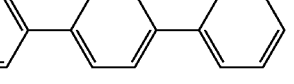 | 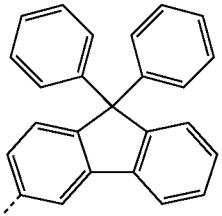 |
| 1-164 | 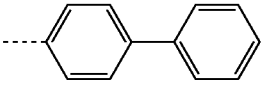 | 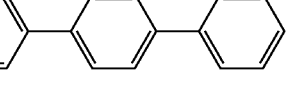 | 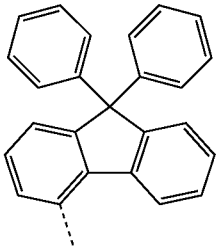 |
| 1-165 | 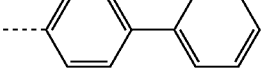 | 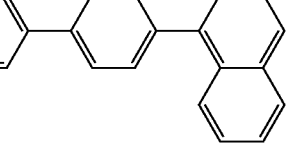 | 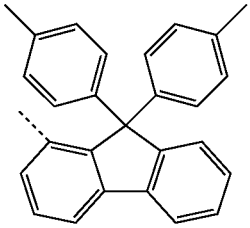 |
| 1-166 | 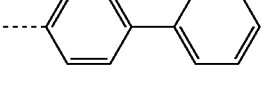 | 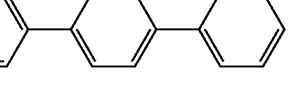 | 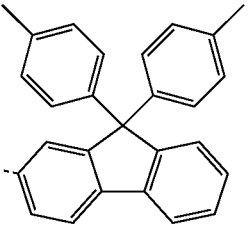 |
| 1-167 | 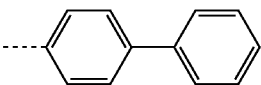 | 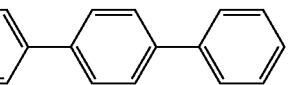 | 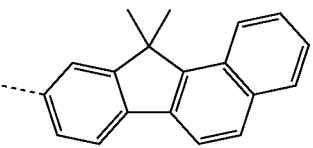 |

-continued

| Compound | ---Ar1 | ---Ar2 | ---Ar3 |
|---|---|---|---|
| 1-168 | | | |
| 1-169 | | | |
| 1-170 | | | |
| 1-172 | | | |
| 1-173 | | | |

-continued

| Compound | --- Ar1 | --- Ar2 | --- Ar3 |
|---|---|---|---|
| 1-174 | biphenyl | 1,3,5-triphenylbenzene | 9,9-diphenylfluoren-2-yl |
| 1-175 | biphenyl | 1,3,5-triphenylbenzene | 9,9-diphenylfluoren-3-yl |
| 1-176 | biphenyl | 1,3,5-triphenylbenzene | 9,9-diphenylfluoren-4-yl |
| 1-178 | biphenyl | 1,3,5-triphenylbenzene | 9,9-bis(4-methylphenyl)fluoren-2-yl |
| 1-179 | biphenyl | 1,3,5-triphenylbenzene | 7,7-dimethyl-7H-benzo[c]fluoren-yl |

-continued

| Compound | ---Ar1 | ---Ar2 | ---Ar3 |
|---|---|---|---|
| 1-180 | | | |
| 1-181 | | | |
| 1-182 | | | |
| 1-183 | | | |
| 1-184 | | | |
| 1-185 | | | |
| 1-186 | | | |

-continued

| Compound | ---Ar1 | ---Ar2 | ---Ar3 |
|---|---|---|---|
| 1-187 | | | |
| 1-188 | | | |
| 1-189 | | | |
| 1-190 | | | |
| 1-191 | | | |

-continued

| Compound | - - - Ar1 | - - - Ar2 | - - - Ar3 |
|---|---|---|---|
| 1-192 | biphenyl | 1,2-diphenylphenyl | 9,9-bis(p-tolyl)fluorenyl |
| 1-193 | biphenyl | 2-naphthyl | 9,9-dimethylfluorenyl |
| 1-194 | biphenyl | 2-naphthyl | 9,9-dimethylfluorenyl |
| 1-195 | biphenyl | 2,2'-binaphthyl | 9,9-dimethylfluorenyl |
| 1-196 | biphenyl | 2-naphthyl | 9,9-dimethylfluorenyl |
| 1-197 | biphenyl | 2-naphthyl | 9,9-diphenylfluorenyl |
| 1-198 | biphenyl | 2-naphthyl | 9,9-diphenylfluorenyl |

-continued

| Compound | ---Ar1 | ---Ar2 | ---Ar3 |
|---|---|---|---|
| 1-199 | 4-biphenyl | 7-phenyl-2-naphthyl | 9,9-diphenyl-fluoren-3-yl |
| 1-200 | 4-biphenyl | 6-phenyl-2-naphthyl | 9,9-diphenyl-fluoren-4-yl |
| 1-201 | 4-biphenyl | 2-naphthyl | 9,9-di(p-tolyl)-fluoren-1-yl |
| 1-202 | 4-biphenyl | 2-naphthyl | 9,9-di(p-tolyl)-fluoren-2-yl |
| 1-203 | 4-biphenyl | 2-naphthyl | 9,9-di(p-tolyl)-fluoren-3-yl |
| 1-204 | 4-biphenyl | 2-naphthyl | 9,9-di(p-tolyl)-fluoren-4-yl |

-continued

| Compound | ---Ar1 | ---Ar2 | ---Ar3 |
|---|---|---|---|
| 1-205 | biphenyl | 1-naphthyl | 9,9-dimethylfluoren-1-yl |
| 1-206 | biphenyl | 1-naphthyl | 9,9-dimethylfluoren-2-yl |
| 1-208 | biphenyl | 1-naphthyl | 9,9-dimethyl-7-phenylfluoren-4-yl |
| 1-209 | biphenyl | 1-naphthyl | 9,9-diphenylfluoren-1-yl |
| 1-210 | biphenyl | 1-naphthyl | 9,9-diphenylfluoren-2-yl |
| 1-211 | biphenyl | 1-naphthyl | 9,9-diphenylfluoren-3-yl |
| 1-212 | biphenyl | 1-naphthyl | 9,9-diphenylfluoren-4-yl |

-continued
| Compound | ---Ar1 | ---Ar2 | ---Ar3 |
|---|---|---|---|
| 1-213 | 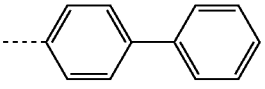 | 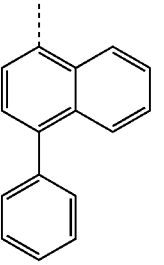 | 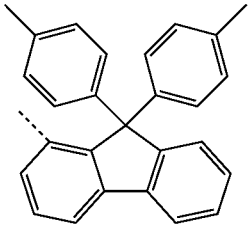 |
| 1-214 | 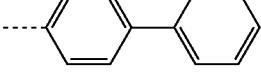 | 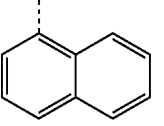 | 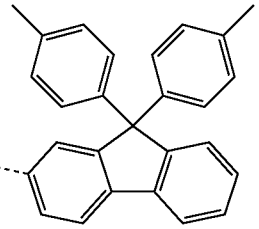 |
| 1-215 | 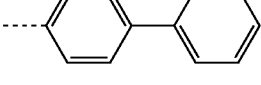 | 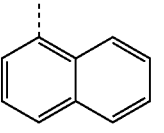 | 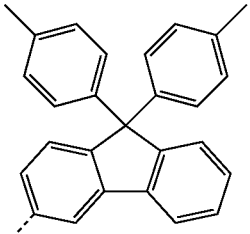 |
| 1-216 | 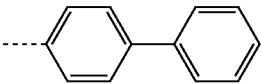 | 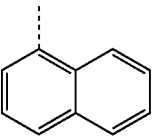 | 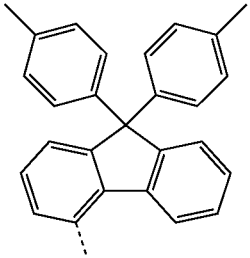 |
| 1-217 | 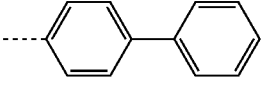 | 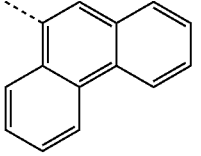 | 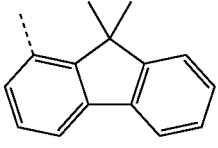 |
| 1-218 | 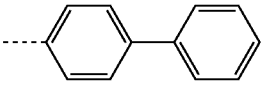 | 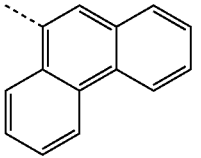 | 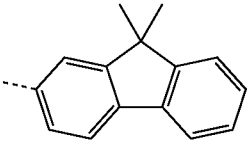 |
| 1-219 | 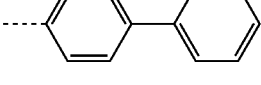 | 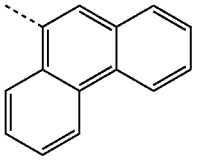 | 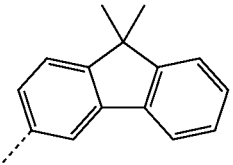 |

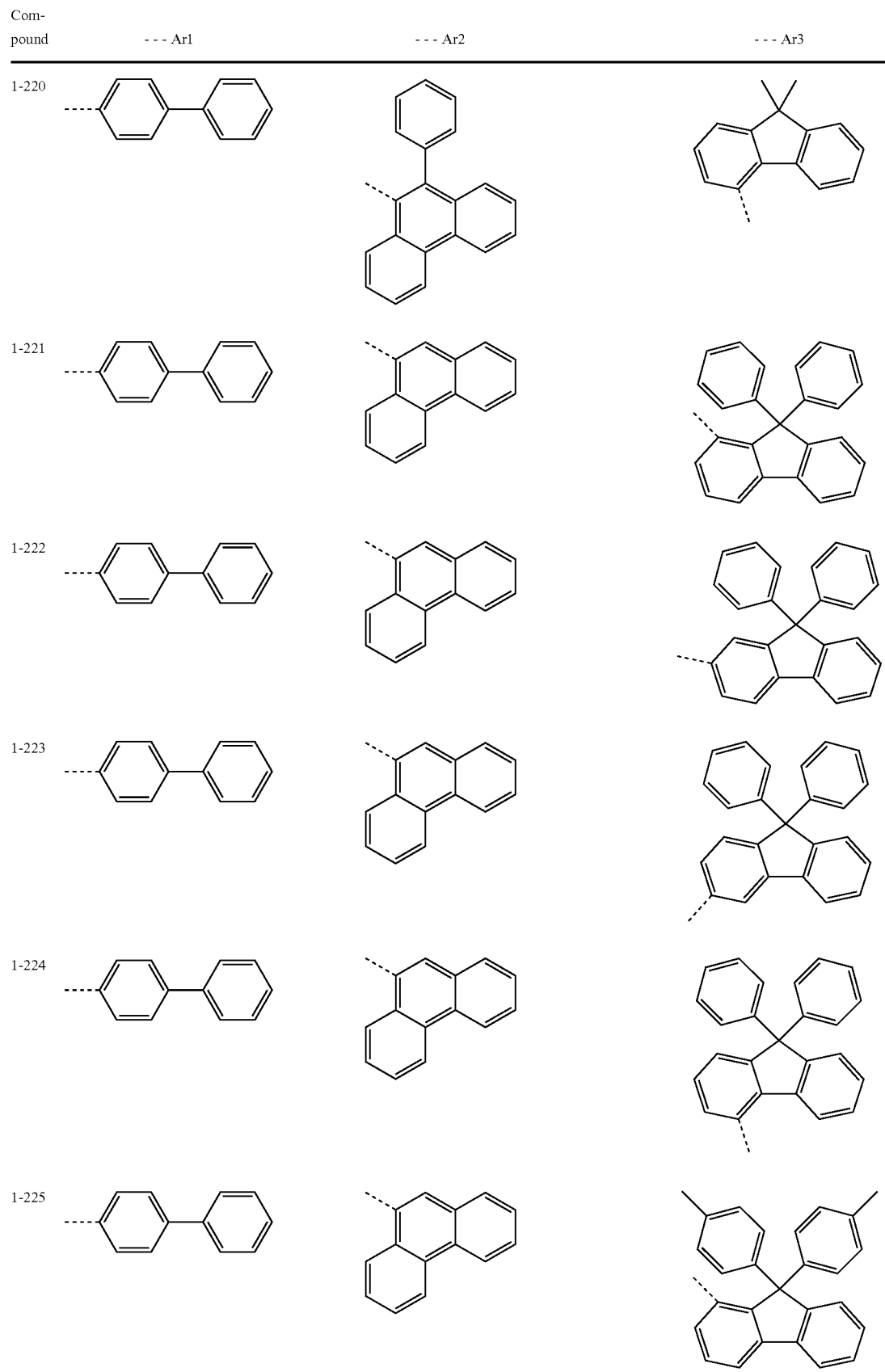

-continued

| Compound | ---Ar1 | ---Ar2 | ---Ar3 |
|---|---|---|---|
| 1-226 | | | |
| 1-227 | | | |
| 1-228 | | | |
| 1-229 | | | |
| 1-230 | | | |
| 1-231 | | | |
| 1-232 | | | |

-continued

| Compound | ---Ar1 | ---Ar2 | ---Ar3 |
|---|---|---|---|
| 1-233 | biphenyl | phenanthrene | 9,9-diphenylfluorene (1-position) |
| 1-234 | biphenyl | phenanthrene | 9,9-diphenylfluorene (2-position) |
| 1-235 | biphenyl | phenanthrene | 9,9-diphenylfluorene (3-position) |
| 1-236 | biphenyl | phenanthrene | 9,9-diphenylfluorene (4-position) |
| 1-237 | biphenyl | phenanthrene | 9,9-dimethylbenzo[c]fluorene |
| 1-238 | biphenyl | phenanthrene | 9,9-di(p-tolyl)fluorene |

-continued

| Compound | ---Ar1 | ---Ar2 | ---Ar3 |
|---|---|---|---|
| 1-239 | | | |
| 1-240 | | | |
| 1-241 | | | |
| 1-242 | | | |
| 1-243 | | | |
| 1-244 | | | |

-continued

| Compound | - - - Ar1 | - - - Ar2 | - - - Ar3 |
|---|---|---|---|
| 1-245 | biphenyl | phenanthrene | 9,9-diphenylfluorene |
| 1-246 | biphenyl | phenanthrene | 9,9-diphenylfluoren-2-yl |
| 1-247 | biphenyl | phenanthrene | 7-tert-butyl-9,9-diphenylfluoren-2-yl |
| 1-248 | biphenyl | phenanthrene | 9,9-diphenylfluoren-4-yl |
| 1-249 | biphenyl | phenanthrene | 9,9-dimethyl-benzofluorenyl |
| 1-250 | biphenyl | phenanthrene | 9,9-di(p-tolyl)fluoren-2-yl |

-continued

| Compound | - - - Ar1 | - - - Ar2 | - - - Ar3 |
|---|---|---|---|
| 1-251 | | | |
| 1-252 | | | |
| 1-253 | | | |
| 1-254 | | | |
| 1-255 | | | |
| 1-256 | | | |
| 1-258 | | | |

-continued
| Compound | ---Ar1 | ---Ar2 | ---Ar3 |
|---|---|---|---|
| 1-259 | 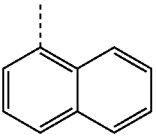 | 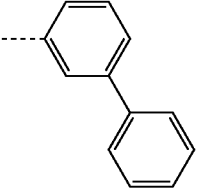 | 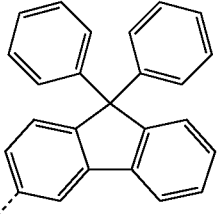 |
| 1-260 | 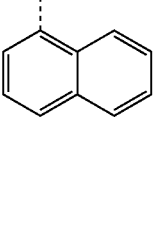 | 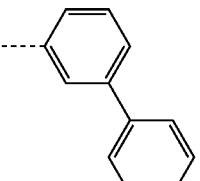 | 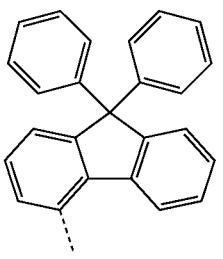 |
| 1-261 | 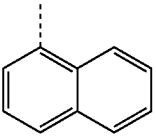 | 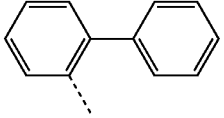 | 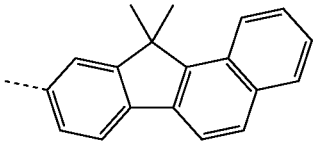 |
| 1-262 | 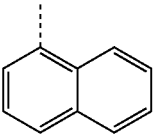 | 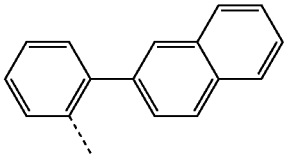 | 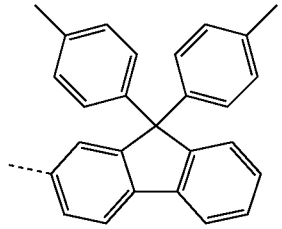 |
| 1-263 | 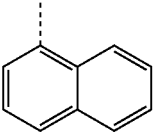 | 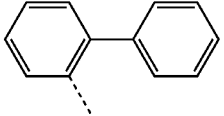 | 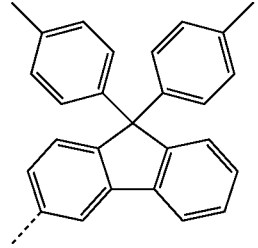 |
| 1-264 | 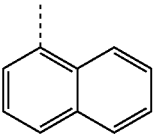 | 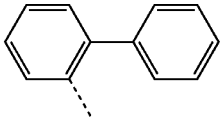 | 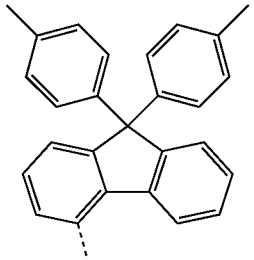 |

-continued
| Compound | ---Ar1 | ---Ar2 | ---Ar3 |
|---|---|---|---|
| 1-265 | 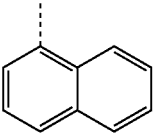 | 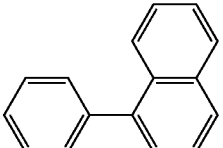 | 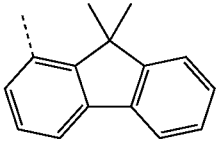 |
| 1-266 | 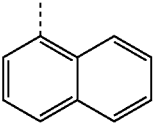 | 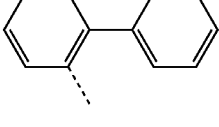 | 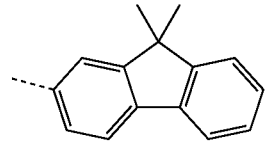 |
| 1-267 | 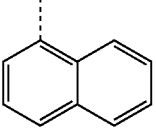 | 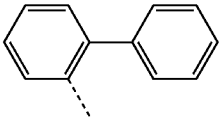 | 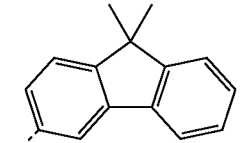 |
| 1-268 | 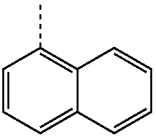 | 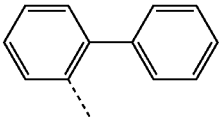 | 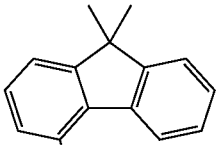 |
| 1-269 | 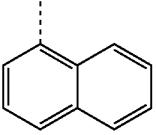 | 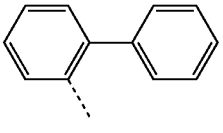 | 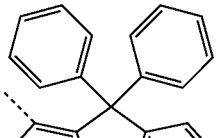 |
| 1-270 | 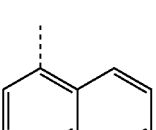 | 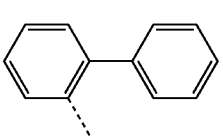 | 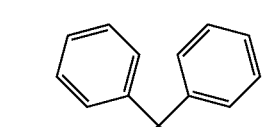 |
| 1-271 | 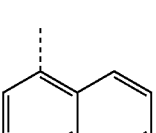 | 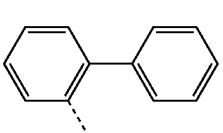 | 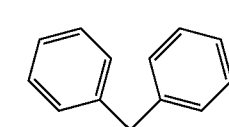 |

-continued

| Compound | ---Ar1 | ---Ar2 | ---Ar3 |
|---|---|---|---|
| 1-272 | | | |
| 1-273 | | | |
| 1-274 | | | |
| 1-275 | | | |
| 1-276 | | | |
| 1-278 | | | |

-continued
| Compound | ---Ar1 | ---Ar2 | ---Ar3 |
|---|---|---|---|
| 1-279 | 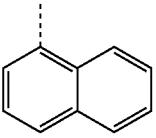 | 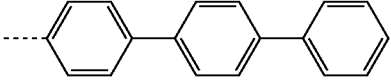 | 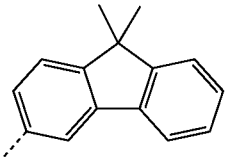 |
| 1-280 | 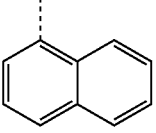 | 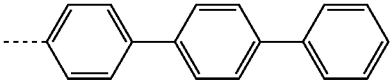 | 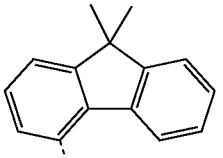 |
| 1-281 | 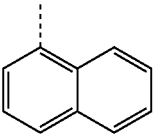 | 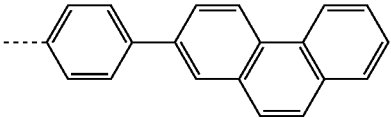 | 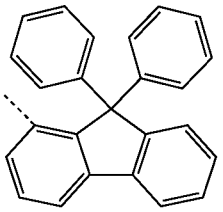 |
| 1-282 | 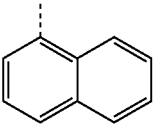 | 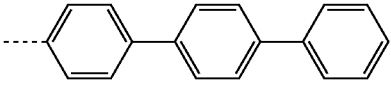 | 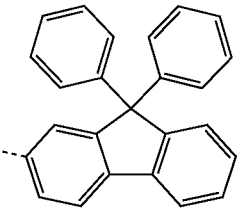 |
| 1-283 | 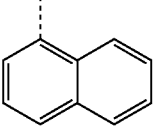 | 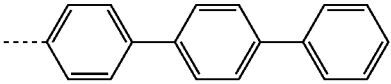 | 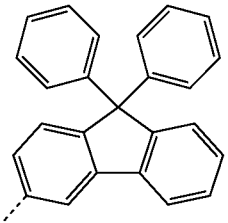 |
| 1-284 | 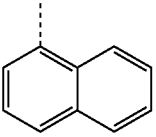 | 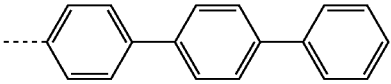 | 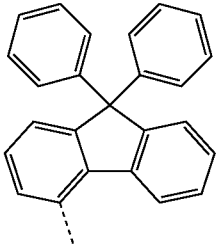 |
| 1-285 | 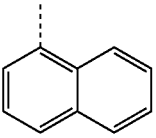 | 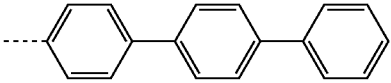 | 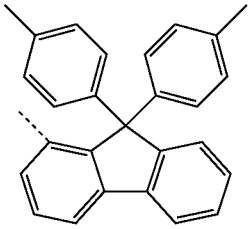 |

-continued
| Compound | ---Ar1 | ---Ar2 | ---Ar3 |
|---|---|---|---|
| 1-286 | 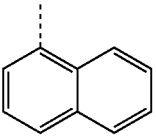 | 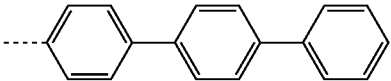 | 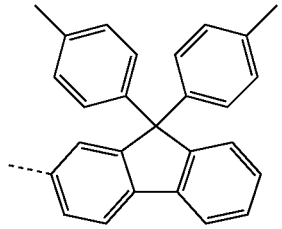 |
| 1-287 | 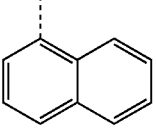 | 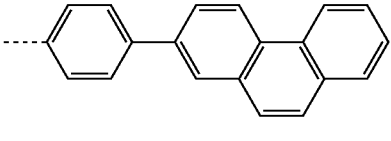 | 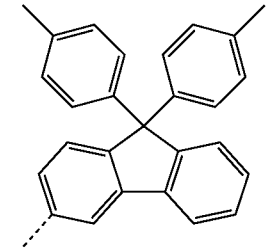 |
| 1-288 | 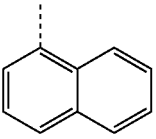 | 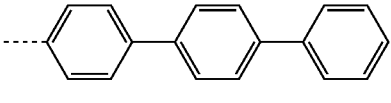 | 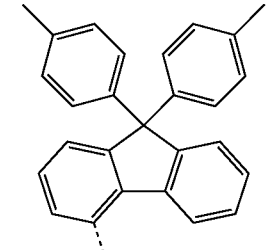 |
| 1-289 | 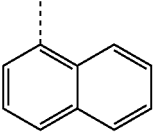 | 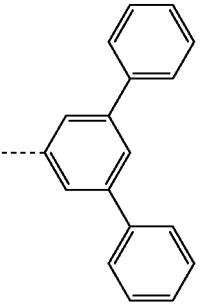 | 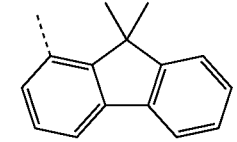 |
| 1-290 | 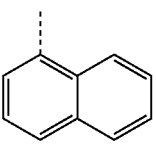 | 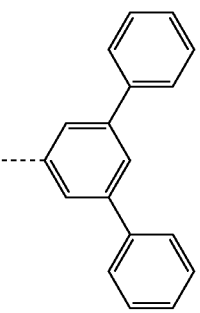 | 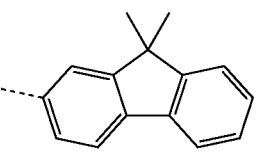 |

-continued
| Compound | - - - Ar1 | - - - Ar2 | - - - Ar3 |
|---|---|---|---|
| 1-292 | 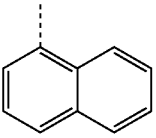 | 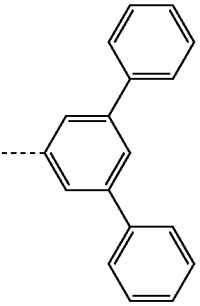 | 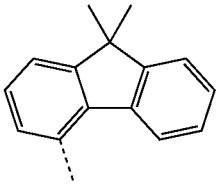 |
| 1-293 | 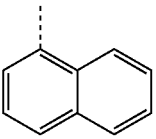 | 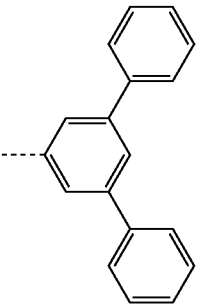 | 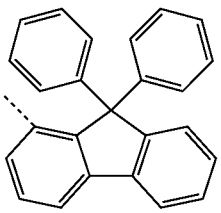 |
| 1-294 | 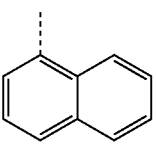 | 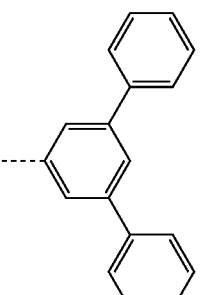 | 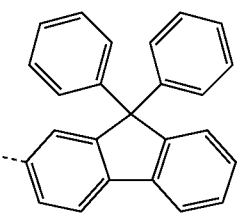 |
| 1-295 | 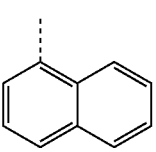 | 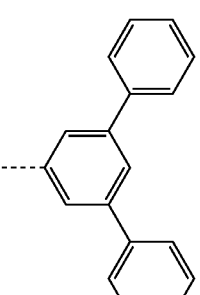 | 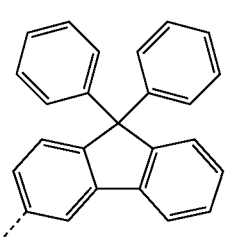 |
| 1-296 | 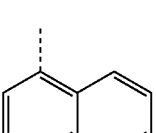 | 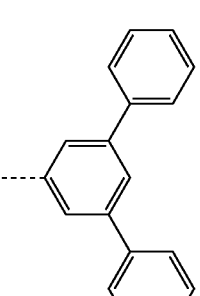 | 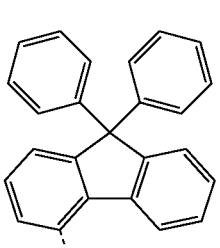 |

-continued
| Compound | ---Ar1 | ---Ar2 | ---Ar3 |
|---|---|---|---|
| 1-297 | 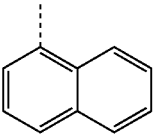 | 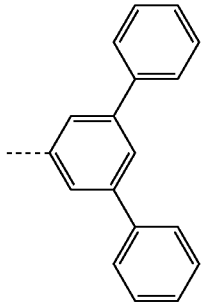 | 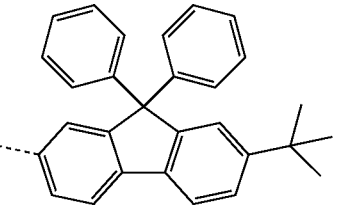 |
| 1-298 | 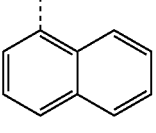 | 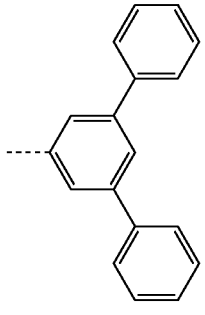 | 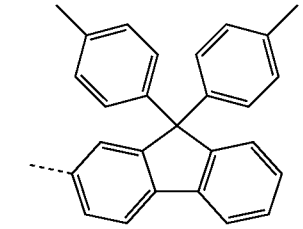 |
| 1-299 | 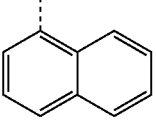 | 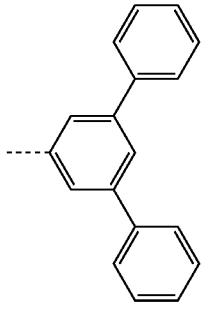 | 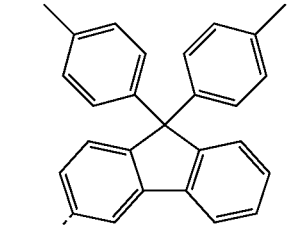 |
| 1-300 | 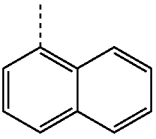 | 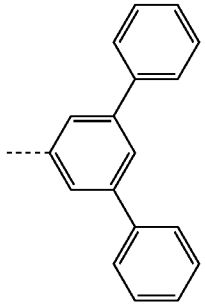 | 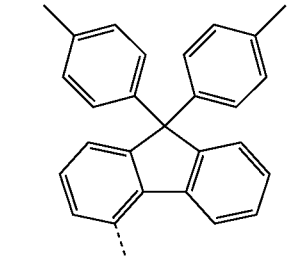 |
| 1-301 | 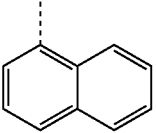 | 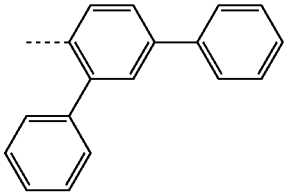 | 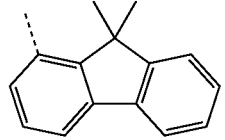 |

-continued
| Compound | ---Ar1 | ---Ar2 | ---Ar3 |
|---|---|---|---|
| 1-302 | 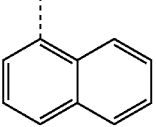 | 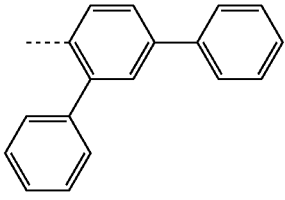 | 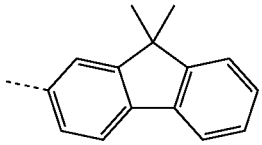 |
| 1-303 | 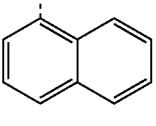 | 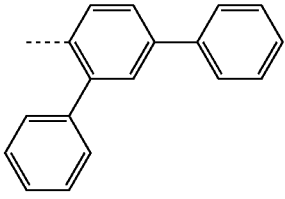 | 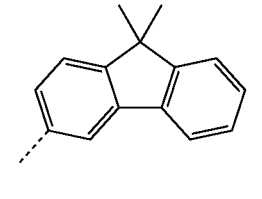 |
| 1-304 | 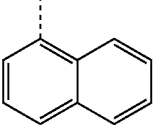 | 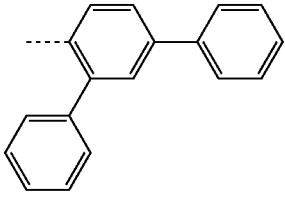 | 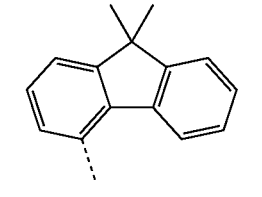 |
| 1-305 | 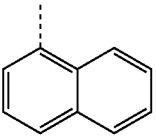 | 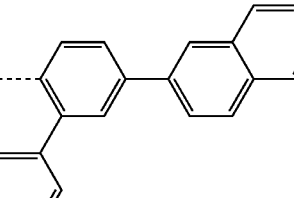 | 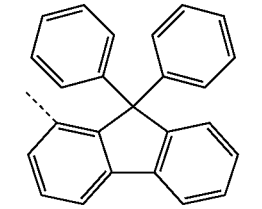 |
| 1-306 | 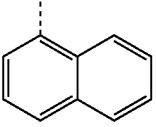 | 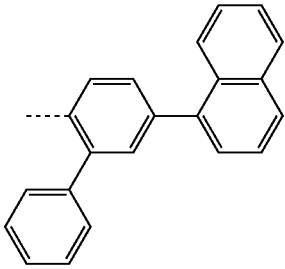 | 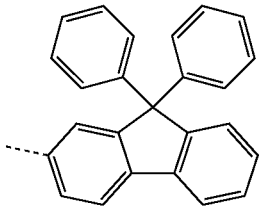 |
| 1-307 | 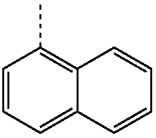 | 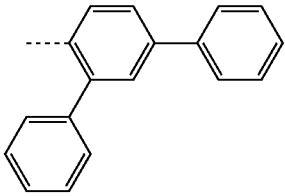 | 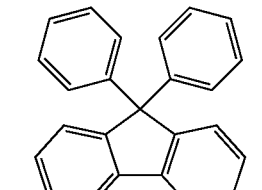 |

-continued

| Compound | ---Ar1 | ---Ar2 | ---Ar3 |
| --- | --- | --- | --- |
| 1-308 | | | |
| 1-309 | | | |
| 1-310 | | | |
| 1-311 | | | |
| 1-312 | | | |
| 1-313 | | | |

-continued
| Compound | ---Ar1 | ---Ar2 | ---Ar3 |
|---|---|---|---|
| 1-314 | 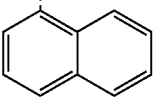 | 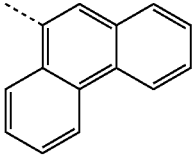 | 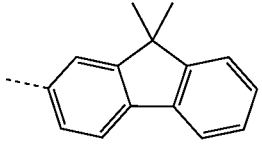 |
| 1-315 | 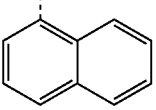 | 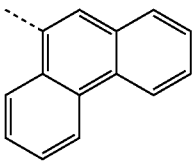 | 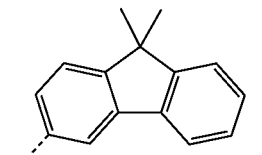 |
| 1-316 | 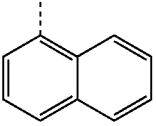 | 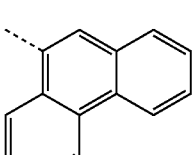 | 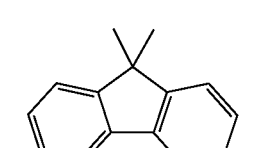 |
| 1-317 | 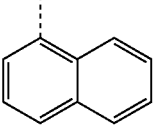 | 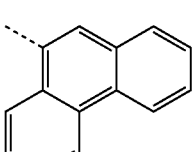 | 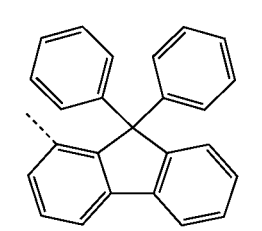 |
| 1-318 | 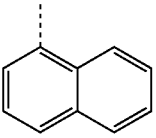 | 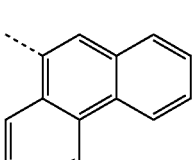 | 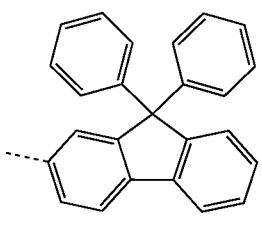 |
| 1-319 | 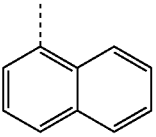 | 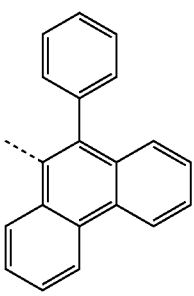 | 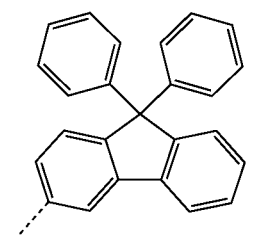 |
| 1-319 | 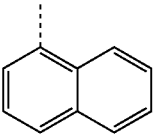 | 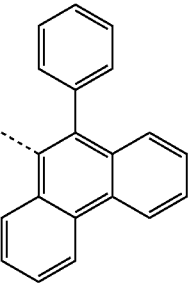 | 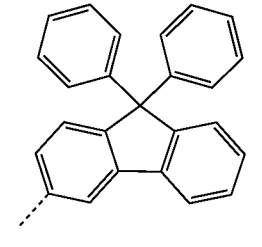 |

-continued
| Compound | ---Ar1 | ---Ar2 | ---Ar3 |
|---|---|---|---|
| 1-320 | | | |
| 1-321 | | | |
| 1-322 | | | |
| 1-323 | | | |
| 1-324 | | | |
| 1-325 | | | |
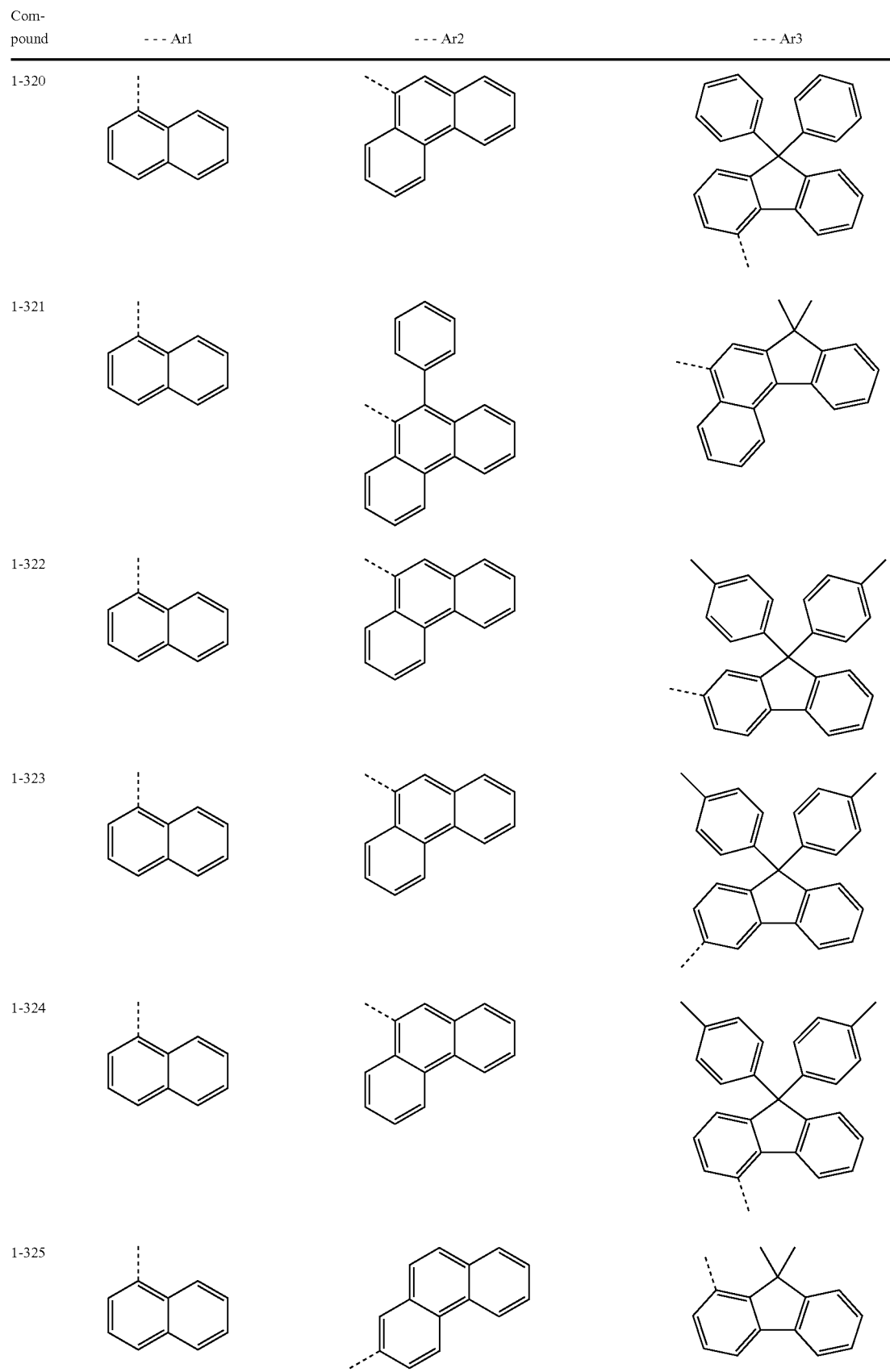

-continued
| Compound | ---Ar1 | ---Ar2 | ---Ar3 |
|---|---|---|---|
| 1-326 | 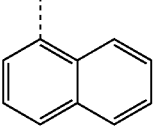 | 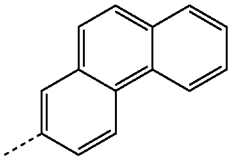 | 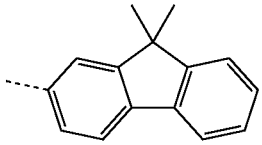 |
| 1-327 | 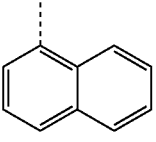 | 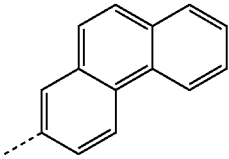 | 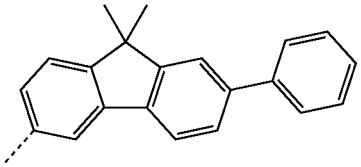 |
| 1-328 | 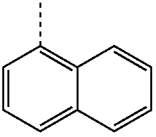 | 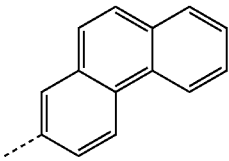 | 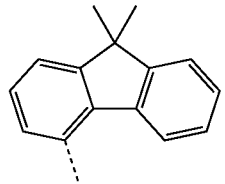 |
| 1-329 | 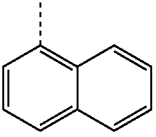 | 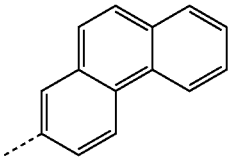 | 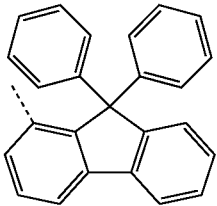 |
| 1-330 | 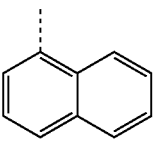 | 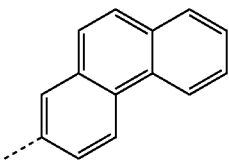 | 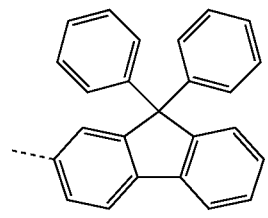 |
| 1-331 | 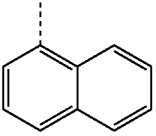 | 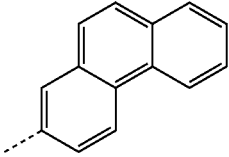 | 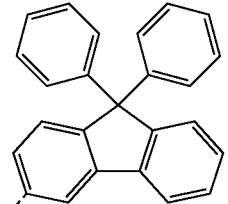 |
| 1-332 | 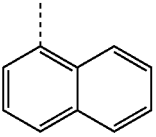 | 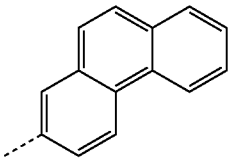 | 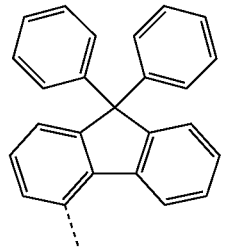 |

-continued
| Compound | - - - Ar1 | - - - Ar2 | - - - Ar3 |
|---|---|---|---|
| 1-333 | 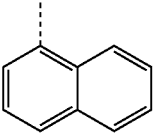 | 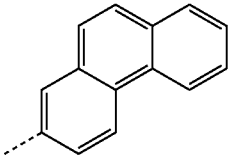 | 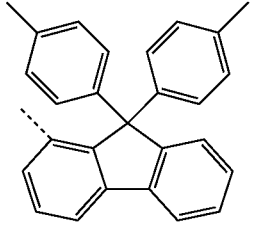 |
| 1-334 | 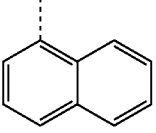 | 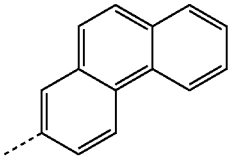 | 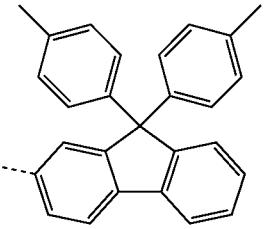 |
| 1-335 | 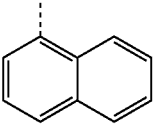 | 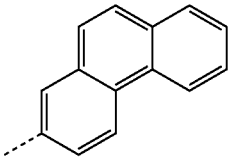 | 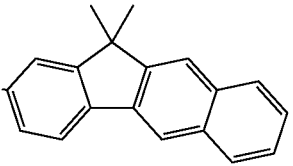 |
| 1-336 | 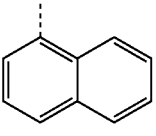 | 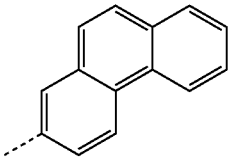 | 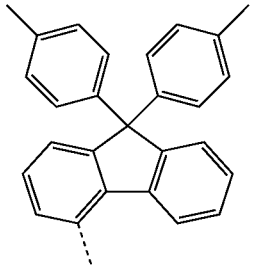 |
| 1-337 | 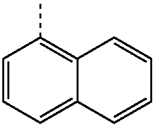 | 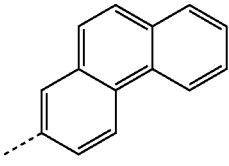 | 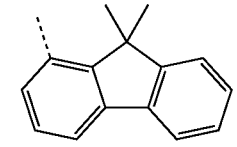 |
| 1-338 | 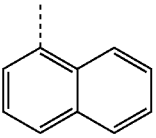 | 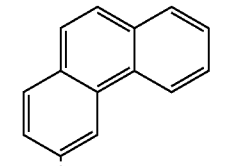 | 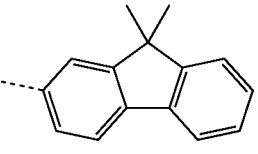 |
| 1-339 | 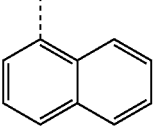 | 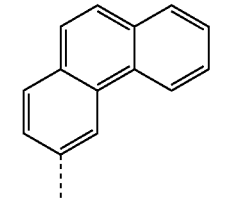 | 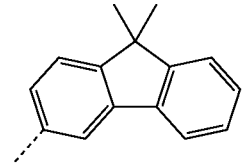 |

-continued

| Compound | ---Ar1 | ---Ar2 | ---Ar3 |
| --- | --- | --- | --- |
| 1-340 | naphthalene | phenanthrene | 9,9-dimethylfluorene |
| 1-341 | naphthalene | phenanthrene | 9,9-diphenylfluorene |
| 1-342 | naphthalene | phenanthrene | 9,9-diphenylfluorene |
| 1-343 | naphthalene | phenyl-phenanthrene | 9,9-diphenylfluorene |
| 1-344 | naphthalene | phenanthrene | 9,9-diphenylfluorene |
| 1-345 | naphthalene | phenanthrene | methyl-benzofluorene |

-continued

| Compound | ---Ar1 | ---Ar2 | ---Ar3 |
|---|---|---|---|
| 1-346 | | | |
| 1-347 | | | |
| 1-348 | | | |
| 1-350 | | | |
| 1-351 | | | |
| 1-352 | | | |

-continued

| Compound | --- Ar1 | --- Ar2 | --- Ar3 |
|---|---|---|---|
| 1-353 | 2-naphthyl | 3-biphenyl | 1-(9,9-diphenylfluorenyl) |
| 1-354 | 2-naphthyl | 3-biphenyl | 2-(9,9-diphenylfluorenyl) |
| 1-355 | 2-naphthyl | 3-biphenyl | 3-(9,9-diphenylfluorenyl) |
| 1-356 | 2-naphthyl | 3-biphenyl | 4-(9,9-diphenylfluorenyl) |
| 1-357 | 2-naphthyl | 2-biphenyl | 1-(9,9-di-p-tolylfluorenyl) |
| 1-358 | 2-naphthyl | 2-biphenyl | 2-(9,9-di-p-tolylfluorenyl) |

-continued

| Compound | - - - Ar1 | - - - Ar2 | - - - Ar3 |
|---|---|---|---|
| 1-360 | 2-naphthyl | 2-biphenyl | 4-(9,9-di-p-tolyl)fluorenyl |
| 1-361 | 2-naphthyl | 2-(anthracen-9-yl)phenyl | 1-(9,9-dimethyl)fluorenyl |
| 1-362 | 2-naphthyl | 2-biphenyl | 2-(9,9-dimethyl)fluorenyl |
| 1-363 | 2-naphthyl | 2-biphenyl | 3-(9,9-dimethyl-6-phenyl)fluorenyl |
| 1-364 | 2-naphthyl | 2-biphenyl | 4-(9,9-dimethyl)fluorenyl |
| 1-365 | 2-naphthyl | 2-biphenyl | 1-(9,9-diphenyl)fluorenyl |
| 1-366 | 2-naphthyl | 2-biphenyl | 2-(9,9-diphenyl)fluorenyl |

-continued

| Compound | ---Ar1 | ---Ar2 | ---Ar3 |
|---|---|---|---|
| 1-367 | 2-naphthyl | 2-biphenyl | 9,9-diphenylfluoren-3-yl |
| 1-368 | 2-naphthyl | 2-biphenyl | 9,9-diphenylfluoren-4-yl |
| 1-369 | 2-naphthyl | 2-biphenyl | 9,9-di(p-tolyl)fluoren-1-yl |
| 1-370 | 2-naphthyl | 2-biphenyl | 9,9-di(p-tolyl)fluoren-2-yl |
| 1-371 | 2-naphthyl | 2-biphenyl | 9,9-di(p-tolyl)fluoren-3-yl |
| 1-372 | 2-naphthyl | 2-biphenyl | 9,9-di(p-tolyl)fluoren-4-yl |

| Compound | --- Ar1 | --- Ar2 | --- Ar3 |
|---|---|---|---|
| 1-373 | 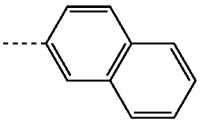 | 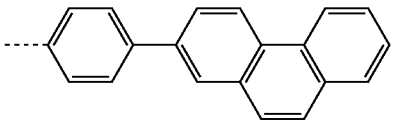 | 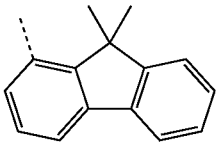 |
| 1-374 | 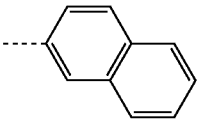 | 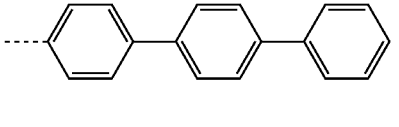 | 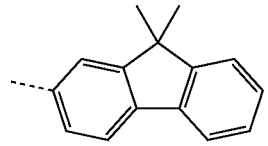 |
| 1-375 | 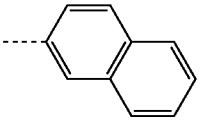 | 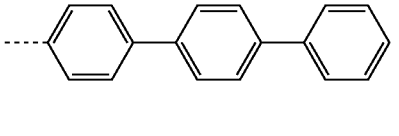 | 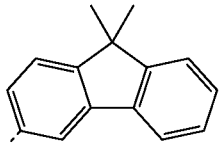 |
| 1-376 | 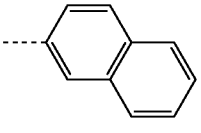 | 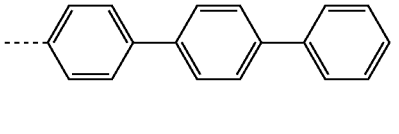 | 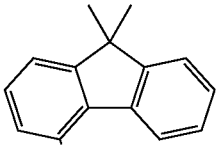 |
| 1-377 | 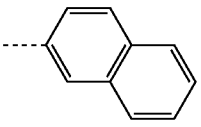 | 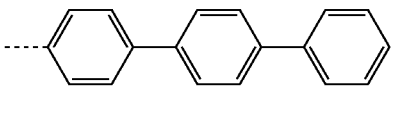 | 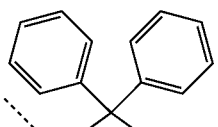 |
| 1-378 | 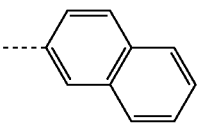 | 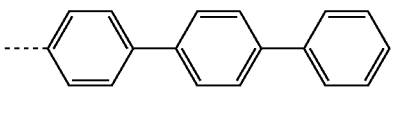 | 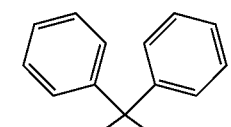 |
| 1-379 | 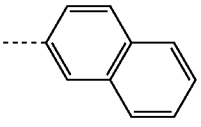 | 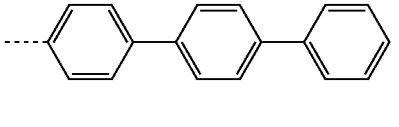 | 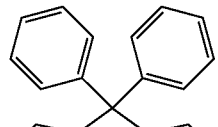 |

-continued
| Compound | - - - Ar1 | - - - Ar2 | - - - Ar3 |
|---|---|---|---|
| 1-380 | 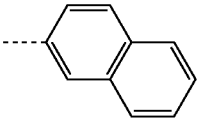 | 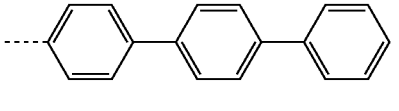 | 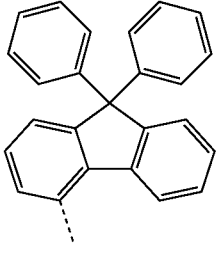 |
| 1-382 | 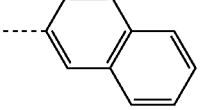 | 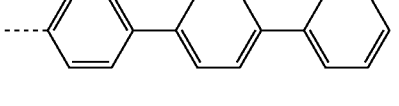 | 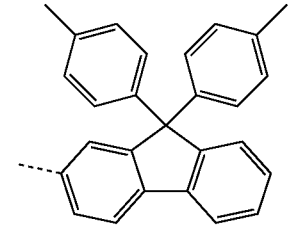 |
| 1-383 | 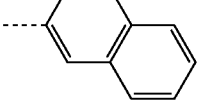 | 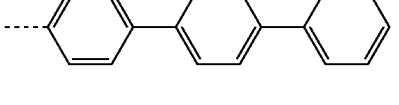 | 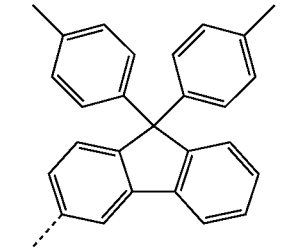 |
| 1-384 | 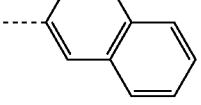 | 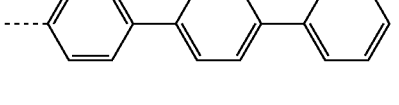 | 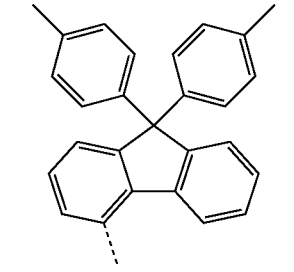 |
| 1-385 | 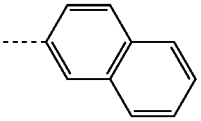 | 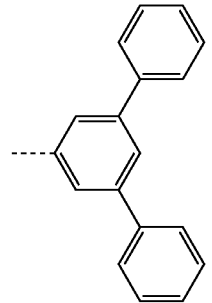 | 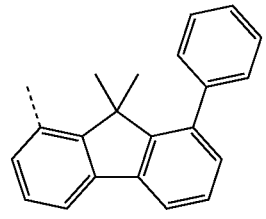 |

-continued
| Compound | --- Ar1 | --- Ar2 | --- Ar3 |
|---|---|---|---|
| 1-386 | 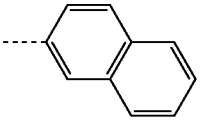 | 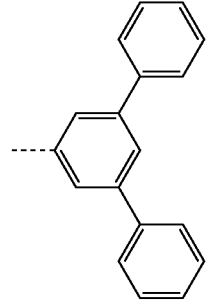 | 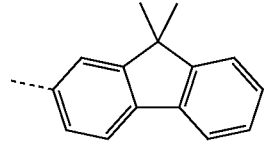 |
| 1-387 | 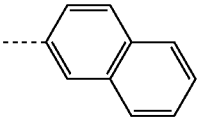 | 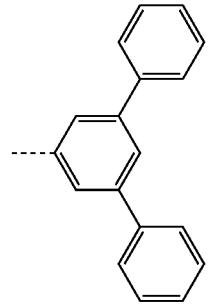 | 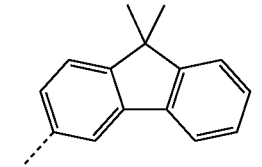 |
| 1-388 | 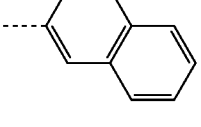 | 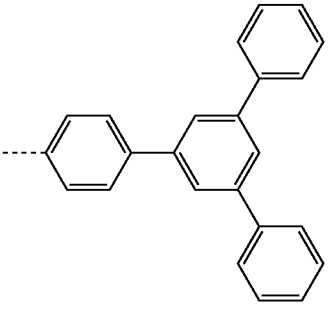 | 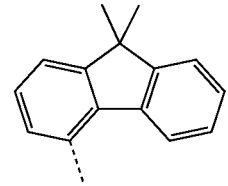 |
| 1-389 | 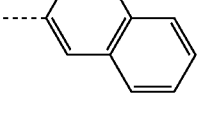 | 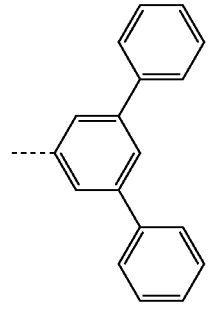 | 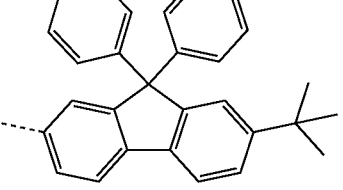 |
| 1-390 | 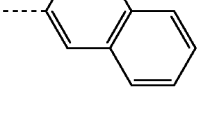 | 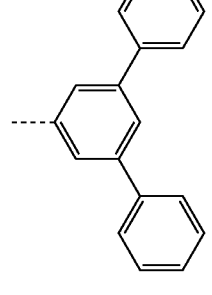 | 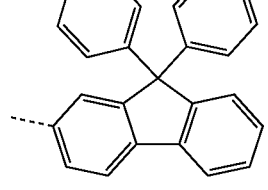 |

-continued
| Compound | ---Ar1 | ---Ar2 | ---Ar3 |
|---|---|---|---|
| 1-391 | 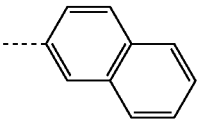 | 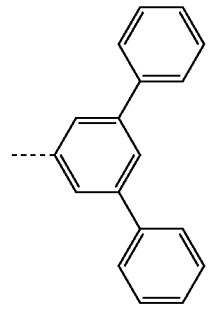 | 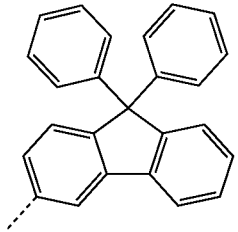 |
| 1-392 | 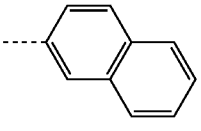 | 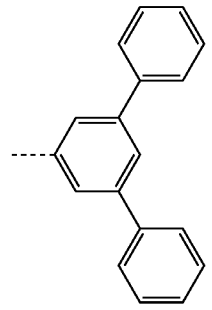 | 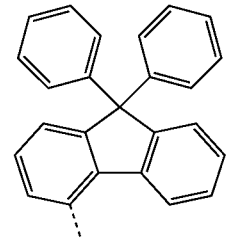 |
| 1-393 | 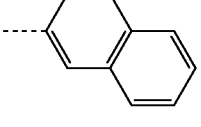 | 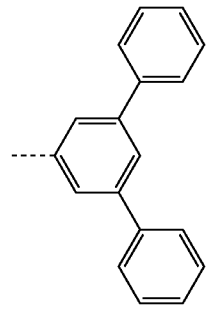 | 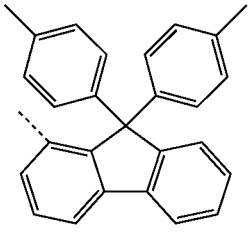 |
| 1-394 | 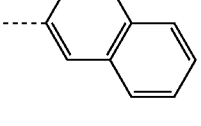 | 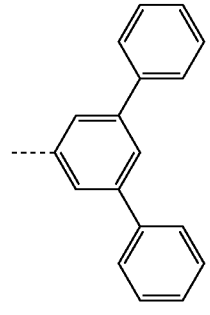 | 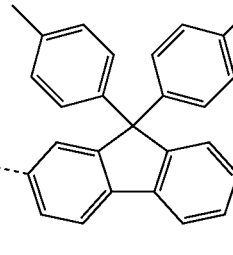 |
| 1-395 | 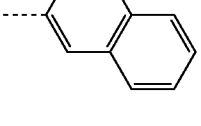 | 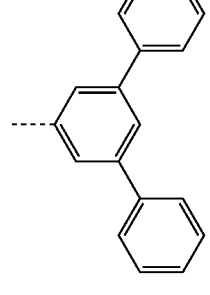 | 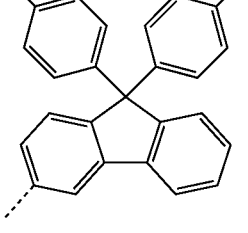 |

-continued
| Compound | ---Ar1 | ---Ar2 | ---Ar3 |
|---|---|---|---|
| 1-396 | 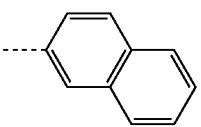 | 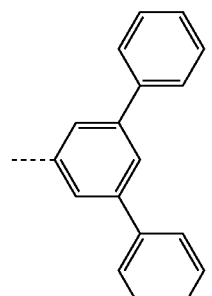 | 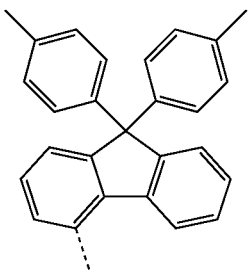 |
| 1-397 | 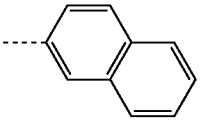 | 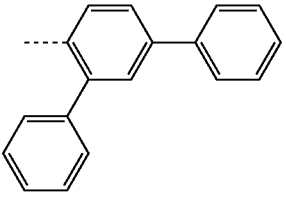 | 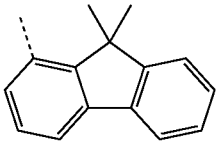 |
| 1-398 | 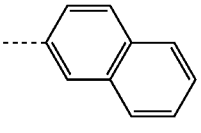 | 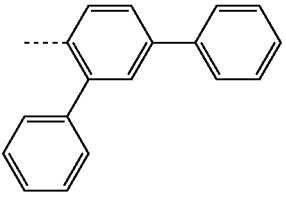 | 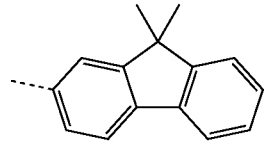 |
| 1-399 | 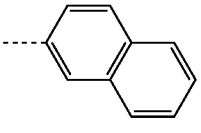 | 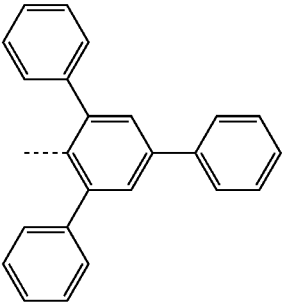 | 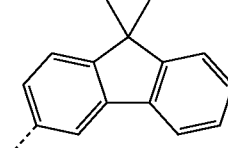 |
| 1-400 | 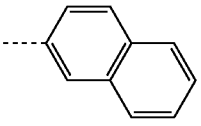 | 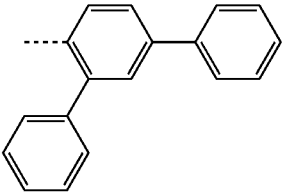 | 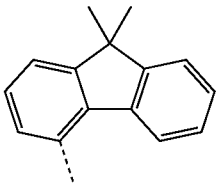 |
| 1-401 | 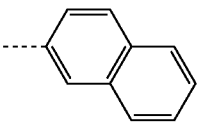 | 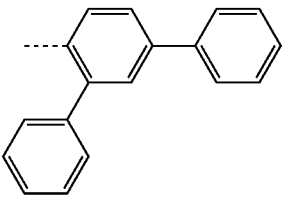 | 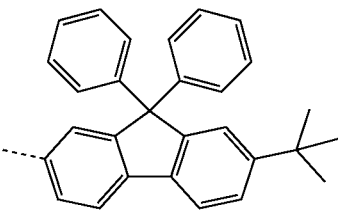 |

-continued
| Compound | --- Ar1 | --- Ar2 | --- Ar3 |
|---|---|---|---|
| 1-402 | 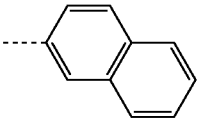 | 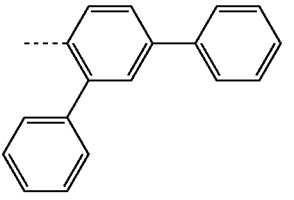 | 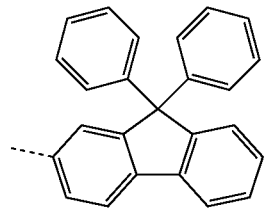 |
| 1-403 | 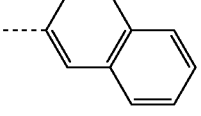 | 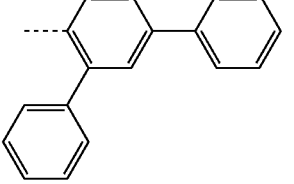 | 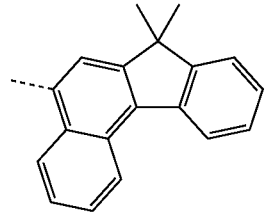 |
| 1-404 | 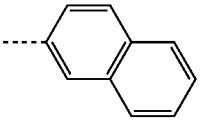 | 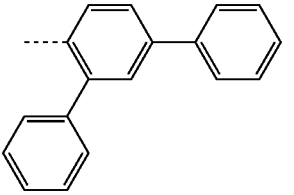 | 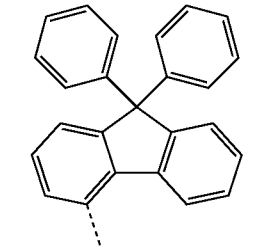 |
| 1-405 | 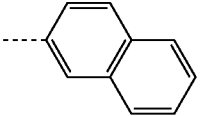 | 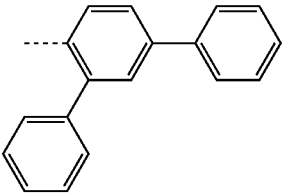 | 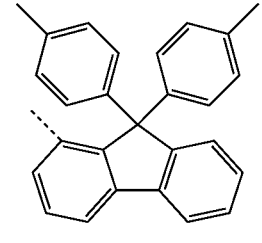 |
| 1-406 | 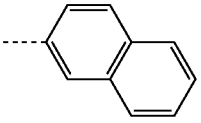 | 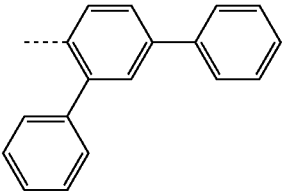 | 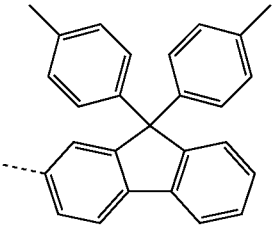 |
| 1-407 | 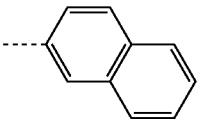 | 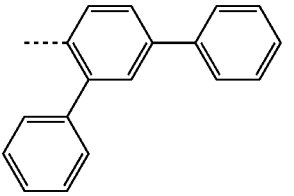 | 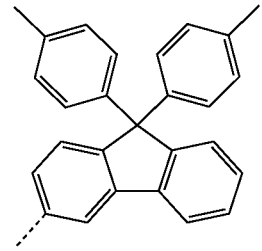 |

-continued
| Compound | ---Ar1 | ---Ar2 | ---Ar3 |
|---|---|---|---|
| 1-408 | 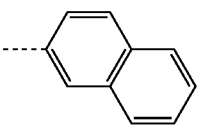 | 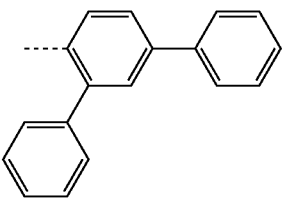 | 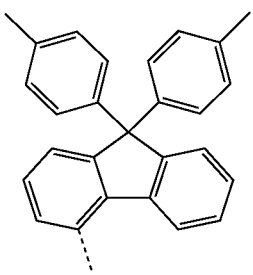 |
| 1-409 | 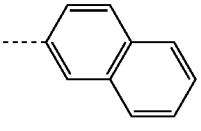 | 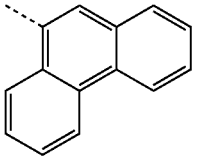 | 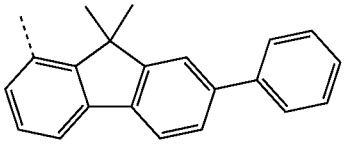 |
| 1-410 | 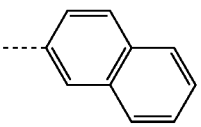 | 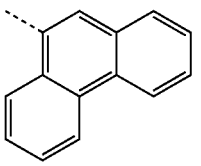 | 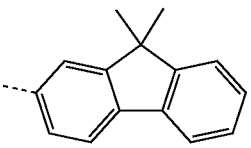 |
| 1-411 | 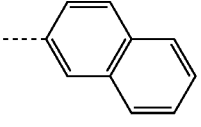 | 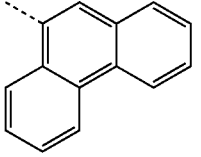 | 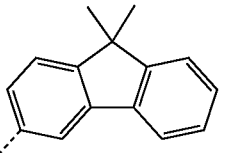 |
| 1-412 | 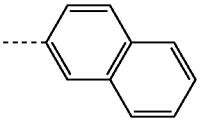 | 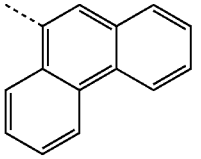 | 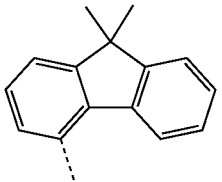 |
| 1-413 | 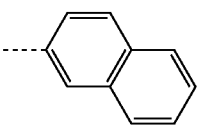 | 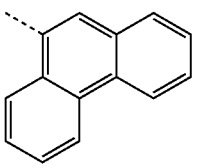 | 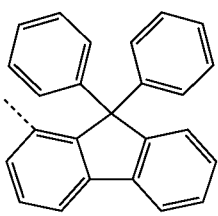 |
| 1-414 | 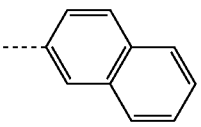 | 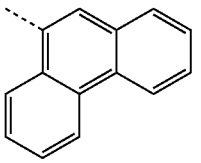 | 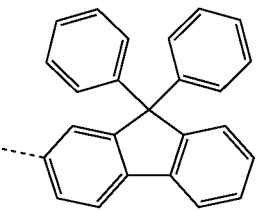 |

-continued
| Compound | --- Ar1 | --- Ar2 | --- Ar3 |
|---|---|---|---|
| 1-415 | 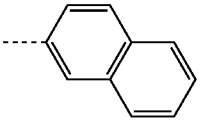 | 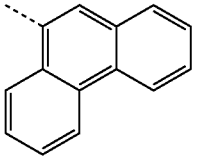 | 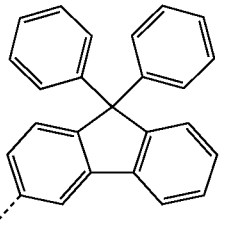 |
| 1-416 | 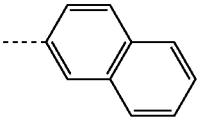 | 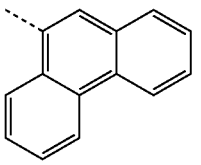 | 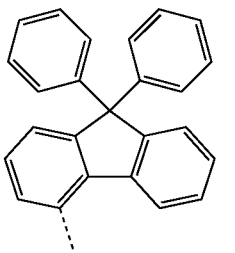 |
| 1-417 | 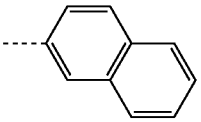 | 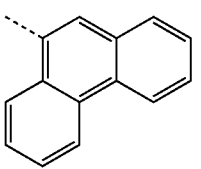 | 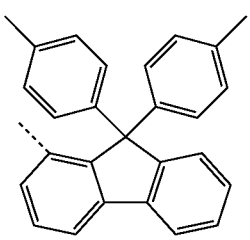 |
| 1-418 | 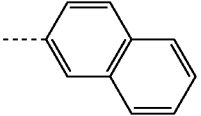 | 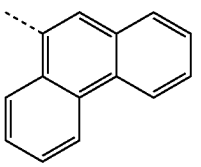 | 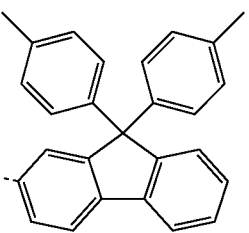 |
| 1-420 | 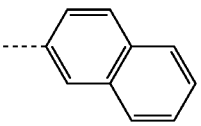 | 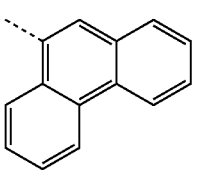 | 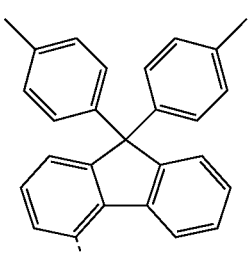 |
| 1-421 | 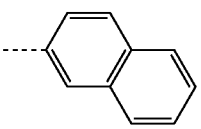 | 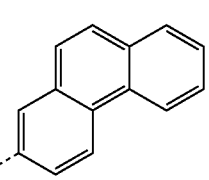 | 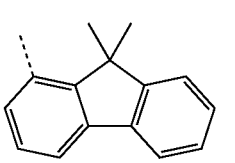 |

-continued
| Compound | ---Ar1 | ---Ar2 | ---Ar3 |
|---|---|---|---|
| 1-422 | 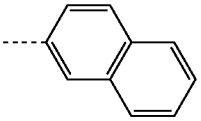 | 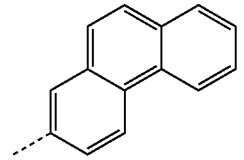 | 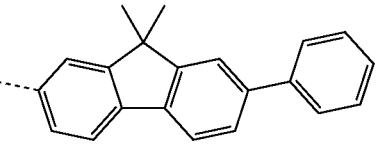 |
| 1-423 | 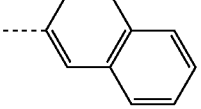 | 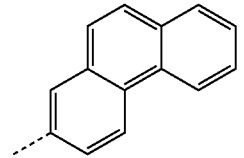 | 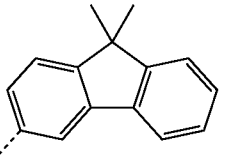 |
| 1-424 | 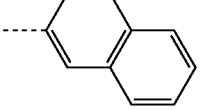 | 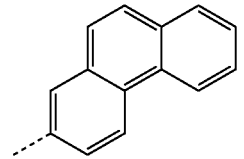 | 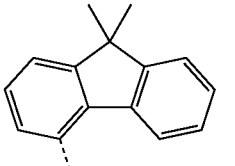 |
| 1-425 | 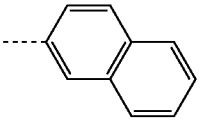 | 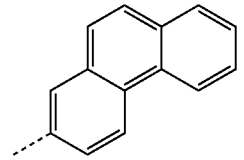 | 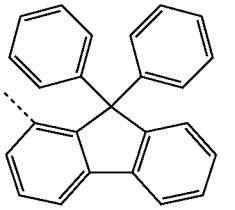 |
| 1-426 | 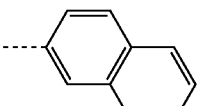 | 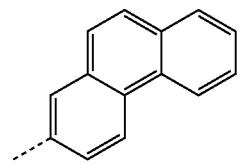 | 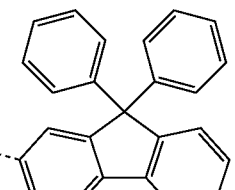 |
| 1-427 | 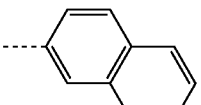 | 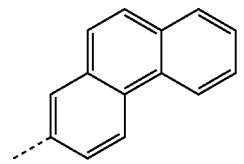 | 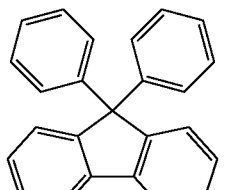 |
| 1-428 | 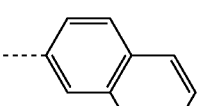 | 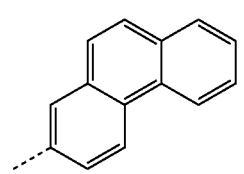 | 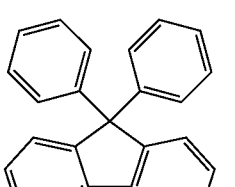 |

-continued

| Compound | --- Ar1 | --- Ar2 | --- Ar3 |
|---|---|---|---|
| 1-429 | | | |
| 1-430 | | | |
| 1-431 | | | |
| 1-432 | | | |
| 1-433 | | | |
| 1-434 | | | |

-continued
| Compound | ---Ar1 | ---Ar2 | ---Ar3 |
|---|---|---|---|
| 1-435 | 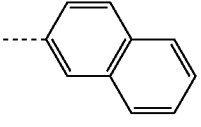 | 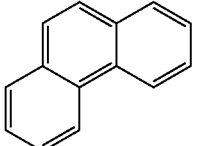 | 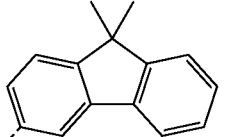 |
| 1-436 | 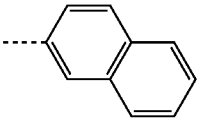 | 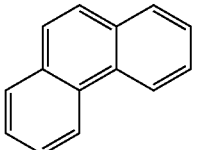 | 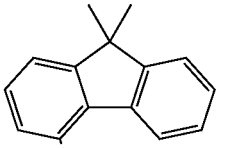 |
| 1-437 | 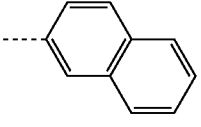 | 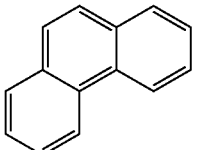 | 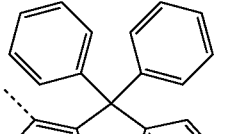 |
| 1-438 | 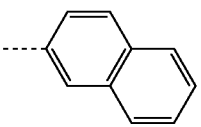 | 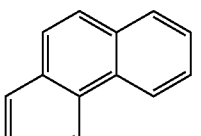 | 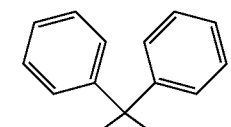 |
| 1-439 | 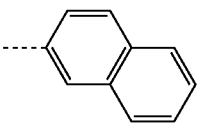 | 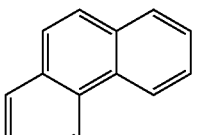 | 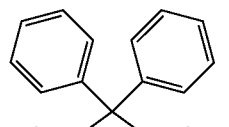 |
| 1-440 | 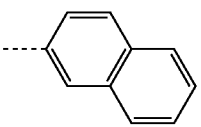 | 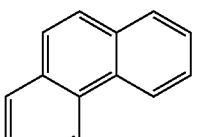 | 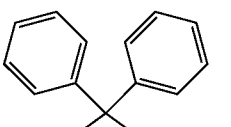 |

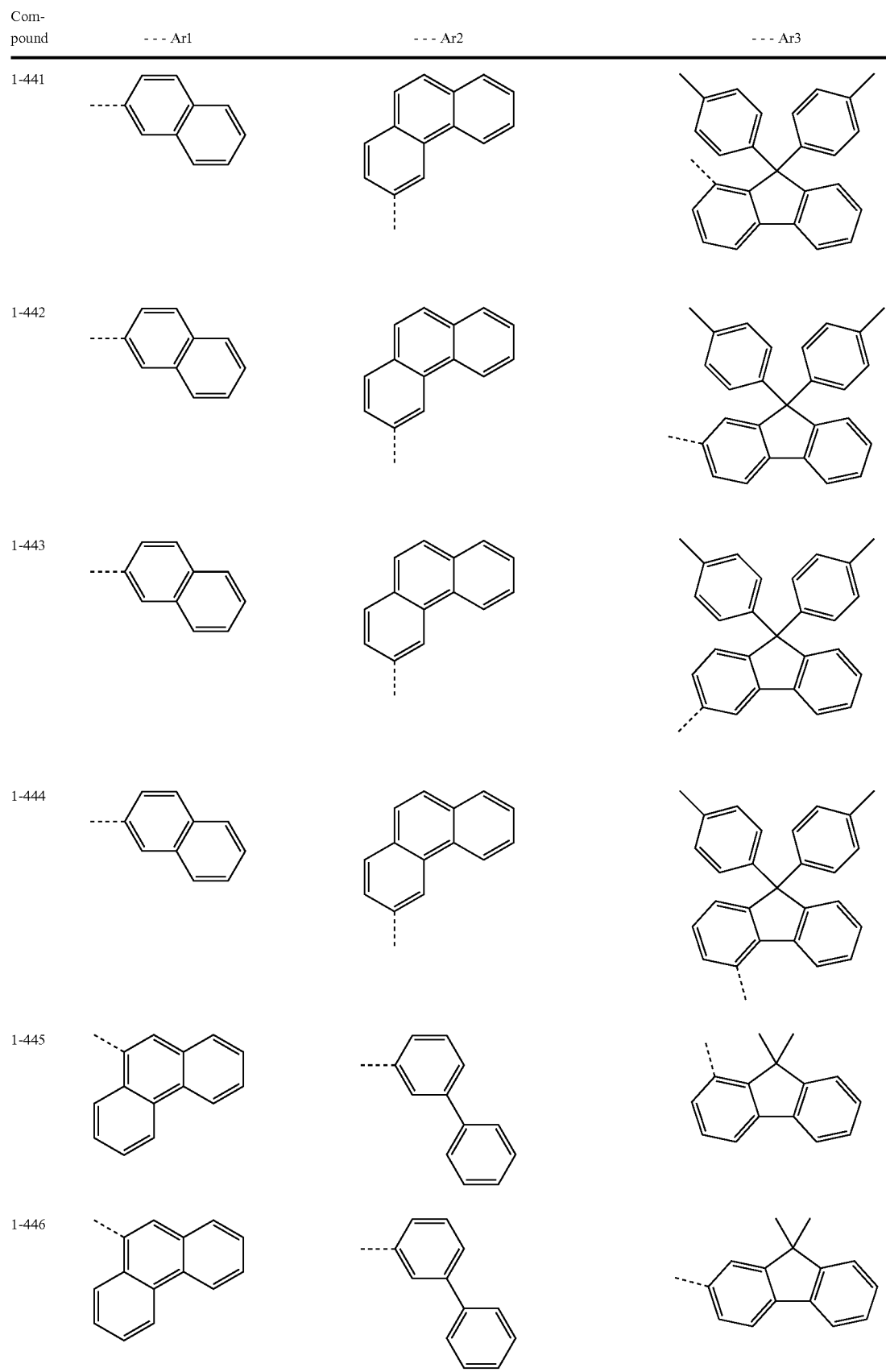

-continued
| Compound | - - - Ar1 | - - - Ar2 | - - - Ar3 |
|---|---|---|---|
| 1-447 | 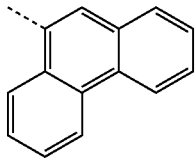 | 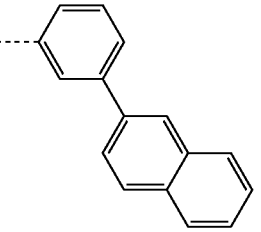 | 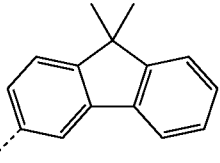 |
| 1-448 | 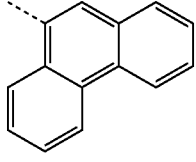 | 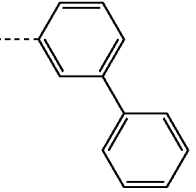 | 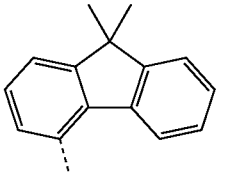 |
| 1-449 | 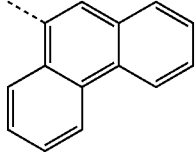 | 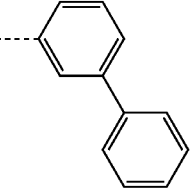 | 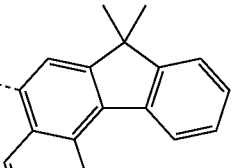 |
| 1-450 | 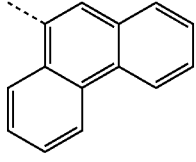 | 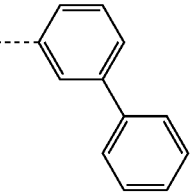 | 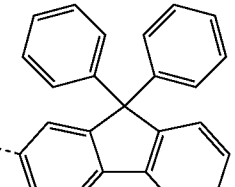 |
| 1-451 | 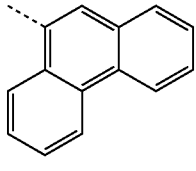 | 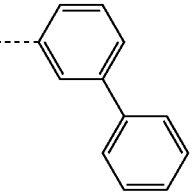 | 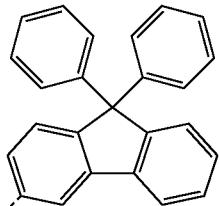 |
| 1-452 | 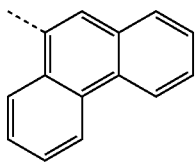 | 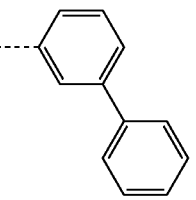 | 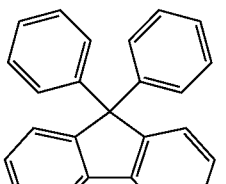 |

-continued
| Compound | ---Ar1 | ---Ar2 | ---Ar3 |
|---|---|---|---|
| 1-453 | 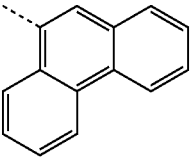 | 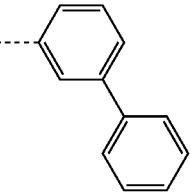 | 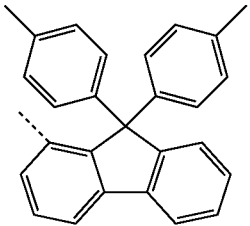 |
| 1-454 | 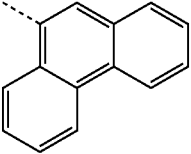 | 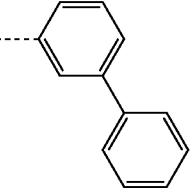 | 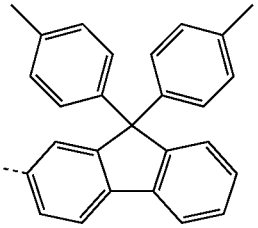 |
| 1-455 | 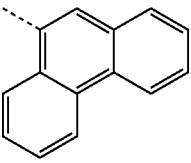 | 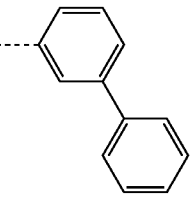 | 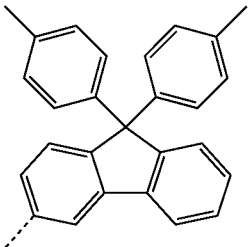 |
| 1-456 | 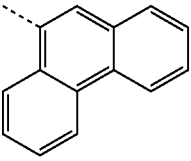 | 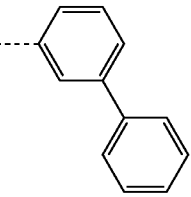 | 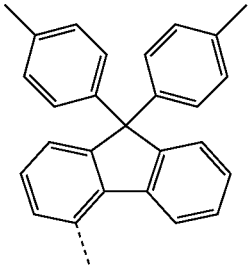 |
| 1-457 | 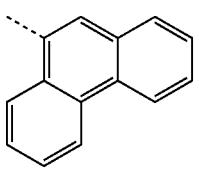 | 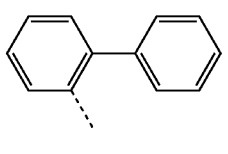 | 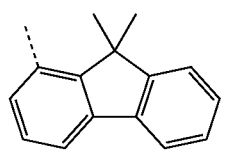 |
| 1-459 | 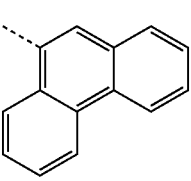 | 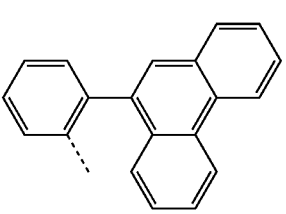 | 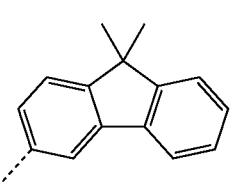 |

-continued

| Compound | - - - Ar1 | - - - Ar2 | - - - Ar3 |
| --- | --- | --- | --- |
| 1-460 | | | |
| 1-461 | | | |
| 1-462 | | | |
| 1-463 | | | |
| 1-464 | | | |
| 1-465 | | | |
| 1-466 | | | |

-continued
| Compound | --- Ar1 | --- Ar2 | --- Ar3 |
|---|---|---|---|
| 1-467 | 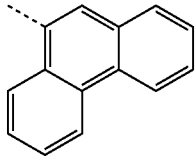 | 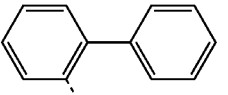 | 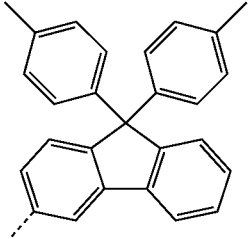 |
| 1-468 | 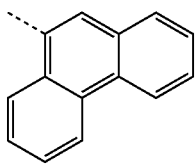 | 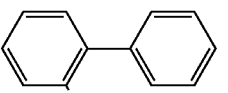 | 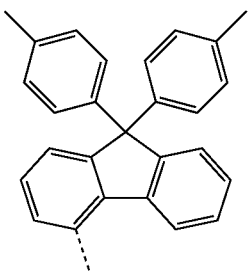 |
| 1-469 | 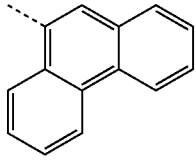 | 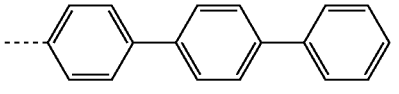 | 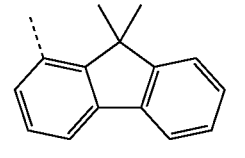 |
| 1-470 | 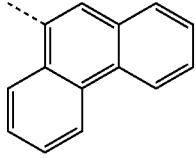 | 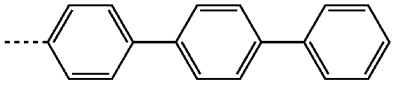 | 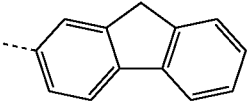 |
| 1-471 | 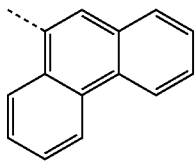 | 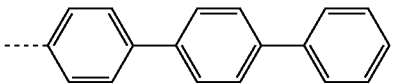 | 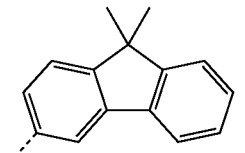 |
| 1-472 | 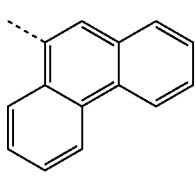 | 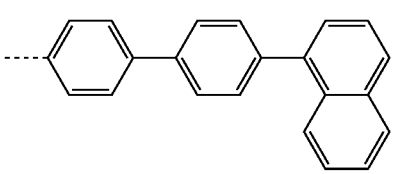 | 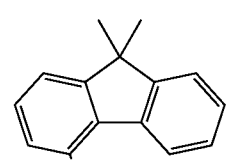 |
| 1-474 | 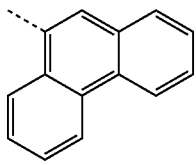 | 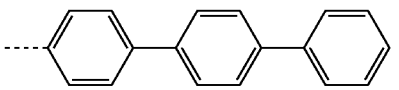 | 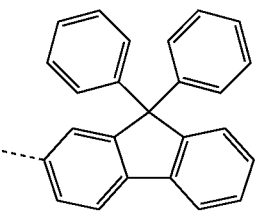 |

-continued

| Compound | - - - Ar1 | - - - Ar2 | - - - Ar3 |
|---|---|---|---|
| 1-475 | phenanthrene | p-terphenyl | 9,9-diphenylfluorene (3-yl) |
| 1-476 | phenanthrene | p-terphenyl | 9,9-diphenylfluorene (4-yl) |
| 1-477 | phenanthrene | p-terphenyl | 9,9-di(p-tolyl)fluorene (1-yl) |
| 1-478 | phenanthrene | p-terphenyl | 9,9-di(p-tolyl)fluorene (2-yl) |
| 1-479 | phenanthrene | p-terphenyl | 9,9-di(p-tolyl)fluorene (3-yl) |
| 1-480 | phenanthrene | p-terphenyl | 9,9-di(p-tolyl)fluorene (4-yl) |

-continued
| Compound | ---Ar1 | ---Ar2 | ---Ar3 |
|---|---|---|---|
| 1-481 | 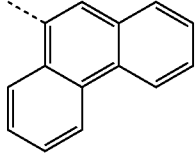 | 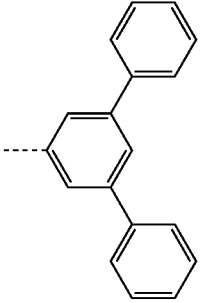 | 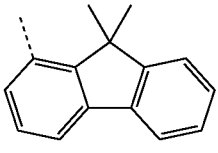 |
| 1-482 | 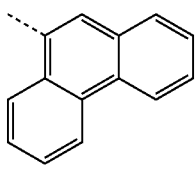 | 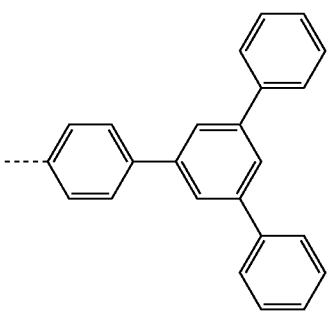 | 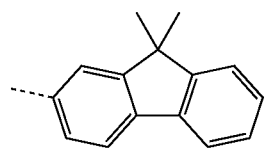 |
| 1-484 | 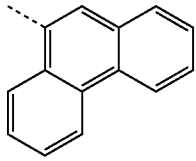 | 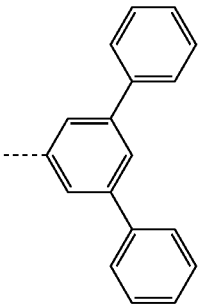 | 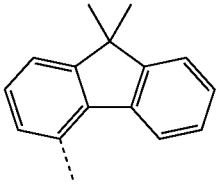 |
| 1-485 | 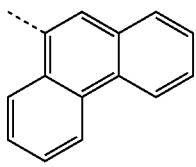 | 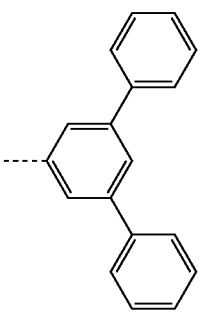 | 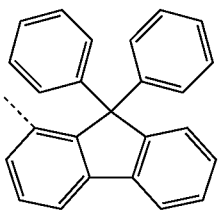 |
| 1-486 | 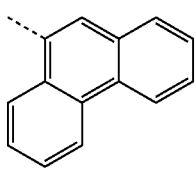 | 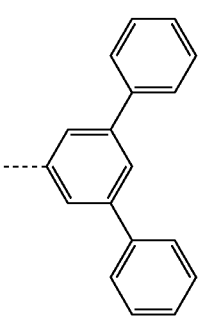 | 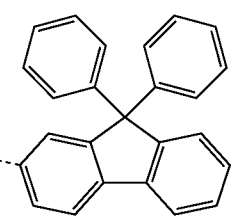 |

-continued

| Compound | --- Ar1 | --- Ar2 | --- Ar3 |
|---|---|---|---|
| 1-487 | | | |
| 1-488 | | | |
| 1-489 | | | |
| 1-490 | | | |
| 1-491 | | | |

-continued
| Compound | - - - Ar1 | - - - Ar2 | - - - Ar3 |
|---|---|---|---|
| 1-492 | 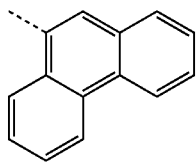 | 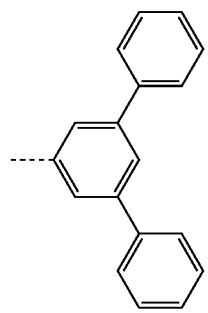 | 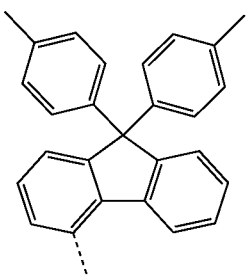 |
| 1-493 | 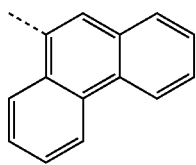 | 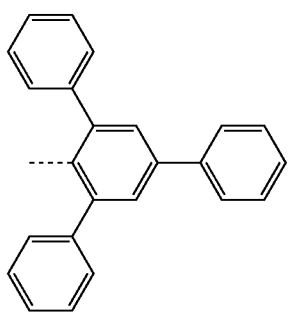 | 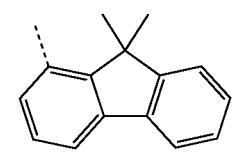 |
| 1-494 | 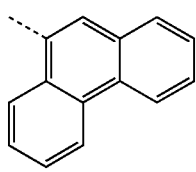 | 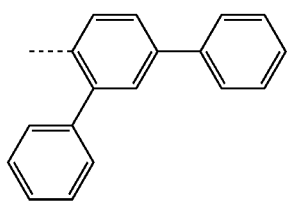 | 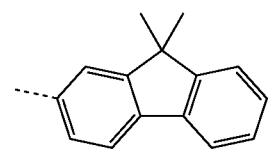 |
| 1-495 | 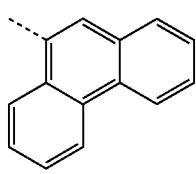 | 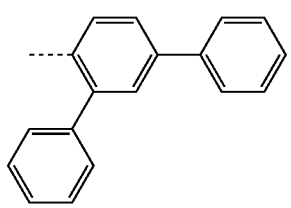 | 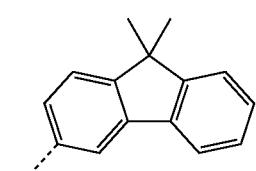 |
| 1-496 | 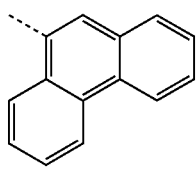 | 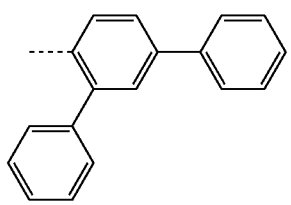 | 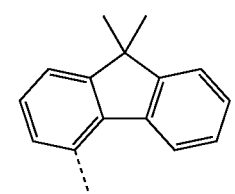 |
| 1-497 | 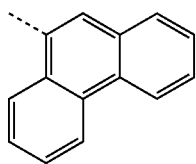 | 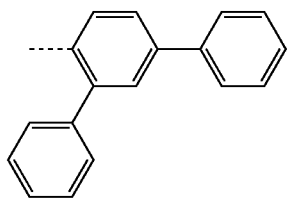 | 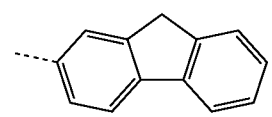 |

-continued
| Compound | --- Ar1 | --- Ar2 | --- Ar3 |
|---|---|---|---|
| 1-498 | 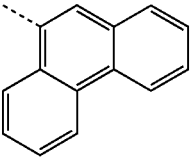 | 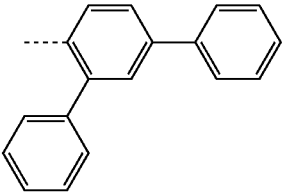 | 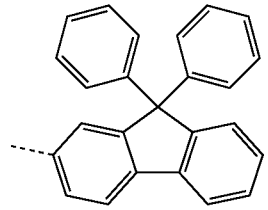 |
| 1-499 | 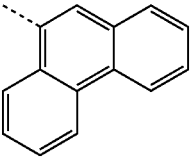 | 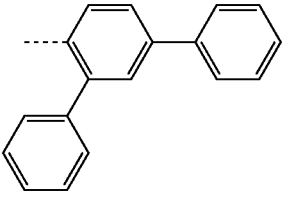 | 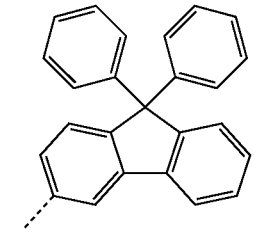 |
| 1-500 | 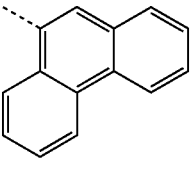 | 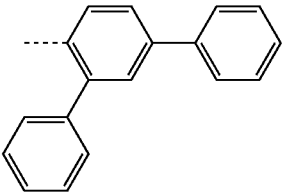 | 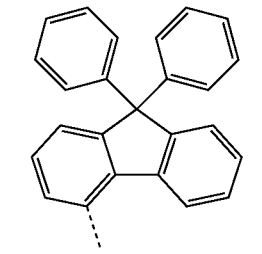 |
| 1-501 | 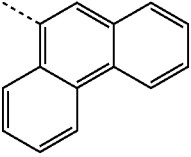 | 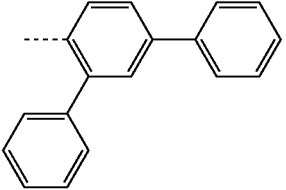 | 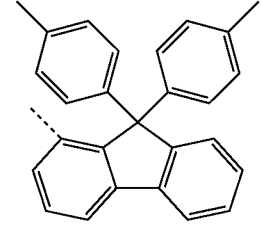 |
| 1-502 | 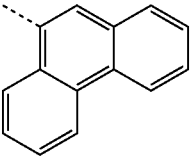 | 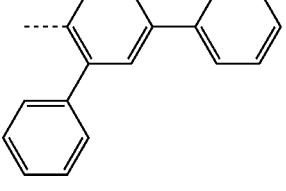 | 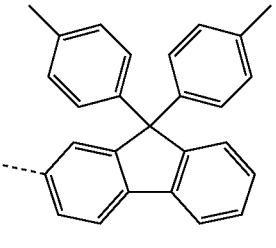 |
| 1-503 | 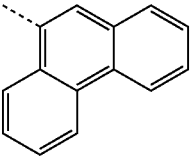 | 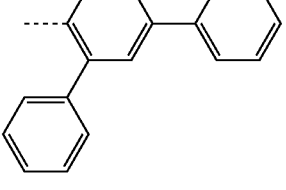 | 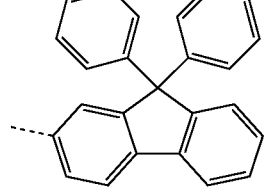 |

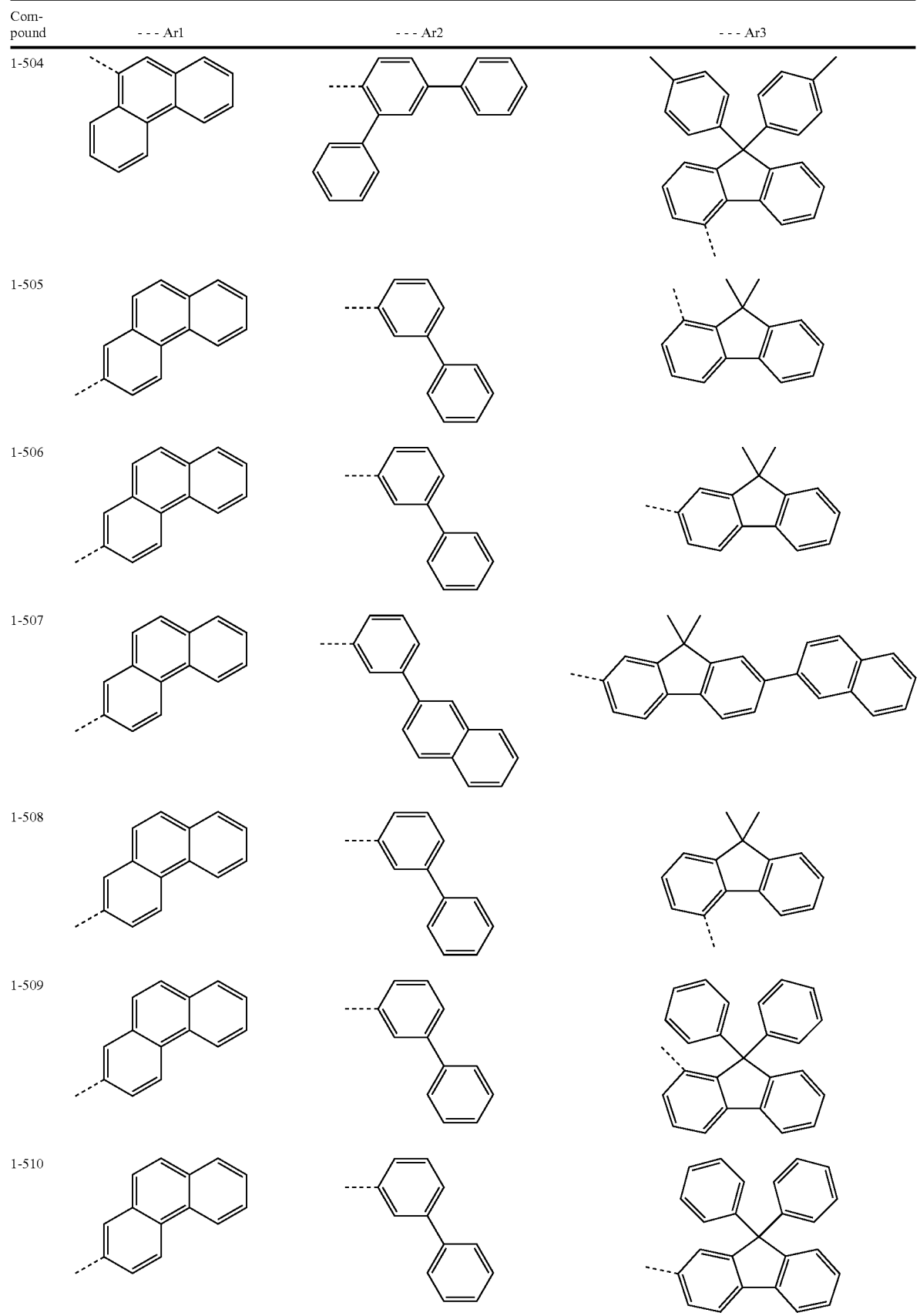

-continued
| Compound | ---Ar1 | ---Ar2 | ---Ar3 |
|---|---|---|---|
| 1-511 | | | |
| 1-512 | | | |
| 1-513 | | | |
| 1-514 | | | |
| 1-516 | | | |
| 1-517 | | | |
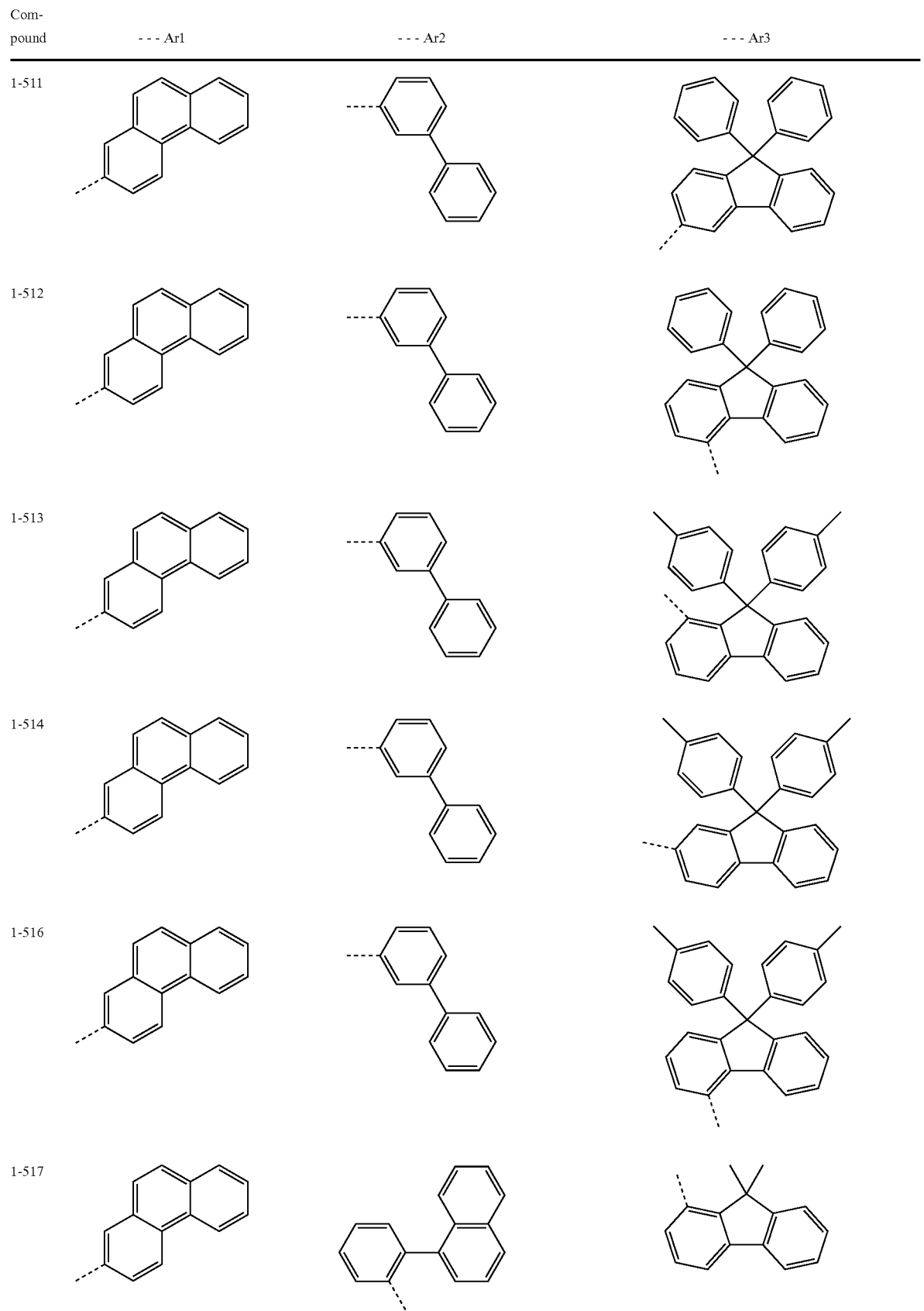

-continued
| Compound | --- Ar1 | --- Ar2 | --- Ar3 |
| --- | --- | --- | --- |
| 1-518 | 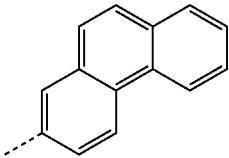 | 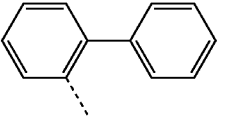 | 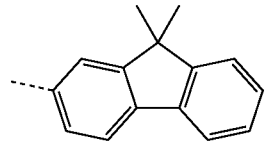 |
| 1-519 | 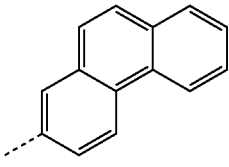 | 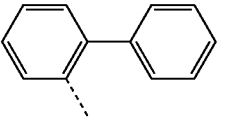 | 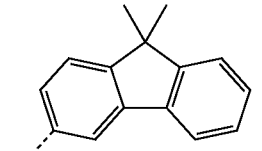 |
| 1-520 | 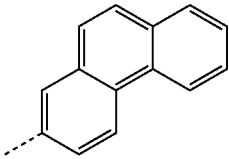 | 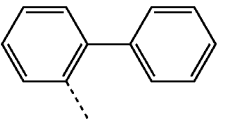 | 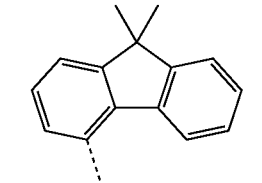 |
| 1-522 | 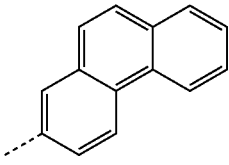 | 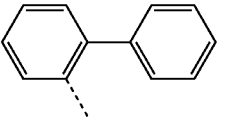 | 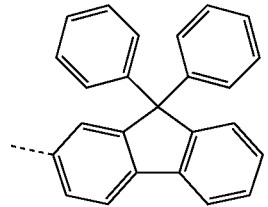 |
| 1-523 | 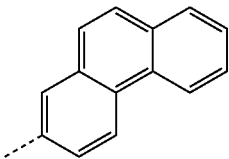 | 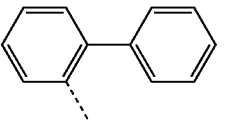 | 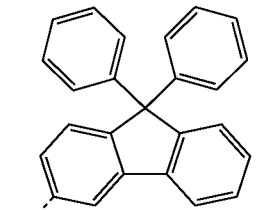 |
| 1-524 | 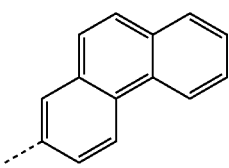 | 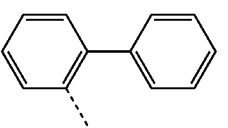 | 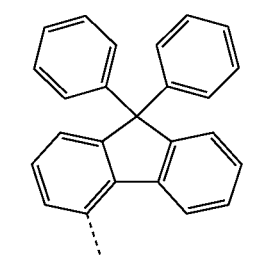 |
| 1-525 | 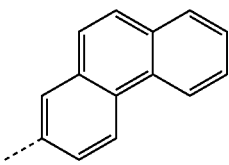 | 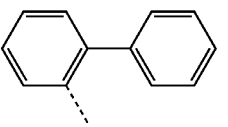 | 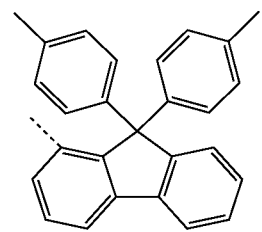 |

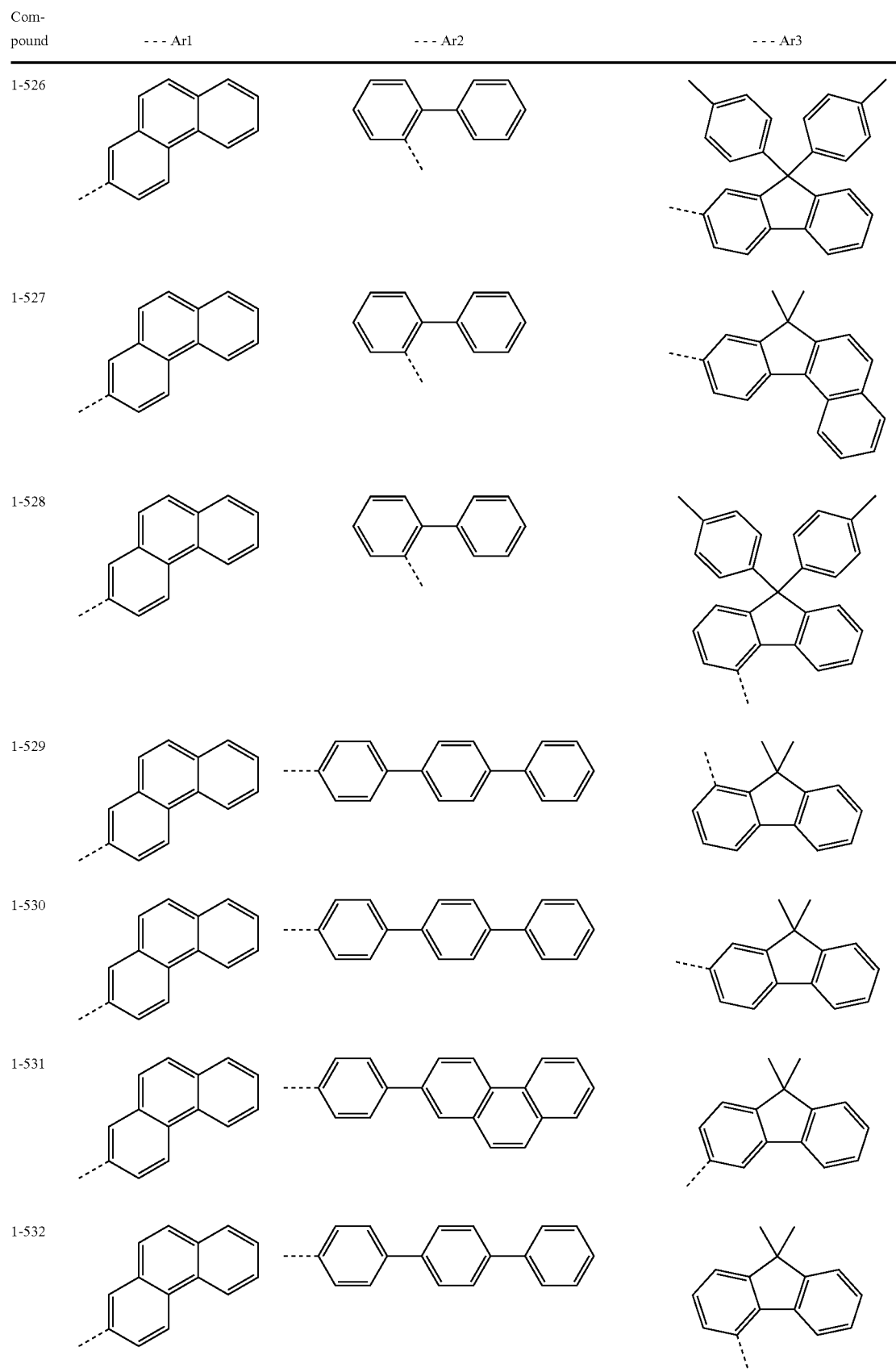

-continued

| Compound | - - - Ar1 | - - - Ar2 | - - - Ar3 |
|---|---|---|---|
| 1-533 | phenanthrenyl | p-terphenyl | 9,9-diphenylfluoren-1-yl |
| 1-534 | phenanthrenyl | p-terphenyl | 9,9-diphenylfluoren-2-yl |
| 1-535 | phenanthrenyl | p-terphenyl | 9,9-diphenylfluoren-3-yl |
| 1-536 | phenanthrenyl | p-terphenyl | 9,9-diphenylfluoren-4-yl |
| 1-537 | phenanthrenyl | p-terphenyl | 9,9-di(p-tolyl)fluoren-1-yl |
| 1-538 | phenanthrenyl | phenyl-phenanthrenyl | 9,9-di(p-tolyl)fluoren-2-yl |

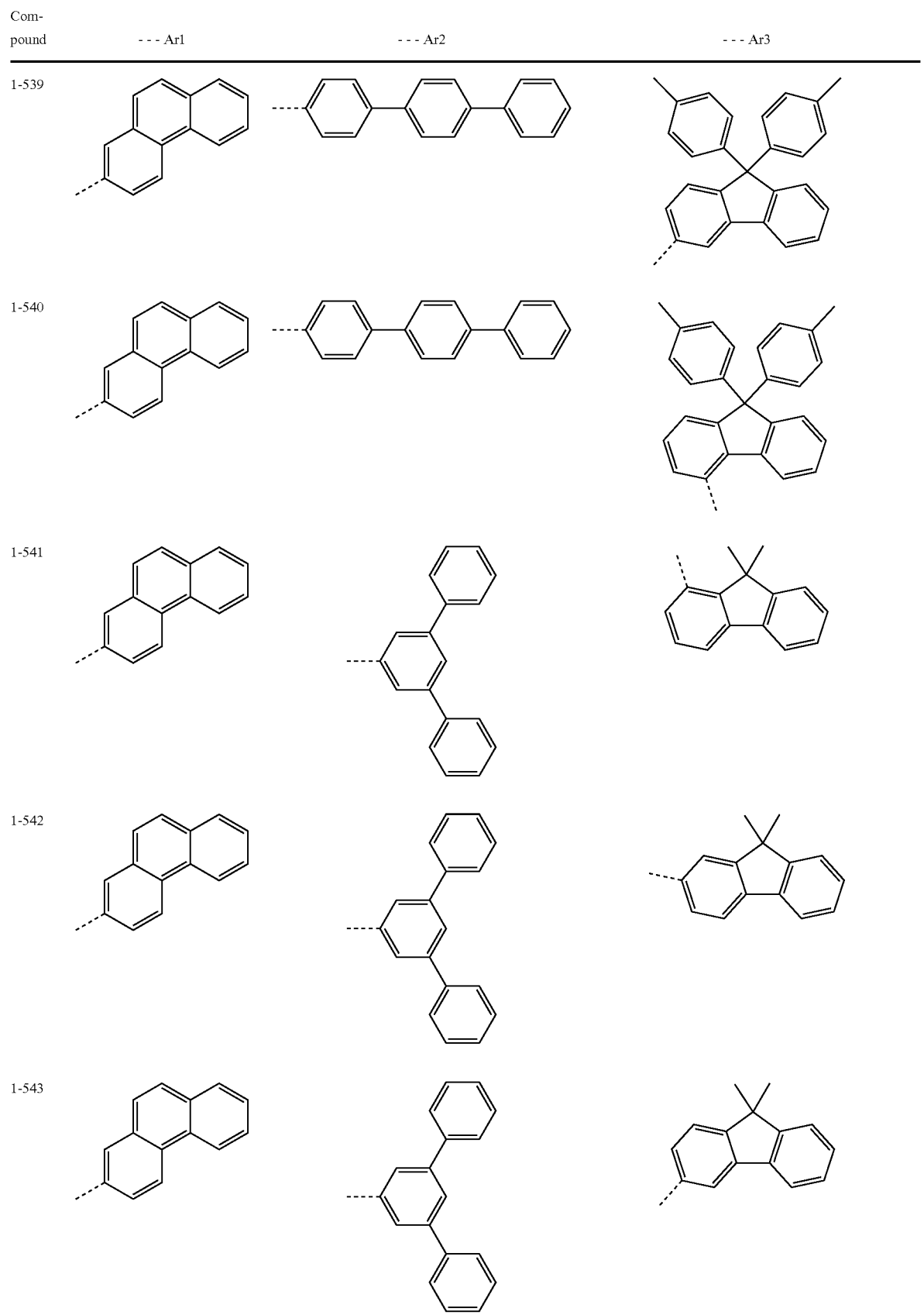

-continued
| Compound | - - - Ar1 | - - - Ar2 | - - - Ar3 |
|---|---|---|---|
| 1-544 | 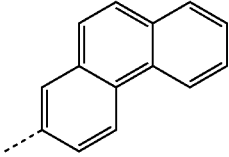 | 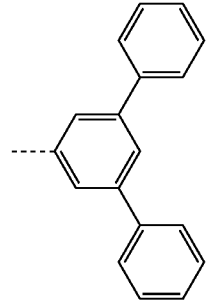 | 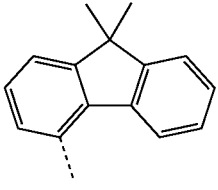 |
| 1-545 | 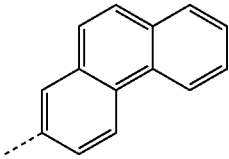 | 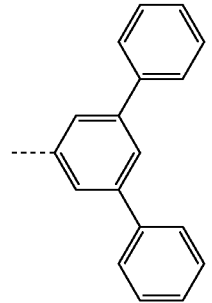 | 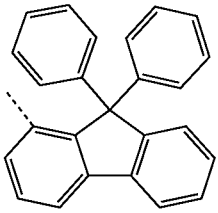 |
| 1-546 | 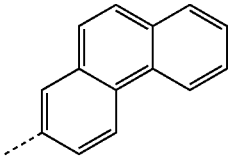 | 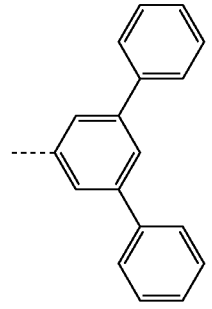 | 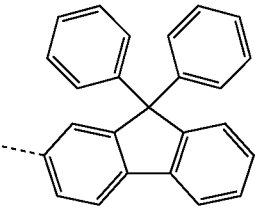 |
| 1-547 | 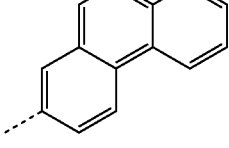 | 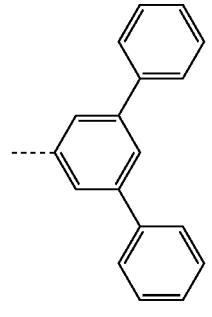 | 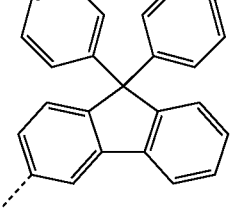 |
| 1-548 | 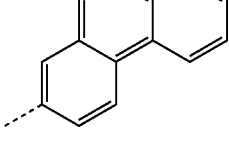 | 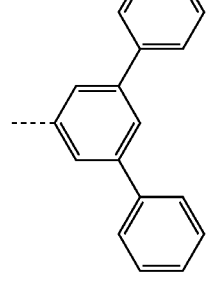 | 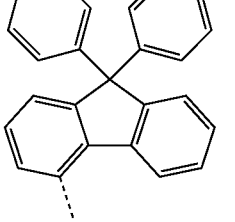 |

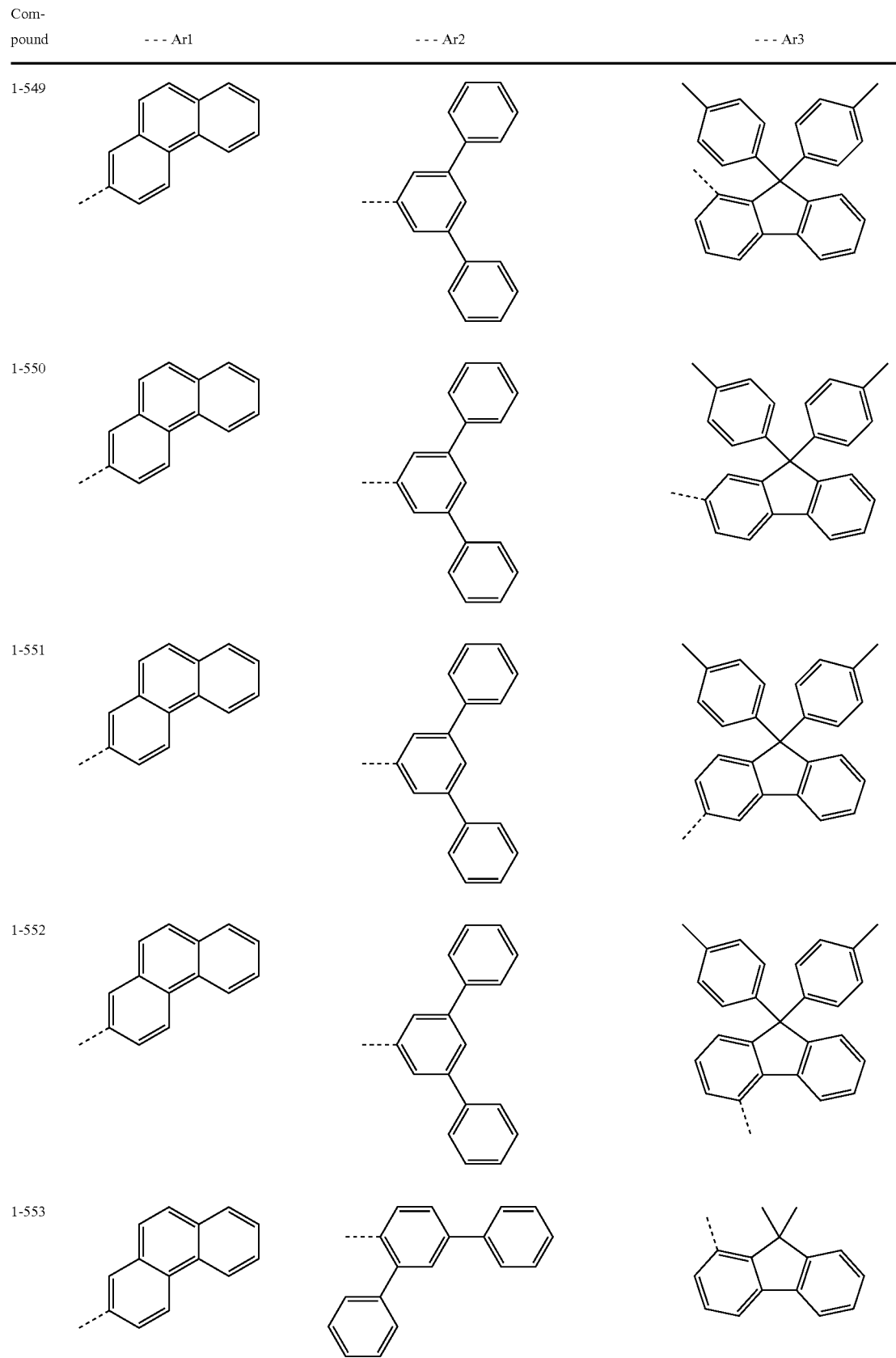

-continued

| Compound | --- Ar1 | --- Ar2 | --- Ar3 |
| --- | --- | --- | --- |
| 1-554 | | | |
| 1-555 | | | |
| 1-556 | | | |
| 1-557 | | | |
| 1-558 | | | |
| 1-559 | | | |
| 1-560 | | | |

-continued
| Compound | ---Ar1 | ---Ar2 | ---Ar3 |
|---|---|---|---|
| 1-561 | | | |
| 1-562 | | | |
| 1-564 | | | |
| 1-565 | | | |
| 1-566 | | | |
| 1-567 | | | |
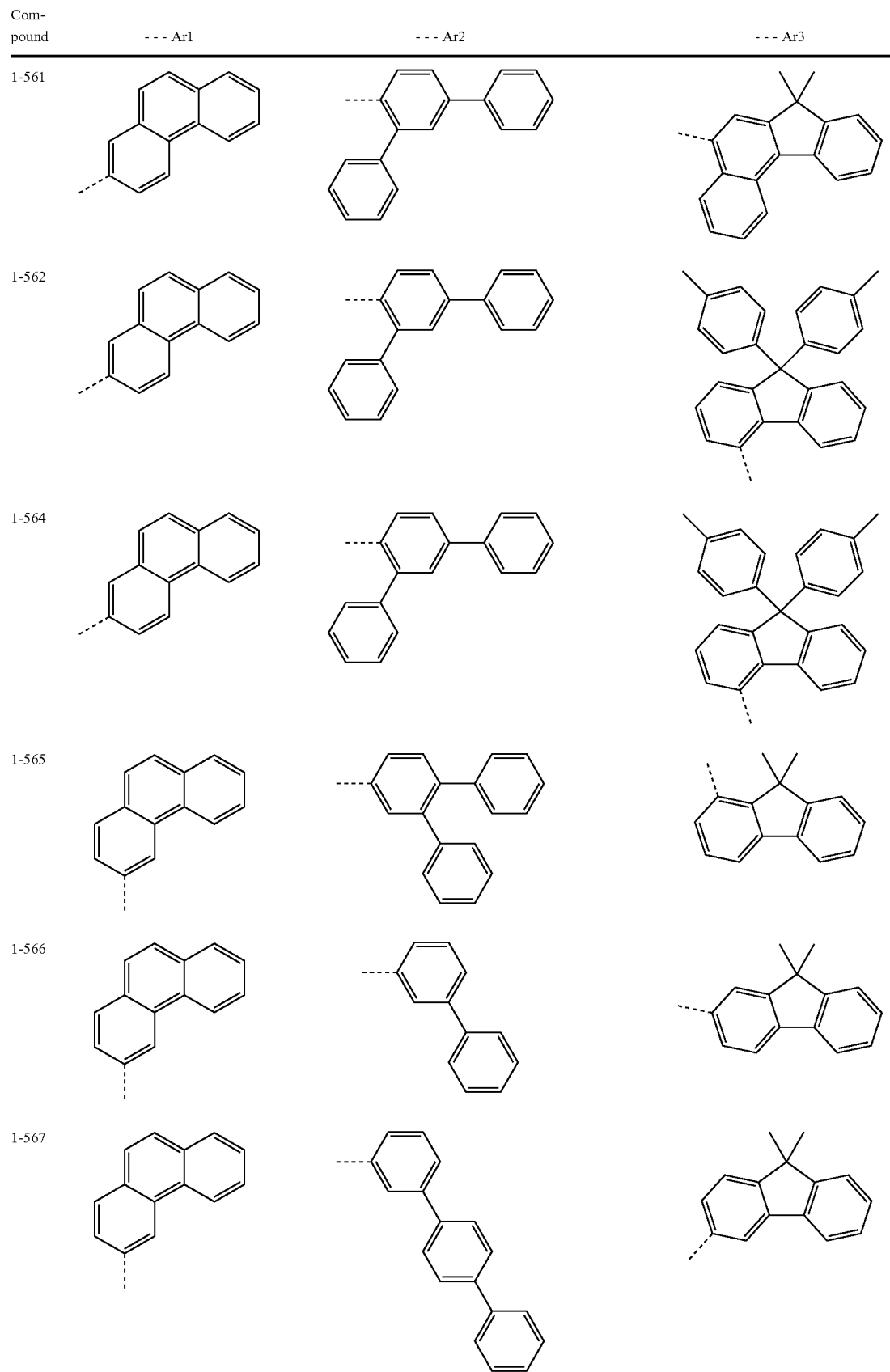

-continued

| Compound | ---Ar1 | ---Ar2 | ---Ar3 |
|---|---|---|---|
| 1-568 | phenanthrene | biphenyl (meta) | 9,9-dimethylfluorene |
| 1-569 | phenanthrene | biphenyl (meta) | 9,9-dimethylbenzofluorene |
| 1-570 | phenanthrene | biphenyl (meta) | 9,9-diphenylfluorene |
| 1-571 | phenanthrene | biphenyl (meta) | 9,9-diphenylfluorene |
| 1-572 | phenanthrene | biphenyl (meta) | 9,9-diphenylfluorene |
| 1-573 | phenanthrene | biphenyl (meta) | 9,9-bis(4-methylphenyl)fluorene |

-continued

| Compound | - - - Ar1 | - - - Ar2 | - - - Ar3 |
|---|---|---|---|
| 1-574 | phenanthrene | biphenyl | 9,9-di(p-tolyl)fluorene |
| 1-575 | phenanthrene | biphenyl | 9,9-di(p-tolyl)fluorene |
| 1-576 | phenanthrene | biphenyl | 9,9-di(p-tolyl)fluorene |
| 1-577 | phenanthrene | terphenyl | 9,9-dimethylfluorene |
| 1-578 | phenanthrene | biphenyl | 9,9-dimethylfluorene |
| 1-579 | phenanthrene | biphenyl | 9,9-dimethylfluorene |

-continued
| Compound | ---Ar1 | ---Ar2 | ---Ar3 |
|---|---|---|---|
| 1-580 | 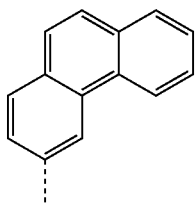 | 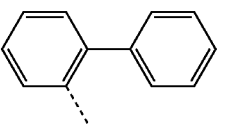 | 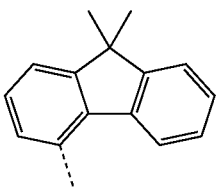 |
| 1-581 | 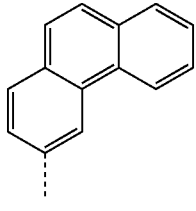 | 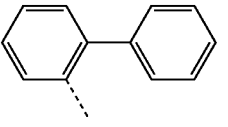 | 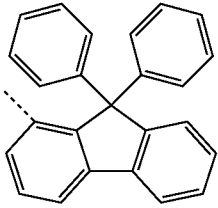 |
| 1-582 | 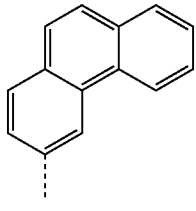 | 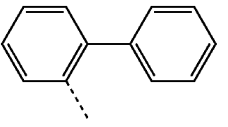 | 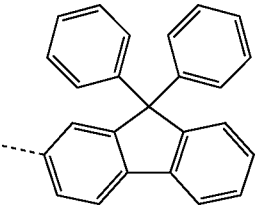 |
| 1-583 | 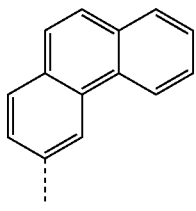 | 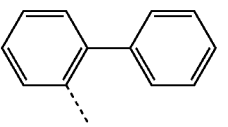 | 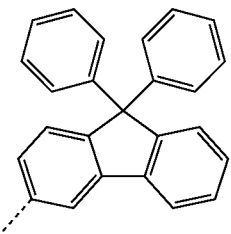 |
| 1-584 | 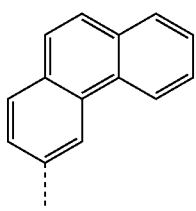 | 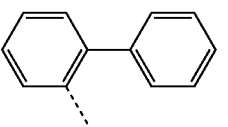 | 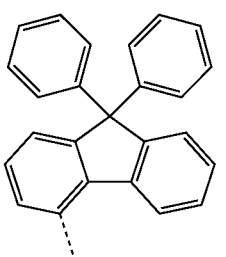 |
| 1-585 | 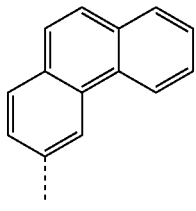 | 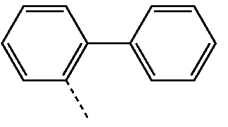 | 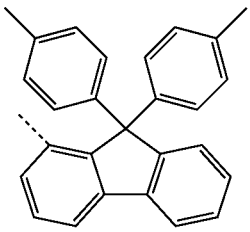 |

-continued
| Compound | ---Ar1 | ---Ar2 | ---Ar3 |
|---|---|---|---|
| 1-586 | 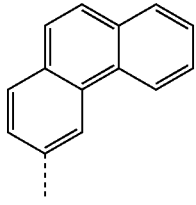 | 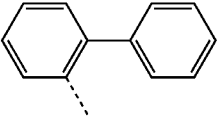 | 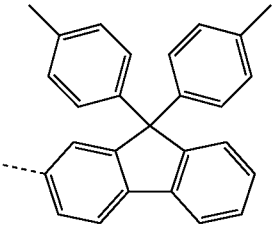 |
| 1-587 | 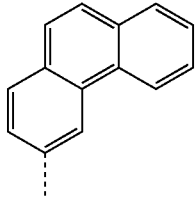 | 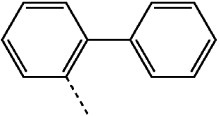 | 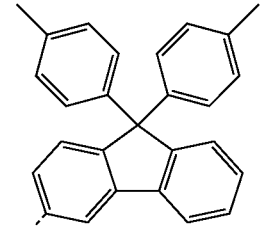 |
| 1-588 | 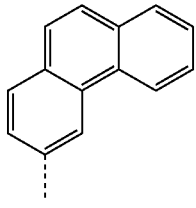 | 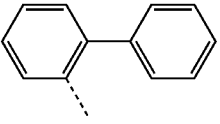 | 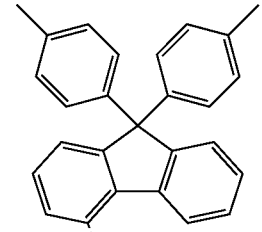 |
| 1-589 | 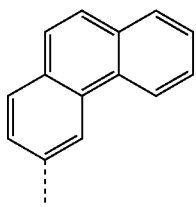 | 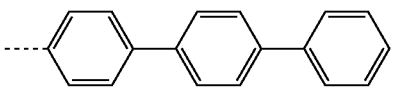 | 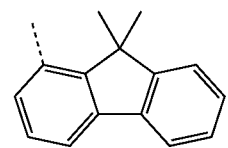 |
| 1-590 | 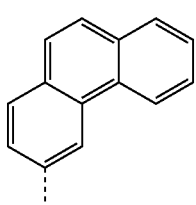 | 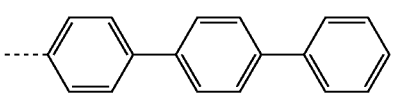 | 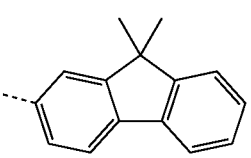 |
| 1-591 | 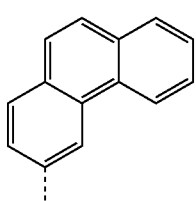 | 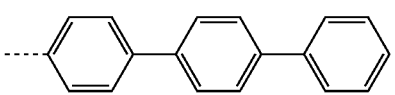 | 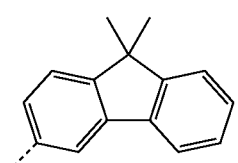 |

-continued

| Compound | ---Ar1 | ---Ar2 | ---Ar3 |
| --- | --- | --- | --- |
| 1-592 | | | |
| 1-593 | | | |
| 1-594 | | | |
| 1-595 | | | |
| 1-596 | | | |
| 1-597 | | | |

-continued
| Compound | - - - Ar1 | - - - Ar2 | - - - Ar3 |
|---|---|---|---|
| 1-598 | 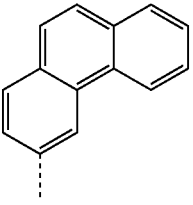 | 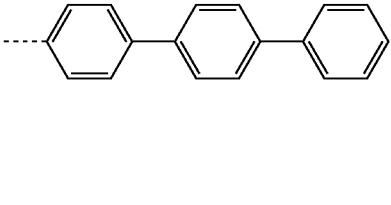 | 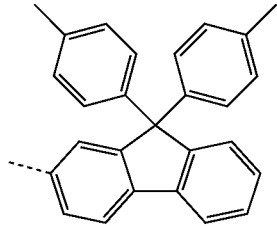 |
| 1-599 | 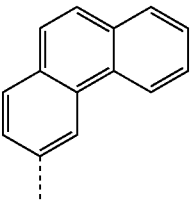 | 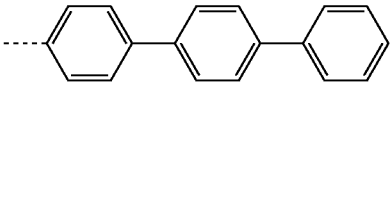 | 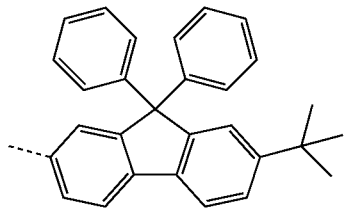 |
| 1-600 | 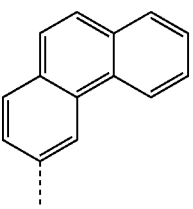 | 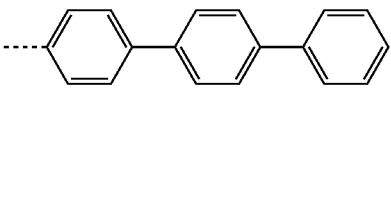 | 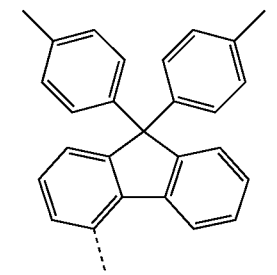 |
| 1-601 | 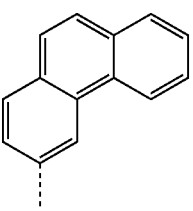 | 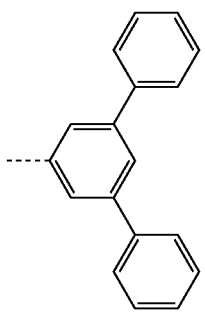 | 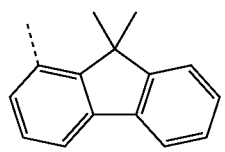 |
| 1-602 | 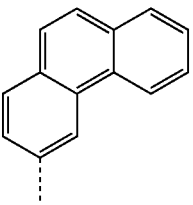 | 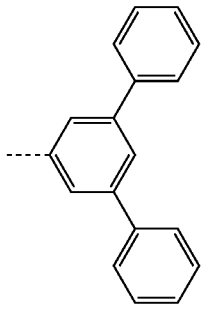 | 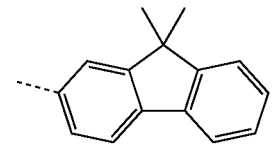 |

-continued
| Compound | --- Ar1 | --- Ar2 | --- Ar3 |
|---|---|---|---|
| 1-603 | 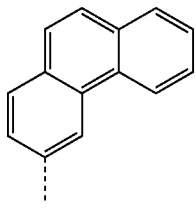 | 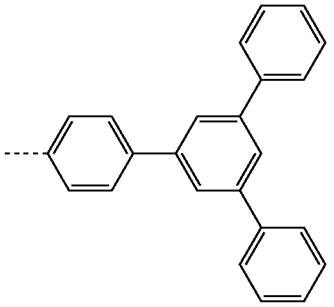 | 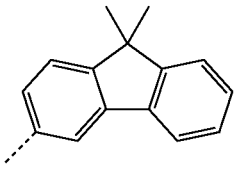 |
| 1-604 | 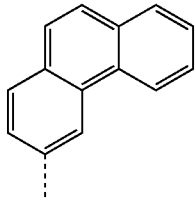 | 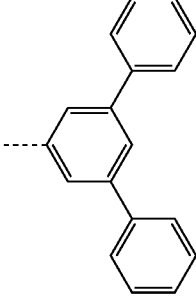 | 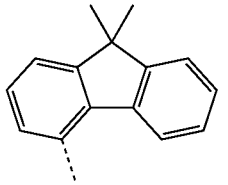 |
| 1-605 | 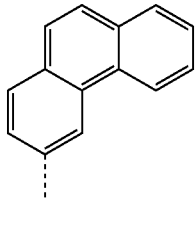 | 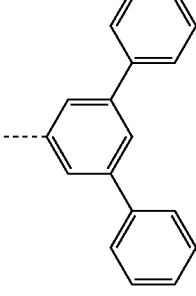 | 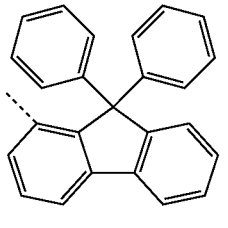 |
| 1-606 | 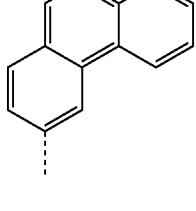 | 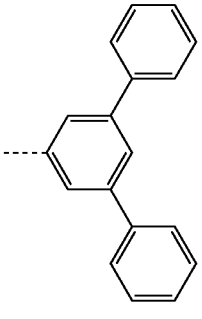 | 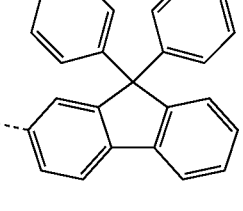 |
| 1-607 | 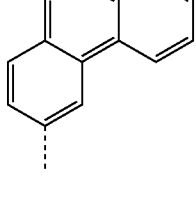 | 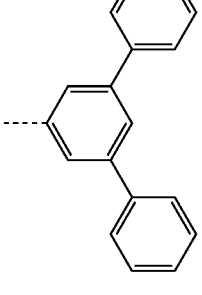 | 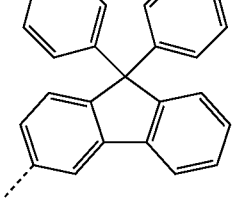 |

-continued

| Compound | - - - Ar1 | - - - Ar2 | - - - Ar3 |
|---|---|---|---|
| 1-608 | phenanthrene | m-terphenyl | 9,9-diphenylfluorene |
| 1-609 | phenanthrene | m-terphenyl | 9,9-dimethylbenzofluorene |
| 1-610 | phenanthrene | m-terphenyl | 9,9-di(p-tolyl)fluorene |
| 1-611 | phenanthrene | m-terphenyl | fluorene |
| 1-612 | phenanthrene | m-terphenyl | 9,9-di(p-tolyl)fluorene |

-continued

| Compound | - - - Ar1 | - - - Ar2 | - - - Ar3 |
|---|---|---|---|
| 1-613 | | | |
| 1-614 | | | |
| 1-615 | | | |
| 1-616 | | | |
| 1-617 | | | |
| 1-618 | | | |

-continued
| Compound | - - - Ar1 | - - - Ar2 | - - - Ar3 |
|---|---|---|---|
| 1-619 | 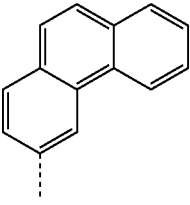 | 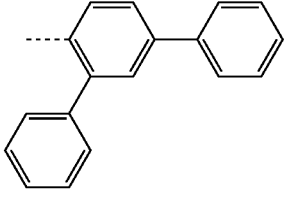 | 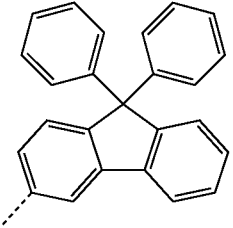 |
| 1-620 | 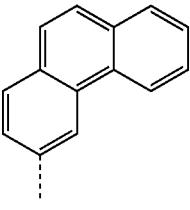 | 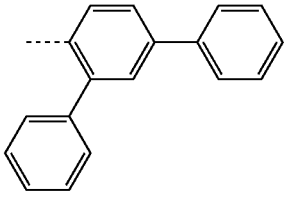 | 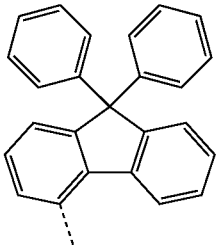 |
| 1-622 | 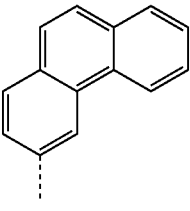 | 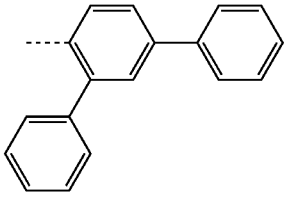 | 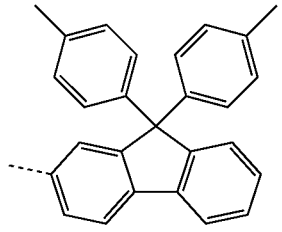 |
| 1-623 | 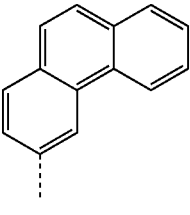 | 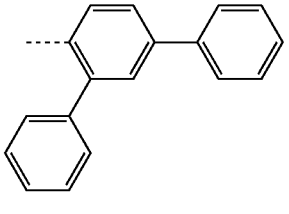 | 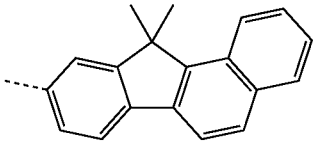 |
| 1-624 | 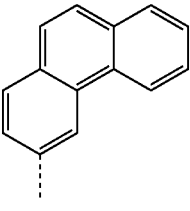 | 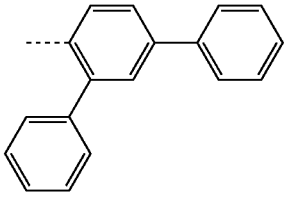 | 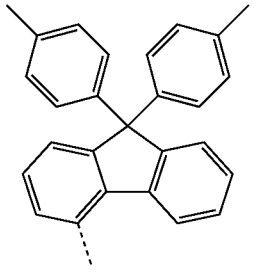 |
| 1-625 | 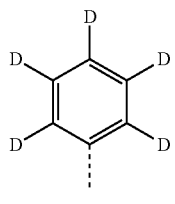 | 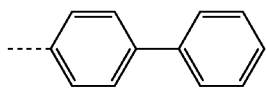 | 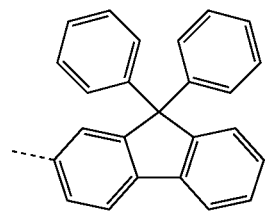 |

| Compound | - - - Ar1 | - - - Ar2 | - - - Ar3 |
|---|---|---|---|
| 1-626 | | | |
| 1-627 | | | |

8. A compound of Formula 1:

[Formula 1]

that is any one selected from the following compounds:

| Compound | - - - -Ar1 | - - - -Ar2 | - - - -Ar3 |
|---|---|---|---|
| 2-1 | | | |
| 2-2 | | | |

-continued
| Compound | ----Ar1 | ----Ar2 | ----Ar3 |
|---|---|---|---|
| 2-3 | 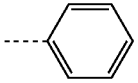 | 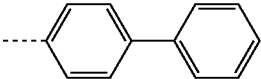 | 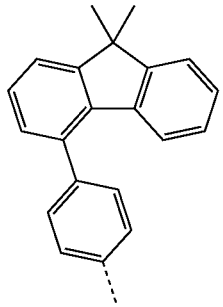 |
| 2-4 | 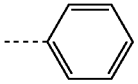 | 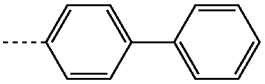 | 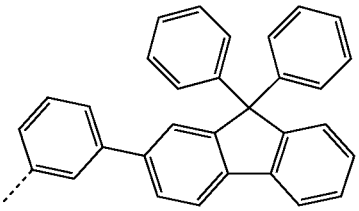 |
| 2-5 | 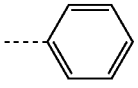 | 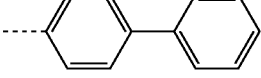 | 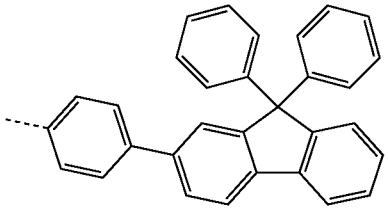 |
| 2-6 | 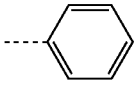 | 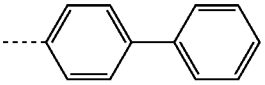 | 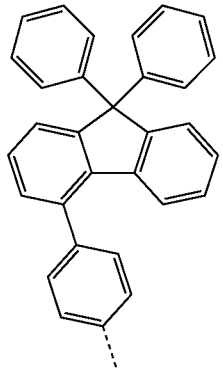 |
| 2-7 | 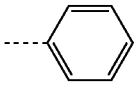 | 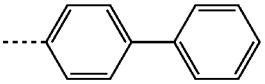 | 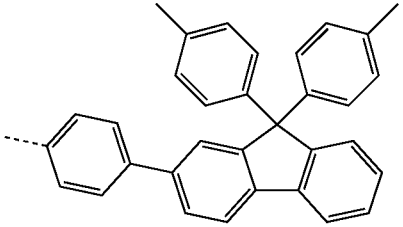 |

-continued

| Compound | ----Ar1 | ----Ar2 | ----Ar3 |
|---|---|---|---|
| 2-8 | phenyl | 4-biphenyl | 4-(7,7-dimethyl-7H-benzo[c]fluorenyl)phenyl |
| 2-9 | phenyl | 2-biphenyl | 4-(9,9-dimethyl-9H-fluoren-1-yl)phenyl |
| 2-10 | phenyl | 2-biphenyl | 4-(9,9-dimethyl-9H-fluoren-2-yl)phenyl |
| 2-11 | phenyl | 2-biphenyl | 4-(9,9-dimethyl-9H-fluoren-3-yl)phenyl |
| 2-12 | phenyl | 2-biphenyl | 4-(9,9-dimethyl-9H-fluoren-4-yl)phenyl |
| 2-13 | phenyl | 2-biphenyl | 4-(9,9-diphenyl-9H-fluoren-2-yl)phenyl |

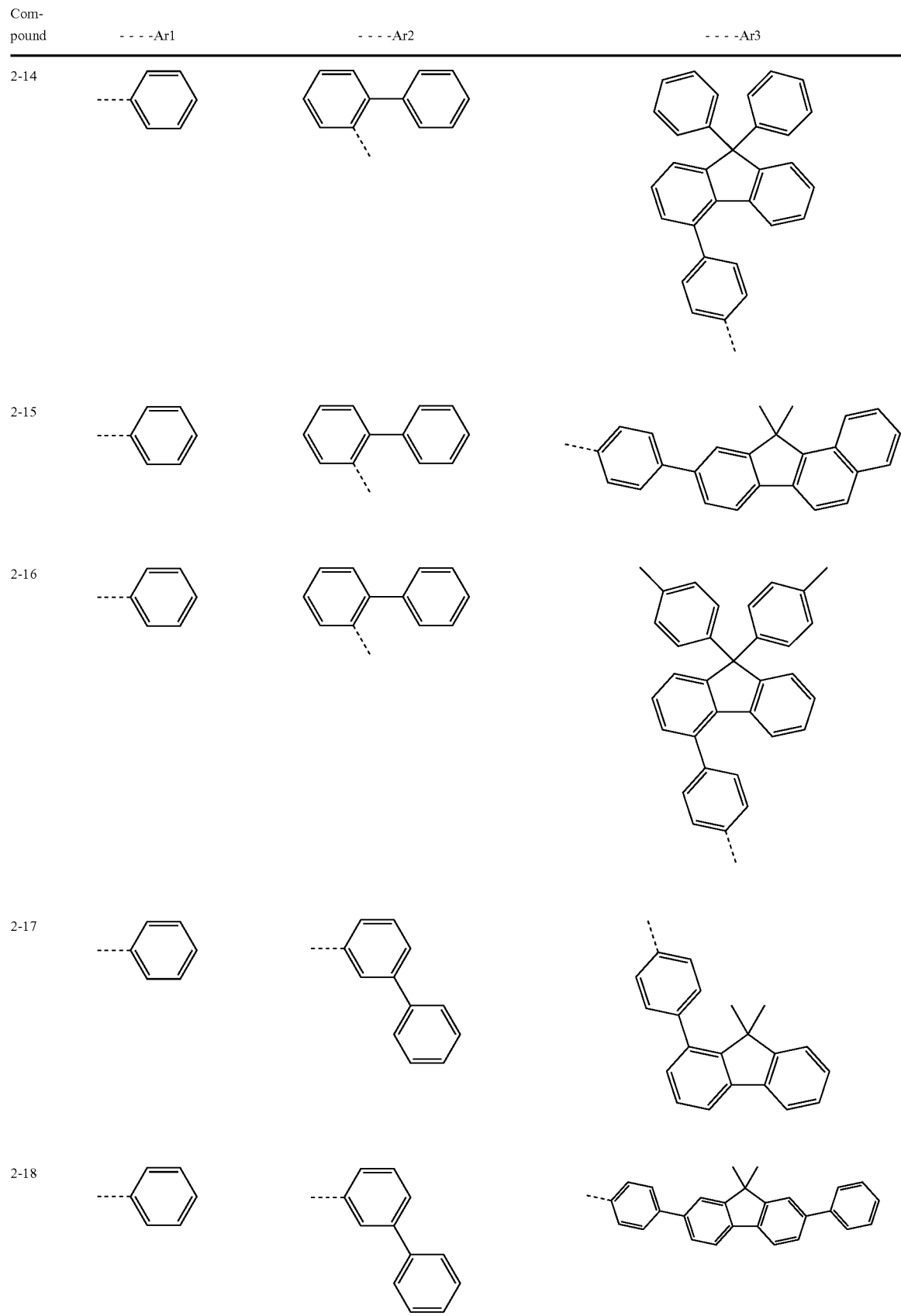

-continued

| Compound | - - - -Ar1 | - - - -Ar2 | - - - -Ar3 |
|---|---|---|---|
| 2-19 | phenyl | biphenyl (meta) | 9,9-dimethyl-benz[b]fluorenyl-phenyl |
| 2-20 | phenyl | 3-(naphthalen-2-yl)phenyl | 4-(9,9-dimethylfluoren-4-yl)phenyl |
| 2-21 | phenyl | biphenyl (meta) | 4-(7-tert-butyl-9,9-diphenylfluoren-2-yl)phenyl |
| 2-22 | phenyl | biphenyl (meta) | 4-(9,9-diphenylfluoren-4-yl)phenyl |
| 2-23 | phenyl | biphenyl (meta) | 4-(9,9-di-p-tolylfluoren-2-yl)phenyl |

-continued
| Compound | ----Ar1 | ----Ar2 | ----Ar3 |
|---|---|---|---|
| 2-24 | 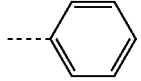 | 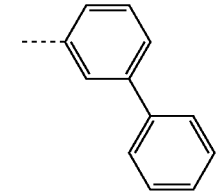 | 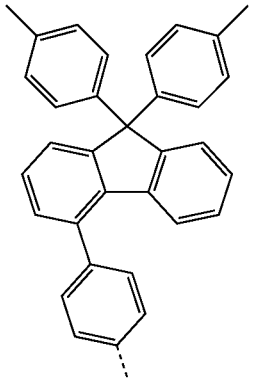 |
| 2-25 | 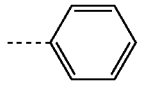 | 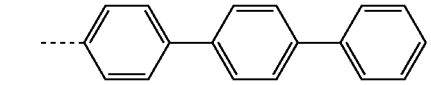 | 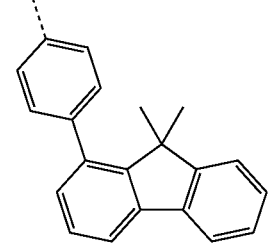 |
| 2-26 | 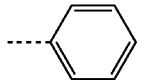 | 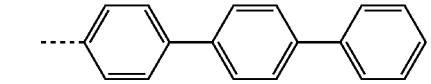 | 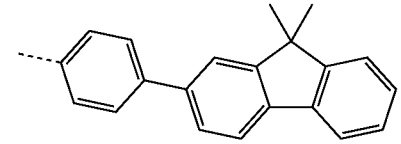 |
| 2-27 | 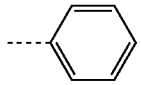 | 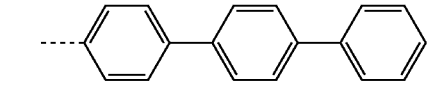 | 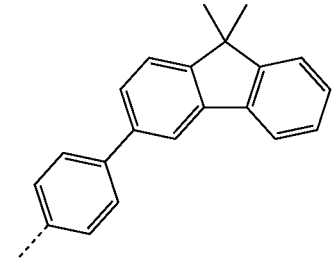 |
| 2-28 | 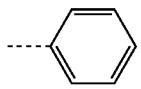 | 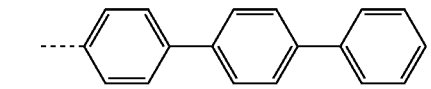 | 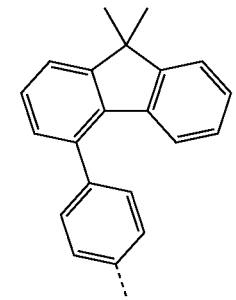 |

-continued
| Compound | ----Ar1 | ----Ar2 | ----Ar3 |
|---|---|---|---|
| 2-29 | 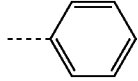 | 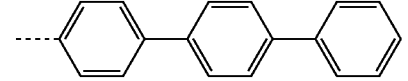 | 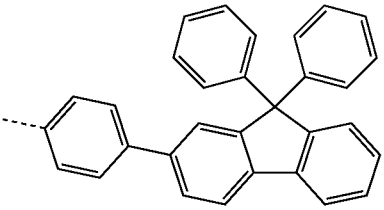 |
| 2-30 | 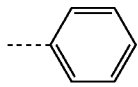 | 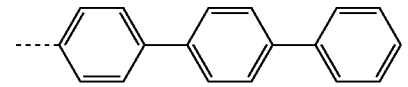 | 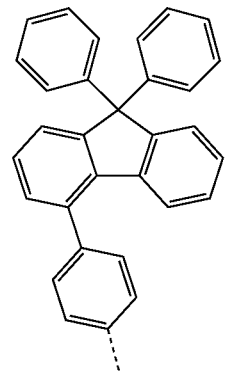 |
| 2-31 | 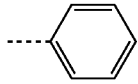 | 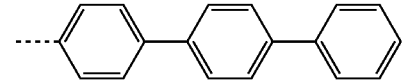 | 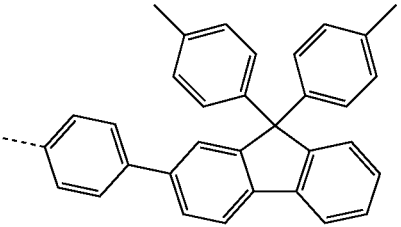 |
| 2-32 | 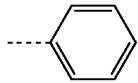 | 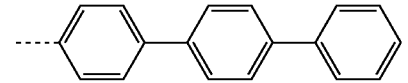 | 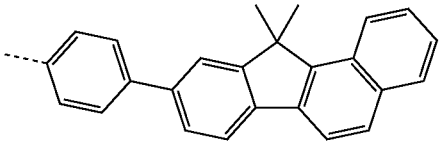 |
| 2-33 | 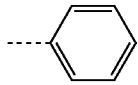 | 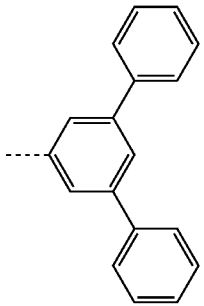 | 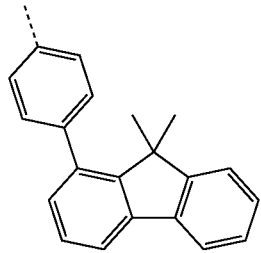 |

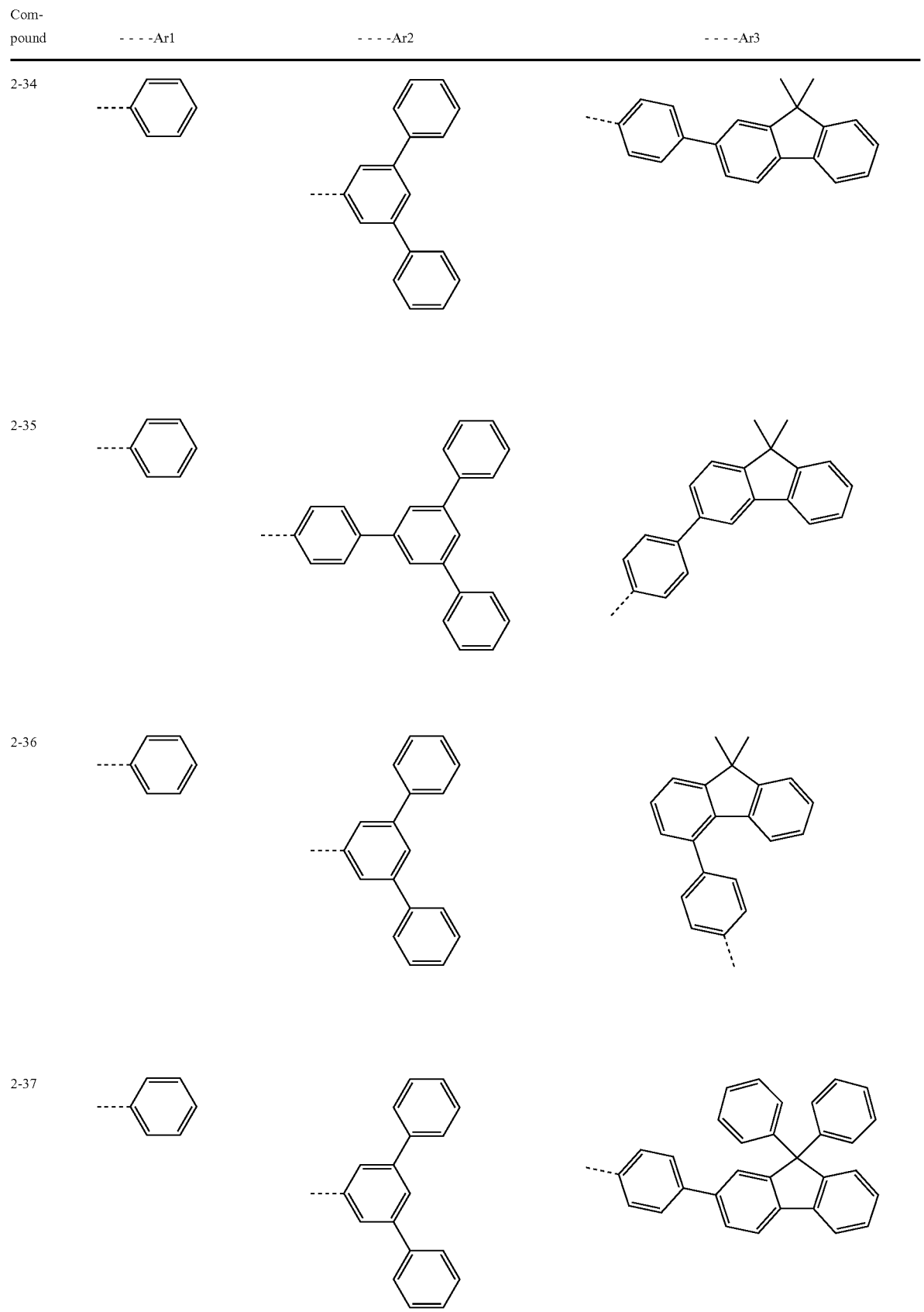

-continued

| Compound | ----Ar1 | ----Ar2 | ----Ar3 |
|---|---|---|---|
| 2-38 | | | |
| 2-39 | | | |
| 2-40 | | | |
| 2-41 | | | |
| 2-42 | | | |

-continued

| Compound | ----Ar1 | ----Ar2 | ----Ar3 |
|---|---|---|---|
| 2-43 | | | |
| 2-44 | | | |
| 2-45 | | | |
| 2-46 | | | |
| 2-47 | | | |

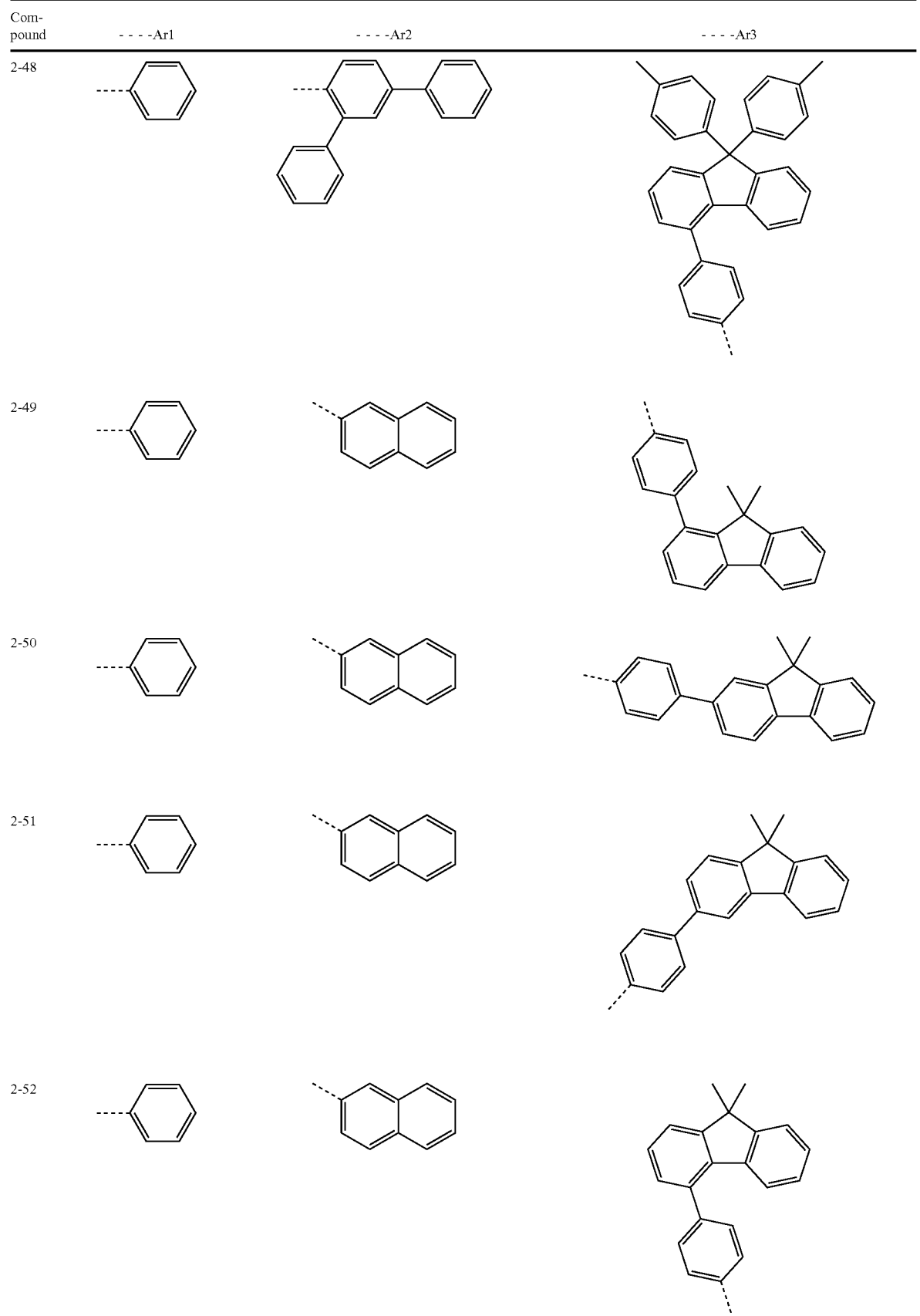

-continued
| Compound | ----Ar1 | ----Ar2 | ----Ar3 |
|---|---|---|---|
| 2-53 | 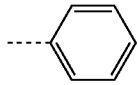 | 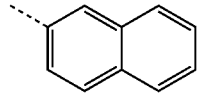 | 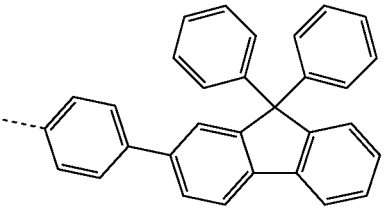 |
| 2-54 | 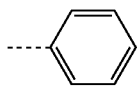 | 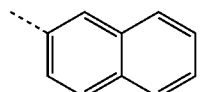 | 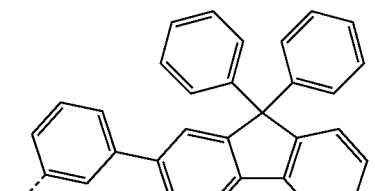 |
| 2-55 | 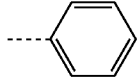 | 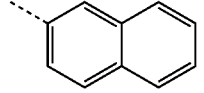 | 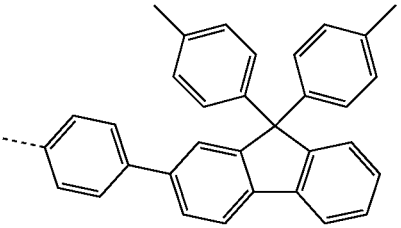 |
| 2-56 | 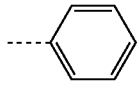 | 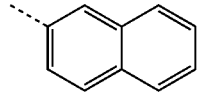 | 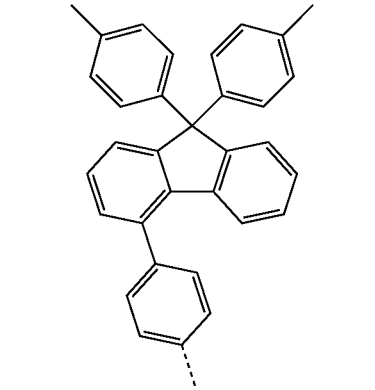 |
| 2-57 | 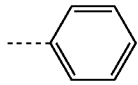 | 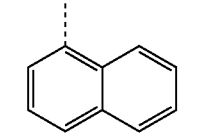 | 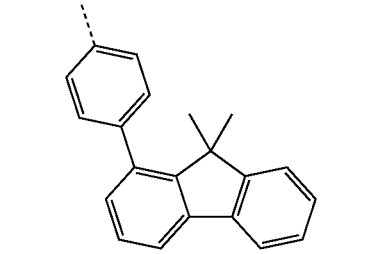 |
| 2-58 | 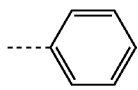 | 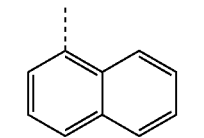 | 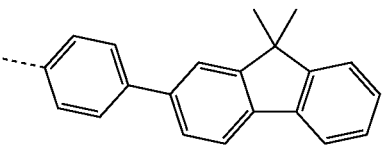 |

-continued

| Compound | ----Ar1 | ----Ar2 | ----Ar3 |
|---|---|---|---|
| 2-59 | phenyl | naphthyl | 9,9-dimethylfluorene-phenyl |
| 2-60 | phenyl | naphthyl | fluorene-biphenyl |
| 2-61 | phenyl | naphthyl | 9,9-diphenylfluorene-phenyl |
| 2-62 | phenyl | naphthyl | 9,9-diphenylfluorene-phenyl |
| 2-63 | phenyl | naphthyl | 9,9-di(p-tolyl)fluorene-phenyl |

-continued
| Compound | - - - -Ar1 | - - - -Ar2 | - - - -Ar3 |
|---|---|---|---|
| 2-64 | | | |
| 2-65 | | | |
| 2-66 | | | |
| 2-67 | | | |
| 2-68 | | | |
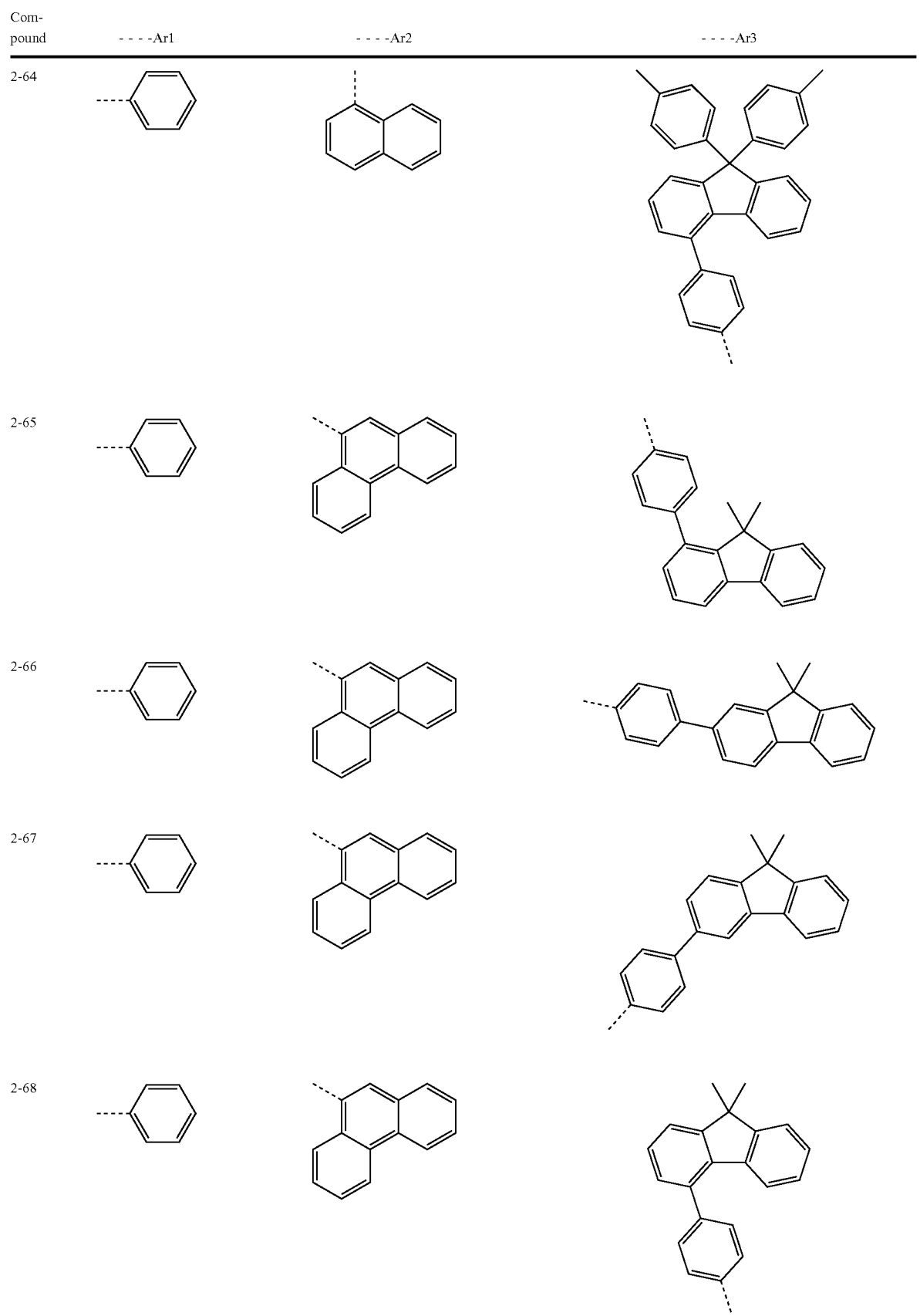

-continued
| Compound | ----Ar1 | ----Ar2 | ----Ar3 |
|---|---|---|---|
| 2-69 | 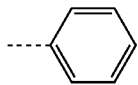 | 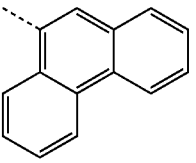 | 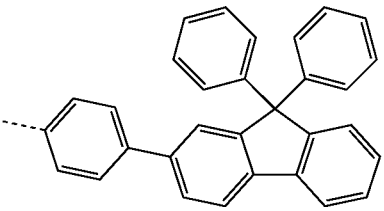 |
| 2-70 | 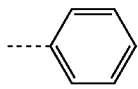 | 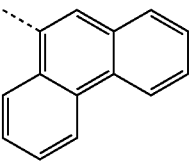 | 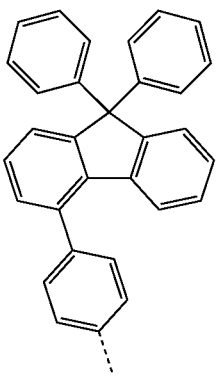 |
| 2-71 | 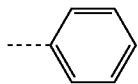 | 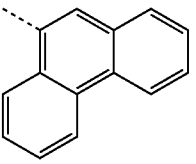 | 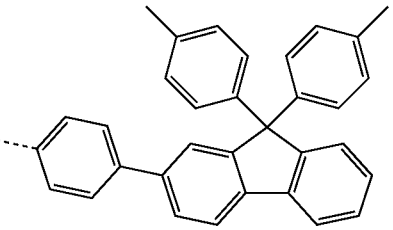 |
| 2-72 | 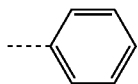 | 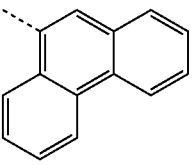 | 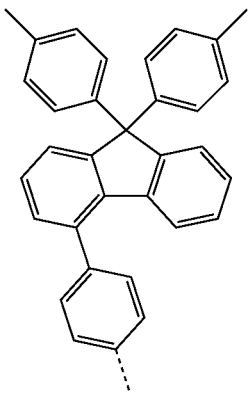 |
| 2-73 | 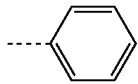 | 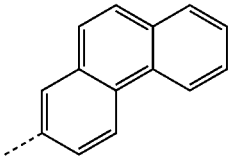 | 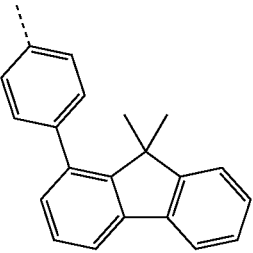 |

-continued

| Compound | ----Ar1 | ----Ar2 | ----Ar3 |
|---|---|---|---|
| 2-74 | phenyl | phenanthrenyl | 9,9-dimethylfluorenyl-phenyl |
| 2-75 | phenyl | phenanthrenyl | 9,9-dimethylfluorenyl-biphenyl |
| 2-76 | phenyl | phenanthrenyl | 9,9-dimethylfluorenyl-phenyl |
| 2-77 | phenyl | phenanthrenyl | 9,9-diphenylfluorenyl-phenyl |
| 2-78 | phenyl | phenanthrenyl | 9,9-diphenylfluorenyl-phenyl |

-continued
| Compound | ----Ar1 | ----Ar2 | ----Ar3 |
|---|---|---|---|
| 2-79 | 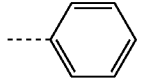 | 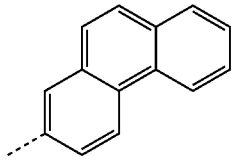 | 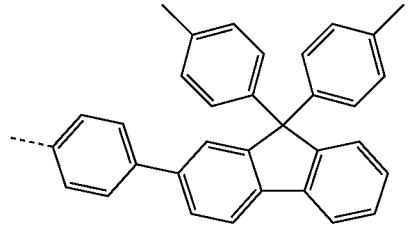 |
| 2-80 | 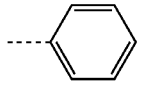 | 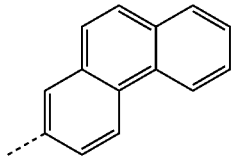 | 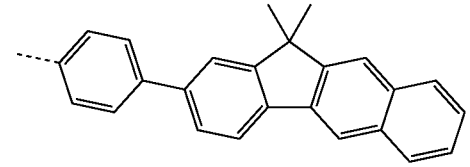 |
| 2-81 | 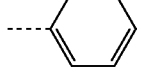 | 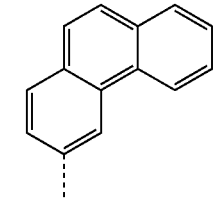 | 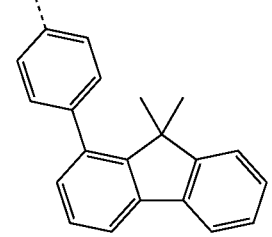 |
| 2-82 | 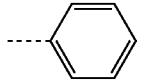 | 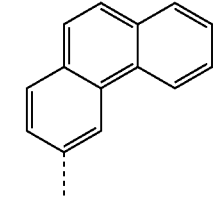 | 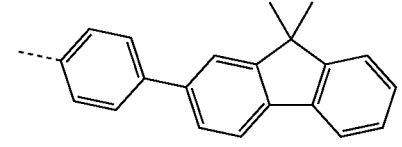 |
| 2-83 | 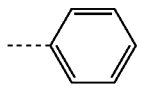 | 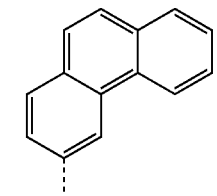 | 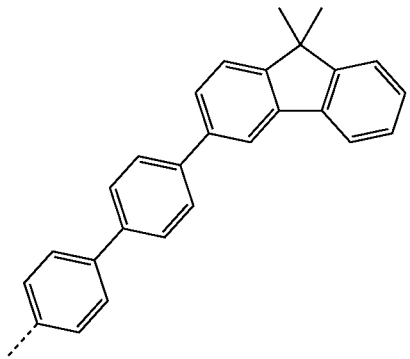 |

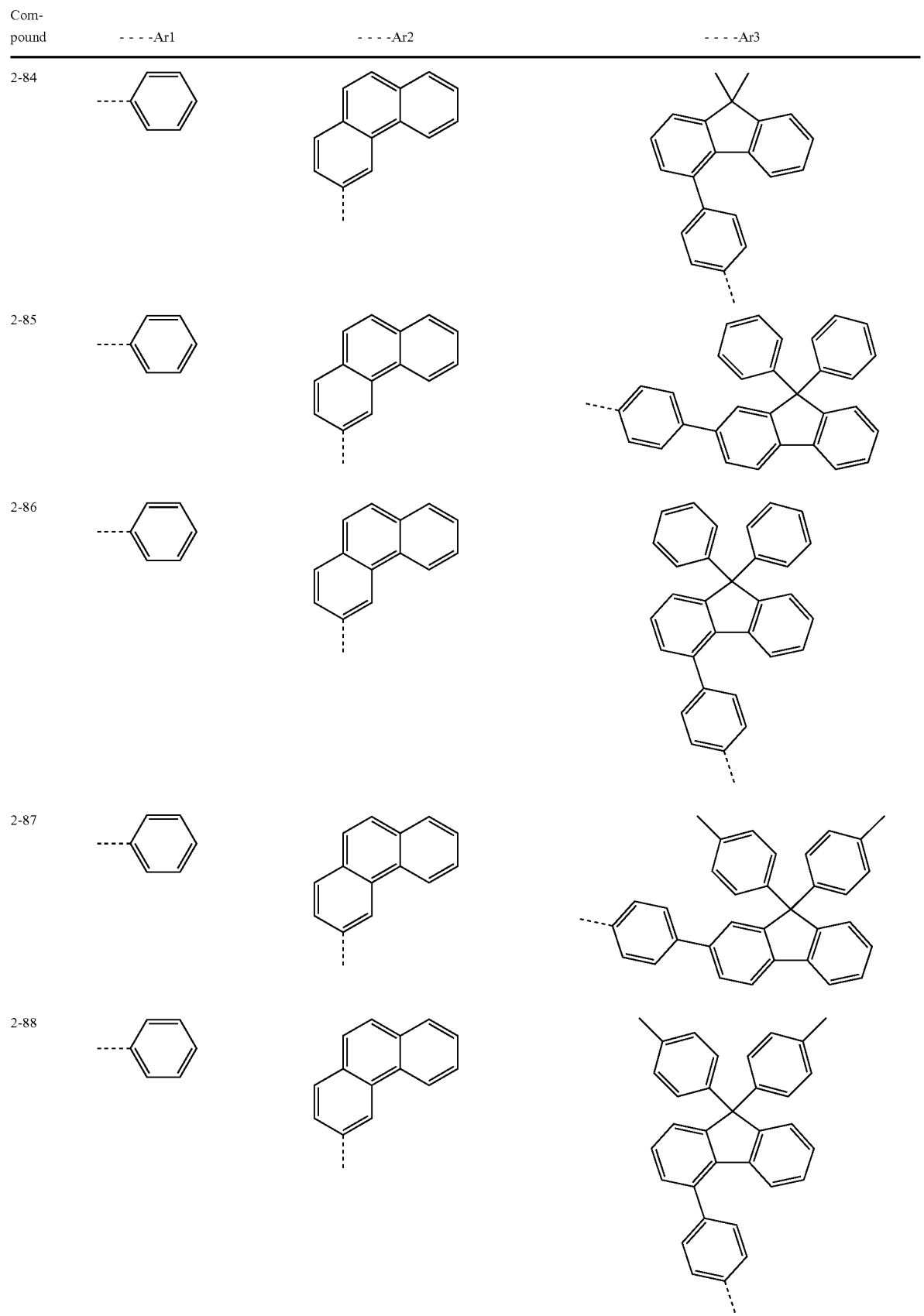

-continued

| Compound | ----Ar1 | ----Ar2 | ----Ar3 |
|---|---|---|---|
| 2-89 | phenyl | biphenyl | 1-(9,9-dimethylfluoren-?-yl)naphthalen-?-yl |
| 2-90 | phenyl | biphenyl | 4-(9,9-dimethylfluoren-2-yl)naphthalen-1-yl |
| 2-91 | phenyl | biphenyl | 4-(9,9-dimethylfluoren-3-yl)naphthalen-1-yl |
| 2-92 | phenyl | biphenyl | 5-(9,9-dimethylfluoren-4-yl)naphthalen-2-yl |
| 2-93 | phenyl | biphenyl | 4-(9,9-diphenylfluoren-2-yl)naphthalen-1-yl |

-continued

| Compound | ----Ar1 | ----Ar2 | ----Ar3 |
|---|---|---|---|
| 2-94 | phenyl | 4-biphenyl | 4-(9,9-diphenylfluoren-4-yl)naphthalen-1-yl |
| 2-95 | phenyl | 4-biphenyl | 6-(9,9-di-p-tolylfluoren-2-yl)naphthalen-2-yl |
| 2-96 | phenyl | 4-biphenyl | 4-(7,7-dimethyl-7H-benzo[c]fluoren-9-yl)naphthalen-1-yl |
| 2-97 | phenyl | 2-biphenyl | 4-(9,9-dimethylfluoren-1-yl)naphthalen-1-yl |
| 2-98 | phenyl | 2-biphenyl | 4-(9,9-dimethylfluoren-2-yl)naphthalen-1-yl |

-continued

| Compound | ----Ar1 | ----Ar2 | ----Ar3 |
|---|---|---|---|
| 2-99 | phenyl | 2-biphenyl | 4-(9,9-dimethylfluoren-3-yl)naphthalen-1-yl |
| 2-100 | phenyl | 2-biphenyl | 4-(9,9-dimethylfluoren-4-yl)naphthalen-1-yl |
| 2-101 | phenyl | 2-biphenyl | 4-(9,9-diphenylfluoren-2-yl)naphthalen-1-yl |
| 2-102 | phenyl | 2-biphenyl | 4-(9,9-diphenylfluoren-4-yl)naphthalen-1-yl |
| 2-103 | phenyl | 2-biphenyl | 8-(9,9-di-p-tolylfluoren-2-yl)naphthalen-1-yl |

-continued

| Compound | ----Ar1 | ----Ar2 | ----Ar3 |
|---|---|---|---|
| 2-104 | phenyl | 2-biphenyl | 9,9-bis(4-methylphenyl)fluorene-naphthyl |
| 2-105 | phenyl | 3-biphenyl | biphenyl-(9,9-dimethylfluoren-1-yl) |
| 2-106 | phenyl | 3-biphenyl | naphthyl-(9,9-dimethylfluoren-2-yl) |
| 2-107 | phenyl | 3-biphenyl | naphthyl-(9,9-dimethylfluoren-3-yl) |
| 2-108 | phenyl | 3-biphenyl | naphthyl-(9,9-dimethylfluoren-4-yl) |

-continued
| Compound | ----Ar1 | ----Ar2 | ----Ar3 |
|---|---|---|---|
| 2-109 | 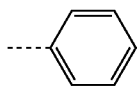 | 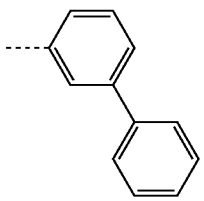 | 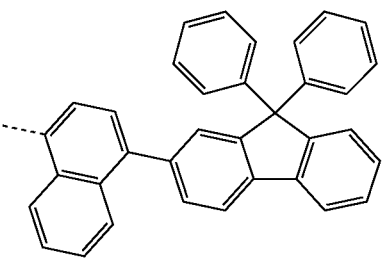 |
| 2-110 | 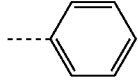 | 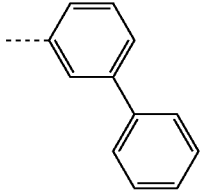 | 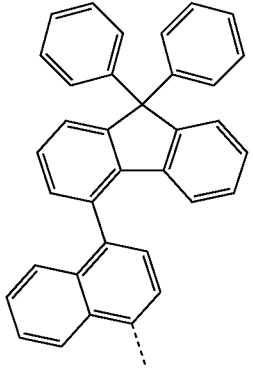 |
| 2-111 | 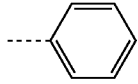 | 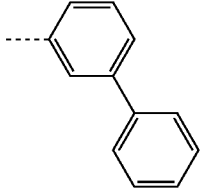 | 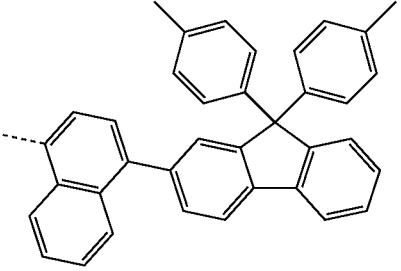 |
| 2-112 | 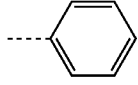 | 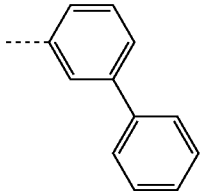 | 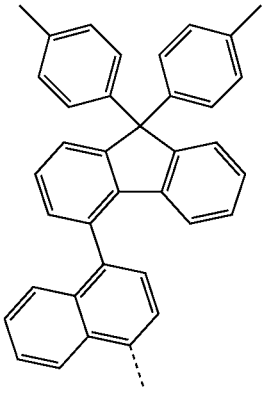 |
| 2-113 | 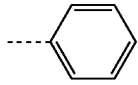 | 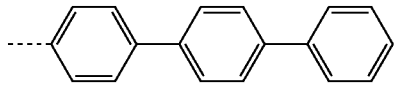 | 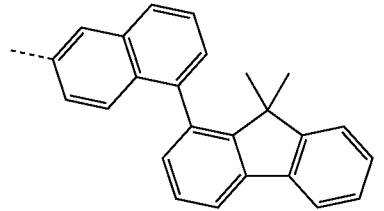 |

-continued
| Compound | ----Ar1 | ----Ar2 | ----Ar3 |
|---|---|---|---|
| 2-114 | 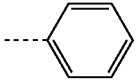 | 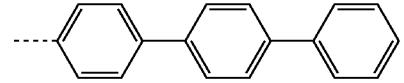 | 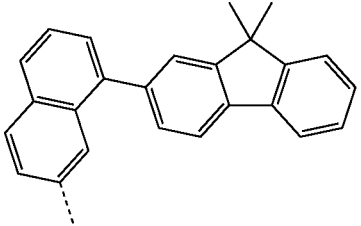 |
| 2-115 | 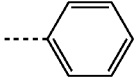 | 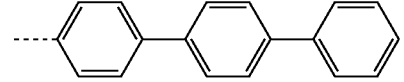 | 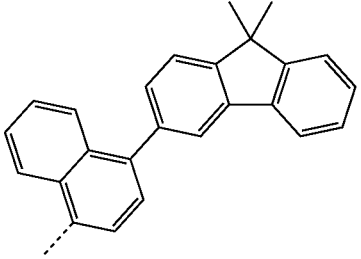 |
| 2-116 | 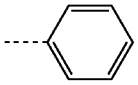 | 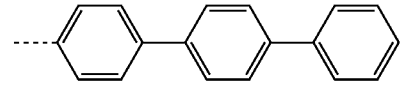 | 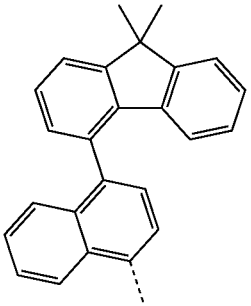 |
| 2-117 | 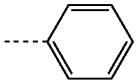 | 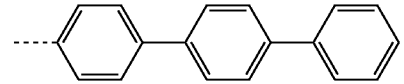 | 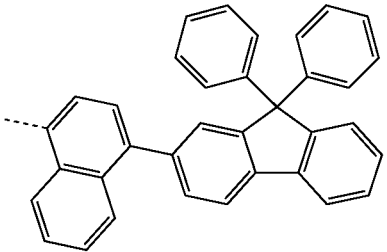 |
| 2-118 | 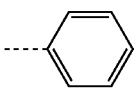 | 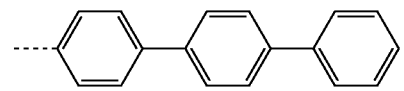 | 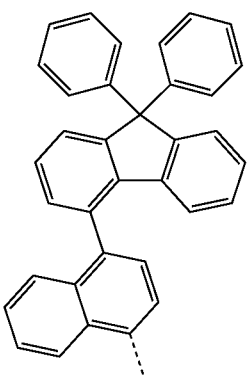 |

-continued

| Compound | ----Ar1 | ----Ar2 | ----Ar3 |
|---|---|---|---|
| 2-119 | | | |
| 2-120 | | | |
| 2-121 | | | |
| 2-122 | | | |

-continued

| Compound | ----Ar1 | ----Ar2 | ----Ar3 |
|---|---|---|---|
| 2-123 | | | |
| 2-124 | | | |
| 2-125 | | | |
| 2-126 | | | |

-continued

| Compound | ----Ar1 | ----Ar2 | ----Ar3 |
|---|---|---|---|
| 2-127 | | | |
| 2-128 | | | |
| 2-129 | | | |
| 2-130 | | | |
| 2-131 | | | |

-continued

| Compound | ----Ar1 | ----Ar2 | ----Ar3 |
|---|---|---|---|
| 2-132 | | | |
| 2-133 | | | |
| 2-134 | | | |
| 2-135 | | | |
| 2-136 | | | |

-continued

| Compound | ----Ar1 | ----Ar2 | ----Ar3 |
|---|---|---|---|
| 2-137 | phenyl | 2-naphthyl | 1-(9,9-dimethylfluoren-4-yl)naphthalen-4-yl |
| 2-138 | phenyl | 2-naphthyl | 4-(9,9-dimethylfluoren-2-yl)naphthalen-1-yl |
| 2-139 | phenyl | 2-naphthyl | 4-(9,9-dimethylfluoren-3-yl)naphthalen-1-yl |
| 2-140 | phenyl | 2-naphthyl | 4-(9,9-dimethylfluoren-4-yl)naphthalen-1-yl |
| 2-141 | phenyl | 2-naphthyl | 2-(9,9-diphenylfluoren-2-yl)naphthalen-3-yl |

-continued
| Compound | ----Ar1 | ----Ar2 | ----Ar3 |
|---|---|---|---|
| 2-142 | 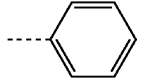 | 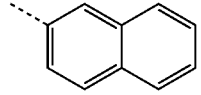 | 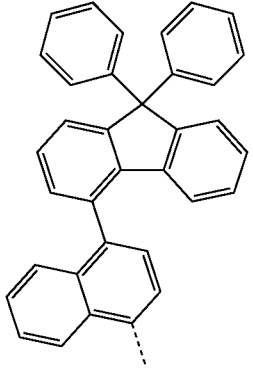 |
| 2-143 | 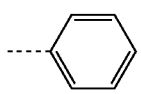 | 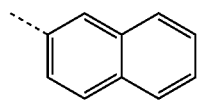 | 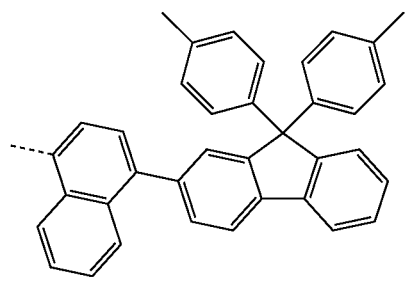 |
| 2-144 | 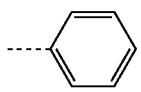 | 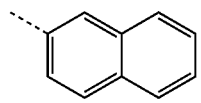 | 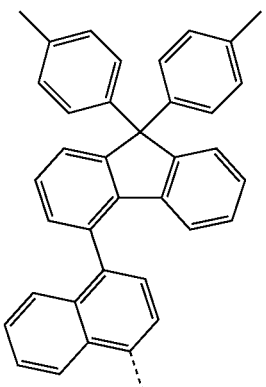 |
| 2-145 | 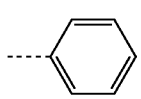 | 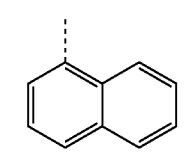 | 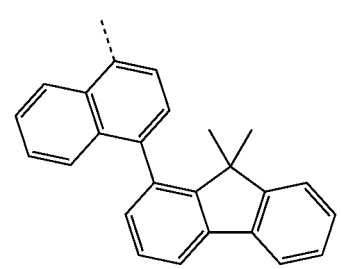 |
| 2-146 | 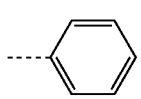 | 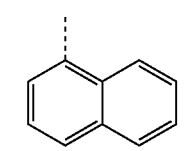 | 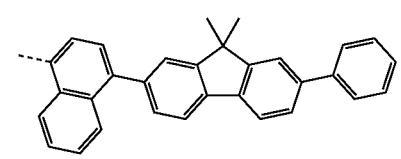 |

-continued

| Compound | ----Ar1 | ----Ar2 | ----Ar3 |
|---|---|---|---|
| 2-147 | phenyl | naphthyl | 4-(9,9-dimethylfluoren-3-yl)naphthalen-1-yl-phenyl |
| 2-148 | phenyl | naphthyl | 4-(9,9-dimethylfluoren-4-yl)naphthalen-1-yl |
| 2-149 | phenyl | naphthyl | 4-(9,9-diphenylfluoren-2-yl)naphthalen-1-yl |
| 2-150 | phenyl | naphthyl | 4-(9,9-diphenylfluoren-4-yl)naphthalen-1-yl |

-continued

| Compound | ----Ar1 | ----Ar2 | ----Ar3 |
| --- | --- | --- | --- |
| 2-151 | phenyl | 1-naphthyl | 4-(9,9-di-p-tolyl-9H-fluoren-2-yl)naphthalen-1-yl |
| 2-152 | phenyl | 1-naphthyl | 4-(9,9-di-p-tolyl-9H-fluoren-4-yl)naphthalen-1-yl |
| 2-153 | phenyl | phenanthren-9-yl | 4-(9,9-dimethyl-9H-fluoren-1-yl)naphthalen-1-yl |
| 2-154 | phenyl | phenanthren-9-yl | 4-(9,9-dimethyl-9H-fluoren-2-yl)naphthalen-1-yl |
| 2-155 | phenyl | phenanthren-9-yl | 4-(9,9-dimethyl-9H-fluoren-3-yl)naphthalen-1-yl |

-continued
| Compound | - - - -Ar1 | - - - -Ar2 | - - - -Ar3 |
| --- | --- | --- | --- |
| 2-156 | 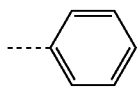 | 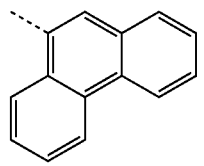 | 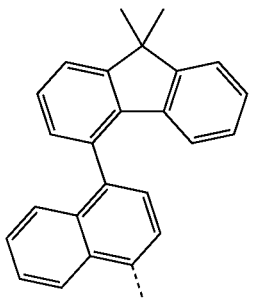 |
| 2-157 | 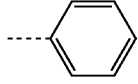 | 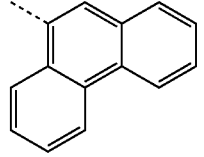 | 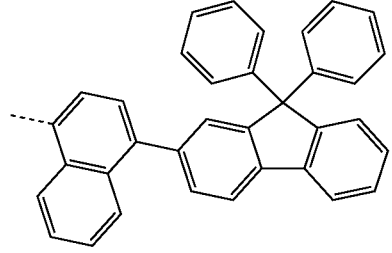 |
| 2-158 | 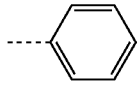 | 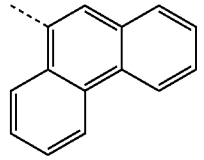 | 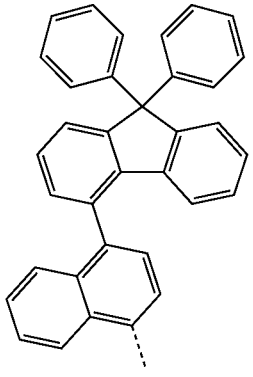 |
| 2-159 | 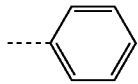 | 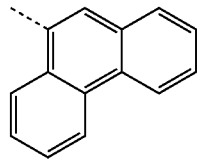 | 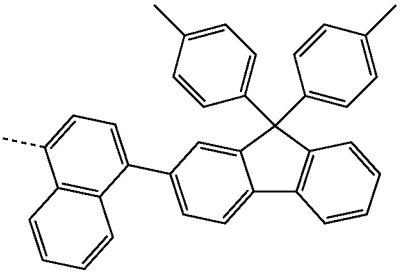 |

| Compound | ----Ar1 | ----Ar2 | ----Ar3 |
|---|---|---|---|
| 2-160 | | | |
| 2-161 | | | |
| 2-162 | | | |
| 2-163 | | | |
| 2-164 | | | |

-continued

| Compound | ----Ar1 | ----Ar2 | ----Ar3 |
|---|---|---|---|
| 2-165 | | | |
| 2-166 | | | |
| 2-167 | | | |
| 2-168 | | | |
| 2-169 | | | |

-continued
| Compound | ----Ar1 | ----Ar2 | ----Ar3 |
|---|---|---|---|
| 2-170 | 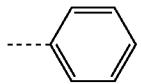 | 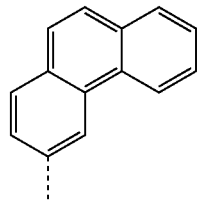 | 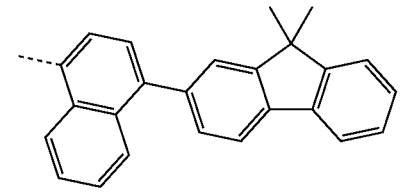 |
| 2-171 | 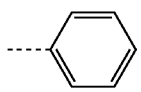 | 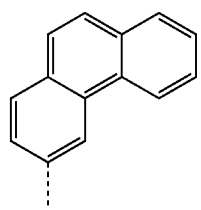 | 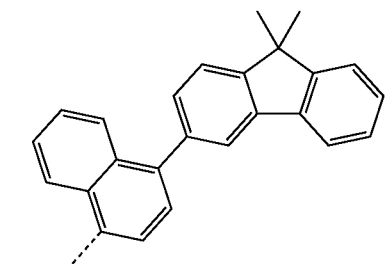 |
| 2-172 | 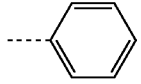 | 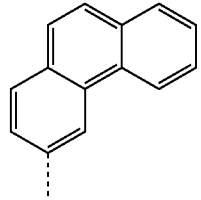 | 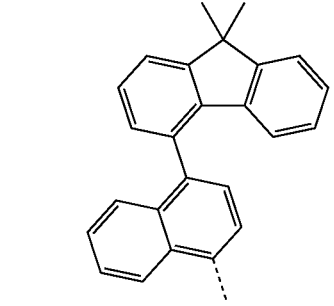 |
| 2-173 | 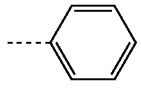 | 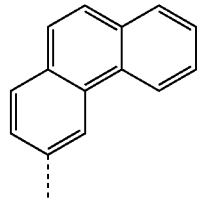 | 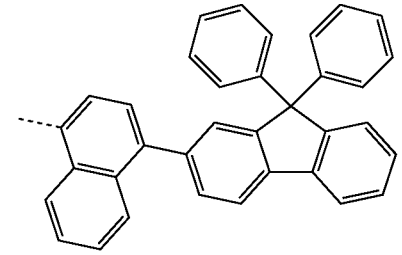 |
| 2-174 | 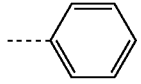 | 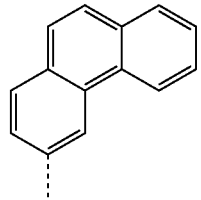 | 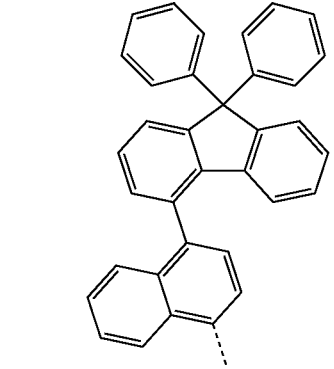 |

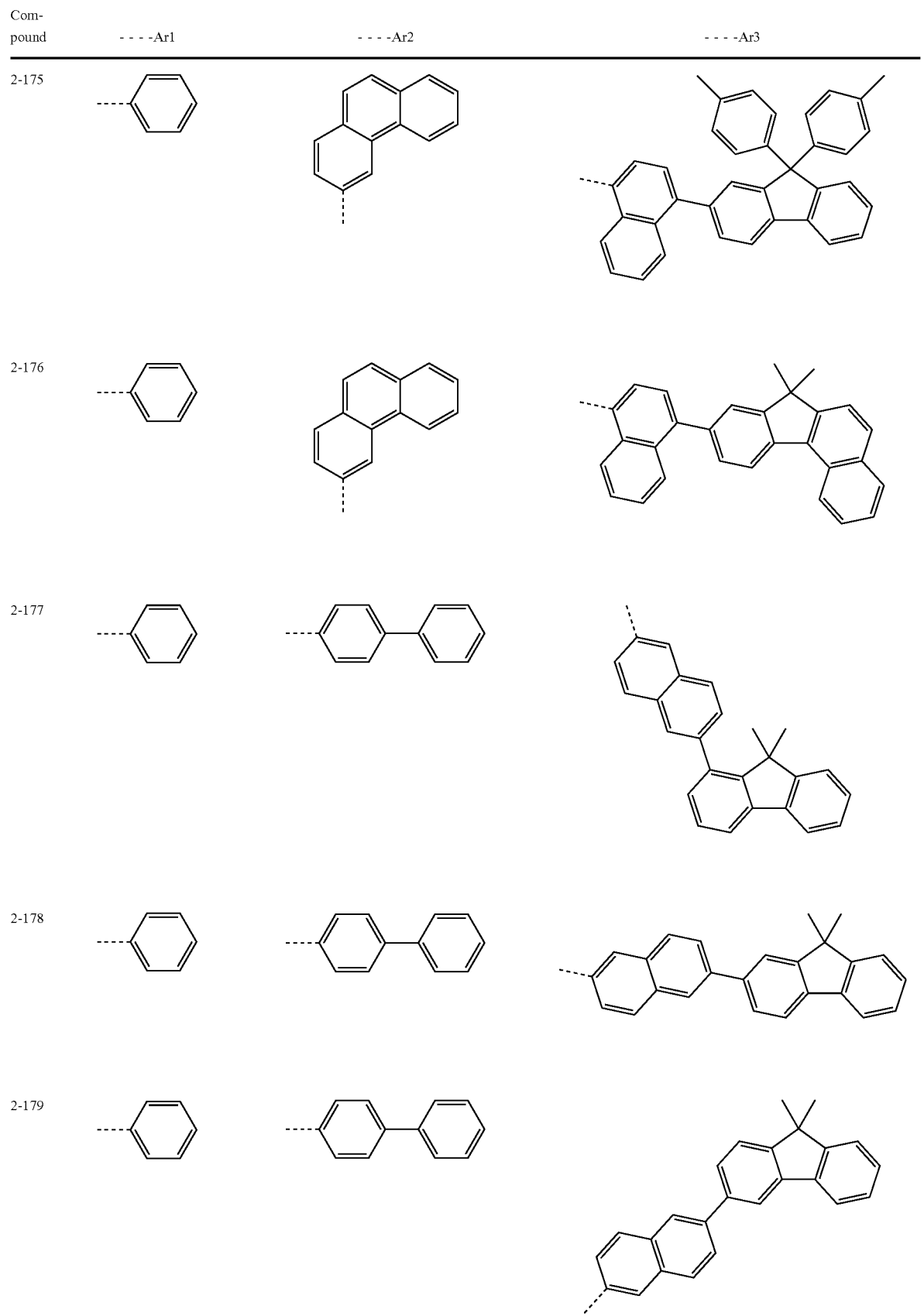

-continued

| Compound | ----Ar1 | ----Ar2 | ----Ar3 |
|---|---|---|---|
| 2-180 | phenyl | biphenyl-4-yl | 4-(6-yl-naphth-2-yl)-9,9-dimethylfluoren-4-yl |
| 2-181 | phenyl | biphenyl-4-yl | 2-(6-yl-naphth-2-yl)-9,9-diphenylfluoren-2-yl |
| 2-182 | phenyl | biphenyl-4-yl | 4-(6-yl-naphth-2-yl)-9,9-diphenylfluoren-4-yl |
| 2-183 | phenyl | biphenyl-4-yl | 2-(6-yl-naphth-2-yl)-9,9-di(p-tolyl)fluoren-2-yl |

741 742
-continued
| Compound | ----Ar1 | ----Ar2 | ----Ar3 |
|---|---|---|---|
| 2-184 | 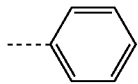 | 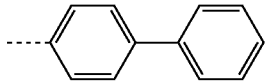 | 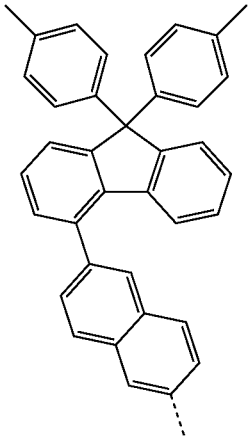 |
| 2-185 | 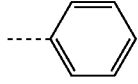 | 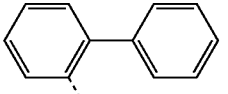 | 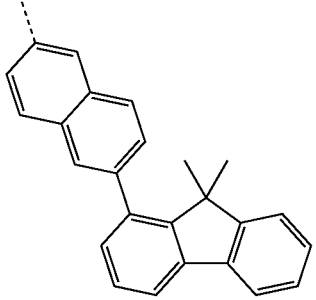 |
| 2-186 | 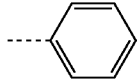 | 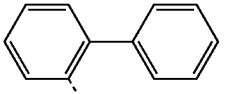 | 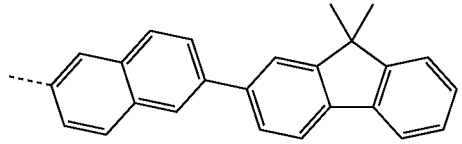 |
| 2-187 | 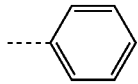 | 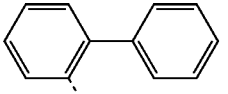 | 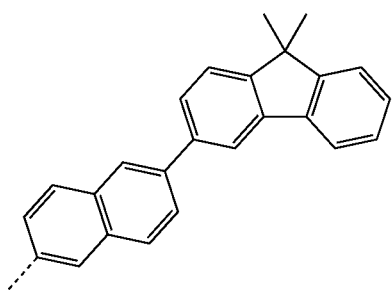 |
| 2-188 | 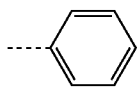 | 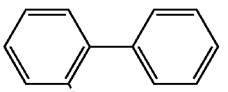 | 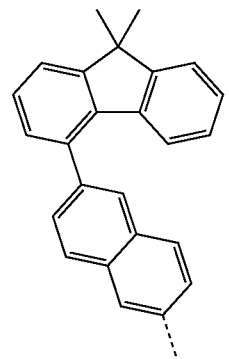 |

-continued

| Compound | ----Ar1 | ----Ar2 | ----Ar3 |
|---|---|---|---|
| 2-189 | phenyl | 2-biphenyl | 6-(9,9-diphenyl-fluoren-2-yl)naphthalen-2-yl |
| 2-190 | phenyl | 2-biphenyl | 6-(9,9-diphenyl-fluoren-4-yl)naphthalen-2-yl |
| 2-191 | phenyl | 2-biphenyl | 6-(9,9-di-p-tolyl-fluoren-2-yl)naphthalen-2-yl |
| 2-192 | phenyl | 2-biphenyl | 6-(9,9-dimethyl-benzofluoren-2-yl)naphthalen-2-yl |
| 2-193 | phenyl | 3-biphenyl | 6-(9,9-dimethyl-fluoren-4-yl)naphthalen-2-yl |

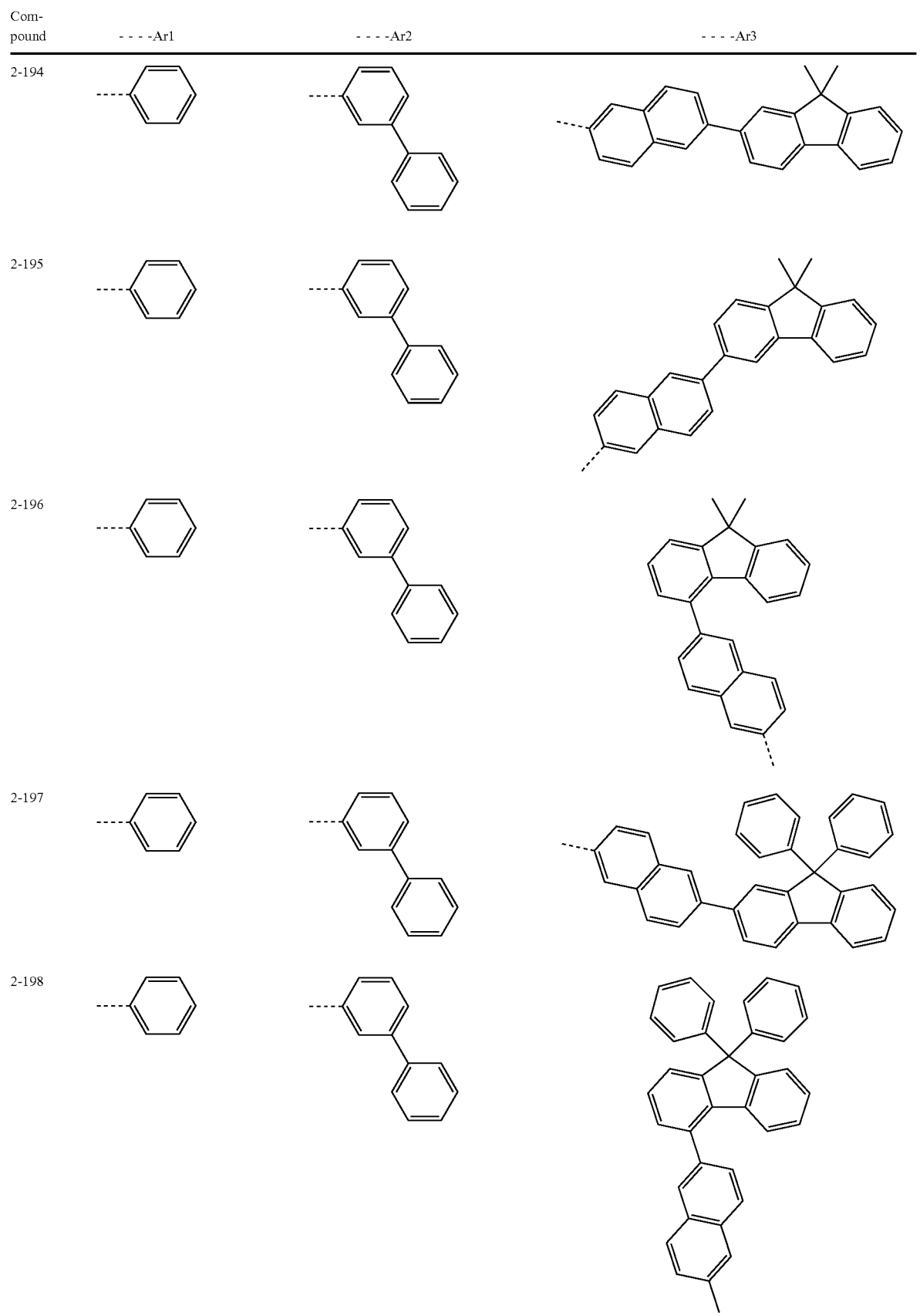

-continued

| Compound | ----Ar1 | ----Ar2 | ----Ar3 |
|---|---|---|---|
| 2-199 | | | |
| 2-200 | | | |
| 2-201 | | | |
| 2-202 | | | |
| 2-203 | | | |

-continued
| Compound | ----Ar1 | ----Ar2 | ----Ar3 |
|---|---|---|---|
| 2-204 | 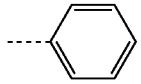 | 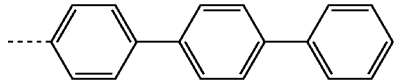 | 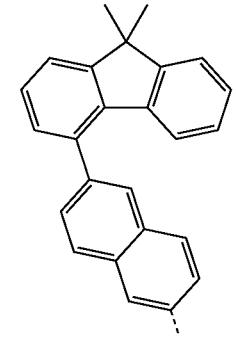 |
| 2-205 | 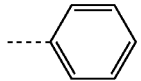 | 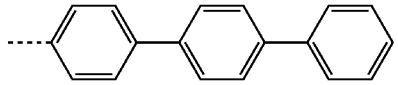 | 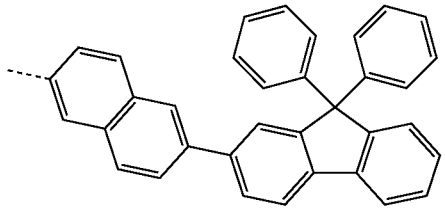 |
| 2-206 | 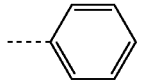 | 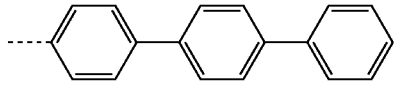 | 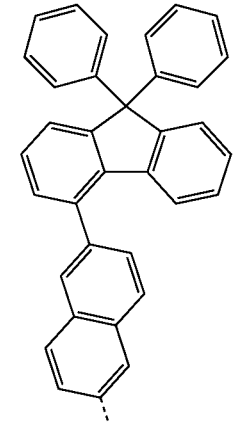 |
| 2-207 | 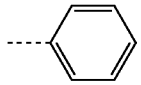 | 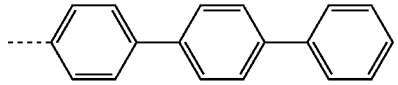 | 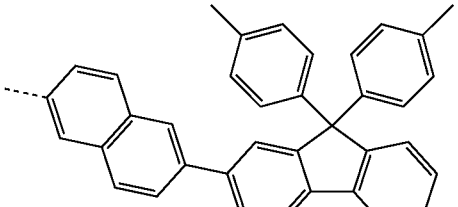 |
| 2-209 | 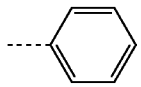 | 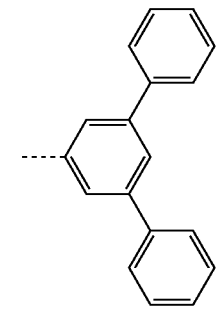 | 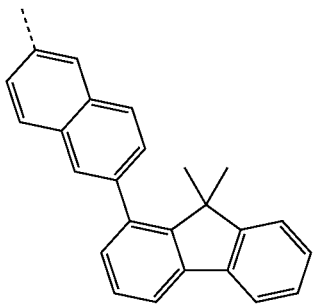 |

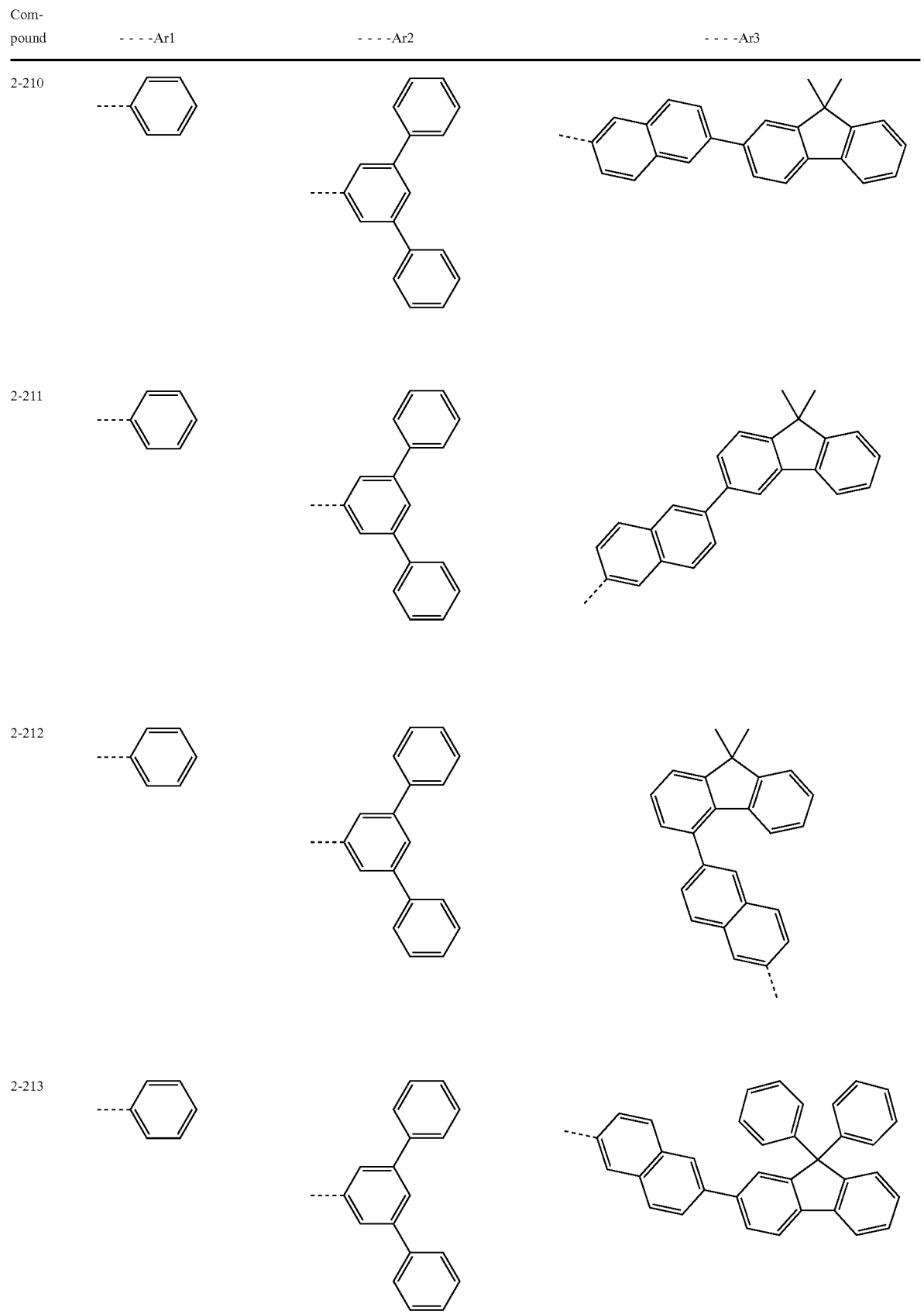

-continued
| Compound | ----Ar1 | ----Ar2 | ----Ar3 |
|---|---|---|---|
| 2-214 | 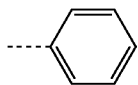 | 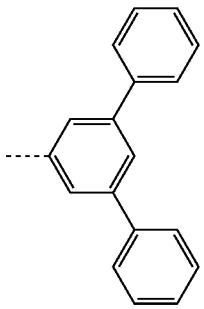 | 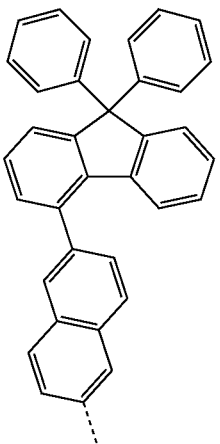 |
| 2-215 | 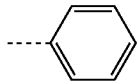 | 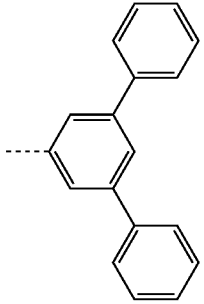 | 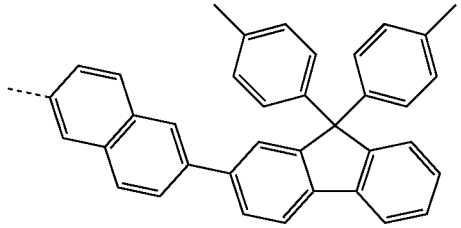 |
| 2-216 | 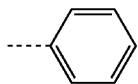 | 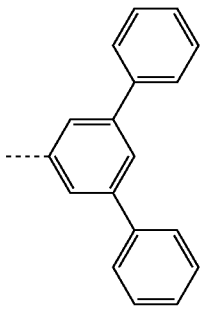 | 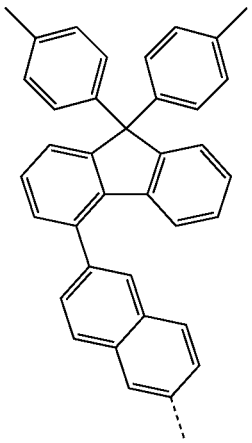 |
| 2-217 | 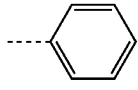 | 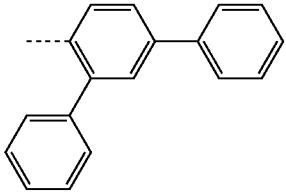 | 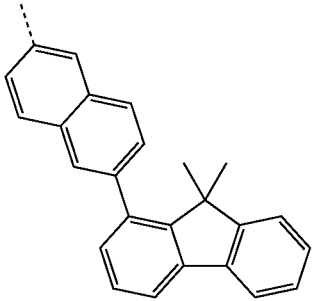 |

-continued
| Compound | ----Ar1 | ----Ar2 | ----Ar3 |
|---|---|---|---|
| 2-218 | | | |
| 2-219 | | | |
| 2-220 | | | |
| 2-221 | | | |
| 2-222 | | | |
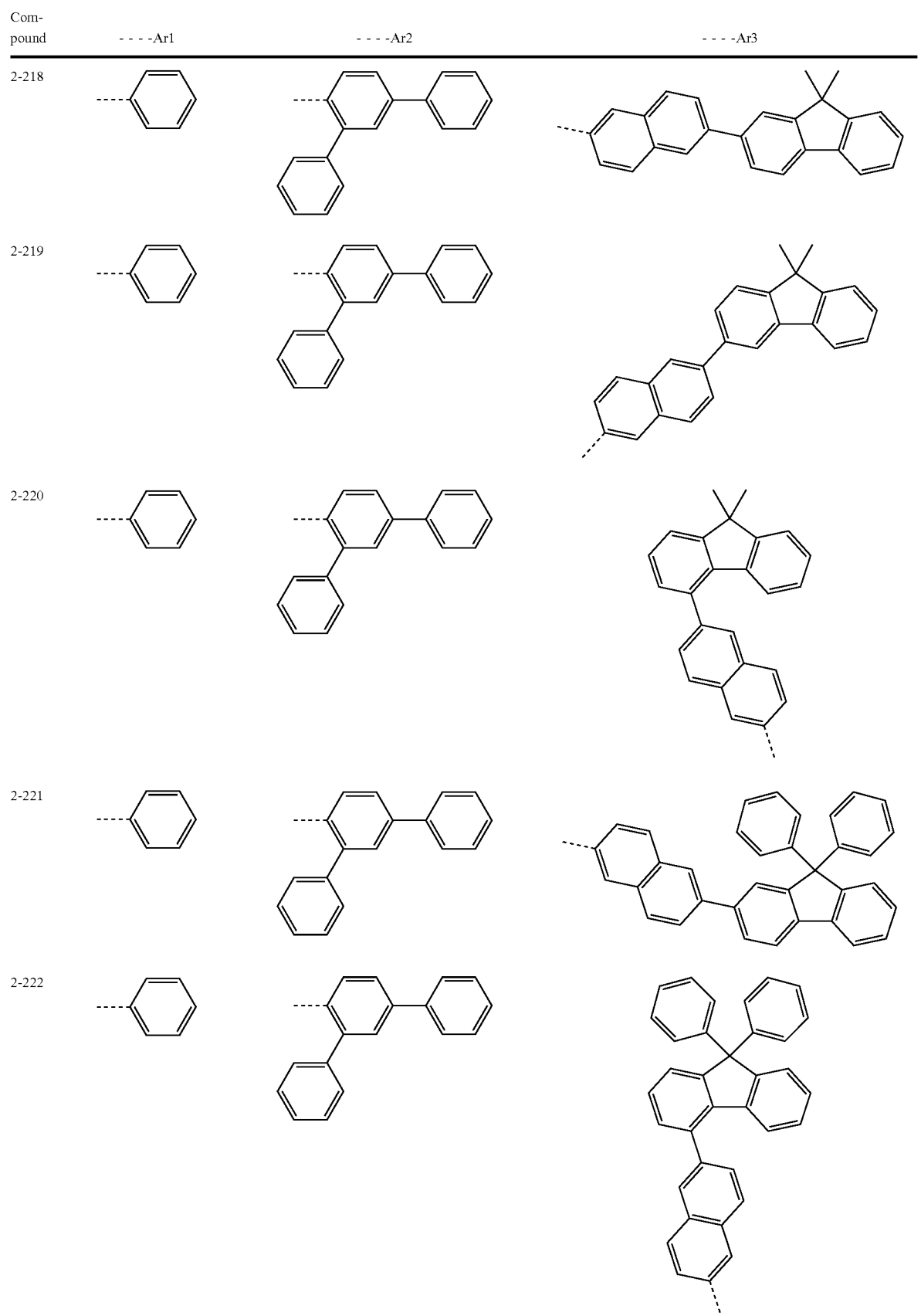

-continued

| Compound | ----Ar1 | ----Ar2 | ----Ar3 |
|---|---|---|---|
| 2-223 | phenyl | 2,5-diphenylphenyl | 6-(9,9-di-p-tolyl-9H-fluoren-2-yl)naphthalen-2-yl |
| 2-224 | phenyl | 3,5-diphenylphenyl | 6-(9,9-di-p-tolyl-9H-fluoren-4-yl)naphthalen-2-yl |
| 2-225 | phenyl | naphthalen-2-yl | 6-(9,9-dimethyl-9H-fluoren-1-yl)naphthalen-2-yl |
| 2-226 | phenyl | naphthalen-2-yl | 6-(9,9-dimethyl-9H-fluoren-2-yl)naphthalen-2-yl |
| 2-227 | phenyl | naphthalen-2-yl | 6-(9,9-dimethyl-9H-fluoren-3-yl)naphthalen-2-yl |

-continued
| Compound | ----Ar1 | ----Ar2 | ----Ar3 |
|---|---|---|---|
| 2-228 | 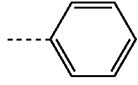 | 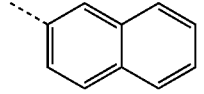 | 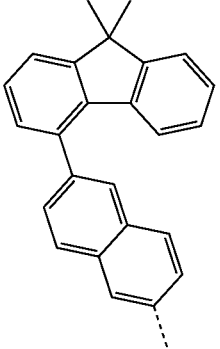 |
| 2-229 | 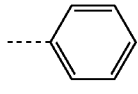 | 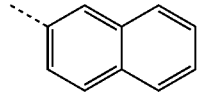 | 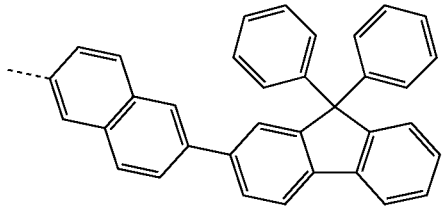 |
| 2-230 | 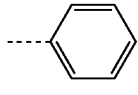 | 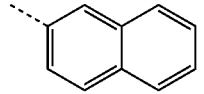 | 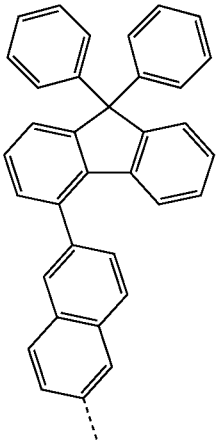 |
| 2-231 | 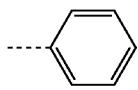 | 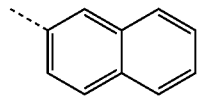 | 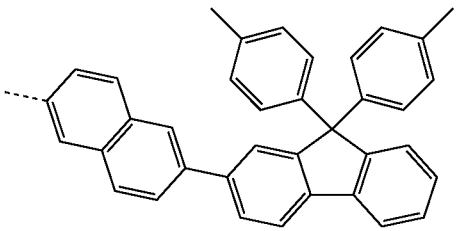 |
| 2-232 | 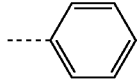 | 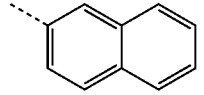 | 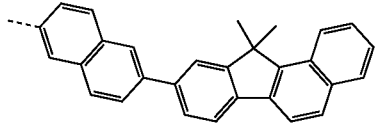 |

-continued
| Compound | ----Ar1 | ----Ar2 | ----Ar3 |
|---|---|---|---|
| 2-233 | 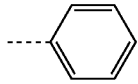 | 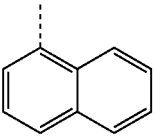 | 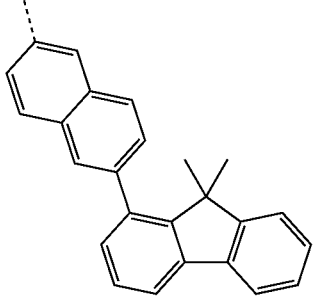 |
| 2-234 | 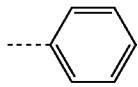 | 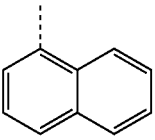 | 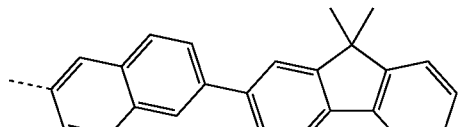 |
| 2-235 | 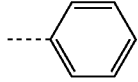 | 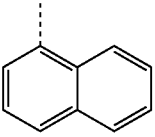 | 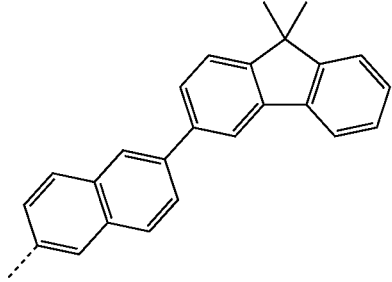 |
| 2-236 | 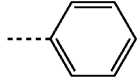 | 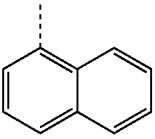 | 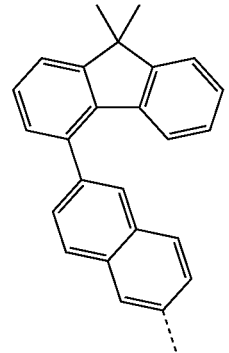 |
| 2-237 | 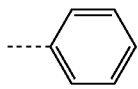 | 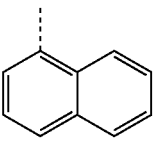 | 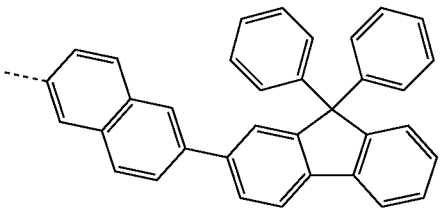 |

-continued
| Compound | - - - -Ar1 | - - - -Ar2 | - - - -Ar3 |
|---|---|---|---|
| 2-238 | 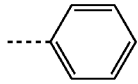 | 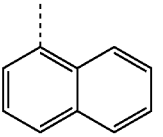 | 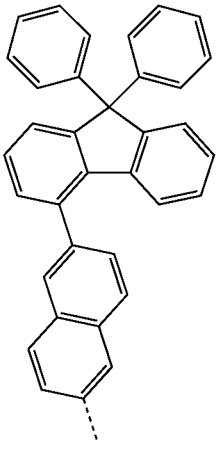 |
| 2-239 | 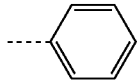 | 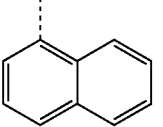 | 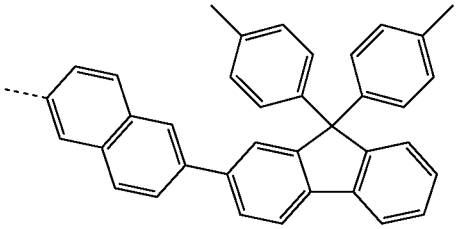 |
| 2-240 | 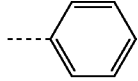 | 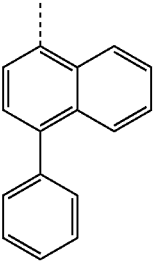 | 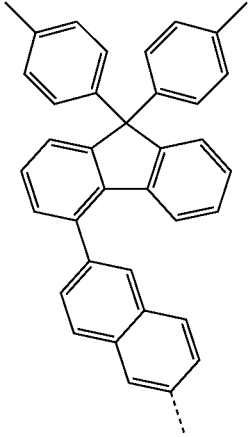 |
| 2-241 | 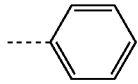 | 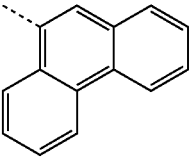 | 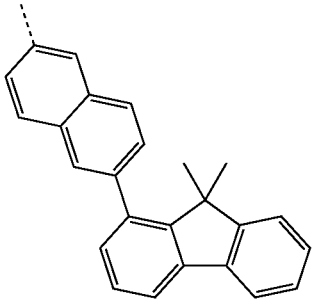 |

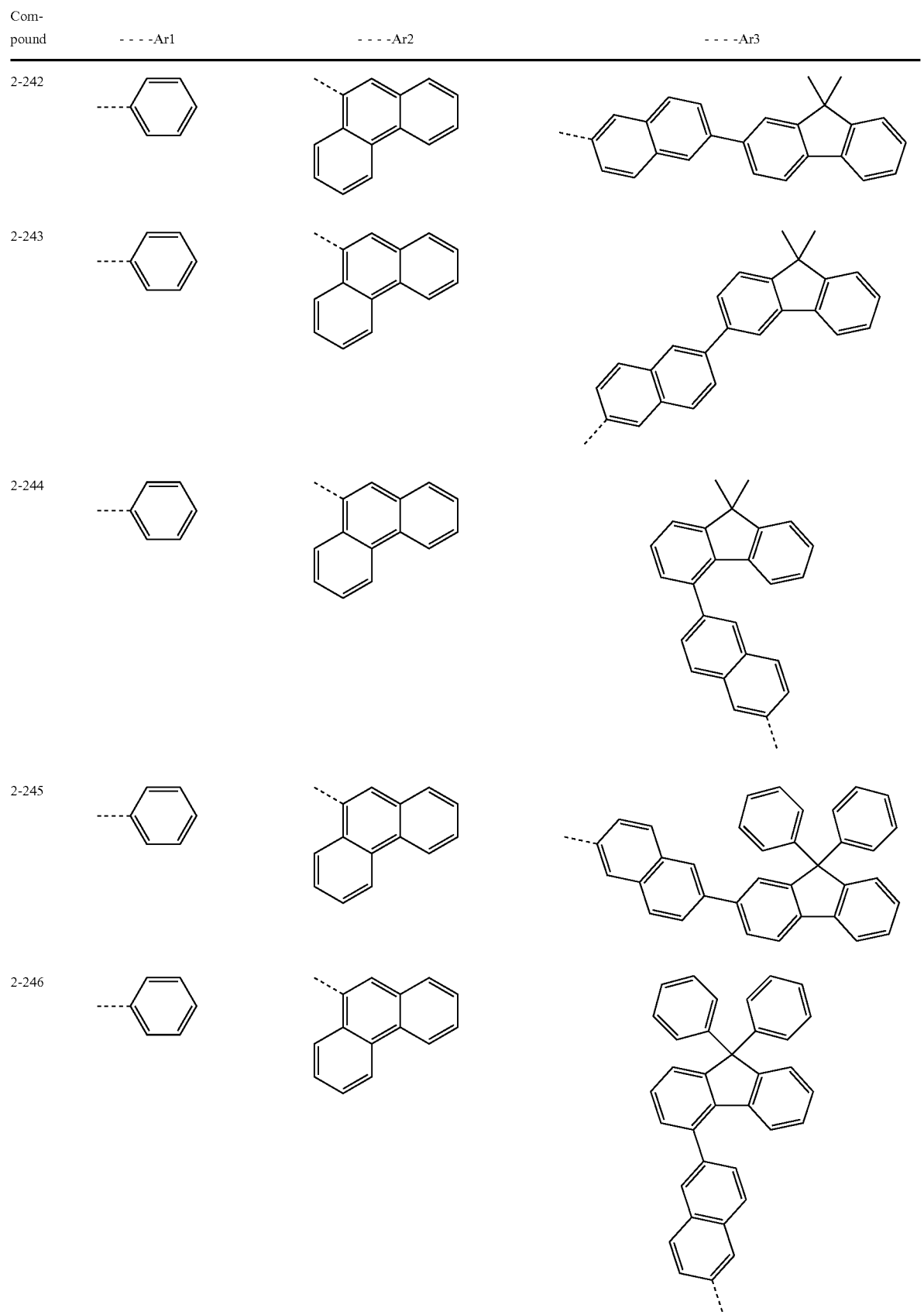

-continued

| Com-pound | ----Ar1 | ----Ar2 | ----Ar3 |
|---|---|---|---|
| 2-248 | phenyl | phenanthrenyl | 9,9-di(p-tolyl)-fluorenyl-naphthyl |
| 2-249 | phenyl | phenanthrenyl | naphthyl-9,9-dimethylfluorenyl |
| 2-250 | phenyl | phenanthrenyl | naphthyl-9,9-dimethylfluorenyl |
| 2-251 | phenyl | phenanthrenyl | 9,9-dimethylfluorenyl-naphthyl |
| 2-252 | phenyl | phenanthrenyl | 9,9-dimethylfluorenyl-naphthyl |

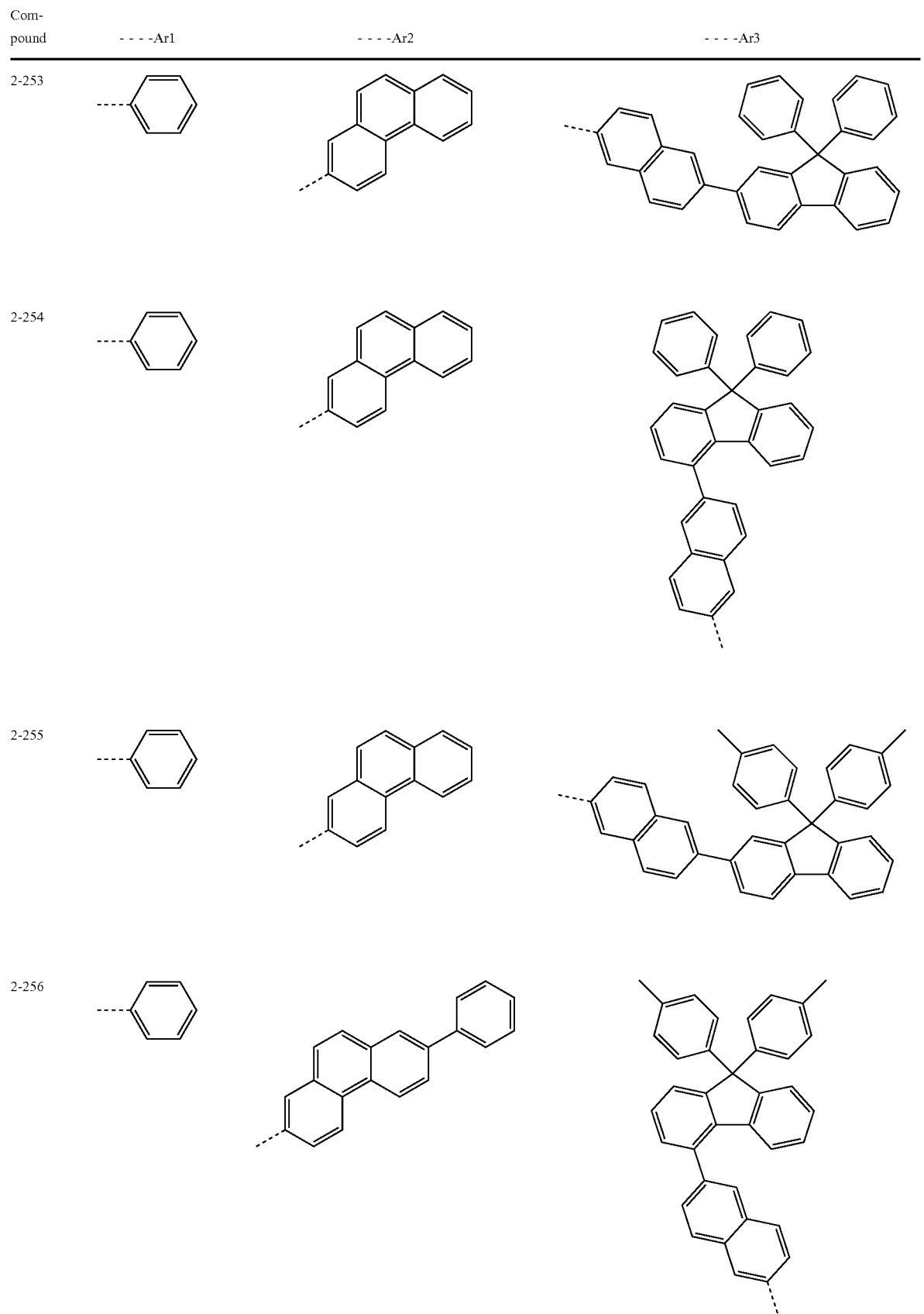

-continued
| Compound | ----Ar1 | ----Ar2 | ----Ar3 |
|---|---|---|---|
| 2-257 | 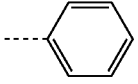 | 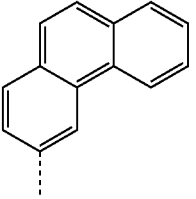 | 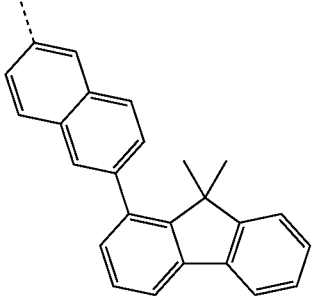 |
| 2-258 | 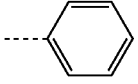 | 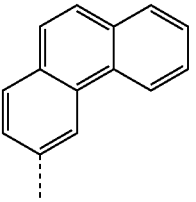 | 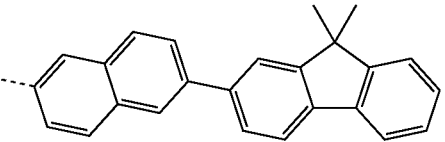 |
| 2-259 | 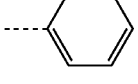 | 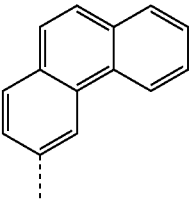 | 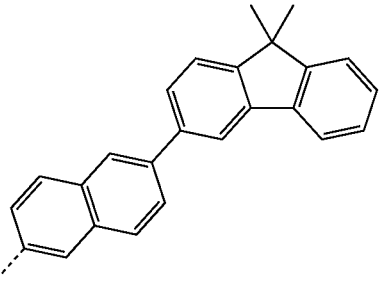 |
| 2-260 | 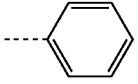 | 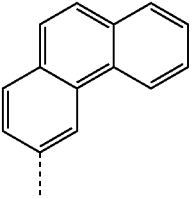 | 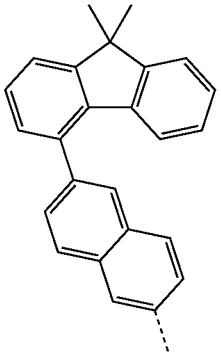 |
| 2-261 | 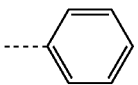 | 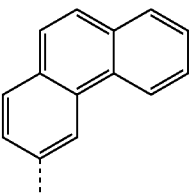 | 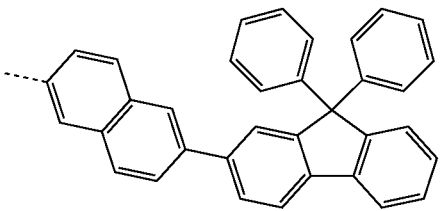 |

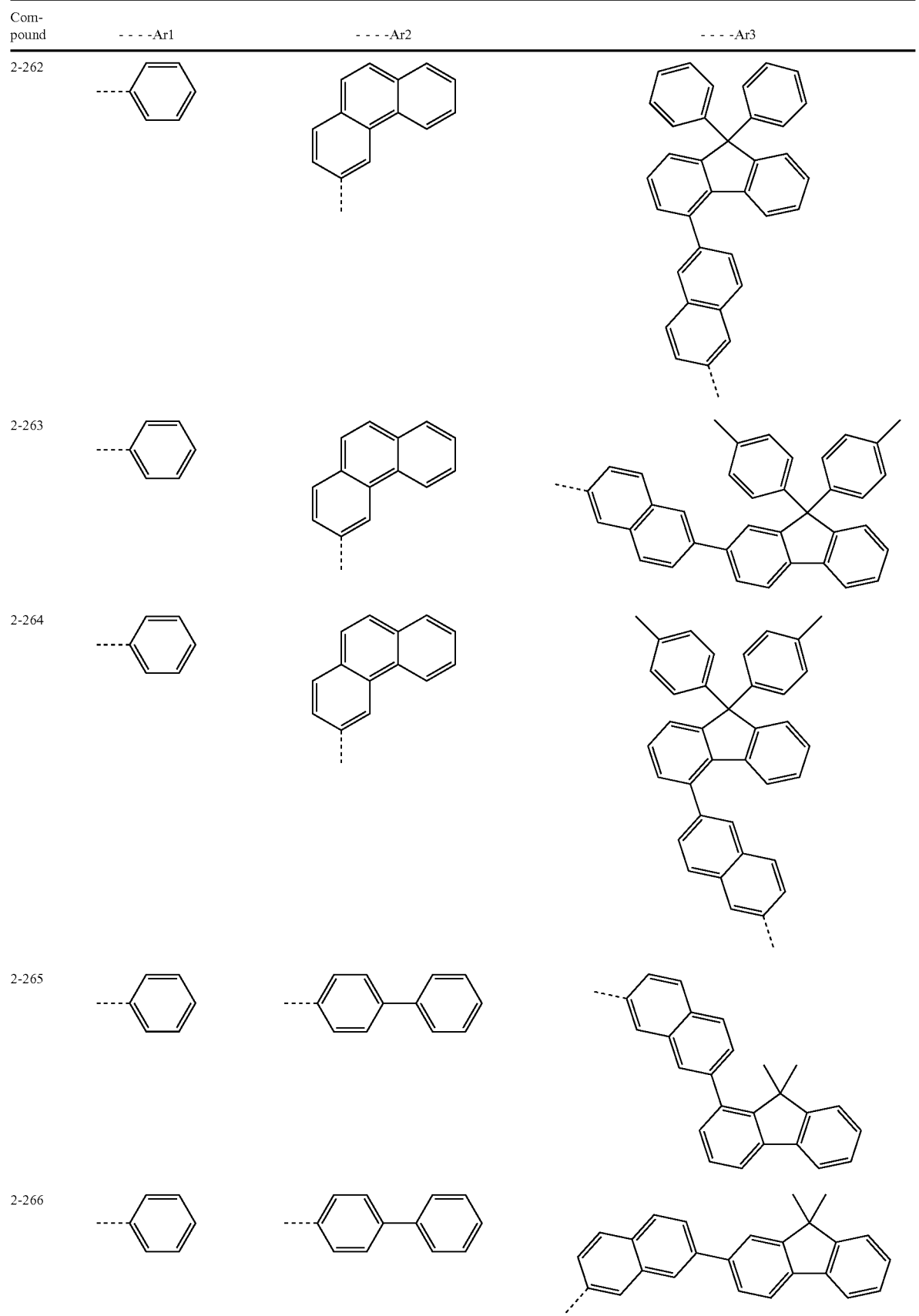

-continued
| Compound | ----Ar1 | ----Ar2 | ----Ar3 |
|---|---|---|---|
| 2-267 | 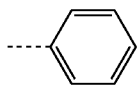 | 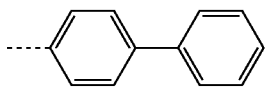 | 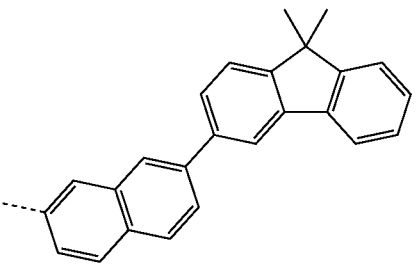 |
| 2-268 | 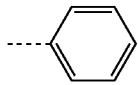 | 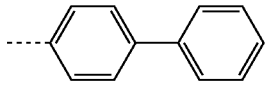 | 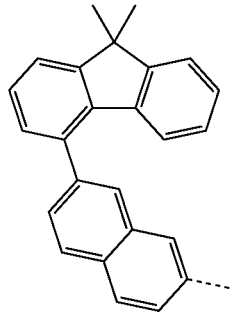 |
| 2-269 | 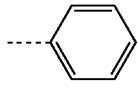 | 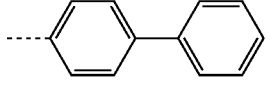 | 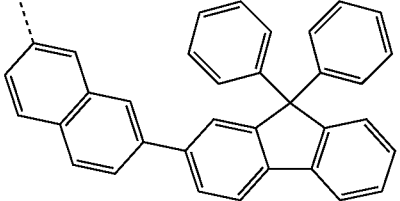 |
| 2-270 | 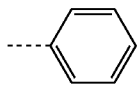 | 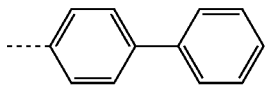 | 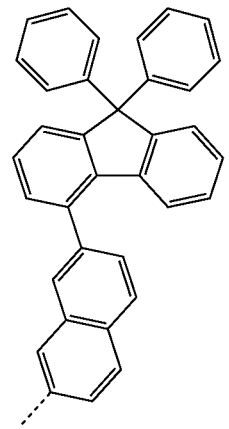 |
| 2-271 | 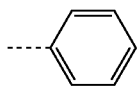 | 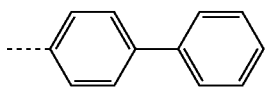 | 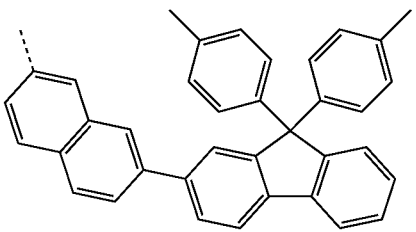 |

-continued

| Compound | ----Ar1 | ----Ar2 | ----Ar3 |
| --- | --- | --- | --- |
| 2-273 | phenyl | 2-biphenyl | 9,9-dimethylfluoren-1-yl-naphthalen-2-yl |
| 2-274 | phenyl | 2-biphenyl | 9,9-dimethylfluoren-2-yl-naphthalen-2-yl |
| 2-275 | phenyl | 9-phenanthrenyl-phenyl | 9,9-dimethylfluoren-3-yl-naphthalen-2-yl |
| 2-276 | phenyl | 1-naphthyl-phenyl | 9,9-dimethylfluoren-4-yl-naphthalen-2-yl |
| 2-277 | phenyl | 2-biphenyl | 9,9-diphenylfluoren-2-yl-naphthalen-2-yl |

-continued

| Compound | ----Ar1 | ----Ar2 | ----Ar3 |
|---|---|---|---|
| 2-278 | phenyl | 2-biphenyl | 9,9-diphenylfluorene-4-yl-naphthalen-2-yl |
| 2-279 | phenyl | 2-biphenyl | 9,9-di(p-tolyl)fluoren-2-yl-naphthalen-2-yl |
| 2-280 | phenyl | 2-biphenyl | 7,7-dimethyl-7H-benzo[c]fluoren-yl-naphthalen-2-yl |
| 2-281 | phenyl | 3-biphenyl | 9,9-dimethylfluoren-1-yl-naphthalen-2-yl |
| 2-282 | phenyl | 3-biphenyl | 9,9-dimethylfluoren-2-yl-naphthalen-2-yl |

-continued
| Compound | ----Ar1 | ----Ar2 | ----Ar3 |
|---|---|---|---|
| 2-283 | 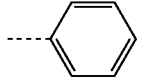 | 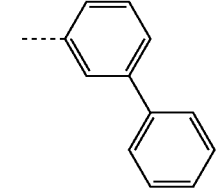 | 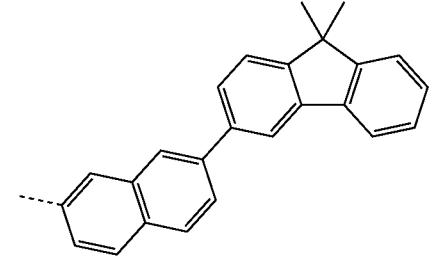 |
| 2-284 | 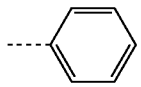 | 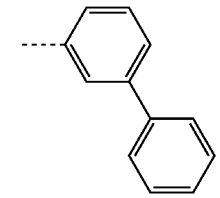 | 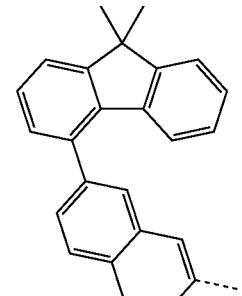 |
| 2-285 | 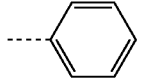 | 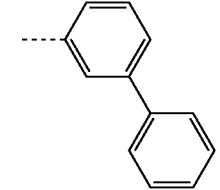 | 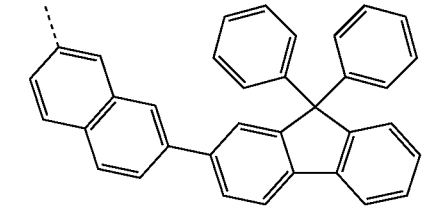 |
| 2-286 | 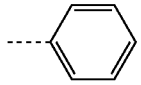 | 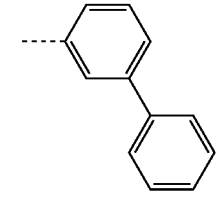 | 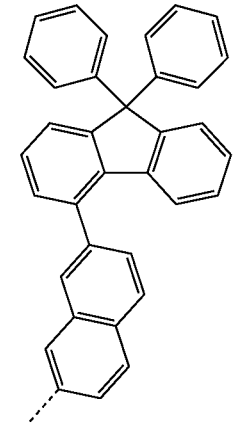 |
| 2-287 | 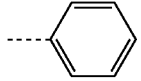 | 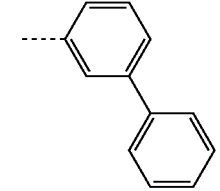 | 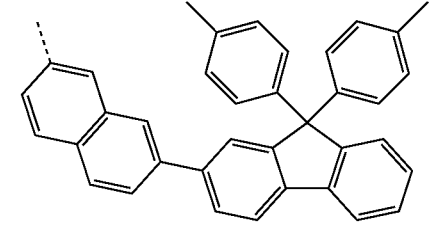 |

-continued

| Compound | ----Ar1 | ----Ar2 | ----Ar3 |
|---|---|---|---|
| 2-288 | phenyl | 3-biphenyl | 9,9-di(p-tolyl)-4-fluorenyl-2-naphthyl |
| 2-289 | phenyl | 4,4'-terphenyl | 9,9-dimethyl-1-fluorenyl-2-naphthyl |
| 2-290 | phenyl | 4,4'-terphenyl | 9,9-dimethyl-2-fluorenyl-2-naphthyl |
| 2-291 | phenyl | 4,4'-terphenyl | 9,9-dimethyl-3-fluorenyl-2-naphthyl |
| 2-292 | phenyl | 4,4'-terphenyl | 9,9-dimethyl-4-fluorenyl-2-naphthyl |

-continued

| Compound | ----Ar1 | ----Ar2 | ----Ar3 |
|---|---|---|---|
| 2-293 | phenyl | p-terphenyl | 2-(9,9-diphenylfluoren-2-yl)naphthalen-6-yl |
| 2-294 | phenyl | p-terphenyl | 6-(9,9-diphenylfluoren-4-yl)naphthalen-2-yl |
| 2-295 | phenyl | p-terphenyl | 2-(9,9-di-p-tolylfluoren-2-yl)naphthalen-6-yl |
| 2-296 | phenyl | p-terphenyl | 2-(9,9-dimethyl-benzo[a]fluoren-2-yl)naphthalen-6-yl |
| 2-297 | phenyl | 3,5-diphenylphenyl | 2-(9,9-dimethylfluoren-4-yl)naphthalen-6-yl |

-continued

| Compound | ----Ar1 | ----Ar2 | ----Ar3 |
|---|---|---|---|
| 2-298 | | | |
| 2-299 | | | |
| 2-300 | | | |
| 2-301 | | | |

-continued
| Compound | ----Ar1 | ----Ar2 | ----Ar3 |
|---|---|---|---|
| 2-302 | 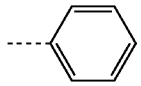 | 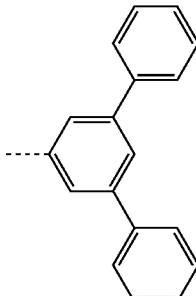 | 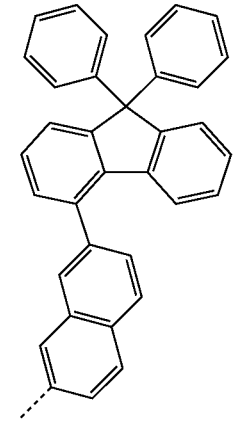 |
| 2-303 | 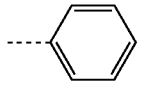 | 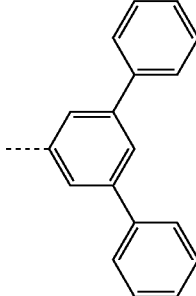 | 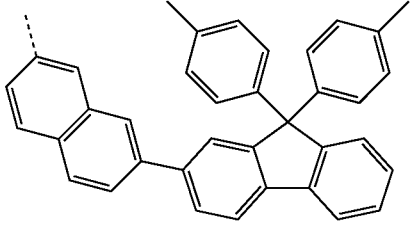 |
| 2-304 | 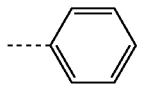 | 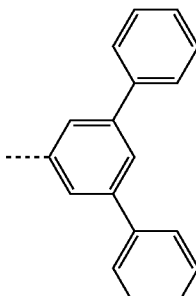 | 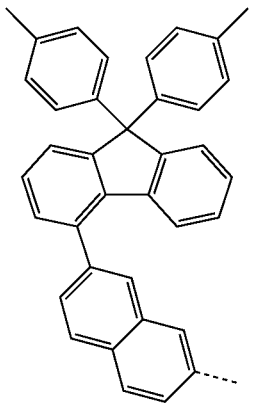 |
| 2-305 | 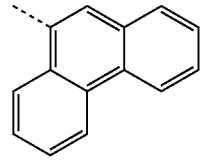 | 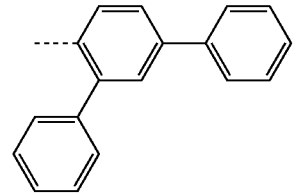 | 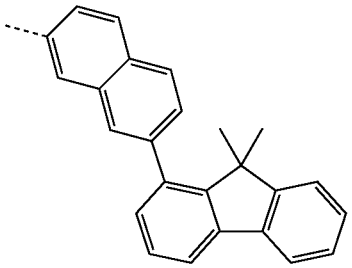 |

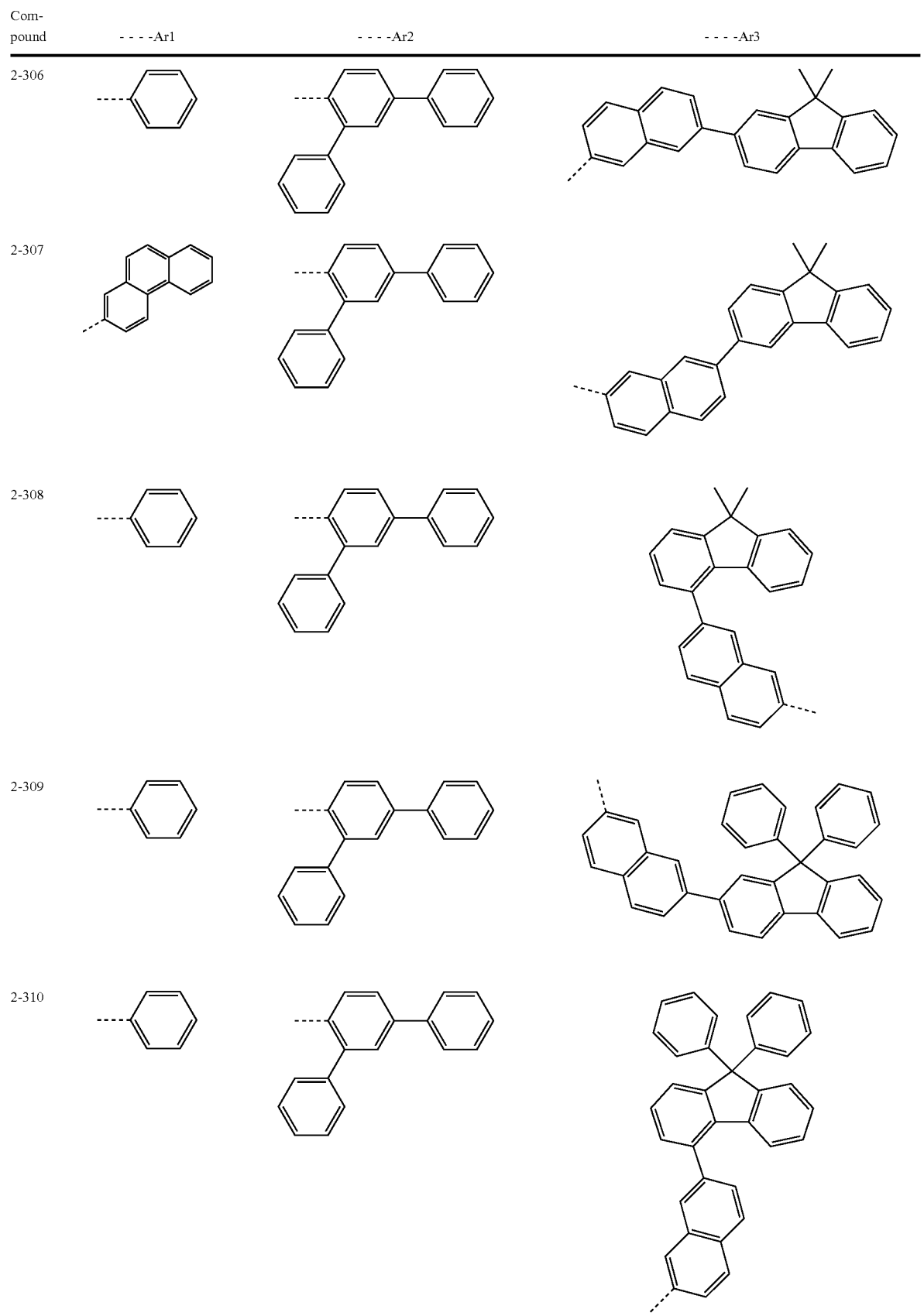

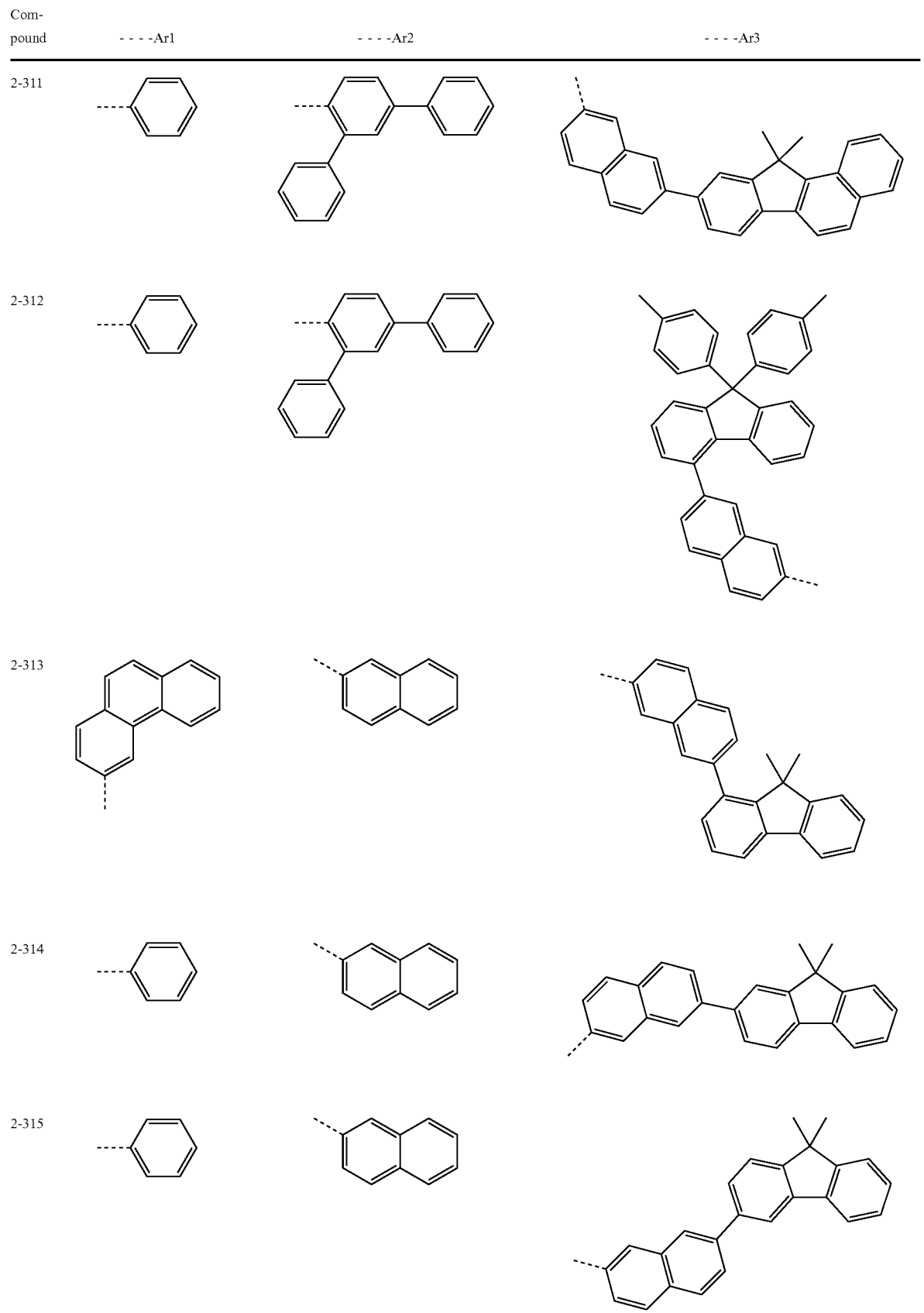

-continued
| Compound | ----Ar1 | ----Ar2 | ----Ar3 |
|---|---|---|---|
| 2-316 | 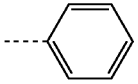 | 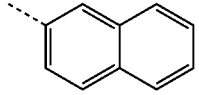 | 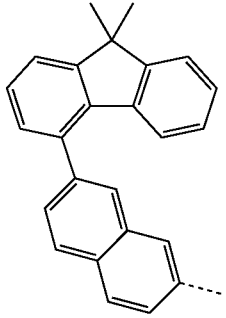 |
| 2-317 | 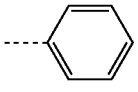 | 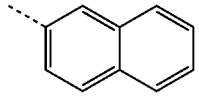 | 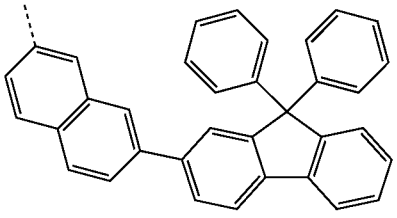 |
| 2-318 | 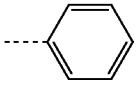 | 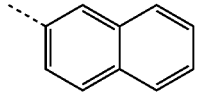 | 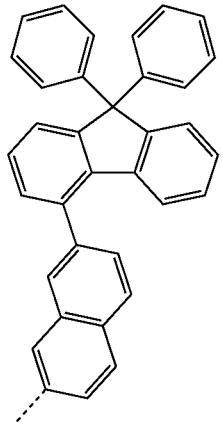 |
| 2-319 | 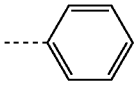 | 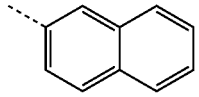 | 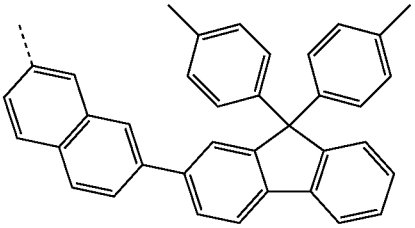 |

-continued

| Compound | ----Ar1 | ----Ar2 | ----Ar3 |
|---|---|---|---|
| 2-320 | phenyl | 2-naphthyl | 9,9-di(tolyl)fluorenyl-naphthyl |
| 2-321 | phenyl | 1-naphthyl | naphthyl-9,9-dimethylfluorenyl |
| 2-322 | phenyl | 1-naphthyl | naphthyl-9,9-dimethylfluorenyl |
| 2-323 | phenyl | 1-naphthyl | 9,9-dimethylfluorenyl-naphthyl |
| 2-324 | phenyl | 1-naphthyl | 9,9-dimethylfluorenyl-naphthyl |

-continued
| Compound | ----Ar1 | ----Ar2 | ----Ar3 |
|---|---|---|---|
| 2-325 | 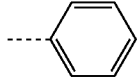 | 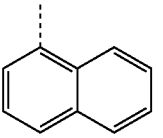 | 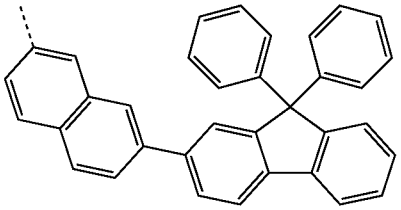 |
| 2-326 | 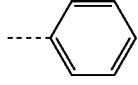 | 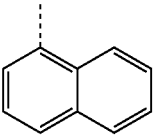 | 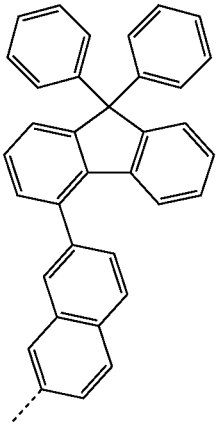 |
| 2-327 | 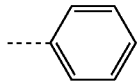 | 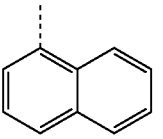 | 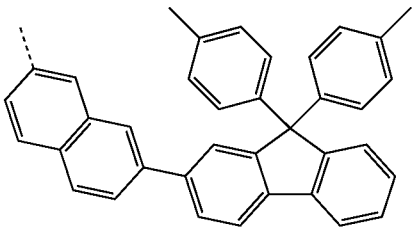 |
| 2-328 | 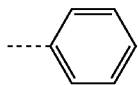 | 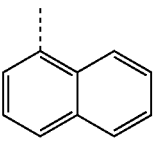 | 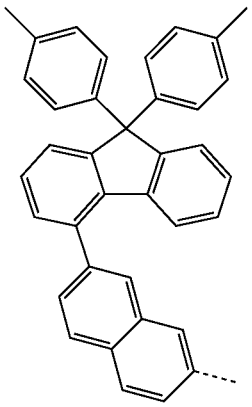 |
| 2-329 | 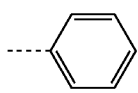 | 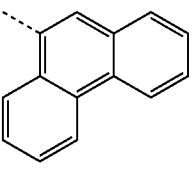 | 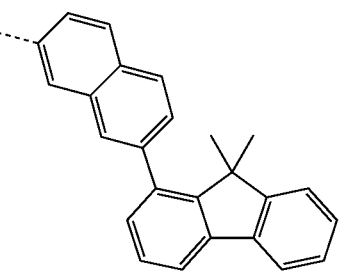 |

| Compound | ----Ar1 | ----Ar2 | ----Ar3 |
|---|---|---|---|
| 2-330 | 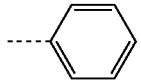 | 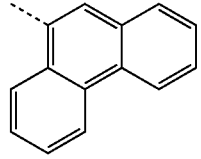 | 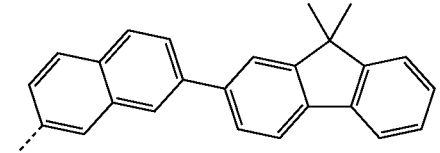 |
| 2-331 | 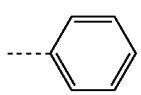 | 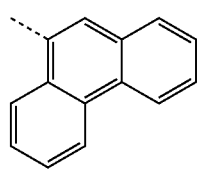 | 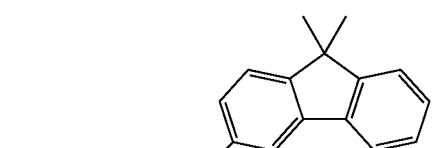 |
| 2-332 | 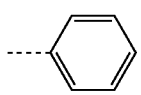 | 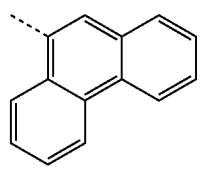 | 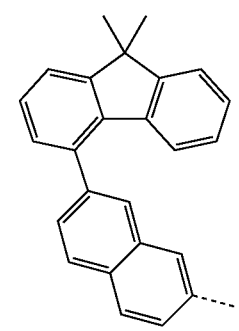 |
| 2-333 | 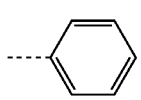 | 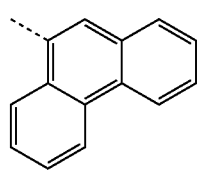 | 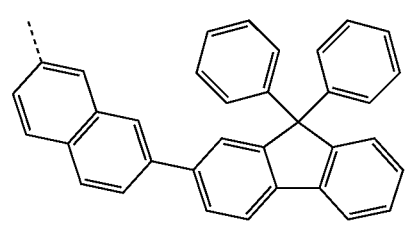 |
| 2-334 | 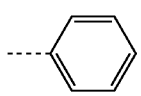 | 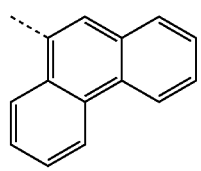 | 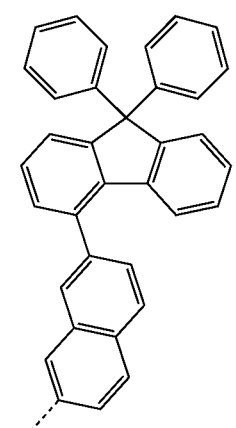 |

-continued

| Compound | ----Ar1 | ----Ar2 | ----Ar3 |
|---|---|---|---|
| 2-335 | | | |
| 2-336 | | | |
| 2-337 | | | |
| 2-338 | | | |
| 2-339 | | | |

-continued
| Compound | - - - -Ar1 | - - - -Ar2 | - - - -Ar3 |
|---|---|---|---|
| 2-340 | 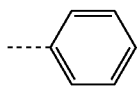 | 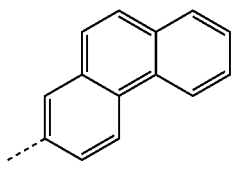 | 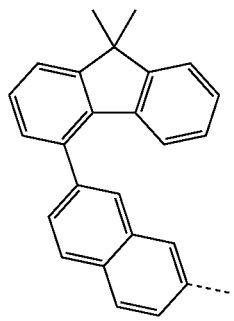 |
| 2-341 | 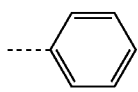 | 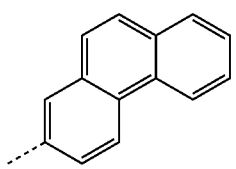 | 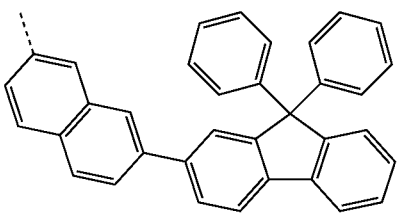 |
| 2-342 | 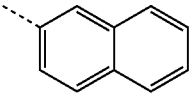 | 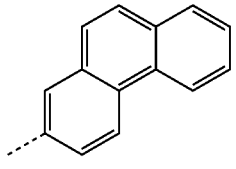 | 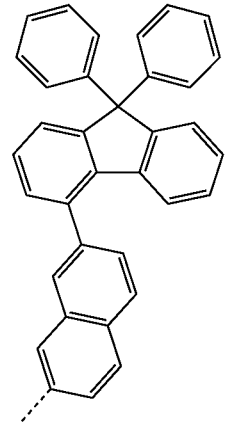 |
| 2-343 | 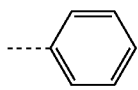 | 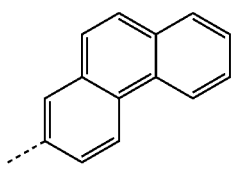 | 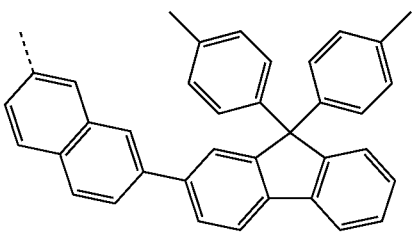 |

-continued

| Compound | ----Ar1 | ----Ar2 | ----Ar3 |
|---|---|---|---|
| 2-344 | | | |
| 2-345 | | | |
| 2-346 | | | |
| 2-347 | | | |
| 2-348 | | | |

-continued
| Compound | ----Ar1 | ----Ar2 | ----Ar3 |
|---|---|---|---|
| 2-349 | 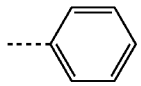 | 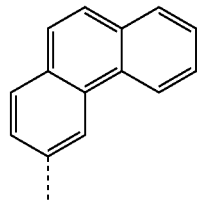 | 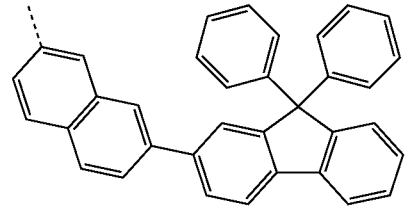 |
| 2-350 | 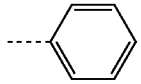 | 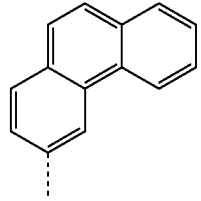 | 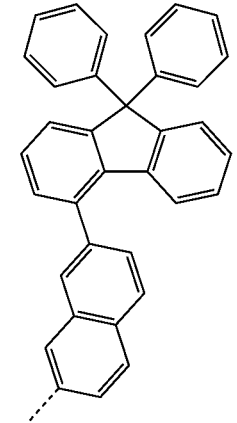 |
| 2-351 | 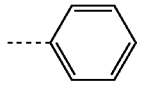 | 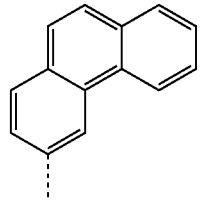 | 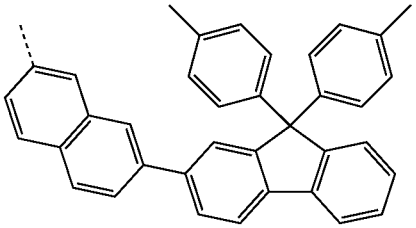 |
| 2-353 | 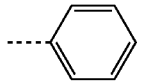 | 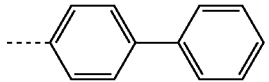 | 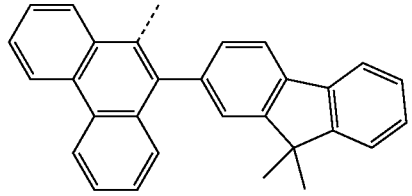 |
| 2-354 | 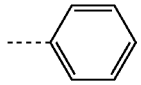 | 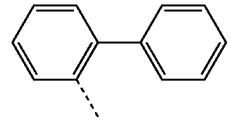 | 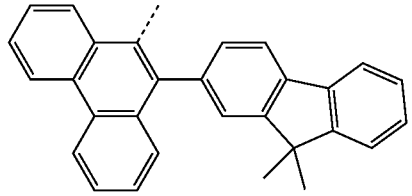 |
| 2-355 | 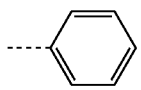 | 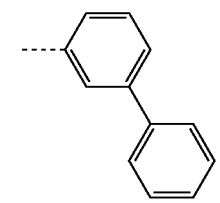 | 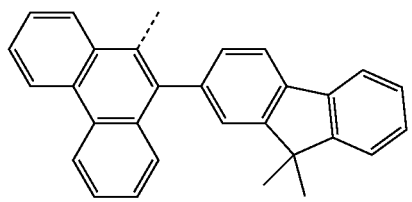 |

-continued

| Compound | ----Ar1 | ----Ar2 | ----Ar3 |
|---|---|---|---|
| 2-356 | | | |
| 2-357 | | | |
| 2-358 | | | |
| 2-359 | | | |
| 2-360 | | | |

-continued

| Compound | - - - -Ar1 | - - - -Ar2 | - - - -Ar3 |
|---|---|---|---|
| 2-361 | phenyl | biphenyl | 9,9-diphenylfluorene with deuterated phenyl linker |
| 2-362 | deuterated phenyl (d5) | biphenyl | 9,9-diphenylfluorene with phenyl linker |
| 2-363 | phenyl | biphenyl with deuterated middle ring (d4) | 9,9-diphenylfluorene with phenyl linker |
| I-7 | phenyl | biphenyl | 9,9-dimethyl-benzo-fused fluorene |
| I-9 | phenyl | biphenyl | 9,9-dimethyl-benzo-fused fluorene (isomer) |
| I-14 | phenyl | 3-biphenyl | 9,9-dimethylfluorene |

-continued
| | | | |
|---|---|---|---|
| I-18 | 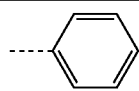 | 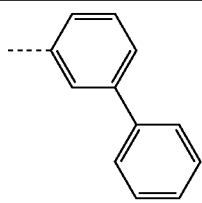 | 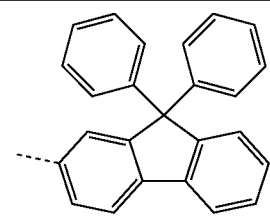 |
| I-22 | 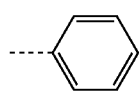 | 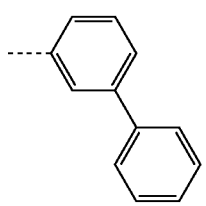 | 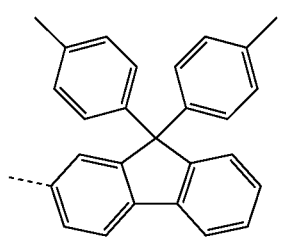 |
| I-23 | 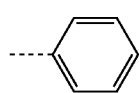 | 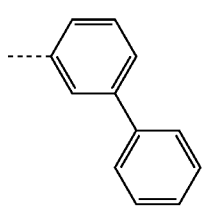 | 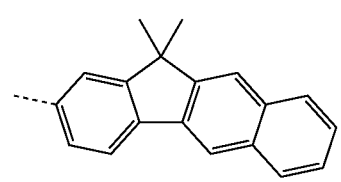 |
| I-26 | 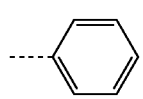 | 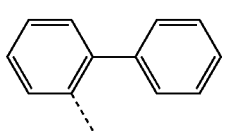 | 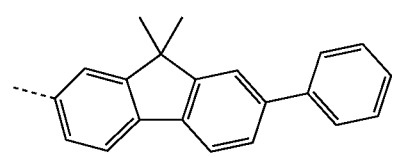 |
| I-30 | 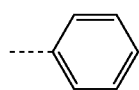 | 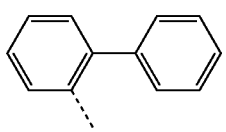 | 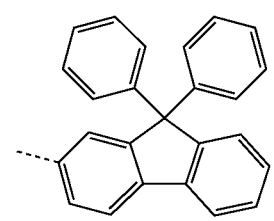 |
| I-33 | 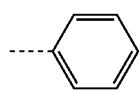 | 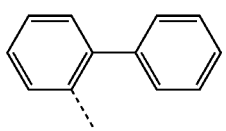 | 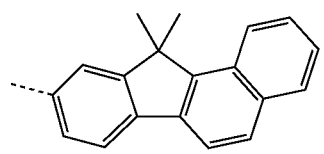 |
| I-34 | 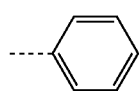 | 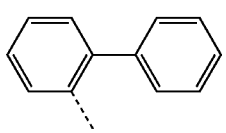 | 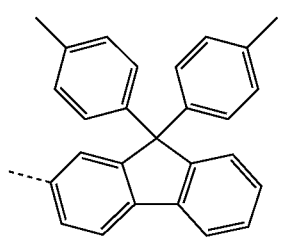 |
| I-38 | 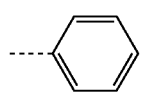 | 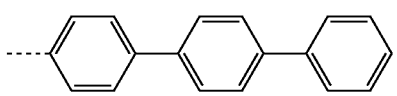 | 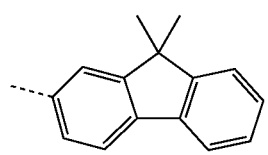 |

-continued
I-42 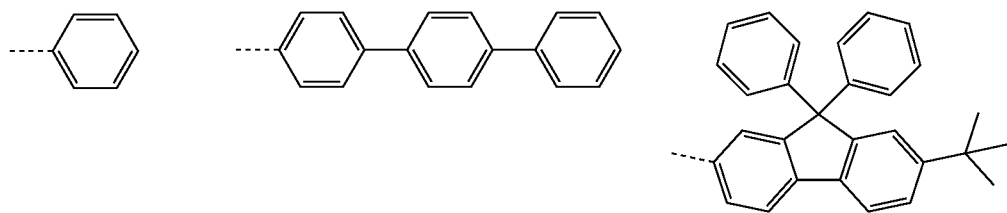
I-45 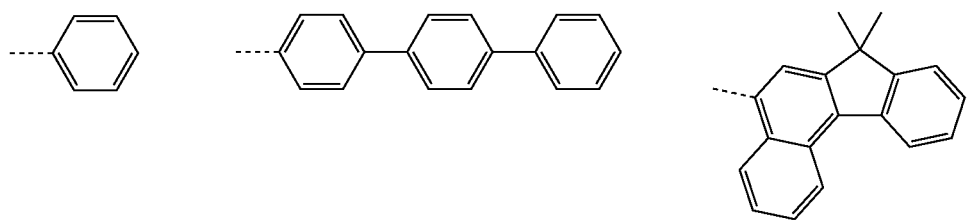
I-46 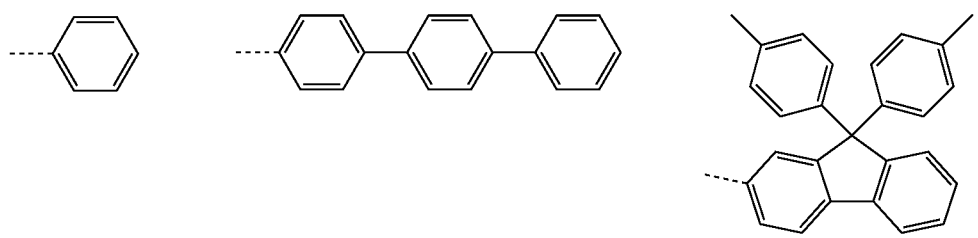
I-50 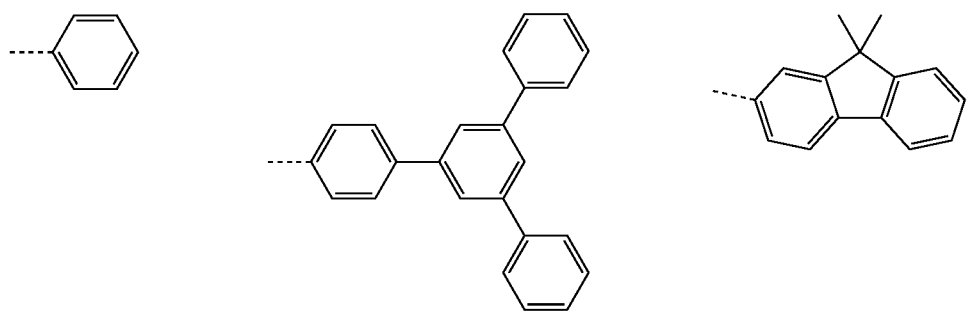
I-54 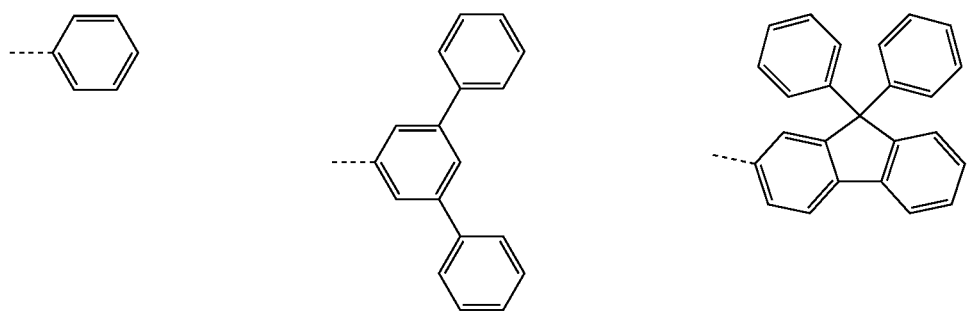
I-57 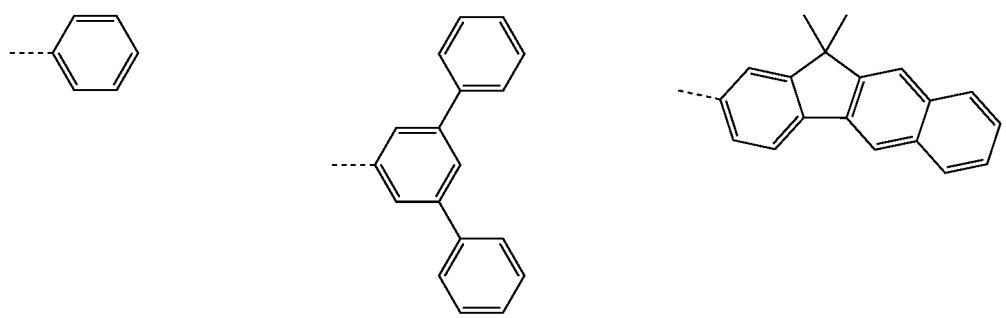

-continued
| | | | |
|---|---|---|---|
| I-58 | 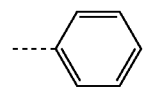 | 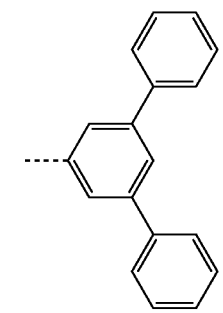 | 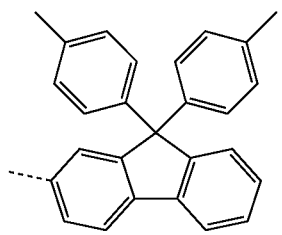 |
| I-62 | 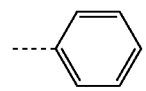 | 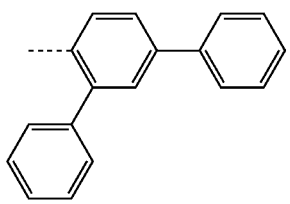 | 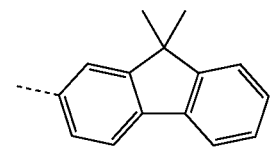 |
| I-66 | 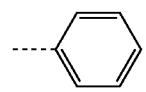 | 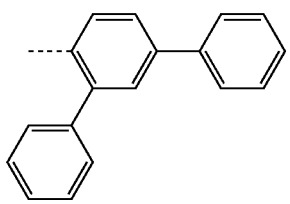 | 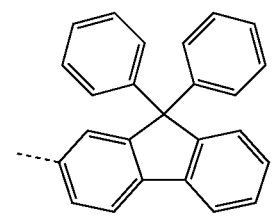 |
| I-69 | 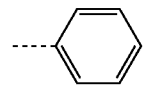 | 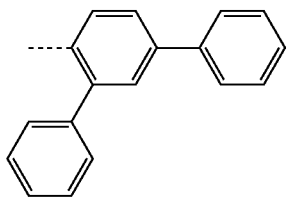 | 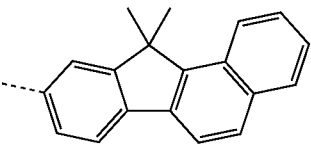 |
| I-70 | 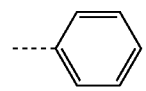 | 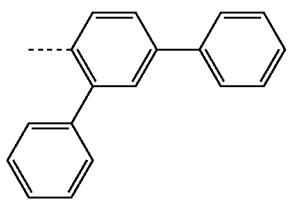 | 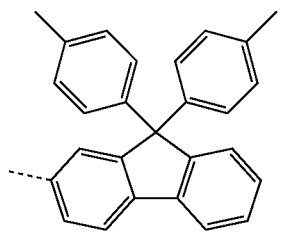 |
| I-74 | 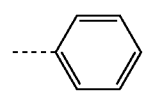 | 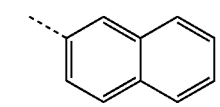 | 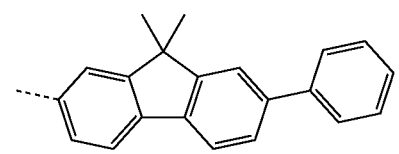 |
| I-78 | 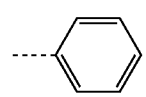 | 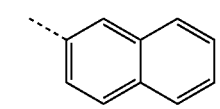 | 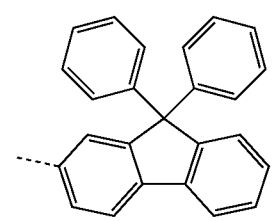 |

-continued
| | | | |
|---|---|---|---|
| I-82 | 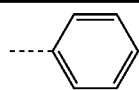 | 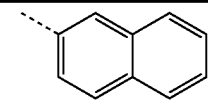 | 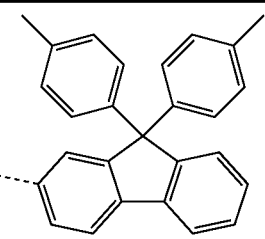 |
| I-86 | 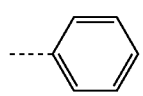 | 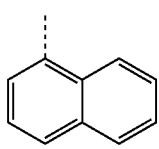 | 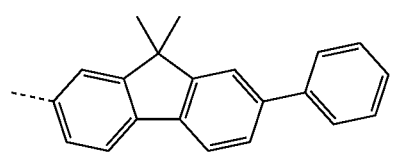 |
| I-90 | 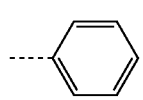 | 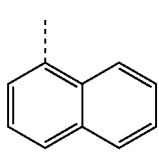 | 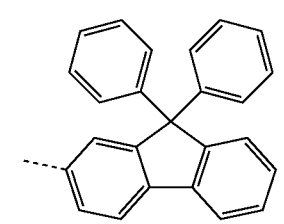 |
| I-94 | 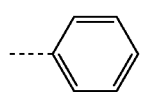 | 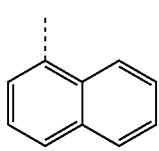 | 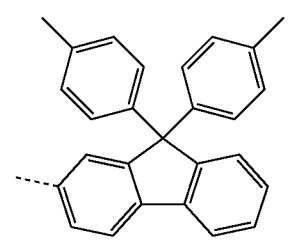 |
| I-98 | 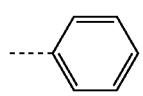 | 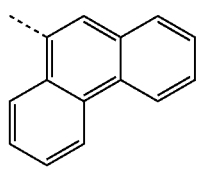 | 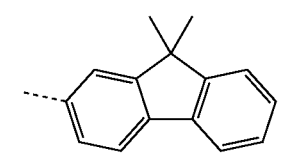 |
| I-102 | 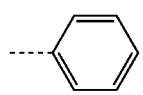 | 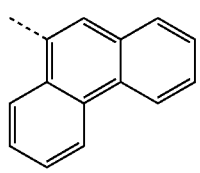 | 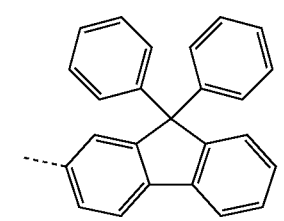 |
| I-105 | 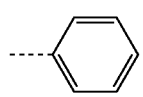 | 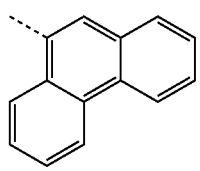 | 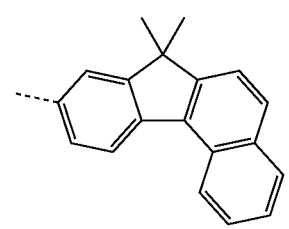 |

-continued
| | | | |
|---|---|---|---|
| I-106 | 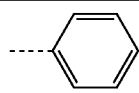 | 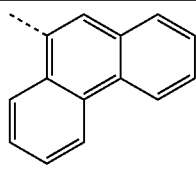 | 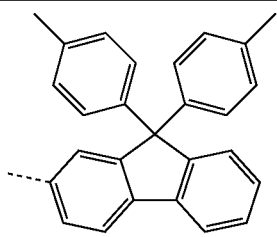 |
| I-110 | 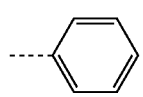 | 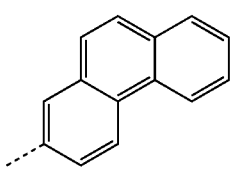 | 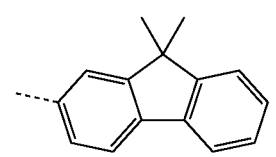 |
| I-114 | 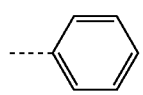 | 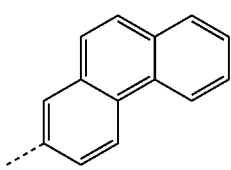 | 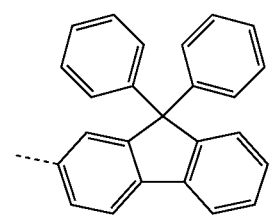 |
| I-118 | 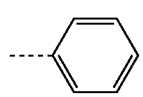 | 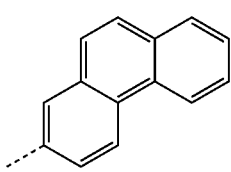 | 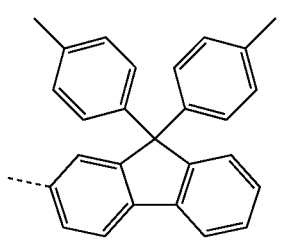 |
| I-119 | 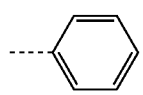 | 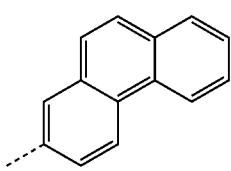 | 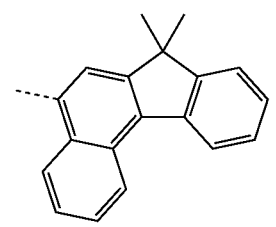 |
| I-122 | 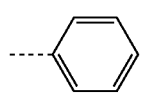 | 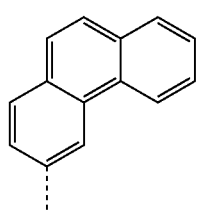 | 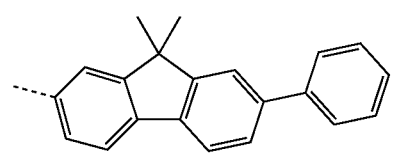 |
| I-126 | 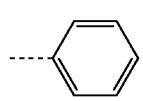 | 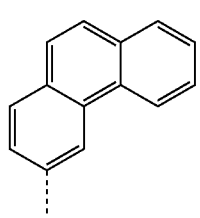 | 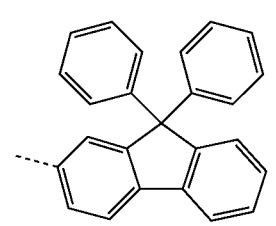 |

-continued
| | | | |
|---|---|---|---|
| I-130 | 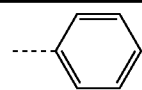 | 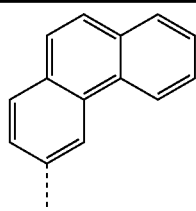 | 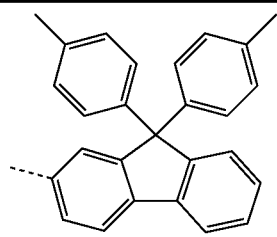 |
| I-134 | 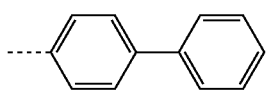 | 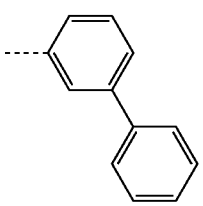 | 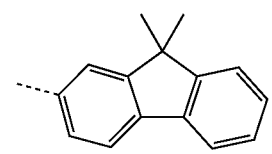 |
| I-138 | 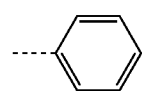 | 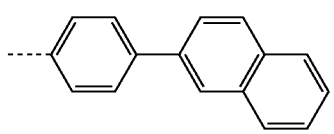 | 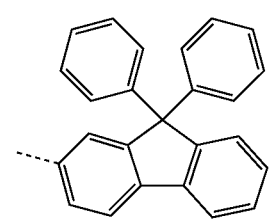 |
| I-142 | 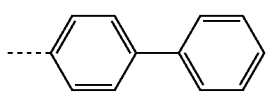 | 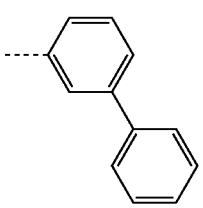 | 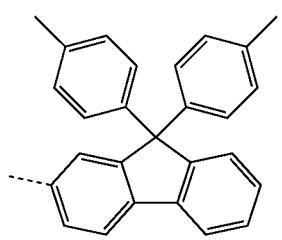 |
| I-143 | 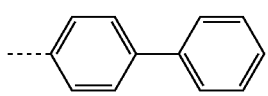 | 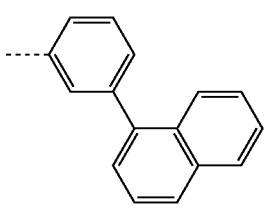 | 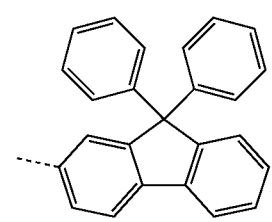 |
| I-146 | 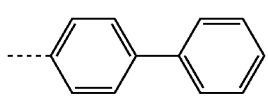 | 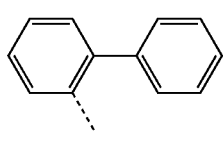 | 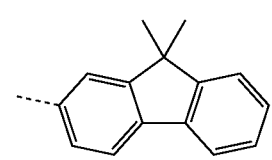 |
| I-149 | 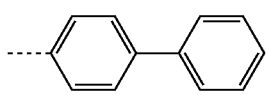 | 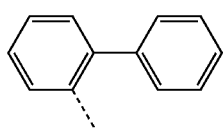 | 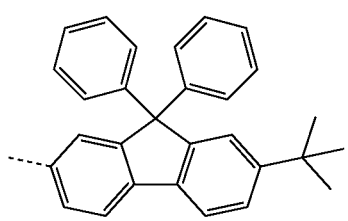 |

-continued
| | | | |
|---|---|---|---|
| I-150 | 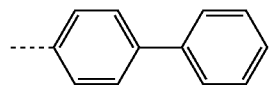 | 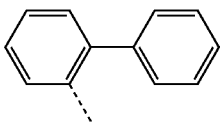 | 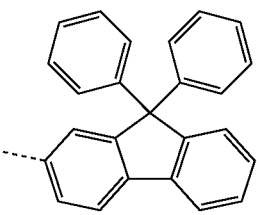 |
| I-153 | 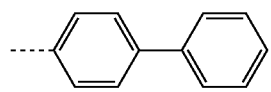 | 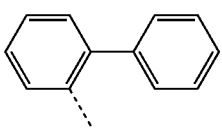 | 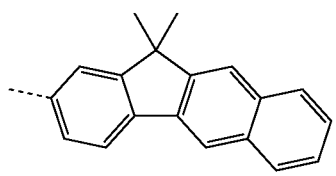 |
| I-154 | 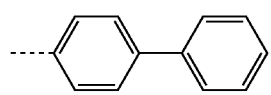 | 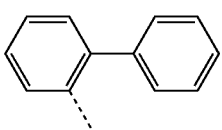 | 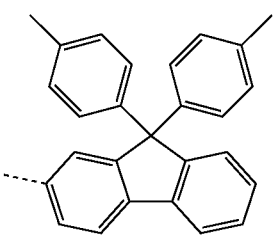 |
| I-158 | 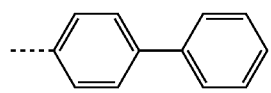 | 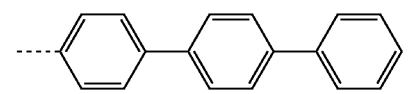 | 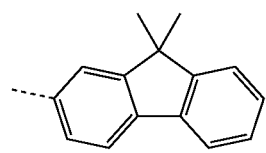 |
| I-162 | 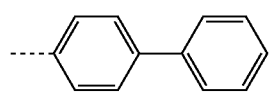 | 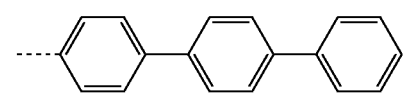 | 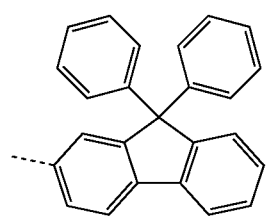 |
| I-166 | 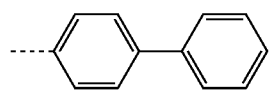 | 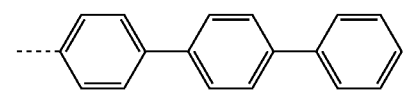 | 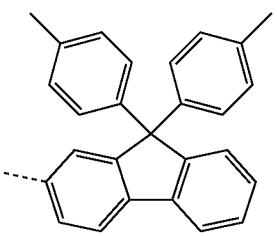 |
| I-167 | 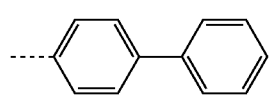 | 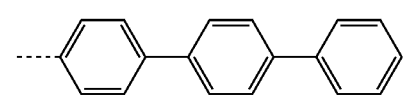 | 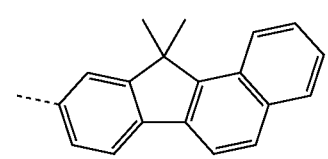 |

-continued
I-170 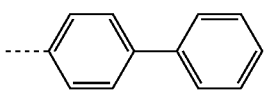 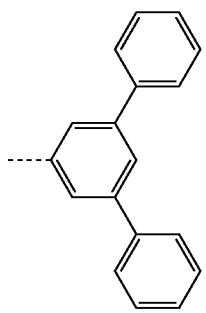 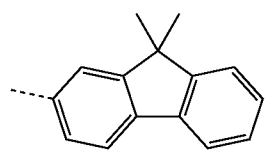
I-174 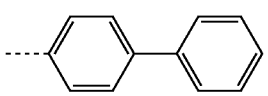 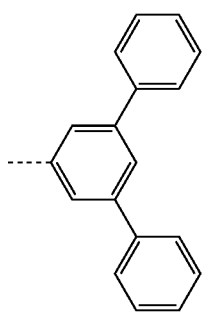 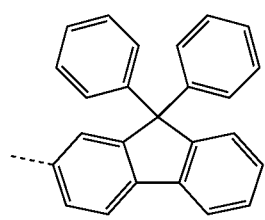
I-178 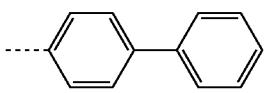 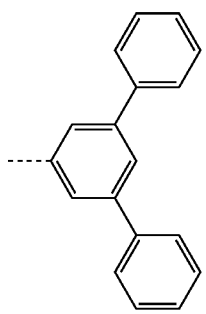 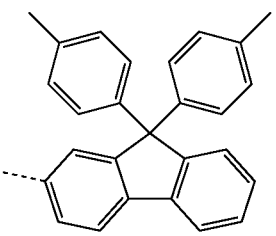
I-179 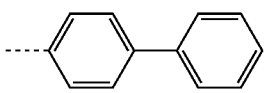 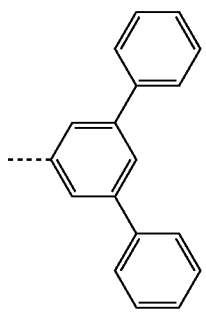 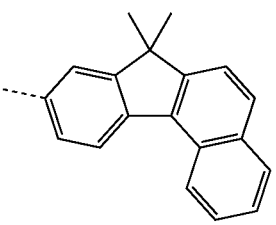
I-182 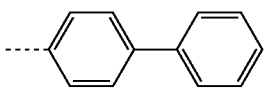 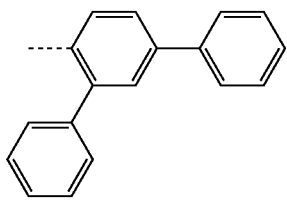 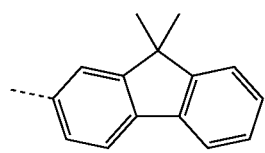

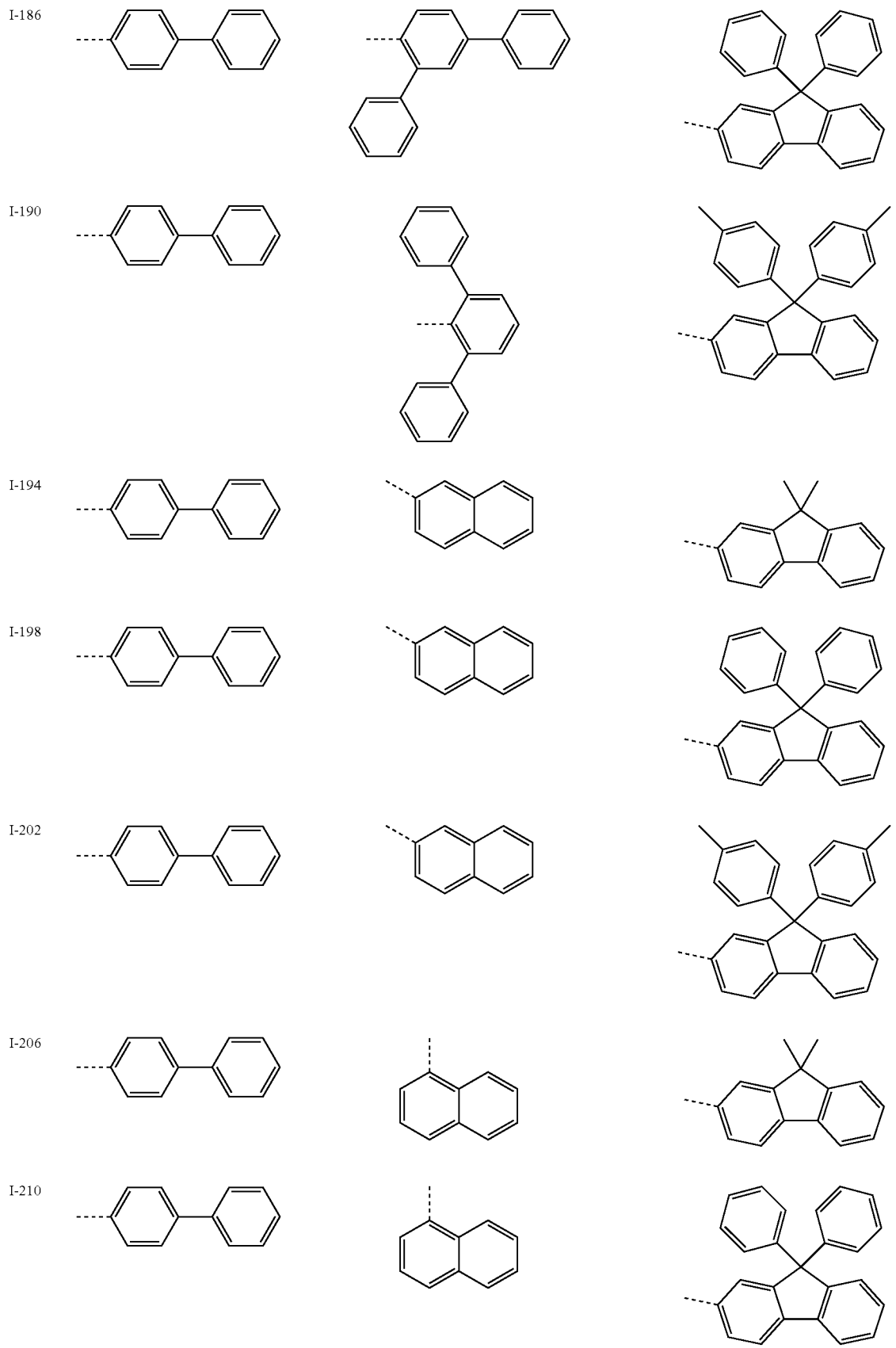

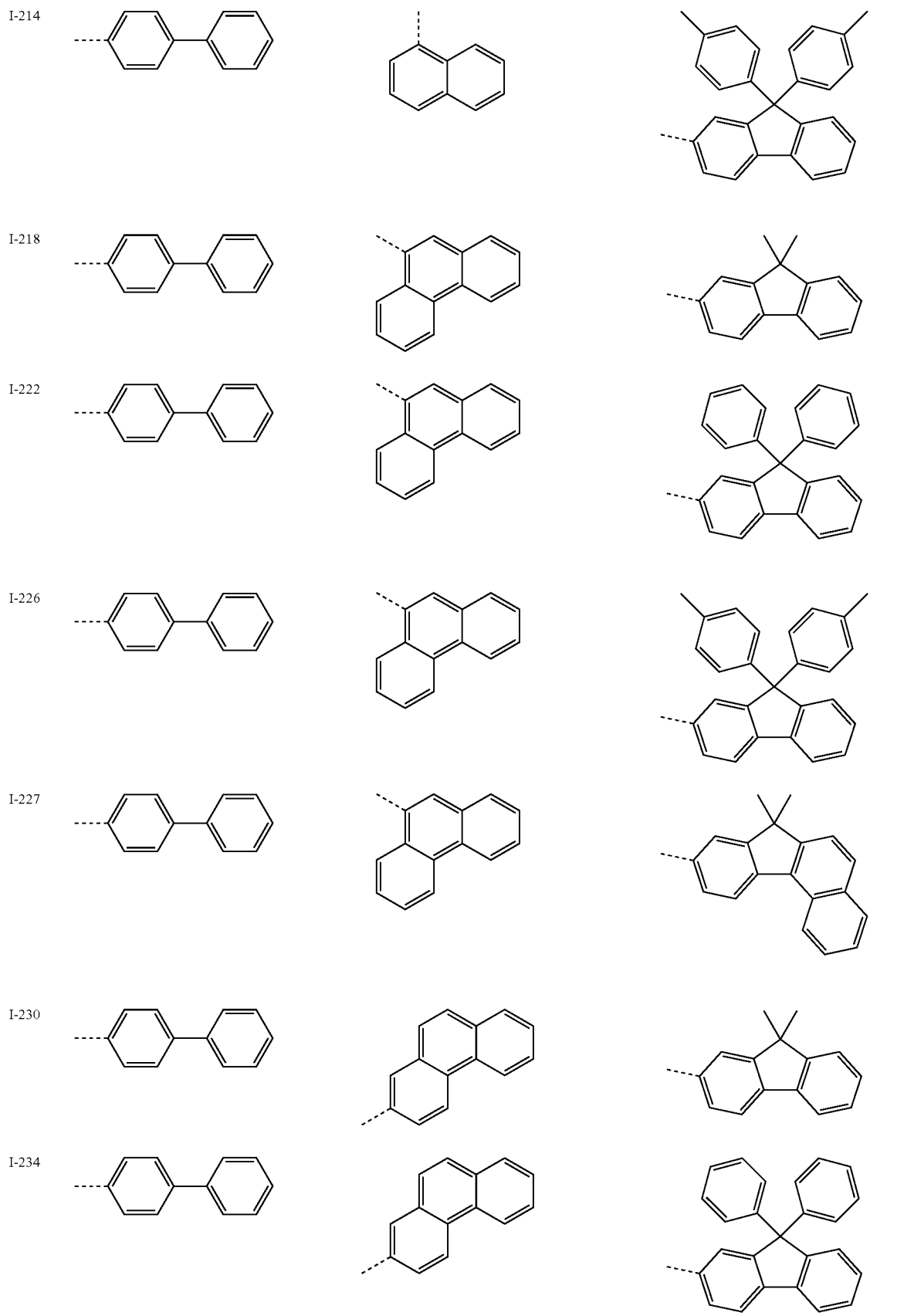

-continued
| | | | |
|---|---|---|---|
| I-237 | 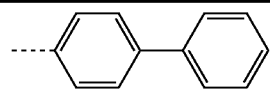 | 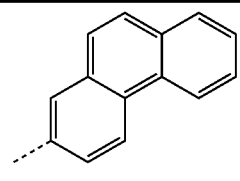 | 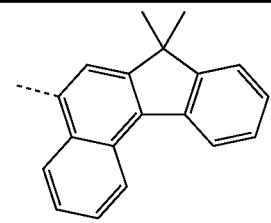 |
| I-238 | 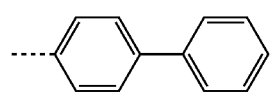 | 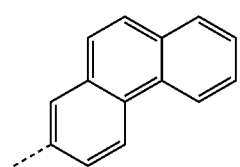 | 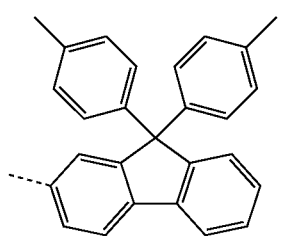 |
| I-242 | 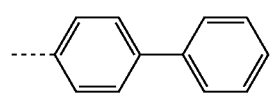 | 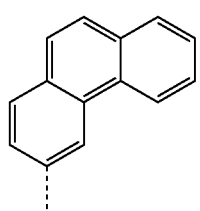 | 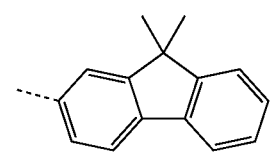 |
| I-246 | 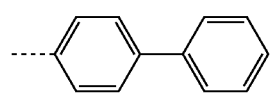 | 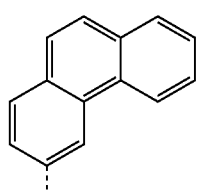 | 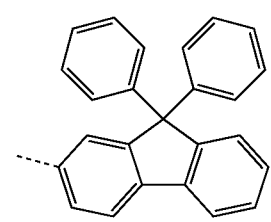 |
| I-247 | 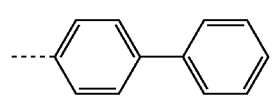 | 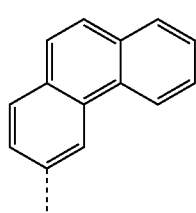 | 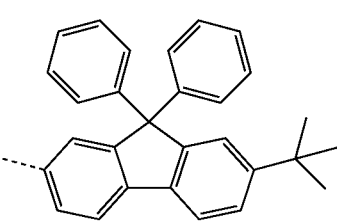 |
| I-249 | 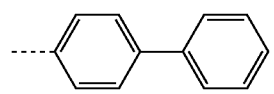 | 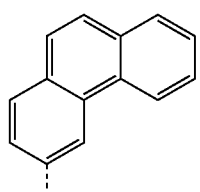 | 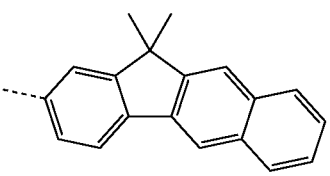 |
| I-250 | 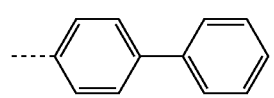 | 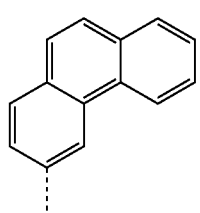 | 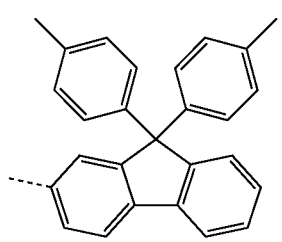 |

-continued
| | | | |
|---|---|---|---|
| I-254 | 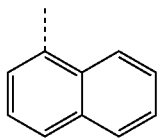 | 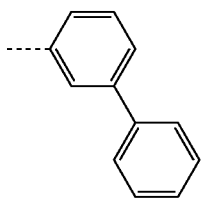 | 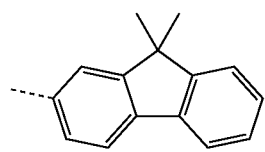 |
| I-258 | 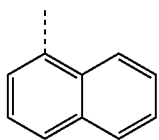 | 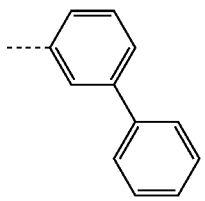 | 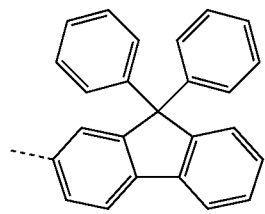 |
| I-261 | 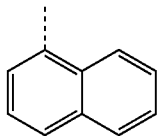 | 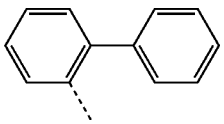 | 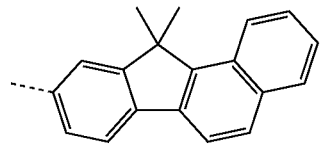 |
| I-262 | 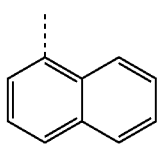 | 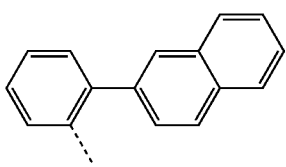 | 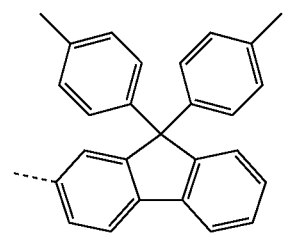 |
| I-266 | 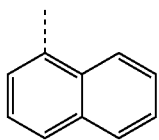 | 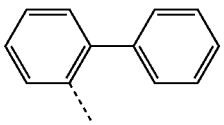 | 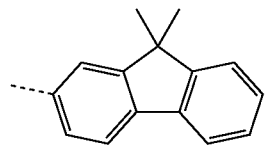 |
| I-270 | 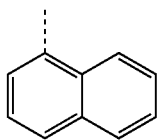 | 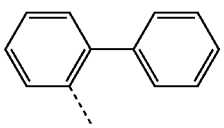 | 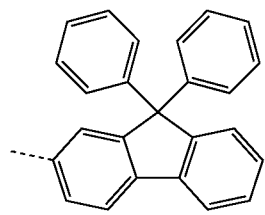 |
| I-273 | 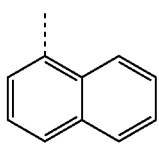 | 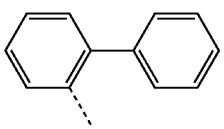 | 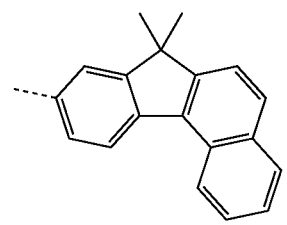 |

-continued
| | | | |
|---|---|---|---|
| I-274 | 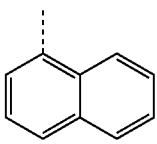 | 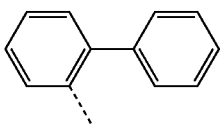 | 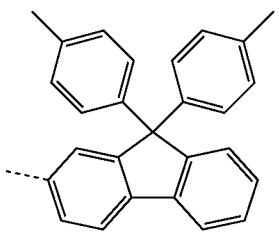 |
| I-278 | 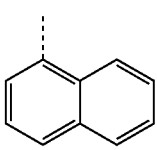 | 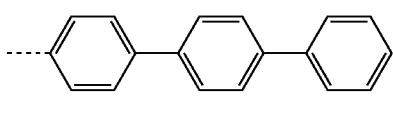 | 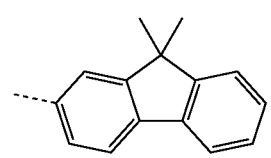 |
| I-282 | 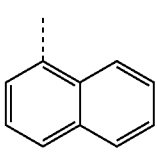 | 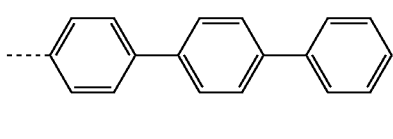 | 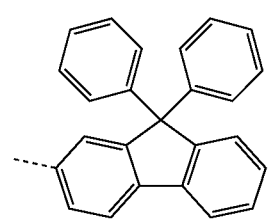 |
| I-286 | 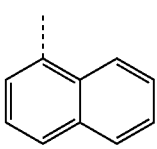 | 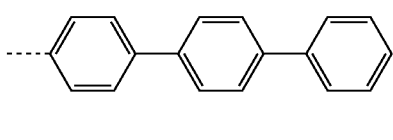 | 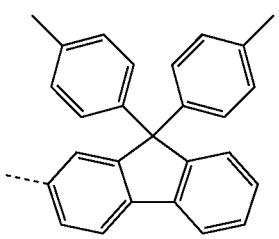 |
| I-290 | 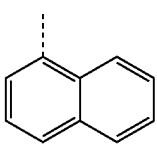 | 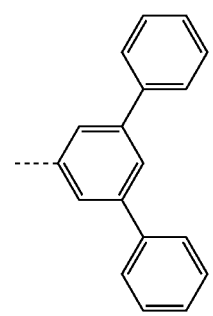 | 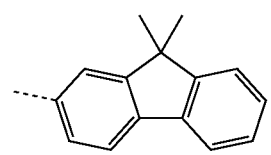 |
| I-294 | 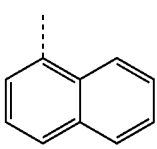 | 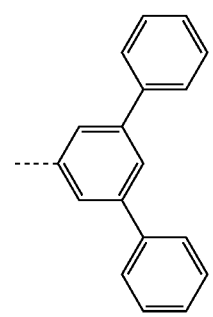 | 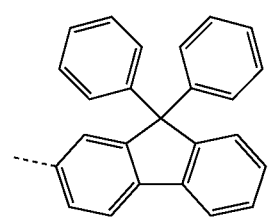 |

-continued
| | 841 | | 842 |
|---|---|---|---|
| I-297 | 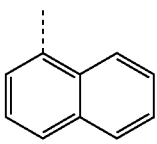 | 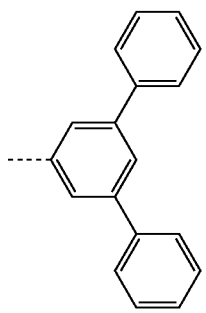 | 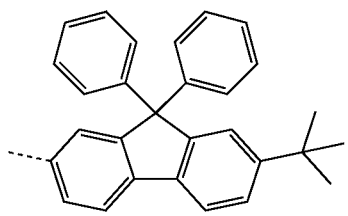 |
| I-298 | 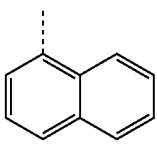 | 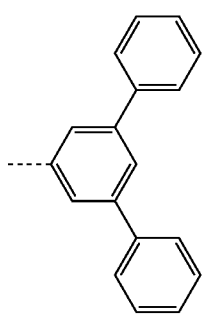 | 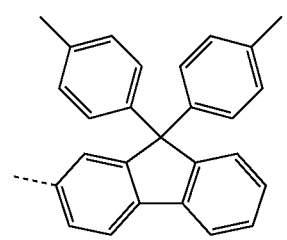 |
| I-302 | 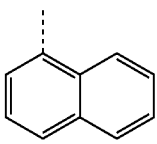 | 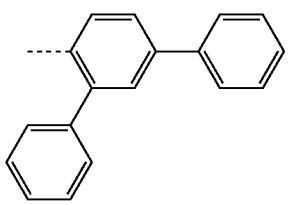 | 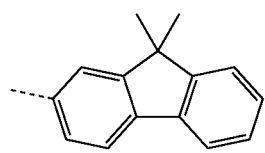 |
| I-306 | 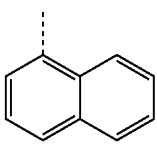 | 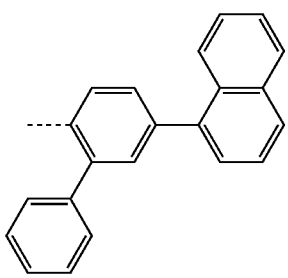 | 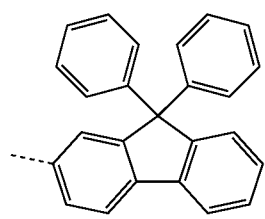 |
| I-310 | 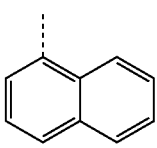 | 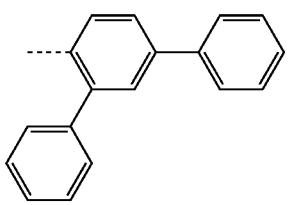 | 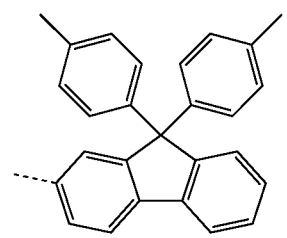 |
| I-314 | 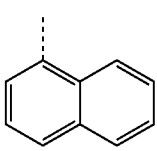 | 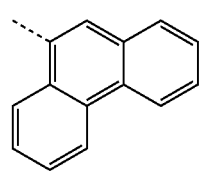 | 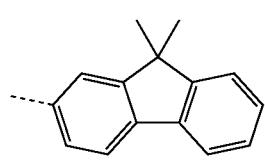 |

-continued
| | | | |
|---|---|---|---|
| I-318 | 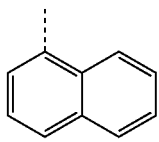 | 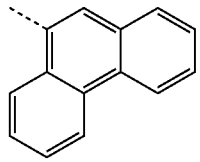 | 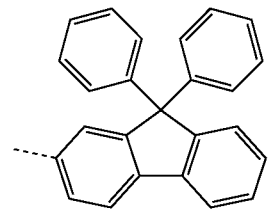 |
| I-321 | 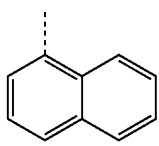 | 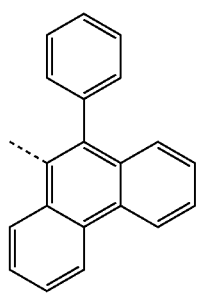 | 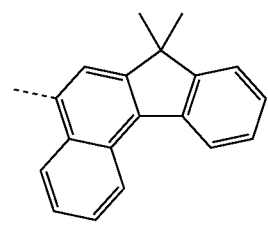 |
| I-322 | 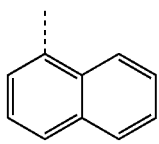 | 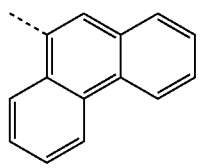 | 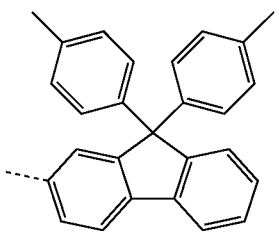 |
| I-326 | 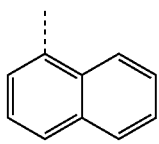 | 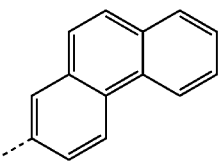 | 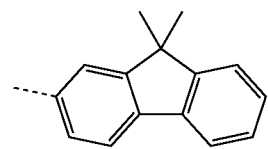 |
| I-330 | 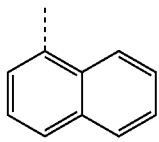 | 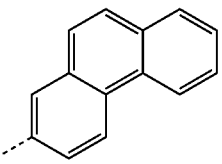 | 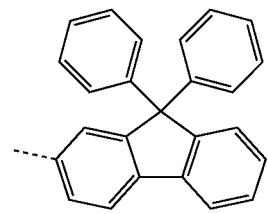 |
| I-334 | 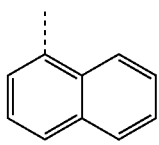 | 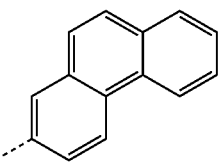 | 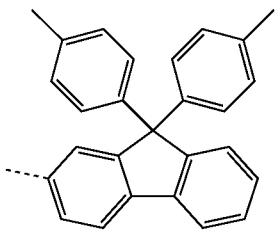 |
| I-335 | 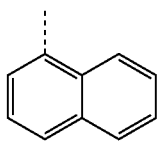 | 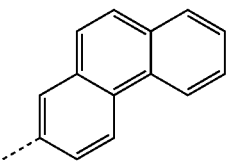 | 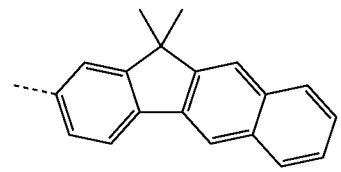 |

| | | | |
|---|---|---|---|
| I-338 | 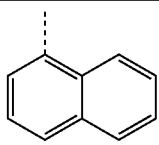 | 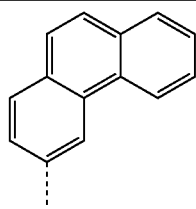 | 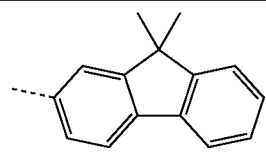 |
| I-342 | 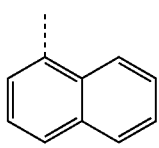 | 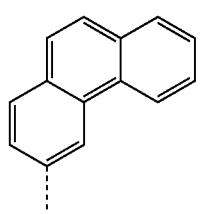 | 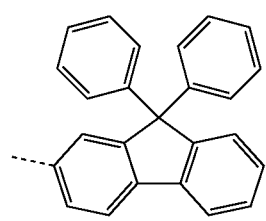 |
| I-345 | 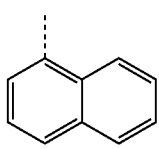 | 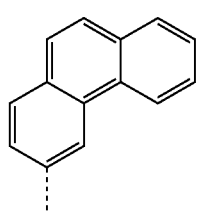 | 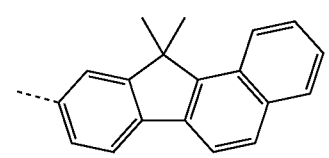 |
| I-346 | 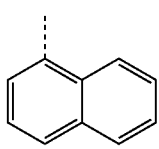 | 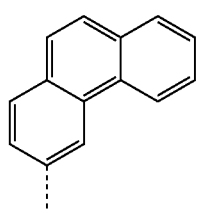 | 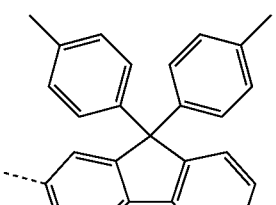 |
| I-350 | 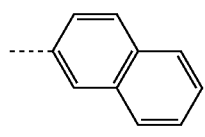 | 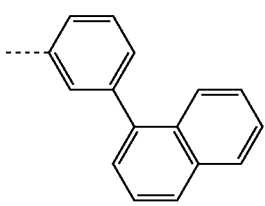 | 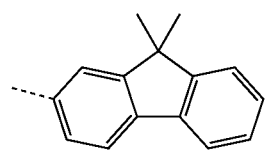 |
| I-354 | 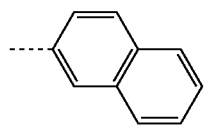 | 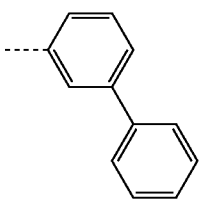 | 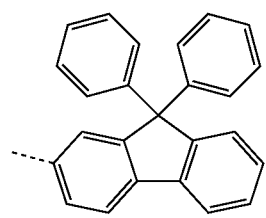 |
| I-358 | 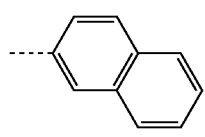 | 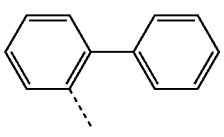 | 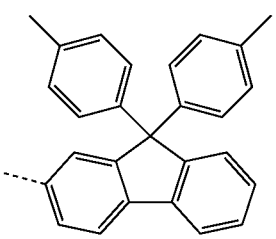 |

-continued
| | | | |
|---|---|---|---|
| I-362 | 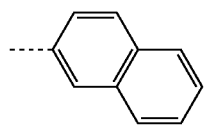 | 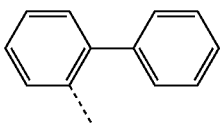 | 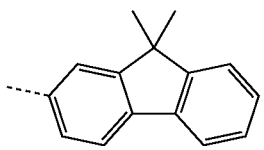 |
| I-366 | 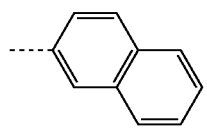 | 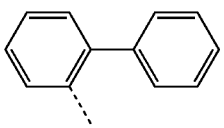 | 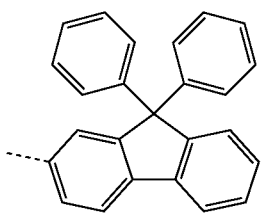 |
| I-370 | 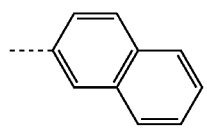 | 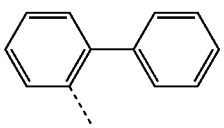 | 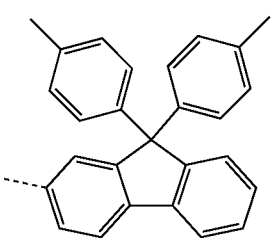 |
| I-374 | 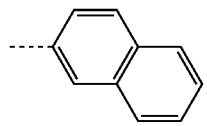 | 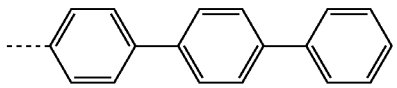 | 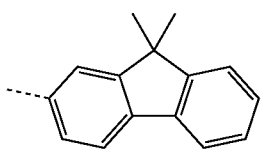 |
| I-378 | 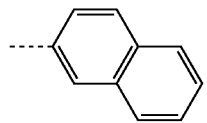 | 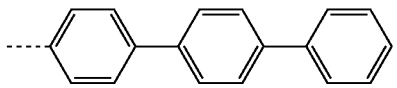 | 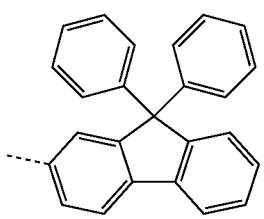 |
| I-382 | 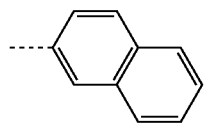 | 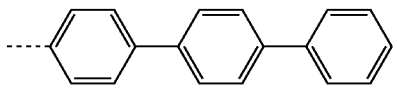 | 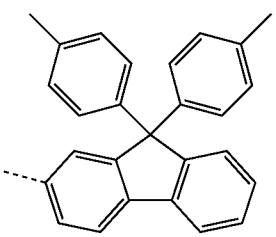 |
| I-386 | 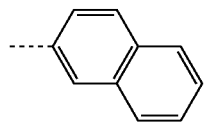 | 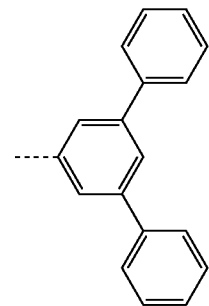 | 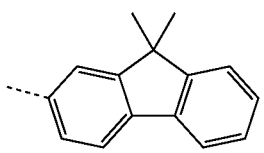 |

-continued
| | | | |
|---|---|---|---|
| I-389 | 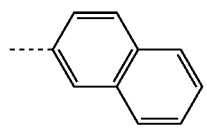 | 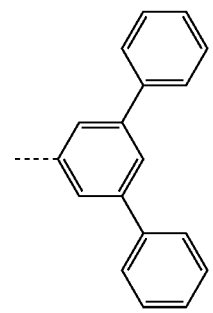 | 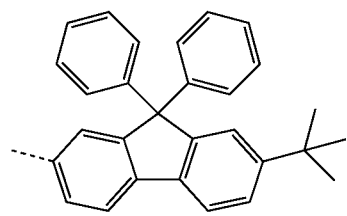 |
| I-390 | 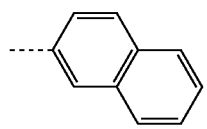 | 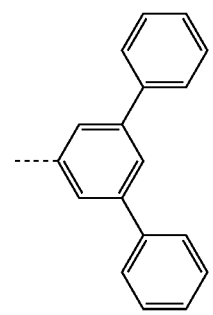 | 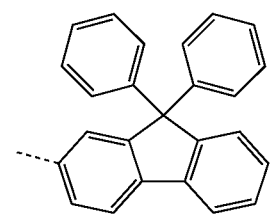 |
| I-394 | 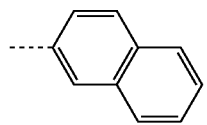 | 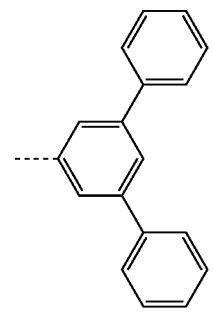 | 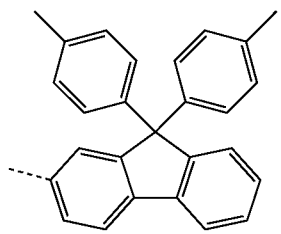 |
| I-398 | 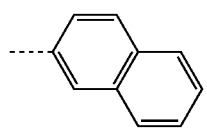 | 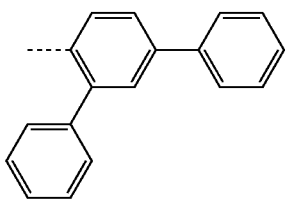 | 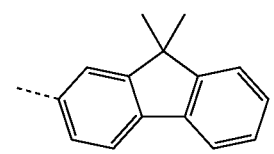 |
| I-401 | 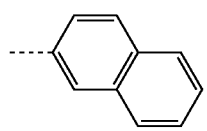 | 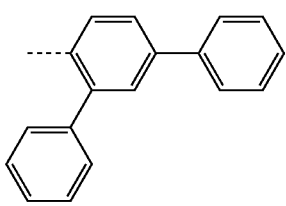 | 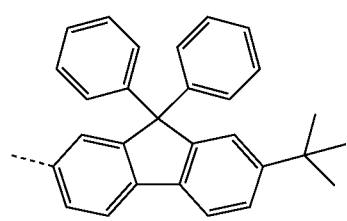 |
| I-402 | 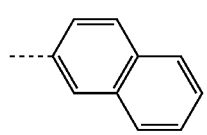 | 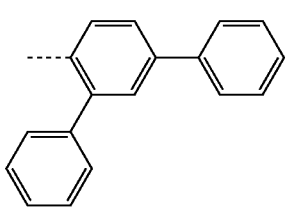 | 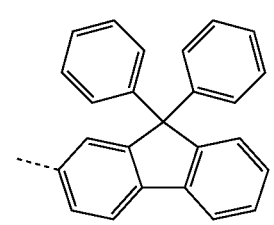 |

| | | | |
|---|---|---|---|
| I-403 | 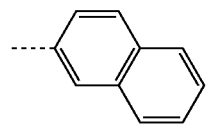 | 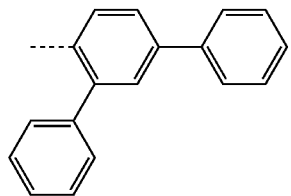 | 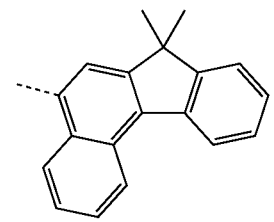 |
| I-406 | 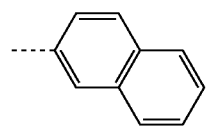 | 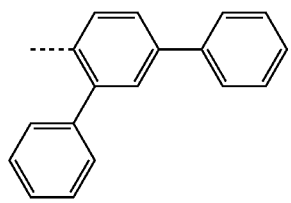 | 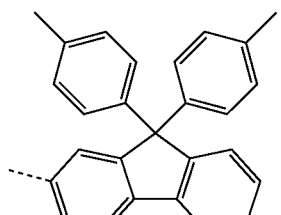 |
| I-410 | 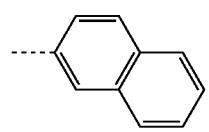 | 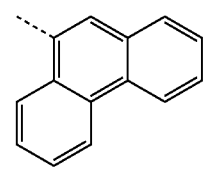 | 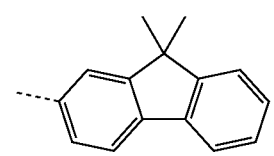 |
| I-414 | 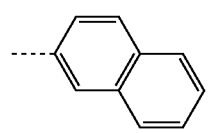 | 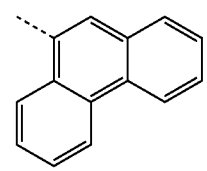 | 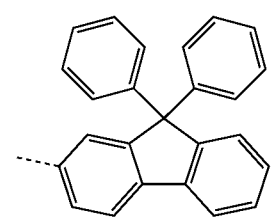 |
| I-418 | 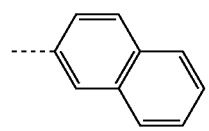 | 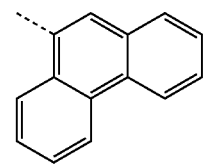 | 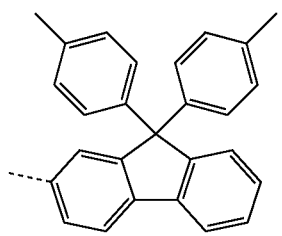 |
| I-422 | 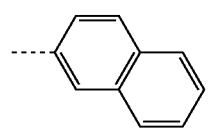 | 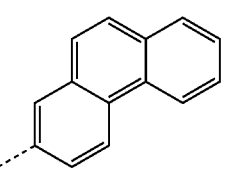 | 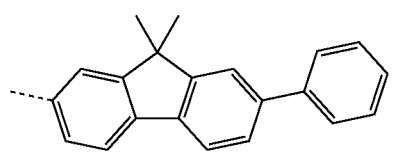 |
| I-426 | 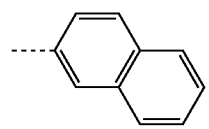 | 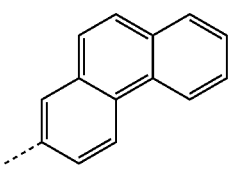 | 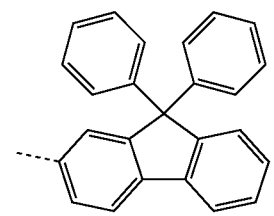 |

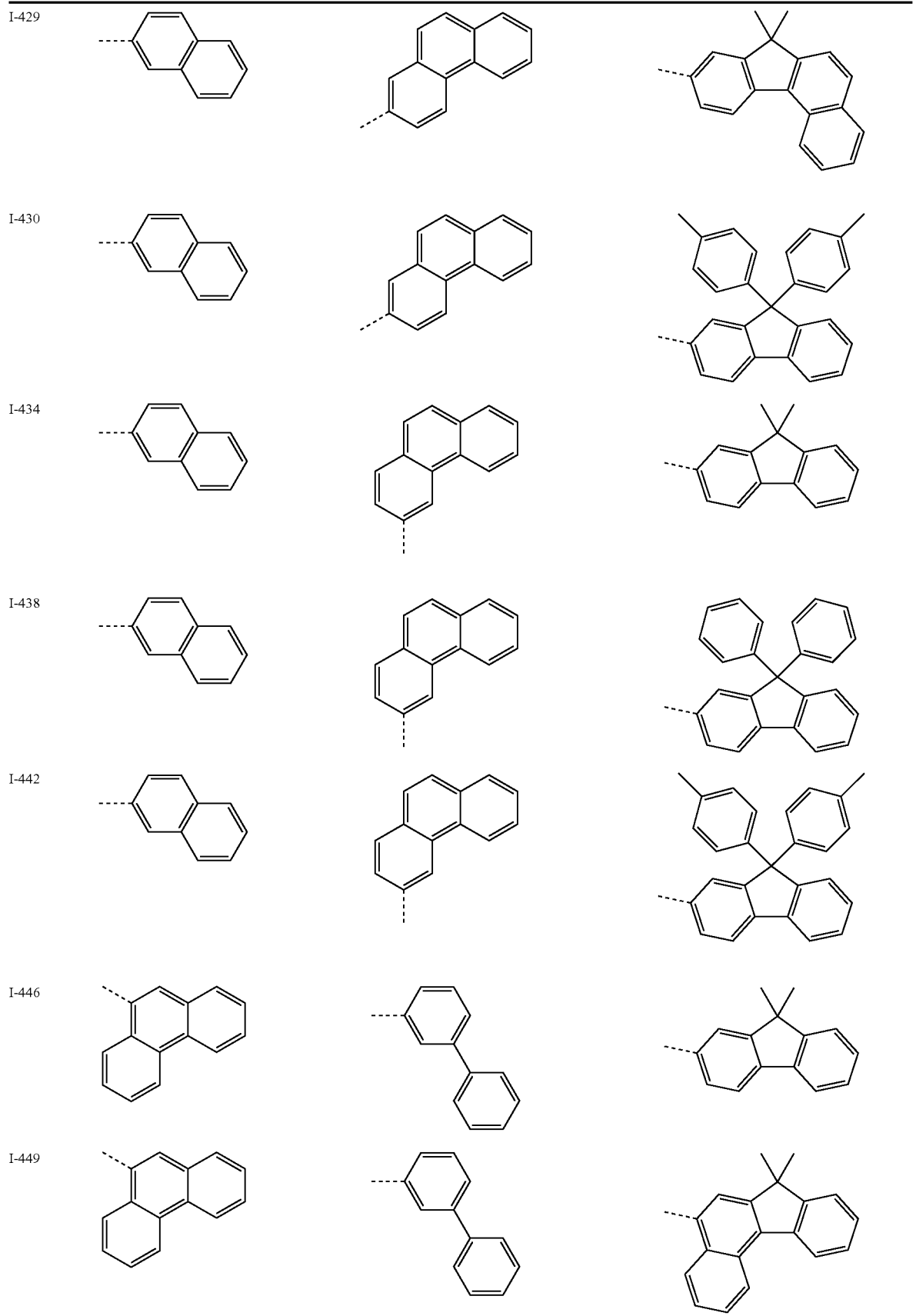

| | 855 | | 856 |
|---|---|---|---|
| I-450 | 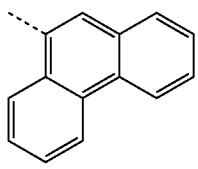 | 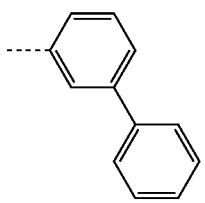 | 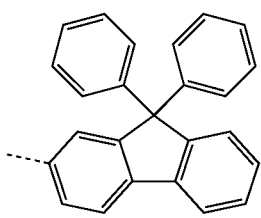 |
| I-454 | 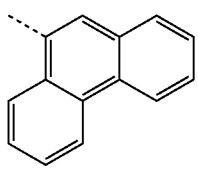 | 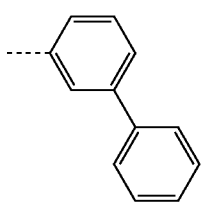 | 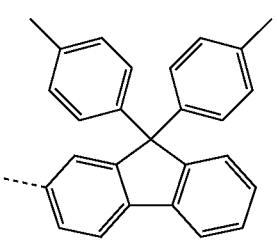 |
| I-462 | 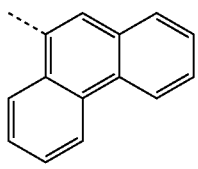 | 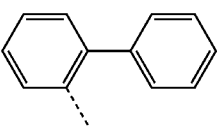 | 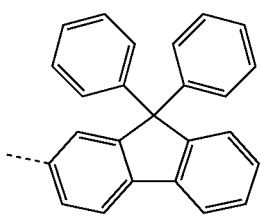 |
| I-463 | 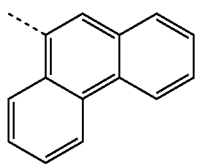 | 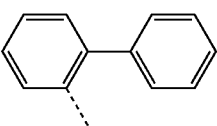 | 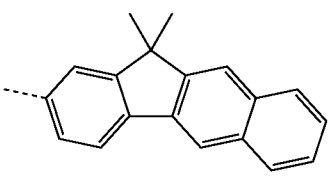 |
| I-466 | 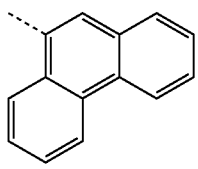 | 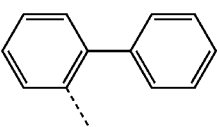 | 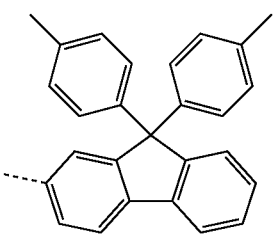 |
| I-470 | 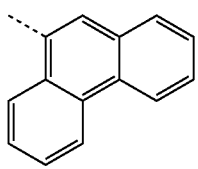 | 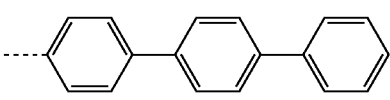 | 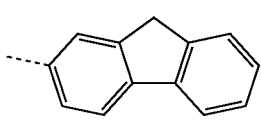 |
| I-474 | 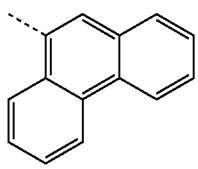 | 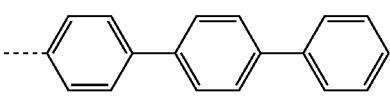 | 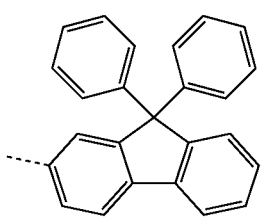 |

-continued
| | | | |
|---|---|---|---|
| I-478 | 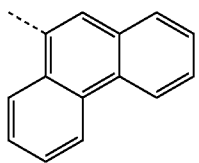 | 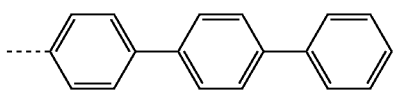 | 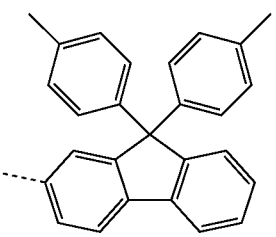 |
| I-482 | 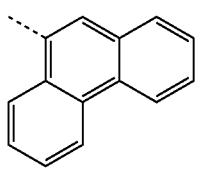 | 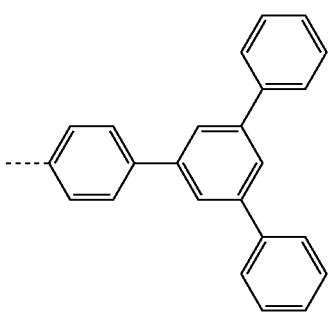 | 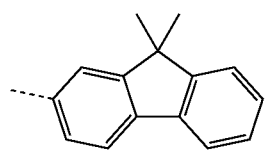 |
| I-486 | 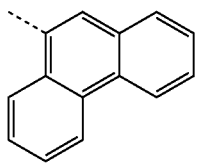 | 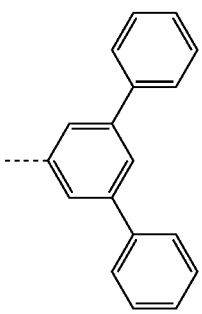 | 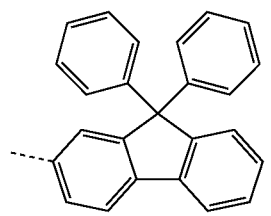 |
| I-489 | 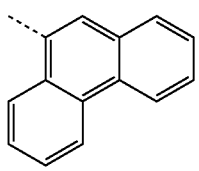 | 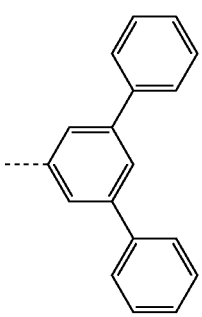 | 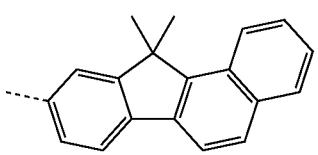 |
| I-490 | 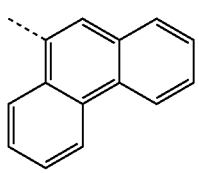 | 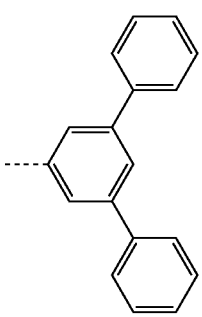 | 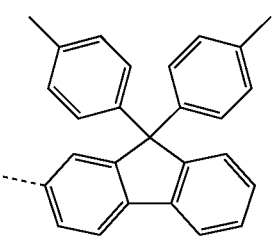 |

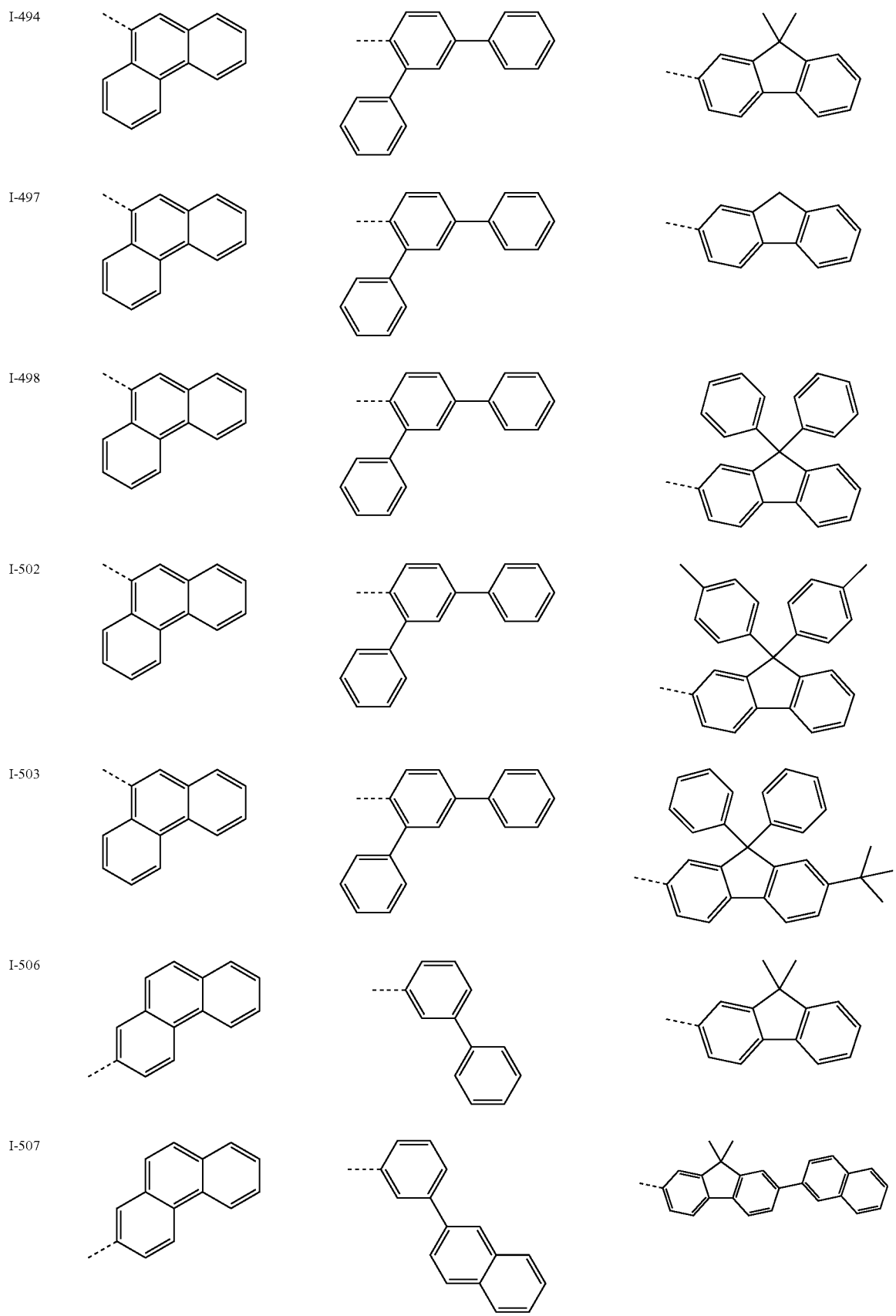

| | | | |
|---|---|---|---|
| I-510 | 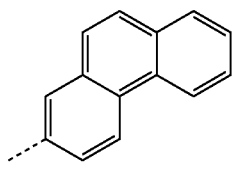 | 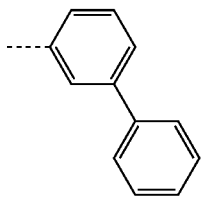 | 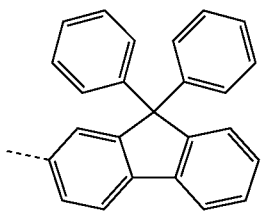 |
| I-514 | 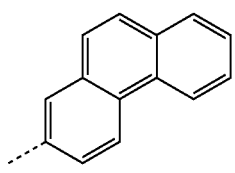 | 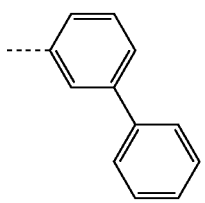 | 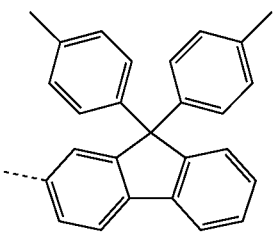 |
| I-518 | 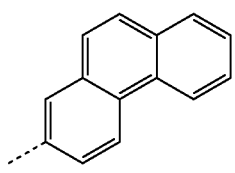 | 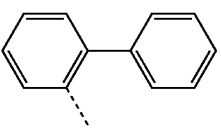 | 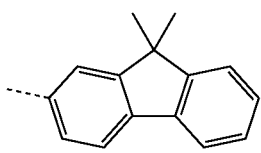 |
| I-522 | 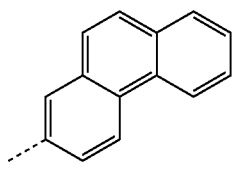 | 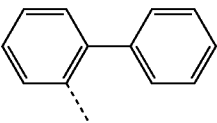 | 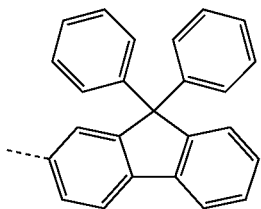 |
| I-526 | 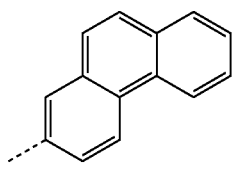 | 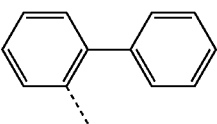 | 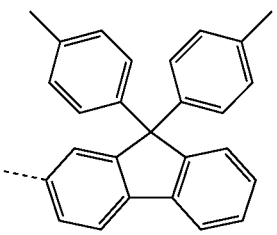 |
| I-527 | 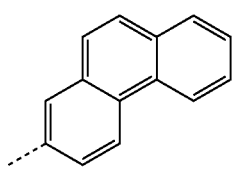 | 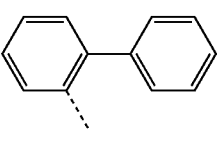 | 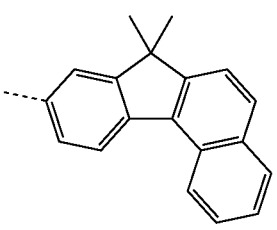 |
| I-530 | 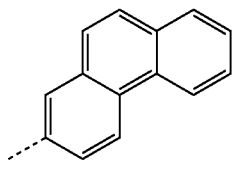 | 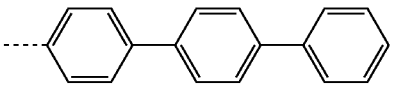 | 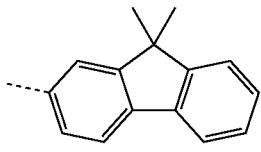 |

-continued
| | | | |
|---|---|---|---|
| I-534 | 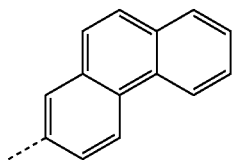 | 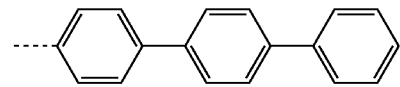 | 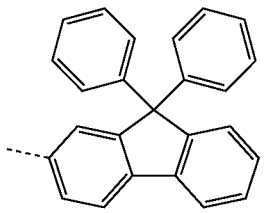 |
| I-538 | 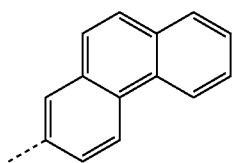 | 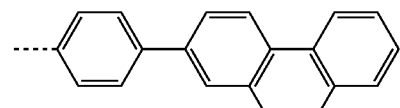 | 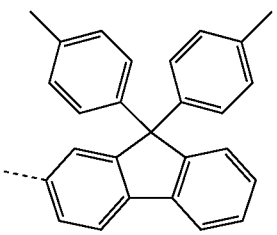 |
| I-542 | 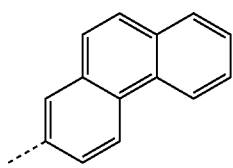 | 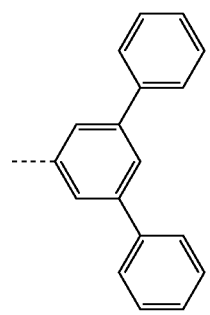 | 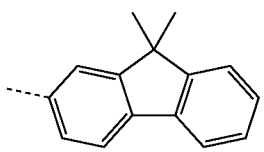 |
| I-546 | 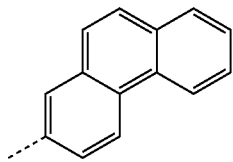 | 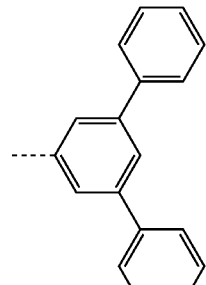 | 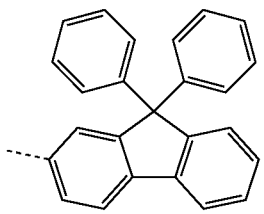 |
| I-550 | 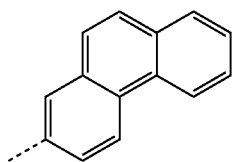 | 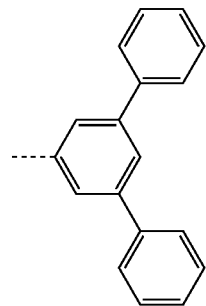 | 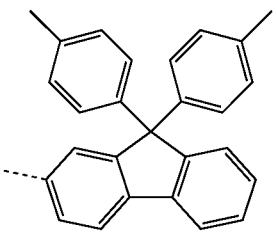 |
| I-554 | 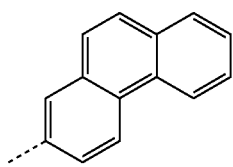 | 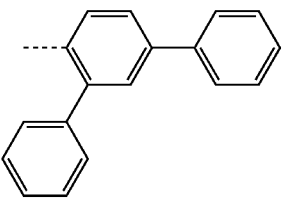 | 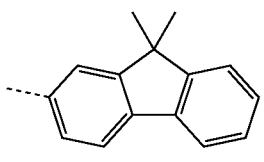 |

-continued
| | | | |
|---|---|---|---|
| I-558 | 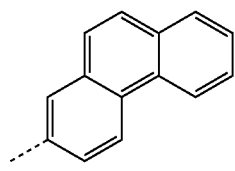 | 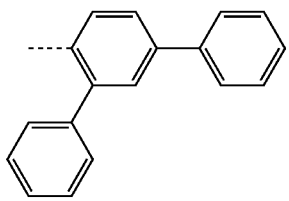 | 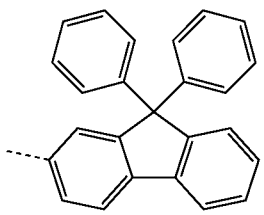 |
| I-561 | 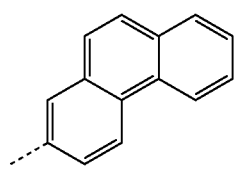 | 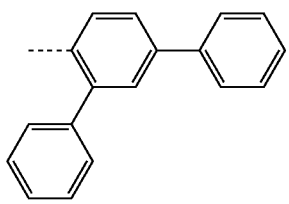 | 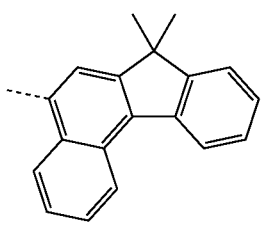 |
| I-562 | 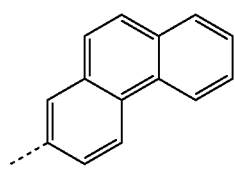 | 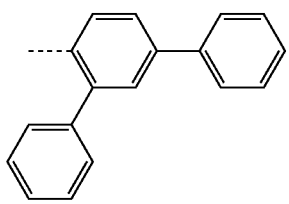 | 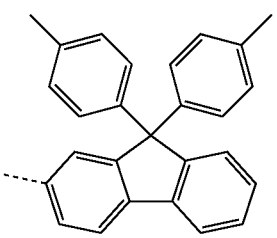 |
| I-566 | 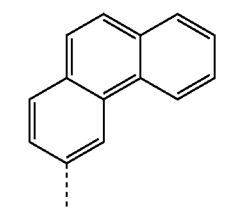 | 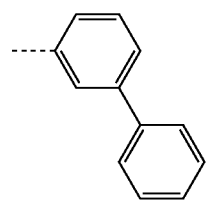 | 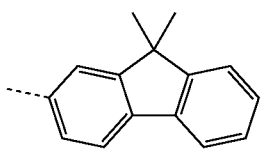 |
| I-569 | 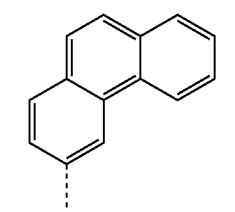 | 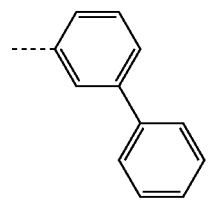 | 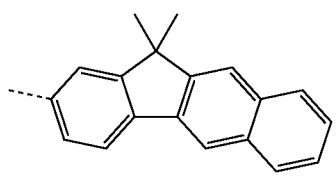 |
| I-570 | 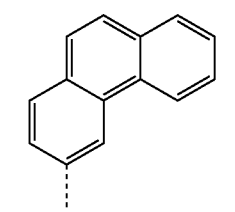 | 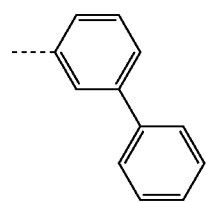 | 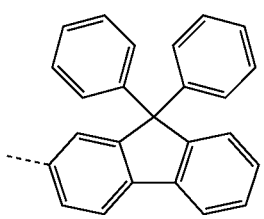 |
| I-574 | 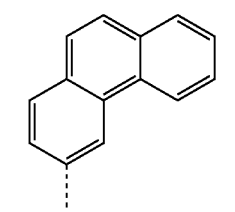 | 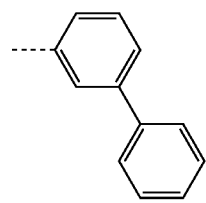 | 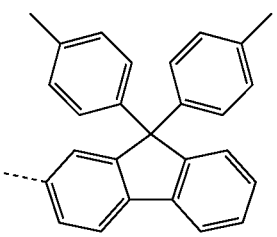 |

-continued
| | | | |
|---|---|---|---|
| I-578 | 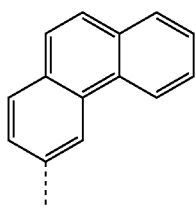 | 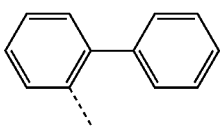 | 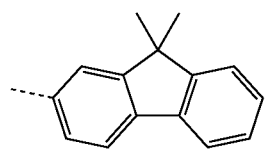 |
| I-582 | 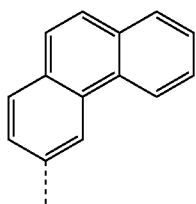 | 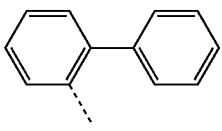 | 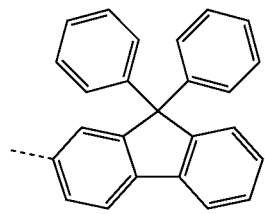 |
| I-586 | 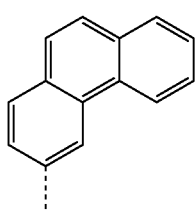 | 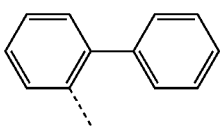 | 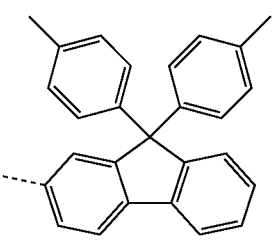 |
| I-590 | 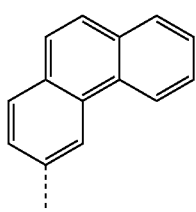 | 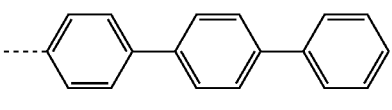 | 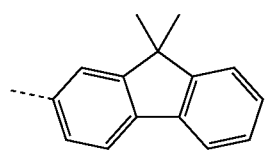 |
| I-594 | 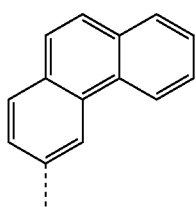 | 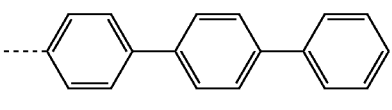 | 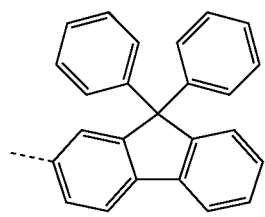 |
| I-597 | 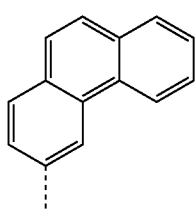 | 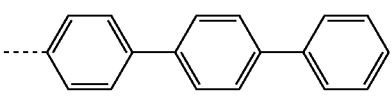 | 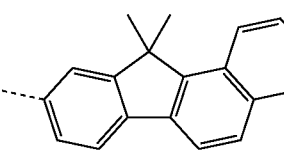 |
| I-598 | 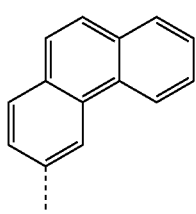 | 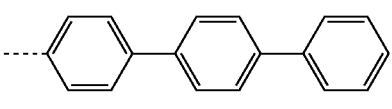 | 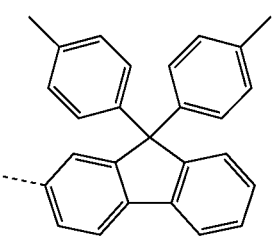 |

-continued
I-599 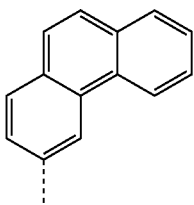 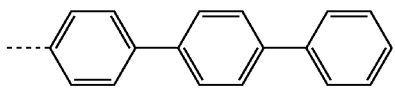 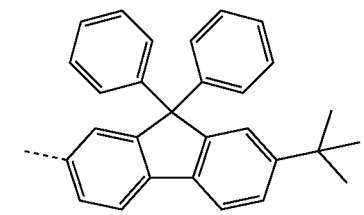
I-602 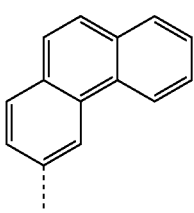 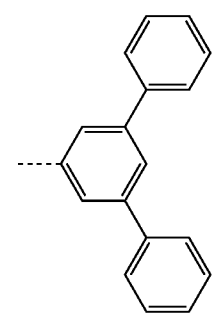 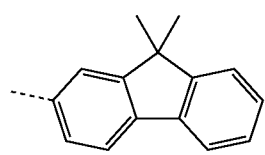
I-606 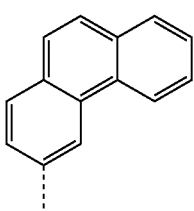 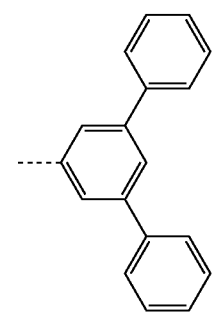 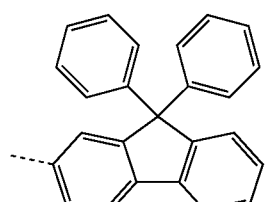
I-609 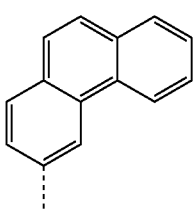 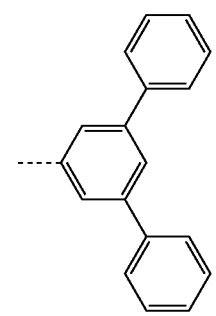 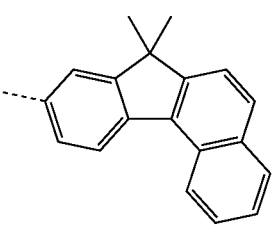
I-610 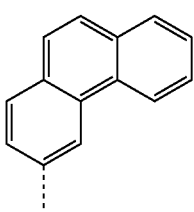 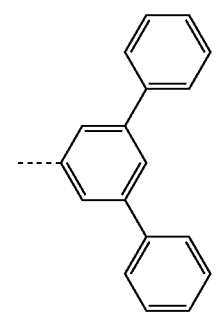 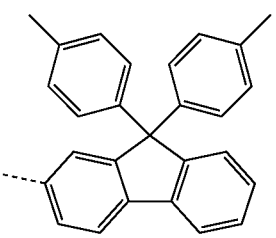

| | | | |
|---|---|---|---|
| I-611 | 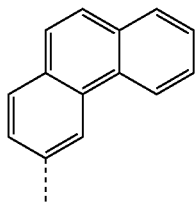 | 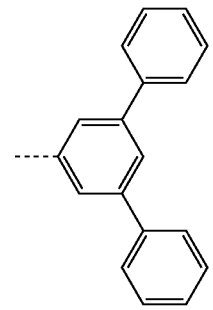 | 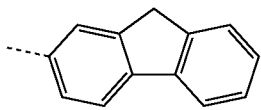 |
| I-614 | 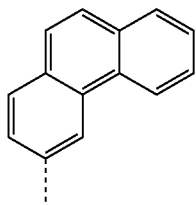 | 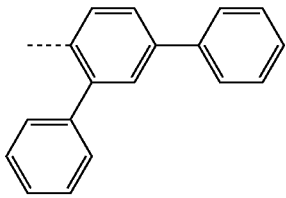 | 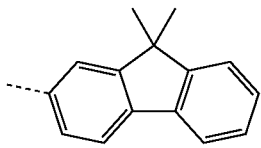 |
| I-618 | 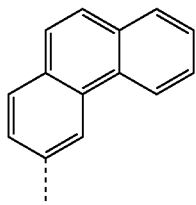 | 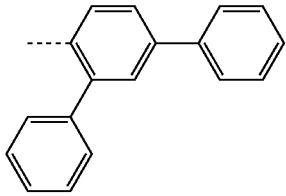 | 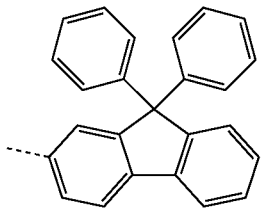 |
| I-622 | 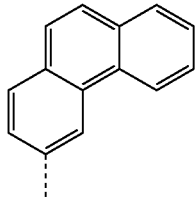 | 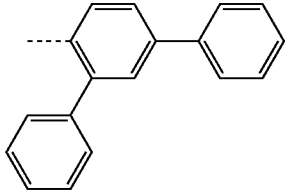 | 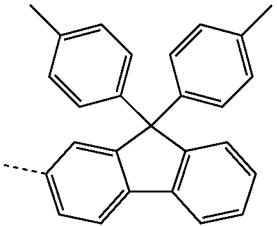 |
| I-623 | 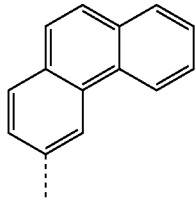 | 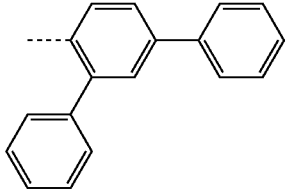 | 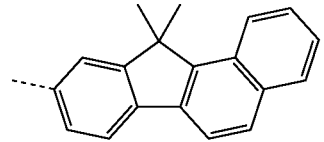 |
| I-625 | 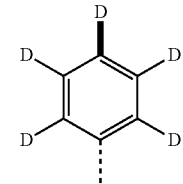 | 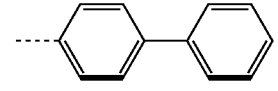 | 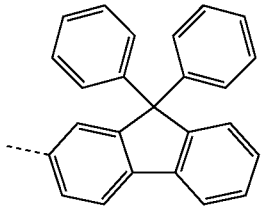 |

-continued

| I-627 | 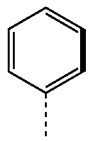 | 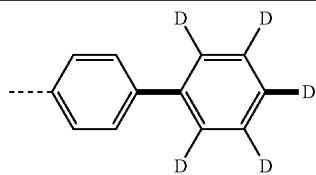 | 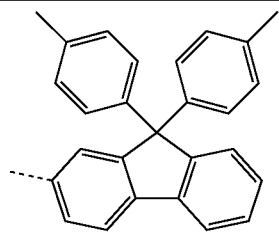 |

9. An organic light emitting device comprising:
an anode;
a cathode; and
one or more organic material layers provided between the anode and the cathode,
wherein one or more layers of the organic material layers comprise the compound of claim 1.

10. The organic light emitting device of claim 9, wherein the organic material layer comprising the compound is one or two or more organic material layers selected from the group consisting of an electron transporting layer, an electron injection layer, a layer which simultaneously injects or transports electrons, and an electron controlling layer.

11. The organic light emitting device of claim 9, wherein the organic material layer comprising the compound comprises the compound as a host and an n-type dopant as a dopant.

12. The organic light emitting device of claim 11, wherein the n-type dopant comprises an alkali metal, an alkali metal compound, an alkaline earth metal, an alkaline earth metal compound, or a combination thereof.

13. The organic light emitting device of claim 11, wherein as the n-type dopant, one or two or more are selected from the group consisting of Li, Na, K, Rb, Cs, Mg, Ca, Sr, Ba, La, Nd, Sm, Eu, Tb, Yb, LiF, $Li_2O$, CsF, or the following compounds:

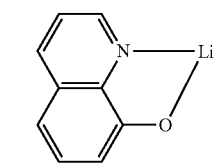

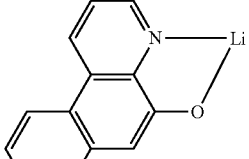

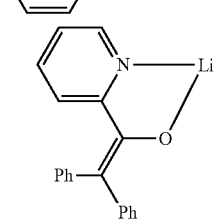

-continued

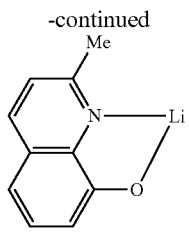

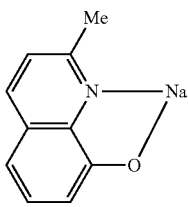

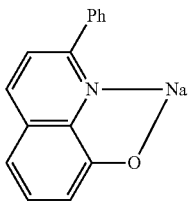

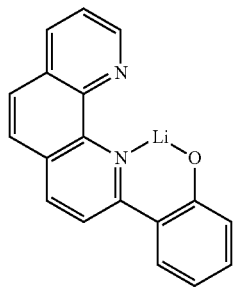

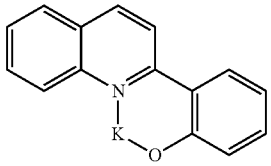

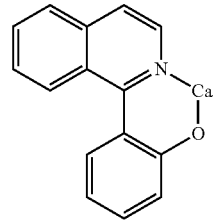

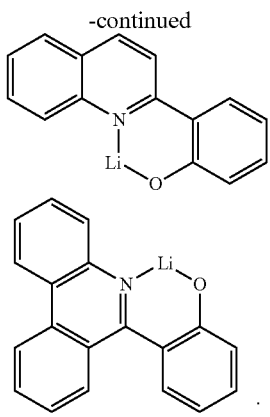

14. An organic light emitting device comprising:
an anode;
a cathode; and
two or more organic material layers provided between the anode and the cathode,
wherein the organic material layer comprises an electron transporting layer and an electron controlling layer,
the electron transporting layer comprises the compound of claim 1 as a host and an n-type dopant as a dopant, and
the electron controlling layer is different from the electron transporting layer.

15. An organic light emitting device comprising:
an anode;
a cathode; and
two or more organic material layers provided between the anode and the cathode,
wherein the organic material layer comprises an electron transporting layer and an electron controlling layer,
the electron controlling layer comprises the compound of claim 1 as a host and an n-type dopant as a dopant, and
the electron transporting layer is different from the electron controlling layer.

16. The organic light emitting device of claim 9, wherein the organic light emitting device comprises:
a light emitting layer provided between the anode and the cathode;
an electron transporting layer provided between the light emitting layer and the cathode; and
an electron controlling layer provided between the electron transporting layer and the light emitting layer, and
the electron controlling layer comprises a compound of Formula 3-1:

[Formula 3-1]

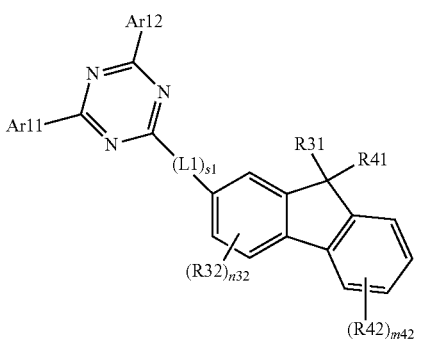

wherein in Formula 3-1:
Ar1 and Ar12 are different from each other, and each independently is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
L1 is a direct bond, a phenylene, a biphenylene, a naphthylene, or a phenanthrylene, which is unsubstituted or substituted with deuterium;
R32 is hydrogen or deuterium, or two or more adjacent R32s combine with each other to form a benzene ring;
R42 is hydrogen, deuterium, a C1 to C6 alkyl group, a phenyl group, a naphthyl group, or a biphenyl group, or two or more adjacent R42s combine with each other to form a benzene ring;
R31 and R41 are the same as or different from each other, and each independently is hydrogen, deuterium, a C1 to C6 alkyl group, a phenyl group, a naphthyl group, or a biphenyl group, which is unsubstituted or substituted with deuterium or a C1-C6 alkyl group;
n32 is an integer of 0 to 3 and m42 is an integer of 0 to 4; and
s1 is an integer of 1 to 5; and
when n32 is 2 or more, the R32's are the same as or different from each other; and
when n42 is 2 or more, the R42's are the same as or different from each other; and
when s1 is 2 or more, the L1's are the same as or different from each other.

17. An organic light emitting device comprising:
an anode;
a cathode;
two or more organic material layers provided between the anode and the cathode, wherein at least one organic material layer is an electron transporting layer and at least one organic material layer is an electron controlling layer; and
a light emitting layer provided between the anode and the cathode;
wherein:
the electron transporting layer is provided between the light emitting layer and the cathode;
the electron controlling layer is provided between the electron transporting layer and the light emitting layer; and
the electron transporting layer comprises a compound of Formula 6-1:

[Formula 6-1]

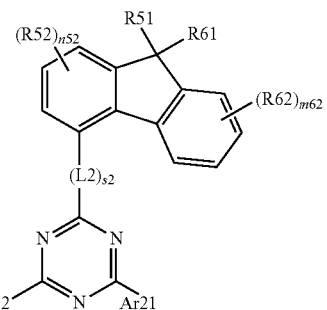

wherein in Formula 6-1:
Ar2 and Ar22 are different from each other, and each independently is a phenyl group, a naphthyl group, biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group, and a phenanthryl group;

L2 is a direct bond, a phenylene, a biphenylene, a naphthylene, or a phenanthrylene, which is unsubstituted or substituted with deuterium;

R52 is hydrogen or deuterium, or two or more adjacent R52s combine with each other to a benzene ring;

R62 is hydrogen, deuterium, a C1 to C6 alkyl group, a phenyl group, a naphthyl group, or a biphenyl group, or two or more adjacent R62s combine with each other to form a benzene ring;

R51 and R61 are the same as or different from each other, and each independently is hydrogen, deuterium, a substituted or unsubstituted C1 to C6 alkyl group, a phenyl group, a naphthyl group, or a biphenyl group, which is unsubstituted or substituted with deuterium or a C1-C6 alkyl group;

n52 is an integer of 0 to 3;

m62 is an integer of 0 to 4; and s2 is an integer of 1 to 5; and when n52 is each 2 or more, the R52's are the same as or different from each other; and when m62 is each 2 or more, the R62's are the same as or different from each other; and when s is each 2 or more, the L2's are the same as or different from each other.

18. An organic light emitting device comprising:
an anode;
a cathode;
a light emitting layer provided between the anode and the cathode; and
an electron transporting layer provided between the light emitting layer and the cathode,
wherein the light emitting layer comprises a host, and
the electron transporting layer comprises the compound of claim 1, which is different from the host and has a HOMO energy level of 6 eV to 7 eV.

19. An organic light emitting device comprising:
an anode;
a cathode;
a light emitting layer provided between the anode and the cathode; and
an electron transporting layer provided between the light emitting layer and the cathode,
wherein the light emitting layer comprises a host, and
the electron transporting layer comprises the compound of claim 1, which is different from the host and has a triplet energy (ET) of 2.2 eV or more.

* * * * *

UNITED STATES PATENT AND TRADEMARK OFFICE
CERTIFICATE OF CORRECTION

PATENT NO. : 10,964,892 B2
APPLICATION NO. : 15/126533
DATED : March 30, 2021
INVENTOR(S) : Jungoh Huh et al.

It is certified that error appears in the above-identified patent and that said Letters Patent is hereby corrected as shown below:

In the Claims

In Claim 1, at Column 465, from Line 15 to Line 25, Formula 5 should appear as follows:

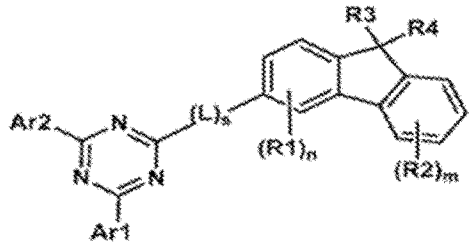

In Claim 7, in Compound 1-2, the formulae for ---Ar2 and ---Ar3 should appear as follows:

| Compound | ---Ar1 | ---Ar2 | ---Ar3 |
|---|---|---|---|
| 1-2 | (phenyl) | (biphenyl) | (fluorenyl) |

In Claim 7, in Compound 1-8, the formula for ---Ar3 should appear as follows:

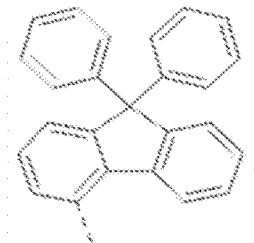

In Claim 7, in Compound 1-40, the formula for ---Ar3 should appear as follows:

Signed and Sealed this
Twenty-ninth Day of June, 2021

Drew Hirshfeld
*Performing the Functions and Duties of the
Under Secretary of Commerce for Intellectual Property and
Director of the United States Patent and Trademark Office*

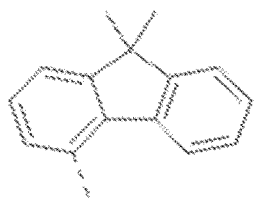

In Claim 7, in Compound 1-46, the formula for ---Ar3 should appear as follows:

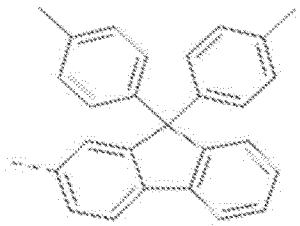

In Claim 7, the extra Compound 1-319 should be deleted

In Claim 7, in Compound 1-337, the formula for ---Ar2 should appear as follows:

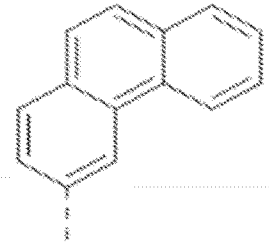

In Claim 7, in Compound 1-503, the formula for ---Ar3 should appear as follows:

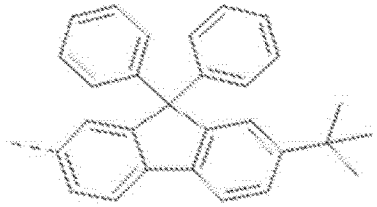

In Claim 7, in Compound 1-534, the formula for ---Ar3 should appear as follows:

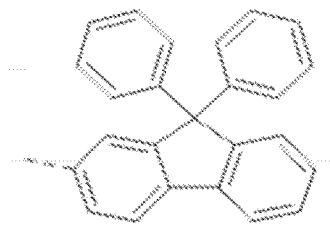

In Claim 7, in Compound 1-562, the formula for ---Ar3 should appear as follows:

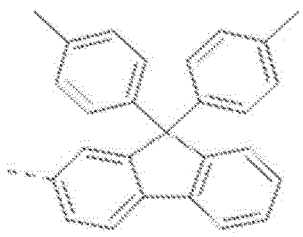
In Claim 8, in Compound 2-198, the formula for ---Ar3 should appear as follows:
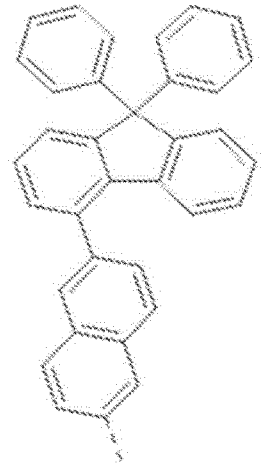
In Claim 8, in Compound 2-361, the formula for ---Ar3 should appear as follows:
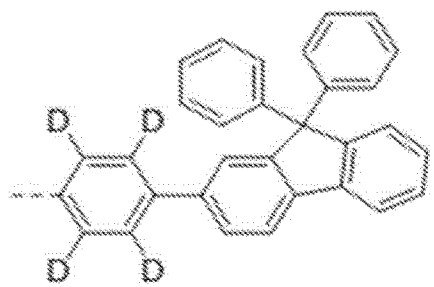
In Claim 8, in Compound 2-363, the formula for ---Ar2 should appear as follows:
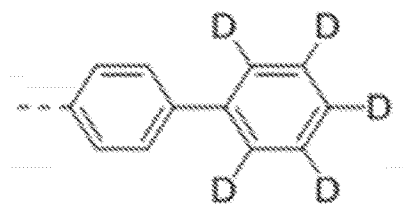
In Claim 8, in Compound 1-625, the formulae for ---Ar1 and ---Ar2 should appear as follows:

| Compound | ---Ar1 | ---Ar2 | ---Ar3 |
|---|---|---|---|
| 1-625 | (deuterated phenyl) | (biphenyl) | (spirobifluorene) |

In Claim 8, in Compound 1-627, the formula for ---Ar1 and ---Ar2 should appear as follows:

| Compound | ---Ar1 | ---Ar2 | ---Ar3 |
|---|---|---|---|
| 1-627 | (phenyl) | (phenyl-deuterated phenyl) | (spirobifluorene) |

At Column 875, Lines 38-67, and at Column 876, Lines 1-28 please replace Claim 16 with the following:

16. The organic light emitting device of claim 9, wherein the organic light emitting device comprises:
    a light emitting layer provided between the anode and the cathode;
    an electron transporting layer provided between the light emitting layer and the cathode; and
    an electron controlling layer provided between the electron transporting layer and the light emitting layer, and
    the electron controlling layer comprises a compound of Formula 3-1:
    [Formula 3-1]

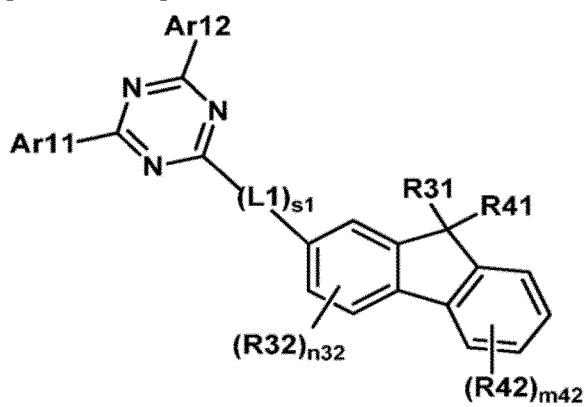

wherein in Formula 3-1:
    Ar11 and Ar12 are different from each other, and each independently is a phenyl group, a naphthyl group, a biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group and a phenanthryl group;
    L1 is a direct bond, a phenylene, a biphenylene, a naphthylene, or a phenanthrylene, which is unsubstituted or substituted with deuterium;

R32 is hydrogen or deuterium, or two or more adjacent R32s combine with each other to form a benzene ring;

R42 is hydrogen, deuterium, a C1 to C6 alkyl group, a phenyl group, a naphthyl group, or a biphenyl group, or two or more adjacent R42s combine with each other to form a benzene ring;

R31 and R41 are the same as or different from each other, and each independently is hydrogen, deuterium, a C1 to C6 alkyl group, a phenyl group, a naphthyl group, or a biphenyl group, which is unsubstituted or substituted with deuterium or a C1-C6 alkyl group;

n32 is an integer of 0 to 3 and m42 is an integer of 0 to 4; and s1 is an integer of 1 to 5; and when n32 is 2 or more, the R32's are the same as or different from each other; and when n42 is 2 or more, the R42's are the same as or different from each other; and when s1 is 2 or more, the L1's are the same as or different from each other.

At Column 876, Lines 29-67, Column 877, Lines 1-24, and Column 878, Lines 1-2 please replace Claim 17 with the following:

17. An organic light emitting device comprising:

an anode;

a cathode;

two or more organic material layers provided between the anode and the cathode, wherein at least one organic material layer is an electron transporting layer and at least one organic material layer is an electron controlling layer; and a light emitting layer provided between the anode and the cathode;

wherein:

the electron transporting layer is provided between the light emitting layer and the cathode;

the electron controlling layer is provided between the electron transporting layer and the light emitting layer; and the electron transporting layer comprises a compound of Formula 6-1:

[Formula 6-1]

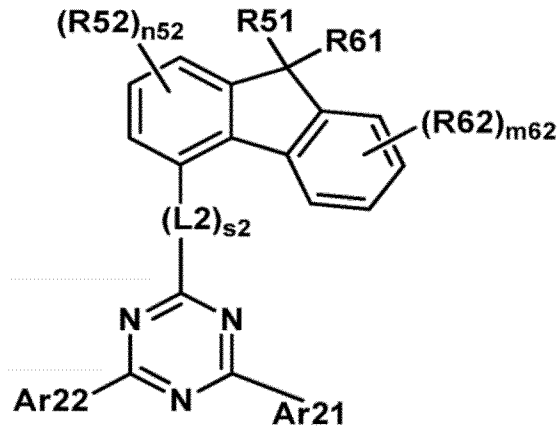

wherein in Formula 6-1:

Ar21 and Ar22 are different from each other, and each independently is a phenyl group, a naphthyl group, biphenyl group, a terphenyl group, a quaterphenyl group, a phenanthryl group, or a chrysenyl group, which is unsubstituted or substituted with one or more substituents selected from the group consisting of deuterium, a phenyl group, a naphthyl group, a terphenyl group, and a phenanthryl group;

$L_2$ is a direct bond, a phenylene, a biphenylene, a naphthylene, or a phenanthrylene, which is unsubstituted or substituted with deuterium;

$R_{52}$ is hydrogen or deuterium, or two or more adjacent $R_{52}$s combine with each other to a benzene ring;

$R_{62}$ is hydrogen, deuterium, a C1 to C6 alkyl group, a phenyl group, a naphthyl group, or a biphenyl group, or two or more adjacent $R_{62}$s combine with each other to form a benzene ring;

$R_{51}$ and $R_{61}$ are the same as or different from each other, and each independently is hydrogen, deuterium, a substituted or unsubstituted C1 to C6 alkyl group, a phenyl group, a naphthyl group, or a biphenyl group, which is unsubstituted or substituted with deuterium or a C1-C6 alkyl group;

$n_{52}$ is an integer of 0 to 3;

$m_{62}$ is an integer of 0 to 4; and $s_2$ is an integer of 1 to 5; and when $n_{52}$ is each 2 or more, the $R_{52}$'s are the same as or different from each other; and when $m_{62}$ is each 2 or more, the $R_{62}$'s are the same as or different from each other; and when s is each 2 or more, the $L_2$'s are the same as or different from each other.

At Column 878, Lines 14-24, please replace Claim 19 with the following:

19. An organic light emitting device comprising:
    an anode;
    a cathode;
    a light emitting layer provided between the anode and the cathode; and
    an electron transporting layer provided between the light emitting layer and the cathode,
    wherein the light emitting layer comprises a host, and
    the electron transporting layer comprises the compound of claim 1, which is different from the host and has a triplet energy ($E_T$) of 2.2 eV or more.